United States Patent
Heffernan et al.

(10) Patent No.: US 11,186,564 B2
(45) Date of Patent: Nov. 30, 2021

(54) DUAL NAV1.2/5HT2A INHIBITORS FOR TREATING CNS DISORDERS

(71) Applicant: Sunovion Pharmaceuticals Inc., Marlborough, MA (US)

(72) Inventors: Michele L. R. Heffernan, Holliston, MA (US); Larry Wendell Hardy, Framingham, MA (US); Scott P. Brown, Framingham, MA (US); Lee W. Herman, Natick, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

(21) Appl. No.: 16/322,278

(22) PCT Filed: Aug. 4, 2016

(86) PCT No.: PCT/US2016/045559
§ 371 (c)(1),
(2) Date: Jan. 31, 2019

(87) PCT Pub. No.: WO2018/026371
PCT Pub. Date: Feb. 8, 2018

(65) Prior Publication Data
US 2019/0194163 A1   Jun. 27, 2019

(51) Int. Cl.
*C07D 211/22* (2006.01)
*C07D 401/08* (2006.01)
(Continued)

(52) U.S. Cl.
CPC ............ *C07D 401/08* (2013.01); *A61P 25/18* (2018.01); *A61P 25/28* (2018.01); *C07D 207/12* (2013.01); *C07D 207/36* (2013.01); *C07D 211/42* (2013.01); *C07D 211/44* (2013.01); *C07D 211/58* (2013.01); *C07D 213/81* (2013.01); *C07D 217/24* (2013.01); *C07D 221/20* (2013.01); *C07D 223/08* (2013.01); *C07D 235/12* (2013.01); *C07D 237/14* (2013.01); *C07D 241/04* (2013.01); *C07D 243/08* (2013.01); *C07D 249/12* (2013.01); *C07D 265/30* (2013.01); *C07D 267/10* (2013.01); *C07D 275/04* (2013.01); *C07D 277/66* (2013.01); *C07D 295/027* (2013.01); *C07D 295/073* (2013.01); *C07D 295/088* (2013.01); *C07D 295/096* (2013.01); *C07D 295/104* (2013.01); *C07D 295/108* (2013.01); *C07D 307/83* (2013.01); *C07D 311/08* (2013.01); *C07D 311/22* (2013.01); *C07D 311/58* (2013.01); *C07D 401/06* (2013.01); *C07D 401/12* (2013.01); *C07D 401/14* (2013.01); *C07D 403/06* (2013.01); *C07D 405/06* (2013.01); *C07D 405/12* (2013.01); *C07D 413/06* (2013.01); *C07D 413/08* (2013.01); *C07D 417/04* (2013.01); *C07D 471/04* (2013.01); *C07D 471/08* (2013.01); *C07D 471/10* (2013.01); *C07D 487/10* (2013.01); *C07D 491/048* (2013.01); *C07D 491/107* (2013.01); *C07D 491/20* (2013.01); *C07D 513/04* (2013.01)

(58) Field of Classification Search
CPC ..................................................... C07D 211/22
See application file for complete search history.

(56) References Cited

U.S. PATENT DOCUMENTS 5,561,145 A * 10/1996 Prucher ................. A61P 25/18
514/326
5,770,221 A * 6/1998 Nakamura ........... A61K 9/7053
424/449
(Continued)

FOREIGN PATENT DOCUMENTS

CN         105732479 A       7/2016
WO    WO-0162728 A1 *    8/2001   ........... C07D 207/12
(Continued)

OTHER PUBLICATIONS

CAS Registry Nos. 1625541-62-9 and 1625324-50-6 (2014) (Year: 2014).*

(Continued)

*Primary Examiner* — Deepak R Rao
(74) *Attorney, Agent, or Firm* — Heslin Rothenberg Farley & Mesiti, P.C.

(57) ABSTRACT

Compounds of formula I:

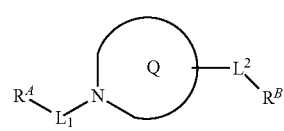

are disclosed, as are pharmaceutical compositions containing such compounds. Methods of treating neurological or psychiatric disorders in a patient in need are also disclosed. Such disorders include depression, bipolar disorder, pain, schizophrenia, obsessive compulsive disorder, addiction, social disorder, attention deficit hyperactivity disorder, an anxiety disorder, autism, a cognitive impairment, or a neuropsychiatric symptom such as apathy, depression, anxiety, psychosis, aggression, agitation, impulse control disorders, and sleep disorders in neurological disorders such as Alzheimer's and Parkinson's diseases.

11 Claims, No Drawings

(51) Int. Cl.

| | |
|---|---|
| *C07D 401/14* | (2006.01) |
| *C07D 401/06* | (2006.01) |
| *C07D 401/12* | (2006.01) |
| *C07D 405/06* | (2006.01) |
| *C07D 471/04* | (2006.01) |
| *C07D 487/10* | (2006.01) |
| *C07D 491/107* | (2006.01) |
| *C07D 311/22* | (2006.01) |
| *C07D 217/24* | (2006.01) |
| *C07D 223/08* | (2006.01) |
| *C07D 235/12* | (2006.01) |
| *C07D 237/14* | (2006.01) |
| *C07D 413/06* | (2006.01) |
| *C07D 241/04* | (2006.01) |
| *C07D 243/08* | (2006.01) |
| *C07D 471/08* | (2006.01) |
| *C07D 491/048* | (2006.01) |
| *C07D 267/10* | (2006.01) |
| *C07D 275/04* | (2006.01) |
| *C07D 211/58* | (2006.01) |
| *C07D 403/06* | (2006.01) |
| *C07D 405/12* | (2006.01) |
| *A61P 25/28* | (2006.01) |
| *C07D 417/04* | (2006.01) |
| *A61P 25/18* | (2006.01) |
| *C07D 513/04* | (2006.01) |
| *C07D 211/42* | (2006.01) |
| *C07D 295/104* | (2006.01) |
| *C07D 207/36* | (2006.01) |
| *C07D 213/81* | (2006.01) |
| *C07D 491/20* | (2006.01) |
| *C07D 249/12* | (2006.01) |
| *C07D 221/20* | (2006.01) |
| *C07D 295/088* | (2006.01) |
| *C07D 311/58* | (2006.01) |
| *C07D 207/12* | (2006.01) |
| *C07D 211/44* | (2006.01) |
| *C07D 265/30* | (2006.01) |
| *C07D 277/66* | (2006.01) |
| *C07D 295/027* | (2006.01) |
| *C07D 295/073* | (2006.01) |
| *C07D 295/096* | (2006.01) |
| *C07D 295/108* | (2006.01) |
| *C07D 307/83* | (2006.01) |
| *C07D 311/08* | (2006.01) |
| *C07D 413/08* | (2006.01) |
| *C07D 471/10* | (2006.01) |

(56) References Cited

U.S. PATENT DOCUMENTS 6,433,182 B1 *  8/2002  Garvey ............... A61K 45/06
                                                  548/301.7
2004/0072851 A1 *  4/2004  Shimoyama ......... A61K 31/18
                                                  514/266.24

FOREIGN PATENT DOCUMENTS

WO   2007/073303 A2   6/2007
WO   2016/117647 A1   1/2011

OTHER PUBLICATIONS

Phrase Construction Searching (2011) (Year: 2011).*
I. Muramatsu et al., 55 Japan J. Pharmacol., 391-398 (1991) (Year: 1991).*
S. Misztal et al., 36 Polish Journal of Pharmacology and Pharmacy, 697-703 (1984) (Year: 1984).*
I. T. Forbes et al., 13 Bioorganic & Medicinal Chemistry Letters, 1055-1058 (2003) (Year: 2003).*
PubChem CID 100906965 (Dec. 11, 2015).*
PubChem CID 47543870 (Nov. 26, 2010).*
International Search Report and Written Opinion issued in PCT/US2016/045559, dated May 18, 2017.

* cited by examiner

DUAL NAV1.2/5HT2A INHIBITORS FOR TREATING CNS DISORDERS

BACKGROUND

Central nervous system disorders affect a wide range of the population with differing severity. Neurological and psychiatric disorders include major depression, schizophrenia, bipolar disorder, obsessive compulsive disorder (OCD), panic disorder, and posttraumatic stress disorder (PTSD), among others. These disorders affect a person's thoughts, mood, behavior and social interactions and can significantly impair daily functioning. See, e.g., *Diagnostic and Statistical Manual of Mental Disorders*, 4th Ed., American Psychiatric Association (2000) ("DSM-IV-TR"); *Diagnostic and Statistical Manual of Mental Disorders*, 5th Ed., American Psychiatric Association (2013) ("DSM-5").

SUMMARY

While medications exist for some aspects of these diseases, there remains a need for effective treatments for various neurological and psychiatric disorders, including mood disorders such as bipolar and related disorders, psychosis and schizophrenia. For example, while mood stabilizers such as lithium and valproate, antidepressants and antipsychotic drugs are used to treat mood disorders, more effective medications are necessary. And current antipsychotics may be successful in treating the positive symptoms of schizophrenia but fare less well for the negative and cognitive symptoms. Additionally, current antidepressants are typically effective only for a proportion of patients suffering from depression. Furthermore, despite the fact that the behavioral and psychiatric symptoms of neurological disease such as Parkinson's disease and Alzheimer's disease are major reasons for the institutionalization of patients, few drugs exist to treat them.

In one aspect, the invention relates to a compound of formula I:

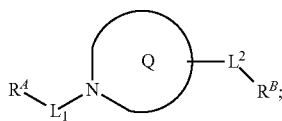

wherein:

Q is an optionally substituted nitrogenous aliphatic monocycle, bicycle or spirocycle attached to $L^1$ at a nitrogen, wherein substituents, when present, are chosen from halogen, hydroxy, $(C_1-C_6)$alkyl, $(C_1-C_6)$alkoxy, and oxo;

$R^A$ is an optionally substituted monocyclic or bicyclic carbocycle or heterocycle wherein substituents, when present, are chosen from halogen, cyano, hydroxy, $(C_1-C_6)$alkyl, $(C_1-C_6)$alkoxy, $(C_1-C_6)$oxaalkyl, oxo, phenyl, halophenyl, phenoxymethyl, benzyl, amino$(C_1-C_6)$oxaalkyl, di$(C_1-C_6)$alkylamino, di$(C_1-C_6)$alkylamino$(C_1-C_6)$alkyl, $(C_1-C_6)$acyl, and N-acetamido;

$L^1$ is a linker chosen from: —(CHR$^1$)—, —(CH$_2$CHR$^1$)—, —C(=O)CH$_2$—, -E-(CH$_2$)$_n$—, -G-CH$_2$CH(OH)CH$_2$—, —OCH$_2$C(=O)—, and —C(=O)NHCH$_2$—, $R^1$ is hydrogen or methyl;

E is chosen from —O—, —CH$_2$—, —CH(OH)—, and —CH(OCH$_3$)—;

n is 2 or 3; and

G is —O— or —NH—;

$L^2$ is a linker chosen from: a direct bond; —O—, —CH$_2$—, —OCH$_2$—, and —NHSO$_2$—; and $R^B$ is an optionally substituted aromatic carbocycle or heterocycle wherein substituents, when present, are chosen from halogen, cyano, $(C_1-C_6)$alkyl, $(C_1-C_6)$alkoxy, $(C_1-C_6)$oxaalkyl, —C(=O)NH$_2$, and di$(C_1-C_6)$alkylamino; or when Q is a spirocycle, $R^B$ may additionally be an optionally substituted, fused aromatic or heteroaromatic ring.

In one aspect the invention relates to a pharmaceutical composition comprising a compound of formula I above.

In one aspect, the invention relates to method for treating a neurological or psychiatric disorder comprising administering an effective amount of a compound of formula I.

In one aspect, the invention relates to a method for treating neuropsychiatric and behavior symptoms in a neurological disorder in a patient, comprising administering to the patient an effective amount of a compound of formula I.

DETAILED DESCRIPTION

In one aspect, the invention relates to compounds of formula I:

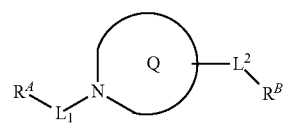

wherein

Q is an optionally substituted nitrogenous aliphatic monocycle, bicycle or spirocycle attached to $L^1$ at a nitrogen, wherein substituents, when present, are chosen from halogen, hydroxy, $(C_1-C_6)$alkyl, $(C_1-C_6)$alkoxy, and oxo;

$R^A$ is an optionally substituted monocyclic or bicyclic carbocycle or heterocycle wherein substituents, when present, are chosen from halogen, cyano, hydroxy, $(C_1-C_6)$alkyl, $(C_1-C_6)$alkoxy, $(C_1-C_6)$oxaalkyl, oxo, phenyl, halophenyl, phenoxymethyl, benzyl, amino$(C_1-C_6)$oxaalkyl, di$(C_1-C_6)$alkylamino, di$(C_1-C_6)$alkylamino$(C_1-C_6)$alkyl, $(C_1-C_6)$acyl, and N-acetamido;

$L^1$ is a linker chosen from: —(CHR$^1$)—, —(CH$_2$CHR$^1$)—, —C(=O)CH$_2$—, -E-(CH$_2$)$_n$—, -G-CH$_2$CH(OH)CH$_2$—, —OCH$_2$C(=O)—, and —C(=O)NHCH$_2$—, $R^1$ is hydrogen or methyl;

E is chosen from —O—, —CH$_2$—, —CH(OH)—, and —CH(OCH$_3$)—;

n is 2 or 3; and

G is —O— or —NH—;

$L^2$ is a linker chosen from: a direct bond; —O—, —CH$_2$—, —OCH$_2$—, and —NHSO$_2$—; and $R^B$ is an optionally substituted aromatic carbocycle or heterocycle wherein substituents, when present, are chosen from halogen, cyano, $(C_1-C_6)$alkyl, $(C_1-C_6)$alkoxy, $(C_1-C_6)$oxaalkyl, —C(=O)NH$_2$, and di$(C_1-C_6)$alkylamino; or when Q is a spirocycle, $R^B$ may additionally be an optionally substituted, fused aromatic or heteroaromatic ring.

In some embodiments, Q is an optionally substituted nitrogenous aliphatic monocycle. In some embodiments, q is chosen from pyrrolidine, piperidine, morpholine, piperazine, azepane, oxazepane, thiazapane and diazepane. In other embodiments, Q is chosen from:

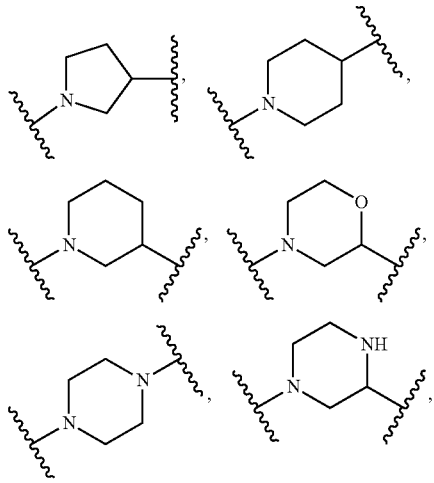

Any of these moieties may be optionally substituted. In still other embodiments, Q is substituted with one or two methyl groups. In yet other embodiments, Q is unsubstituted. In further embodiments, Q is an optionally substituted nitrogenous aliphatic bicycle. In some embodiments, Q is an optionally substituted diazabicycloheptane or optionally substituted diazabicyclooctane. In other embodiments, Q is an optionally substituted nitrogenous aliphatic bicycle chosen from:

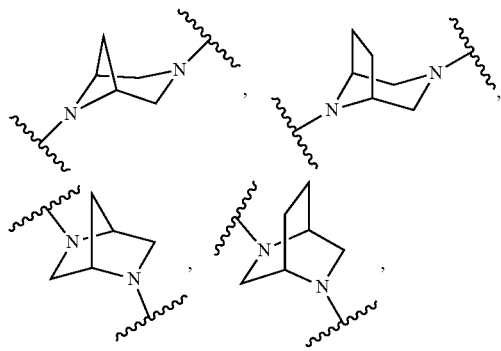

-continued

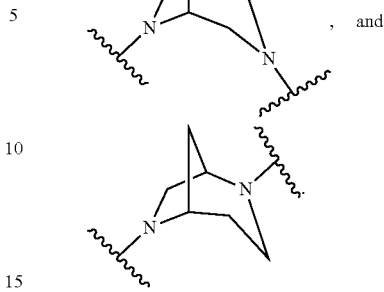

In still other embodiments, Q is an optionally substituted nitrogenous aliphatic spirocycle. In yet other embodiments, Q is chosen from diazaspiro[4.4]nonane and diazaspiro[4.5]decane. In some of these embodiments, Q is chosen from:

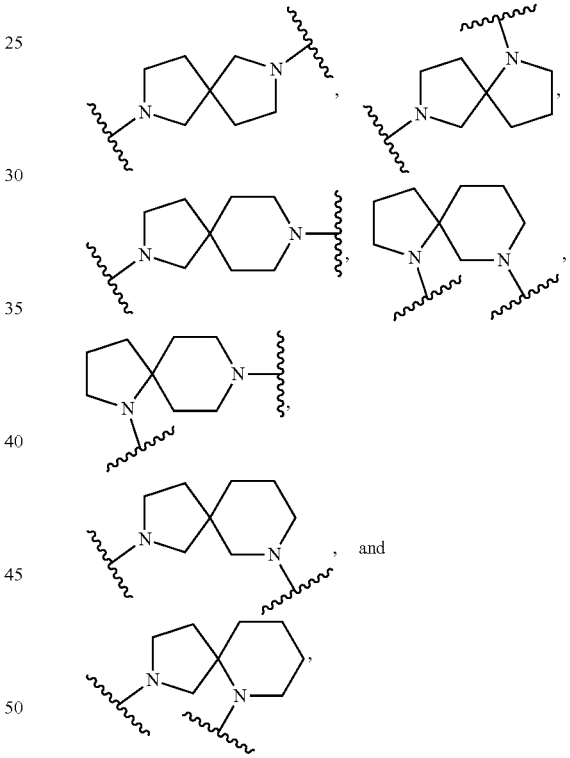

any of which may be optionally substituted. In further embodiments, Q is an optionally substituted nitrogenous aliphatic spirocycle chosen from oxazaspiro[3.4]octane, oxazaspiro[3.4]octene, azaspiro[4.4]nonane, and oxazaspiro[4.5]decane. In some of these embodiments, Q is chosen from:

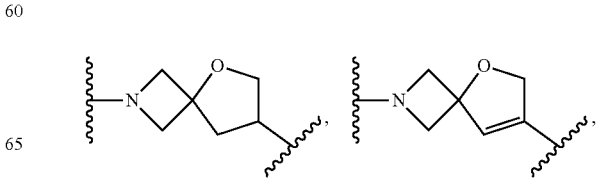

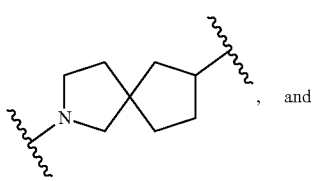, and

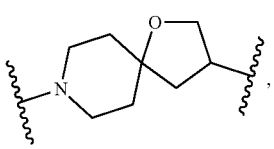, any of which may be unsubstituted or substituted.

In some embodiments, when Q is a spirocycle, $R^B$ may additionally be an optionally substituted, fused aromatic or heteroaromatic ring. In some of these embodiments when Q is an optionally substituted nitrogenous aliphatic spirocycle and $R^B$ is an optionally substituted, fused aromatic or heteroaromatic ring, Q is chosen from:

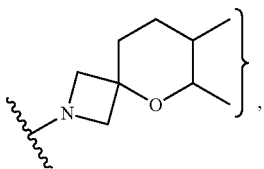,

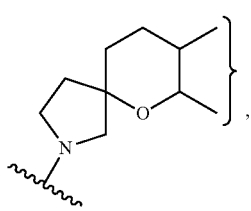,

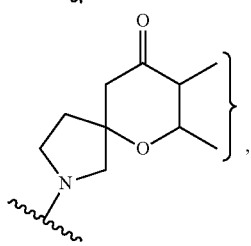,

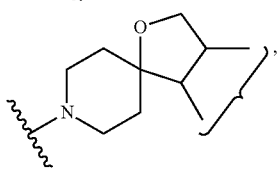,

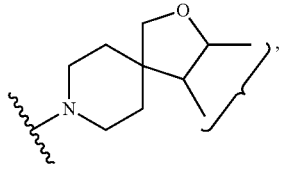,

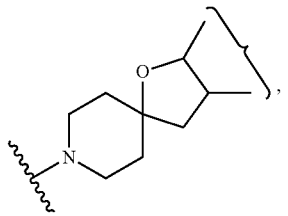,

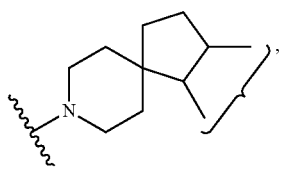,

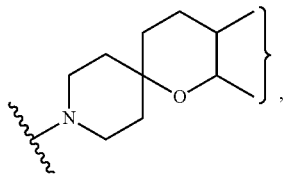,

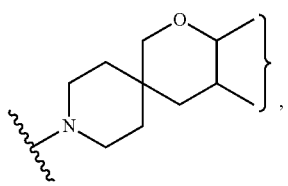,

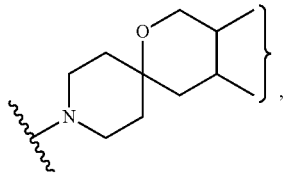,

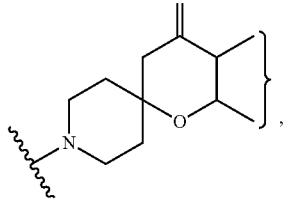,

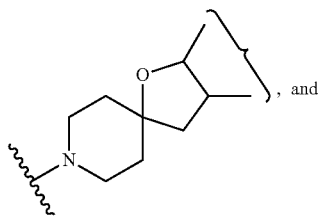, and

-continued

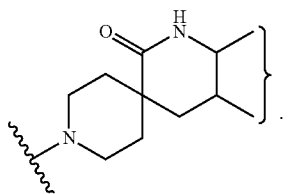

In some of these embodiments, $R^B$ is chosen from:

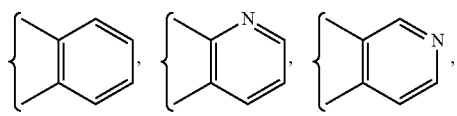

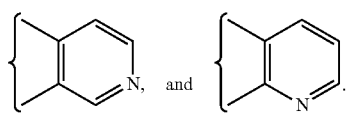

In further embodiments, Q and $R^B$ taken together are chosen from:

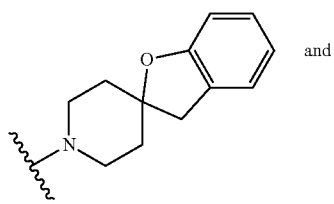

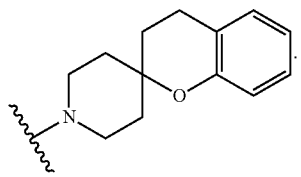

In some embodiments, Q is unsubstituted. In other embodiments, Q is substituted. In those embodiments in which Q is substituted, the substituents are chosen from halogen, hydroxy, $(C_1-C_6)$alkyl, $(C_1-C_6)$alkoxy, and oxo. In other embodiments, Q is methyl, fluoro, chloro, methoxy, hydroxy, or oxo. In still other embodiments, Q is substituted with one or two substituents. In some embodiments, Q is substituted with one or two methyl groups. In other embodiments, Q is substituted with oxo.

In some embodiments, $R^A$ is an optionally substituted monocyclic carbocycle or heterocycle. In other embodiments, $R^A$ is an optionally substituted monocycle chosen from benzene, cyclohexane, tetrahydropyridazine and tetrahydropyran. In some embodiments, $R^A$ is an optionally substituted bicyclic carbocycle or heterocycle. In still other embodiments, $R^A$ is an optionally substituted fused bicycle containing an aromatic 6-membered ring and a non-aromatic 5-membered ring. In some of these embodiments, $R^A$ is chosen from

In some of these embodiments, one of $W^1$, $W^2$, $W^3$, and $W^4$ is nitrogen and the other three are carbon. In other of these embodiments, all of $W^1$, $W^2$, $W^3$, and $W^4$ are carbon. In some of these embodiments, Y is oxygen. In other of these embodiments, Y is carbon. In some embodiments, $R^A$ is an optionally substituted fused bicycle containing an aromatic 6-membered ring and a 5-membered ring. In some of these embodiments, $R^A$ is

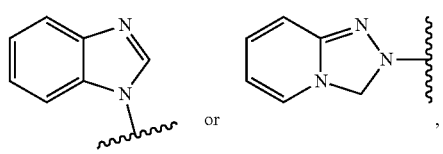 [SMILES: *n1cnc2ccccc21 ; *N1CN2C=CC=CC2=N1]

either of which may be unsubstituted or substituted. In further embodiments, $R^A$ is an optionally substituted fused bicycle containing an aromatic 6-membered ring and a non-aromatic 6-membered ring. In some of these embodiments, $R^A$ is chosen from substituted or unsubstituted

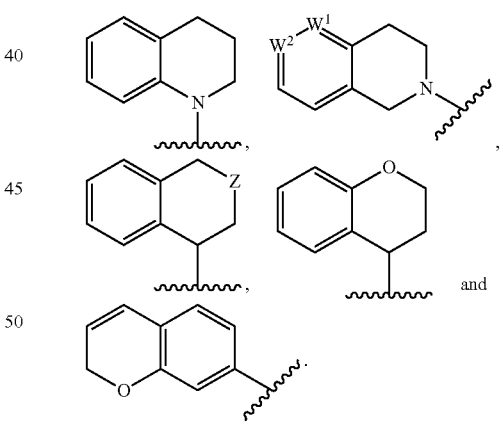

In some of these embodiments, one of $W^1$ and $W^2$ is nitrogen and the other is carbon. In other of these embodiments, both of $W^1$ and $W^2$ are carbon. In some of these embodiments, Z is nitrogen, oxygen or carbon. In some of these embodiments, $R^A$ is an optionally substituted fused bicycle containing two aromatic 6-membered rings. In other embodiments, $R^A$ is chosen from naphthalene, quinoline, isoquinoline, and pyrido[2,3-d]pyrimidine, any of which may be substituted or unsubstituted. In some embodiments, $R^A$ is an optionally substituted fused bicycle containing an aromatic 6-membered ring and a non-aromatic 7-membered ring. In other embodiments, $R^A$ is optionally substituted tetrahydrobenzoannulene or tetrahydrobenzoazepine. In still other embodiments, $R^A$ is chosen from substituted or unsubstituted

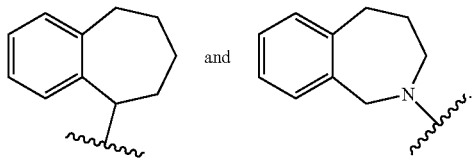 [SMILES: *C1CCCCc2ccccc21 ; *N1CCCc2ccccc2C1]

In some embodiments, $R^A$ is chosen from indane, cyclohexane, dihydrobenzofuran, 3-methyldihydrobenzofuran, benzene, methylbenzene, naphthalene, tetrahydrobenzoannulene, chroman, isochromanol, indane, methylindane, haloindane, cyanoindane, methoxyindane, isochroman, halobenzoazepinone, and dihydroisoquinolinone.

In some embodiments, $R^A$ is unsubstituted. In other embodiments, $R^A$ is substituted, and the substituents are chosen from halogen, cyano, hydroxy, $(C_1-C_6)$alkyl, $(C_1-C_6)$alkoxy, $(C_1-C_6)$oxaalkyl, oxo, phenyl, halophenyl, phenoxymethyl, benzyl, amino$(C_1-C_6)$oxaalkyl, di$(C_1-C_6)$alkylamino, di$(C_1-C_6)$alkylamino$(C_1-C_6)$alkyl, $(C_1-C_6)$acyl, and N-acetamido. In some embodiments, $R^A$ is substituted with oxo. In other embodiments, the oxo substituent is adjacent a heteroatom.

In some embodiments, $R^B$ is an optionally substituted aromatic carbocycle or heterocycle. In other embodiments, $R^B$ is an optionally substituted aromatic monocycle. In still other embodiments, $R^B$ is chosen from benzene, pyridine, pyrimidine, thiophene, furan, pyrrole and thiazole. In yet other embodiments, $R^B$ is an optionally substituted aromatic bicycle chosen from benzothiazole, benzoisothiazole, and quinoline. In some embodiments, $R^B$ is unsubstituted. In other embodiments, $R^B$ is substituted with one or more substituents chosen from halogen, cyano, $(C_1-C_6)$alkyl, $(C_1-C_6)$alkoxy, $(C_1-C_6)$oxaalkyl, $—C(=O)NH_2$, and di$(C_1-C_6)$ alkylamino. In some embodiments, $R^B$ is chosen from benzene, halobenzene, methylbenzene, dimethylbenzene, methoxybenzene, benzothiazole, benzoisothiazole, and benzene fused to Q.

In some embodiments, $L^1$ is a linker $—(CHR^1)—$, and $R^1$ is hydrogen or methyl. In some embodiments, $L^1$ is $—CH_2—$. In some embodiments, $L^1$ is a linker $—(CH_2CHR^1)—$, and $R^1$ is hydrogen or methyl. In other embodiments, $L^1$ is $—CH_2CH_2—$. In still other embodiments, $L^1$ is a linker $—C(=O)CH_2—$. In yet other embodiments, $L^1$ is a linker -E-$(CH_2)_n$-. In some of these embodiments, E is chosen from $—O—$, $—CH_2—$, $—CH(OH)—$, and $—CH(OCH_3)—$. In some of these embodiments, n is 2. In other of these embodiments, n is 3. In some embodiments, $L^1$ is a linker -G-$CH_2CH(OH)CH_2—$, and G is selected from $—O—$ or $—NH—$. In other embodiments, $L^1$ is a linker $—OCH_2C(=O)—$. In still other embodiments, $L^1$ is a linker $—C(=O)NHCH_2—$. In yet other embodiments, $L^1$ is $—O—CH_2CH(OH)CH_2—$. In some embodiments, $L^1$ is $—OCH_2CH_2—$.

In some embodiments, $L^2$ is a direct bond. In other embodiments, $L^2$ is $—O—$. In still other embodiments, $L^2$ is $—CH_2—$. In yet other embodiments, $L^2$ is $—OCH_2—$. In further embodiments, $L^2$ is $—NHSO_2—$.

In some embodiments, $L^1$ is $—O—CH_2CH(OH)CH_2—$ and $R^A$ is chosen from indane, cyclohexane, dihydrobenzofuran, 3-methyldihydrobenzofuran, benzene, methylbenzene, naphthalene, and tetrahydrobenzoannulene. In other embodiments, $L^1$ is $—O—CH_2CH(OH)CH_2—$ and $R^B$ is chosen from benzene, halobenzene, methylbenzene, dimethylbenzene, benzothiazole, methoxybenzene, and benzene fused to Q. In still other embodiments, $L^1$ is $—O—CH_2CH(OH)CH_2—$; $R^A$ is chosen from indane, cyclohexane, dihydrobenzofuran, 3-methyldihydrobenzofuran, benzene, methylbenzene, naphthalene, and tetrahydrobenzoannulene; and $R^B$ is chosen from benzene, halobenzene, methylbenzene, dimethylbenzene, benzothiazole, methoxybenzene, and benzene fused to Q.

In some embodiments, $L^1$ is $—CH_2—$ and $R^A$ is chosen from chroman, isochromanol, indane, methylindane, haloindane, cyanoindane, methoxyindane, and dihydrobenzofuran. In other embodiments, $L^1$ is $—CH_2—$ and $R^B$ is chosen from benzene, halobenzene, methylbenzene, dimethylbenzene, methoxybenzene, and benzene fused to Q. In still other embodiments, $L^1$ is $—CH_2—$; $R^A$ is chosen from chroman, isochromanol, indane, methylindane, haloindane, cyanoindane, methoxyindane, and dihydrobenzofuran; and $R^B$ is chosen from benzene, halobenzene, methylbenzene, dimethylbenzene, methoxybenzene, and benzene fused to Q.

In some embodiments, $L^1$ is $—CH_2CH_2—$ and $R^A$ is chosen from isochroman, indane, halobenzoazepinone, and dihydroisoquinolinone. In other embodiments, $L^1$ is $—CH_2CH_2—$ and $R^B$ is chosen from benzene, halobenzene, methylbenzene, dimethylbenzene, methoxybenzene, and benzene fused to Q. In still other embodiments, $L^1$ is $—CH_2CH_2—$; $R^A$ is chosen from isochroman, indane, halobenzoazepinone, and dihydroisoquinolinone; and $R^B$ is chosen from benzene, halobenzene, methylbenzene, dimethylbenzene, methoxybenzene, and benzene fused to Q.

In some embodiments, $L^1$ is $—OCH_2CH_2—$ and $R^A$ is indane and $R^B$ is chosen from benzoisothiazole and benzene fused to Q.

In some embodiments, $L^2$ is $—O—$ and Q is chosen from pyrrolidine; piperidine; piperazine; methylpiperidine; azepane; 2,6-diazabicyclo[3.2.1]octane; 3,8-diazabicyclo[3.2.1]octane; 2,5-diazabicyclo[2.2.2]octane; 2,7-diazaspiro[4.4]nonane; 2,7-diazaspiro[4.5]decane; 5-oxa-2-azaspiro[3.4]octane; and 1-oxa-8-azaspiro[4.5]decane.

The methods of the invention relate to the use of compounds of formula I above to treat neurological or psychiatric disorders or impairments. In some embodiments, the neurological or psychiatric disorder is depression, bipolar disorder, pain, schizophrenia, obsessive compulsive disorder, addiction, social disorder, attention deficit hyperactivity disorder, an anxiety disorder, autism or cognitive impairments. In one embodiment, the disorder is depression, particularly treatment-resistant depression (TRD), major depressive disorder (MDD), unipolar depression, bipolar depression or depression associated with another disease or disorder.

Compounds and Definitions

Compounds of this invention include those described generally above, and are further illustrated by the classes, subclasses, and species disclosed herein. As used herein, the following definitions shall apply unless otherwise indicated. A comprehensive list of abbreviations utilized by organic chemists (i.e. persons of ordinary skill in the art) appears in the first issue of each volume of the Journal of Organic Chemistry. The definitions therein, which are typically presented in a table entitled "Standard List of Abbreviations" are the definitions used herein.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; solid and broken bold lines are geometric descriptors indicating the relative configuration shown but not necessarily denoting racemic character; and wedge outlines and dotted or broken lines denote enantiomerically pure compounds of indeterminate absolute configuration. For example, the graphic representation

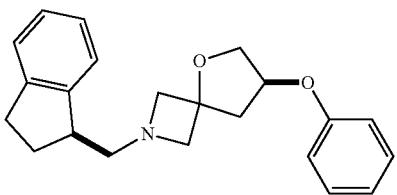 [SMILES: c1ccc(O[C@@H]2COC3(C2)CN(C[C@H]2CCc4ccccc42)C3)cc1]

indicates a cis relationship between the two chiral centers, that is, either or both of the two representations below:

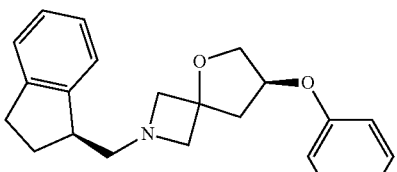

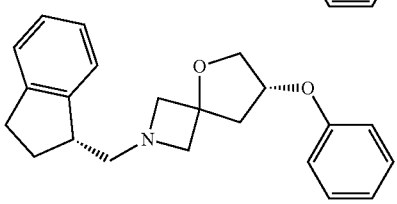

in any ratio, from pure enantiomers to racemates, while the representation:

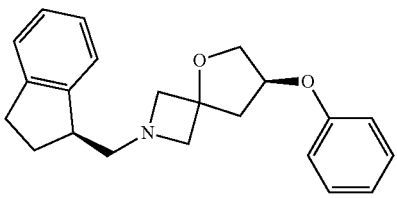 [SMILES: c1ccc(O[C@@H]2COC3(C2)CN(C[C@H]2CCc4ccccc42)C3)cc1]

indicates pure (S)-2-(((S)-2,3-dihydro-1H-inden-1-yl)methyl)-7-phenoxy-5-oxa-2-azaspiro[3.4]octane. For the purpose of the present disclosure, a "pure" or "substantially pure" enantiomer is intended to mean that the enantiomer is at least 95% of the configuration shown and 5% or less of other enantiomers. Similarly, a "pure" or "substantially pure" diastereomer is intended to mean that the diastereomer is at least 95% of the relative configuration shown and 5% or less of other diastereomers. In the text describing the stereochemistry of the examples, the convention of Chemical Abstracts is used. Thus "(R)-1-((R)-5-rel-..." indicates that the two chiral centers are in that relative relationship, which would be depicted in a structural diagram by solid bold and dashed lines, whereas "(R)-1-((R)-5-..." without the "rel" indicates a single enantiomer of that absolute configuration, which would be depicted in a structural diagram by solid and broken wedges.

Hydrocarbyl refers to any substituent comprised of hydrogen and carbon as the only elemental constituents. $C_1$ to $C_{20}$ hydrocarbon includes, for example, alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Aromatic hydrocarbons include benzene (phenyl), naphthalene (naphthyl), anthracene, etc. Aliphatic hydrocarbons are hydrocarbons that are not aromatic; they may be saturated or unsaturated, cyclic, linear or branched, or combinations thereof. Aliphatic hydrocarbons include, for example, alkyl, alkenyl, alkynyl, cycloalkyl, cycloalkenyl, cycloalkynyl, and combinations thereof. Non-limiting examples of aliphatic hydrocarbons include isopropyl, 2-butenyl, 2-butynyl, cyclopentyl, cyclopropylmethyl, norbornyl, and the like.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cyclopropyl, cyclobutyl, cyclopentyl, norbornyl and the like.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene (phenyl) and cyclohexene; ($C_8$-$C_{12}$) carbopolycycle refers to such systems as norbornane, decalin, indane and naphthalene. Carbocycle, if not otherwise limited, refers to monocycles, bicycles and polycycles, including bridged structures.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Heterocycle, if not otherwise limited, refers to monocycles, bicycles and polycycles, including bridged structures. Examples of heterocycles include, but are not limited to, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, atrophine, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Hydrocarbyloxy refers to groups of from 1 to 20 carbon atoms, preferably 1 to 10 carbon atoms, more preferably 1 to 6 carbon atoms attached to the parent structure through an oxygen. Alkoxy is a subset of hydrocarbyloxy and includes groups of a straight or branched configuration. Examples include methoxy, ethoxy, propoxy, isopropoxy and the like. Lower-alkoxy refers to groups containing one to four carbons. The term "halogen" means fluorine, chlorine, bromine or iodine atoms.

The term "halogen" means fluorine, chlorine, bromine or iodine. In one embodiment, halogen may be fluorine or chlorine.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, hydrocarbyl, acyl, alkoxyalkyl, hydroxy lower alkyl, carbonyl, phenyl, heteroaryl, benzenesulfonyl, hydroxy, hydrocarbyloxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)NH$_2$], alkylaminocarbonyl [—C(=O)NH-alkyl], dialkylaminocarbonyl [—C(=O)N(alkyl)$_2$], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In particular embodiments, substituents are halogen, halo(C$_1$-C$_4$)hydrocarbyl, halo(C$_1$-C$_4$)hydrocarbyloxy, cyano, thiocyanato, (C$_1$-C$_4$)hydrocarbylsulfinyl, (C$_1$-C$_4$)hydrocarbyl-sulfonyl, aminosulfonyl, nitro, acetyl, and acetamido. Preferred substituents are halogen, (C$_1$-C$_4$)alkyl, (C$_1$-C$_4$)alkoxy, (C$_1$-C$_4$) fluoroalkyl, (C$_1$-C$_4$)fluoroalkoxy, hydroxy, amino, (C$_1$-C$_4$) alkylamino, di(C$_1$-C$_4$)alkylamino, (C$_1$-C$_4$)acylamino, (C$_1$-C$_4$)fluoroalkyl and (C$_1$-C$_4$)fluoroalkoxy.

Substituents R" are generally defined when introduced and retain that definition throughout the specification and claims.

As used herein, and as would be understood by the person of skill in the art, the recitation of "a compound"—unless expressly further limited—is intended to include salts of that compound. Thus, for example, the recitation "a compound of formula I" as depicted above, which contains a basic amine residue

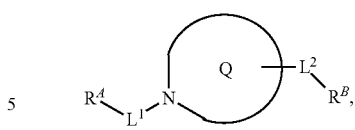

would include salts

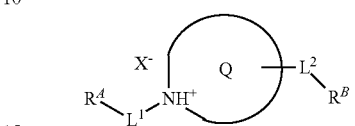

wherein X$^-$ is any counterion. In a particular embodiment, the term "compound of formula I" refers to the compound or a pharmaceutically acceptable salt thereof; this term refers to a pharmaceutically acceptable salt of the compound, even if not explicitly stated. Unless otherwise stated or depicted, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. In addition to therapeutic uses, such compounds are useful, for example, as analytical tools or probes in biological assays.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Although pharmaceutically acceptable counter ions will be preferred for preparing pharmaceutical formulations, other anions are quite acceptable as synthetic intermediates. Thus X may be pharmaceutically undesirable anions, such as iodide, oxalate, trifluoromethanesulfonate and the like, when such salts are chemical intermediates.

Unless otherwise specified, the word "includes" (or any variation thereon, e.g., "include", "including", etc.) is intended to be open-ended. For example, "A includes 1, 2 and 3" means that A includes but is not limited to 1, 2 and 3.

Unless otherwise specified, the phrase "such as" is intended to be open-ended. For example, "A can be a halogen, such as chlorine or bromine" means that A can be, but is not limited to, chlorine or bromine.

According to another embodiment, the invention provides a composition comprising a compound of this invention (or its pharmaceutically acceptable salt) and a pharmaceutically acceptable carrier, adjuvant, or vehicle. In some embodiments, the amount of compound in compositions of this invention is such that is effective to treat, prevent, and/or manage various neurological and/or psychiatric disorders and/or symptoms in a patient. In some embodiments, a composition of this invention is formulated for administration to a patient in need of such composition. In some embodiments, a composition of this invention is formulated for oral administration to a patient. The term "patient," as used herein, means an animal, preferably a mammal, and most preferably a human.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. Pharmaceutically acceptable compositions of this invention may be orally administered in any orally acceptable dosage form including capsules, tablets, aqueous suspensions or solutions.

The amount of compounds of the present invention that may be combined with the carrier materials to produce a composition in a single dosage form will vary depending upon a variety of factors, including the host treated and the particular mode of administration. It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the invention provides a method for treating a neurological or psychiatric disorder in a patient, comprising administering to the patient an effective amount of a compound of this invention (or its pharmaceutically acceptable salt), or composition comprising a compound of this invention (or its pharmaceutically acceptable salt). Neurological and/or psychiatric disorders diseases can exhibit a variety of psychiatric and behavioral symptoms, including apathy, depression, anxiety, cognitive impairment, psychosis, aggression, agitation, poor impulse control and sleep disruptions.

In some embodiments, the neurological or psychiatric disorder is selected from a psychosis, including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (e.g., phencyclidine, ketamine and other dissociative anesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both positive, negative, and cognitive symptoms of schizophrenia and other psychoses; cognitive disorders including dementia (semantic dementia, frontotemporal dementia, dementia with depressive features, persisting, subcortical dementia, dementia with Lewy Bodies, Parkinsonism-ALS Dementia Complex, and dementia associated with Alzheimer's disease, ischemia, multi-infarct dementia, trauma, vascular problems, stroke, HIV disease, Parkinson's disease, Huntington's disease, Down syndrome, Pick's disease, Creutzfeldt-Jacob disease, perinatal hypoxia, or substance abuse), delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa, pica and compulsive eating disorders; bipolar disorders, mood disorders including depressive disorders; depression including unipolar depression, seasonal depression and post-partum depression, atypical depression, catatonic depression, elderly depression, endogenous depression, melancholic depression, perinatal depression, situational depression, chronic depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; disorders such as autism, depression, benign forgetfulness, childhood learning disorders, specific learning disorders, intellectual development disorders, and closed head injury; movement disorders; epilepsy; urinary incontinence; neuronal damage including ocular damage, retinopathy or macular degeneration of the eye, tinnitus, hearing impairment and loss, and brain edema; emesis; and sleep disorders including insomnia and narcolepsy.

In some embodiments, the neurological or psychiatric disorder is Alzheimer's disease, Parkinson's disease, depression, cognitive impairment, stroke, schizophrenia, Down syndrome, or Fetal Alcohol Syndrome. In some embodiments, the neurological or psychiatric disorder is Alzheimer's disease. In some embodiments, the neurological or psychiatric disorder is Parkinson's disease. In some embodiments, the neurological or psychiatric disorder is depression. In some embodiments, the neurological or psychiatric disorder is cognitive impairment. In some embodiments, the cognitive impairment is cognitive dysfunction associated with depression, for example, major depressive disorder. In some embodiments, the neurological or psychiatric disorder is stroke. In some embodiments, the neurological or psychiatric disorder is schizophrenia. In some embodiments, the neurological or psychiatric disorder is Down syndrome. In some embodiments, the neurological or psychiatric disorder is Fetal Alcohol Syndrome.

In some embodiments, the neurological or psychiatric disorder is bipolar disease. Bipolar disorder is a serious psychiatric disorder that has a prevalence of approximately 2% of the population, and affects both genders alike. It is a relapsing-remitting condition characterized by cycling between elevated (i.e., manic) and depressed moods, which distinguishes it from other disorders such as major depressive disorder and schizophrenia. Bipolar I is defined by the occurrence of a full manic episode, although most individuals experience significant depression. Symptoms of mania include elevated or irritable mood, hyperactivity, grandiosity, decreased need for sleep, racing thoughts and in some cases, psychosis. The depressive episodes are characterized by anhedonia, sad mood, hopelessness, poor self-esteem, diminished concentration and lethargy. Bipolar II is defined as the occurrence of a major depressive episode and hypomanic (less severe mania) episode although patients spend considerable more time in the depressive state. Other related conditions include cyclothymic disorder.

In some embodiments, the neurological or psychiatric disorder is schizophrenia. Schizophrenia is a disorder of unknown origin, which usually appears for the first time in early adulthood and is marked by characteristics such as psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g., loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g., catatonia). Other symptoms are also associated with this disorder. Schizophrenia is classified into subgroups: the paranoid type, characterized by delusions and hallucinations and absence of thought disorder, disorganized behavior, and affective flattening; the disorganized type, also named "hebephrenic schizophrenia," in which thought disorder and flat affect are present together; the cataconic type, in which prominent psychomotor disturbances are evident, and symptoms may include catatonic stupor and waxy flexibility; and the undifferentiated type, in which psychotic symptoms are present but the criteria for paranoid, disorganized, or catatonic types have not been met. The symptoms of schizophrenia normally manifest themselves in three broad categories: positive, negative and cognitive symptoms. Positive symptoms are those which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making.

In some embodiments, the neurological or psychiatric disorder is anxiety disorder. Anxiety disorders are characterized by fear, worry, and uneasiness, usually generalized and unfocused as an overreaction to a situation. Anxiety disorders differ in the situations or types of objects that induce fear, anxiety, or avoidance behavior, and the associated cognitive ideation. Anxiety differs from fear in that anxiety is an emotional response to a perceived future threat while fear is associated with a perceived or real immediate threat. They also differ in the content of the associated thoughts or beliefs. Examples of anxiety disorders include separation anxiety disorder, selective mutism, specific phobia, social anxiety disorder (social phobia), panic disorder, panic attack specifier, agoraphobia, generalized anxiety disorder, substance/medication-induced anxiety disorder, anxiety disorder due to another medical condition, illness anxiety disorder, social (pragmatic) communication disorder, other specified anxiety disorder, and unspecified anxiety disorder; stressor-related disorders, including reactive attachment disorder, disinhibited social engagement disorder, posttraumatic stress disorder (PTSD), acute stress disorder, and adjustment disorders.

Cognitive impairment includes a decline in cognitive functions or cognitive domains, e.g., working memory, attention and vigilance, verbal learning and memory, visual learning and memory, reasoning and problem solving (e.g., executive function, speed of processing and/or social cognition). In particular, cognitive impairment may indicate deficits in attention, disorganized thinking, slow thinking, difficulty in understanding, poor concentration, impairment of problem solving, poor memory, difficulties in expressing thoughts, and/or difficulties in integrating thoughts, feelings and behavior, or difficulties in extinction of irrelevant thoughts.

In some embodiments, the neurological or psychiatric disorder involves a deficit in cognition (cognitive domains as defined by the DSM-5 are: complex attention, executive function, learning and memory, language, perceptual-motor, social cognition). In some embodiments, the neurological or psychiatric disorder is associated with a deficit in dopamine signaling. In some embodiments, the neurological or psychiatric disorder is associated with basal ganglia dysfunction. In some embodiments, the neurological or psychiatric disorder is associated with dysregulated locomotor activity. In some embodiments, the neurological or psychiatric disorder is associated with impairment of prefrontal cortex functioning.

In some embodiments, the present invention provides a method of treating one or more symptoms of a neurological and/or psychiatric disorder provided herein. Such disorders include mood disorders, including bipolar I disorder, bipolar II disorder, bipolar depression, mania, cyclothymic disorder, substance/medication-induced bipolar and related disorders, bipolar and related disorder due to another medical condition, other specified bipolar and related disorder, and unspecified bipolar and related disorders; psychotic disorders, including schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), schizoaffective disorder, agitation, aggression, delirium, catalepsy, catatonia, disssociative identity disorder, paranoid personality disorder, psychotic depression, Schizotypical Personality Disorder, Childhood Disintegrative Disorder (Heller's Syndrome), Disintegrative Psychosis, Dissociative Amnesia, Somatic Symptom Disorder, Parkinson's psychosis, excitative psychosis, Tourette's syndrome, and organic or NOS psychosis; depressive disorders, including disruptive mood dysregulation disorder, major depressive disorder (MDD) (including major depressive episode), dysthymia, persistent depressive disorder (dysthymia), treatment resistant depression, premenstrual dysphoric disorder, substance/medication-induced depressive disorder, depressive disorder due to another medical condition, other specified depressive disorder, and unspecified depressive disorder; anxiety disorders; and other disorders including substance abuse or dependency (e.g., nicotine, alcohol, cocaine), addiction, internet gaming disorder, eating disorders, behavior disorder, seizure, vertigo, epilepsy, agitation, aggression, neurodegenerative disease, Alzheimer's disease, Parkinson's disease, dyskinesias, Huntington's disease, dementia, premenstrual dysphoria, attention deficit disorder (ADD) and attention deficit hyperactivity disorder (ADHD)), hyperkinetic syndrome, autism, autism spectrum disorder, obsessive-compulsive disorder, pain, fibromyalgia, migraine, cognitive impairment, movement disorder, restless leg syndrome (RLS), multiple sclerosis, Primary Progressive Multiple Sclerosis, multiple sclerosis, sleep disorder, sleep apnea, narcolepsy, excessive daytime sleepiness, jet lag, drowsy side effect of medications, insomnia, sexual dysfunction, hypertension, emesis, Lesche-Nyhane disease, Wilson's disease, Rett syndrome, and Huntington's chorea. In some embodiments, the neurological and/or psychiatric disorders include agitation and aggression.

In some embodiments, the agitation and aggression are associated with Alzheimer's disease, Parkinson's disease, and/or autism.

In some embodiments, the neurological and/or psychiatric disorders are obsessive-compulsive disorder and related disorders (e.g., body dysmorphic disorder, hoarding disorder, trichotillomania, excoriation disorder).

In some embodiments, the neurological and/or psychiatric disorders are disruptive, impulse-control, and conduct disorders including oppositional defiant disorder, intermittent explosive disorder, conduct disorder, antisocial personality disorder, pyromania, kleptomania, other specified disruptive, impulse-control, and conduct disorder, unspecified disruptive, impulse-control, and conduct disorder.

Depressive disorders include major depressive disorder and dysthymia, and are associated with depressed mood (sadness), poor concentration, insomnia, fatigue, appetite disturbances, excessive guilt and thoughts of suicide.

In some embodiments, the present invention provides a method of treating one or more symptoms including depression (e.g., major depressive disorder or dysthymia); bipolar disorder, seasonal affective disorder; cognitive deficit; sleep related disorder (e.g., sleep apnea, insomnia, narcolepsy, cataplexy) including those sleep disorders which are produced by psychiatric conditions; chronic fatigue syndrome; anxieties (e.g., general anxiety disorder, social anxiety disorder, panic disorder); obsessive compulsive disorder; postmenopausal vasomotor symptoms (e.g., hot flashes, night sweats); neurodegenerative disease (e.g., Parkinson's disease, Alzheimer's disease, amyotrophic lateral sclerosis, primary lateral sclerosis, progressive muscular atrophy, progressive bulbar (atrophy) palsy, pseudobulbar palsy spinal muscular atrophy diseases (e.g., SMA type I, also called Werdnig-Hoffmann disease, SMA type II, SMA type III, also called Kugelberg-Welander disease, and Kennedy Disease, also called progressive spinobulbar muscular atrophy), Hallervorden-Spatz disease, Seitelberger disease (Infantile Neuroaxonal Dystrophy), adrenoleukodystrophy, Alexander Disease, autosomal dominant cerebellar ataxia (ADCA), pure autonomic failure (Bradbury-Eggleston Syndrome), CADASIL Syndrome, and neuronal ceroids lipofuscinose disorders such as Batten Disease (Spielmeyer-Vogt-Sjögren)); manic disorder; dysthymic disorder; and obesity.

In some embodiments, a depressive disorder is associated with acute suicidality or suicide ideation. The United States Food and Drug Administration has adopted a "black box" label warning indicating that antidepressants may increase the risk of suicidal thinking and behavior in some children, adolescents and young adults (up to age 24) with a depressive disorder such as MDD. In some embodiments, a provided compound does not increase the risk of suicidal thinking and/or behavior in children, adolescents and/or young adults with a depressive disorder, e.g., with MDD. In some embodiments, the present invention provides a method of treating one or more symptoms of a depressive disorder (e.g., MDD) in children, adolescents and/or young adults without increasing the risk of suicidal thinking and/or behavior.

In some embodiments, the present invention provides a method of treating one or more symptoms including senile dementia, Early Onset Alzheimer's Disease, Alzheimer's type dementia, cognition, memory loss, amnesia/amnestic syndrome, disturbances of consciousness, coma, lowering of attention, speech disorder, agnosia, aphasia, apraxia, Mild Cognitive Impairment (MCI), benign forgetfulness, mild neurocognitive disorder, major neurocognitive disorder, neurocognitive disorder due to disease (e.g., Huntington's Disease, Parkinson's disease, Prion Disease, Traumatic Brain Injury, HIV or AIDS), Binswanger's Disease (subcortical leukoencephalopathy), and Capgras Syndrome.

In some embodiments, the present invention provides a method of treating one or more symptoms of pain, e.g., neuropathic pain, sensitization accompanying neuropathic pain, or inflammatory pain. In some embodiments, the pain is neuropathic pain, including post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use). In some embodiments, the pain is acute pain, nociceptive pain, arthritis pain, rheumatoid arthritis, osteoarthritis, joint pain, muscoskeletal pain, back pain, dorsalgia, bulging disc, hip pain, visceral pain, headache, tension headache, acute tension headache, chronic tension headache, chronic cluster headache, common migraine, classic migraine, cluster headache, mixed headache, post-traumatic headache, eye strain headache, Short-lasting Unilateral Neuralgiform (SUNCT) headache, SUNCT Syndrome, herpes zoster, acute herpes zoster, shingles, postherpetic neuralgia (shingles), causalgia, central pain, central pain syndrome, chronic back pain, neuralgia, neuropathic pain syndrome, neuropathy, diabetic neuropathy, diabetes-related neuropathy, diabetes-related nerve pain, fibrositis, peripheral neuropathy caused by chemotherapy, peripheral nerve disease, peripheral neuropathy, nerve pain, nerve trauma, sensitization accompanying neuropathic pain, complex regional pain syndrome, compression neuropathy, craniofacial pain, chronic joint pain, chronic knee pain, chronic pain syndrome, cancer pain, trigeminal neuralgia, tic doloreaux, reflex sympathetic causalgia, painful peripheral neuropathy, spinal nerve injury, arachnoiditis, spinal pain, Bernhardt-Roth Syndrome (meralgia parasthetica), carpal tunnel syndrome, cerebrospinal fluid syndrome, Charcot-Marie-tooth disease, hereditary motor and sensory neuropathy, peroneal muscular atrophy, cluster-tic syndrome, coccygeal pain syndromes, compartment syndrome, degenerative disc disease, failed back surgery syndrome, genito-pelvic pain/penetration disorder, gout, inflammatory pain, lumbar radiculopathy, neuroma (painful scar), pain associated with multiple sclerosis, pelvic floor disorders, phantom limb pain, piriformis syndrome, psychogenic pain, radicular pain syndrome, Raeder's syndrome, referred pain, reflex sympathetic dystrophy syndrome, sciatica, sciatica pain, scoliosis, slipped disc, somatic pain, spinal stenosis, stiff-person syndrome/stiff-man syndrome, stump pain, sympathetically maintained pain, tolosa-hunt syndrome, whiplash, or pain associated with Lyme disease.

In some embodiments, the present invention provides a method of treating one or more symptoms including obesity; migraine or migraine headache; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

In some embodiments, the present invention provides a method of suppressing rapid eye movement (REM) during both sleep and daytime equivalent.

In some embodiments, the present invention provides a method of suppressing or eliminating pathological or excessive REM during the night or daytime equivalent.

In some embodiments, the present invention provides a method of treating one or more symptoms including cataplexy (sudden involuntary transient bouts of muscle weakness or paralysis while awake); nighttime sleep disturbance/sleep fragmentation associated with narcolepsy or other conditions; sleep paralysis associated with narcolepsy or other conditions; hypnagogic and hypnapompic hallucinations associated with narcolepsy or other conditions; and excessive daytime sleepiness associated with narcolepsy, sleep apnea or shift work disorder and other medical conditions such as cancer, chronic fatigue syndrome and fibromyalgia.

In some embodiments, the present invention provides a method of treating one or more symptoms of movement disorders, including akinesias, akinetic-rigid syndromes, dyskinesias and dystonias. Examples of akinesias and akinetic-rigid syndromes include Parkinson's disease, drug-induced Parkinsonism, postencephalitic Parkinsonism, secondary Parkinsonism, Parkinson plus syndromes, atypical Parkinsonism, idiopathic Parkinsonism, progressive supranuclear palsy, multiple system atrophy, corticobasal degeneration, Parkinsonism-ALS dementia complex and basal ganglia calcification, medication-induced Parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors. Examples of dyskinesias include drug (e.g. L-DOPA) induced dyskinesia tremor (such as rest tremor, postural tremor, intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics). Examples of dystonias include generalised dystonia, iodiopathic dystonia, drug-induced dystonia, symptomatic dystonia, paroxymal dystonia, focal dystonia, blepharospasm, oromandibular dystonia, spasmodic dysphonia, spasmodic torticollis, axial dystonia, dystonic writer's cramp and hemiplegic dystonia. Other examples of movement disorders include stereotypic movement disorder, persistent (chronic) motor disorder, medication-Induced movement disorder, psychogenic movement disorders, substance/medication-Induced movement disorder, extrapyramidal movement disorders, hyperkinetic movement disorders, hypokinetic movement disorders, alternating hemiplegia, Angelman syndrome, Hallervorden-Spatz Disease, ataxia, dentate cerebellar ataxia, ataxia telangiectasia (Louis-Bar syndrome), Friedreich's Ataxia, hereditary spinal ataxia, hereditary spinal sclerosis, Machado-Joseph Disease, spinocerebellar ataxia, progressive myoclonic ataxia, athetosis, ballismus, blepharospasm (eye twitching), cerebral palsy, tardive dystonia, tardive dyskinesia, idiopathic torsion dystonia, torsion dystonia, focal dystonia, idiopathic familial dystonia, Idiopathic nonfamilial dystonia, cervical dystonia (spasmodic torticollis), primary dystonia, orofacial dystonia, developmental coordination disorder, bulbospinal muscular atrophy (Kennedy's Disease), Shy-Drager Syndrome, and Stiff-Person (Stiff-Man) Syndrome.

In some embodiments, the present invention provides a method of treating one or more symptoms of epilepsy and/or seizures, including abdominal epilepsy, absence seizure, acquired epilepsy, acquired epileptiform aphasia, Aicardi syndrome, Alpers' disease, Alpers-Huttenlocher syndrome, Angelman syndrome, benign focal epilepsy, benign focal epilepsy of childhood, benign intracranial hypertension, benign rolandic epilepsy (BRE), CDKL5 disorder, childhood absense epilepsy, dentate cerebellar ataxia, Doose syndrome, Dravet syndrome, dyscognitive focal seizure, epilepsy with grand mal seizures, epilepsy with myoclonicabsences, epileptic hemiplegia, febrile seizures, focal seizure, frontal lobe epilepsy, generalized tonic-clonic seizures, genetic epilepsy, Glut1 deficiency syndrome, hypothalmic hamartoma, idiopathic epilepsy, idiopathic generalized epilepsy, idopathic localization-related epilepsies, idopathic partial epilepsy, idopathic seizure, junenile absense epilepsy, junvenile myoclonic epilepsy, Lafora disease, Lafora progressive myoclonus epilepsy, Landau-Kleffner syndrome, Lassueur-Graham-Little syndrome, Lennox syndrome, Lennox-Gastaut syndrome, medically refractory epilepsy, mesial-temporal lobe sclerosis, myoclonic seizure, neonatal epilepsy, occipital lobe epilepsy, Ohtahara syndrome, Panayiotopoulos syndrome, parietal lobe epilepsy, PCDH19 epilepsy, photosensitive epilepsy, progressive myoclonic epilepsies, Rasmussen's encephalitis, Rasmussen's syndrome, refractory epilepsy, seizure disorder, status epilepticus, Sturge-Weber syndrome, symptomatic generalized epilepsy, symptomatic parital epilepsy, TBCK-related ID syndrome, temporal lobe epilepsy, temporal lobe seizures, tonic-clonic seizure, West syndrome, tremor, cerebellar tremor, cerebellar outflow tremor, intention tremor, essential tremor, benign essential tremor, Parkinsonian tremor, and medication-induced postural tremor.

In some embodiments, the present invention provides a method of treating a neurological and/or psychiatric disorder described herein, comprising administering a compound of the invention in conjunction with one or more pharmaceutical agents. Suitable pharmaceutical agents that may be used in combination with the compounds of the present invention include anti-Parkinson's drugs, anti-Alzheimer's drugs, anti-depressants, anti-psychotics, anti-ischemics, CNS depressants, anti-cholinergics, nootropics, epilepsy medication, attention (e.g., ADD/ADHD) medications, sleep-promoting medications, wakefulness-promoting medications, and pain medications. In some embodiments, suitable pharmaceutical agents are anxiolytics.

Suitable anti-Parkinson's drugs include dopamine replacement therapy (e.g. L-DOPA, carbidopa, COMT inhibitors such as entacapone or tolcapone), dopamine agonists (e.g. D1 agonists, D2 agonists, mixed D1/D2 agonists, bromocriptine, pergolide, cabergoline, ropinirole, pramipexole, piribedil, or apomorphine in combination with domperidone), histamine H2 antagonists, monoamine oxidase inhibitors (such as selegiline, rasagiline, safinamide and tranylcypromine), certain atypical antipsychotics such as pimavanserin (a non-dopaminergic atypical antipsychotic and inverse agonist of the serotonin 5-$HT_{2A}$ receptor), and amantadine.

In some embodiments, compounds of the invention can be used in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone or tolcapone, MAO A/B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexole are commonly used in a non-salt form.

Suitable anti-Alzheimer's drugs include beta-secretase inhibitors, gamma-secretase inhibitors, cholinesterase inhibitors such as donepezil, galantamine or rivastigmine, HMG-CoA reductase inhibitors, NSAID's including ibuprofen, vitamin E, and anti-amyloid antibodies. In some embodiments, an anti-Alzheimer's drug is memantine.

Suitable anti-depressants and anti-anxiety agents include norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists.

Specific suitable anti-depressant and anti-anxiety agents include amitriptyline, clomipramine, doxepin, imipramine and trimipramine; amoxapine, desipramine, citalopram, escitalopram, maprotiline, nortriptyline and protriptyline; fluoxetine, fluvoxamine, paroxetine and sertraline; isocarboxazid, phenelzine, tranylcypromine and selegiline; moclobemide: venlafaxine; desvenlafaxine, duloxetine; aprepitant; bupropion, vilazodone, mirtazapine, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, reboxetine, vortioxetine, clorazepate, and pharmaceutically acceptable salts thereof. In some embodiments, suitable anti-depressant and anti-anxiety agents are tianeptine, or pharmaceutically acceptable salts thereof.

Suitable anti-psychotic and mood stabilizer agents include D2 antagonists, 5HT2A antagonists, atypical antipsychotics, lithium, and anticonvulsants.

Specific suitable anti-psychotic and mood stabilizer agents include chlorpromazine, fluphenazine, haloperidol, amisulpride, perphenazine, thioridazine, trifluoperazine, aripiprazole, asenapine, clozapine, olanzapine, paliperidone, quetiapine, risperidone, ziprasidone, lurasidone, flupentixol, levomepromazine, pericyazine, perphenazine, pimozide, prochlorperazine, zuclopenthixol, olanzapine and fluoxetine, lithium, carbamazepine, lamotrigine, valproic acid, iloperidone, thiothixene and pharmaceutically acceptable salts thereof.

Suitable epilepsy medications include levetiracetam, oxcarbazepine, clobazam, retigabine, zonisamide, felbamate, esclicarbazepine acetate, lacosamide, carbamazepine, tiagabine, methsuximide, progabide, valproic acid, lamotrigine, brivaracetam, rufinamide, topiramate and perampanel.

Suitable attention medications include methyl phenidate, atomoxetine, guanfacine, D-amphetamine, lisdexamphetamine, methylamphetamine, and clonidine.

Suitable sleep-promoting medications include ramelteon, triazolam, zopiclone, eszopiclone, zolpidem, temazepam, and trazodone.

Suitable wakefulness-promoting medications include Modafinil, D-Amphetamine, caffeine, and armodafinil.

Suitable pain medications include dextromethorphan, tapentadol, buprenorphine, codeine, fentanyl, hydrocodone, hydromorphone, morphine, naloxegol, oxycodone, tramadol, gabapentil, difluprednate, pregabalin, acetyl salicyclic acid, bromfenac, diclofenac, diflunisal, indomethacin, ketorolac, meoxican, and naproxen.

In some embodiments, compounds of the invention may be used in combination with other therapies. Suitable therapies include psychotherapy, cognitive behavioral therapy, electroconvulsive therapy, transcranial magnetic stimulation, vagus nerve stimulation, and deep-brain stimulation.

The exact amount required will vary from subject to subject, depending on the species, age, and general condition of the subject, the severity of the condition, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In some embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In some embodiments, a combination of two or more therapeutic agents may be administered together with the compounds of the invention. In some embodiments, a combination of three or more therapeutic agents may be administered with the compounds of the invention.

Other examples of agents the compounds of this invention may also be combined with include: vitamins and nutritional supplements, antiemetics (e.g. 5-HT3 receptor antagonists, dopamine antagonists, NK1 receptor antagonists, histamine receptor antagonists, cannabinoids, benzodiazepines, or anticholinergics), agents for treating Multiple Sclerosis (MS) such as beta interferon (e.g., Avonex® and Rebif®, dalfampridine, alemtuzumab), Copaxone®, and mitoxantrone; treatments for Huntington's disease such as tetrabenazine; treatments for asthma such as albuterol and Singulair®; anti-inflammatory agents such as corticosteroids, TNF blockers, IL-1 RA, azathioprine, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In some embodiments, a compound of the present invention, or a pharmaceutically acceptable salt thereof, is administered in combination with an antisense agent, a monoclonal or polyclonal antibody, or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, or a pharmaceutically acceptable salt thereof, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the present invention provides a medicament comprising at least one compound of formula I, or a pharmaceutically acceptable salt thereof, and a pharmaceutically acceptable carrier, adjuvant, or vehicle.

In some embodiments, the present invention provides the use of a compound of formula I, or a pharmaceutically acceptable salt thereof, in the manufacture of a medicament for the treatment of a neurological and/or psychiatric disorder.

EXAMPLES

As depicted in the Examples below, in some embodiments, compounds are prepared according to the following procedures. It will be appreciated that, although the general methods depict the synthesis of certain compounds of the present invention, the following methods, and other methods known to persons skilled in the art, can be applied to all compounds and subclasses and species of each of these, as described herein.

Synthesis of Compounds—Definition of Abbreviations Used in the Synthetic Examples Ac=acetyl; AcOH=acetic acid; aq=aqueous; BINAP=(2,2'-bis(diphenylphosphino)-1,1'-binaphthyl); Boc=t-butoxy carbonyl; Bu=butyl; n-Bu=n-butyl; t-butyl=t-butyl; Bz=benzoyl; Cbz=benzyloxycarbonyl; conc=concentrated; d=day(s); dba=dibenzylideneacetone; DCM=dichloromethane; DEAD=diethyl azodicarboxylate; Dess-Martin periodinane=1,1,1-tris(acetyloxy)-1,1-dihydro-1,2-benziodoxol-3-(1H)-one; DIAD=diisoproyl azodicarboxylate; DMAP=4-(N,N-dimethylamino)pyridine; DMF=4-(N,N-dimethylamino)pyridine; DMSB=dimethyl sulfide borane; DMSO=dimethyl sulfoxide; EDCI=1-ethyl-3-(3-dimethylaminopropyl)carbodiimide; EtOAc=ethyl acetate; h=hour(s); HATU=(1-[bis(dimethylamino)methylene]-1H-1,2,3-triazolo[4,5-b]pyridinium 3-oxid hexafluorophosphate); Hex=hexane; HOBT=HOBt=hydroxybenzotriazole; HPLC=high-performance liquid chromatography; LC-MS=liquid chromatography-mass spectrometry; LiHMDS=lithium hexamethyldisilazane; MBTE=methyl t-butyl ether; MeOH=methanol; min=minute(s); Ms=methylsulfonyl; NBS=N-bromosuccinimide; NaHMDS=sodium hexamethyldisilazane; STAB=sodium triacetoxyborohydride; t-=tert-; TBAB: tetra-n-butylammonium bromide; TFA=trifluoroacetic acid; THF=tetrahydrofuran; TLC=thin layer chromatography; TMEDA=Tetramethylethylenediamine; TTIP=titanium tetraisopropoxide

TABLE 1

$R^4$ Group Examples. The representative $R^4$ group synthetic coupling partners in Table 1 were synthesized according to Example $R^4$ and Example T.

| Group # | $R^4$ Group (with X, $R^1$ and $R^2$, as defined independently for each ex.) | Representative $R^4$-group Synthetic Coupling Partners |
|---|---|---|
| $R^4$-1 | 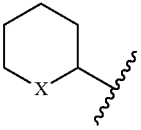 X = CH$_2$, O | 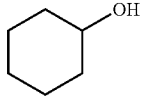 |
| $R^4$-2 | 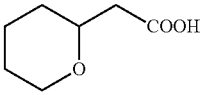 | 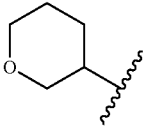 [SMILES: *C1CCCOC1] |
| $R^4$-3 | 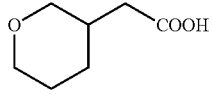 | 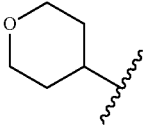 [SMILES: *C1CCOCC1] |
| $R^4$-4 | 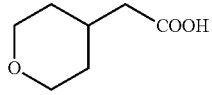 $R^1$ = H, Me, $R^2$ = H, Me, $R^3$ = H, F, OMe, OCH$_2$CH$_2$NH$_2$, NH$_2$, NMe$_2$, CN | 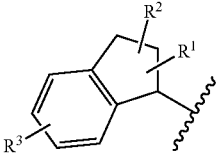 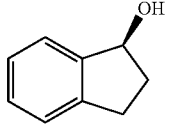 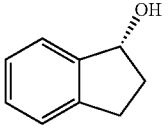 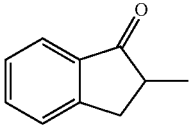 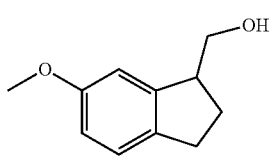 |

TABLE 1-continued
R⁴ Group Examples. The representative R⁴ group synthetic coupling partners in Table 1 were synthesized according to Example R⁴ and Example T.
| Group # | R⁴ Group (with X, R¹ and R², as defined independently for each ex.) | Representative R⁴-group Synthetic Coupling Partners |
|---|---|---|
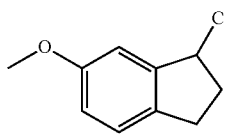
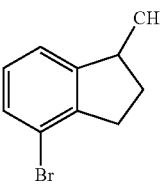
R⁴-5 with X = N, C—CN TABLE 1-continued R⁴ Group Examples. The representative R⁴ group synthetic coupling partners in Table 1 were synthesized according to Example R⁴ and Example T.

| Group # | R⁴ Group (with X, R¹ and R², as defined independently for each ex.) | Representative R⁴-group Synthetic Coupling Partners |
|---|---|---|
| R⁴-6 | 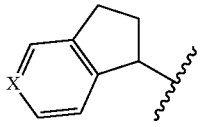<br>X = N, C—CN | 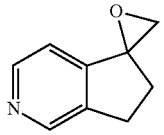 [SMILES: c1cc2c(cn1)CCC21CO1] 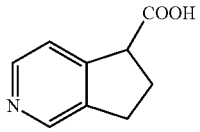 [SMILES: O=C(O)C1CCc2cnccc21]<br>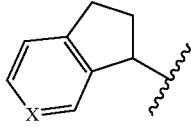 |
| R⁴-7 | 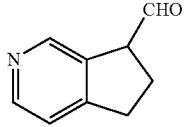<br>X = N, C—OMe,<br>C—NH₂, C—NMe₂,<br>C—OCH₂CH₂NH₂ | 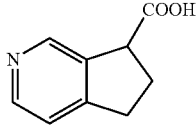 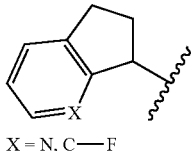<br>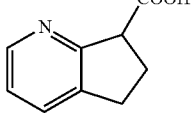 |
| R⁴-8 | 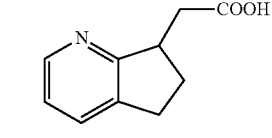 [SMILES: O=C(O)CC1CCc2cccnc21]<br>X = N, C—F | 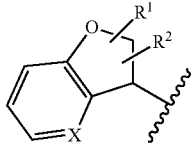 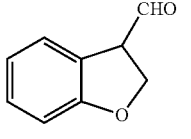 [SMILES: O=CC1COc2ccccc21] |
| R⁴-9 | 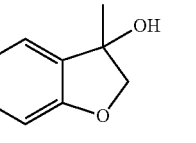<br>X = CH, N; R¹ = H, Me;<br>R² = H, Me | 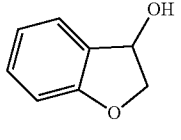 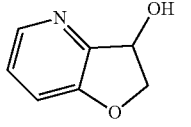 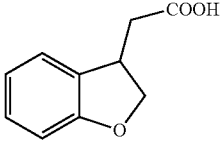 [SMILES: O=C(O)CC1COc2ccccc21]<br>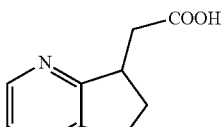 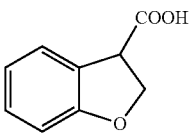 [SMILES: O=C(O)C1COc2ccccc21] |

TABLE 1-continued
R[4] Group Examples. The representative R[4] group synthetic coupling partners in Table 1 were synthesized according to Example R[4] and Example T.
| Group # | R[4] Group (with X, R[1] and R[2], as defined independently for each ex.) | Representative R[4]-group Synthetic Coupling Partners |
|---|---|---|
| R[4]-10 | 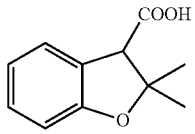 X = CH, N; R = H, Me | 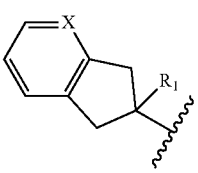 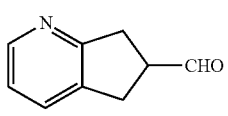 [SMILES: O=CC1Cc2cccnc2C1] 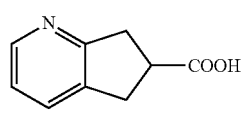 [SMILES: O=C(O)C1Cc2cccnc2C1] 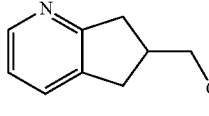 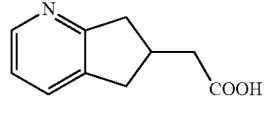 [SMILES: O=C(O)CC1Cc2cccnc2C1] 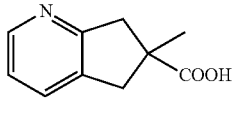 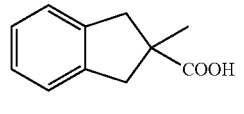 |
| R[4]-11 | 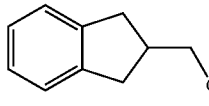 X = CH, N; R = H, Me | 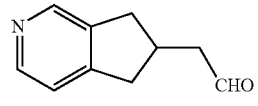 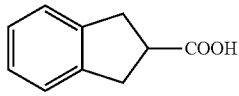 [SMILES: O=C(O)C1Cc2ccccc2C1]  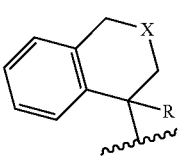 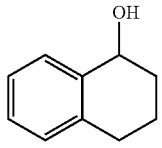 |
| R[4]-12 | 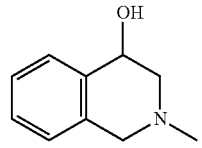 X = CH$_2$, O, NMe, R = H, OH | 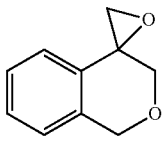 [SMILES: c1ccc2c(c1)COCC21CO1] 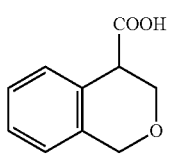 [SMILES: O=C(O)C1COCc2ccccc21] 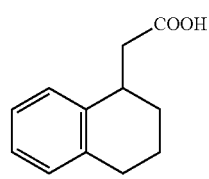 [SMILES: O=C(O)CC1CCCc2ccccc21] 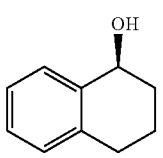 [SMILES: O[C@H]1CCCc2ccccc21] |

TABLE 1-continued
R[4] Group Examples. The representative R[4] group synthetic coupling partners in Table 1 were synthesized according to Example R[4] and Example T.
| Group # | R[4] Group (with X, R[1] and R[2], as defined independently for each ex.) | Representative R[4]-group Synthetic Coupling Partners |
|---|---|---|
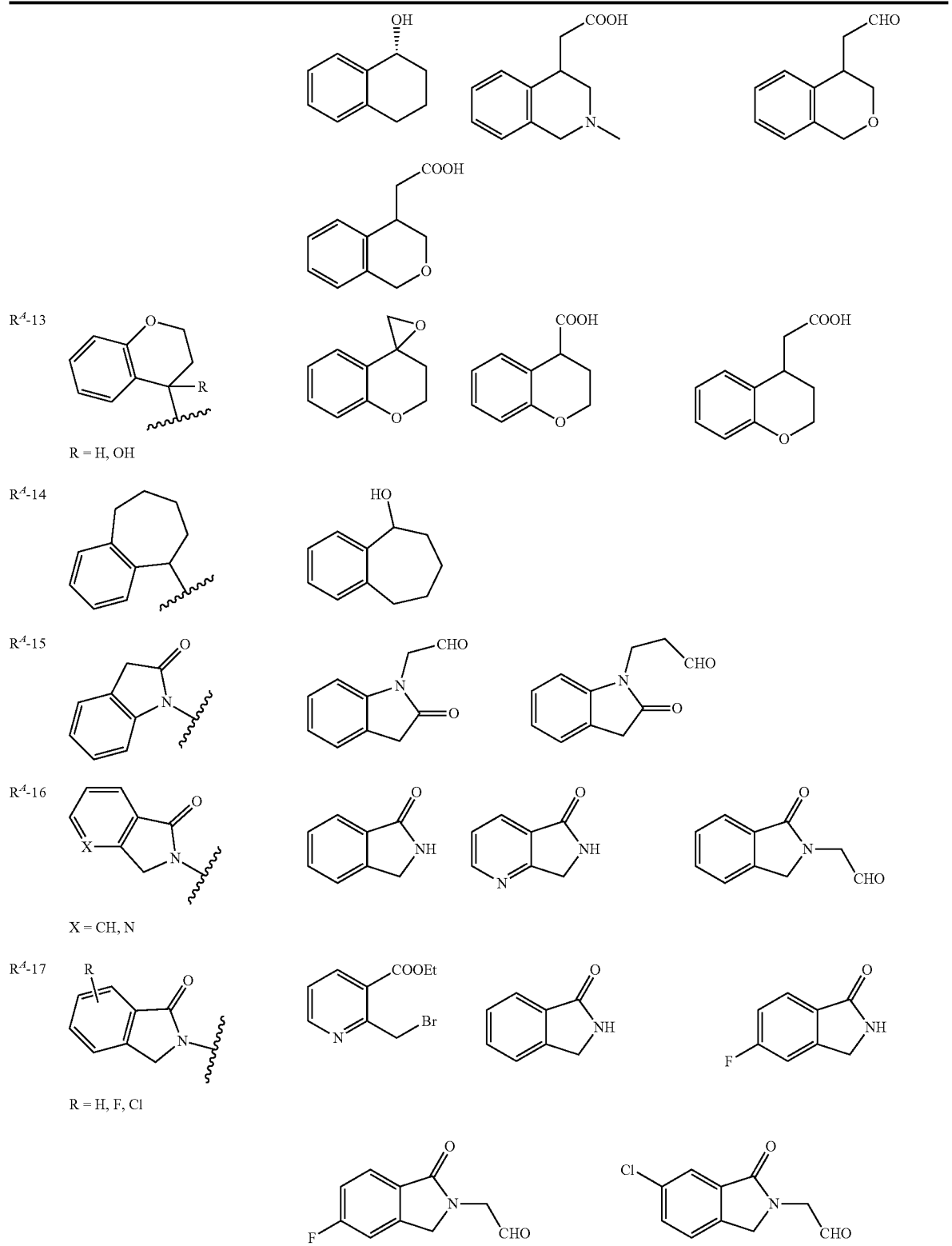
R[4]-13
R = H, OH
R[4]-14
R[4]-15
R[4]-16
X = CH, N
R[4]-17
R = H, F, Cl TABLE 1-continued R⁴ Group Examples. The representative R⁴ group synthetic coupling partners in Table 1 were synthesized according to Example R⁴ and Example T.

| Group # | R⁴ Group (with X, R¹ and R², as defined independently for each ex.) | Representative R⁴-group Synthetic Coupling Partners |
|---|---|---|
| R⁴-18 | | |
| R⁴-19 | X = CH, N, R = CH₂, CHMe | |
| R⁴-20 | | |
| R⁴-21 | R = H, OMe, Br, Cl, CH₂NMe₂ | |

TABLE 1-continued
R[4] Group Examples. The representative R[4] group synthetic coupling partners in Table 1 were synthesized according to Example R[4] and Example T.
| R[4] Group (with X, R[1] and R[2], as | |
|---|---|
| Group # defined independently for each ex.) | Representative R[4]-group Synthetic Coupling Partners |
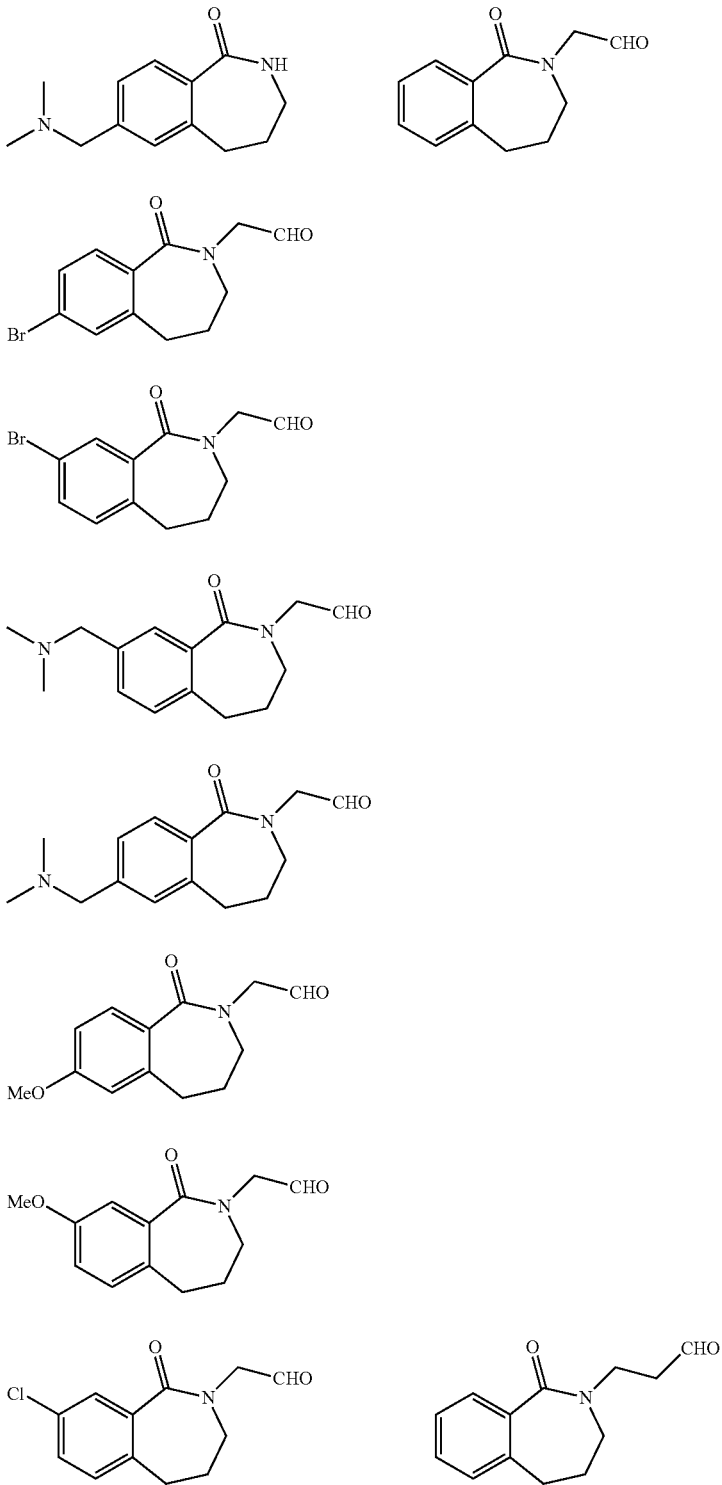

TABLE 1-continued $R^4$ Group Examples. The representative $R^4$ group synthetic coupling partners in Table 1 were synthesized according to Example $R^4$ and Example T.

| Group # | $R^4$ Group (with X, $R^1$ and $R^2$, as defined independently for each ex.) | Representative $R^4$-group Synthetic Coupling Partners |
|---|---|---|
| $R^4$-22 | 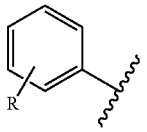<br>R = H, F, Cl, Me, OMe, CN, C(O)CH$_2$CH$_3$, NHC(O)Me | 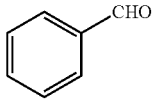 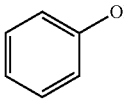 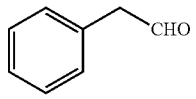<br>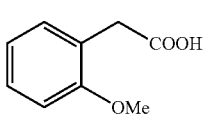 [SMILES: COc1ccccc1CC(=O)O] 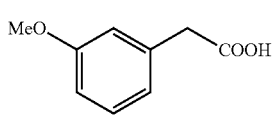<br>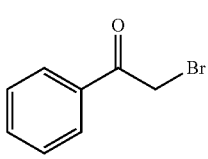 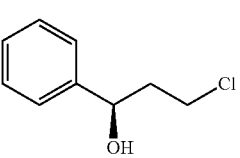 [SMILES: O[C@H](CCCl)c1ccccc1]<br>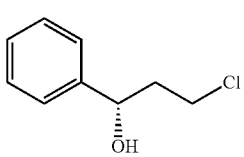 [SMILES: O[C@@H](CCCl)c1ccccc1] 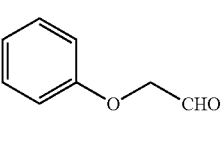<br>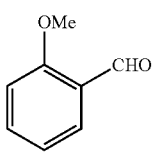 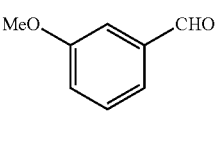<br>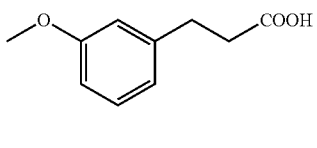 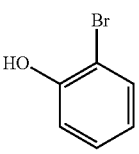 |
| $R^4$-23 | 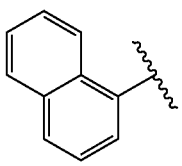 [SMILES: *c1cccc2ccccc12] | |
| $R^4$-24 | 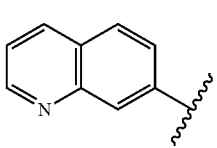 [SMILES: *c1ccc2cccnc2c1] | 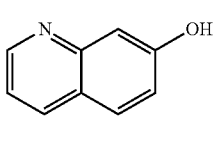 [SMILES: Oc1ccc2cccnc2c1] 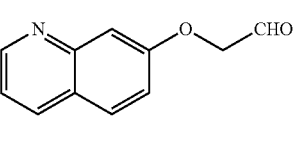 [SMILES: O=CCOc1ccc2cccnc2c1] |
| $R^4$-25 | 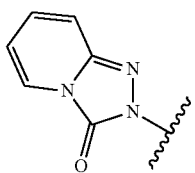 [SMILES: *n1nc2ccccn2c1=O] | |

TABLE 1-continued

R[4] Group Examples. The representative R[4] group synthetic coupling partners in Table 1 were synthesized according to Example R[4] and Example T.

| Group # | R[4] Group (with X, R[1] and R[2], as defined independently for each ex.) Representative R[4]-group Synthetic Coupling Partners |
|---|---|
| R[4]-26 | (benzimidazole with N-CH2-O-phenyl substituent) |
| R[4]-27 | (6-(4-fluorophenyl)-4,5-dihydropyridazin-3(2H)-one, N-substituted and NH forms) |
| R[4]-28 | (pyrido[2,3-d]pyrimidin-4(3H)-one, N-substituted) |
| R[4]-29 | (4-methylcoumarin, 7-substituted) |

TABLE 2

L[1] Group Examples. The L[1] groups were used to couple the Q coupling intermediates to R[4] group synthetic coupling partners according to the Example L[1].

| Linker L[1] | L[1]-Linker (with X and R, as defined independently for each example) |
|---|---|
| L[1]-1 | CHR, R = H, alkyl |
| L[1]-2 | CH2-CHR, R = H, Me |
| L[1]-3 | CH2-C(=O)-CH2 |
| L[1]-4 | X-CH2-CH2, X = O, CH2, CHOH, CHOMe |
| L[1]-5 | X-CH2-CH2-CH2, X = O, CH2 |
| L[1]-6 | X-CH2-CH(OH)-CH2, X = O, NH |

TABLE 2-continued

L¹ Group Examples. The L¹ groups were used to couple the Q coupling intermediates to R^A group synthetic coupling partners according to the Example L¹.

| Linker L¹ | L¹-Linker (with X and R, as defined independently for each example) |
|---|---|
| L¹-7 | 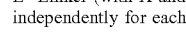 |
| L¹-8 |  |

TABLE 3

Q Group Examples. The Q-group coupling partners were synthesized according to Example Q and Example T, and were coupled to R^A-group synthetic coupling partners from Table 1 according to Example L¹ and coupled to R^B-coupling partners according to Example L².

| Q # | Q | Representative Q groups |
|---|---|---|
| Q-1 |  R = H, Me | |
| Q-2 |  | |
| Q-3 | 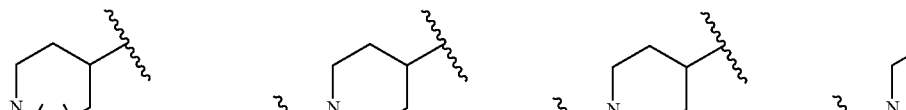 R¹ = H, Me; R² = H, Me | |
| Q-4 |  | |
| Q-5 | | |

TABLE 3-continued

Q Group Examples. The Q-group coupling partners were synthesized according to Example Q and Example T, and were coupled to $R^A$-group synthetic coupling partners from Table 1 according to Example $L^1$ and coupled to $R^B$-coupling partners according to Example $L^2$.

| Q # | Q | Representative Q groups |
|---|---|---|
| Q-6 | | |
| Q-7 | | |
| Q-8 | | |
| Q-9 | | |
| Q-10 | | |
| Q-11 | | |
| Q-12 | | |
| Q-13 | | |
| Q-14 | | |

TABLE 3-continued

Q Group Examples. The Q-group coupling partners were synthesized according to Example Q and Example T, and were coupled to R$^A$-group synthetic coupling partners from Table 1 according to Example L$^1$ and coupled to R$^B$-coupling partners according to Example L$^2$.

| Q # | Q | Representative Q groups |
|---|---|---|
| Q-15 | | |
| Q-16 | | |
| Q-17 | | |
| Q-18 | | |
| Q-19 | | |
| Q-20 | | |
| Q-21 | | |
| Q-22 | | |

TABLE 3-continued

Q Group Examples. The Q-group coupling partners were synthesized according to Example Q and Example T, and were coupled to $R^A$-group synthetic coupling partners from Table 1 according to Example $L^1$ and coupled to $R^B$-coupling partners according to Example $L^2$.

| Q # | Q | Representative Q groups |
|---|---|---|
| Q-23 | | |
| Q-24 | | |
| Q-25 | | |
| Q-26 | | |
| Q-27 | | |
| Q-28 | | |
| Q-29 | | |
| Q-30 | | |

TABLE 3-continued

Q Group Examples. The Q-group coupling partners were synthesized according to Example Q and Example T, and were coupled to R$^A$-group synthetic coupling partners from Table 1 according to Example L$^1$ and coupled to R$^B$-coupling partners according to Example L$^2$.

| Q # | Q | Representative Q groups |
|---|---|---|
| Q-31 | (1-oxa-6-azaspiro[3.4]oct-7-ene structure) | |
| Q-32 | (1-oxa-6-azaspiro[3.4]octane structure with R substituent); R = H, OH | |
| Q-33 | (2-azaspiro[4.4]nonane structure) | |
| Q-34 | (1-oxa-8-azaspiro[4.5]decane structure with R substituent); R = H, OH | |
| Q-35 | (1-oxa-6-azaspiro[3.5]nonane structure) | |
| Q-36 | (oxo-substituted 1-oxa-6-azaspiro[3.5]nonane structure) | |
| Q-37 | (1-oxa-8-azaspiro[4.5]decane structure) | |

TABLE 3-continued

Q Group Examples. The Q-group coupling partners were synthesized according to Example Q and Example T, and were coupled to $R^A$-group synthetic coupling partners from Table 1 according to Example $L^1$ and coupled to $R^B$-coupling partners according to Example $L^2$.

| Q # | Q | Representative Q groups |
|---|---|---|
| Q-38 | | |
| Q-39 | | |
| Q-40 | | |
| Q-41 | | |
| Q-42 | | |
| Q-43 | R = H, Me | |
| Q-44 | | |

TABLE 3-continued

Q Group Examples. The Q-group coupling partners were synthesized according to Example Q and Example T, and were coupled to $R^A$-group synthetic coupling partners from Table 1 according to Example $L^1$ and coupled to $R^B$-coupling partners according to Example $L^2$.

| Q # | Q | Representative Q groups |
|---|---|---|
| Q-45 | 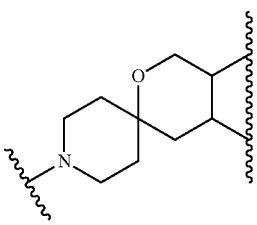 | |
| Q-46 | 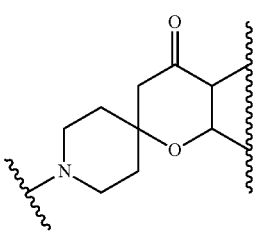 | |
| Q-47 | 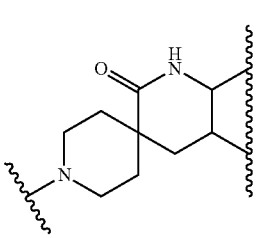 | |

TABLE 4

Representative $R^B$-group Synthetic Coupling Partners

| Linker $L^2$ used to couple with $R^B$ | Representative $R^B$-group Synthetic Coupling Partners | | | |
|---|---|---|---|---|
| $L^2$-1 | bond | 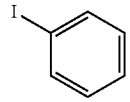 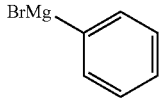 | 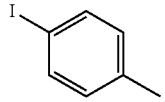 | 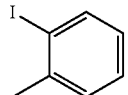 |
| $L^2$-2 | —O— | 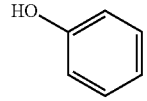 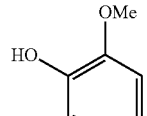 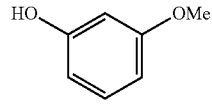 | 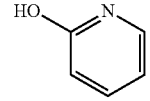 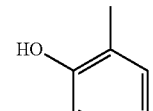 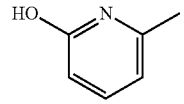 | 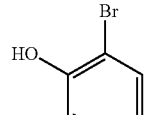 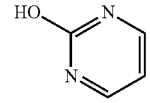 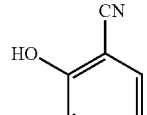 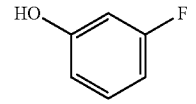 |

TABLE 4-continued

Representative R$^B$-group Synthetic Coupling Partners

| Linker L$^2$ used to couple with R$^B$ | Representative R$^B$-group Synthetic Coupling Partners |
|---|---|
| L$^2$-3  —CH$_2$— | benzyl bromide |
| L$^2$-4  —OCH$_2$— | 4-fluorobenzyl bromide; 2-methoxybenzyl chloride; 3-(bromomethyl)pyridine; 2-chlorobenzyl bromide; 3-methoxybenzyl bromide; 2-fluorobenzyl bromide; 4-(bromomethyl)pyridine |
| L$^2$-5  —NHSO$_2$— | 4-fluorobenzenesulfonyl chloride; thiazole-2-sulfonyl chloride |
| L$^2$-6  —CH$_2$O— | 4-fluorophenol |

Additional R$^B$-group coupling partners shown at top of table: 3-chlorophenol, 3-hydroxypyridine, 3-hydroxybenzonitrile, 4-fluorophenol, 4-hydroxypyridine, 4-methoxyphenol, methyl 4-hydroxybenzoate, 4-hydroxybenzonitrile, 5-hydroxypyrimidine, 2-methoxy-4-nitrophenol, 7-hydroxyquinoline, 2-fluoro-3-methoxy-nitrobenzene.

TABLE 5

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 1 | 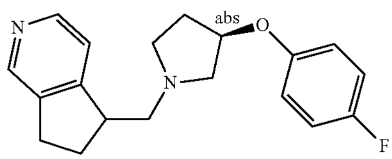 [SMILES: Fc1ccc(O[C@@H]2CCN(CC3CCc4cnccc43)C2)cc1] | 5-(((R)-3-(4-fluorophenoxy)pyrrolidin-1-yl)methyl)-6,7-dihydro-5H-cyclopenta[c]pyridine | $R^A$-6 | $L^1$-1 | Q-1 | $L^2$-2 |
| 2 | 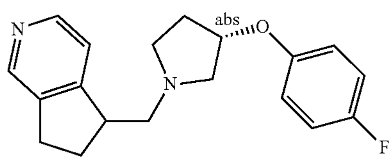 [SMILES: Fc1ccc(O[C@H]2CCN(CC3CCc4cnccc43)C2)cc1] | 5-(((S)-3-(4-fluorophenoxy)pyrrolidin-1-yl)methyl)-6,7-dihydro-5H-cyclopenta[c]pyridine | $R^A$-6 | $L^1$-1 | Q-1 | $L^2$-2 |
| 3 | 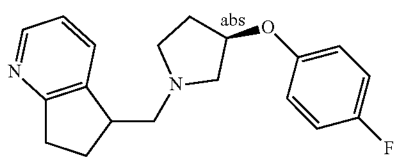 [SMILES: Fc1ccc(O[C@@H]2CCN(CC3CCc4ncccc43)C2)cc1] | 5-(((R)-3-(4-fluorophenoxy)pyrrolidin-1-yl)methyl)-6,7-dihydro-5H-cyclopenta[b]pyridine | $R^A$-6 | $L^1$-1 | Q-1 | $L^2$-2 |
| 4 | 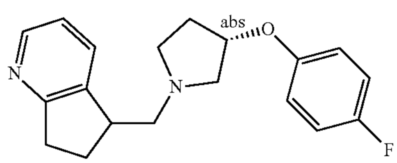 [SMILES: Fc1ccc(O[C@H]2CCN(CC3CCc4ncccc43)C2)cc1] | 5-(((S)-3-(4-fluorophenoxy)pyrrolidin-1-yl)methyl)-6,7-dihydro-5H-cyclopenta[b]pyridine | $R^A$-6 | $L^1$-1 | Q-1 | $L^2$-2 |
| 5 | 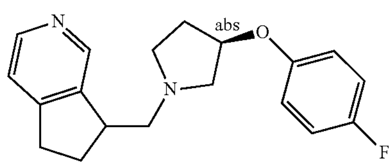 [SMILES: Fc1ccc(O[C@@H]2CCN(CC3CCc4ccncc43)C2)cc1] | 7-(((R)-3-(4-fluorophenoxy)pyrrolidin-1-yl)methyl)-6,7-dihydro-5H-cyclopenta[c]pyridine | $R^A$-7 | $L^1$-1 | Q-1 | $L^2$-2 |
| 6 | 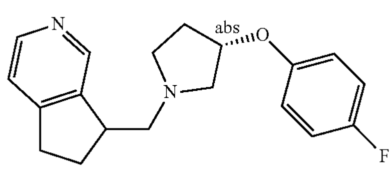 [SMILES: Fc1ccc(O[C@H]2CCN(CC3CCc4ccncc43)C2)cc1] | 7-(((S)-3-(4-fluorophenoxy)pyrrolidin-1-yl)methyl)-6,7-dihydro-5H-cyclopenta[c]pyridine | $R^A$-7 | $L^1$-1 | Q-1 | $L^2$-2 |
| 7 | 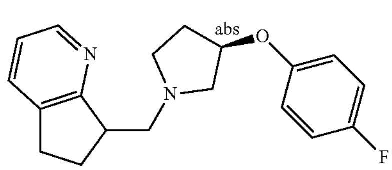 [SMILES: Fc1ccc(O[C@@H]2CCN(CC3CCc4cccnc43)C2)cc1] | 7-(((R)-3-(4-fluorophenoxy)pyrrolidin-1-yl)methyl)-6,7-dihydro-5H-cyclopenta[b]pyridine | $R^A$-8 | $L^1$-1 | Q-1 | $L^2$-2 |
| 8 | 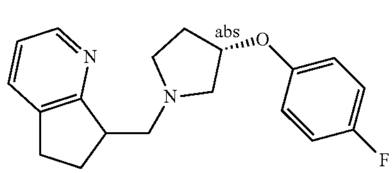 [SMILES: Fc1ccc(O[C@H]2CCN(CC3CCc4cccnc43)C2)cc1] | 7-(((S)-3-(4-fluorophenoxy)pyrrolidin-1-yl)methyl)-6,7-dihydro-5H-cyclopenta[b]pyridine | $R^A$-7 | $L^1$-1 | Q-1 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 9 | 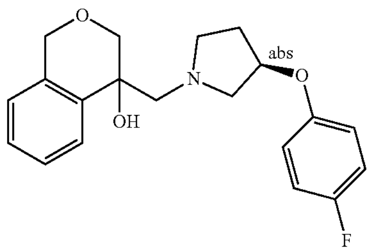 [SMILES: OC1(CN2CC[C@@H](Oc3ccc(F)cc3)C2)COCc2ccccc21] | 4-(((R)-3-(4-fluorophenoxy)pyrrolidin-1-yl)methyl)isochroman-4-ol | $R^A$-12 | $L^1$-1 | Q-1 | $L^2$-2 |
| 10 | 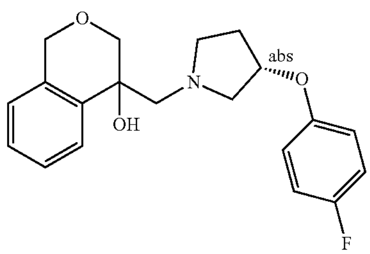 [SMILES: OC1(CN2CC[C@H](Oc3ccc(F)cc3)C2)COCc2ccccc21] | 4-(((S)-3-(4-fluorophenoxy)pyrrolidin-1-yl)methyl)isochroman-4-ol | $R^A$-12 | $L^1$-1 | Q-1 | $L^2$-2 |
| 11 | 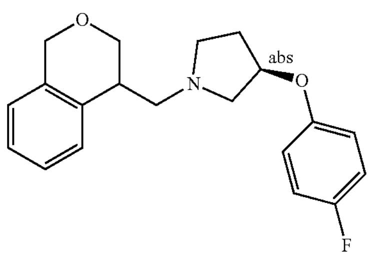 [SMILES: Fc1ccc(O[C@@H]2CCN(CC3COCc4ccccc43)C2)cc1] | (3R)-3-(4-fluorophenoxy)-1-(isochroman-4-ylmethyl)pyrrolidine | $R^A$-12 | $L^1$-1 | Q-1 | $L^2$-2 |
| 12 | 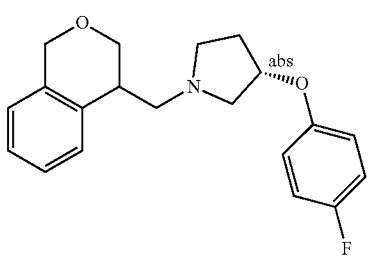 [SMILES: Fc1ccc(O[C@H]2CCN(CC3COCc4ccccc43)C2)cc1] | (3S)-3-(4-fluorophenoxy)-1-(isochroman-4-ylmethyl)pyrrolidine | $R^A$-12 | $L^1$-1 | Q-1 | $L^2$-2 |
| 13 | 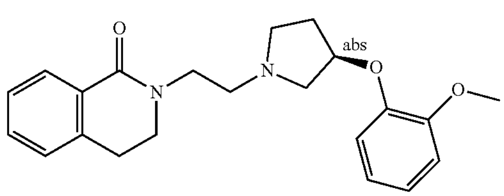 [SMILES: COc1ccccc1O[C@@H]1CCN(CCN2CCc3ccccc3C2=O)C1] | (R)-2-(2-(3-(2-methoxyphenoxy)pyrrolidin-1-yl)ethyl)-3,4-dihydroisoquinolin-1(2H)-one | $R^A$-19 | $L^1$-2 | Q-1 | $L^2$-2 |
| 14 | 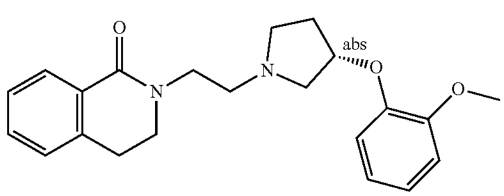 [SMILES: COc1ccccc1O[C@H]1CCN(CCN2CCc3ccccc3C2=O)C1] | (S)-2-(2-(3-(2-methoxyphenoxy)pyrrolidin-1-yl)ethyl)-3,4-dihydroisoquinolin-1(2H)-one | $R^A$-19 | $L^1$-2 | Q-1 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 15 | 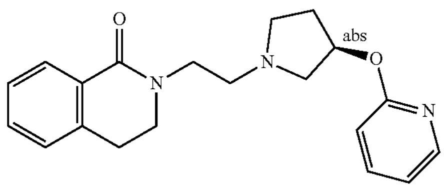 [SMILES: O=C1c2ccccc2CCN1CCN1CC[C@@H](Oc2ccccn2)C1] | (R)-2-(2-(3-(pyridin-2-yloxy)pyrrolidin-1-yl)ethyl)-3,4-dihydroisoquinolin-1(2H)-one | $R^A$-19 | $L^1$-2 | Q-1 | $L^2$-2 |
| 16 | 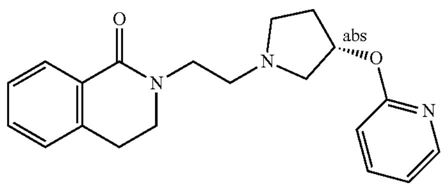 [SMILES: O=C1c2ccccc2CCN1CCN1CC[C@H](Oc2ccccn2)C1] | (S)-2-(2-(3-(pyridin-2-yloxy)pyrrolidin-1-yl)ethyl)-3,4-dihydroisoquinolin-1(2H)-one | $R^A$-19 | $L^1$-2 | Q-1 | $L^2$-2 |
| 17 | 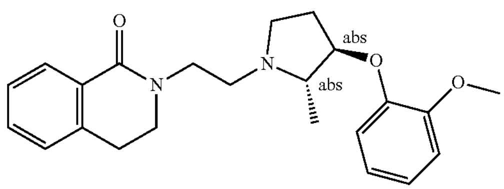 [SMILES: COc1ccccc1O[C@@H]1CCN(CCN2CCc3ccccc3C2=O)[C@H]1C] | 2-(2-((2S,3R)-3-(2-methoxyphenoxy)-2-methylpyrrolidin-1-yl)ethyl)-3,4-dihydroisoquinolin-1(2H)-one | $R^A$-19 | $L^1$-2 | Q-1 | $L^2$-2 |
| 18 | 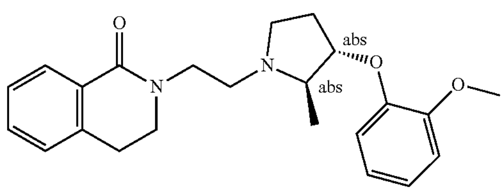 [SMILES: COc1ccccc1O[C@H]1CCN(CCN2CCc3ccccc3C2=O)[C@@H]1C] | 2-(2-((2R,3S)-3-(2-methoxyphenoxy)-2-methylpyrrolidin-1-yl)ethyl)-3,4-dihydroisoquinolin-1(2H)-one | $R^A$-19 | $L^1$-2 | Q-1 | $L^2$-2 |
| 19 | 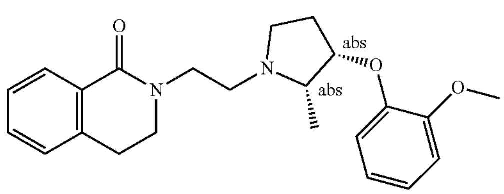 [SMILES: COc1ccccc1O[C@H]1CCN(CCN2CCc3ccccc3C2=O)[C@H]1C] | 2-(2-((2S,3S)-3-(2-methoxyphenoxy)-2-methylpyrrolidin-1-yl)ethyl)-3,4-dihydroisoquinolin-1(2H)-one | $R^A$-19 | $L^1$-2 | Q-1 | $L^2$-2 |
| 20 | 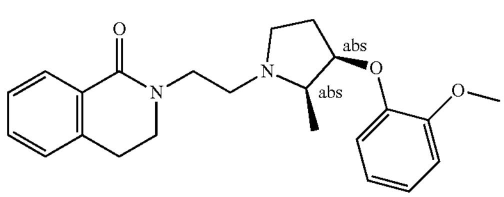 [SMILES: COc1ccccc1O[C@@H]1CCN(CCN2CCc3ccccc3C2=O)[C@@H]1C] | 2-(2-((2R,3R)-3-(2-methoxyphenoxy)-2-methylpyrrolidin-1-yl)ethyl)-3,4-dihydroisoquinolin-1(2H)-one | $R^A$-19 | $L^1$-2 | Q-1 | $L^2$-2 |
| 21 | 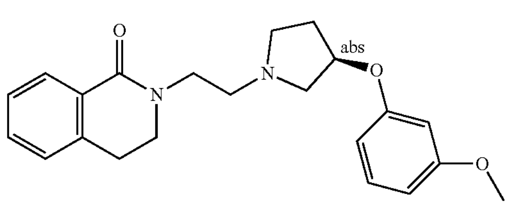 [SMILES: COc1cccc(O[C@@H]2CCN(CCN3CCc4ccccc4C3=O)C2)c1] | (R)-2-(2-(3-(3-methoxyphenoxy)pyrrolidin-1-yl)ethyl)-3,4-dihydroisoquinolin-1(2H)-one | $R^A$-19 | $L^1$-2 | Q-1 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| Structure | Chem Name | $R^A$ | $L^1$ | Q | $L^2$ |
|---|---|---|---|---|---|
| 22 | (S)-2-(2-(3-(3-methoxyphenoxy)pyrrolidin-1-yl)ethyl)-3,4-dihydroisoquinolin-1(2H)-one | $R^A$-19 | $L^1$-2 | Q-1 | $L^2$-2 |
| 23 | (R)-2-(2-(3-(pyridin-3-yloxy)pyrrolidin-1-yl)ethyl)-3,4-dihydroisoquinolin-1(2H)-one | $R^A$-19 | $L^1$-2 | Q-1 | $L^2$-2 |
| 24 | (S)-2-(2-(3-(pyridin-3-yloxy)pyrrolidin-1-yl)ethyl)-3,4-dihydroisoquinolin-1(2H)-one | $R^A$-19 | $L^1$-2 | Q-1 | $L^2$-2 |
| 25 | (R)-2-(2-(3-(4-fluorophenoxy)pyrrolidin-1-yl)ethyl)-3,4-dihydroisoquinolin-1(2H)-one | $R^A$-19 | $L^1$-2 | Q-1 | $L^2$-2 |
| 26 | (S)-2-(2-(3-(4-fluorophenoxy)pyrrolidin-1-yl)ethyl)-3,4-dihydroisoquinolin-1(2H)-one | $R^A$-19 | $L^1$-2 | Q-1 | $L^2$-2 |
| 27 | (R)-2-(2-(3-(4-methoxyphenoxy)pyrrolidin-1-yl)ethyl)-3,4-dihydroisoquinolin-1(2H)-one | $R^A$-19 | $L^1$-2 | Q-1 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 28 | 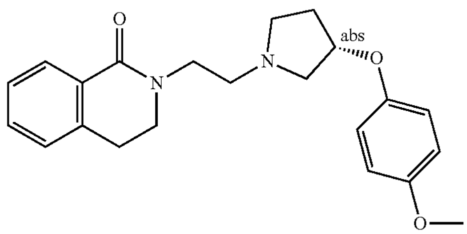 [SMILES: COc1ccc(O[C@H]2CCN(CCN3CCc4ccccc4C3=O)C2)cc1] | (S)-2-(2-(3-(4-methoxyphenoxy)pyrrolidin-1-yl)ethyl)-3,4-dihydroisoquinolin-1(2H)-one | $R^A$-19 | $L^1$-2 | Q-1 | $L^2$-2 |
| 29 | 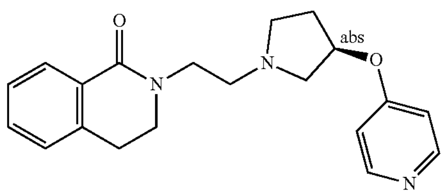 [SMILES: O=C1c2ccccc2CCN1CCN1CC[C@@H](Oc2ccncc2)C1] | (R)-2-(2-(3-(pyridin-4-yloxy)pyrrolidin-1-yl)ethyl)-3,4-dihydroisoquinolin-1(2H)-one | $R^A$-19 | $L^1$-2 | Q-1 | $L^2$-2 |
| 30 | 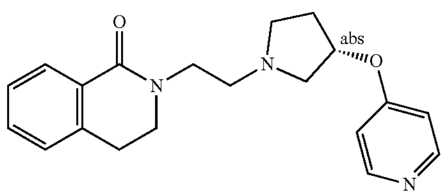 [SMILES: O=C1c2ccccc2CCN1CCN1CC[C@H](Oc2ccncc2)C1] | (S)-2-(2-(3-(pyridin-4-yloxy)pyrrolidin-1-yl)ethyl)-3,4-dihydroisoquinolin-1(2H)-one | $R^A$-19 | $L^1$-2 | Q-1 | $L^2$-2 |
| 31 | 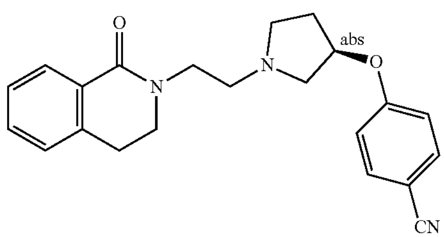 [SMILES: N#Cc1ccc(O[C@@H]2CCN(CCN3CCc4ccccc4C3=O)C2)cc1] | (R)-4-((1-(2-(1-oxo-3,4-dihydroisoquinolin-2(1H)-yl)ethyl)pyrrolidin-3-yl)oxy)benzonitrile | $R^A$-19 | $L^1$-2 | Q-1 | $L^2$-2 |
| 32 | 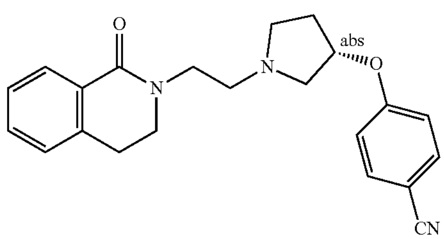 [SMILES: N#Cc1ccc(O[C@H]2CCN(CCN3CCc4ccccc4C3=O)C2)cc1] | (S)-4-((1-(2-(1-oxo-3,4-dihydroisoquinolin-2(1H)-yl)ethyl)pyrrolidin-3-yl)oxy)benzonitrile | $R^A$-19 | $L^1$-2 | Q-1 | $L^2$-2 |
| 33 | 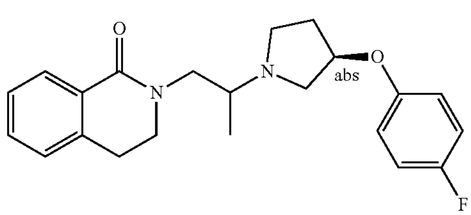 [SMILES: CC(CN1CCc2ccccc2C1=O)N1CC[C@@H](Oc2ccc(F)cc2)C1] | 2-(2-((R)-3-(4-fluorophenoxy)pyrrolidin-1-yl)propyl)-3,4-dihydroisoquinolin-1(2H)-one | $R^A$-19 | $L^1$-2 | Q-1 | $L^2$-2 |

TABLE 5-continued

Summary of synthesis of Compounds. Compounds were synthesized by coupling the R$^A$ group coupling partners to the Q group coupling partners through the L$^1$ linker and coupling the R$^B$ group coupling partners to the Q group coupling partners through the L$^2$ linker. The R$^A$ coupling chemistry used is described in Example L$^1$. The R$^B$ coupling chemistry is described in Example L$^2$. Synthetic details for the transformations described in Examples Example L$^1$, Example L$^2$, Example R$^A$ and Example R$^B$ are in Example T.
The table below lists the R$^A$, L$^1$, Q, L$^2$ and R$^B$ groups whose coupling partners were used in the syntheses.

| | Structure | Chem Name | R$^A$ | L$^1$ | Q | L$^2$ |
|---|---|---|---|---|---|---|
| 34 | 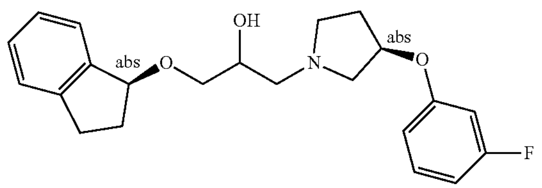 [SMILES: OC(CO[C@H]1CCc2ccccc21)CN1CC[C@@H](Oc2cccc(F)c2)C1] | 1-(((S)-2,3-dihydro-1H-inden-1-yl)oxy)-3-((R)-3-(3-fluorophenoxy)pyrrolidin-1-yl)propan-2-ol | R$^A$-4 | L$^1$-6 | Q-1 | L$^2$-2 |
| 35 | 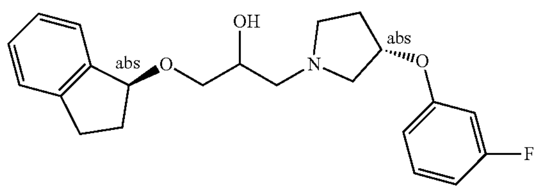 [SMILES: OC(CO[C@H]1CCc2ccccc21)CN1CC[C@H](Oc2cccc(F)c2)C1] | 1-(((S)-2,3-dihydro-1H-inden-1-yl)oxy)-3-((S)-3-(3-fluorophenoxy)pyrrolidin-1-yl)propan-2-ol | R$^A$-4 | L$^1$-6 | Q-1 | L$^2$-2 |
| 36 | 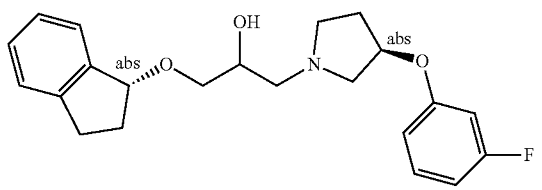 [SMILES: OC(CO[C@@H]1CCc2ccccc21)CN1CC[C@@H](Oc2cccc(F)c2)C1] | 1-(((R)-2,3-dihydro-1H-inden-1-yl)oxy)-3-((R)-3-(3-fluorophenoxy)pyrrolidin-1-yl)propan-2-ol | R$^A$-4 | L$^1$-6 | Q-1 | L$^2$-2 |
| 37 | 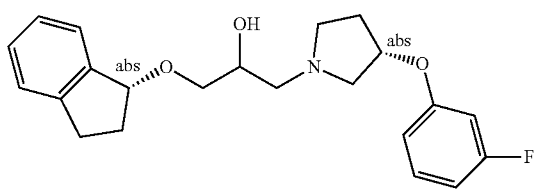 [SMILES: OC(CO[C@@H]1CCc2ccccc21)CN1CC[C@H](Oc2cccc(F)c2)C1] | 1-(((R)-2,3-dihydro-1H-inden-1-yl)oxy)-3-((S)-3-(3-fluorophenoxy)pyrrolidin-1-yl)propan-2-ol | R$^A$-4 | L$^1$-6 | Q-1 | L$^2$-2 |
| 38 | 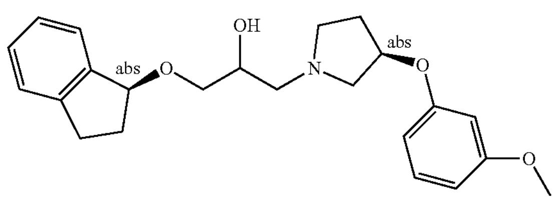 [SMILES: COc1cccc(O[C@@H]2CCN(CC(O)CO[C@H]3CCc4ccccc43)C2)c1] | 1-(((S)-2,3-dihydro-1H-inden-1-yl)oxy)-3-((R)-3-(3-methoxyphenoxy)pyrrolidin-1-yl)propan-2-ol | R$^A$-4 | L$^1$-6 | Q-1 | L$^2$-2 |
| 39 | 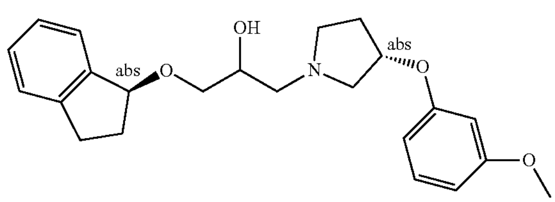 [SMILES: COc1cccc(O[C@H]2CCN(CC(O)CO[C@H]3CCc4ccccc43)C2)c1] | 1-(((S)-2,3-dihydro-1H-inden-1-yl)oxy)-3-((S)-3-(3-methoxyphenoxy)pyrrolidin-1-yl)propan-2-ol | R$^A$-4 | L$^1$-6 | Q-1 | L$^2$-2 |
| 40 | 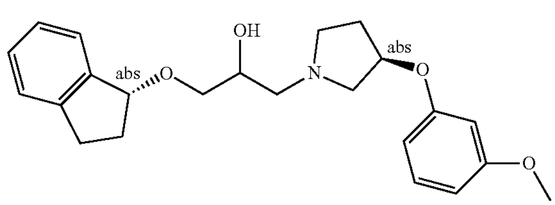 [SMILES: COc1cccc(O[C@@H]2CCN(CC(O)CO[C@@H]3CCc4ccccc43)C2)c1] | 1-(((R)-2,3-dihydro-1H-inden-1-yl)oxy)-3-((R)-3-(3-methoxyphenoxy)pyrrolidin-1-yl)propan-2-ol | R$^A$-4 | L$^1$-6 | Q-1 | L$^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 41 | 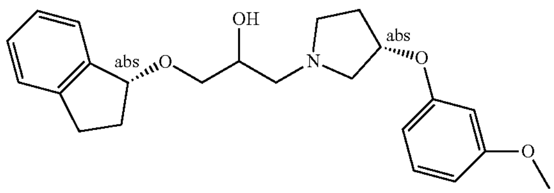 [SMILES: COc1cccc(O[C@H]2CCN(CC(O)CO[C@@H]3CCc4ccccc43)C2)c1] | 1-(((R)-2,3-dihydro-1H-inden-1-yl)oxy)-3-((S)-3-(3-methoxyphenoxy)pyrrolidin-1-yl)propan-2-ol | $R^A$-4 | $L^1$-6 | Q-1 | $L^2$-2 |
| 42 | 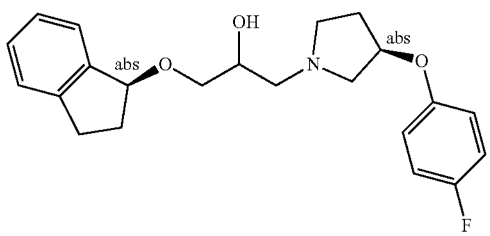 [SMILES: OC(CO[C@H]1CCc2ccccc21)CN1CC[C@@H](Oc2ccc(F)cc2)C1] | 1-(((S)-2,3-dihydro-1H-inden-1-yl)oxy)-3-((R)-3-(4-fluorophenoxy)pyrrolidin-1-yl)propan-2-ol | $R^A$-4 | $L^1$-6 | Q-1 | $L^2$-2 |
| 43 | 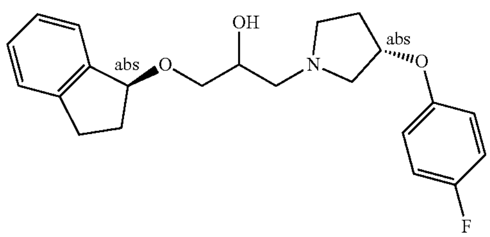 [SMILES: OC(CO[C@H]1CCc2ccccc21)CN1CC[C@H](Oc2ccc(F)cc2)C1] | 1-(((S)-2,3-dihydro-1H-inden-1-yl)oxy)-3-((S)-3-(4-fluorophenoxy)pyrrolidin-1-yl)propan-2-ol | $R^A$-4 | $L^1$-6 | Q-1 | $L^2$-2 |
| 44 | 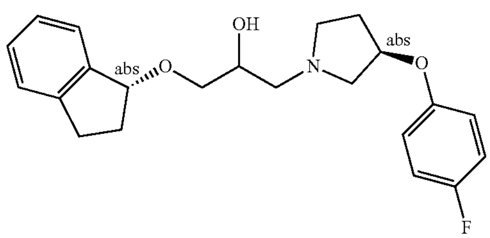 [SMILES: OC(CO[C@@H]1CCc2ccccc21)CN1CC[C@@H](Oc2ccc(F)cc2)C1] | 1-(((R)-2,3-dihydro-1H-inden-1-yl)oxy)-3-((R)-3-(4-fluorophenoxy)pyrrolidin-1-yl)propan-2-ol | $R^A$-4 | $L^1$-6 | Q-1 | $L^2$-2 |
| 45 | 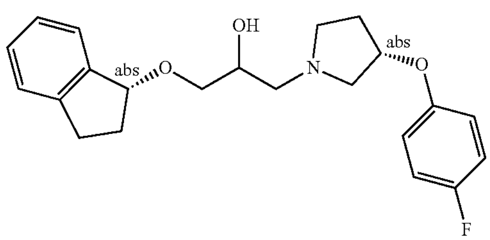 [SMILES: OC(CO[C@@H]1CCc2ccccc21)CN1CC[C@H](Oc2ccc(F)cc2)C1] | 1-(((R)-2,3-dihydro-1H-inden-1-yl)oxy)-3-((S)-3-(4-fluorophenoxy)pyrrolidin-1-yl)propan-2-ol | $R^A$-4 | $L^1$-6 | Q-1 | $L^2$-2 |
| 46 | 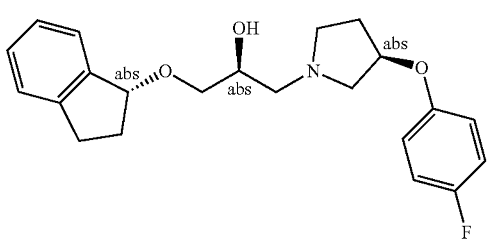 [SMILES: O[C@H](CO[C@@H]1CCc2ccccc21)CN1CC[C@@H](Oc2ccc(F)cc2)C1] | (S)-1-(((R)-2,3-dihydro-1H-inden-1-yl)oxy)-3-((R)-3-(4-fluorophenoxy)pyrrolidin-1-yl)propan-2-ol | $R^A$-4 | $L^1$-6 | Q-1 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 47 | 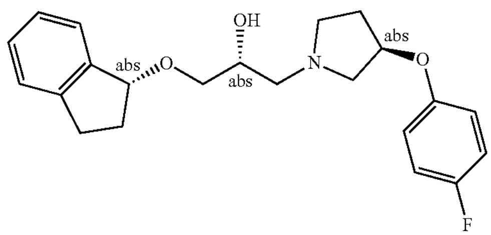 [SMILES: O[C@@H](CO[C@@H]1CCc2ccccc21)CN1CC[C@@H](Oc2ccc(F)cc2)C1] | (R)-1-(((R)-2,3-dihydro-1H-inden-1-yl)oxy)-3-((R)-3-(4-fluorophenoxy)pyrrolidin-1-yl)propan-2-ol | $R^A$-4 | $L^1$-6 | Q-1 | $L^2$-2 |
| 48 | 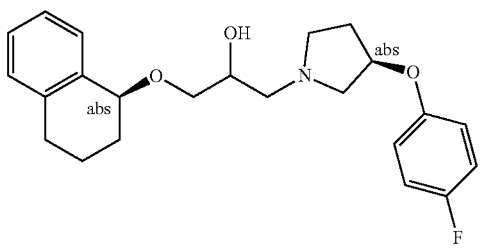 [SMILES: OC(CO[C@H]1CCCc2ccccc21)CN1CC[C@@H](Oc2ccc(F)cc2)C1] | 1-((R)-3-(4-fluorophenoxy)pyrrolidin-1-yl)-3-(((S)-1,2,3,4-tetrahydronaphthalen-1-yl)oxy)propan-2-ol | $R^A$-12 | $L^1$-6 | Q-1 | $L^2$-2 |
| 49 | 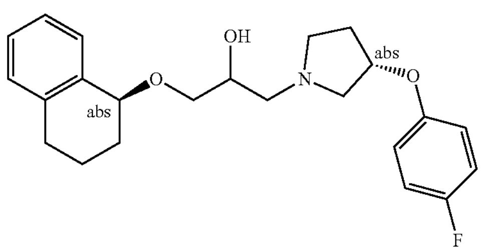 [SMILES: OC(CO[C@H]1CCCc2ccccc21)CN1CC[C@H](Oc2ccc(F)cc2)C1] | 1-((S)-3-(4-fluorophenoxy)pyrrolidin-1-yl)-3-(((S)-1,2,3,4-tetrahydronaphthalen-1-yl)oxy)propan-2-ol | $R^A$-12 | $L^1$-6 | Q-1 | $L^2$-2 |
| 50 | 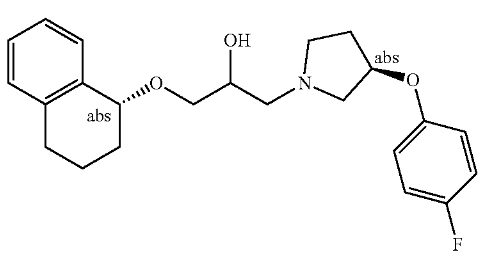 [SMILES: OC(CO[C@@H]1CCCc2ccccc21)CN1CC[C@@H](Oc2ccc(F)cc2)C1] | 1-((R)-3-(4-fluorophenoxy)pyrrolidin-1-yl)-3-(((R)-1,2,3,4-tetrahydronaphthalen-1-yl)oxy)propan-2-ol | $R^A$-12 | $L^1$-6 | Q-1 | $L^2$-2 |
| 51 | 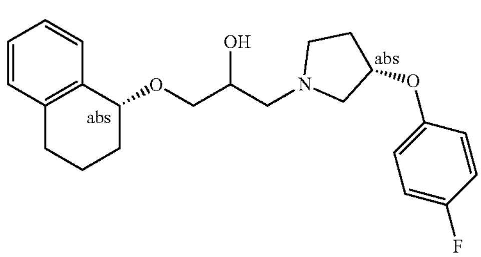 [SMILES: OC(CO[C@@H]1CCCc2ccccc21)CN1CC[C@H](Oc2ccc(F)cc2)C1] | 1-((S)-3-(4-fluorophenoxy)pyrrolidin-1-yl)-3-(((R)-1,2,3,4-tetrahydronaphthalen-1-yl)oxy)propan-2-ol | $R^A$-12 | $L^1$-6 | Q-1 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 52 | 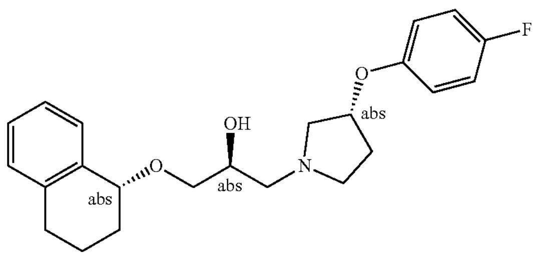 [SMILES: O[C@H](CO[C@@H]1CCCc2ccccc21)CN1CC[C@@H](Oc2ccc(F)cc2)C1] | (S)-1-((R)-3-(4-fluorophenoxy)pyrrolidin-1-yl)-3-(((R)-1,2,3,4-tetrahydronaphthalen-1-yl)oxy)propan-2-ol | $R^A$-12 | $L^1$-6 | Q-1 | $L^2$-2 |
| 53 | 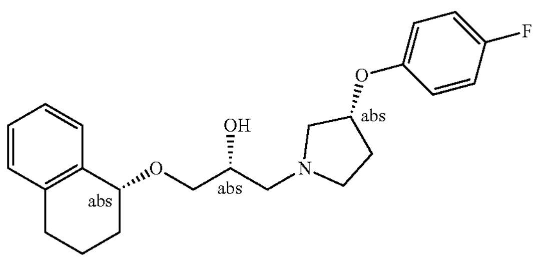 [SMILES: O[C@@H](CO[C@@H]1CCCc2ccccc21)CN1CC[C@@H](Oc2ccc(F)cc2)C1] | (R)-1-((R)-3-(4-fluorophenoxy)pyrrolidin-1-yl)-3-(((R)-1,2,3,4-tetrahydronaphthalen-1-yl)oxy)propan-2-ol | $R^A$-12 | $L^1$-6 | Q-1 | $L^2$-2 |
| 54 | 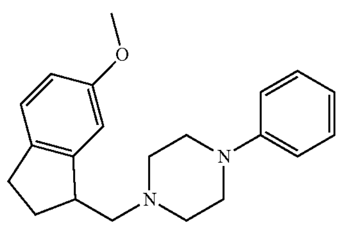 [SMILES: COc1ccc2c(c1)C(CN1CCN(c3ccccc3)CC1)CC2] | 1-((6-methoxy-2,3-dihydro-1H-inden-1-yl)methyl)-4-phenylpiperazine | $R^A$-4 | $L^1$-1 | Q-2 | $L^2$-1 |
| 55 | 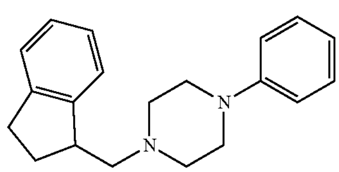 [SMILES: c1ccc(N2CCN(CC3CCc4ccccc43)CC2)cc1] | 1-((2,3-dihydro-1H-inden-1-yl)methyl)-4-phenylpiperazine | $R^A$-4 | $L^1$-1 | Q-2 | $L^2$-1 |
| 56 | 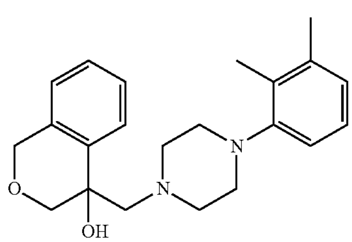 [SMILES: Cc1cccc(N2CCN(CC3(O)COCc4ccccc43)CC2)c1C] | 4-((4-(2,3-dimethylphenyl)piperazin-1-yl)methyl)isochroman-4-ol | $R^A$-12 | $L^1$-1 | Q-2 | $L^2$-1 |
| 57 | 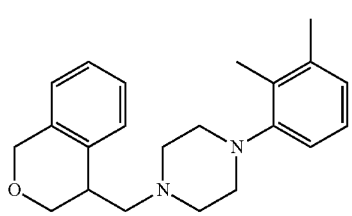 [SMILES: Cc1cccc(N2CCN(CC3COCc4ccccc43)CC2)c1C] | 1-(2,3-dimethylphenyl)-4-(isochroman-4-ylmethyl)piperazine | $R^A$-12 | $L^1$-1 | Q-2 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 58 | 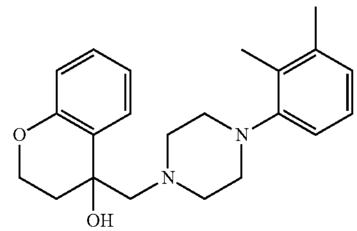 [SMILES: Cc1cccc(N2CCN(CC3(O)CCOc4ccccc43)CC2)c1C] | 4-((4-(2,3-dimethylphenyl)piperazin-1-yl)methyl)chroman-4-ol | $R^A$-13 | $L^1$-1 | Q-2 | $L^2$-1 |
| 59 | 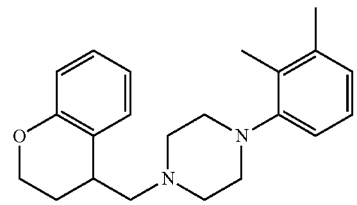 [SMILES: Cc1cccc(N2CCN(CC3CCOc4ccccc43)CC2)c1C] | 1-(chroman-4-ylmethyl)-4-(2,3-dimethylphenyl)piperazine | $R^A$-13 | $L^1$-1 | Q-2 | $L^2$-1 |
| 60 | 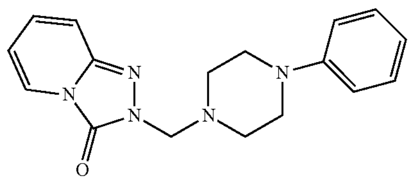 [SMILES: O=c1n(CN2CCN(c3ccccc3)CC2)nc2ccccn12] | 2-((4-phenylpiperazin-1-yl)methyl)-[1,2,4]triazolo[4,3-a]pyridin-3(2H)-one | $R^A$-25 | $L^1$-1 | Q-2 | $L^2$-1 |
| 61 | 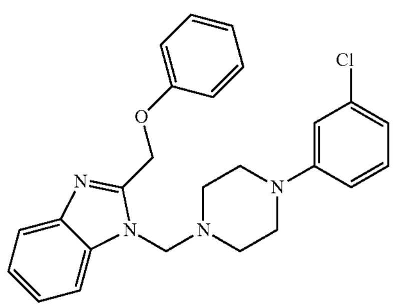 [SMILES: Clc1cccc(N2CCN(Cn3c(COc4ccccc4)nc4ccccc43)CC2)c1] | 1-((4-(3-chlorophenyl)piperazin-1-yl)methyl)-2-(phenoxymethyl)-1H-benzo[d]imidazole | $R^A$-26 | $L^1$-1 | Q-2 | $L^2$-1 |
| 62 | 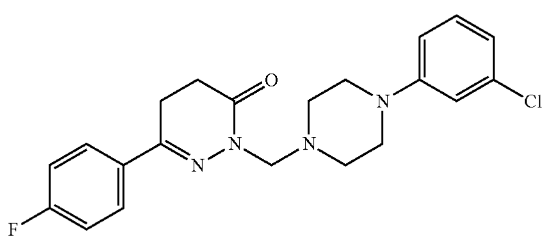 [SMILES: O=C1CCC(c2ccc(F)cc2)=NN1CN1CCN(c2cccc(Cl)c2)CC1] | 2-((4-(3-chlorophenyl)piperazin-1-yl)methyl)-6-(4-fluorophenyl)-4,5-dihydropyridazin-3(2H)-one | $R^A$-27 | $L^1$-1 | Q-2 | $L^2$-1 |
| 63 | 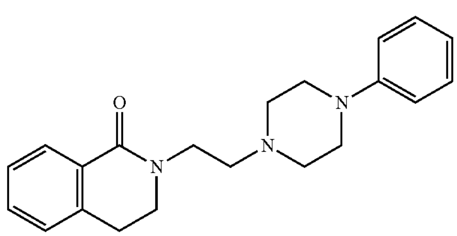 [SMILES: O=C1c2ccccc2CCN1CCN1CCN(c2ccccc2)CC1] | 2-(2-(4-phenylpiperazin-1-yl)ethyl)-3,4-dihydroisoquinolin-1(2H)-one | $R^A$-19 | $L^1$-2 | Q-2 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 64 | 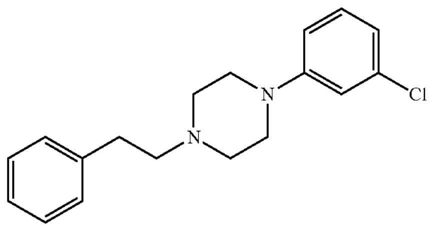 [SMILES: Clc1cccc(N2CCN(CCc3ccccc3)CC2)c1] | 1-(3-chlorophenyl)-4-phenethylpiperazine | $R^A$-22 | $L^1$-2 | Q-2 | $L^2$-1 |
| 65 | 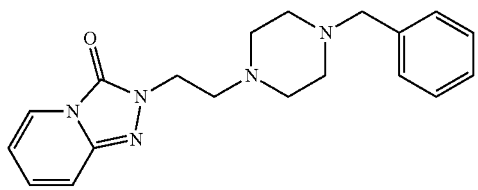 [SMILES: O=c1n(CCN2CCN(Cc3ccccc3)CC2)nc2ccccn12] | 2-(2-(4-benzylpiperazin-1-yl)ethyl)-[1,2,4]triazolo[4,3-a]pyridin-3(2H)-one | $R^A$-25 | $L^1$-2 | Q-2 | $L^2$-3 |
| 66 | 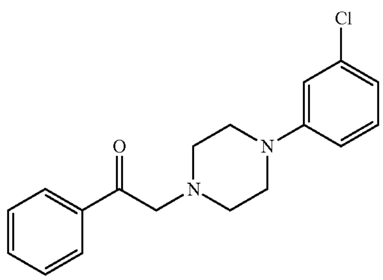 [SMILES: O=C(CN1CCN(c2cccc(Cl)c2)CC1)c1ccccc1] | 2-(4-(3-chlorophenyl)piperazin-1-yl)-1-phenylethan-1-one | $R^A$-22 | $L^1$-3 | Q-2 | $L^2$-1 |
| 67 | 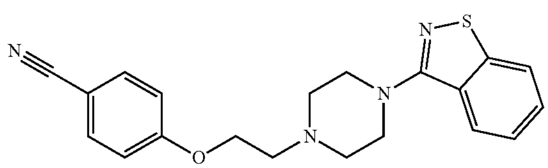 [SMILES: N#Cc1ccc(OCCN2CCN(c3nsc4ccccc34)CC2)cc1] | 4-(2-(4-(benzo[d]isothiazol-3-yl)piperazin-1-yl)ethoxy)benzonitrile | $R^A$-22 | $L^1$-4 | Q-2 | $L^2$-1 |
| 68 | 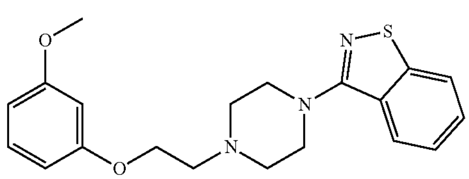 [SMILES: COc1cccc(OCCN2CCN(c3nsc4ccccc34)CC2)c1] | 3-(4-(2-(3-methoxyphenoxy)ethyl)piperazin-1-yl)benzo[d]isothiazole | $R^A$-22 | 4 | Q-2 | $L^2$-1 |
| 69 | 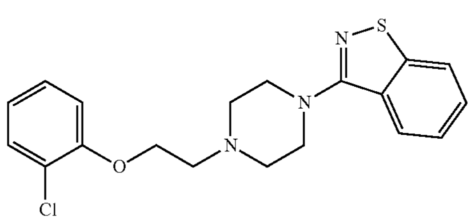 [SMILES: Clc1ccccc1OCCN1CCN(c2nsc3ccccc23)CC1] | 3-(4-(2-(2-chlorophenoxy)ethyl)piperazin-1-yl)benzo[d]isothiazole | $R^A$-22 | $L^1$-4 | Q-2 | $L^2$-1 |
| 70 | 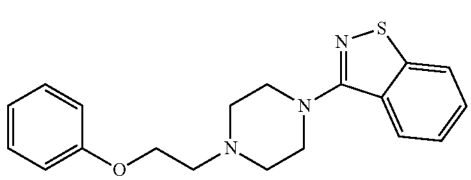 [SMILES: c1ccc(OCCN2CCN(c3nsc4ccccc34)CC2)cc1] | 3-(4-(2-phenoxyethyl)piperazin-1-yl)benzo[d]isothiazole | $R^A$-22 | $L^1$-4 | Q-2 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 71 | 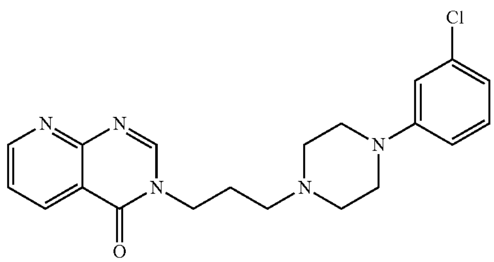 [SMILES: O=c1c2cccnc2ncn1CCCN1CCN(c2cccc(Cl)c2)CC1] | 3-(3-(4-(3-chlorophenyl)piperazin-1-yl)propyl)pyrido[2,3-d]pyrimidin-4(3H)-one | $R^A$-28 | $L^1$-4 | Q-2 | $L^2$-1 |
| 72 | 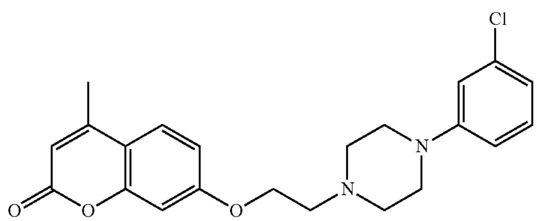 [SMILES: Cc1cc(=O)oc2cc(OCCN3CCN(c4cccc(Cl)c4)CC3)ccc12] | 7-(2-(4-(3-chlorophenyl)piperazin-1-yl)ethoxy)-4-methyl-2H-chromen-2-one | $R^A$-29 | $L^1$-4 | Q-2 | $L^2$-1 |
| 73 | 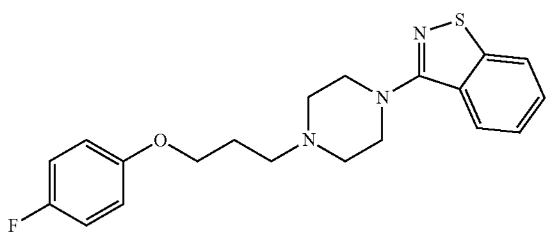 [SMILES: Fc1ccc(OCCCN2CCN(c3nsc4ccccc34)CC2)cc1] | 3-(4-(3-(4-fluorophenoxy)propyl)piperazin-1-yl)benzo[d]isothiazole | $R^A$-22 | $L^1$-5 | Q-2 | $L^2$-1 |
| 74 | 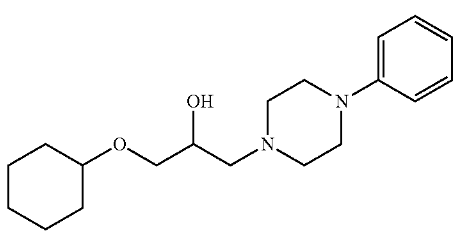 [SMILES: OC(COC1CCCCC1)CN1CCN(c2ccccc2)CC1] | 1-(cyclohexyloxy)-3-(4-phenylpiperazin-1-yl)propan-2-ol | $R^A$-4 | $L^1$-6 | Q-2 | $L^2$-1 |
| 75 | 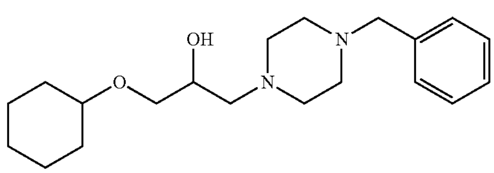 [SMILES: OC(COC1CCCCC1)CN1CCN(Cc2ccccc2)CC1] | 1-(4-benzylpiperazin-1-yl)-3-(cyclohexyloxy)propan-2-ol | $R^A$-4 | $L^1$-6 | Q-2 | $L^2$-3 |
| 76 | 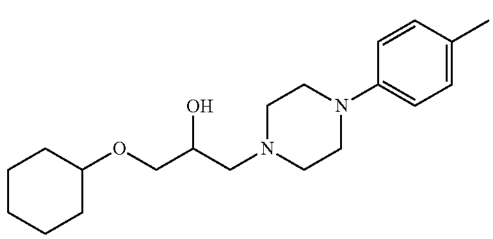 [SMILES: Cc1ccc(N2CCN(CC(O)COC3CCCCC3)CC2)cc1] | 1-(cyclohexyloxy)-3-(4-(p-tolyl)piperazin-1-yl)propan-2-ol | $R^A$-4 | $L^1$-6 | Q-2 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 77 | 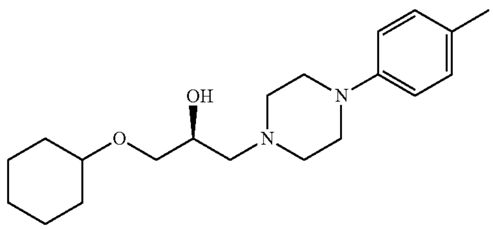 [SMILES: Cc1ccc(N2CCN(C[C@H](O)COC3CCCCC3)CC2)cc1] | (S)-1-(cyclohexyloxy)-3-(4-(p-tolyl)piperazin-1-yl)propan-2-ol | $R^A$-4 | $L^1$-6 | Q-2 | $L^2$-1 |
| 78 | 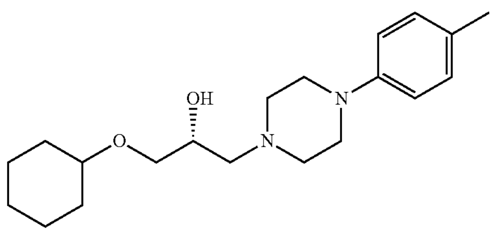 [SMILES: Cc1ccc(N2CCN(C[C@@H](O)COC3CCCCC3)CC2)cc1] | (R)-1-(cyclohexyloxy)-3-(4-(p-tolyl)piperazin-1-yl)propan-2-ol | $R^A$-4 | $L^1$-6 | Q-2 | $L^2$-1 |
| 79 | 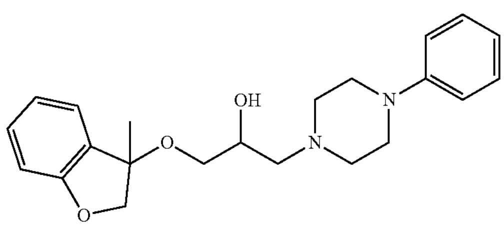 [SMILES: CC1(OCC(O)CN2CCN(c3ccccc3)CC2)COc2ccccc21] | 1-((3-methyl-2,3-dihydrobenzofuran-3-yl)oxy)-3-(4-phenylpiperazin-1-yl)propan-2-ol | $R^A$-9 | $L^1$-6 | Q-2 | $L^2$-1 |
| 80 | 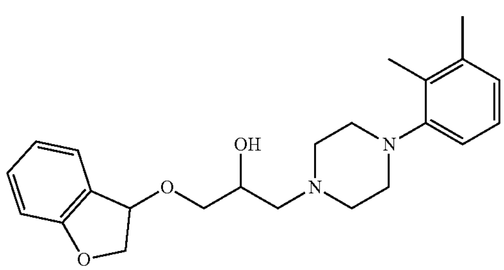 [SMILES: Cc1cccc(N2CCN(CC(O)COC3COc4ccccc43)CC2)c1C] | 1-((2,3-dihydrobenzofuran-3-yl)oxy)-3-(4-(2,3-dimethylphenyl)piperazin-1-yl)propan-2-ol | $R^A$-9 | $L^1$-6 | Q-2 | $L^2$-1 |
| 81 | 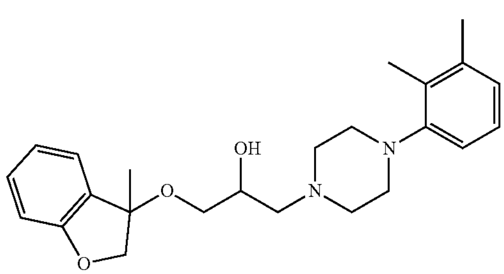 [SMILES: Cc1cccc(N2CCN(CC(O)COC3(C)COc4ccccc43)CC2)c1C] | 1-(4-(2,3-dimethylphenyl)piperazin-1-yl)-3-((3-methyl-2,3-dihydrobenzofuran-3-yl)oxy)propan-2-ol | $R^A$-9 | $L^1$-6 | Q-2 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 82 | 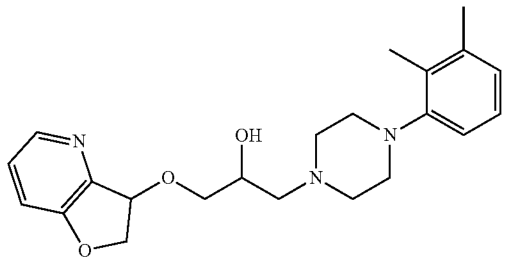 [SMILES: Cc1cccc(N2CCN(CC(O)COC3COc4cccnc43)CC2)c1C] | 1-((2,3-dihydrofuro[3,2-b]pyridin-3-yl)oxy)-3-(4-(2,3-dimethylphenyl)piperazin-1-yl)propan-2-ol | $R^A$-9 | $L^1$-6 | Q-2 | $L^2$-1 |
| 83 | 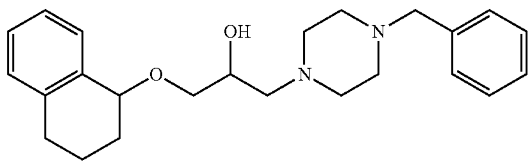 [SMILES: OC(COC1CCCc2ccccc21)CN1CCN(Cc2ccccc2)CC1] | 1-(4-benzylpiperazin-1-yl)-3-((1,2,3,4-tetrahydronaphthalen-1-yl)oxy)propan-2-ol | $R^A$-12 | $L^1$-6 | Q-2 | $L^2$-3 |
| 84 | 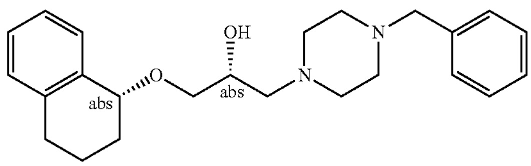 [SMILES: O[C@@H](CO[C@@H]1CCCc2ccccc21)CN1CCN(Cc2ccccc2)CC1] | (R)-1-(4-benzylpiperazin-1-yl)-3-(((R)-1,2,3,4-tetrahydronaphthalen-1-yl)oxy)propan-2-ol | $R^A$-12 | $L^1$-6 | Q-2 | $L^2$-3 |
| 85 | 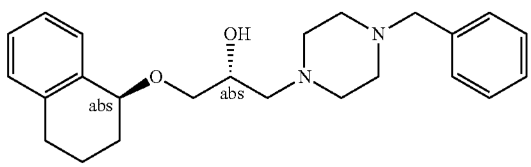 [SMILES: O[C@@H](CO[C@H]1CCCc2ccccc21)CN1CCN(Cc2ccccc2)CC1] | (R)-1-(4-benzylpiperazin-1-yl)-3-(((S)-1,2,3,4-tetrahydronaphthalen-1-yl)oxy)propan-2-ol | $R^A$-12 | $L^1$-6 | Q-2 | $L^2$-3 |
| 86 | 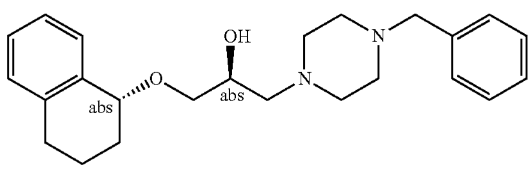 [SMILES: O[C@H](CO[C@@H]1CCCc2ccccc21)CN1CCN(Cc2ccccc2)CC1] | (S)-1-(4-benzylpiperazin-1-yl)-3-(((R)-1,2,3,4-tetrahydronaphthalen-1-yl)oxy)propan-2-ol | $R^A$-12 | $L^1$-6 | Q-2 | $L^2$-3 |
| 87 | 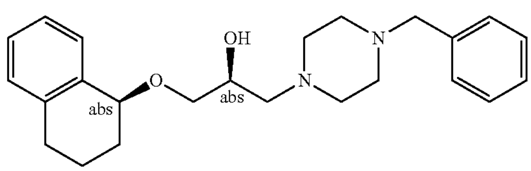 [SMILES: O[C@H](CO[C@H]1CCCc2ccccc21)CN1CCN(Cc2ccccc2)CC1] | (S)-1-(4-benzylpiperazin-1-yl)-3-(((S)-1,2,3,4-tetrahydronaphthalen-1-yl)oxy)propan-2-ol | $R^A$-12 | $L^1$-6 | Q-2 | $L^2$-3 |
| 88 | 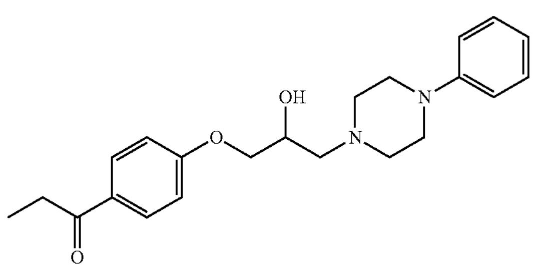 [SMILES: CCC(=O)c1ccc(OCC(O)CN2CCN(c3ccccc3)CC2)cc1] | 1-(4-(2-hydroxy-3-(4-phenylpiperazin-1-yl)propoxy)phenyl)propan-1-one | $R^A$-22 | $L^1$-6 | Q-2 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 89 | 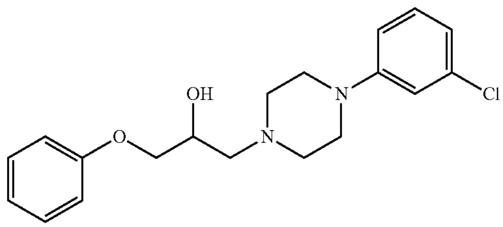 [SMILES: OC(COc1ccccc1)CN1CCN(c2cccc(Cl)c2)CC1] | 1-(4-(3-chlorophenyl)piperazin-1-yl)-3-phenoxypropan-2-ol | $R^A$-22 | $L^1$-6 | Q-2 | $L^2$-1 |
| 90 | 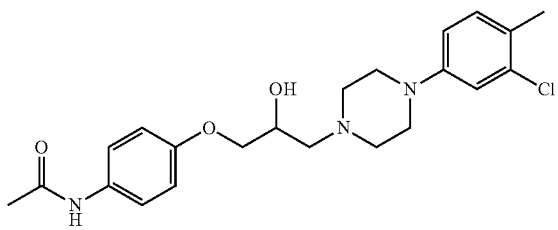 [SMILES: CC(=O)Nc1ccc(OCC(O)CN2CCN(c3ccc(C)c(Cl)c3)CC2)cc1] | N-(4-(3-(4-(3-chloro-4-methylphenyl)piperazin-1-yl)-2-hydroxypropoxy)phenyl)acetamide | $R^A$-22 | $L^1$-6 | Q-2 | $L^2$-1 |
| 91 | 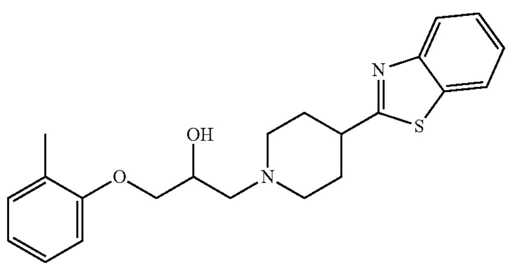 [SMILES: Cc1ccccc1OCC(O)CN1CCC(c2nc3ccccc3s2)CC1] | 1-(4-(benzo[d]thiazol-2-yl)piperidin-1-yl)-3-(o-tolyloxy)propan-2-ol | $R^A$-22 | $L^1$-6 | Q-2 | $L^2$-1 |
| 92 | 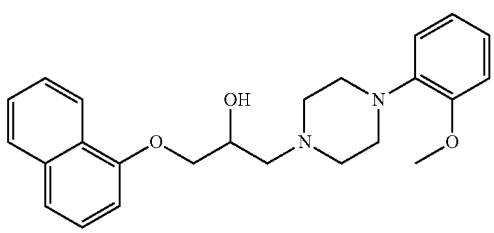 [SMILES: COc1ccccc1N1CCN(CC(O)COc2cccc3ccccc23)CC1] | 1-(4-(2-methoxyphenyl)piperazin-1-yl)-3-(naphthalen-1-yloxy)propan-2-ol | $R^A$-23 | $L^1$-6 | Q-2 | $L^2$-1 |
| 93 | 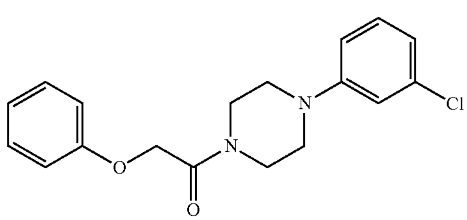 [SMILES: O=C(COc1ccccc1)N1CCN(c2cccc(Cl)c2)CC1] | 1-(4-(3-chlorophenyl)piperazin-1-yl)-2-phenoxyethan-1-one | $R^A$-22 | $L^1$-7 | Q-2 | $L^2$-1 |
| 94 | 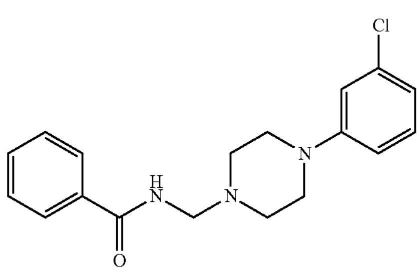 [SMILES: O=C(NCN1CCN(c2cccc(Cl)c2)CC1)c1ccccc1] | N-((4-(3-chlorophenyl)piperazin-1-yl)methyl)benzamide | $R^A$-22 | $L^1$-8 | Q-2 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 95 | 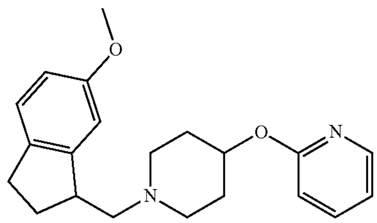 [SMILES: COc1ccc2c(c1)C(CN1CCC(Oc3ccccn3)CC1)CC2] | 2-((1-((6-methoxy-2,3-dihydro-1H-inden-1-yl)methyl)piperidin-4-yl)oxy)pyridine | $R^A$-4 | $L^1$-1 | Q-3 | $L^2$-2 |
| 96 | 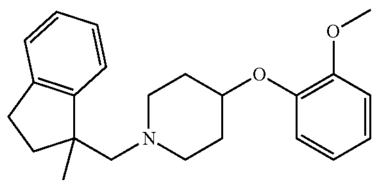 [SMILES: COc1ccccc1OC1CCN(CC2(C)CCc3ccccc32)CC1] | 4-(2-methoxyphenoxy)-1-((1-methyl-2,3-dihydro-1H-inden-1-yl)methyl)piperidine | $R^A$-4 | $L^1$-1 | Q-3 | $L^2$-2 |
| 97 | 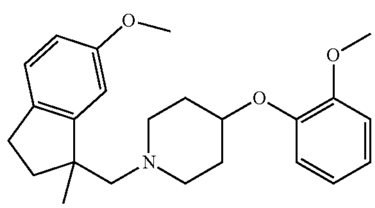 [SMILES: COc1ccc2c(c1)C(C)(CN1CCC(Oc3ccccc3OC)CC1)CC2] | 1-((6-methoxy-1-methyl-2,3-dihydro-1H-inden-1-yl)methyl)-4-(2-methoxyphenoxy)piperidine | $R^A$-4 | $L^1$-1 | Q-3 | $L^2$-2 |
| 98 | 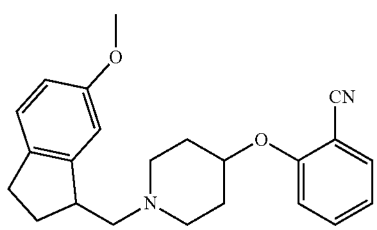 [SMILES: COc1ccc2c(c1)C(CN1CCC(Oc3ccccc3C#N)CC1)CC2] | 2-((1-((6-methoxy-2,3-dihydro-1H-inden-1-yl)methyl)piperidin-4-yl)oxy)benzonitrile | $R^A$-4 | $L^1$-1 | Q-3 | $L^2$-2 |
| 99 | 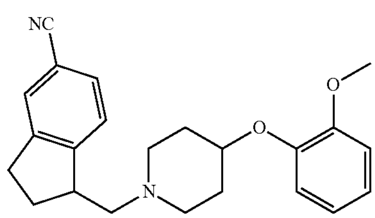 [SMILES: COc1ccccc1OC1CCN(CC2CCc3cc(C#N)ccc32)CC1] | 1-((4-(2-methoxyphenoxy)piperidin-1-yl)methyl)-2,3-dihydro-1H-indene-5-carbonitrile | $R^A$-4 | $L^1$-1 | Q-3 | $L^2$-2 |
| 100 | 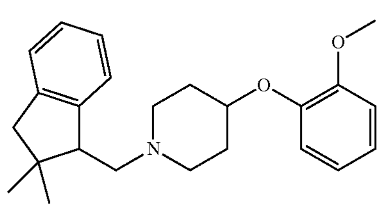 | 1-(2,2-dimethyl-2,3-dihydro-1H-inden-1-yl)methyl)-4-(2-methoxyphenoxy)piperidine | $R^A$-4 | $L^1$-1 | Q-3 | $L^2$-2 |
| 101 | 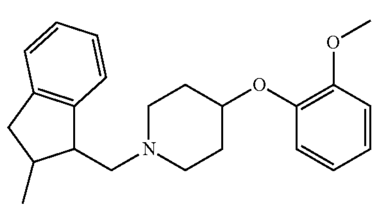 [SMILES: COc1ccccc1OC1CCN(CC2c3ccccc3CC2C)CC1] | 4-(2-methoxyphenoxy)-1-((2-methyl-2,3-dihydro-1H-inden-1-yl)methyl)piperidine | $R^A$-4 | $L^1$-1 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 102 | 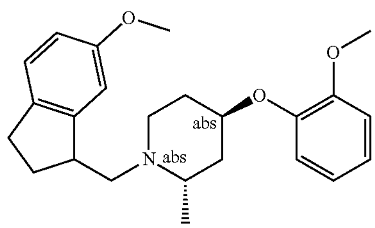 [SMILES: COc1ccc2c(c1)C(CN1CC[C@@H](Oc3ccccc3OC)C[C@@H]1C)CC2] | (2S,4R)-1-((6-methoxy-2,3-dihydro-1H-inden-1-yl)methyl)-4-(2-methoxyphenoxy)-2-methylpiperidine | $R^A$-4 | $L^1$-1 | Q-3 | $L^2$-2 |
| 103 | 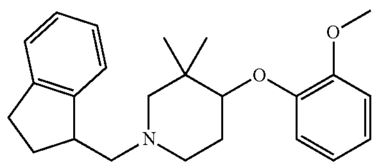 [SMILES: COc1ccccc1OC1CCN(CC2CCc3ccccc32)CC1(C)C] | 1-((2,3-dihydro-1H-inden-1-yl)methyl)-4-(2-methoxyphenoxy)-3,3-dimethylpiperidine | $R^A$-4 | $L^1$-1 | Q-3 | $L^2$-2 |
| 104 | 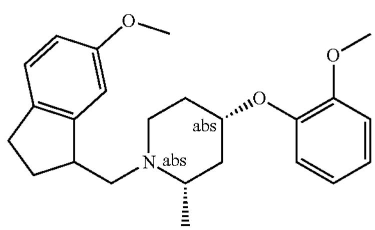 [SMILES: COc1ccc2c(c1)C(CN1CC[C@H](Oc3ccccc3OC)C[C@@H]1C)CC2] | (2S,4S)-1-((6-methoxy-2,3-dihydro-1H-inden-1-yl)methyl)-4-(2-methoxyphenoxy)-2-methylpiperidine | $R^A$-4 | $L^1$-1 | Q-3 | $L^2$-2 |
| 105 | 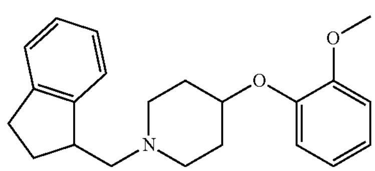 [SMILES: COc1ccccc1OC1CCN(CC2CCc3ccccc32)CC1] | 1-((2,3-dihydro-1H-inden-1-yl)methyl)-4-(2-methoxyphenoxy)piperidine | $R^A$-4 | $L^1$-1 | Q-3 | $L^2$-2 |
| 106 | 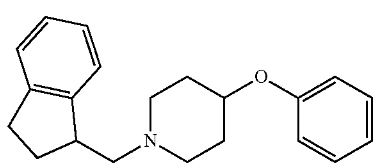 [SMILES: c1ccc(OC2CCN(CC3CCc4ccccc43)CC2)cc1] | 1-((2,3-dihydro-1H-inden-1-yl)methyl)-4-phenoxypiperidine | $R^A$-4 | $L^1$-1 | Q-3 | $L^2$-2 |
| 107 | 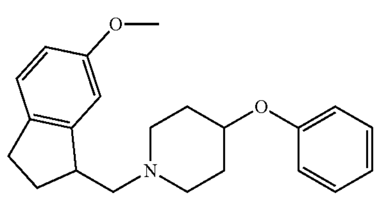 [SMILES: COc1ccc2c(c1)C(CN1CCC(Oc3ccccc3)CC1)CC2] | 1-((6-methoxy-2,3-dihydro-1H-inden-1-yl)methyl)-4-phenoxypiperidine | $R^A$-4 | $L^1$-1 | Q-3 | $L^2$-2 |
| 108 | 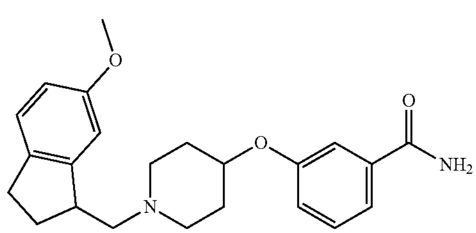 [SMILES: COc1ccc2c(c1)C(CN1CCC(Oc3cccc(C(N)=O)c3)CC1)CC2] | 3-((1-((6-methoxy-2,3-dihydro-1H-inden-1-yl)methyl)piperidin-4-yl)oxy)benzamide | $R^A$-4 | $L^1$-1 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 109 | 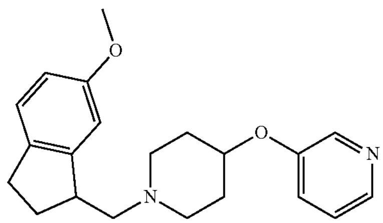 [SMILES: COc1ccc2c(c1)C(CN1CCC(Oc3cccnc3)CC1)CC2] | 3-((1-((6-methoxy-2,3-dihydro-1H-inden-1-yl)methyl)piperidin-4-yl)oxy)pyridine | $R^A$-4 | $L^1$-1 | Q-3 | $L^2$-2 |
| 110 | 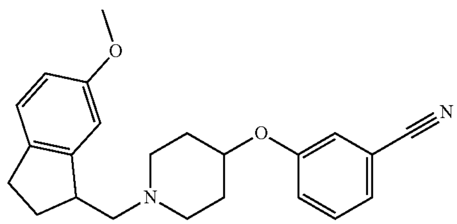 [SMILES: COc1ccc2c(c1)C(CN1CCC(Oc3cccc(C#N)c3)CC1)CC2] | 3-((1-((6-methoxy-2,3-dihydro-1H-inden-1-yl)methyl)piperidin-4-yl)oxy)benzonitrile | $R^A$-4 | $L^1$-1 | Q-3 | $L^2$-2 |
| 111 | 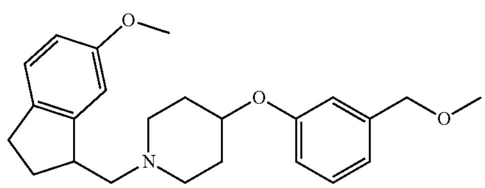 [SMILES: COCc1cccc(OC2CCN(CC3CCc4ccc(OC)cc43)CC2)c1] | 1-((6-methoxy-2,3-dihydro-1H-inden-1-yl)methyl)-4-(3-(methoxymethyl)phenoxy)piperidine | $R^A$-4 | $L^1$-1 | Q-3 | $L^2$-2 |
| 112 | 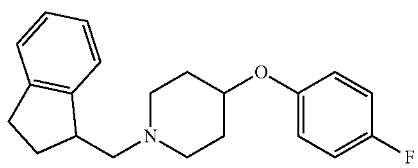 [SMILES: Fc1ccc(OC2CCN(CC3CCc4ccccc43)CC2)cc1] | 1-((2,3-dihydro-1H-inden-1-yl)methyl)-4-(4-fluorophenoxy)piperidine | $R^A$-4 | $L^1$-1 | Q-3 | $L^2$-2 |
| 113 | 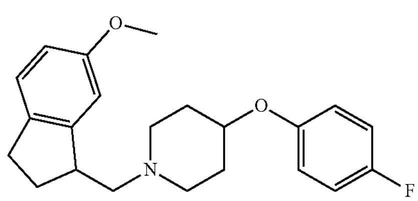 [SMILES: COc1ccc2c(c1)C(CN1CCC(Oc3ccc(F)cc3)CC1)CC2] | 4-(4-fluorophenoxy)-1-((6-methoxy-2,3-dihydro-1H-inden-1-yl)methyl)piperidine | $R^A$-4 | $L^1$-1 | Q-3 | $L^2$-2 |
| 114 | 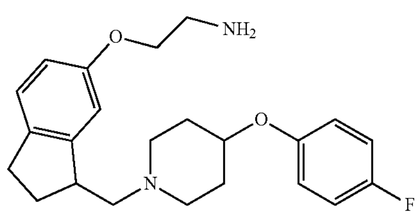 [SMILES: NCCOc1ccc2c(c1)C(CN1CCC(Oc3ccc(F)cc3)CC1)CC2] | 2-((3-((4-(4-fluorophenoxy)piperidin-1-yl)methyl)-2,3-dihydro-1H-inden-5-yl)oxy)ethan-1-amine | $R^A$-4 | $L^1$-1 | Q-3 | $L^2$-2 |
| 115 | 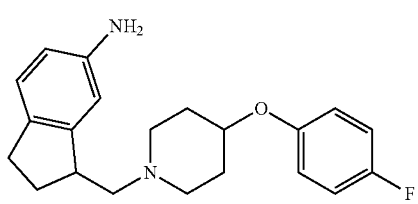 [SMILES: Nc1ccc2c(c1)C(CN1CCC(Oc3ccc(F)cc3)CC1)CC2] | 3-((4-(4-fluorophenoxy)piperidin-1-yl)methyl)-2,3-dihydro-1H-inden-5-amine | $R^A$-4 | $L^1$-1 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 116 | 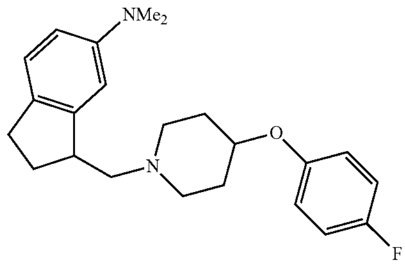 [SMILES: CN(C)c1ccc2c(c1)C(CN1CCC(Oc3ccc(F)cc3)CC1)CC2] | 3-((4-(4-fluorophenoxy)piperidin-1-yl)methyl)-N,N-dimethyl-2,3-dihydro-1H-inden-5-amine | $R^A$-4 | $L^1$-1 | Q-3 | $L^2$-2 |
| 117 | 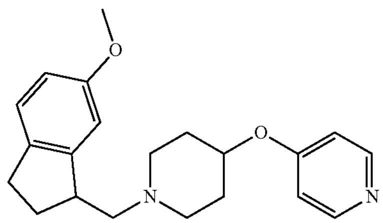 [SMILES: COc1ccc2c(c1)C(CN1CCC(Oc3ccncc3)CC1)CC2] | 4-((1-((6-methoxy-2,3-dihydro-1H-inden-1-yl)methyl)piperidin-4-yl)oxy)pyridine | $R^A$-4 | $L^1$-1 | Q-3 | $L^2$-2 |
| 118 | 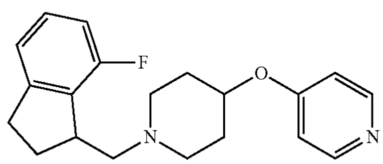 [SMILES: Fc1cccc2c1C(CN1CCC(Oc3ccncc3)CC1)CC2] | 4-((1-((7-fluoro-2,3-dihydro-1H-inden-1-yl)methyl)piperidin-4-yl)oxy)pyridine | $R^A$-4 | $L^1$-1 | Q-3 | $L^2$-2 |
| 119 | 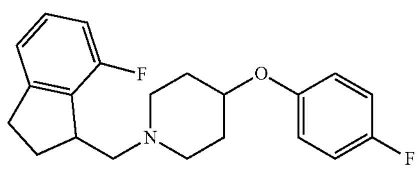 [SMILES: Fc1ccc(OC2CCN(CC3CCc4cccc(F)c43)CC2)cc1] | 1-((7-fluoro-2,3-dihydro-1H-inden-1-yl)methyl)-4-(4-fluorophenoxy)piperidine | $R^A$-4 | $L^1$-1 | Q-3 | $L^2$-2 |
| 120 | 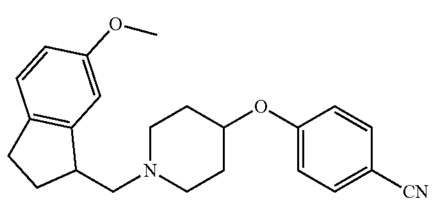 [SMILES: COc1ccc2c(c1)C(CN1CCC(Oc3ccc(C#N)cc3)CC1)CC2] | 4-((1-((6-methoxy-2,3-dihydro-1H-inden-1-yl)methyl)piperidin-4-yl)oxy)benzonitrile | $R^A$-4 | $L^1$-1 | Q-3 | $L^2$-2 |
| 121 | 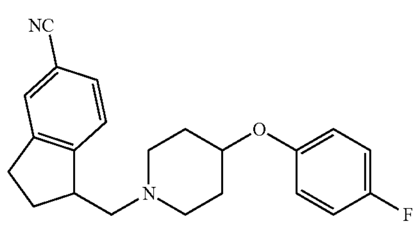 [SMILES: N#Cc1ccc2c(c1)CCC2CN1CCC(Oc2ccc(F)cc2)CC1] | 1-((4-(4-fluorophenoxy)piperidin-1-yl)methyl)-2,3-dihydro-1H-indene-5-carbonitrile | $R^A$-4 | $L^1$-1 | Q-3 | $L^2$-2 |
| 122 | 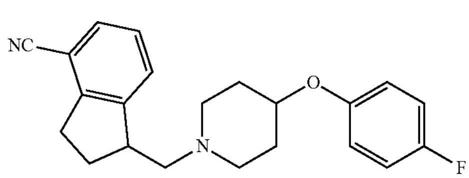 [SMILES: N#Cc1cccc2c1CCC2CN1CCC(Oc2ccc(F)cc2)CC1] | 1-((4-(4-fluorophenoxy)piperidin-1-yl)methyl)-2,3-dihydro-1H-indene-4-carbonitrile | $R^A$-4 | $L^1$-1 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 123 | 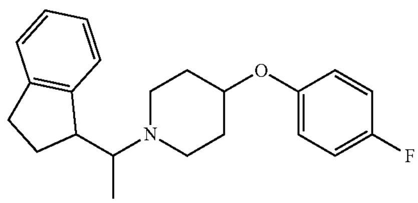 [SMILES: CC(C1CCc2ccccc21)N1CCC(Oc2ccc(F)cc2)CC1] | 1-(1-(2,3-dihydro-1H-inden-1-yl)ethyl)-4-(4-fluorophenoxy)piperidine | $R^A$-4 | $L^1$-1 | Q-3 | $L^2$-2 |
| 124 | 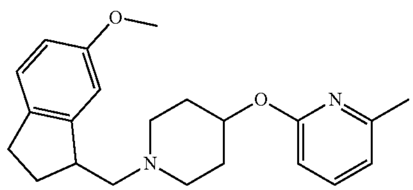 [SMILES: COc1ccc2c(c1)C(CN1CCC(Oc3cccc(C)n3)CC1)CC2] | 2-((1-((6-methoxy-2,3-dihydro-1H-inden-1-yl)methyl)piperidin-4-yl)oxy)-6-methylpyridine | $R^A$-4 | $L^1$-1 | Q-3 | $L^2$-2 |
| 125 | 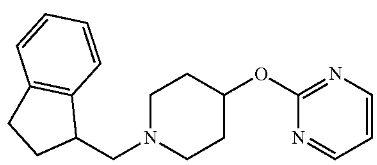 [SMILES: c1cnc(OC2CCN(CC3CCc4ccccc43)CC2)nc1] | 2-((1-((2,3-dihydro-1H-inden-1-yl)methyl)piperidin-4-yl)oxy)pyrimidine | $R^A$-4 | $L^1$-1 | Q-3 | $L^2$-2 |
| 126 | 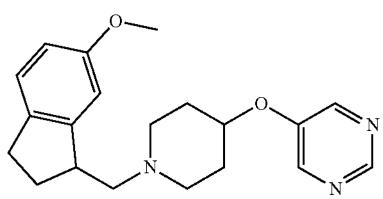 [SMILES: COc1ccc2c(c1)C(CN1CCC(Oc3cncnc3)CC1)CC2] | 5-((1-((6-methoxy-2,3-dihydro-1H-inden-1-yl)methyl)piperidin-4-yl)oxy)pyrimidine | $R^A$-4 | $L^1$-1 | Q-3 | $L^2$-2 |
| 127 | 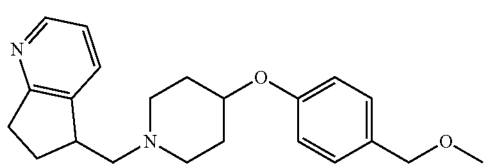 [SMILES: COCc1ccc(OC2CCN(CC3CCc4ncccc43)CC2)cc1] | 5-((4-(4-(methoxymethyl)phenoxy)piperidin-1-yl)methyl)-6,7-dihydro-5H-cyclopenta[b]pyridine | $R^A$-5 | $L^1$1 | Q-3 | $L^2$-2 |
| 128 | 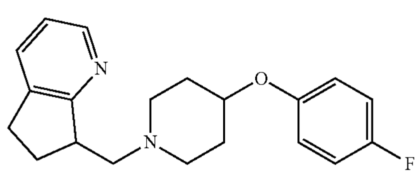 [SMILES: Fc1ccc(OC2CCN(CC3CCc4cccnc43)CC2)cc1] | 7-((4-(4-fluorophenoxy)piperidin-1-yl)methyl)-6,7-dihydro-5H-cyclopenta[b]pyridine | $R^A$-8 | $L^1$-1 | Q-3 | $L^2$-2 |
| 129 | 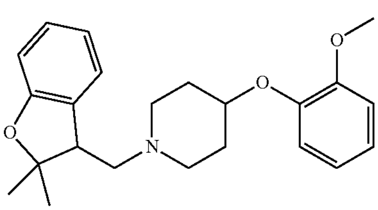 | 1-((2,2-dimethyl-2,3-dihydrobenzofuran-3-yl)methyl)-4-(2-methoxyphenoxy)piperidine | $R^A$-9 | $L^1$-1 | Q-3 | $L^2$-2 |
| 130 | 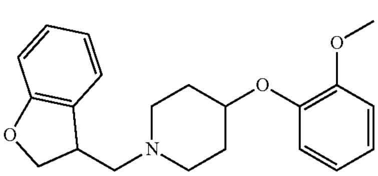 [SMILES: COc1ccccc1OC1CCN(CC2COc3ccccc32)CC1] | 1-((2,3-dihydrobenzofuran-3-yl)methyl)-4-(2-methoxyphenoxy)piperidine | $R^A$-9 | $L^1$-1 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 131 | 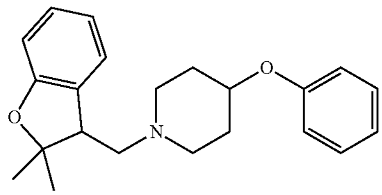 [SMILES: CC1(C)Oc2ccccc2C1CN1CCC(Oc2ccccc2)CC1] | 1-((2,2-dimethyl-2,3-dihydrobenzofuran-3-yl)methyl)-4-phenoxypiperidine | $R^A$-9 | $L^1$-1 | Q-3 | $L^2$-2 |
| 132 | 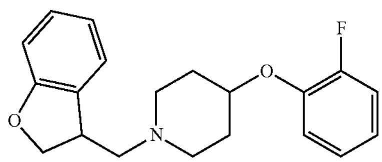 [SMILES: Fc1ccccc1OC1CCN(CC2COc3ccccc32)CC1] | 1-((2,3-dihydrobenzofuran-3-yl)methyl)-4-(2-fluorophenoxy)piperidine | $R^A$-9 | $L^1$-1 | Q-3 | $L^2$-2 |
| 133 | 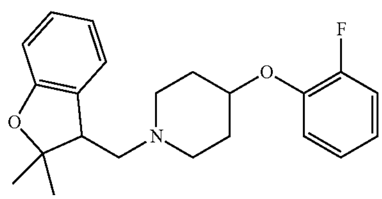 [SMILES: CC1(C)Oc2ccccc2C1CN1CCC(Oc2ccccc2F)CC1] | 1-((2,2-dimethyl-2,3-dihydrobenzofuran-3-yl)methyl)-4-(2-fluorophenoxy)piperidine | $R^A$-9 | $L^1$-1 | Q-3 | $L^2$-2 |
| 134 | 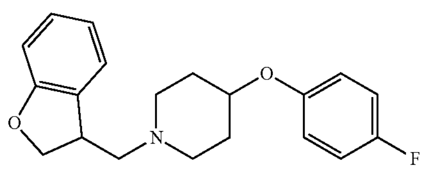 [SMILES: Fc1ccc(OC2CCN(CC3COc4ccccc43)CC2)cc1] | 1-((2,3-dihydrobenzofuran-3-yl)methyl)-4-(4-fluorophenoxy)piperidine | $R^A$-9 | $L^1$-1 | Q-3 | $L^2$-2 |
| 135 | 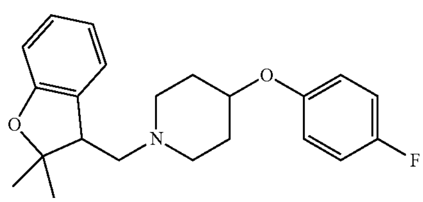 [SMILES: CC1(C)Oc2ccccc2C1CN1CCC(Oc2ccc(F)cc2)CC1] | 1-((2,2-dimethyl-2,3-dihydrobenzofuran-3-yl)methyl)-4-(4-fluorophenoxy)piperidine | $R^A$-9 | $L^1$-1 | Q-3 | $L^2$-2 |
| 136 | 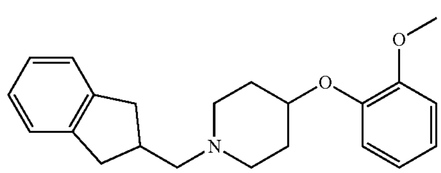 [SMILES: COc1ccccc1OC1CCN(CC2Cc3ccccc3C2)CC1] | 1-((2,3-dihydro-1H-inden-2-yl)methyl)-4-(2-methoxyphenoxy)piperidine | $R^A$-10 | $L^1$-1 | Q-3 | $L^2$-2 |
| 137 | 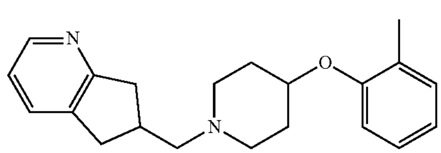 [SMILES: Cc1ccccc1OC1CCN(CC2Cc3cccnc3C2)CC1] | 6-((4-(o-tolyloxy)piperidin-1-yl)methyl)-6,7-dihydro-5H-cyclopenta[b]pyridine | $R^A$-10 | $L^1$-1 | Q-3 | $L^2$-2 |
| 138 | 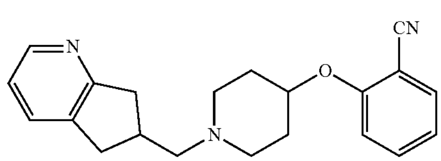 [SMILES: N#Cc1ccccc1OC1CCN(CC2Cc3cccnc3C2)CC1] | 2-((1-((6,7-dihydro-5H-cyclopenta[b]pyridin-6-yl)methyl)piperidin-4-yl)oxy)benzonitrile | $R^A$-10 | $L^1$-1 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 139 | 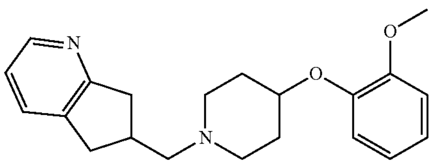 [SMILES: COc1ccccc1OC1CCN(CC2Cc3cccnc3C2)CC1] | 6-((4-(2-methoxyphenoxy)piperidin-1-yl)methyl)-6,7-dihydro-5H-cyclopenta[b]pyridine | $R^A$-10 | $L^1$-1 | Q-3 | $L^2$-2 |
| 140 | 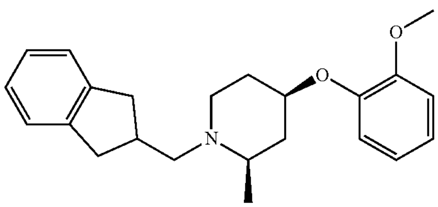 [SMILES: COc1ccccc1O[C@@H]1CCN(CC2Cc3ccccc3C2)[C@H](C)C1] | (2R,4R)-1-((2,3-dihydro-1H-inden-2-yl)methyl)-4-(2-methoxyphenoxy)-2-methylpiperidine | $R^A$-10 | $L^1$-1 | Q-3 | $L^2$-2 |
| 141 | 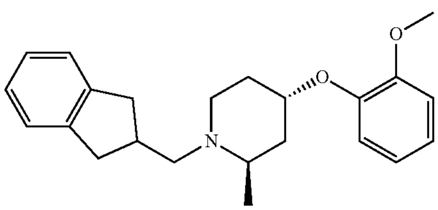 [SMILES: COc1ccccc1O[C@H]1CCN(CC2Cc3ccccc3C2)[C@H](C)C1] | (2R,4S)-1-((2,3-dihydro-1H-inden-2-yl)methyl)-4-(2-methoxyphenoxy)-2-methylpiperidine | $R^A$-10 | $L^1$-1 | Q-3 | $L^2$-2 |
| 142 | 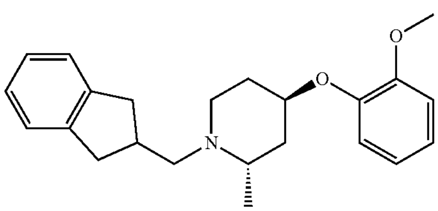 [SMILES: COc1ccccc1O[C@@H]1CCN(CC2Cc3ccccc3C2)[C@@H](C)C1] | (2S,4R)-1-((2,3-dihydro-1H-inden-2-yl)methyl)-4-(2-methoxyphenoxy)-2-methylpiperidine | $R^A$-10 | $L^1$-1 | Q-3 | $L^2$-2 |
| 143 | 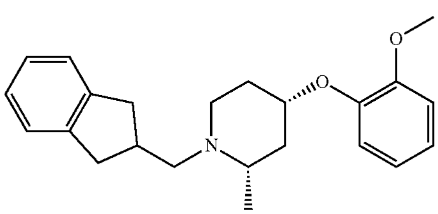 [SMILES: COc1ccccc1O[C@H]1CCN(CC2Cc3ccccc3C2)[C@@H](C)C1] | (2S,4S)-1-((2,3-dihydro-1H-inden-2-yl)methyl)-4-(2-methoxyphenoxy)-2-methylpiperidine | $R^A$-10 | $L^1$-1 | Q-3 | $L^2$-2 |
| 144 | 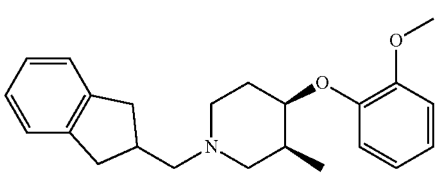 [SMILES: COc1ccccc1O[C@@H]1CCN(CC2Cc3ccccc3C2)C[C@@H]1C] | (3S,4R)-1-((2,3-dihydro-1H-inden-2-yl)methyl)-4-(2-methoxyphenoxy)-3-methylpiperidine | $R^A$-10 | $L^1$-1 | Q-3 | $L^2$-2 |
| 145 | 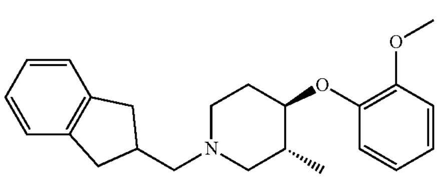 [SMILES: COc1ccccc1O[C@@H]1CCN(CC2Cc3ccccc3C2)C[C@H]1C] | (3R,4R)-1-((2,3-dihydro-1H-inden-2-yl)methyl)-4-(2-methoxyphenoxy)-3-methylpiperidine | $R^A$-10 | $L^1$-1 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 146 | 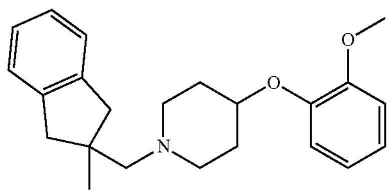 [SMILES: COc1ccccc1OC1CCN(CC2(C)Cc3ccccc3C2)CC1] | 4-(2-methoxyphenoxy)-1-((2-methyl-2,3-dihydro-1H-inden-2-yl)methyl)piperidine | $R^A$-10 | $L^1$-1 | Q-3 | $L^2$-2 |
| 147 | 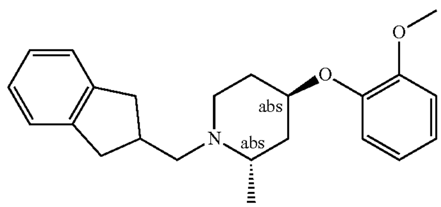 [SMILES: COc1ccccc1O[C@@H]1CCN(CC2Cc3ccccc3C2)[C@@H](C)C1] | (2S,4R)-1-((2,3-dihydro-1H-inden-2-yl)methyl)-4-(2-methoxyphenoxy)-2-methylpiperidine | $R^A$-10 | $L^1$-1 | Q-3 | $L^2$-2 |
| 148 | 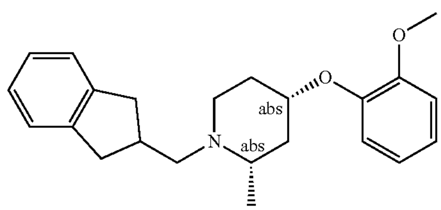 [SMILES: COc1ccccc1O[C@H]1CCN(CC2Cc3ccccc3C2)[C@@H](C)C1] | (2S,4S)-1-((2,3-dihydro-1H-inden-2-yl)methyl)-4-(2-methoxyphenoxy)-2-methylpiperidine | $R^A$-10 | $L^1$-1 | Q-3 | $L^2$-2 |
| 149 | 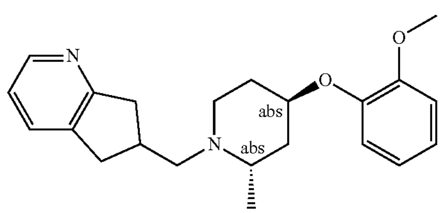 [SMILES: COc1ccccc1O[C@@H]1CCN(CC2Cc3cccnc3C2)[C@@H](C)C1] | 6-(((2S,4R)-4-(2-methoxyphenoxy)-2-methylpiperidin-1-yl)methyl)-6,7-dihydro-5H-cyclopenta[b]pyridine | $R^A$-10 | $L^1$-1 | Q-3 | $L^2$-2 |
| 150 | 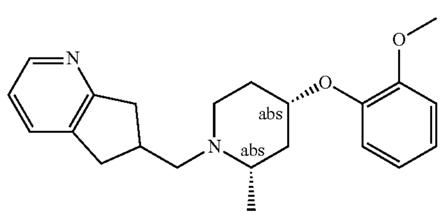 [SMILES: COc1ccccc1O[C@H]1CCN(CC2Cc3cccnc3C2)[C@@H](C)C1] | 6-(((2S,4S)-4-(2-methoxyphenoxy)-2-methylpiperidin-1-yl)methyl)-6,7-dihydro-5H-cyclopenta[b]pyridine | $R^A$-10 | $L^1$-1 | Q-3 | $L^2$-2 |
| 151 | 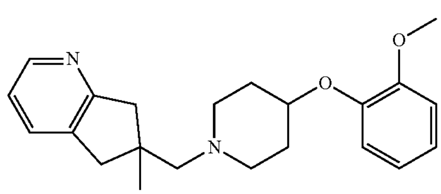 [SMILES: COc1ccccc1OC1CCN(CC2(C)Cc3cccnc3C2)CC1] | 6-((4-(2-methoxyphenoxy)piperidin-1-yl)methyl)-6-methyl-6,7-dihydro-5H-cyclopenta[b]pyridine | $R^A$-10 | $L^1$-1 | Q-3 | $L^2$-2 |
| 152 | 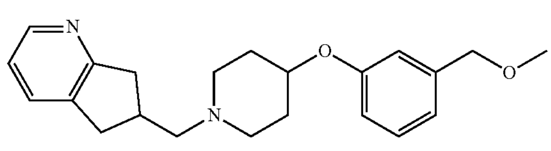 [SMILES: COCc1cccc(OC2CCN(CC3Cc4cccnc4C3)CC2)c1] | 6-((4-(3-(methoxymethyl)phenoxy)piperidin-1-yl)methyl)-6,7-dihydro-5H-cyclopenta[b]pyridine | $R^A$-10 | $L^1$-1 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 153 | 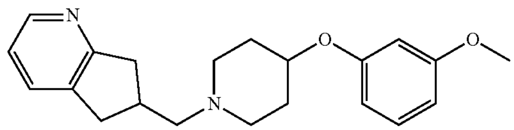 [SMILES: COc1cccc(OC2CCN(CC3Cc4cccnc4C3)CC2)c1] | 6-((4-(3-methoxyphenoxy)piperidin-1-yl)methyl)-6,7-dihydro-5H-cyclopenta[b]pyridine | $R^A$-10 | $L^1$-1 | Q-3 | $L^2$-2 |
| 154 | 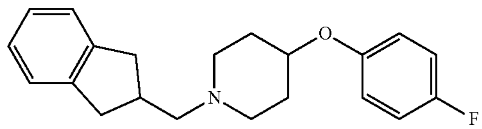 [SMILES: Fc1ccc(OC2CCN(CC3Cc4ccccc4C3)CC2)cc1] | 1-((2,3-dihydro-1H-inden-2-yl)methyl)-4-(4-fluorophenoxy)piperidine | $R^A$-10 | $L^1$-1 | Q-3 | $L^2$-2 |
| 155 | 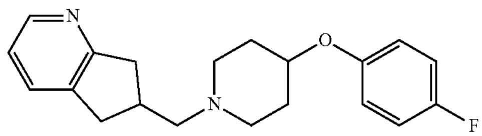 [SMILES: Fc1ccc(OC2CCN(CC3Cc4cccnc4C3)CC2)cc1] | 6-((4-(4-fluorophenoxy)piperidin-1-yl)methyl)-6,7-dihydro-5H-cyclopenta[b]pyridine | $R^A$-10 | $L^1$-1 | Q-3 | $L^2$-2 |
| 156 | 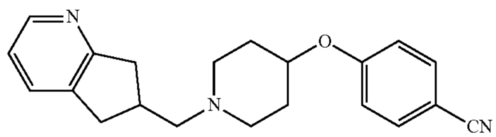 [SMILES: N#Cc1ccc(OC2CCN(CC3Cc4cccnc4C3)CC2)cc1] | 4-((1-((6,7-dihydro-5H-cyclopenta[b]pyridin-6-yl)methyl)piperidin-4-yl)oxy)benzonitrile | $R^A$-10 | $L^1$-1 | Q-3 | $L^2$-2 |
| 157 | 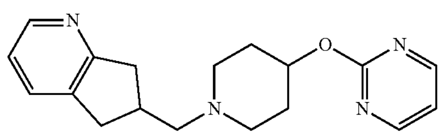 [SMILES: c1cnc(OC2CCN(CC3Cc4cccnc4C3)CC2)nc1] | 6-((4-(pyrimidin-2-yloxy)piperidin-1-yl)methyl)-6,7-dihydro-5H-cyclopenta[b]pyridine | $R^A$-11 | $L^1$-1 | Q-3 | $L^2$-2 |
| 158 | 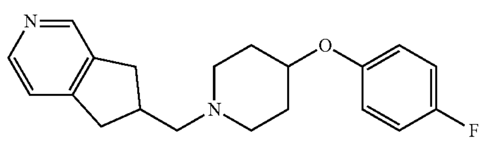 [SMILES: Fc1ccc(OC2CCN(CC3Cc4ccncc4C3)CC2)cc1] | 6-((4-(4-fluorophenoxy)piperidin-1-yl)methyl)-6,7-dihydro-5H-cyclopenta[c]pyridine | $R^A$-11 | $L^1$-1 | Q-3 | $L^2$-2 |
| 159 | 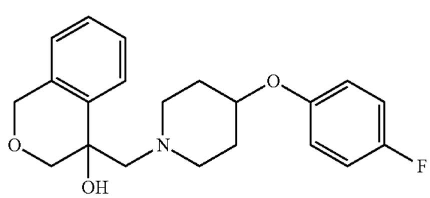 [SMILES: OC1(CN2CCC(Oc3ccc(F)cc3)CC2)COCc2ccccc21] | 4-((4-(4-fluorophenoxy)piperidin-1-yl)methyl)isochroman-4-ol | $R^A$-12 | $L^1$-1 | Q-3 | $L^2$-2 |
| 160 | 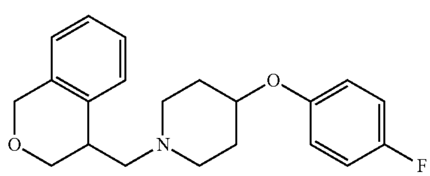 [SMILES: Fc1ccc(OC2CCN(CC3COCc4ccccc43)CC2)cc1] | 4-(4-fluorophenoxy)-1-(isochroman-4-ylmethyl)piperidine | $R^A$-12 | $L^1$-1 | Q-3 | $L^2$-2 |
| 161 | 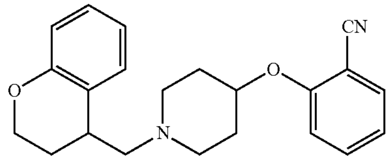 [SMILES: N#Cc1ccccc1OC1CCN(CC2CCOc3ccccc32)CC1] | 2-((1-(chroman-4-ylmethyl)piperidin-4-yl)oxy)benzonitrile | $R^A$-13 | $L^1$-1 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 162 | 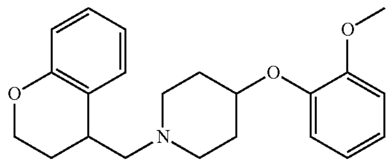 [SMILES: COc1ccccc1OC1CCN(CC2CCOc3ccccc32)CC1] | 1-(chroman-4-ylmethyl)-4-(2-methoxyphenoxy)piperidine | $R^A$-13 | $L^1$-1 | Q-3 | $L^2$-2 |
| 163 | 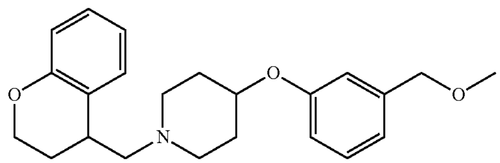 [SMILES: COCc1cccc(OC2CCN(CC3CCOc4ccccc43)CC2)c1] | 1-(chroman-4-ylmethyl)-4-(3-(methoxymethyl)phenoxy)piperidine | $R^A$-13 | $L^1$-1 | Q-3 | $L^2$-2 |
| 164 | 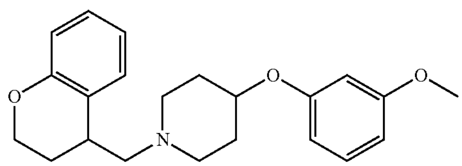 [SMILES: COc1cccc(OC2CCN(CC3CCOc4ccccc43)CC2)c1] | 1-(chroman-4-ylmethyl)-4-(3-methoxyphenoxy)piperidine | $R^A$-13 | $L^1$-1 | Q-3 | $L^2$-2 |
| 165 | 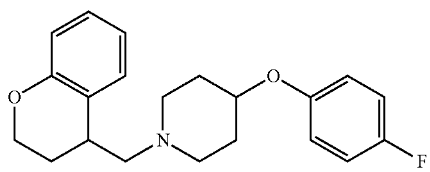 [SMILES: Fc1ccc(OC2CCN(CC3CCOc4ccccc43)CC2)cc1] | 1-(chroman-4-ylmethyl)-4-(4-fluorophenoxy)piperidine | $R^A$-13 | $L^1$-1 | Q-3 | $L^2$-2 |
| 166 | 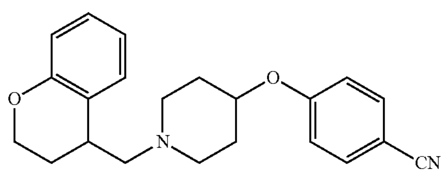 [SMILES: N#Cc1ccc(OC2CCN(CC3CCOc4ccccc43)CC2)cc1] | 4-((1-(chroman-4-ylmethyl)piperidin-4-yl)oxy)benzonitrile | $R^A$-13 | $L^1$-1 | Q-3 | $L^2$-2 |
| 167 | 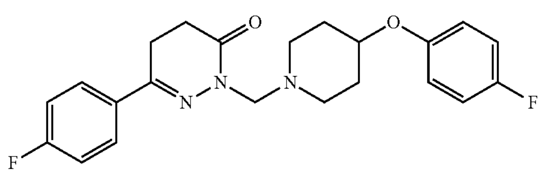 [SMILES: O=C1CCC(c2ccc(F)cc2)=NN1CN1CCC(Oc2ccc(F)cc2)CC1] | 2-((4-(4-fluorophenoxy)piperidin-1-yl)methyl)-6-(4-fluorophenyl)-4,5-dihydropyridazin-3(2H)-one | $R^A$-27 | $L^1$-1 | Q-3 | $L^2$-2 |
| 168 | 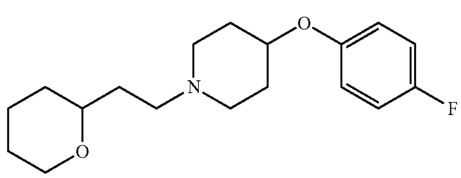 [SMILES: Fc1ccc(OC2CCN(CCC3CCCCO3)CC2)cc1] | 4-(4-fluorophenoxy)-1-(2-(tetrahydro-2H-pyran-2-yl)ethyl)piperidine | $R^A$-1 | $L^1$-2 | Q-3 | $L^2$-2 |
| 169 | 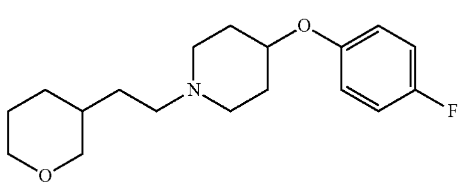 [SMILES: Fc1ccc(OC2CCN(CCC3CCCOC3)CC2)cc1] | 4-(4-fluorophenoxy)-1-(2-(tetrahydro-2H-pyran-3-yl)ethyl)piperidine | $R^A$-2 | $L^1$-2 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 170 | 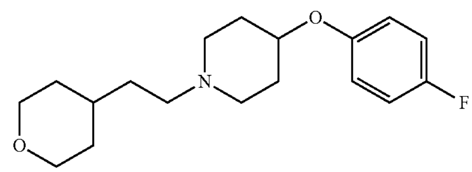 [SMILES: Fc1ccc(OC2CCN(CCC3CCOCC3)CC2)cc1] | 4-(4-fluorophenoxy)-1-(2-(tetrahydro-2H-pyran-4-yl)ethyl)piperidine | $R^A$-3 | $L^1$-2 | Q-3 | $L^2$-2 |
| 171 | 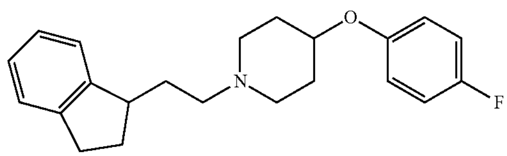 [SMILES: Fc1ccc(OC2CCN(CCC3CCc4ccccc43)CC2)cc1] | 1-(2-(2,3-dihydro-1H-inden-1-yl)ethyl)-4-(4-fluorophenoxy)piperidine | $R^A$-4 | $L^1$-2 | Q-3 | $L^2$-2 |
| 172 | 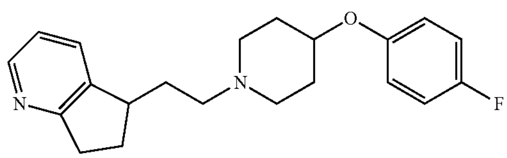 [SMILES: Fc1ccc(OC2CCN(CCC3CCc4ncccc43)CC2)cc1] | 5-(2-(4-(4-fluorophenoxy)piperidin-1-yl)ethyl)-6,7-dihydro-5H-cyclopenta[b]pyridine | $R^A$-5 | $L^1$-2 | Q-3 | $L^2$-2 |
| 173 | 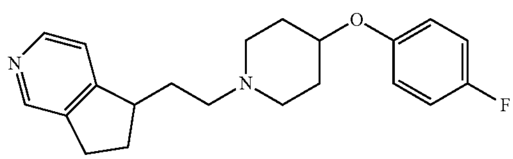 [SMILES: Fc1ccc(OC2CCN(CCC3CCc4cnccc43)CC2)cc1] | 5-(2-(4-(4-fluorophenoxy)piperidin-1-yl)ethyl)-6,7-dihydro-5H-cyclopenta[c]pyridine | $R^A$-6 | $L^1$-2 | Q-3 | $L^2$-2 |
| 174 | 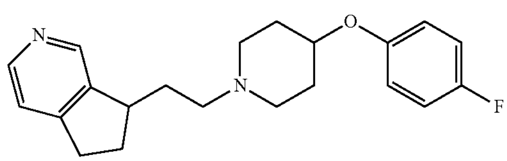 [SMILES: Fc1ccc(OC2CCN(CCC3CCc4ccncc43)CC2)cc1] | 7-(2-(4-(4-fluorophenoxy)piperidin-1-yl)ethyl)-6,7-dihydro-5H-cyclopenta[c]pyridine | $R^A$-7 | $L^1$-2 | Q-3 | $L^2$-2 |
| 175 | 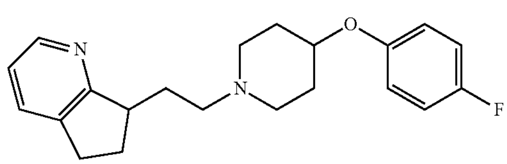 [SMILES: Fc1ccc(OC2CCN(CCC3CCc4cccnc43)CC2)cc1] | 7-(2-(4-(4-fluorophenoxy)piperidin-1-yl)ethyl)-6,7-dihydro-5H-cyclopenta[b]pyridine | $R^A$-8 | $L^1$-2 | Q-3 | $L^2$-2 |
| 176 | 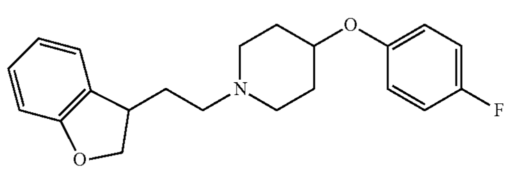 [SMILES: Fc1ccc(OC2CCN(CCC3COc4ccccc43)CC2)cc1] | 1-(2-(2,3-dihydrobenzofuran-3-yl)ethyl)-4-(4-fluorophenoxy)piperidine | $R^A$-9 | $L^1$-2 | Q-3 | $L^2$-2 |
| 177 | 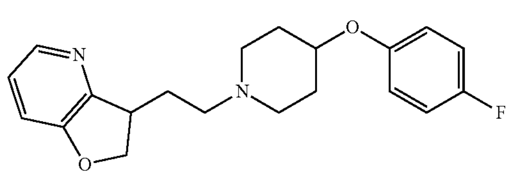 [SMILES: Fc1ccc(OC2CCN(CCC3COc4cccnc43)CC2)cc1] | 3-(2-(4-(4-fluorophenoxy)piperidin-1-yl)ethyl)-2,3-dihydrofuro[3,2-b]pyridine | $R^A$-10 | $L^1$-2 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 178 | 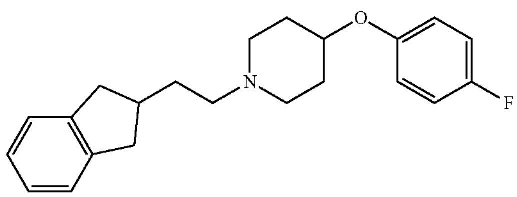 [SMILES: Fc1ccc(OC2CCN(CCC3Cc4ccccc4C3)CC2)cc1] | 1-(2-(2,3-dihydro-1H-inden-2-yl)ethyl)-4-(4-fluorophenoxy)piperidine | $R^A$-10 | $L^1$-2 | Q-3 | $L^2$-2 |
| 179 | 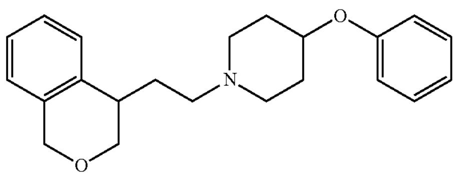 [SMILES: c1ccc(OC2CCN(CCC3COCc4ccccc43)CC2)cc1] | 1-(2-(isochroman-4-yl)ethyl)-4-phenoxypiperidine | $R^A$-12 | $L^1$-2 | Q-3 | $L^2$-2 |
| 180 | 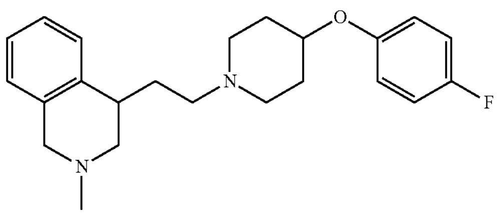 [SMILES: CN1Cc2ccccc2C(CCN2CCC(Oc3ccc(F)cc3)CC2)C1] | 4-(2-(4-(4-fluorophenoxy)piperidin-1-yl)ethyl)-2-methyl-1,2,3,4-tetrahydroisoquinoline | $R^A$-12 | $L^1$-2 | Q-3 | $L^2$-2 |
| 181 | 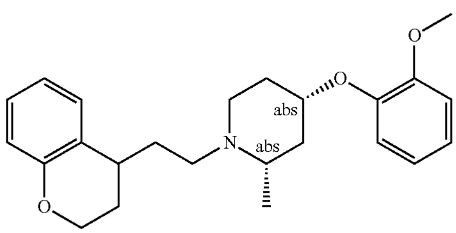 [SMILES: COc1ccccc1O[C@H]1CCN(CCC2CCOc3ccccc32)[C@@H](C)C1] | (2S,4S)-1-(2-(chroman-4-yl)ethyl)-4-(2-methoxyphenoxy)-2-methylpiperidine | $R^A$-13 | $L^1$-2 | Q-3 | $L^2$-2 |
| 182 | 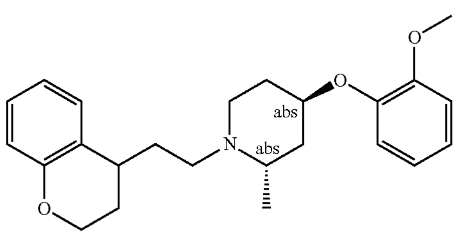 [SMILES: COc1ccccc1O[C@@H]1CCN(CCC2CCOc3ccccc32)[C@@H](C)C1] | (2S,4R)-1-(2-(chroman-4-yl)ethyl)-4-(2-methoxyphenoxy)-2-methylpiperidine | $R^A$-13 | $L^1$-2 | Q-3 | $L^2$-2 |
| 183 | 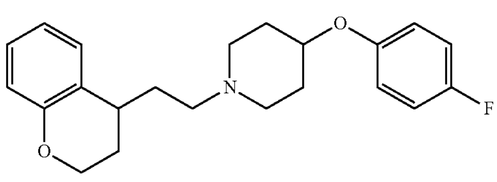 [SMILES: Fc1ccc(OC2CCN(CCC3CCOc4ccccc43)CC2)cc1] | 1-(2-(chroman-4-yl)ethyl)-4-(4-fluorophenoxy)piperidine | $R^A$-13 | $L^1$-2 | Q-3 | $L^2$-2 |
| 184 | 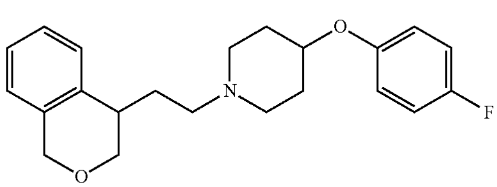 [SMILES: Fc1ccc(OC2CCN(CCC3COCc4ccccc43)CC2)cc1] | 4-(4-fluorophenoxy)-1-(2-(isochroman-4-yl)ethyl)piperidine | $R^A$-13 | $L^1$-2 | Q-3 | $L^2$-2 |

TABLE 5-continued

Summary of synthesis of Compounds. Compounds were synthesized by coupling the R$^A$ group coupling partners to the Q group coupling partners through the L$^1$ linker and coupling the R$^B$ group coupling partners to the Q group coupling partners through the L$^2$ linker. The R$^A$ coupling chemistry used is described in Example L$^1$. The R$^B$ coupling chemistry is described in Example L$^2$. Synthetic details for the transformations described in Examples Example L$^1$, Example L$^2$, Example R$^A$ and Example R$^B$ are in Example T.
The table below lists the R$^A$, L$^1$, Q, L$^2$ and R$^B$ groups whose coupling partners were used in the syntheses.

| | Structure | Chem Name | R$^A$ | L$^1$ | Q | L$^2$ |
|---|---|---|---|---|---|---|
| 185 | 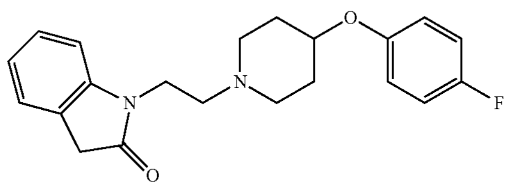 [SMILES: O=C1Cc2ccccc2N1CCN1CCC(Oc2ccc(F)cc2)CC1] | 1-(2-(4-(4-fluorophenoxy)piperidin-1-yl)ethyl)indolin-2-one | R$^A$-15 | L$^1$-2 | Q-3 | L$^2$-2 |
| 186 | 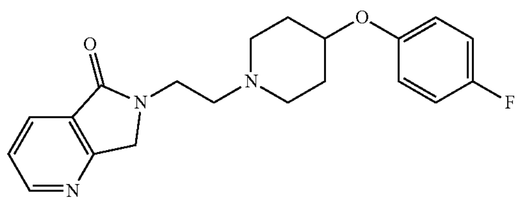 [SMILES: O=C1c2cccnc2CN1CCN1CCC(Oc2ccc(F)cc2)CC1] | 6-(2-(4-(4-fluorophenoxy)piperidin-1-yl)ethyl)-6,7-dihydro-5H-pyrrolo[3,4-b]pyridin-5-one | R$^A$-16 | L$^1$-2 | Q-3 | L$^2$-2 |
| 187 | 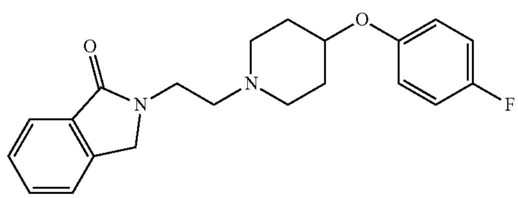 [SMILES: O=C1c2ccccc2CN1CCN1CCC(Oc2ccc(F)cc2)CC1] | 2-(2-(4-(4-fluorophenoxy)piperidin-1-yl)ethyl)isoindolin-1-one | R$^A$-17 | L$^1$-2 | Q-3 | L$^2$-2 |
| 188 | 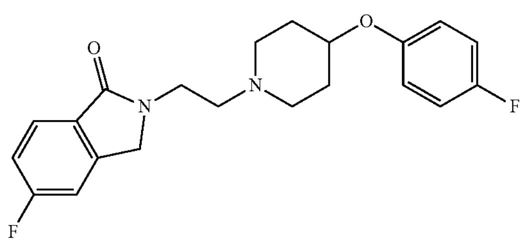 [SMILES: O=C1c2ccc(F)cc2CN1CCN1CCC(Oc2ccc(F)cc2)CC1] | 5-fluoro-2-(2-(4-(4-fluorophenoxy)piperidin-1-yl)ethyl)isoindolin-1-one | R$^A$-17 | L$^1$-2 | Q-3 | L$^2$-2 |
| 189 | 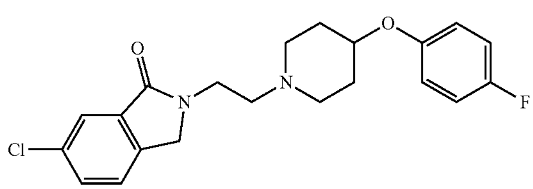 [SMILES: O=C1c2cc(Cl)ccc2CN1CCN1CCC(Oc2ccc(F)cc2)CC1] | 6-chloro-2-(2-(4-(4-fluorophenoxy)piperidin-1-yl)ethyl)isoindolin-1-one | R$^A$-17 | L$^1$-2 | Q-3 | L$^2$-2 |
| 190 | 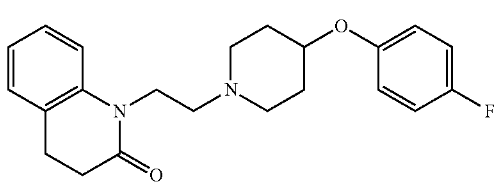 [SMILES: O=C1CCc2ccccc2N1CCN1CCC(Oc2ccc(F)cc2)CC1] | 1-(2-(4-(4-fluorophenoxy)piperidin-1-yl)ethyl)-3,4-dihydroquinolin-2(1H)-one | R$^A$-18 | L$^1$-2 | Q-3 | L$^2$-2 |
| 191 | 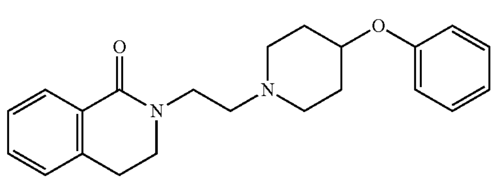 [SMILES: O=C1c2ccccc2CCN1CCN1CCC(Oc2ccccc2)CC1] | 2-(2-(4-phenoxypiperidin-1-yl)ethyl)-3,4-dihydroisoquinolin-1(2H)-one | R$^A$-19 | L$^1$-2 | Q-3 | L$^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 192 | 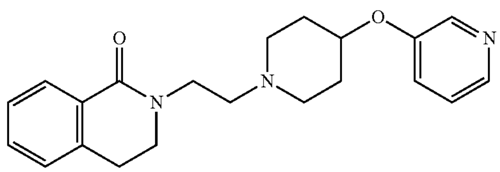 [SMILES: O=C1c2ccccc2CCN1CCN1CCC(Oc2cccnc2)CC1] | 2-(2-(4-(pyridin-3-yloxy)piperidin-1-yl)ethyl)-3,4-dihydroisoquinolin-1(2H)-one | $R^A$-19 | $L^1$-2 | Q-3 | $L^2$-2 |
| 193 | 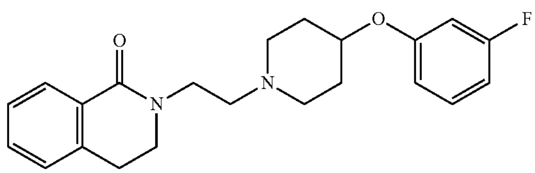 [SMILES: O=C1c2ccccc2CCN1CCN1CCC(Oc2cccc(F)c2)CC1] | 2-(2-(4-(3-fluorophenoxy)piperidin-1-yl)ethyl)-3,4-dihydroisoquinolin-1(2H)-one | $R^A$-19 | $L^1$-2 | Q-3 | $L^2$-2 |
| 194 | 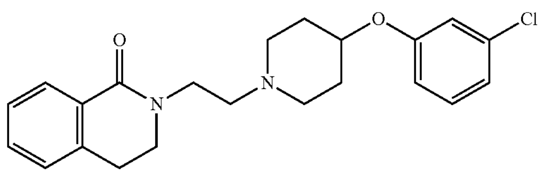 [SMILES: O=C1c2ccccc2CCN1CCN1CCC(Oc2cccc(Cl)c2)CC1] | 2-(2-(4-(3-chlorophenoxy)piperidin-1-yl)ethyl)-3,4-dihydroisoquinolin-1(2H)-one | $R^A$-19 | $L^1$-2 | Q-3 | $L^2$-2 |
| 195 | 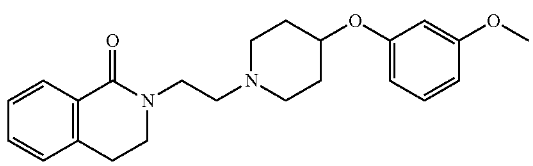 [SMILES: COc1cccc(OC2CCN(CCN3CCc4ccccc4C3=O)CC2)c1] | 2-(2-(4-(3-methoxyphenoxy)piperidin-1-yl)ethyl)-3,4-dihydroisoquinolin-1(2H)-one | $R^A$-19 | $L^1$-2 | Q-3 | $L^2$-2 |
| 196 | 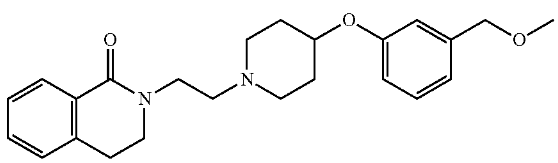 [SMILES: COCc1cccc(OC2CCN(CCN3CCc4ccccc4C3=O)CC2)c1] | 2-(2-(4-(3-(methoxymethyl)phenoxy)piperidin-1-yl)ethyl)-3,4-dihydroisoquinolin-1(2H)-one | $R^A$-19 | $L^1$-2 | Q-3 | $L^2$-2 |
| 197 | 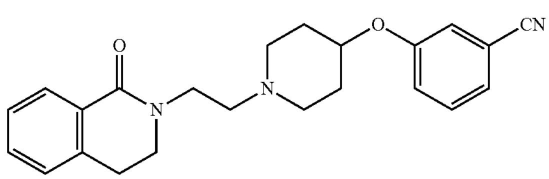 [SMILES: N#Cc1cccc(OC2CCN(CCN3CCc4ccccc4C3=O)CC2)c1] | 3-((1-(2-(1-oxo-3,4-dihydroisoquinolin-2(1H)-yl)ethyl)piperidin-4-yl)oxy)benzonitrile | $R^A$-19 | $L^1$-2 | Q-3 | $L^2$-2 |
| 198 | 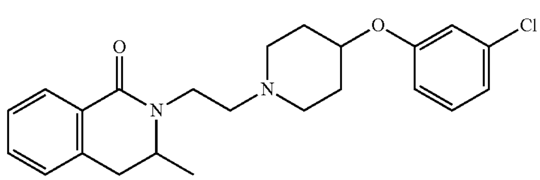 [SMILES: CC1Cc2ccccc2C(=O)N1CCN1CCC(Oc2cccc(Cl)c2)CC1] | 2-(2-(4-(3-chlorophenoxy)piperidin-1-yl)ethyl)-3-methyl-3,4-dihydroisoquinolin-1(2H)-one | $R^A$-19 | $L^1$-2 | Q-3 | $L^2$-2 |
| 199 | 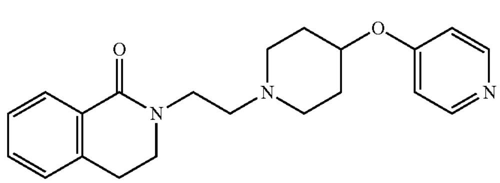 [SMILES: O=C1c2ccccc2CCN1CCN1CCC(Oc2ccncc2)CC1] | 2-(2-(4-(pyridin-4-yloxy)piperidin-1-yl)ethyl)-3,4-dihydroisoquinolin-1(2H)-one | $R^A$-19 | $L^1$-2 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 200 | 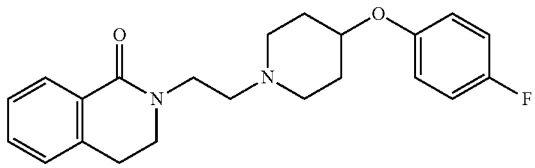 [SMILES: O=C1c2ccccc2CCN1CCN1CCC(Oc2ccc(F)cc2)CC1] | 2-(2-(4-(4-fluorophenoxy)piperidin-1-yl)ethyl)-3,4-dihydroisoquinolin-1(2H)-one | $R^A$-19 | $L^1$-2 | Q-3 | $L^2$-2 |
| 201 | 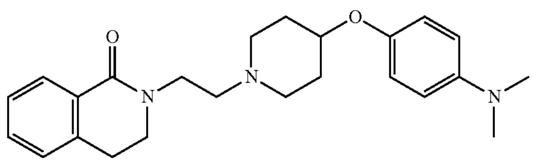 [SMILES: CN(C)c1ccc(OC2CCN(CCN3CCc4ccccc4C3=O)CC2)cc1] | 2-(2-(4-(4-(dimethylamino)phenoxy)piperidin-1-yl)ethyl)-3,4-dihydroisoquinolin-1(2H)-one | $R^A$-19 | $L^1$-2 | Q-3 | $L^2$-2 |
| 202 | 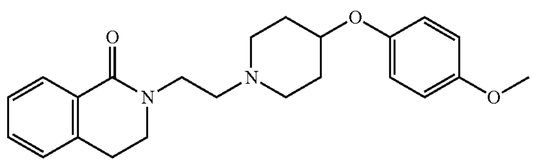 [SMILES: COc1ccc(OC2CCN(CCN3CCc4ccccc4C3=O)CC2)cc1] | 2-(2-(4-(4-methoxyphenoxy)piperidin-1-yl)ethyl)-3,4-dihydroisoquinolin-1(2H)-one | $R^A$-19 | $L^1$-2 | Q-3 | $L^2$-2 |
| 203 | 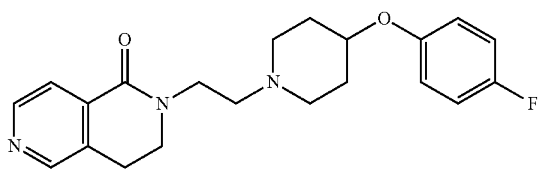 [SMILES: O=C1c2ccncc2CCN1CCN1CCC(Oc2ccc(F)cc2)CC1] | 2-(2-(4-(4-fluorophenoxy)piperidin-1-yl)ethyl)-3,4-dihydro-2,6-naphthyridin-1(2H)-one | $R^A$-19 | $L^1$-2 | Q-3 | $L^2$-2 |
| 204 | 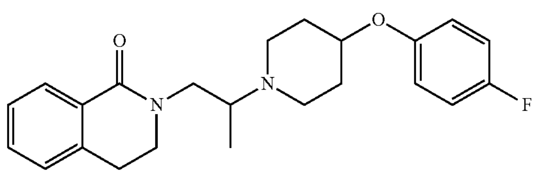 [SMILES: CC(CN1CCc2ccccc2C1=O)N1CCC(Oc2ccc(F)cc2)CC1] | 2-(2-(4-(4-fluorophenoxy)piperidin-1-yl)propyl)-3,4-dihydroisoquinolin-1(2H)-one | $R^A$-19 | $L^1$-2 | Q-3 | $L^2$-2 |
| 205 | 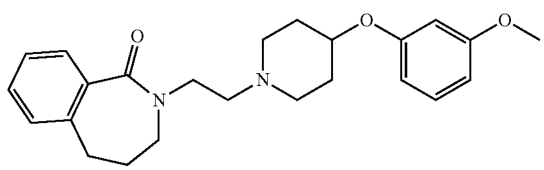 [SMILES: COc1cccc(OC2CCN(CCN3CCCc4ccccc4C3=O)CC2)c1] | 2-(2-(4-(3-methoxyphenoxy)piperidin-1-yl)ethyl)-2,3,4,5-tetrahydro-1H-benzo[c]azepin-1-one | $R^A$-21 | $L^1$-2 | Q-3 | $L^2$-2 |
| 206 | 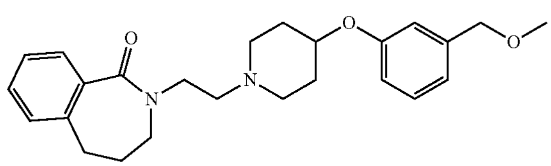 [SMILES: COCc1cccc(OC2CCN(CCN3CCCc4ccccc4C3=O)CC2)c1] | 2-(2-(4-(3-(methoxymethyl)phenoxy)piperidin-1-yl)ethyl)-2,3,4,5-tetrahydro-1H-benzo[c]azepin-1-one | $R^A$-21 | $L^1$-2 | Q-3 | $L^2$-2 |
| 207 | 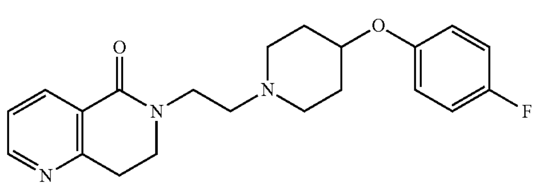 [SMILES: O=C1c2cccnc2CCN1CCN1CCC(Oc2ccc(F)cc2)CC1] | 6-(2-(4-(4-fluorophenoxy)piperidin-1-yl)ethyl)-7,8-dihydro-1,6-naphthyridin-5(6H)-one | $R^A$-21 | $L^1$-2 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 208 | 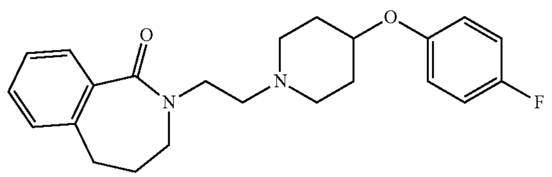 [SMILES: O=C1c2ccccc2CCCN1CCN1CCC(Oc2ccc(F)cc2)CC1] | 2-(2-(4-(4-fluorophenoxy)piperidin-1-yl)ethyl)-2,3,4,5-tetrahydro-1H-benzo[c]azepin-1-one | $R^A$-21 | $L^1$-2 | Q-3 | $L^2$-2 |
| 209 | 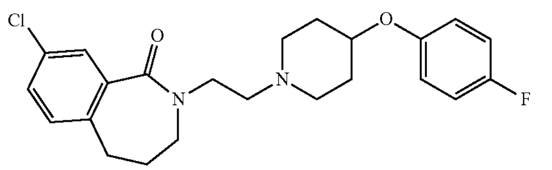 [SMILES: O=C1c2cc(Cl)ccc2CCCN1CCN1CCC(Oc2ccc(F)cc2)CC1] | 8-chloro-2-(2-(4-(4-fluorophenoxy)piperidin-1-yl)ethyl)-2,3,4,5-tetrahydro-1H-benzo[c]azepin-1-one | $R^A$-21 | $L^1$-2 | Q-3 | $L^2$-2 |
| 210 | 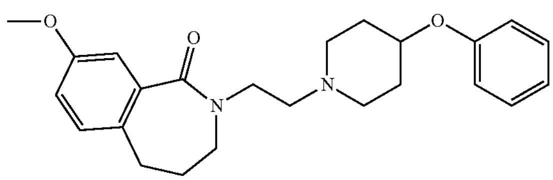 [SMILES: COc1ccc2c(c1)C(=O)N(CCN1CCC(Oc3ccccc3)CC1)CCC2] | 2-(2-(4-(4-fluorophenoxy)piperidin-1-yl)ethyl)-8-methoxy-2,3,4,5-tetrahydro-1H-benzo[c]azepin-1-one | $R^A$-21 | $L^1$-2 | Q-3 | $L^2$-2 |
| 211 | 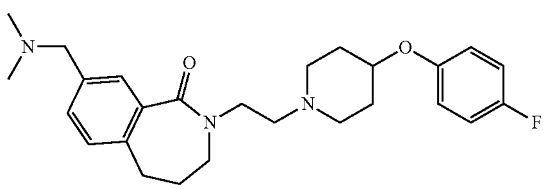 [SMILES: CN(C)Cc1ccc2c(c1)C(=O)N(CCN1CCC(Oc3ccc(F)cc3)CC1)CCC2] | 8-((dimethylamino)methyl)-2-(2-(4-(4-fluorophenoxy)piperidin-1-yl)ethyl)-2,3,4,5-tetrahydro-1H-benzo[c]azepin-1-one | $R^A$-21 | $L^1$-2 | Q-3 | $L^2$-2 |
| 212 | 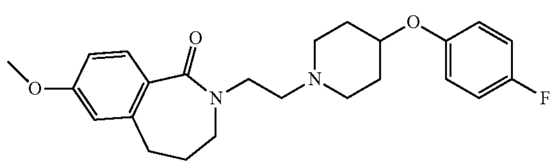 [SMILES: COc1ccc2c(c1)CCCN(CCN1CCC(Oc3ccc(F)cc3)CC1)C2=O] | 2-(2-(4-(4-fluorophenoxy)piperidin-1-yl)ethyl)-7-methoxy-2,3,4,5-tetrahydro-1H-benzo[c]azepin-1-one | $R^A$-21 | $L^1$-2 | Q-3 | $L^2$-2 |
| 213 | 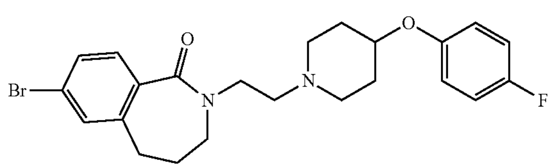 [SMILES: O=C1c2ccc(Br)cc2CCCN1CCN1CCC(Oc2ccc(F)cc2)CC1] | 7-bromo-2-(2-(4-(4-fluorophenoxy)piperidin-1-yl)ethyl)-2,3,4,5-tetrahydro-1H-benzo[c]azepin-1-one | $R^A$-21 | $L^1$-2 | Q-3 | $L^2$-2 |
| 214 | 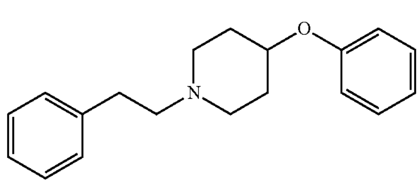 [SMILES: c1ccc(CCN2CCC(Oc3ccccc3)CC2)cc1] | 1-phenethyl-4-phenoxypiperidine | $R^A$-22 | $L^1$-2 | Q-3 | $L^2$-2 |
| 215 | 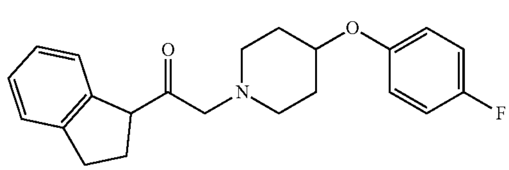 [SMILES: O=C(CN1CCC(Oc2ccc(F)cc2)CC1)C1CCc2ccccc21] | 1-(2,3-dihydro-1H-inden-1-yl)-2-(4-(4-fluorophenoxy)piperidin-1-yl)ethan-1-one | $R^A$-4 | $L^1$-3 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 216 | 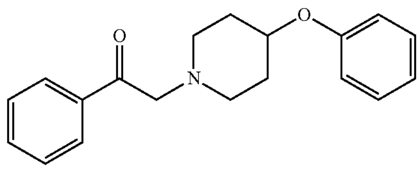 [SMILES: O=C(CN1CCC(Oc2ccccc2)CC1)c1ccccc1] | 2-(4-phenoxypiperidin-1-yl)-1-phenylethan-1-one | $R^A$-22 | $L^1$-3 | Q-3 | $L^2$-2 |
| 217 | 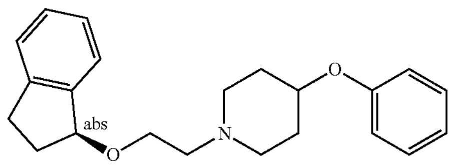 [SMILES: c1ccc(OC2CCN(CCO[C@H]3CCc4ccccc43)CC2)cc1] | (S)-1-(2-((2,3-dihydro-1H-inden-1-yl)oxy)ethyl)-4-phenoxypiperidine | $R^A$-4 | $L^1$-4 | Q-3 | $L^2$-2 |
| 218 | 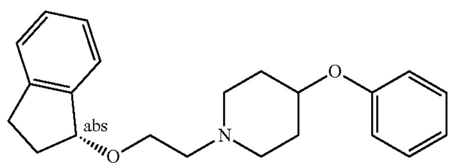 [SMILES: c1ccc(OC2CCN(CCO[C@@H]3CCc4ccccc43)CC2)cc1] | (R)-1-(2-((2,3-dihydro-1H-inden-1-yl)oxy)ethyl)-4-phenoxypiperidine | $R^A$-4 | $L^1$-4 | Q-3 | $L^2$-2 |
| 219 | 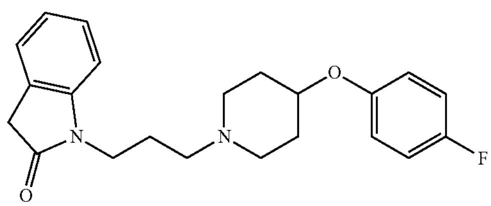 [SMILES: O=C1Cc2ccccc2N1CCCN1CCC(Oc2ccc(F)cc2)CC1] | 1-(3-(4-(4-fluorophenoxy)piperidin-1-yl)propyl)indolin-2-one | $R^A$-15 | $L^1$-4 | Q-3 | $L^2$-2 |
| 220 | 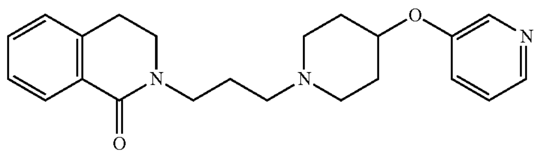 [SMILES: O=C1c2ccccc2CCN1CCCN1CCC(Oc2cccnc2)CC1] | 2-(3-(4-(pyridin-3-yloxy)piperidin-1-yl)propyl)-3,4-dihydroisoquinolin-1(2H)-one | $R^A$-19 | $L^1$-4 | Q-3 | $L^2$-2 |
| 221 | 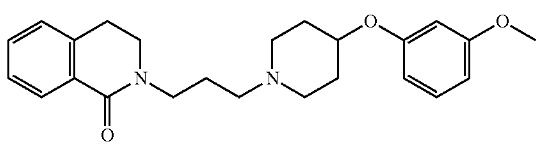 [SMILES: COc1cccc(OC2CCN(CCCN3CCc4ccccc4C3=O)CC2)c1] | 2-(3-(4-(3-methoxyphenoxy)piperidin-1-yl)propyl)-3,4-dihydroisoquinolin-1(2H)-one | $R^A$-19 | $L^1$-4 | Q-3 | $L^2$-2 |
| 222 | 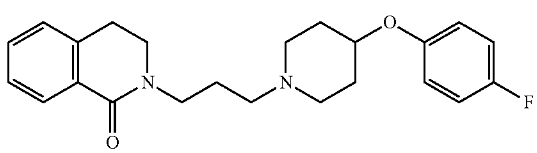 [SMILES: O=C1c2ccccc2CCN1CCCN1CCC(Oc2ccc(F)cc2)CC1] | 2-(3-(4-(4-fluorophenoxy)piperidin-1-yl)propyl)-3,4-dihydroisoquinolin-1(2H)-one | $R^A$-19 | $L^1$-4 | Q-3 | $L^2$-2 |
| 223 | 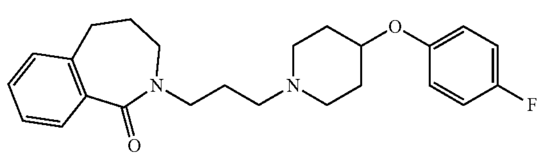 [SMILES: O=C1c2ccccc2CCCN1CCCN1CCC(Oc2ccc(F)cc2)CC1] | 2-(3-(4-(4-fluorophenoxy)piperidin-1-yl)propyl)-2,3,4,5-tetrahydro-1H-benzo[c]azepin-1-one | $R^A$-21 | $L^1$-4 | Q-3 | $L^2$-2 |
| 224 | 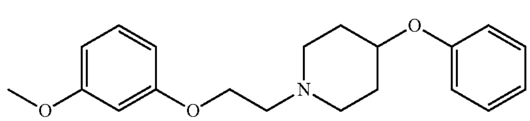 [SMILES: COc1cccc(OCCN2CCC(Oc3ccccc3)CC2)c1] | 1-(2-(3-methoxyphenoxy)ethyl)-4-phenoxypiperidine | $R^A$-22 | $L^1$-4 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 225 | 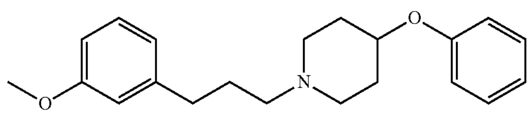 [SMILES: COc1cccc(CCCN2CCC(Oc3ccccc3)CC2)c1] | 1-(3-(3-methoxyphenyl)propyl)-4-phenoxypiperidine | $R^A$-22 | $L^1$-4 | Q-3 | $L^2$-2 |
| 226 | 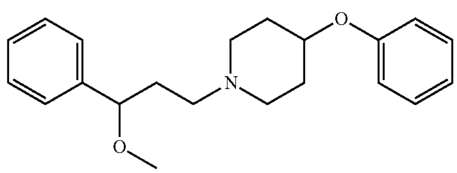 [SMILES: COC(CCN1CCC(Oc2ccccc2)CC1)c1ccccc1] | 1-(3-methoxy-3-phenylpropyl)-4-phenoxypiperidine | $R^A$-22 | $L^1$-4 | Q-3 | $L^2$-2 |
| 227 | 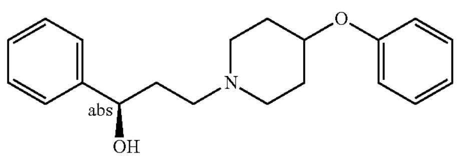 [SMILES: O[C@H](CCN1CCC(Oc2ccccc2)CC1)c1ccccc1] | (R)-3-(4-phenoxypiperidin-1-yl)-1-phenylpropan-1-ol | $R^A$-22 | $L^1$-4 | Q-3 | $L^2$-2 |
| 228 | 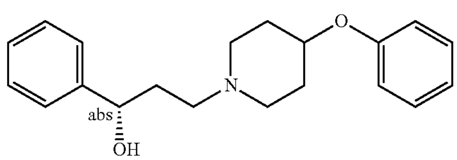 [SMILES: O[C@@H](CCN1CCC(Oc2ccccc2)CC1)c1ccccc1] | (S)-3-(4-phenoxypiperidin-1-yl)-1-phenylpropan-1-ol | $R^A$-22 | $L^1$-4 | Q-3 | $L^2$-2 |
| 229 | 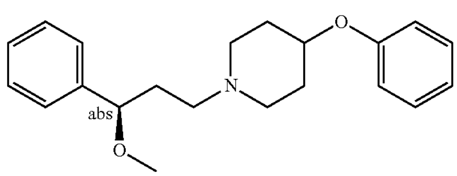 [SMILES: CO[C@H](CCN1CCC(Oc2ccccc2)CC1)c1ccccc1] | (R)-1-(3-methoxy-3-phenylpropyl)-4-phenoxypiperidine | $R^A$-22 | $L^1$-4 | Q-3 | $L^2$-2 |
| 230 | 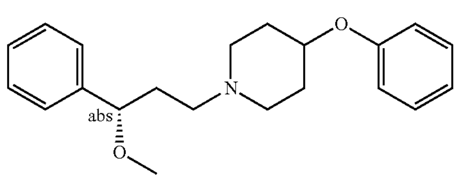 [SMILES: CO[C@@H](CCN1CCC(Oc2ccccc2)CC1)c1ccccc1] | (S)-1-(3-methoxy-3-phenylpropyl)-4-phenoxypiperidine | $R^A$-22 | $L^1$-4 | Q-3 | $L^2$-2 |
| 231 | 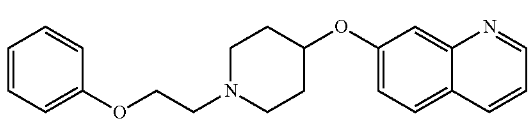 [SMILES: c1ccc(OCCN2CCC(Oc3ccc4cccnc4c3)CC2)cc1] | 7-((1-(2-phenoxyethyl)piperidin-4-yl)oxy)quinoline | $R^A$-22 | $L^1$-4 | Q-3 | $L^2$-2 |
| 232 | 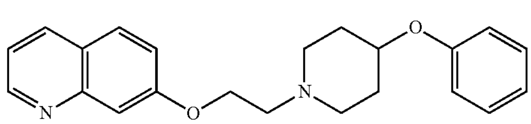 [SMILES: c1ccc(OC2CCN(CCOc3ccc4cccnc4c3)CC2)cc1] | 7-(2-(4-phenoxypiperidin-1-yl)ethoxy)quinoline | $R^A$-24 | $L^1$-4 | Q-3 | $L^2$-2 |
| 233 | 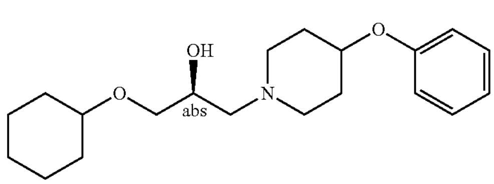 [SMILES: O[C@H](COC1CCCCC1)CN1CCC(Oc2ccccc2)CC1] | (S)-1-(cyclohexyloxy)-3-(4-phenoxypiperidin-1-yl)propan-2-ol | $R^A$-1 | $L^1$-6 | Q-3 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 234 | 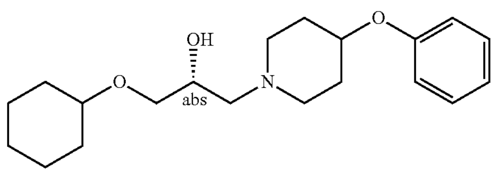 [SMILES: O[C@@H](COC1CCCCC1)CN1CCC(Oc2ccccc2)CC1] | (R)-1-(cyclohexyloxy)-3-(4-phenoxypiperidin-1-yl)propan-2-ol | $R^A$-1 | $L^1$-6 | Q-3 | $L^2$-2 |
| 235 | 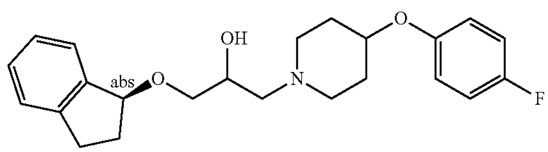 [SMILES: OC(CO[C@H]1CCc2ccccc21)CN1CCC(Oc2ccc(F)cc2)CC1] | 1-(((S)-2,3-dihydro-1H-inden-1-yl)oxy)-3-(4-(4-fluorophenoxy)piperidin-1-yl)propan-2-ol | $R^A$-4 | $L^1$-6 | Q-3 | $L^2$-2 |
| 236 | 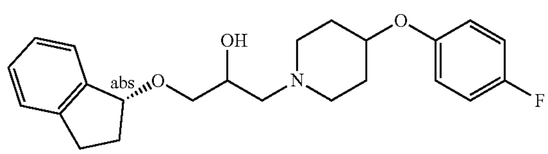 [SMILES: OC(CO[C@@H]1CCc2ccccc21)CN1CCC(Oc2ccc(F)cc2)CC1] | 1-(((R)-2,3-dihydro-1H-inden-1-yl)oxy)-3-(4-(4-fluorophenoxy)piperidin-1-yl)propan-2-ol | $R^A$-4 | $L^1$-6 | Q-3 | $L^2$-2 |
| 237 | 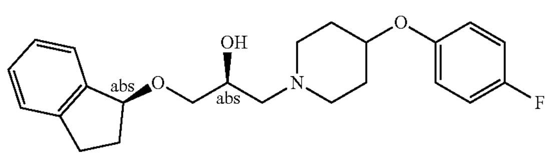 [SMILES: O[C@H](CO[C@H]1CCc2ccccc21)CN1CCC(Oc2ccc(F)cc2)CC1] | (R)-1-(((S)-2,3-dihydro-1H-inden-1-yl)oxy)-3-(4-(4-fluorophenoxy)piperidin-1-yl)propan-2-ol | $R^A$-4 | $L^1$-6 | Q-3 | $L^2$-2 |
| 238 | 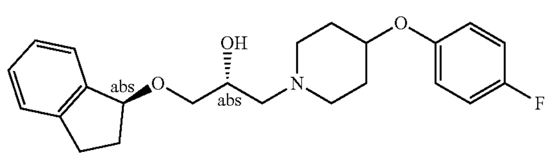 [SMILES: O[C@@H](CO[C@H]1CCc2ccccc21)CN1CCC(Oc2ccc(F)cc2)CC1] | (R)-1-(((S)-2,3-dihydro-1H-inden-1-yl)oxy)-3-(4-(4-fluorophenoxy)piperidin-1-yl)propan-2-ol | $R^A$-4 | $L^1$-6 | Q-3 | $L^2$-2 |
| 239 | 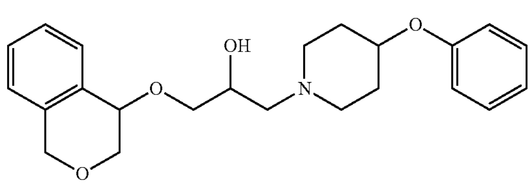 [SMILES: OC(COC1COCc2ccccc21)CN1CCC(Oc2ccccc2)CC1] | 1-(isochroman-4-yloxy)-3-(4-phenoxypiperidin-1-yl)propan-2-ol | $R^A$-12 | $L^1$-6 | Q-3 | $L^2$-2 |
| 240 | 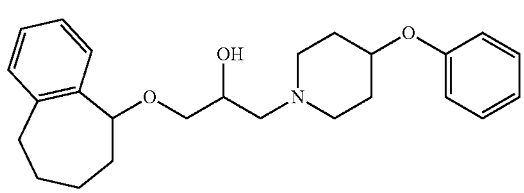 [SMILES: OC(COC1CCCCc2ccccc21)CN1CCC(Oc2ccccc2)CC1] | 1-(4-phenoxypiperidin-1-yl)-3-((6,7,8,9-tetrahydro-5H-benzo[7]annulen-5-yl)oxy)propan-2-ol | $R^A$-4 | $L^1$-6 | Q-3 | $L^2$-2 |
| 242 | 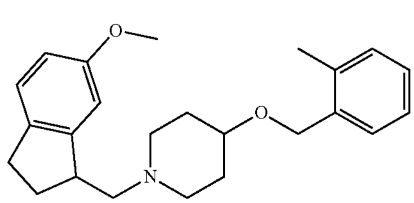 [SMILES: COc1ccc2c(c1)C(CN1CCC(OCc3ccccc3C)CC1)CC2] | 1-((6-methoxy-2,3-dihydro-1H-inden-1-yl)methyl)-4-((2-methylbenzyl)oxy)piperidine | $R^A$-4 | $L^1$-1 | Q-3 | $L^2$-4 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 243 | 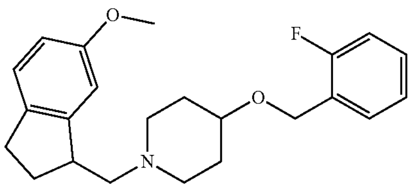 [SMILES: COc1ccc2c(c1)C(CN1CCC(OCc3ccccc3F)CC1)CC2] | 4-((2-fluorobenzyl)oxy)-1-((6-methoxy-2,3-dihydro-1H-inden-1-yl)methyl)piperidine | $R^A$-4 | $L^1$-1 | Q-3 | $L^2$-4 |
| 244 | 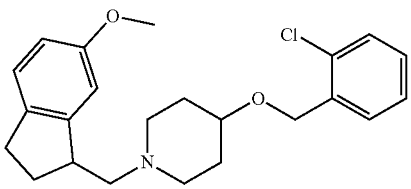 [SMILES: COc1ccc2c(c1)C(CN1CCC(OCc3ccccc3Cl)CC1)CC2] | 4-((2-chlorobenzyl)oxy)-1-((6-methoxy-2,3-dihydro-1H-inden-1-yl)methyl)piperidine | $R^A$-4 | $L^1$-1 | Q-3 | $L^2$-4 |
| 245 | 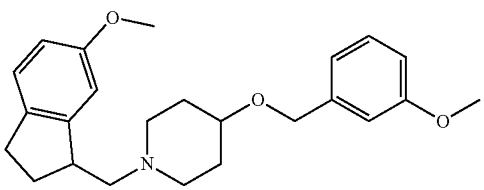 [SMILES: COc1cccc(COC2CCN(CC3CCc4ccc(OC)cc43)CC2)c1] | 1-((6-methoxy-2,3-dihydro-1H-inden-1-yl)methyl)-4-((3-methoxybenzyl)oxy)piperidine | $R^A$-4 | $L^1$-1 | Q-3 | $L^2$-4 |
| 246 | 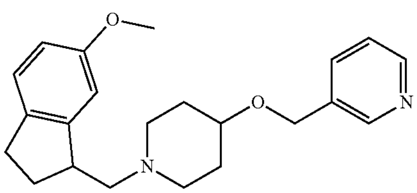 [SMILES: COc1ccc2c(c1)C(CN1CCC(OCc3cccnc3)CC1)CC2] | 3-(((1-((6-methoxy-2,3-dihydro-1H-inden-1-yl)methyl)piperidin-4-yl)oxy)methyl)pyridine | $R^A$-4 | $L^1$-1 | Q-3 | $L^2$-4 |
| 247 | 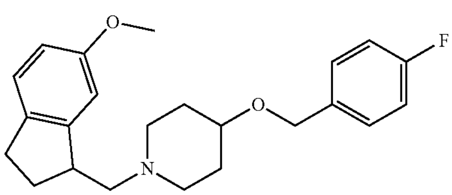 [SMILES: COc1ccc2c(c1)C(CN1CCC(OCc3ccc(F)cc3)CC1)CC2] | 4-((4-fluorobenzyl)oxy)-1-((6-methoxy-2,3-dihydro-1H-inden-1-yl)methyl)piperidine | $R^A$-4 | $L^1$-1 | Q-3 | $L^2$-4 |
| 248 | 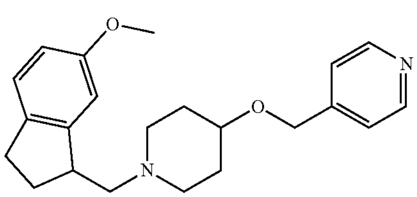 [SMILES: COc1ccc2c(c1)C(CN1CCC(OCc3ccncc3)CC1)CC2] | 4-(((1-((6-methoxy-2,3-dihydro-1H-inden-1-yl)methyl)piperidin-4-yl)oxy)methyl)pyridine | $R^A$-4 | $L^1$-1 | Q-3 | $L^2$-4 |
| 249 | 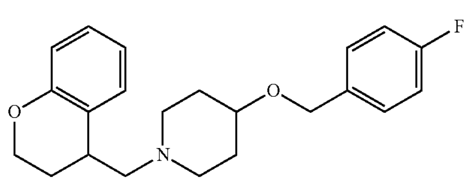 [SMILES: Fc1ccc(COC2CCN(CC3CCOc4ccccc43)CC2)cc1] | 1-(chroman-4-ylmethyl)-4-((4-fluorobenzyl)oxy)piperidine | $R^A$-13 | $L^1$-1 | Q-3 | $L^2$-4 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 250 | 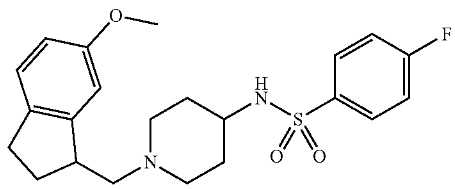 [SMILES: COc1ccc2c(c1)C(CN1CCC(NS(=O)(=O)c3ccc(F)cc3)CC1)CC2] | 4-fluoro-N-(1-((6-methoxy-2,3-dihydro-1H-inden-1-yl)methyl)piperidin-4-yl)benzenesulfonamide | $R^A$-4 | $L^1$-1 | Q-3 | $L^2$-5 |
| 251 | 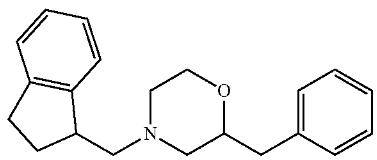 [SMILES: c1ccc(CC2CN(CC3CCc4ccccc43)CCO2)cc1] | 2-benzyl-4-((2,3-dihydro-1H-inden-1-yl)methyl)morpholine | $R^A$-4 | $L^1$-1 | Q-4 | $L^2$-3 |
| 252 | 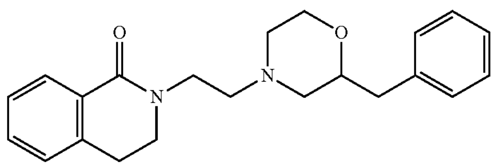 [SMILES: O=C1c2ccccc2CCN1CCN1CCOC(Cc2ccccc2)C1] | 2-(2-(2-benzylmorpholino)ethyl)-3,4-dihydroisoquinolin-1(2H)-one | $R^A$-19 | $L^1$2 | Q-4 | $L^2$-3 |
| 253 | 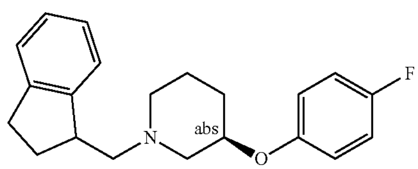 [SMILES: Fc1ccc(O[C@@H]2CCCN(CC3CCc4ccccc43)C2)cc1] | (3R)-1-((2,3-dihydro-1H-inden-1-yl)methyl)-3-(4-fluorophenoxy)piperidine | $R^A$-4 | $L^1$-1 | Q-5 | $L^2$-2 |
| 254 | 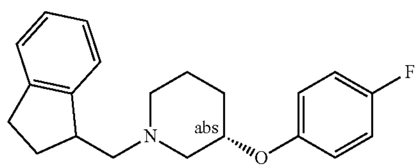 [SMILES: Fc1ccc(O[C@H]2CCCN(CC3CCc4ccccc43)C2)cc1] | (3S)-1-((2,3-dihydro-1H-inden-1-yl)methyl)-3-(4-fluorophenoxy)piperidine | $R^A$-4 | $L^1$-1 | Q-5 | $L^2$-2 |
| 255 | 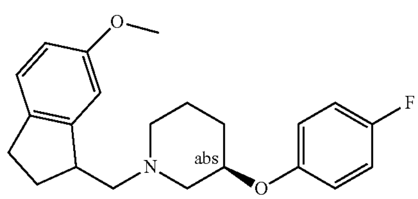 [SMILES: COc1ccc2c(c1)C(CN1CCC[C@@H](Oc3ccc(F)cc3)C1)CC2] | (3R)-3-(4-fluorophenoxy)-1-((6-methoxy-2,3-dihydro-1H-inden-1-yl)methyl)piperidine | $R^A$-4 | $L^1$-1 | Q-5 | $L^2$-2 |
| 256 | 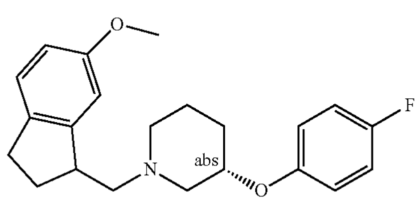 [SMILES: COc1ccc2c(c1)C(CN1CCC[C@H](Oc3ccc(F)cc3)C1)CC2] | (3S)-3-(4-fluorophenoxy)-1-((6-methoxy-2,3-dihydro-1H-inden-1-yl)methyl)piperidine | $R^A$-4 | $L^1$-1 | Q-5 | $L^2$-2 |
| 257 | 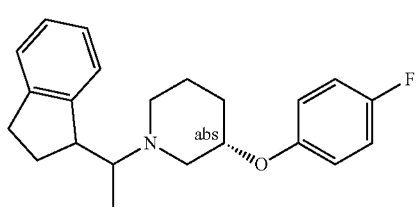 [SMILES: CC(C1CCc2ccccc21)N1CCC[C@H](Oc2ccc(F)cc2)C1] | (3S)-1-(1-(2,3-dihydro-1H-inden-1-yl)ethyl)-3-(4-fluorophenoxy)piperidine | $R^A$-4 | $L^1$-1 | Q-5 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 258 | 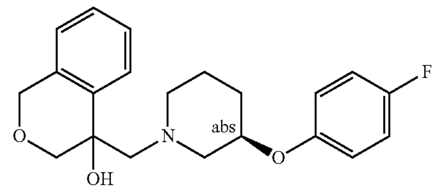 [SMILES: OC1(CN2CCC[C@@H](Oc3ccc(F)cc3)C2)COCc2ccccc21] | 4-(((R)-3-(4-fluorophenoxy)piperidin-1-yl)methyl)isochroman-4-ol | $R^A$-12 | $L^1$-1 | Q-5 | $L^2$-2 |
| 259 | 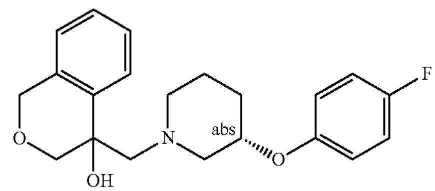 [SMILES: OC1(CN2CCC[C@H](Oc3ccc(F)cc3)C2)COCc2ccccc21] | 4-(((S)-3-(4-fluorophenoxy)piperidin-1-yl)methyl)isochroman-4-ol | $R^A$-12 | $L^1$-1 | Q-5 | $L^2$-2 |
| 260 | 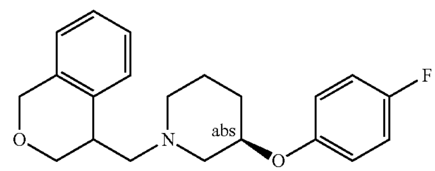 [SMILES: Fc1ccc(O[C@@H]2CCCN(CC3COCc4ccccc43)C2)cc1] | (3R)-3-(4-fluorophenoxy)-1-(isochroman-4-ylmethyl)piperidine | $R^A$-12 | $L^1$-1 | Q-5 | $L^2$-2 |
| 261 | 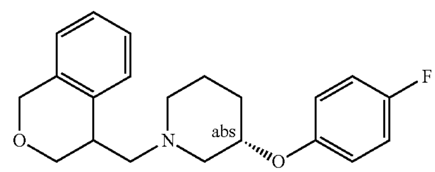 [SMILES: Fc1ccc(O[C@H]2CCCN(CC3COCc4ccccc43)C2)cc1] | (3S)-3-(4-fluorophenoxy)-1-(isochroman-4-ylmethyl)piperidine | $R^A$-12 | $L^1$-1 | Q-5 | $L^2$-2 |
| 262 | 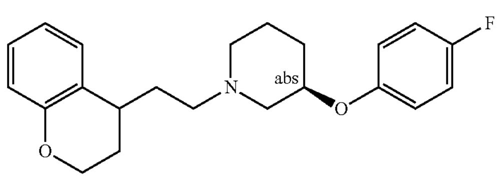 [SMILES: Fc1ccc(O[C@@H]2CCCN(CCC3CCOc4ccccc43)C2)cc1] | (3R)-1-(2-(chroman-4-yl)ethyl)-3-(4-fluorophenoxy)piperidine | $R^A$-13 | $L^1$-2 | Q-5 | $L^2$-2 |
| 263 | 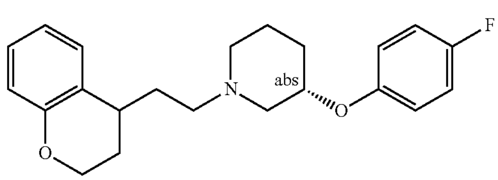 [SMILES: Fc1ccc(O[C@H]2CCCN(CCC3CCOc4ccccc43)C2)cc1] | (3S)-1-(2-(chroman-4-yl)ethyl)-3-(4-fluorophenoxy)piperidine | $R^A$-13 | $L^1$-2 | Q-5 | $L^2$-2 |
| 264 | 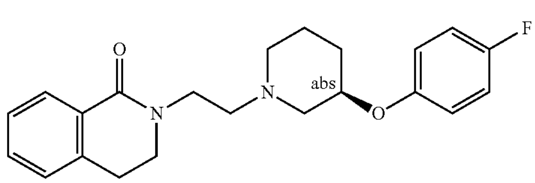 [SMILES: O=C1c2ccccc2CCN1CCN1CCC[C@@H](Oc2ccc(F)cc2)C1] | (R)-2-(2-(3-(4-fluorophenoxy)piperidin-1-yl)ethyl)-3,4-dihydroisoquinolin-1(2H)-one | $R^A$-19 | $L^1$-2 | Q-5 | $L^2$-2 |
| 265 | 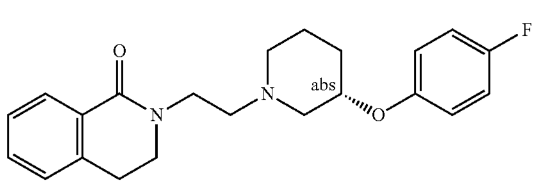 [SMILES: O=C1c2ccccc2CCN1CCN1CCC[C@H](Oc2ccc(F)cc2)C1] | (S)-2-(2-(3-(4-fluorophenoxy)piperidin-1-yl)ethyl)-3,4-dihydroisoquinolin-1(2H)-one | $R^A$-19 | $L^1$-2 | Q-5 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 266 | 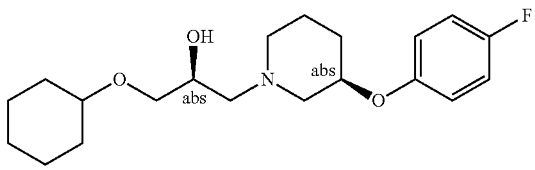 [SMILES: O[C@H](COC1CCCCC1)CN1CCC[C@@H](Oc2ccc(F)cc2)C1] | (S)-1-(cyclohexyloxy)-3-((R)-3-(4-fluorophenoxy)piperidin-1-yl)propan-2-ol | $R^A$-1 | $L^1$-6 | Q-5 | $L^2$-2 |
| 267 | 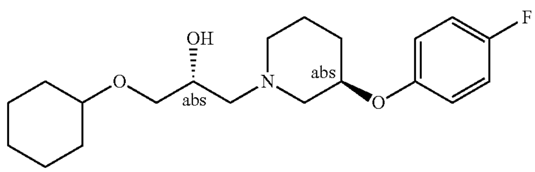 [SMILES: O[C@@H](COC1CCCCC1)CN1CCC[C@@H](Oc2ccc(F)cc2)C1] | (R)-1-(cyclohexyloxy)-3-((R)-3-(4-fluorophenoxy)piperidin-1-yl)propan-2-ol | $R^A$-1 | $L^1$-6 | Q-5 | $L^2$-2 |
| 268 | 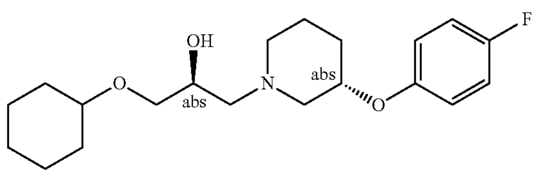 [SMILES: O[C@H](COC1CCCCC1)CN1CCC[C@H](Oc2ccc(F)cc2)C1] | (S)-1-(cyclohexyloxy)-3-((S)-3-(4-fluorophenoxy)piperidin-1-yl)propan-2-ol | $R^A$-1 | $L^1$-6 | Q-5 | $L^2$-2 |
| 269 | 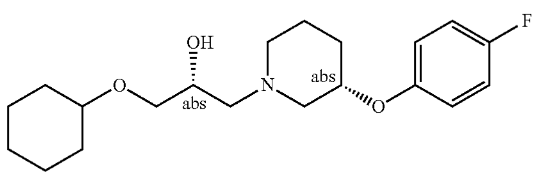 [SMILES: O[C@@H](COC1CCCCC1)CN1CCC[C@H](Oc2ccc(F)cc2)C1] | (R)-1-(cyclohexyloxy)-3-((S)-3-(4-fluorophenoxy)piperidin-1-yl)propan-2-ol | $R^A$-1 | $L^1$-6 | Q-5 | $L^2$-2 |
| 270 | 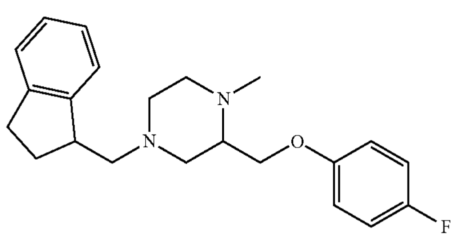 [SMILES: CN1CCN(CC2CCc3ccccc32)CC1COc1ccc(F)cc1] | 4-((2,3-dihydro-1H-inden-1-yl)methyl)-2-((4-fluorophenoxy)methyl)-1-methylpiperazine | $R^A$-4 | $L^1$-1 | Q-6 | $L^2$-6 |
| 271 | 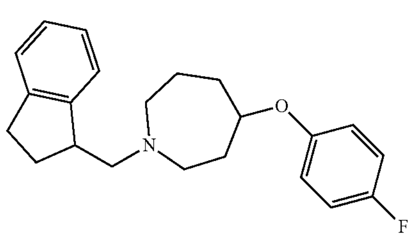 [SMILES: Fc1ccc(OC2CCCN(CC3CCc4ccccc43)CC2)cc1] | 1-((2,3-dihydro-1H-inden-1-yl)methyl)-4-(4-fluorophenoxy)azepane | $R^A$-4 | $L^1$-1 | Q-7 | $L^2$-2 |
| 272 | 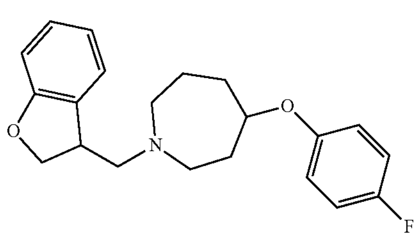 [SMILES: Fc1ccc(OC2CCCN(CC3COc4ccccc43)CC2)cc1] | 1-((2,3-dihydrobenzofuran-3-yl)methyl)-4-(4-fluorophenoxy)azepane | $R^A$-9 | $L^1$-1 | Q-7 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 273 | 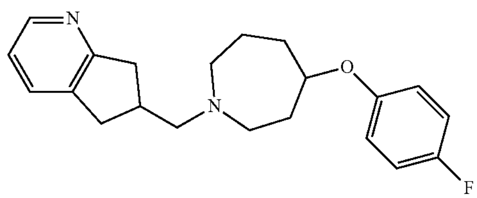 [SMILES: Fc1ccc(OC2CCCN(CC3Cc4cccnc4C3)CC2)cc1] | 6-((4-(4-fluorophenoxy)azepan-1-yl)methyl)-6,7-dihydro-5H-cyclopenta[b]pyridine | $R^A$-10 | $L^1$-1 | Q-7 | $L^2$-2 |
| 274 | 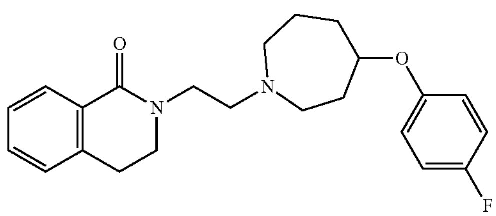 [SMILES: O=C1c2ccccc2CCN1CCN1CCCC(Oc2ccc(F)cc2)CC1] | 2-(2-(4-(4-fluorophenoxy)azepan-1-yl)ethyl)-3,4-dihydroisoquinolin-1(2H)-one | $R^A$-19 | $L^1$-2 | Q-7 | $L^2$-2 |
| 275 | 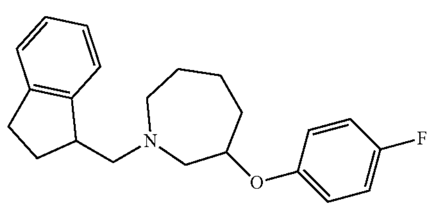 [SMILES: Fc1ccc(OC2CCCCN(CC3CCc4ccccc43)C2)cc1] | 1-((2,3-dihydro-1H-inden-1-yl)methyl)-3-(4-fluorophenoxy)azepane | $R^A$-4 | $L^1$-1 | Q-8 | $L^2$-2 |
| 276 | 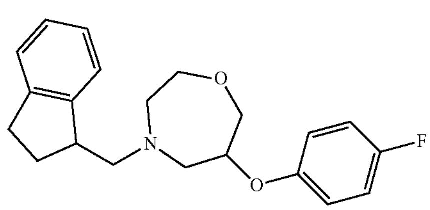 [SMILES: Fc1ccc(OC2COCCN(CC3CCc4ccccc43)C2)cc1] | 4-((2,3-dihydro-1H-inden-1-yl)methyl)-6-(4-fluorophenoxy)-1,4-oxazepane | $R^A$-4 | $L^1$-1 | Q-9 | $L^2$-2 |
| 277 | 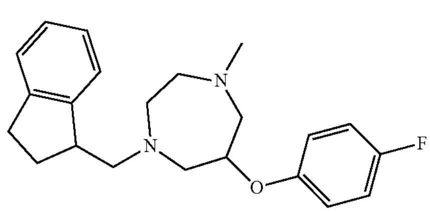 [SMILES: CN1CCN(CC2CCc3ccccc32)CC(Oc2ccc(F)cc2)C1] | 1-((2,3-dihydro-1H-inden-1-yl)methyl)-6-(4-fluorophenoxy)-4-methyl-1,4-diazepane | $R^A$-4 | $L^1$-1 | Q-10 | $L^2$-2 |
| 278 | 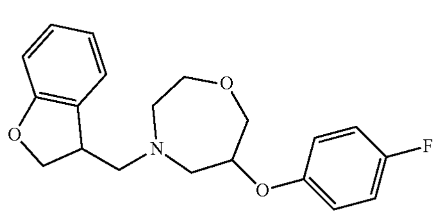 [SMILES: Fc1ccc(OC2COCCN(CC3COc4ccccc43)C2)cc1] | 4-((2,3-dihydrobenzofuran-3-yl)methyl)-6-(4-fluorophenoxy)-1,4-oxazepane | $R^A$-9 | $L^1$-1 | Q-9 | $L^2$-2 |
| 279 | 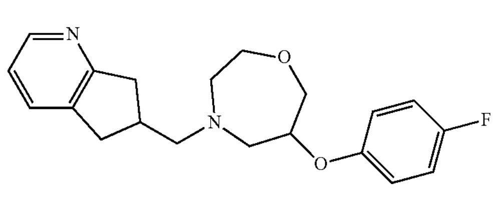 [SMILES: Fc1ccc(OC2COCCN(CC3Cc4cccnc4C3)C2)cc1] | 4-((6,7-dihydro-5H-cyclopenta[b]pyridin-6-yl)methyl)-6-(4-fluorophenoxy)-1,4-oxazepane | $R^A$-10 | $L^1$-1 | Q-9 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 280 | 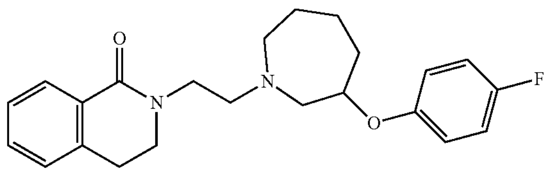 [SMILES: O=C1c2ccccc2CCN1CCN1CCCCC(Oc2ccc(F)cc2)C1] | 2-(2-(3-(4-fluorophenoxy)azepan-1-yl)ethyl)-3,4-dihydroisoquinolin-1(2H)-one | $R^A$-19 | $L^1$-2 | Q-9 | $L^2$-2 |
| 281 | 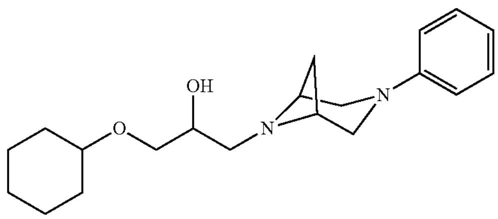 [SMILES: OC(COC1CCCCC1)CN1C2CC1CN(c1ccccc1)C2] | 1-(cyclohexyloxy)-3-((1R,5S)-3-phenyl-3,6-diazabicyclo[3.1.1]heptan-6-yl)propan-2-ol | $R^A$-1 | $L^1$-6 | Q-11 | $L^2$-1 |
| 286 | 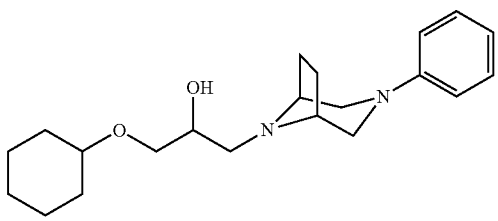 [SMILES: OC(COC1CCCCC1)CN1C2CCC1CN(c1ccccc1)C2] | 1-(cyclohexyloxy)-3-((1R,5S)-3-phenyl-3,8-diazabicyclo[3.2.1]octan-8-yl)propan-2-ol | $R^A$-1 | $L^1$-6 | Q-12 | $L^2$-1 |
| 287 | 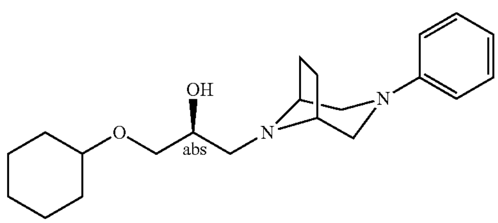 [SMILES: O[C@H](COC1CCCCC1)CN1C2CCC1CN(c1ccccc1)C2] | (S)-1-(cyclohexyloxy)-3-((1R,5S)-3-phenyl-3,8-diazabicyclo[3.2.1]octan-8-yl)propan-2-ol | $R^A$-1 | $L^1$-6 | Q-12 | $L^2$-1 |
| 288 | 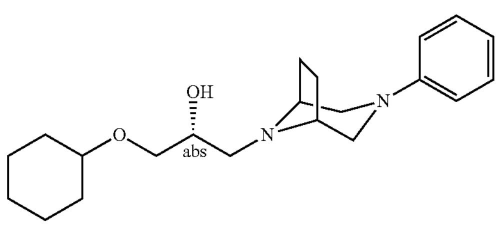 [SMILES: O[C@@H](COC1CCCCC1)CN1C2CCC1CN(c1ccccc1)C2] | (R)-1-(cyclohexyloxy)-3-((1R,5S)-3-phenyl-3,8-diazabicyclo[3.2.1]octan-8-yl)propan-2-ol | $R^A$-1 | $L^1$-6 | Q-12 | $L^2$-1 |
| 289 | 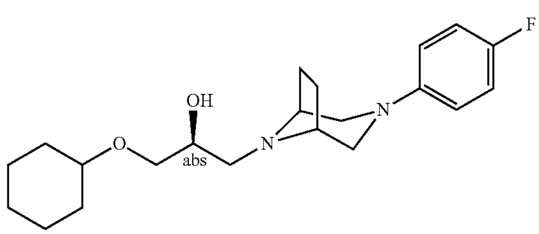 [SMILES: O[C@H](COC1CCCCC1)CN1C2CCC1CN(c1ccc(F)cc1)C2] | (S)-1-(cyclohexyloxy)-3-((1R,5S)-3-(4-fluorophenyl)-3,8-diazabicyclo[3.2.1]octan-8-yl)propan-2-ol | $R^A$-1 | $L^1$-6 | Q-12 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 290 | 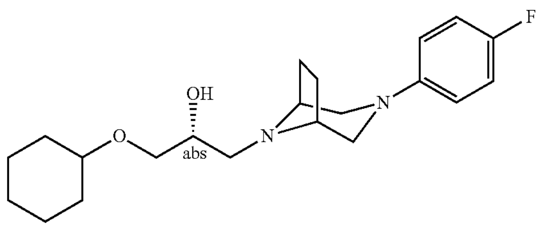 [SMILES: O[C@@H](COC1CCCCC1)CN1C2CCC1CN(c1ccc(F)cc1)C2] | (R)-1-(cyclohexyloxy)-3-((1R,5S)-3-(4-fluorophenyl)-3,8-diazabicyclo[3.2.1]octan-8-yl)propan-2-ol | $R^A$-1 | $L^1$-6 | Q-12 | $L^2$-1 |
| 291 | 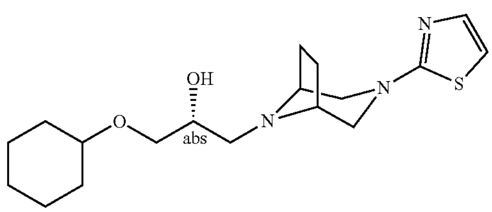 [SMILES: O[C@@H](COC1CCCCC1)CN1C2CCC1CN(c1nccs1)C2] | (R)-1-(cyclohexyloxy)-3-((1R,5S)-3-(thiazol-2-yl)-3,8-diazabicyclo[3.2.1]octan-8-yl)propan-2-ol | $R^A$-1 | $L^1$-6 | Q-12 | $L^2$-1 |
| 292 | 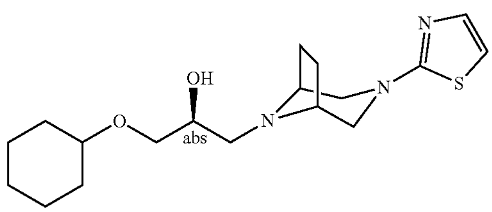 [SMILES: O[C@H](COC1CCCCC1)CN1C2CCC1CN(c1nccs1)C2] | (S)-1-(cyclohexyloxy)-3-((1R,5S)-3-(thiazol-2-yl)-3,8-diazabicyclo[3.2.1]octan-8-yl)propan-2-ol | $R^A$-1 | $L^1$-6 | Q-12 | $L^2$-1 |
| 293 | 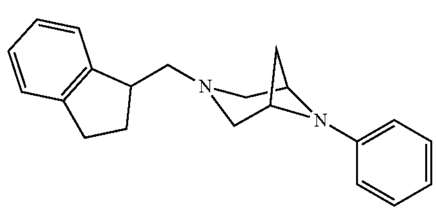 [SMILES: c1ccc(N2C3CC2CN(CC2CCc4ccccc42)C3)cc1] | (1R,5S)-3-((2,3-dihydro-1H-inden-1-yl)methyl)-6-phenyl-3,6-diazabicyclo[3.1.1]heptane | $R^A$-4 | $L^1$-1 | Q-13 | $L^2$-1 |
| 294 | 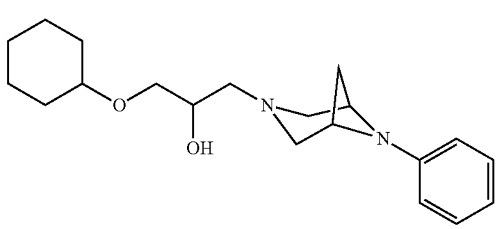 [SMILES: OC(COC1CCCCC1)CN1CC2CC(C1)N2c1ccccc1] | 1-(cyclohexyloxy)-3-((1R,5S)-6-phenyl-3,6-diazabicyclo[3.1.1]heptan-3-yl)propan-2-ol | $R^A$-1 | $L^1$-6 | Q-13 | $L^2$-1 |
| 295 | 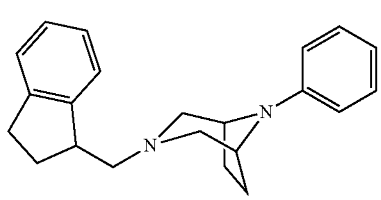 [SMILES: c1ccc(N2C3CCC2CN(CC2CCc4ccccc42)C3)cc1] | (1R,5S)-3-((2,3-dihydro-1H-inden-1-yl)methyl)-8-phenyl-3,8-diazabicyclo[3.2.1]octane | $R^A$-4 | $L^1$-1 | Q-14 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 296 | 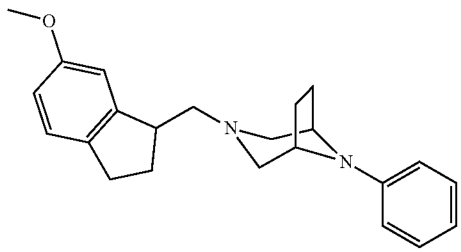 [SMILES: COc1ccc2c(c1)C(CN1CC3CCC(C1)N3c1ccccc1)CC2] | (1R,5S)-3-((6-methoxy-2,3-dihydro-1H-inden-1-yl)methyl)-8-phenyl-3,8-diazabicyclo[3.2.1]octane | $R^A$-4 | $L^1$-1 | Q-14 | $L^2$-1 |
| 297 | 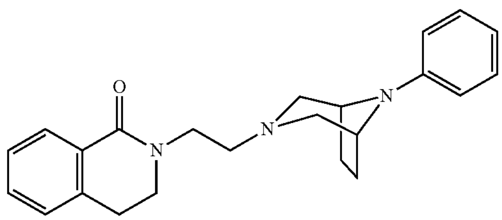 [SMILES: O=C1c2ccccc2CCN1CCN1CC2CCC(C1)N2c1ccccc1] | 2-(2-((1R,5S)-8-phenyl-3,8-diazabicyclo[3.2.1]octan-3-yl)ethyl)-3,4-dihydroisoquinolin-1(2H)-one | $R^A$-19 | $L^1$-2 | Q-14 | $L^2$-1 |
| 298 | 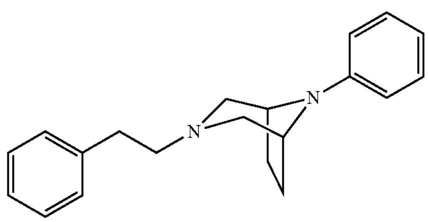 [SMILES: c1ccc(CCN2CC3CCC(C2)N3c2ccccc2)cc1] | (1R,5S)-3-phenethyl-8-phenyl-3,8-diazabicyclo[3.2.1]octane | $R^A$-22 | $L^1$-2 | Q-14 | $L^2$-1 |
| 299 | 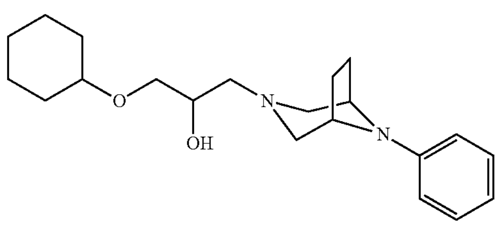 [SMILES: OC(COC1CCCCC1)CN1CC2CCC(C1)N2c1ccccc1] | 1-(cyclohexyloxy)-3-((1R,5S)-8-phenyl-3,8-diazabicyclo[3.2.1]octan-3-yl)propan-2-ol | $R^A$-1 | $L^1$-6 | Q-14 | $L^2$-1 |
| 300 | 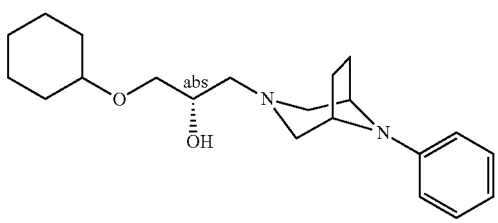 [SMILES: O[C@H](COC1CCCCC1)CN1CC2CCC(C1)N2c1ccccc1] | (S)-1-(cyclohexyloxy)-3-((1R,5S)-8-phenyl-3,8-diazabicyclo[3.2.1]octan-3-yl)propan-2-ol | $R^A$-1 | $L^1$-6 | Q-14 | $L^2$-1 |
| 301 | 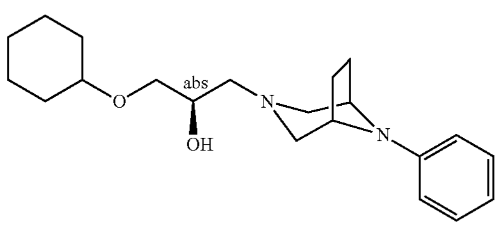 [SMILES: O[C@@H](COC1CCCCC1)CN1CC2CCC(C1)N2c1ccccc1] | (R)-1-(cyclohexyloxy)-3-((1R,5S)-8-phenyl-3,8-diazabicyclo[3.2.1]octan-3-yl)propan-2-ol | $R^A$-1 | $L^1$-6 | Q-14 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 302 | 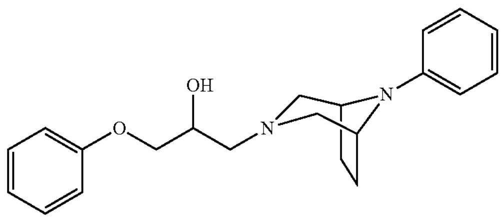 [SMILES: OC(COc1ccccc1)CN1CC2CCC(C1)N2c1ccccc1] | 1-phenoxy-3-((1R,5S)-8-phenyl-3,8-diazabicyclo[3.2.1]octan-3-yl)propan-2-ol | $R^A$-22 | $L^1$-6 | Q-14 | $L^2$-1 |
| 303 | 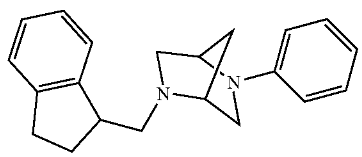 [SMILES: c1ccc(N2CC3CC2CN3CC2CCc3ccccc32)cc1] | (1S,4S)-2-((2,3-dihydro-1H-inden-1-yl)methyl)-5-phenyl-2,5-diazabicyclo[2.2.1]heptane | $R^A$-4 | $L^1$-1 | Q-15 | $L^2$-1 |
| 304 | 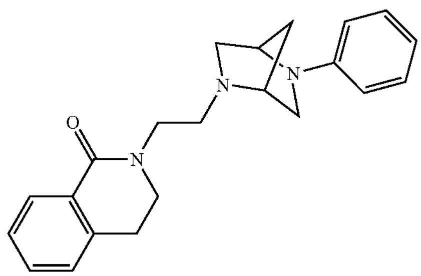 [SMILES: O=C1c2ccccc2CCN1CCN1CC2CC1CN2c1ccccc1] | 2-(2-((1S,4S)-5-phenyl-2,5-diazabicyclo[2.2.1]heptan-2-yl)ethyl)-3,4-dihydroisoquinolin-1(2H)-one | $R^A$-19 | $L^1$-2 | Q-15 | $L^2$-1 |
| 305 | 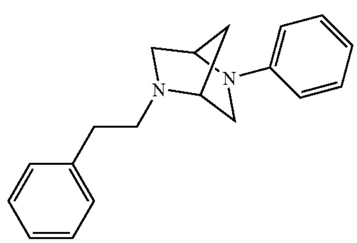 [SMILES: c1ccc(CCN2CC3CC2CN3c2ccccc2)cc1] | (1S,4S)-2-phenethyl-5-phenyl-2,5-diazabicyclo[2.2.1]heptane | $R^A$-22 | $L^1$-2 | Q-15 | $L^2$-1 |
| 306 | 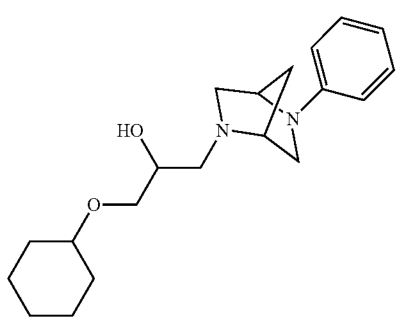 [SMILES: OC(COC1CCCCC1)CN1CC2CC1CN2c1ccccc1] | 1-(cyclohexyloxy)-3-((1S,4S)-5-phenyl-2,5-diazabicyclo[2.2.1]heptan-2-yl)propan-2-ol | $R^A$-1 | $L^1$-6 | Q-15 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 307 | 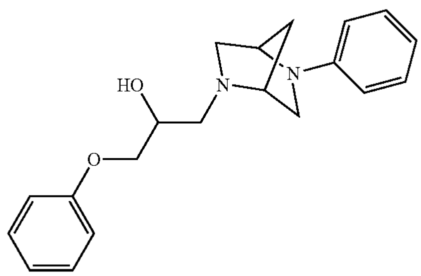 [SMILES: OC(COc1ccccc1)CN1CC2CC1CN2c1ccccc1] | 1-phenoxy-3-((1S,4S)-5-phenyl-2,5-diazabicyclo[2.2.1]heptan-2-yl)propan-2-ol | $R^A$-22 | $L^1$-6 | Q-15 | $L^2$-1 |
| 308 | 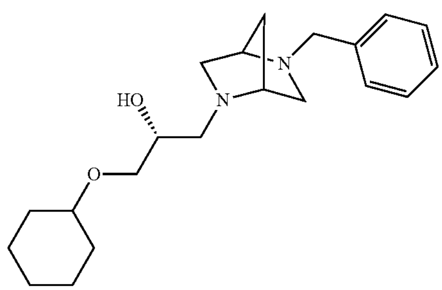 [SMILES: O[C@@H](COC1CCCCC1)CN1CC2CC1CN2Cc1ccccc1] | (R)-1-((1S,4S)-5-benzyl-2,5-diazabicyclo[2.2.1]heptan-2-yl)-3-(cyclohexyloxy)propan-2-ol | $R^A$-1 | $L^1$-6 | Q-15 | $L^2$-3 |
| 309 | 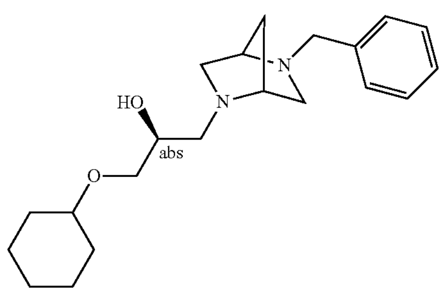 [SMILES: O[C@H](COC1CCCCC1)CN1CC2CC1CN2Cc1ccccc1] | (S)-1-((1S,4S)-5-benzyl-2,5-diazabicyclo[2.2.1]heptan-2-yl)-3-(cyclohexyloxy)propan-2-ol | $R^A$-1 | $L^1$-6 | Q-15 | $L^2$-3 |
| 310 | 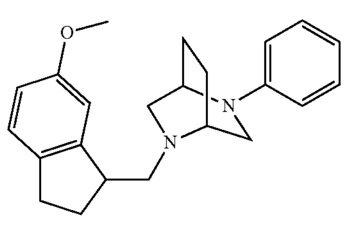 [SMILES: COc1ccc2c(c1)C(CN1CC3CCC1CN3c1ccccc1)CC2] | 2-((6-methoxy-2,3-dihydro-1H-inden-1-yl)methyl)-5-phenyl-2,5-diazabicyclo[2.2.2]octane | $R^A$-4 | $L^1$-1 | Q-16 | $L^2$-1 |
| 311 | 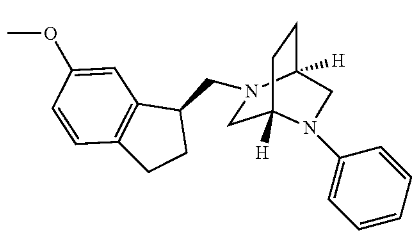 [SMILES: COc1ccc2c(c1)[C@@H](CN1C[C@@H]3CC[C@H]1CN3c1ccccc1)CC2] | (1S,4S)-2-(((S)-6-methoxy-2,3-dihydro-1H-inden-1-yl)methyl)-5-phenyl-2,5-diazabicyclo[2.2.2]octane | $R^A$-4 | $L^1$-1 | Q-16 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 312 | 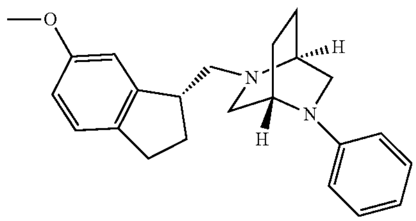 [SMILES: COc1ccc2c(c1)[C@H](CN1C[C@@H]3CC[C@H]1CN3c1ccccc1)CC2] | (1S,4S)-2-(((R)-6-methoxy-2,3-dihydro-1H-inden-1-yl)methyl)-5-phenyl-2,5-diazabicyclo[2.2.2]octane | $R^A$-4 | $L^1$-1 | Q-16 | $L^2$-1 |
| 313 | 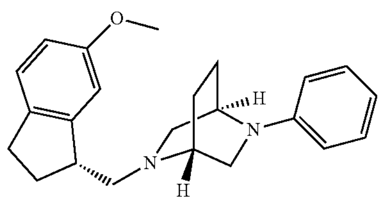 [SMILES: COc1ccc2c(c1)[C@H](CN1C[C@H]3CC[C@@H]1CN3c1ccccc1)CC2] | (1R,4R)-2-(((S)-6-methoxy-2,3-dihydro-1H-inden-1-yl)methyl)-5-phenyl-2,5-diazabicyclo[2.2.2]octane | $R^A$-4 | $L^1$-1 | Q-16 | $L^2$-1 |
| 314 | 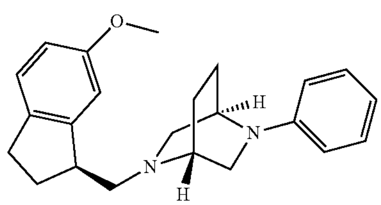 [SMILES: COc1ccc2c(c1)[C@@H](CN1C[C@H]3CC[C@@H]1CN3c1ccccc1)CC2] | (1R,4R)-2-(((R)-6-methoxy-2,3-dihydro-1H-inden-1-yl)methyl)-5-phenyl-2,5-diazabicyclo[2.2.2]octane | $R^A$-4 | $L^1$-1 | Q-16 | $L^2$-1 |
| 315 | 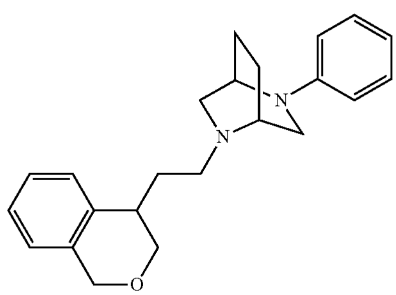 [SMILES: c1ccc(N2CC3CCC2CN3CCC2COCc3ccccc32)cc1] | (1S,4S)-2-(2-(isochroman-4-yl)ethyl)-5-phenyl-2,5-diazabicyclo[2.2.2]octane | $R^A$-12 | $L^1$-2 | Q-16 | $L^2$-1 |
| 316 | 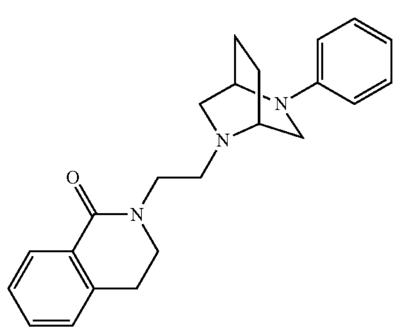 [SMILES: O=C1c2ccccc2CCN1CCN1CC2CCC1CN2c1ccccc1] | 2-(2-((1S,4S)-5-phenyl-2,5-diazabicyclo[2.2.2]octan-2-yl)ethyl)-3,4-dihydroisoquinolin-1(2H)-one | $R^A$-19 | $L^1$-2 | Q-16 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 317 | 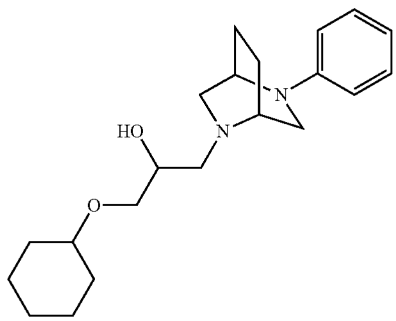 [SMILES: OC(COC1CCCCC1)CN1CC2CCC1CN2c1ccccc1] | 1-(cyclohexyloxy)-3-((1S,4S)-5-phenyl-2,5-diazabicyclo[2.2.2]octan-2-yl)propan-2-ol | $R^A$-1 | $L^1$-6 | Q-16 | $L^2$-1 |
| 318 | 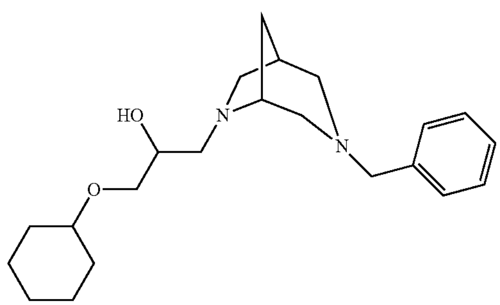 [SMILES: OC(COC1CCCCC1)CN1CC2CC1CN(Cc1ccccc1)C2] | 1-((1S,5R)-3-benzyl-3,6-diazabicyclo[3.2.1]octan-6-yl)-3-(cyclohexyloxy)propan-2-ol | $R^A$-1 | $L^1$-6 | Q-17 | $L^2$-3 |
| 319 | 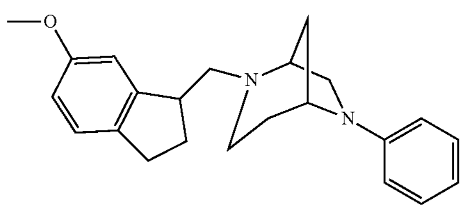 [SMILES: COc1ccc2c(c1)C(CN1CCC3CC1CN3c1ccccc1)CC2] | (1S,5R)-2-((6-methoxy-2,3-dihydro-1H-inden-1-yl)methyl)-6-phenyl-2,6-diazabicyclo[3.2.1]octane | $R^A$-4 | $L^1$-1 | Q-18 | $L^2$-1 |
| 320 | 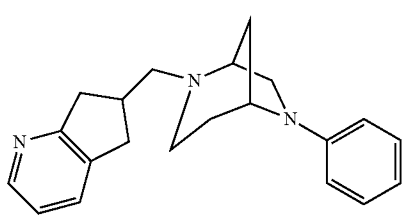 [SMILES: c1ccc(N2CC3CC2CCN3CC2Cc3cccnc3C2)cc1] | 6-(((1S,5R)-6-phenyl-2,6-diazabicyclo[3.2.1]octan-2-yl)methyl)-6,7-dihydro-5H-cyclopenta[b]pyridine | $R^A$-10 | $L^1$-1 | Q-18 | $L^2$-1 |
| 321 | 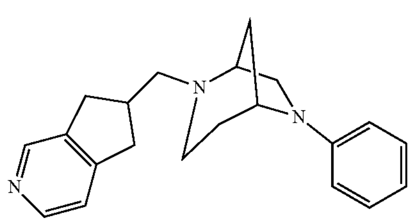 [SMILES: c1ccc(N2CC3CC2CCN3CC2Cc3ccncc3C2)cc1] | 6-(((1S,5R)-6-phenyl-2,6-diazabicyclo[3.2.1]octan-2-yl)methyl)-6,7-dihydro-5H-cyclopenta[c]pyridine | $R^A$-11 | $L^1$-1 | Q-18 | $L^2$-1 |
| 322 | 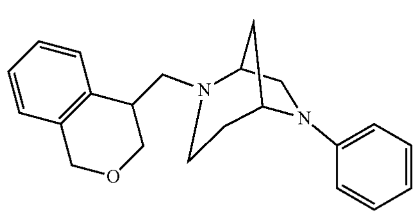 [SMILES: c1ccc(N2CC3CC2CCN3CC2COCc3ccccc32)cc1] | (1S,5R)-2-(isochroman-4-ylmethyl)-6-phenyl-2,6-diazabicyclo[3.2.1]octane | $R^A$-12 | $L^1$-1 | Q-18 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 323 | 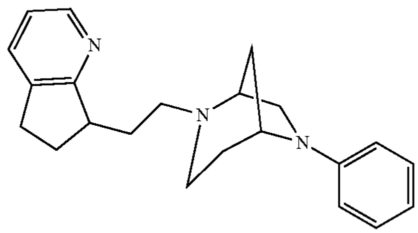 [SMILES: c1ccc(N2CC3CC2CCN3CCC2CCc3cccnc32)cc1] | 7-(2-((1S,5R)-6-phenyl-2,6-diazabicyclo[3.2.1]octan-2-yl)ethyl)-6,7-dihydro-5H-cyclopenta[b]pyridine | $R^A$-8 | $L^1$-2 | Q-18 | $L^2$-1 |
| 324 | 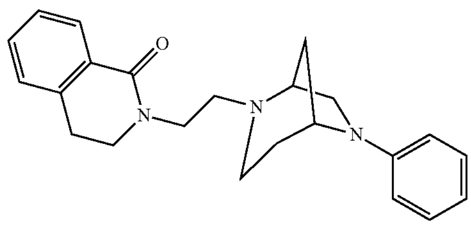 [SMILES: O=C1c2ccccc2CCN1CCN1CCC2CC1CN2c1ccccc1] | 2-(2-((1S,5R)-6-phenyl-2,6-diazabicyclo[3.2.1]octan-2-yl)ethyl)-3,4-dihydroisoquinolin-1(2H)-one | $R^A$-19 | $L^1$-2 | Q-18 | $L^2$-1 |
| 325 | 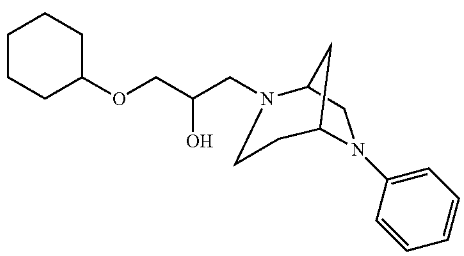 [SMILES: OC(COC1CCCCC1)CN1CCC2CC1CN2c1ccccc1] | 1-(cyclohexyloxy)-3-((1R,5S)-6-phenyl-2,6-diazabicyclo[3.2.1]octan-2-yl)propan-2-ol | $R^A$-1 | $L^1$-6 | Q-18 | $L^2$-1 |
| 326 | 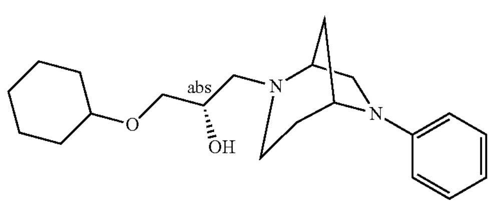 [SMILES: O[C@H](COC1CCCCC1)CN1CCC2CC1CN2c1ccccc1] | (S)-1-(cyclohexyloxy)-3-((1S,5R)-6-phenyl-2,6-diazabicyclo[3.2.1]octan-2-yl)propan-2-ol | $R^A$-1 | $L^1$-6 | Q-18 | $L^2$-1 |
| 327 | 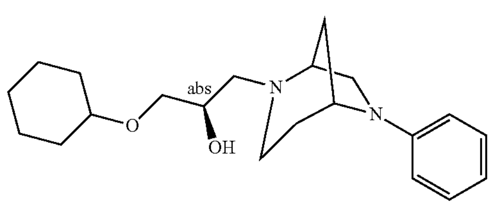 [SMILES: O[C@@H](COC1CCCCC1)CN1CCC2CC1CN2c1ccccc1] | (R)-1-(cyclohexyloxy)-3-((1S,5R)-6-phenyl-2,6-diazabicyclo[3.2.1]octan-2-yl)propan-2-ol | $R^A$-1 | $L^1$-6 | Q-18 | $L^2$-1 |
| 328 | 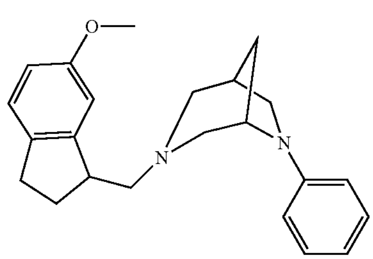 [SMILES: COc1ccc2c(c1)C(CN1CC3CC(C1)N(c1ccccc1)C3)CC2] | 3-((6-methoxy-2,3-dihydro-1H-inden-1-yl)methyl)-6-phenyl-3,6-diazabicyclo[3.2.1]octane | $R^A$-4 | $L^1$-1 | Q-19 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 329 | 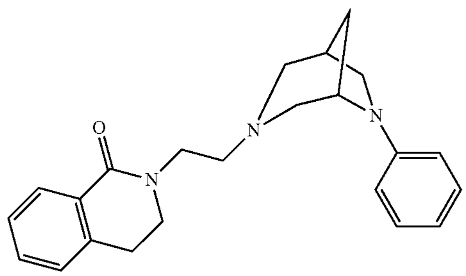 [SMILES: O=C1c2ccccc2CCN1CCN1CC2CC(C1)N(c1ccccc1)C2] | 2-(2-((1S,5R)-6-phenyl-3,6-diazabicyclo[3.2.1]octan-3-yl)ethyl)-3,4-dihydroisoquinolin-1(2H)-one | $R^A$-19 | $L^1$-2 | Q-19 | $L^2$-1 |
| 330 | 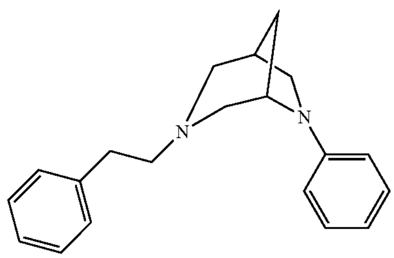 [SMILES: c1ccc(CCN2CC3CC(C2)N(c2ccccc2)C3)cc1] | (1S,5R)-3-phenethyl-6-phenyl-3,6-diazabicyclo[3.2.1]octane | $R^A$-22 | $L^1$-2 | Q-19 | $L^2$-1 |
| 331 | 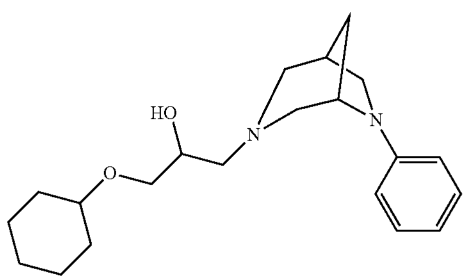 [SMILES: OC(COC1CCCCC1)CN1CC2CC(C1)N(c1ccccc1)C2] | 1-(cyclohexyloxy)-3-((1S,5R)-6-phenyl-3,6-diazabicyclo[3.2.1]octan-3-yl)propan-2-ol | $R^A$-1 | $L^1$-6 | Q-19 | $L^2$-1 |
| 332 | 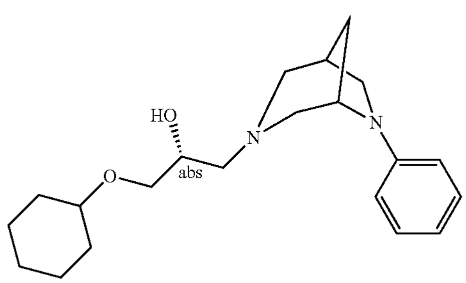 [SMILES: O[C@@H](COC1CCCCC1)CN1CC2CC(C1)N(c1ccccc1)C2] | (R)-1-(cyclohexyloxy)-3-((1S,5R)-6-phenyl-3,6-diazabicyclo[3.2.1]octan-3-yl)propan-2-ol | $R^A$-1 | $L^1$-6 | Q-19 | $L^2$-1 |
| 333 | 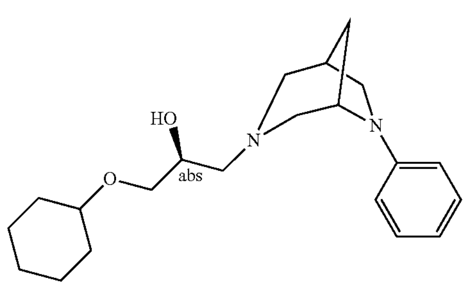 [SMILES: O[C@H](COC1CCCCC1)CN1CC2CC(C1)N(c1ccccc1)C2] | (S)-1-(cyclohexyloxy)-3-((1S,5R)-6-phenyl-3,6-diazabicyclo[3.2.1]octan-3-yl)propan-2-ol | $R^A$-1 | $L^1$-6 | Q-19 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 334 | 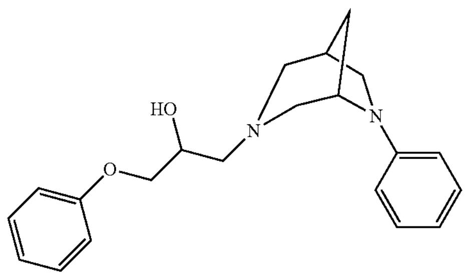 [SMILES: OC(COc1ccccc1)CN1CC2CC(C1)N(c1ccccc1)C2] | 1-phenoxy-3-((1S,5R)-6-phenyl-3,6-diazabicyclo[3.2.1]octan-3-yl)propan-2-ol | $R^A$-22 | $L^1$-6 | Q-20 | $L^2$-1 |
| 335 | 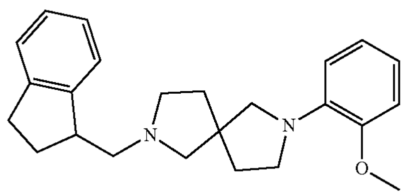 [SMILES: COc1ccccc1N1CCC2(CCN(CC3CCc4ccccc43)C2)C1] | 2-((2,3-dihydro-1H-inden-1-yl)methyl)-7-(2-methoxyphenyl)-2,7-diazaspiro[4.4]nonane | $R^A$-4 | $L^1$-1 | Q-20 | $L^2$-1 |
| 336 | 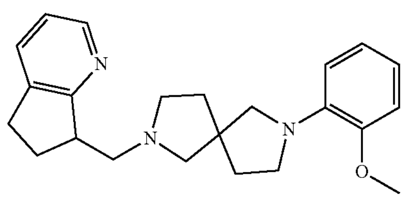 [SMILES: COc1ccccc1N1CCC2(CCN(CC3CCc4cccnc43)C2)C1] | 2-((6,7-dihydro-5H-cyclopenta[b]pyridin-7-yl)methyl)-7-(2-methoxyphenyl)-2,7-diazaspiro[4.4]nonane | $R^A$-8 | $L^1$-1 | Q-20 | $L^2$-1 |
| 337 | 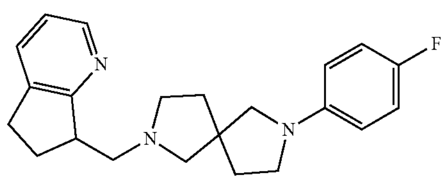 [SMILES: Fc1ccc(N2CCC3(CCN(CC4CCc5cccnc54)C3)C2)cc1] | 2-((6,7-dihydro-5H-cyclopenta[b]pyridin-7-yl)methyl)-7-(4-fluorophenyl)-2,7-diazaspiro[4.4]nonane | $R^A$-8 | $L^1$-1 | Q-20 | $L^2$-1 |
| 338 | 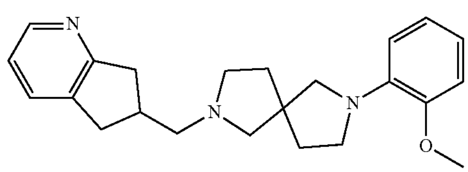 [SMILES: COc1ccccc1N1CCC2(CCN(CC3Cc4cccnc4C3)C2)C1] | 2-((6,7-dihydro-5H-cyclopenta[b]pyridin-6-yl)methyl)-7-(2-methoxyphenyl)-2,7-diazaspiro[4.4]nonane | $R^A$-10 | $L^1$-1 | Q-20 | $L^2$-1 |
| 339 | 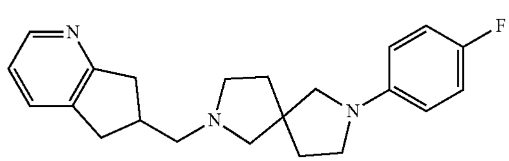 [SMILES: Fc1ccc(N2CCC3(CCN(CC4Cc5cccnc5C4)C3)C2)cc1] | 2-((6,7-dihydro-5H-cyclopenta[b]pyridin-6-yl)methyl)-7-(4-fluorophenyl)-2,7-diazaspiro[4.4]nonane | $R^A$-10 | $L^1$-1 | Q-20 | $L^2$-1 |
| 340 | 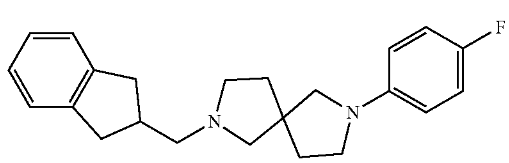 [SMILES: Fc1ccc(N2CCC3(CCN(CC4Cc5ccccc5C4)C3)C2)cc1] | 2-((2,3-dihydro-1H-inden-2-yl)methyl)-7-(4-fluorophenyl)-2,7-diazaspiro[4.4]nonane | $R^A$-10 | $L^1$-1 | Q-20 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 341 | 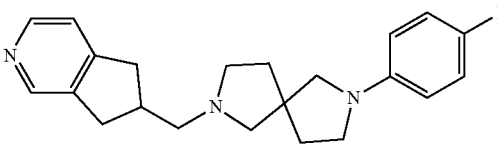 | 2-((6,7-dihydro-5H-cyclopenta[c]pyridin-6-yl)methyl)-7-(4-fluorophenyl)-2,7-diazaspiro[4.4]nonane | $R^A$-11 | $L^1$-1 | Q-20 | $L^2$-1 |
| 342 | 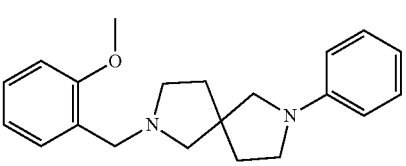 [SMILES: COc1ccccc1CN1CCC2(CCN(c3ccccc3)C2)C1] | 2-(2-methoxybenzyl)-7-phenyl-2,7-diazaspiro[4.4]nonane | $R^A$-22 | $L^1$-1 | Q-20 | $L^2$-1 |
| 343 | 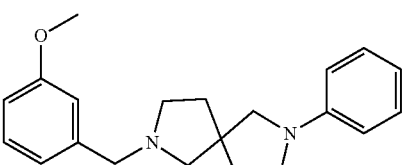 | 2-(3-methoxybenzyl)-7-phenyl-2,7-diazaspiro[4.4]nonane | $R^A$-22 | $L^1$-1 | Q-20 | $L^2$-1 |
| 344 | 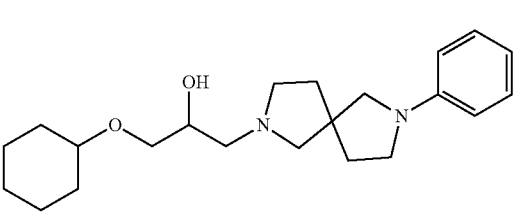 [SMILES: OC(COC1CCCCC1)CN1CCC2(CCN(c3ccccc3)C2)C1] | 1-(cyclohexyloxy)-3-(7-phenyl-2,7-diazaspiro[4.4]nonan-2-yl)propan-2-ol | $R^A$-1 | $L^1$-6 | Q-20 | $L^2$-1 |
| 345 | 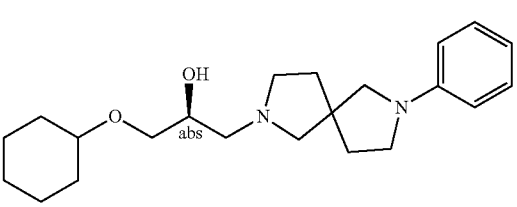 [SMILES: O[C@H](COC1CCCCC1)CN1CCC2(CCN(c3ccccc3)C2)C1] | (2S)-1-(cyclohexyloxy)-3-(7-phenyl-2,7-diazaspiro[4.4]nonan-2-yl)propan-2-ol | $R^A$-1 | $L^1$-6 | Q-20 | $L^2$-1 |
| 346 | 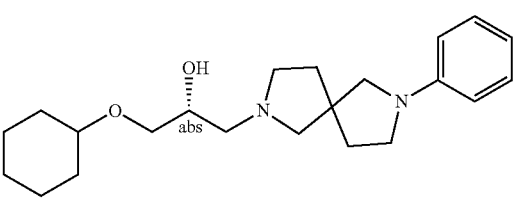 [SMILES: O[C@@H](COC1CCCCC1)CN1CCC2(CCN(c3ccccc3)C2)C1] | (2R)-1-(cyclohexyloxy)-3-(7-phenyl-2,7-diazaspiro[4.4]nonan-2-yl)propan-2-ol | $R^A$-1 | $L^1$-6 | Q-20 | $L^2$-1 |
| 347 | 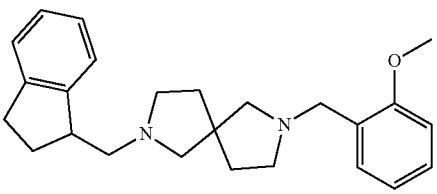 [SMILES: COc1ccccc1CN1CCC2(CCN(CC3CCc4ccccc43)C2)C1] | 2-((2,3-dihydro-1H-inden-1-yl)methyl)-7-(2-methoxybenzyl)-2,7-diazaspiro[4.4]nonane | $R^A$-4 | $L^1$-1 | Q-20 | $L^2$-3 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 348 | 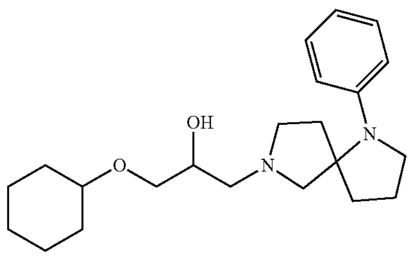 [SMILES: OC(COC1CCCCC1)CN1CCC2(CCCN2c2ccccc2)C1] | 1-(cyclohexyloxy)-3-(1-phenyl-1,7-diazaspiro[4.4]nonan-7-yl)propan-2-ol | $R^A$-1 | $L^1$-6 | Q-21 | $L^2$-1 |
| 349 | 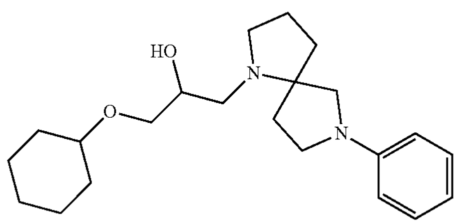 [SMILES: OC(COC1CCCCC1)CN1CCCC12CCN(c1ccccc1)C2] | 1-(cyclohexyloxy)-3-(7-phenyl-1,7-diazaspiro[4.4]nonan-1-yl)propan-2-ol | $R^A$-1 | $L^1$-6 | Q-22 | $L^2$-1 |
| 350 | 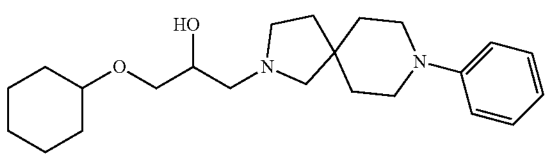 [SMILES: OC(COC1CCCCC1)CN1CCC2(CCN(c3ccccc3)CC2)C1] | 1-(cyclohexyloxy)-3-(8-phenyl-2,8-diazaspiro[4.5]decan-2-yl)propan-2-ol | $R^A$-1 | $L^1$-6 | Q-23 | $L^2$-1 |
| 351 | 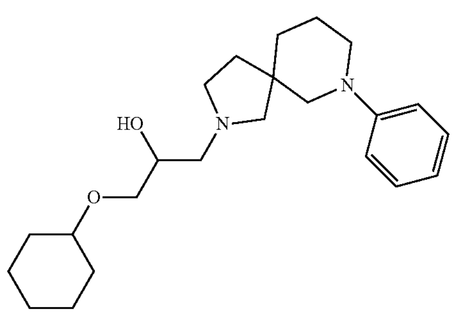 [SMILES: OC(COC1CCCCC1)CN1CCC2(CCCN(c3ccccc3)C2)C1] | 1-(cyclohexyloxy)-3-(7-phenyl-2,7-diazaspiro[4.5]decan-2-yl)propan-2-ol | $R^A$-1 | $L^1$-6 | Q-24 | $L^2$-1 |
| 352 | 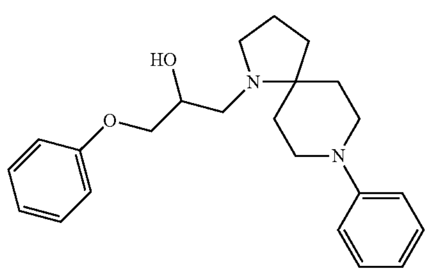 [SMILES: OC(COc1ccccc1)CN1CCCC12CCN(c1ccccc1)CC2] | 1-phenoxy-3-(8-phenyl-1,8-diazaspiro[4.5]decan-1-yl)propan-2-ol | $R^A$-22 | $L^1$-6 | Q-25 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 353 | 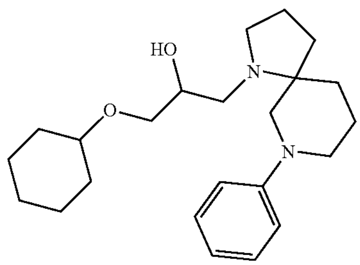 [SMILES: OC(COC1CCCCC1)CN1CCCC12CCCN(c1ccccc1)C2] | 1-(cyclohexyloxy)-3-(7-phenyl-1,7-diazaspiro[4.5]decan-1-yl)propan-2-ol | $R^A$-1 | $L^1$-6 | Q-26 | $L^2$-1 |
| 354 | 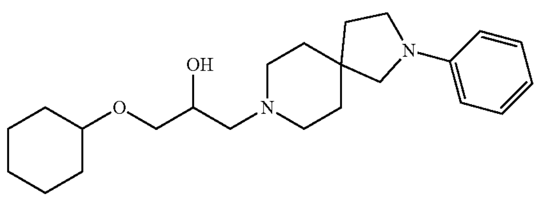 [SMILES: OC(COC1CCCCC1)CN1CCC2(CC1)CCN(c1ccccc1)C2] | 1-(cyclohexyloxy)-3-(2-phenyl-2,8-diazaspiro[4.5]decan-8-yl)propan-2-ol | $R^A$-1 | $L^1$-6 | Q-27 | $L^2$-1 |
| 355 | 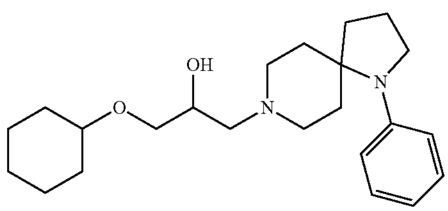 [SMILES: OC(COC1CCCCC1)CN1CCC2(CCCN2c2ccccc2)CC1] | 1-(cyclohexyloxy)-3-(1-phenyl-1,8-diazaspiro[4.5]decan-8-yl)propan-2-ol | $R^A$-1 | $L^1$-6 | Q-28 | $L^2$-1 |
| 356 | 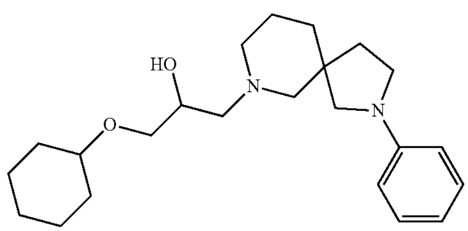 [SMILES: OC(COC1CCCCC1)CN1CCCC2(CCN(c3ccccc3)C2)C1] | 1-(cyclohexyloxy)-3-(2-phenyl-2,7-diazaspiro[4.5]decan-7-yl)propan-2-ol | $R^A$-1 | $L^1$-6 | Q-29 | $L^2$-1 |
| 357 | 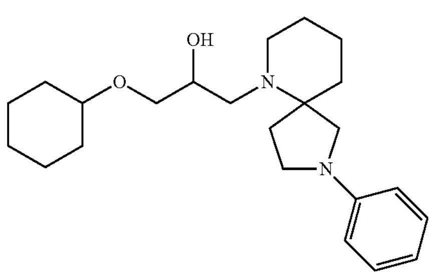 [SMILES: OC(COC1CCCCC1)CN1CCCCC12CCN(c1ccccc1)C2] | 1-(cyclohexyloxy)-3-(2-phenyl-2,6-diazaspiro[4.5]decan-6-yl)propan-2-ol | $R^A$-1 | $L^1$-6 | Q-30 | $L^2$-1 |
| 358 | 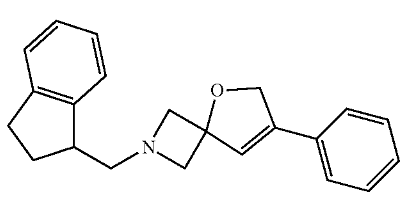 [SMILES: C1=C(c2ccccc2)COC12CN(CC1CCc3ccccc31)C2] | 2-((2,3-dihydro-1H-inden-1-yl)methyl)-7-phenyl-5-oxa-2-azaspiro[3.4]oct-7-ene | $R^A$-4 | $L^1$-1 | Q-31 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 359 | 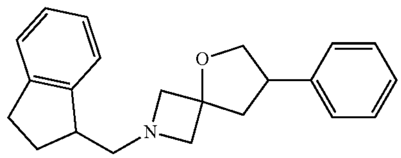 [SMILES: c1ccc(C2COC3(C2)CN(CC2CCc4ccccc42)C3)cc1] | 2-((2,3-dihydro-1H-inden-1-yl)methyl)-7-phenyl-5-oxa-2-azaspiro[3.4]octane | $R^A$-4 | $L^1$-1 | Q-32 | $L^2$-1 |
| 360 | 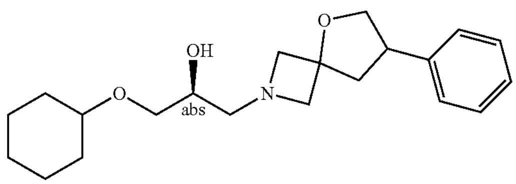 [SMILES: O[C@H](COC1CCCCC1)CN1CC2(CC(c3ccccc3)CO2)C1] | (2S)-1-(cyclohexyloxy)-3-(7-phenyl-5-oxa-2-azaspiro[3.4]octan-2-yl)propan-2-ol | $R^A$-1 | $L^1$-6 | Q-32 | $L^2$-1 |
| 361 | 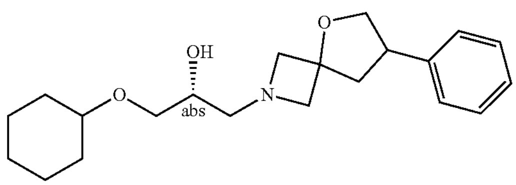 [SMILES: O[C@@H](COC1CCCCC1)CN1CC2(CC(c3ccccc3)CO2)C1] | (2R)-1-(cyclohexyloxy)-3-(7-phenyl-5-oxa-2-azaspiro[3.4]octan-2-yl)propan-2-ol | $R^A$-1 | $L^1$-6 | Q-32 | $L^2$-1 |
| 362 | 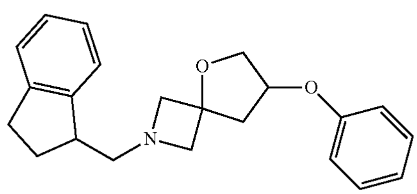 [SMILES: c1ccc(OC2COC3(C2)CN(CC2CCc4ccccc42)C3)cc1] | 2-((2,3-dihydro-1H-inden-1-yl)methyl)-7-phenoxy-5-oxa-2-azaspiro[3.4]octane | $R^A$-4 | $L^1$-1 | Q-32 | $L^2$-2 |
| 363 | 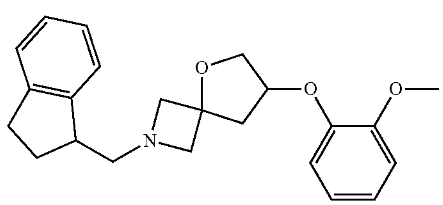 [SMILES: COc1ccccc1OC1COC2(C1)CN(CC1CCc3ccccc31)C2] | 2-((2,3-dihydro-1H-inden-1-yl)methyl)-7-(2-methoxyphenoxy)-5-oxa-2-azaspiro[3.4]octane | $R^A$-4 | $L^1$-1 | Q-32 | $L^2$-2 |
| 364 | 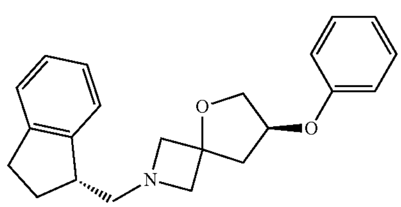 [SMILES: c1ccc(O[C@@H]2COC3(C2)CN(C[C@@H]2CCc4ccccc42)C3)cc1] | (S)-2-(((R)-2,3-dihydro-1H-inden-1-yl)methyl)-7-phenoxy-5-oxa-2-azaspiro[3.4]octane | $R^A$-4 | $L^1$-1 | Q-32 | $L^2$-2 |
| 365 | 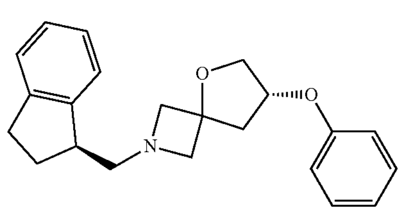 [SMILES: c1ccc(O[C@H]2COC3(C2)CN(C[C@H]2CCc4ccccc42)C3)cc1] | (R)-2-(((S)-2,3-dihydro-1H-inden-1-yl)methyl)-7-phenoxy-5-oxa-2-azaspiro[3.4]octane | $R^A$-4 | $L^1$-1 | Q-32 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 366 | 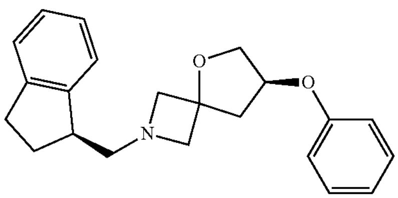 [SMILES: c1ccc(O[C@@H]2COC3(C2)CN(C[C@H]2CCc4ccccc42)C3)cc1] | (S)-2-(((S)-2,3-dihydro-1H-inden-1-yl)methyl)-7-phenoxy-5-oxa-2-azaspiro[3.4]octane | $R^A$-4 | $L^1$-1 | Q-32 | $L^2$-2 |
| 367 | 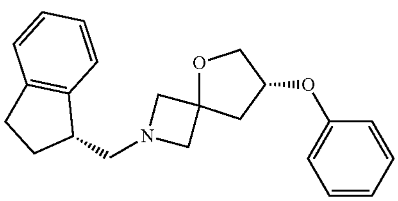 [SMILES: c1ccc(O[C@H]2COC3(C2)CN(C[C@@H]2CCc4ccccc42)C3)cc1] | (R)-2-(((R)-2,3-dihydro-1H-inden-1-yl)methyl)-7-phenoxy-5-oxa-2-azaspiro[3.4]octane | $R^A$-4 | $L^1$-1 | Q-32 | $L^2$-2 |
| 368 | 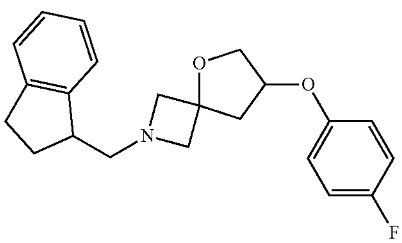 [SMILES: Fc1ccc(OC2COC3(C2)CN(CC2CCc4ccccc42)C3)cc1] | 2-((2,3-dihydro-1H-inden-1-yl)methyl)-7-(4-fluorophenoxy)-5-oxa-2-azaspiro[3.4]octane | $R^A$-4 | $L^1$-1 | Q-32 | $L^2$-2 |
| 369 | 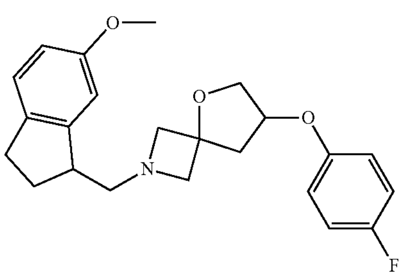 [SMILES: COc1ccc2c(c1)C(CN1CC3(CC(Oc4ccc(F)cc4)CO3)C1)CC2] | 7-(4-fluorophenoxy)-2-((6-methoxy-2,3-dihydro-1H-inden-1-yl)methyl)-5-oxa-2-azaspiro[3.4]octane | $R^A$-4 | $L^1$-1 | Q-32 | $L^2$-2 |
| 370 | 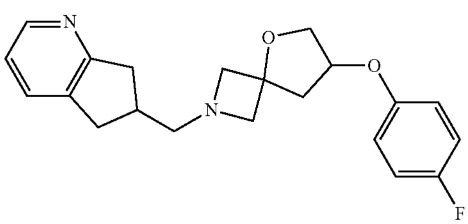 [SMILES: Fc1ccc(OC2COC3(C2)CN(CC2Cc4cccnc4C2)C3)cc1] | 2-((6,7-dihydro-5H-cyclopenta[b]pyridin-6-yl)methyl)-7-(4-fluorophenoxy)-5-oxa-2-azaspiro[3.4]octane | $R^A$-10 | $L^1$-1 | Q-32 | $L^2$-2 |
| 371 | 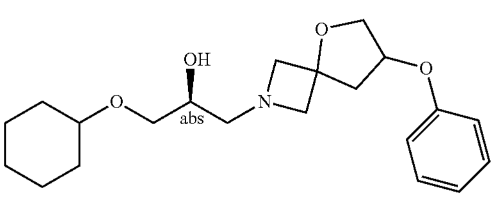 [SMILES: O[C@H](COC1CCCCC1)CN1CC2(CC(Oc3ccccc3)CO2)C1] | (2S)-1-(cyclohexyloxy)-3-(7-phenoxy-5-oxa-2-azaspiro[3.4]octan-2-yl)propan-2-ol | $R^A$-1 | $L^1$-6 | Q-32 | $L^2$-2 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 372 | 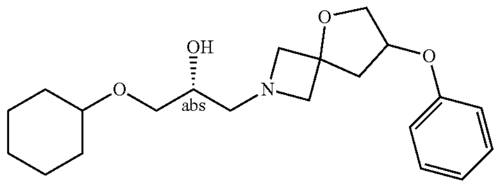 [SMILES: O[C@@H](COC1CCCCC1)CN1CC2(CC(Oc3ccccc3)CO2)C1] | (2R)-1-(cyclohexyloxy)-3-(7-phenoxy-5-oxa-2-azaspiro[3.4]octan-2-yl)propan-2-ol | $R^A$-1 | $L^1$-6 | Q-32 | $L^2$-2 |
| 373 | 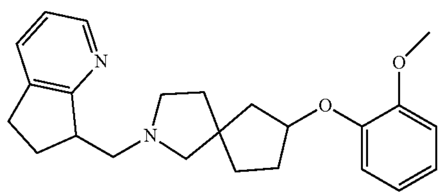 [SMILES: COc1ccccc1OC1CCC2(CCN(CC3CCc4cccnc43)C2)C1] | 2-((6,7-dihydro-5H-cyclopenta[b]pyridin-7-yl)methyl)-7-(2-methoxyphenoxy)-2-azaspiro[4.4]nonane | $R^A$-8 | $L^1$-1 | Q-33 | $L^2$-2 |
| 374 | 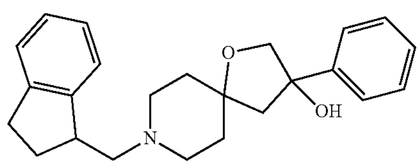 [SMILES: OC1(c2ccccc2)COC2(CCN(CC3CCc4ccccc43)CC2)C1] | 8-((2,3-dihydro-1H-inden-1-yl)methyl)-3-phenyl-1-oxa-8-azaspiro[4.5]decan-3-ol | $R^A$-4 | $L^1$-1 | Q-34 | $L^2$-1 |
| 375 | 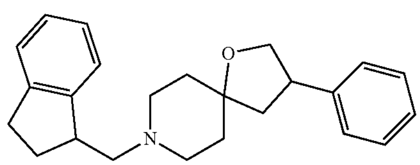 [SMILES: c1ccc(C2COC3(CCN(CC4CCc5ccccc54)CC3)C2)cc1] | 8-((2,3-dihydro-1H-inden-1-yl)methyl)-3-phenyl-1-oxa-8-azaspiro[4.5]decane | $R^A$-4 | $L^1$-1 | Q-34 | $L^2$-1 |
| 376 | 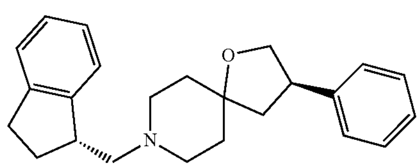 [SMILES: c1ccc([C@@H]2COC3(CCN(C[C@@H]4CCc5ccccc54)CC3)C2)cc1] | (R)-8-(((R)-2,3-dihydro-1H-inden-1-yl)methyl)-3-phenyl-1-oxa-8-azaspiro[4.5]decane | $R^A$-4 | $L^1$-1 | Q-34 | $L^2$-1 |
| 377 | 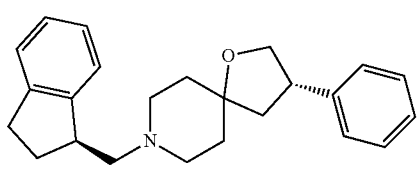 [SMILES: c1ccc([C@H]2COC3(CCN(C[C@H]4CCc5ccccc54)CC3)C2)cc1] | (S)-8-(((S)-2,3-dihydro-1H-inden-1-yl)methyl)-3-phenyl-1-oxa-8-azaspiro[4.5]decane | $R^A$-4 | $L^1$-1 | Q-34 | $L^2$-1 |
| 378 | 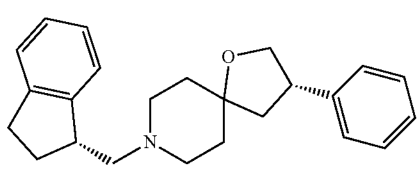 [SMILES: c1ccc([C@H]2COC3(CCN(C[C@@H]4CCc5ccccc54)CC3)C2)cc1] | (S)-8-(((R)-2,3-dihydro-1H-inden-1-yl)methyl)-3-phenyl-1-oxa-8-azaspiro[4.5]decane | $R^A$-4 | $L^1$-1 | Q-34 | $L^2$-1 |
| 379 | 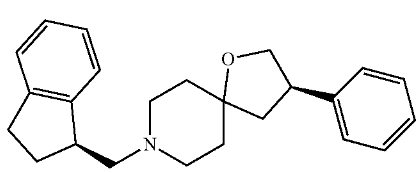 [SMILES: c1ccc([C@@H]2COC3(CCN(C[C@H]4CCc5ccccc54)CC3)C2)cc1] | (R)-8-(((S)-2,3-dihydro-1H-inden-1-yl)methyl)-3-phenyl-1-oxa-8-azaspiro[4.5]decane | $R^A$-4 | $L^1$-1 | Q-34 | $L^2$-1 |

TABLE 5-continued

Summary of synthesis of Compounds. Compounds were synthesized by coupling the R$^A$ group coupling partners to the Q group coupling partners through the L$^1$ linker and coupling the R$^B$ group coupling partners to the Q group coupling partners through the L$^2$ linker. The R$^A$ coupling chemistry used is described in Example L$^1$. The R$^B$ coupling chemistry is described in Example L$^2$. Synthetic details for the transformations described in Examples Example L$^1$, Example L$^2$, Example R$^A$ and Example R$^B$ are in Example T. The table below lists the R$^A$, L$^1$, Q, L$^2$ and R$^B$ groups whose coupling partners were used in the syntheses.

| | Structure | Chem Name | R$^A$ | L$^1$ | Q | L$^2$ |
|---|---|---|---|---|---|---|
| 380 | 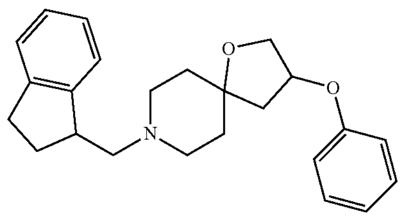 [SMILES: c1ccc(OC2COC3(CCN(CC4CCc5ccccc54)CC3)C2)cc1] | 8-((2,3-dihydro-1H-inden-1-yl)methyl)-3-phenoxy-1-oxa-8-azaspiro[4.5]decane | R$^A$-4 | L$^1$-1 | Q-34 | L$^2$-2 |
| 381 | 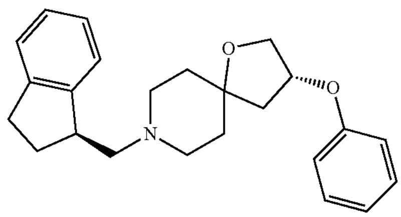 [SMILES: c1ccc(O[C@H]2COC3(CCN(C[C@H]4CCc5ccccc54)CC3)C2)cc1] | (R)-8-(((S)-2,3-dihydro-1H-inden-1-yl)methyl)-3-phenoxy-1-oxa-8-azaspiro[4.5]decane | R$^A$-4 | L$^1$-1 | Q-34 | L$^2$-2 |
| 382 | 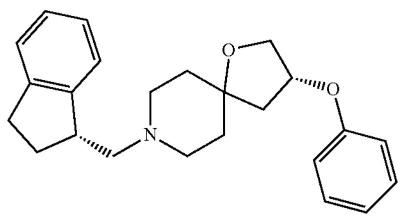 [SMILES: c1ccc(O[C@H]2COC3(CCN(C[C@@H]4CCc5ccccc54)CC3)C2)cc1] | (R)-8-(((R)-2,3-dihydro-1H-inden-1-yl)methyl)-3-phenoxy-1-oxa-8-azaspiro[4.5]decane | R$^A$-4 | L$^1$-1 | Q-34 | L$^2$-2 |
| 383 | 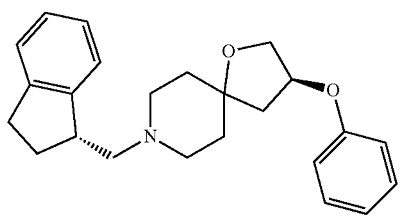 [SMILES: c1ccc(O[C@@H]2COC3(CCN(C[C@@H]4CCc5ccccc54)CC3)C2)cc1] | (S)-8-(((R)-2,3-dihydro-1H-inden-1-yl)methyl)-3-phenoxy-1-oxa-8-azaspiro[4.5]decane | R$^A$-4 | L$^1$-1 | Q-34 | L$^2$-2 |
| 384 | 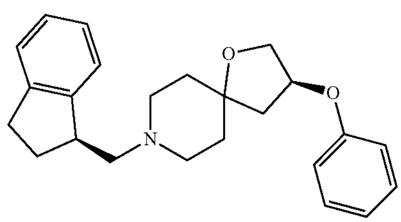 [SMILES: c1ccc(O[C@@H]2COC3(CCN(C[C@H]4CCc5ccccc54)CC3)C2)cc1] | (S)-8-(((S)-2,3-dihydro-1H-inden-1-yl)methyl)-3-phenoxy-1-oxa-8-azaspiro[4.5]decane | R$^A$-4 | L$^1$-1 | Q-34 | L$^2$-2 |
| 385 | 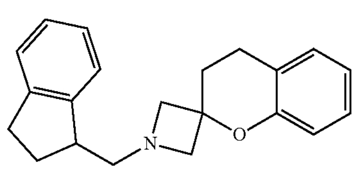 [SMILES: c1ccc2c(c1)CCC1(CN(CC3CCc4ccccc43)C1)O2] | 1-((2,3-dihydro-1H-inden-1-yl)methyl)spiro[azetidine-3,2'-chromane] | R$^A$-4 | L$^1$-1 | Q-35 | L$^2$-1 |
| 386 | 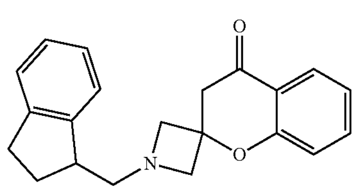 [SMILES: O=C1CC2(CN(CC3CCc4ccccc43)C2)Oc2ccccc21] | 1-((2,3-dihydro-1H-inden-1-yl)methyl)spiro[azetidine-3,2'-chroman]-4'-one | R$^A$-4 | L$^1$-1 | Q-36 | L$^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 387 | 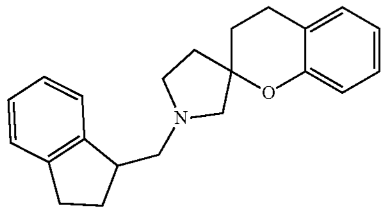 [SMILES: c1ccc2c(c1)CCC1(CCN(CC3CCc4ccccc43)C1)O2] | 1'-((2,3-dihydro-1H-inden-1-yl)methyl)spiro[chromane-2,3'-pyrrolidine] | $R^A$-4 | $L^1$-1 | Q-37 | $L^2$-1 |
| 388 | 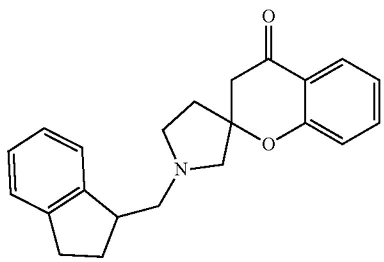 [SMILES: O=C1CC2(CCN(CC3CCc4ccccc43)C2)Oc2ccccc21] | 1'-((2,3-dihydro-1H-inden-1-yl)methyl)spiro[chromane-2,3'-pyrrolidin]-4-one | $R^A$-4 | $L^1$-1 | Q-38 | $L^2$-1 |
| 389 | 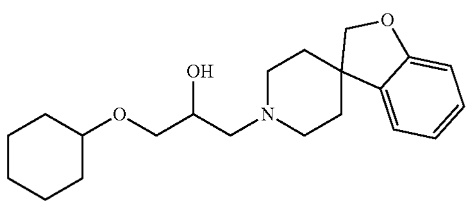 [SMILES: OC(COC1CCCCC1)CN1CCC2(CC1)COc1ccccc12] | 1-(cyclohexyloxy)-3-(2H-spiro[benzofuran-3,4'-piperidin]-1'-yl)propan-2-ol | $R^A$-1 | $L^1$-6 | Q-39 | $L^2$-1 |
| 390 | 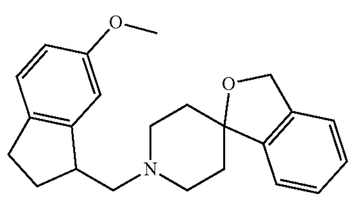 [SMILES: COc1ccc2c(c1)C(CN1CCC3(CC1)OCc1ccccc13)CC2] | 1'-((6-methoxy-2,3-dihydro-1H-inden-1-yl)methyl)-3H-spiro[isobenzofuran-1,4'-piperidine] | $R^A$-4 | $L^1$-1 | Q-40 | $L^2$-1 |
| 391 | 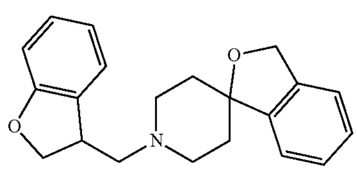 [SMILES: c1ccc2c(c1)COC21CCN(CC2COc3ccccc32)CC1] | 1'-((2,3-dihydrobenzofuran-3-yl)methyl)-3H-spiro[isobenzofuran-1,4'-piperidine] | $R^A$-9 | $L^1$-1 | Q-40 | $L^2$-1 |
| 392 | 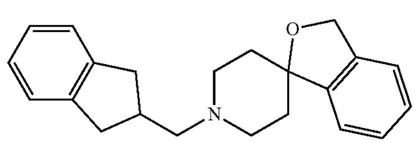 [SMILES: c1ccc2c(c1)CC(CN1CCC3(CC1)OCc1ccccc13)C2] | 1'-((2,3-dihydro-1H-inden-2-yl)methyl)-3H-spiro[isobenzofuran-1,4'-piperidine] | $R^A$-10 | $L^1$-1 | Q-40 | $L^2$-1 |
| 393 | 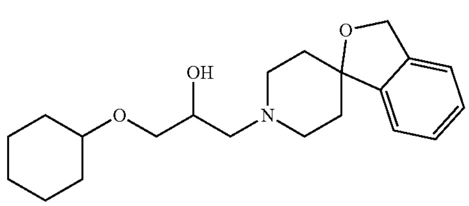 [SMILES: OC(COC1CCCCC1)CN1CCC2(CC1)OCc1ccccc12] | 1'-(cyclohexyloxy)-3-(3H-spiro[isobenzofuran-1,4'-piperidin]-1'-yl)propan-2-ol | $R^A$-1 | $L^1$-6 | Q-40 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| # | Structure | Chem Name | $R^A$ | $L^1$ | Q | $L^2$ |
|---|---|---|---|---|---|---|
| 394 | 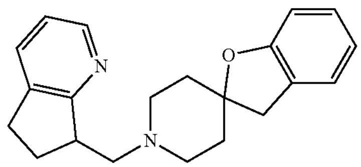 [SMILES: c1ccc2c(c1)CC1(CCN(CC3CCc4cccnc43)CC1)O2] | 1'-((6,7-dihydro-5H-cyclopenta[b]pyridin-7-yl)methyl)-3H-spiro[benzofuran-2,4'-piperidine] | $R^A$-8 | $L^1$-1 | Q-41 | $L^2$-1 |
| 395 | 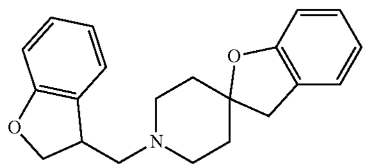 [SMILES: c1ccc2c(c1)CC1(CCN(CC3COc4ccccc43)CC1)O2] | 1'-((2,3-dihydrobenzofuran-3-yl)methyl)-3H-spiro[benzofuran-2,4'-piperidine] | $R^A$-9 | $L^1$-1 | Q-41 | $L^2$-1 |
| 396 | 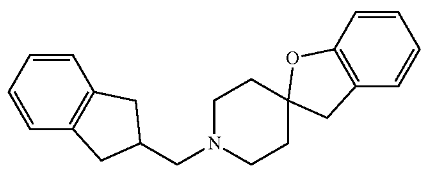 | 1'-((2,3-dihydro-1H-inden-2-yl)methyl)-3H-spiro[benzofuran-2,4'-piperidine] | $R^A$-10 | $L^1$-1 | Q-41 | $L^2$-1 |
| 397 | 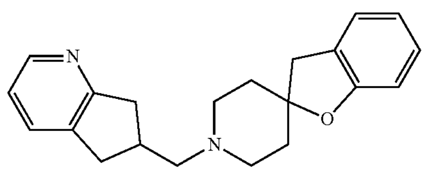 [SMILES: c1ccc2c(c1)CC1(CCN(CC3Cc4cccnc4C3)CC1)O2] | 1'-((6,7-dihydro-5H-cyclopenta[b]pyridin-6-yl)methyl)-3H-spiro[benzofuran-2,4'-piperidine] | $R^A$-10 | $L^1$-1 | Q-41 | $L^2$-1 |
| 398 | 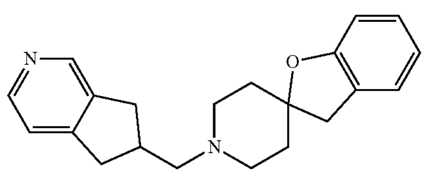 [SMILES: c1ccc2c(c1)CC1(CCN(CC3Cc4ccncc4C3)CC1)O2] | 1'-((6,7-dihydro-5H-cyclopenta[c]pyridin-6-yl)methyl)-3H-spiro[benzofuran-2,4'-piperidine] | $R^A$-11 | $L^1$-1 | Q-41 | $L^2$-1 |
| 399 | 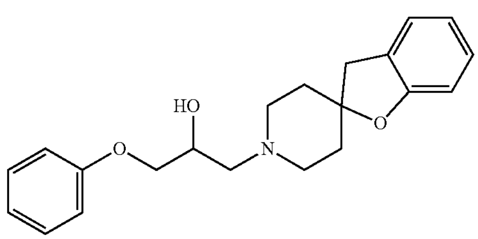 [SMILES: OC(COc1ccccc1)CN1CCC2(CC1)Cc1ccccc1O2] | 1-phenoxy-3-(3H-spiro[benzofuran-2,4'-piperidin]-1'-yl)propan-2-ol | $R^A$-22 | $L^1$-6 | Q-41 | $L^2$-1 |
| 400 | 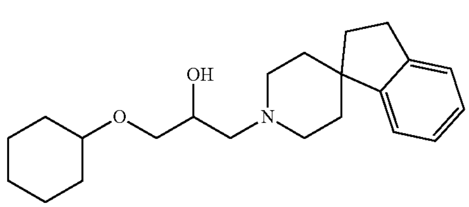 [SMILES: OC(COC1CCCCC1)CN1CCC2(CCc3ccccc32)CC1] | 1-(cyclohexyloxy)-3-(2,3-dihydrospiro[indene-1,4'-piperidin]-1'-yl)propan-2-ol | $R^A$-1 | $L^1$-6 | Q-42 | $L^2$-1 |
| 401 | 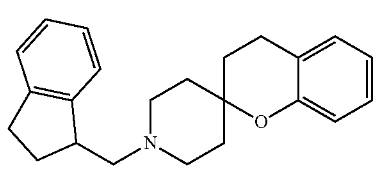 [SMILES: c1ccc2c(c1)CCC1(CCN(CC3CCc4ccccc43)CC1)O2] | 1'-((2,3-dihydro-1H-inden-1-yl)methyl)spiro[chromane-2,4'-piperidine] | $R^A$-4 | $L^1$-1 | Q-43 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 402 | 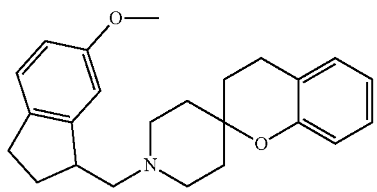 [SMILES: COc1ccc2c(c1)C(CN1CCC3(CCc4ccccc4O3)CC1)CC2] | 1'-((6-methoxy-2,3-dihydro-1H-inden-1-yl)methyl)spiro[chromane-2,4'-piperidine] | $R^A$-4 | $L^1$-1 | Q-43 | $L^2$-1 |
| 403 | 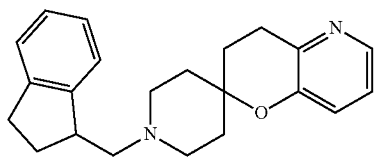 [SMILES: c1ccc2c(c1)CCC2CN1CCC2(CCc3ncccc3O2)CC1] | 1-((2,3-dihydro-1H-inden-1-yl)methyl)-3',4'-dihydrospiro[piperidine-4,2'-pyrano[3,2-b]pyridine] | $R^A$-4 | $L^1$-1 | Q-43 | $L^2$-1 |
| 404 | 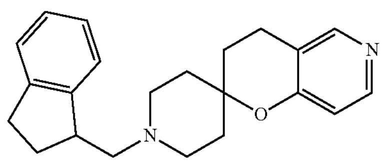 [SMILES: c1ccc2c(c1)CCC2CN1CCC2(CCc3cnccc3O2)CC1] | 1-((2,3-dihydro-1H-inden-1-yl)methyl)-3',4'-dihydrospiro[piperidine-4,2'-pyrano[3,2-c]pyridine] | $R^A$-4 | $L^1$-1 | Q-43 | $L^2$-1 |
| 405 | 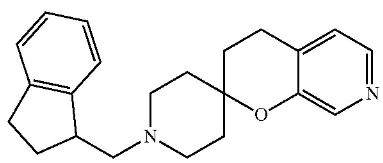 [SMILES: c1ccc2c(c1)CCC2CN1CCC2(CCc3ccncc3O2)CC1] | 1-((2,3-dihydro-1H-inden-1-yl)methyl)-3',4'-dihydrospiro[piperidine-4,2'-pyrano[2,3-c]pyridine] | $R^A$-4 | $L^1$-1 | Q-43 | $L^2$-1 |
| 406 | 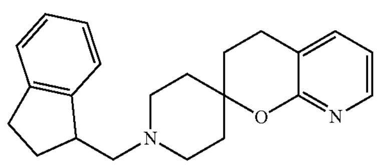 [SMILES: c1ccc2c(c1)CCC2CN1CCC2(CCc3cccnc3O2)CC1] | 1-((2,3-dihydro-1H-inden-1-yl)methyl)-3',4'-dihydrospiro[piperidine-4,2'-pyrano[2,3-b]pyridine] | $R^A$-4 | $L^1$-1 | Q-43 | $L^2$-1 |
| 407 | 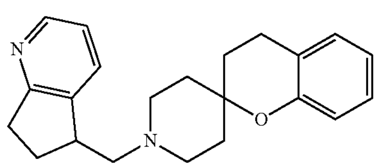 [SMILES: c1ccc2c(c1)CCC1(CCN(CC3CCc4ncccc43)CC1)O2] | 1'-((6,7-dihydro-5H-cyclopenta[b]pyridin-5-yl)methyl)spiro[chromane-2,4'-piperidine] | $R^A$-5 | $L^1$-1 | Q-43 | $L^2$-1 |
| 408 | 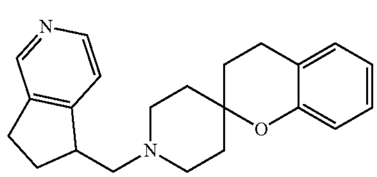 [SMILES: c1ccc2c(c1)CCC1(CCN(CC3CCc4cnccc43)CC1)O2] | 1'-((6,7-dihydro-5H-cyclopenta[c]pyridin-5-yl)methyl)spiro[chromane-2,4'-piperidine] | $R^A$-6 | $L^1$-1 | Q-43 | $L^2$-1 |
| 409 | 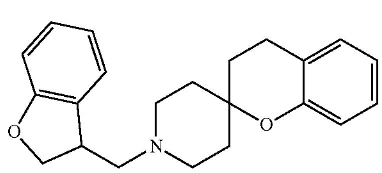 [SMILES: c1ccc2c(c1)CCC1(CCN(CC3COc4ccccc43)CC1)O2] | 1'-((2,3-dihydrobenzofuran-3-yl)methyl)spiro[chromane-2,4'-piperidine | $R^A$-9 | $L^1$-1 | Q-43 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 410 | 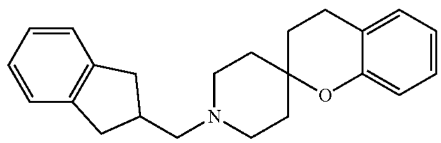 [SMILES: c1ccc2c(c1)CC(CN1CCC3(CCc4ccccc4O3)CC1)C2] | 1'-((2,3-dihydro-1H-inden-2-yl)methyl)spiro[chromane-2,4'-piperidine] | $R^A$-10 | $L^1$-1 | Q-43 | $L^2$-1 |
| 411 | 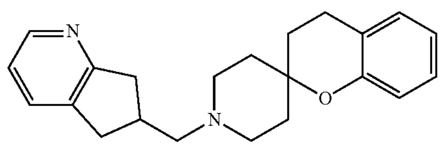 [SMILES: c1ccc2c(c1)CCC1(CCN(CC3Cc4cccnc4C3)CC1)O2] | 1'-((6,7-dihydro-5H-cyclopenta[b]pyridin-6-yl)methyl)spiro[chromane-2,4'-piperidine] | $R^A$-10 | $L^1$-1 | Q-43 | $L^2$-1 |
| 412 | 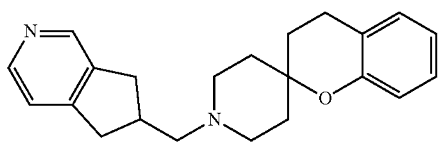 | 1'-((6,7-dihydro-5H-cyclopenta[c]pyridin-6-yl)methyl)spiro[chromane-2,4'-piperidine] | $R^A$-11 | $L^1$-1 | Q-43 | $L^2$-1 |
| 413 | 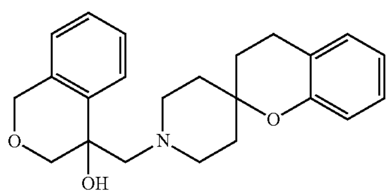 [SMILES: OC1(CN2CCC3(CCc4ccccc4O3)CC2)COCc2ccccc21] | 4-(spiro[chromane-2,4'-piperidin]-1'-ylmethyl)isochroman-4-ol | $R^A$-12 | $L^1$-1 | Q-43 | $L^2$-1 |
| 414 | 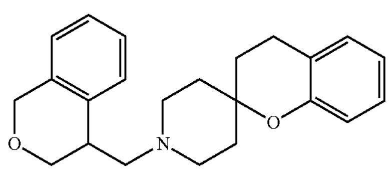 [SMILES: c1ccc2c(c1)CCC1(CCN(CC3COCc4ccccc43)CC1)O2] | 1'-(isochroman-4-ylmethyl)spiro[chromane-2,4'-piperidine] | $R^A$-12 | $L^1$-1 | Q-43 | $L^2$-1 |
| 415 | 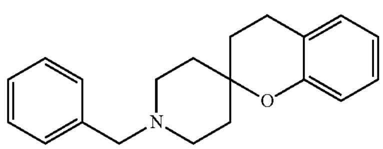 [SMILES: c1ccc(CN2CCC3(CCc4ccccc4O3)CC2)cc1] | 1'-benzylspiro[chromane-2,4'-piperidine] | $R^A$-22 | $L^1$-1 | Q-43 | $L^2$-1 |
| 416 | 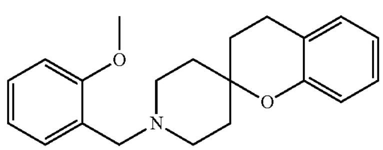 [SMILES: COc1ccccc1CN1CCC2(CCc3ccccc3O2)CC1] | 1'-(2-methoxybenzyl)spiro[chromane-2,4'-piperidine] | $R^A$-22 | $L^1$-1 | Q-43 | $L^2$-1 |
| 417 | 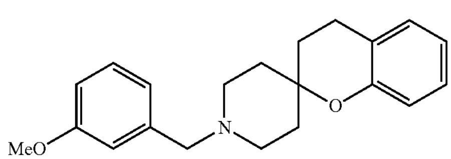 [SMILES: COc1cccc(CN2CCC3(CCc4ccccc4O3)CC2)c1] | 1'-(3-methoxybenzyl)spiro[chromane-2,4'-piperidine] | $R^A$-22 | $L^1$-1 | Q-43 | $L^2$-1 |
| 418 | 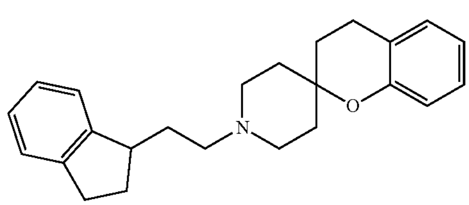 [SMILES: c1ccc2c(c1)CCC1(CCN(CCC3CCc4ccccc43)CC1)O2] | 1'-(2-(2,3-dihydro-1H-inden-1-yl)ethyl)spiro[chromane-2,4'-piperidine] | $R^A$-4 | $L^1$-2 | Q-43 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 419 | 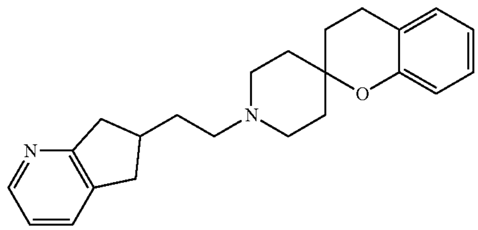 [SMILES: c1ccc2c(c1)CCC1(CCN(CCC3Cc4cccnc4C3)CC1)O2] | 1'-(2-(6,7-dihydro-5H-cyclopenta[b]pyridin-6-yl)ethyl)spiro[chromane-2,4'-piperidine] | $R^A$-10 | $L^1$-2 | Q-43 | $L^2$-1 |
| 420 | 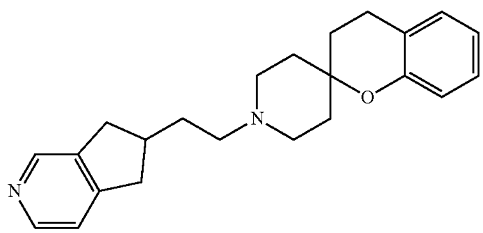 [SMILES: c1ccc2c(c1)CCC1(CCN(CCC3Cc4ccncc4C3)CC1)O2] | 1'-(2-(6,7-dihydro-5H-cyclopenta[c]pyridin-6-yl)ethyl)spiro[chromane-2,4'-piperidine] | $R^A$-11 | $L^1$-2 | Q-43 | $L^2$-1 |
| 421 | 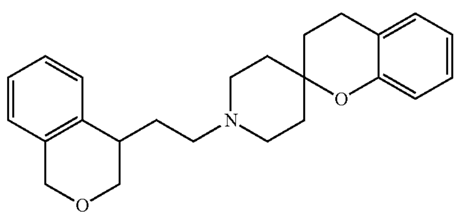 [SMILES: c1ccc2c(c1)CCC1(CCN(CCC3COCc4ccccc43)CC1)O2] | 1'-(2-(isochroman-4-yl)ethyl)spiro[chromane-2,4'-piperidine] | $R^A$-12 | $L^1$-2 | Q-43 | $L^2$-1 |
| 422 | 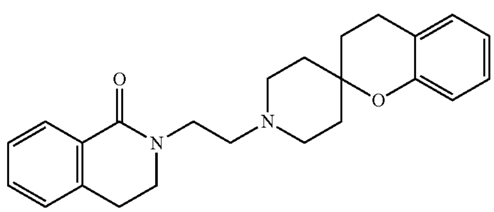 [SMILES: O=C1c2ccccc2CCN1CCN1CCC2(CCc3ccccc3O2)CC1] | 2-(2-(spiro[chromane-2,4'-piperidin]-1'-yl)ethyl)-3,4-dihydroisoquinolin-1(2H)-one | $R^A$-19 | $L^1$-2 | Q-43 | $L^2$-1 |
| 423 | 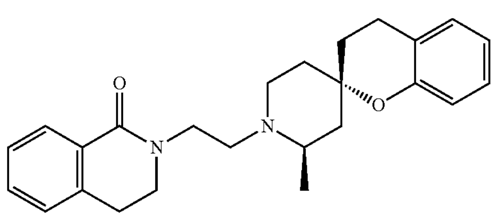 [SMILES: C[C@@H]1C[C@]2(CCc3ccccc3O2)CCN1CCN1CCc2ccccc2C1=O] | 2-(2-((2S,2'R)-2'-methylspiro[chromane-2,4'-piperidin]-1'-yl)ethyl)-3,4-dihydroisoquinolin-1(2H)-one | $R^A$-19 | $L^1$-2 | Q-43 | $L^2$-1 |
| 424 | 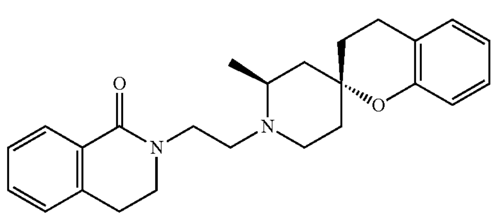 [SMILES: C[C@H]1C[C@@]2(CCc3ccccc3O2)CCN1CCN1CCc2ccccc2C1=O] | 2-(2-((2R,2'S)-2'-methylspiro[chromane-2,4'-piperidin]-1'-yl)ethyl)-3,4-dihydroisoquinolin-1(2H)-one | $R^A$-19 | $L^1$-2 | Q-43 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 425 | 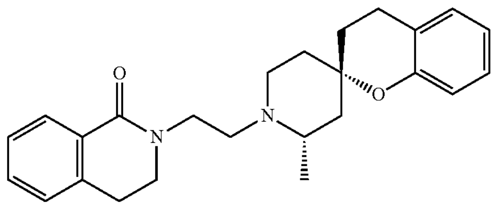 [SMILES: C[C@H]1C[C@]2(CCc3ccccc3O2)CCN1CCN1CCc2ccccc2C1=O] | 2-(2-((2S,2'S)-2'-methylspiro[chromane-2,4'-piperidin]-1'-yl)ethyl)-3,4-dihydroisoquinolin-1(2H)-one | $R^A$-19 | $L^1$-2 | Q-43 | $L^2$-1 |
| 426 | 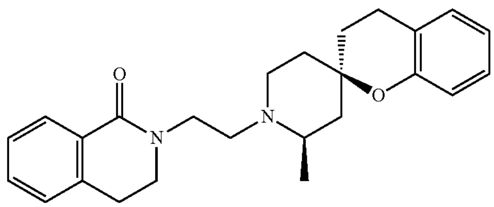 [SMILES: C[C@@H]1C[C@@]2(CCc3ccccc3O2)CCN1CCN1CCc2ccccc2C1=O] | 2-(2-((2R,2'R)-2'-methylspiro[chromane-2,4'-piperidin]-1'-yl)ethyl)-3,4-dihydroisoquinolin-1(2H)-one | $R^A$-19 | $L^1$-2 | Q-43 | $L^2$-1 |
| 427 | 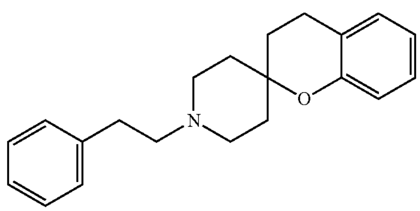 [SMILES: c1ccc(CCN2CCC3(CCc4ccccc4O3)CC2)cc1] | 1'-phenethylspiro[chromane-2,4'-piperidine] | $R^A$-22 | $L^1$-2 | Q-43 | $L^2$-1 |
| 428 | 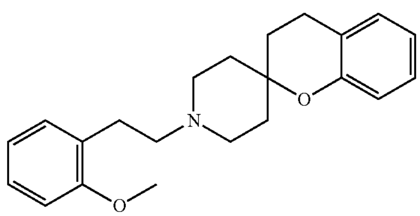 [SMILES: COc1ccccc1CCN1CCC2(CCc3ccccc3O2)CC1] | 1'-(2-methoxyphenethyl)spiro[chromane-2,4'-piperidine] | $R^A$-22 | $L^1$-2 | Q-43 | $L^2$-1 |
| 429 | 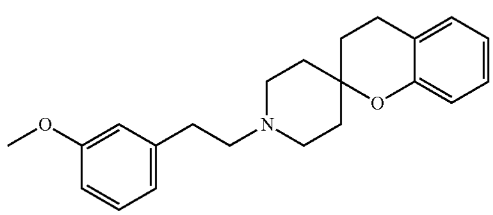 [SMILES: COc1cccc(CCN2CCC3(CCc4ccccc4O3)CC2)c1] | 1'-(3-methoxyphenethyl)spiro[chromane-2,4'-piperidine] | $R^A$-22 | $L^1$-2 | Q-43 | $L^2$-1 |
| 431 | 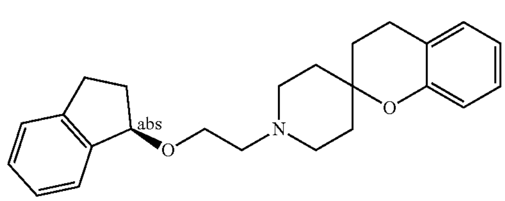 [SMILES: c1ccc2c(c1)CCC1(CCN(CCO[C@@H]3CCc4ccccc43)CC1)O2] | (R)-1'-(2-((2,3-dihydro-1H-inden-1-yl)oxy)ethyl)spiro[chromane-2,4'-piperidine] | $R^A$-4 | $L^1$-4 | Q-43 | $L^2$-1 |
| 432 | 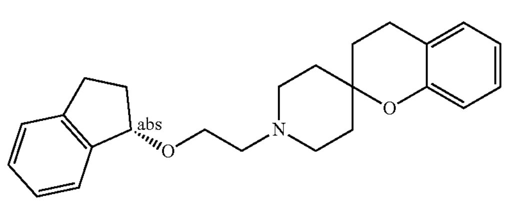 [SMILES: c1ccc2c(c1)CCC1(CCN(CCO[C@H]3CCc4ccccc43)CC1)O2] | (S)-1'-(2-((2,3-dihydro-1H-inden-1-yl)oxy)ethyl)spiro[chromane-2,4'-piperidine] | $R^A$-4 | $L^1$-4 | Q-43 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T.
The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 433 | 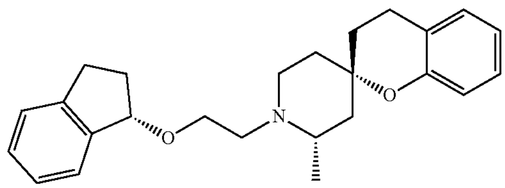 [SMILES: C[C@H]1C[C@]2(CCc3ccccc3O2)CCN1CCO[C@H]1CCc2ccccc21] | (2S,2'S)-1'-(2-(((S)-2,3-dihydro-1H-inden-1-yl)oxy)ethyl)-2'-methylspiro[chromane-2,4'-piperidine] | $R^A$-4 | $L^1$-4 | Q-43 | $L^2$-1 |
| 434 | 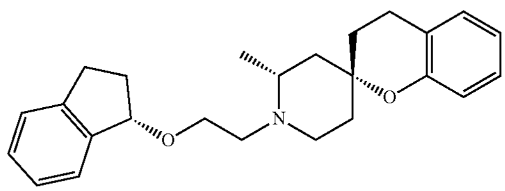 [SMILES: C[C@@H]1C[C@@]2(CCc3ccccc3O2)CCN1CCO[C@H]1CCc2ccccc21] | (2R,2'R)-1'-(2-(((S)-2,3-dihydro-1H-inden-1-yl)oxy)ethyl)-2'-methylspiro[chromane-2,4'-piperidine] | $R^A$-4 | $L^1$-4 | Q-43 | $L^2$-1 |
| 435 | 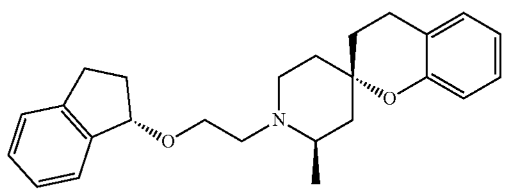 [SMILES: C[C@@H]1C[C@]2(CCc3ccccc3O2)CCN1CCO[C@H]1CCc2ccccc21] | (2S,2'R)-1'-(2-(((S)-2,3-dihydro-1H-inden-1-yl)oxy)ethyl)-2'-methylspiro[chromane-2,4'-piperidine] | $R^A$-4 | $L^1$-4 | Q-43 | $L^2$-1 |
| 436 | 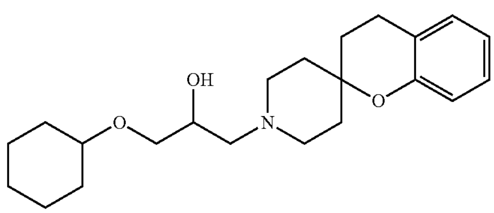 [SMILES: OC(COC1CCCCC1)CN1CCC2(CCc3ccccc3O2)CC1] | 1-(cyclohexyloxy)-3-(spiro[chromane-2,4'-piperidin]-1'-yl)propan-2-ol | $R^A$-1 | $L^1$-6 | Q-43 | $L^2$-1 |
| 437 | 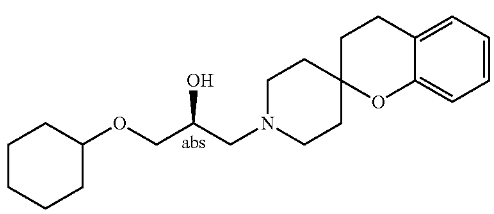 [SMILES: O[C@H](COC1CCCCC1)CN1CCC2(CCc3ccccc3O2)CC1] | (S)-1-(cyclohexyloxy)-3-(spiro[chromane-2,4'-piperidin]-1'-yl)propan-2-ol | $R^A$-1 | $L^1$-6 | Q-43 | $L^2$-1 |
| 438 | 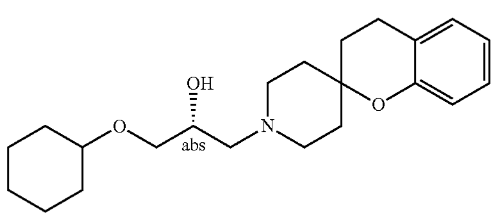 [SMILES: O[C@@H](COC1CCCCC1)CN1CCC2(CCc3ccccc3O2)CC1] | (R)-1-(cyclohexyloxy)-3-(spiro[chromane-2,4'-piperidin]-1'-yl)propan-2-ol | $R^A$-1 | $L^1$-6 | Q-43 | $L^2$-1 |
| 439 | 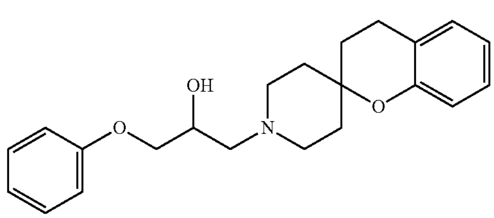 [SMILES: OC(COc1ccccc1)CN1CCC2(CCc3ccccc3O2)CC1] | 1-phenoxy-3-(spiro[chromane-2,4'-piperidin]-1'-yl)propan-2-ol | $R^A$-22 | $L^2$-6 | Q-43 | $L^2$-1 |

TABLE 5-continued

Summary of synthesis of Compounds. Compounds were synthesized by coupling the $R^A$ group coupling partners to the Q group coupling partners through the $L^1$ linker and coupling the $R^B$ group coupling partners to the Q group coupling partners through the $L^2$ linker. The $R^A$ coupling chemistry used is described in Example $L^1$. The $R^B$ coupling chemistry is described in Example $L^2$. Synthetic details for the transformations described in Examples Example $L^1$, Example $L^2$, Example $R^A$ and Example $R^B$ are in Example T. The table below lists the $R^A$, $L^1$, Q, $L^2$ and $R^B$ groups whose coupling partners were used in the syntheses.

| | Structure | Chem Name | $R^A$ | $L^1$ | Q | $L^2$ |
|---|---|---|---|---|---|---|
| 440 | 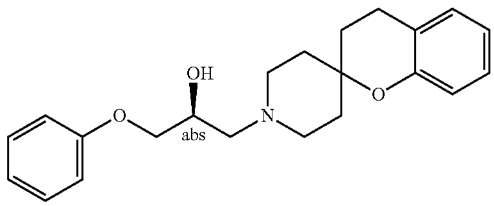 [SMILES: O[C@H](COc1ccccc1)CN1CCC2(CCc3ccccc3O2)CC1] | (S)-1-phenoxy-3-(spiro[chromane-2,4'-piperidin]-1'-yl)propan-2-ol | $R^A$-22 | $L^2$-6 | Q-43 | $L^2$-1 |
| 441 | 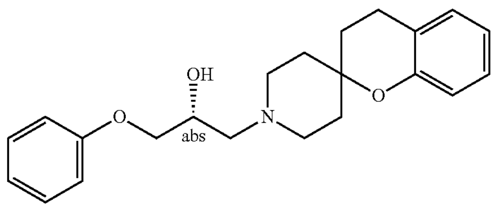 [SMILES: O[C@@H](COc1ccccc1)CN1CCC2(CCc3ccccc3O2)CC1] | (R)-1-phenoxy-3-(spiro[chromane-2,4'-piperidin]-1'-yl)propan-2-ol | $R^A$-22 | $L^1$-6 | Q-43 | $L^2$-1 |
| 442 | 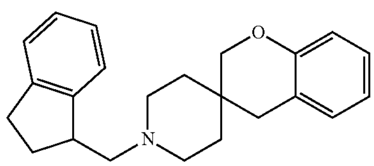 [SMILES: c1ccc2c(c1)CC1(CCN(CC3CCc4ccccc43)CC1)CO2] | 1'-((2,3-dihydro-1H-inden-1-yl)methyl)spiro[chromane-3,4'-piperidine] | $R^A$-4 | $L^1$-1 | Q-44 | $L^2$-1 |
| 443 | 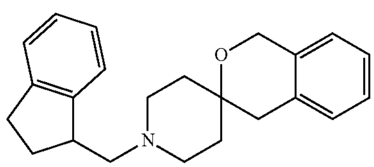 [SMILES: c1ccc2c(c1)COC1(CCN(CC3CCc4ccccc43)CC1)C2] | 1'-((2,3-dihydro-1H-inden-1-yl)methyl)spiro[isochromane-3,4'-piperidine] | $R^A$-4 | $L^1$-1 | Q-45 | $L^2$-1 |
| 444 | 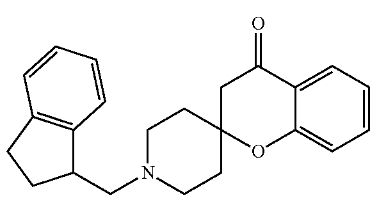 [SMILES: O=C1CC2(CCN(CC3CCc4ccccc43)CC2)Oc2ccccc21] | 1'-((2,3-dihydro-1H-inden-1-yl)methyl)spiro[chromane-2,4'-piperidin]-4-one | $R^A$-4 | $L^1$-1 | Q-46 | $L^2$-1 |
| 445 | 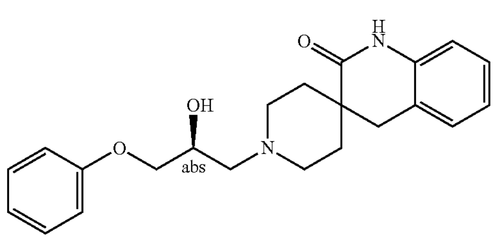 [SMILES: O=C1Nc2ccccc2CC12CCN(C[C@H](O)COc1ccccc1)CC2] | (S)-1-(2-hydroxy-3-phenoxypropyl)-1',4'-dihydro-2'H-spiro[piperidine-4,3'-quinolin]-2'-one | $R^A$-22 | $L^1$-6 | Q-47 | $L^2$-1 |
| 446 | 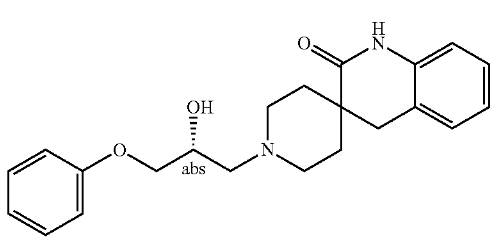 [SMILES: O=C1Nc2ccccc2CC12CCN(C[C@@H](O)COc1ccccc1)CC2] | (R)-1-(2-hydroxy-3-phenoxypropyl)-1',4'-dihydro-2'H-spiro[piperidine-4,3'-quinolin]-2'-one | $R^A$-22 | $L^1$-6 | Q-47 | $L^2$-1 |

Example $L^1$. Coupling of $R^A$ groups to Q. Compounds of the invention are made by coupling the $R^A$-coupling partners with the Q through linker $L^1$, and by coupling the $R^B$ coupling partners with the Q through linker $L^2$. Example $L^1$ contains the synthetic methods used to couple $R^A$ groups to the Q.

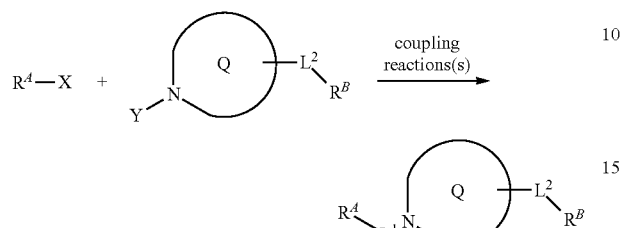

In this example, X, Y represent independently H or coupling-compatible functional groups Example $L^1$-1a. Coupling of $R^A$-groups to form linker $L^1$-1

General Scheme

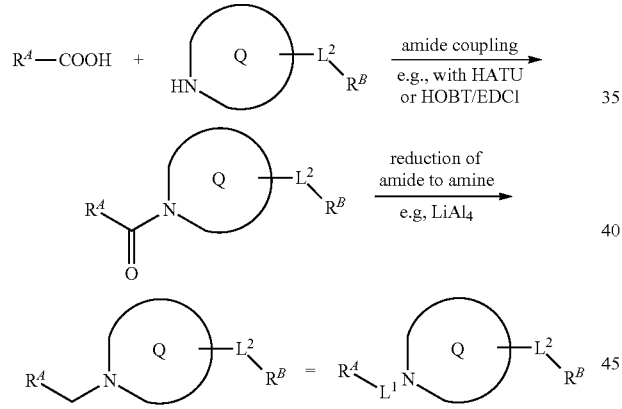

Representative Example 1

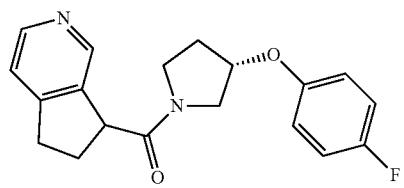

Representative Example 2

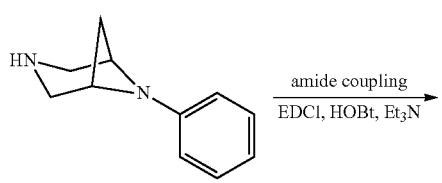

Example $L^1$-1b. Coupling of $R^A$-groups to form linker $L^1$-1

General Scheme

191
-continued
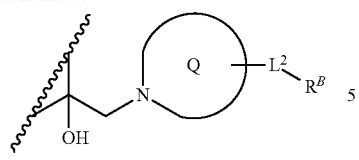
Representative Example
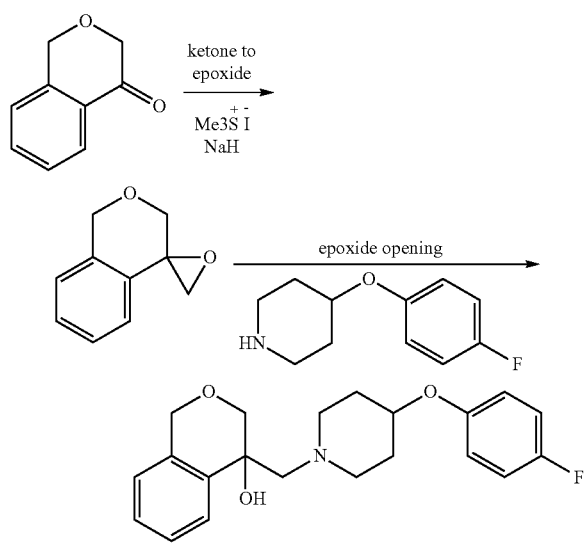
Example L¹-1c. Coupling of R^A-groups to form linker L¹-1
General Scheme
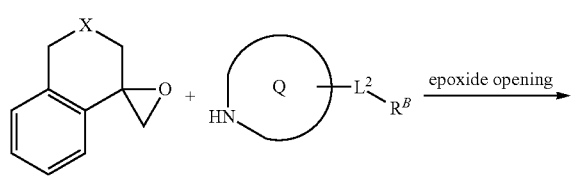
In this example, X = O, CH₂
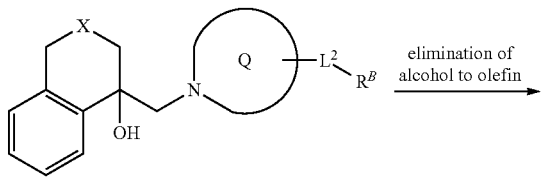
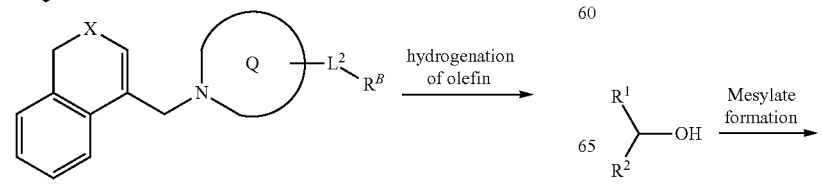
192
-continued
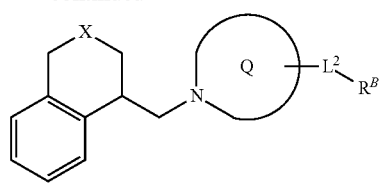
Representative Example
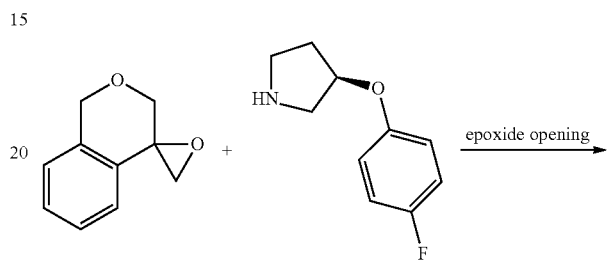
Example L¹-1d. Coupling of R^A-groups to form linker L¹-1
General Scheme 193
-continued
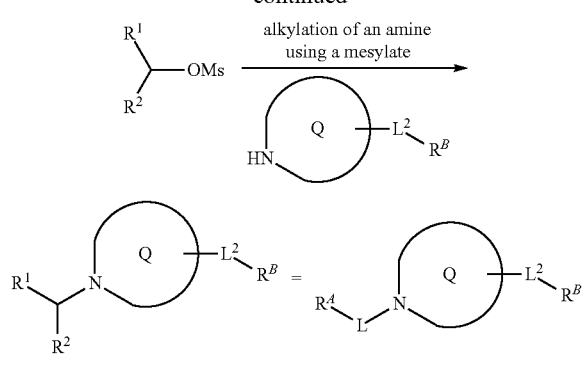
Representative Example
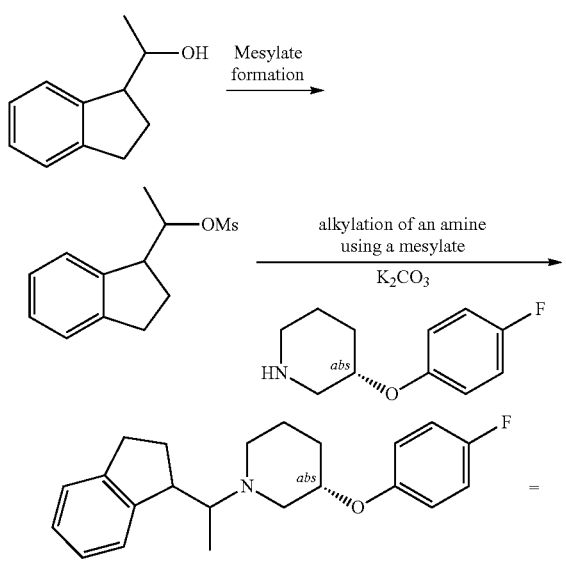
Representative Example
194
-continued
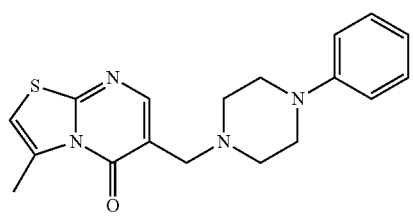
Example L¹-1e. Coupling of R$^A$-groups to form linker L¹-1
General Scheme
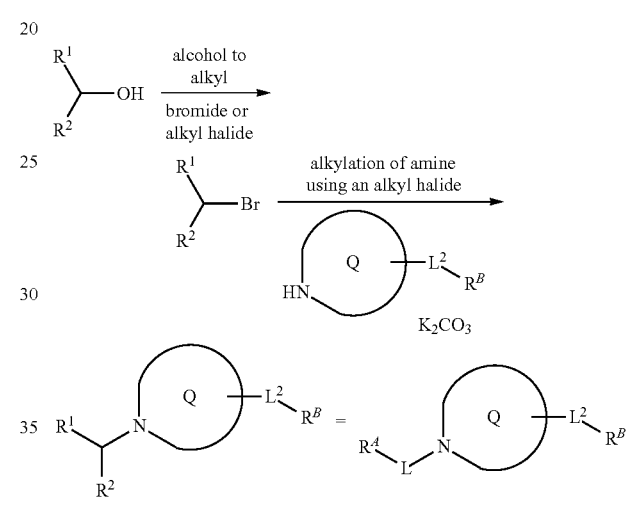
Representative Example
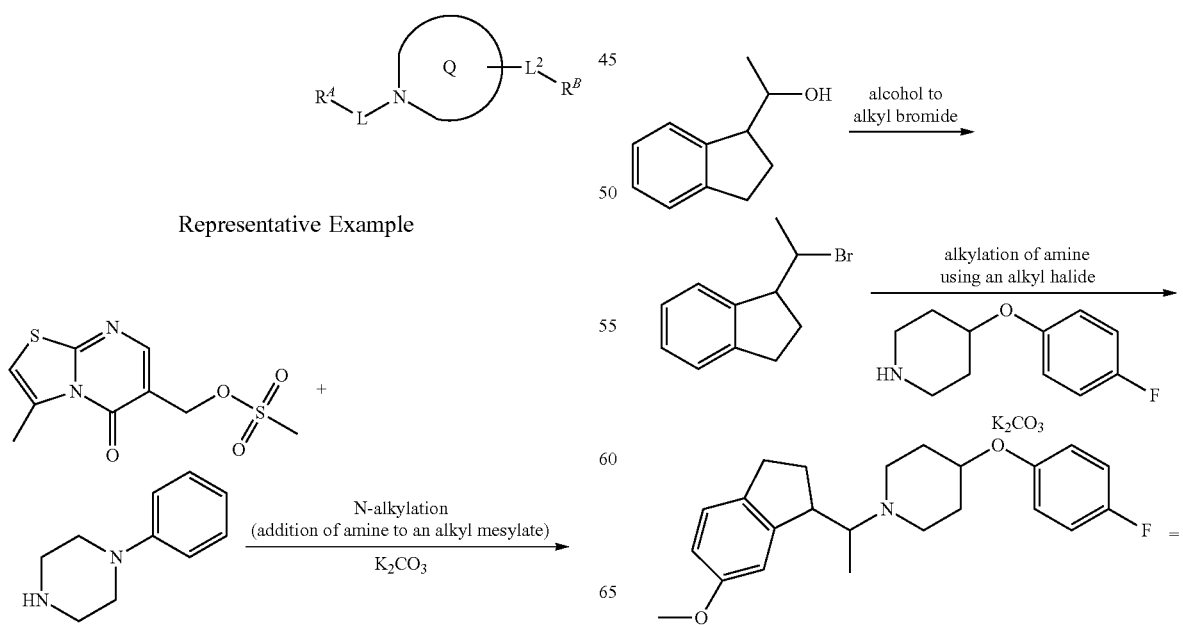

195
-continued
Representative Example
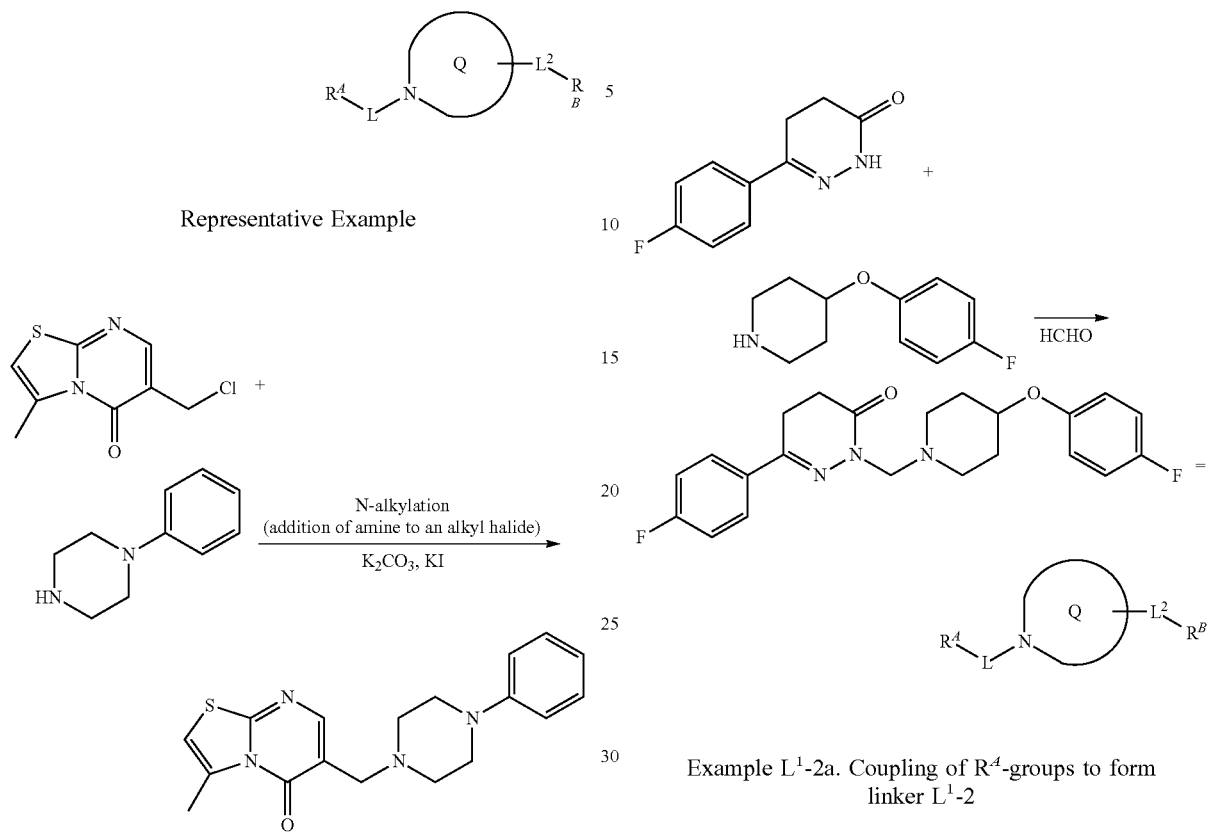
Example L¹-1f. Coupling of R^A-groups to form linker L¹-1
General Scheme
196
Representative Example
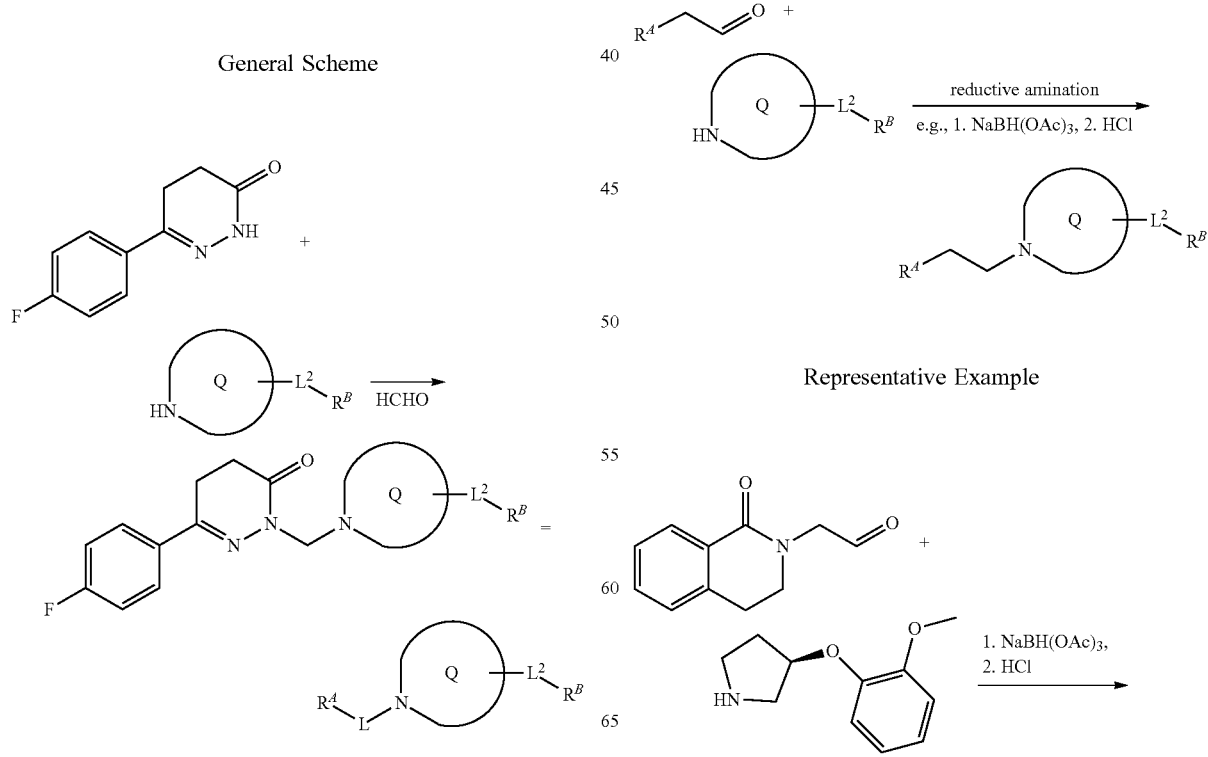
Example L¹-2a. Coupling of R^A-groups to form linker L¹-2
General Scheme
Representative Example

197
-continued
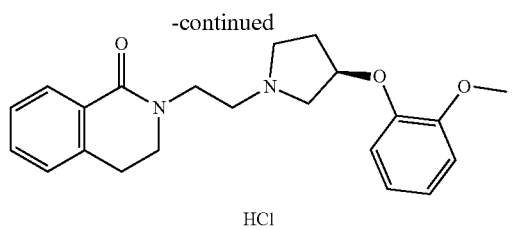
HCl
Example L¹-2b. Coupling of R^A-groups to form linker L¹-2
General Scheme
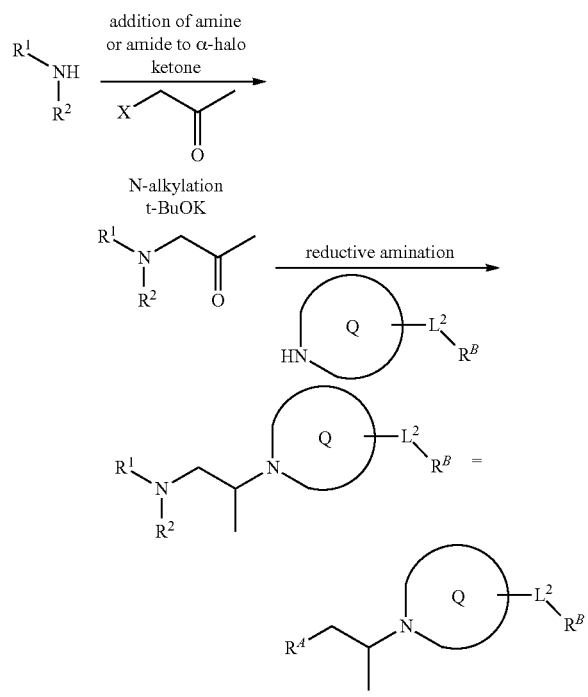
Representative Example
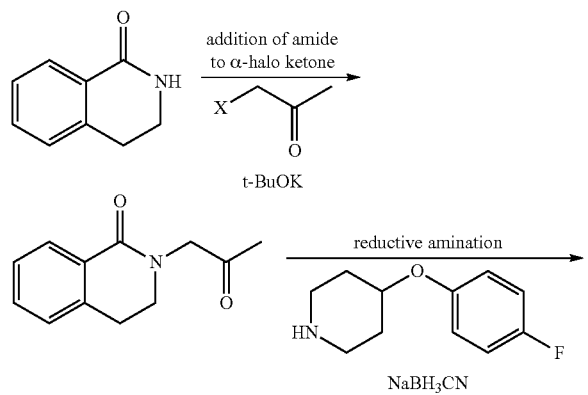
198
-continued
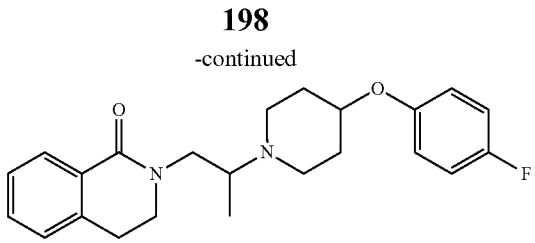
Example L¹-2c. Coupling of R^A-groups to form linker L¹-2
General Scheme
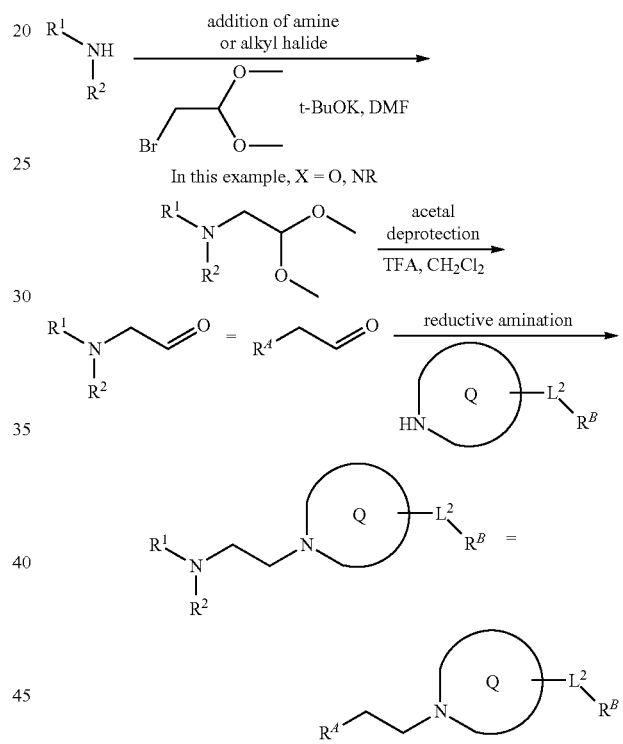
Representative Example
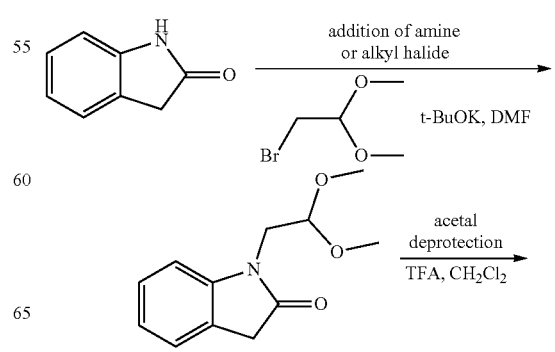

199
-continued
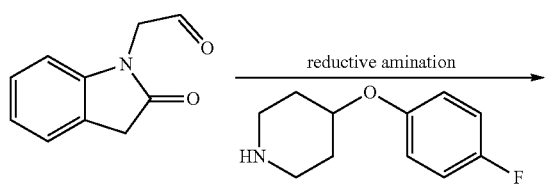
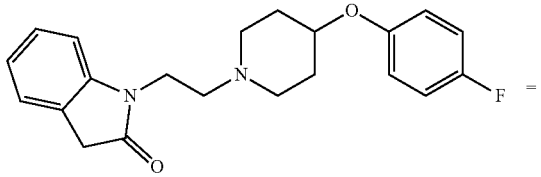
Example L¹-2d. Coupling of R^A-groups to form linker L¹-2
General Scheme
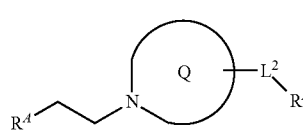
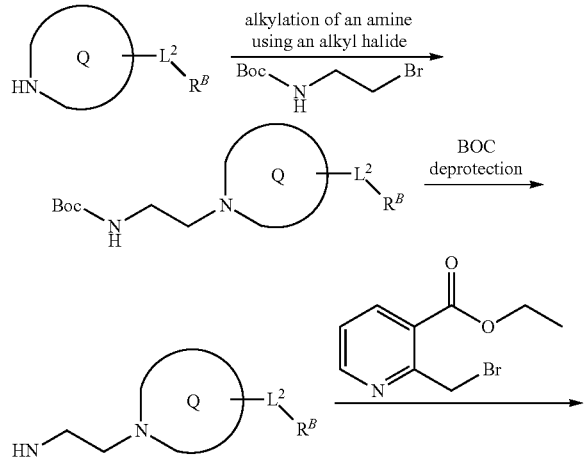
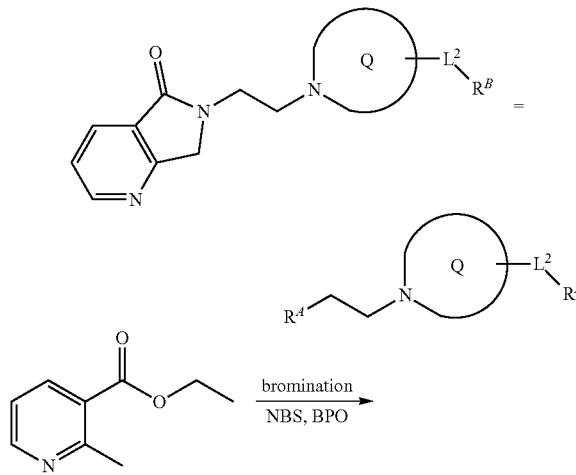
200
-continued
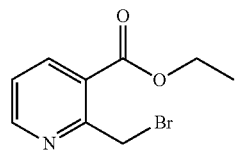
Representative Example
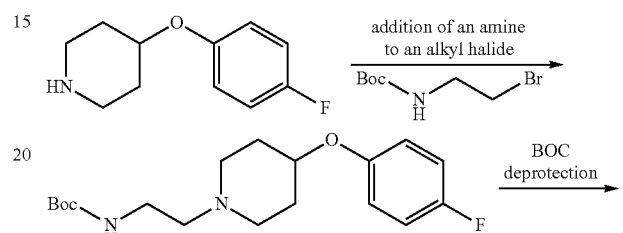
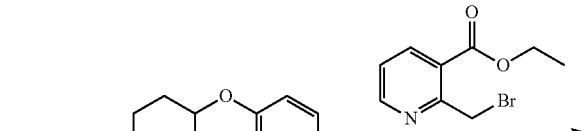
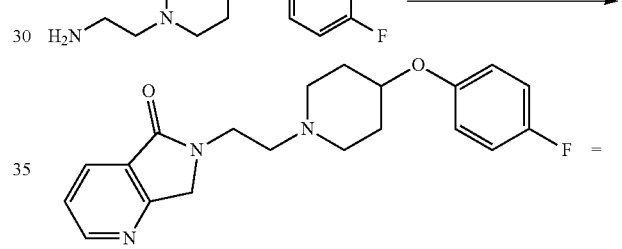
Example L¹-3. Coupling of R^A-groups to form linker L¹-3
General Scheme
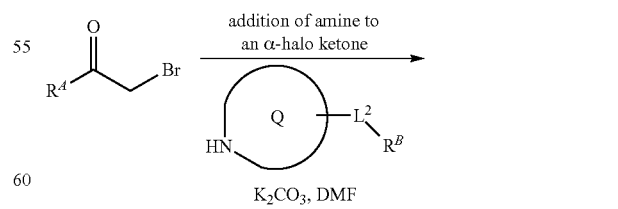
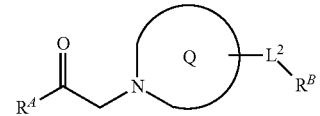

201
Representative Example
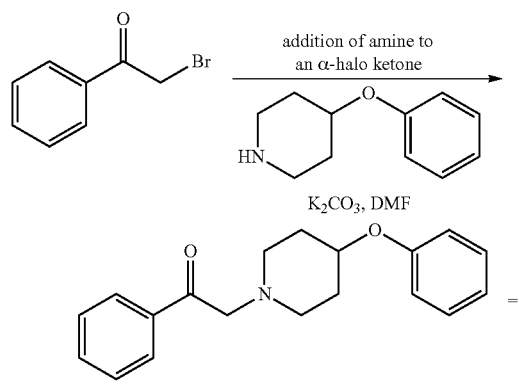
Example L¹-4a. Coupling of R$^A$-groups to form linker L¹-4
General Scheme
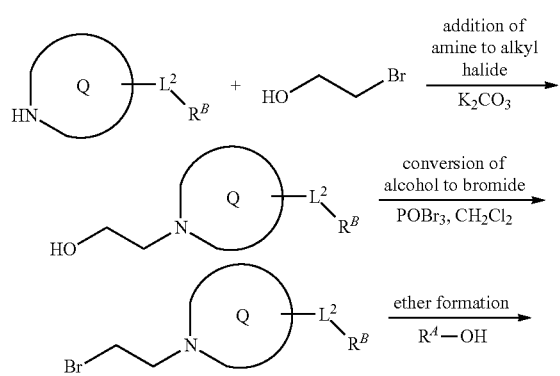
Representative Example
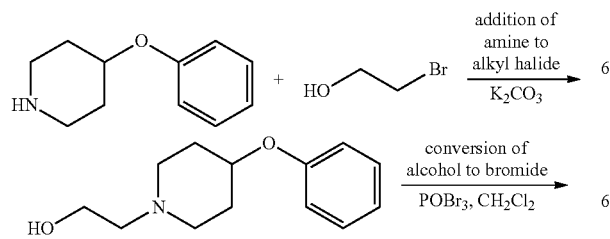
202
-continued
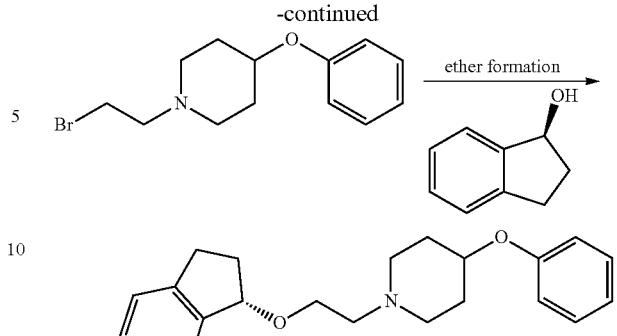
Example L¹-4b. Coupling of R$^A$-groups to form linker L¹-4
General Scheme
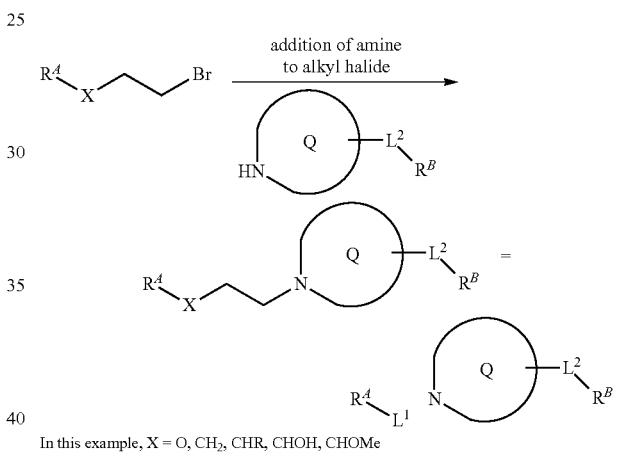
In this example, X = O, CH$_2$, CHR, CHOH, CHOMe
Representative Example
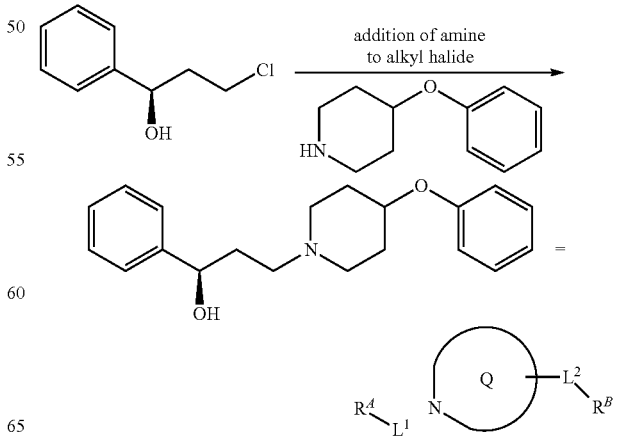

203
Example L¹-4c. Coupling of R$^A$-groups to form linker L¹-4
General Scheme
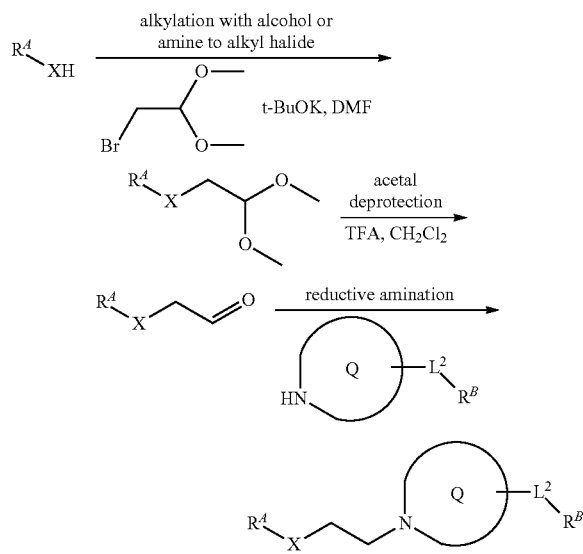
In this example, X = O, NR
Representative Example
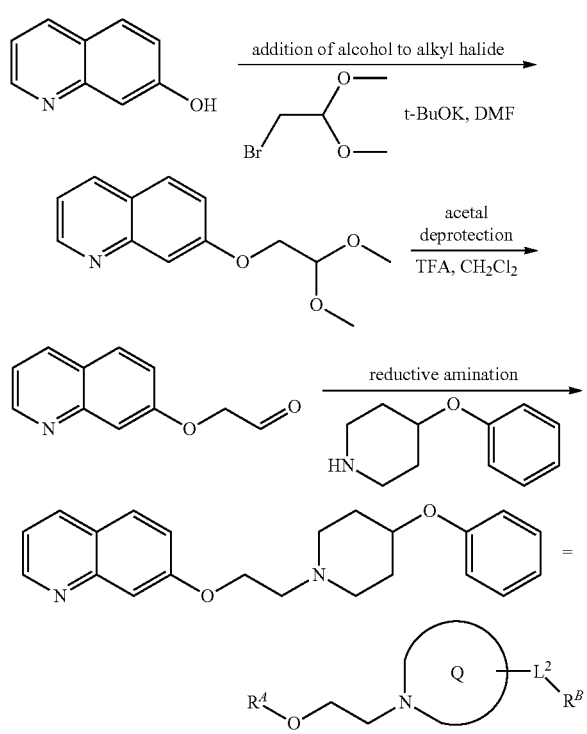
204
Example L¹-6a. Coupling of R$^A$-groups to form linker L¹-6
General Scheme
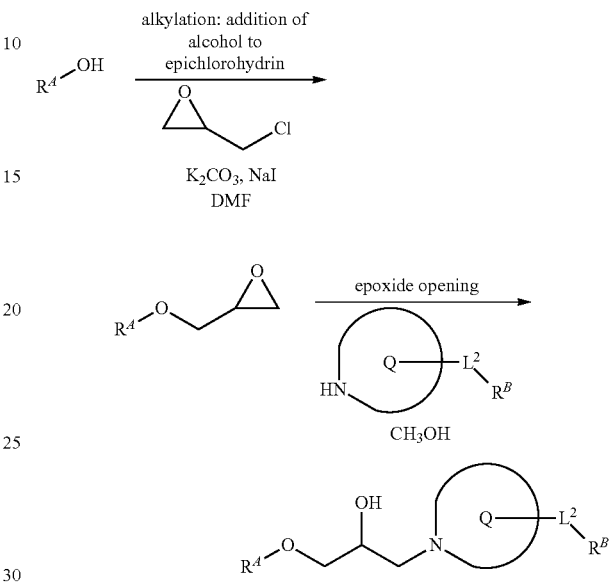
Representative Example
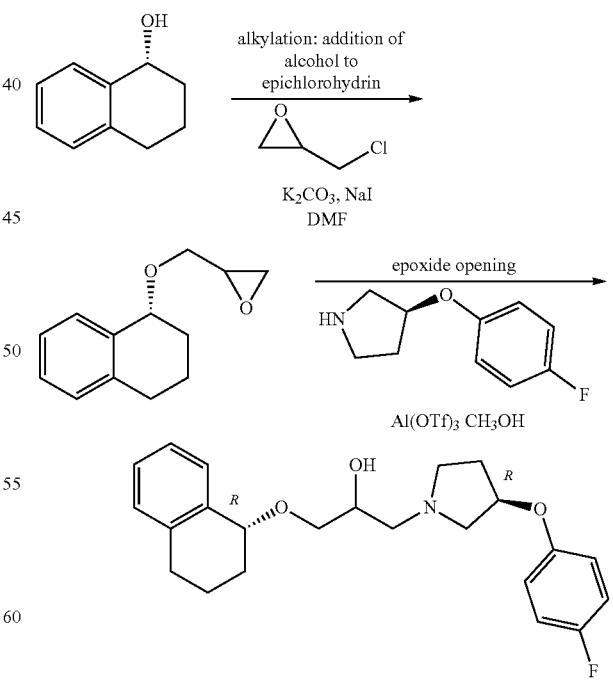
Example L². Coupling of R$^B$ groups to Q. Example L² contains the synthetic methods used to couple R$^B$ groups to the Q.

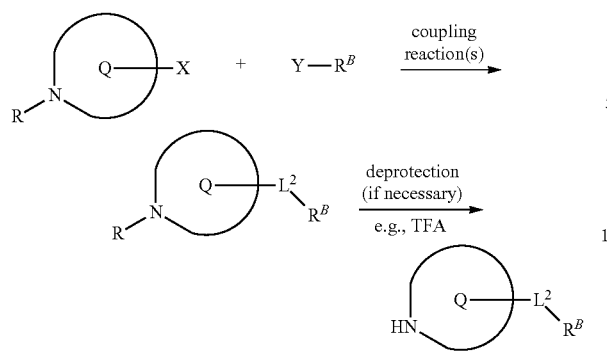

In this example, R= H, protecting group, $L^1 = R^A$
In this example, X, Y represent independently H or coupling-compatible functional groups

Example $L^2$-1a. Coupling of $R^A$-groups to form linker $L^2$-1

General Scheme

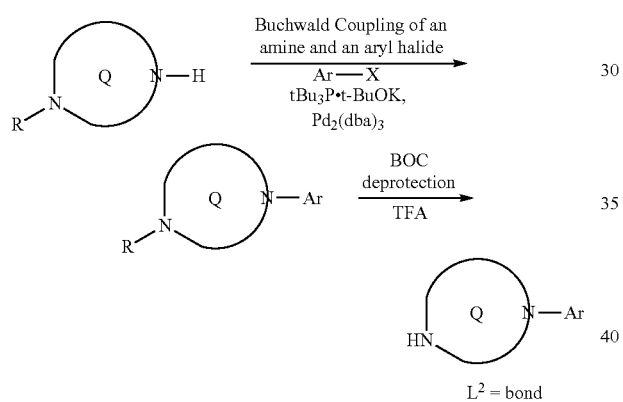

In this example, X = halide

Representative Example

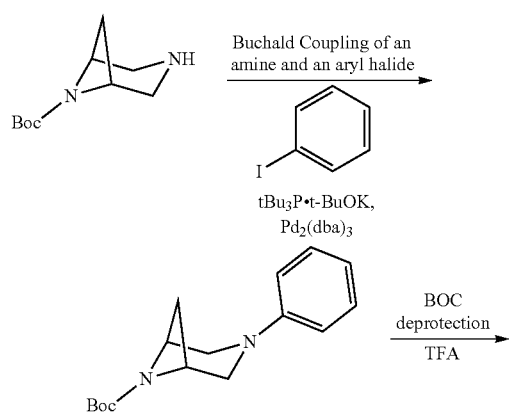

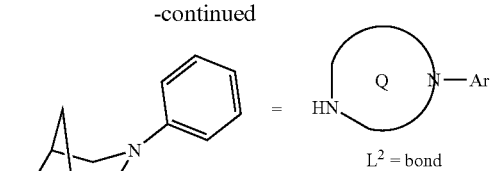

Example $L^2$-1b. Coupling of $R^A$-groups to form linker $L^2$-1

General Scheme

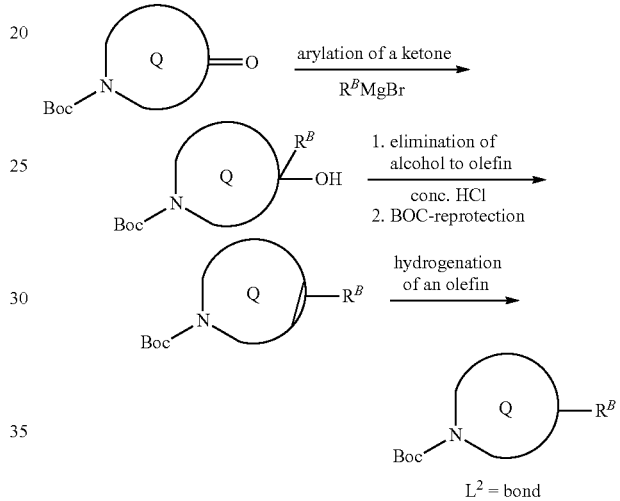

Representative Example

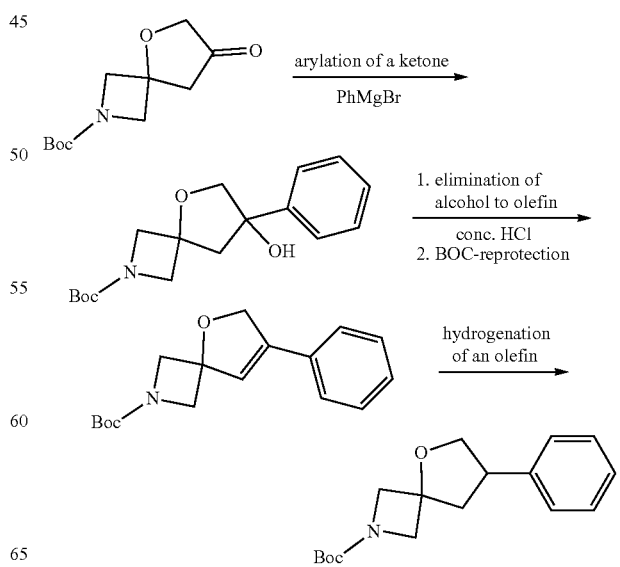

Example L²-2a. Coupling of R^A-groups to form linker L²-2
General Scheme
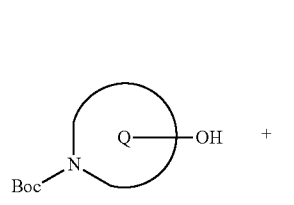
Representative Example
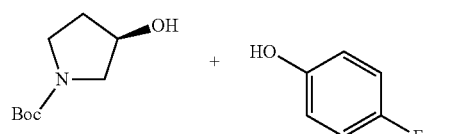 +  →
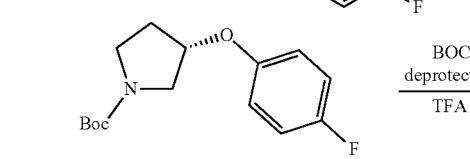
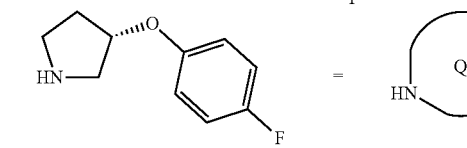
Example L²-2b. Coupling of R^A-groups to form linker L²-2
General Scheme
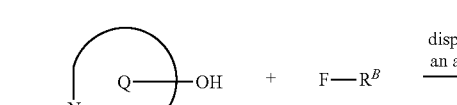 + 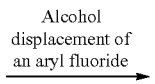 →
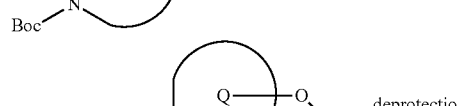
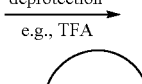
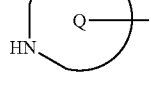
Representative Example
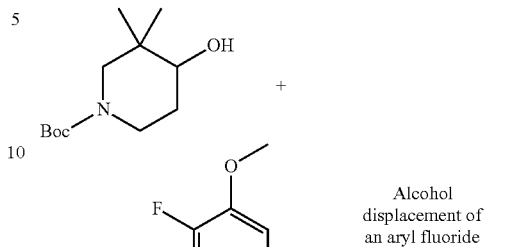
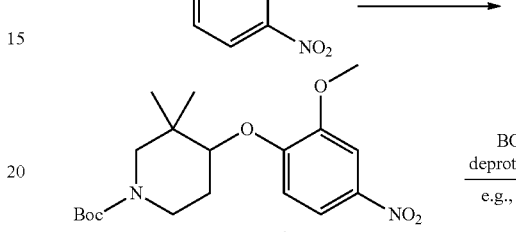
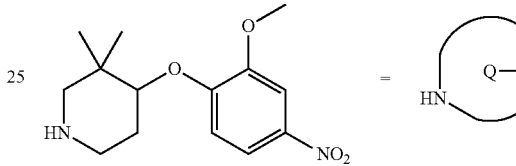
Example L²-2c. Coupling of R^A-groups to form linker L²-2
General Scheme
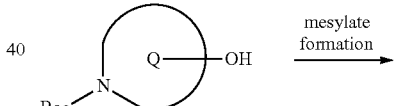
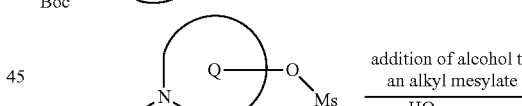
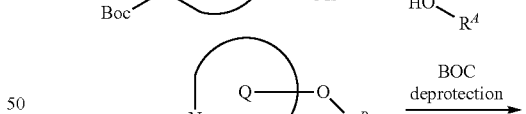
Representative Example
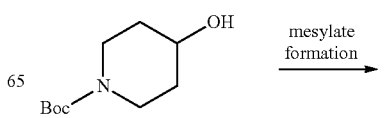

-continued addition of alcohol to an alkyl mesylate

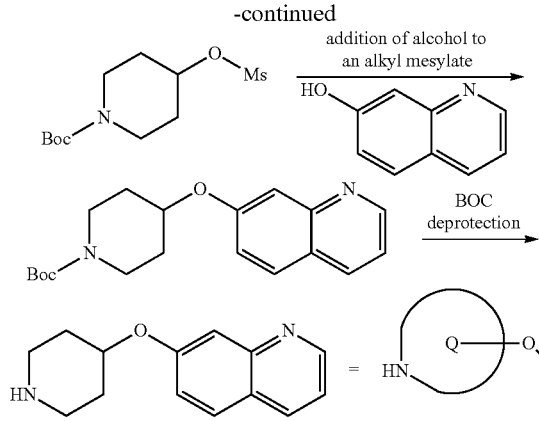

Example L²-4. Coupling of R^A-groups to form linker L²-4

General Scheme

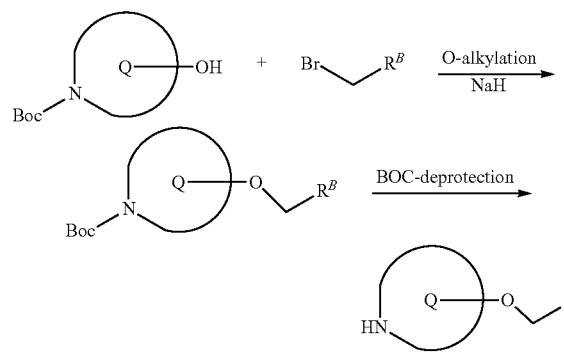

Representative Example

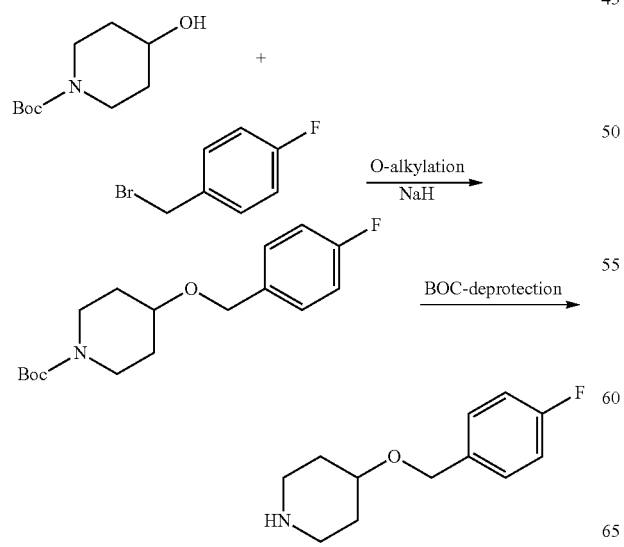

Example L²-5. Coupling of R^A-groups to form linker L²-3

General Scheme

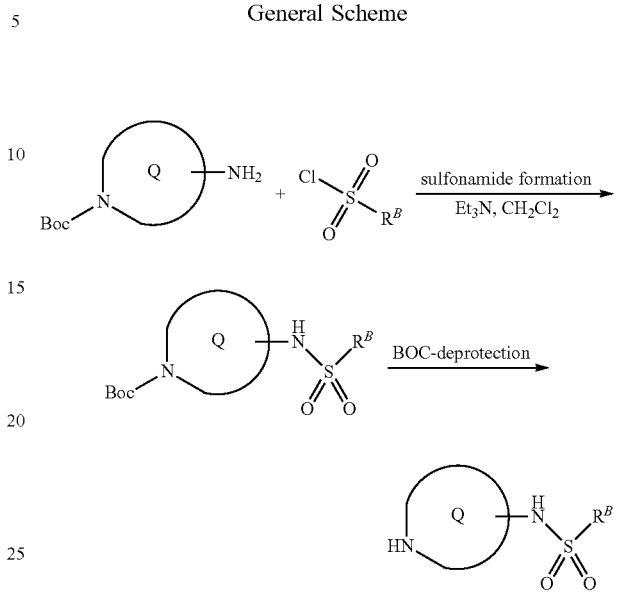

Representative Example

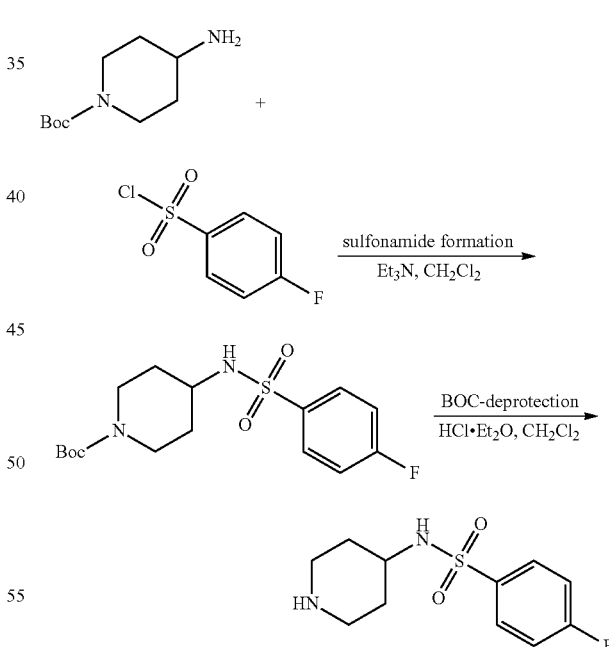

Example R^A. Synthesis of R^A group coupling partners to be used in Example L¹. Compounds of the invention are made by coupling the R^A-coupling partners with the Q through linker L¹, and by coupling the R^B coupling partners with the Q through linker L². Example R^A contains the synthetic methods used to synthesis the R^A coupling partners. Other R^A coupling partners were commercially available.

211
Example R^A-4a. Synthesis R^A Group Coupling Partner R^A-4
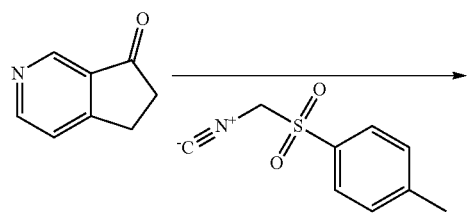
Example R^A-4b. Synthesis R^A Group Coupling Partner R^A-4. See Homologation. Ketone to acid
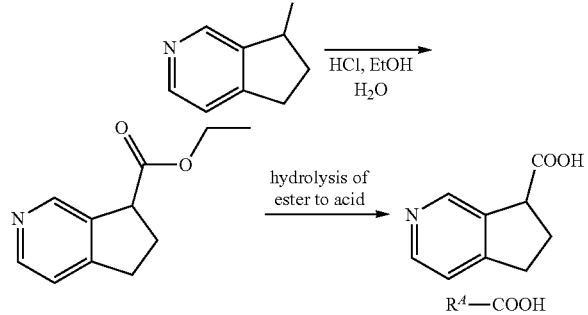
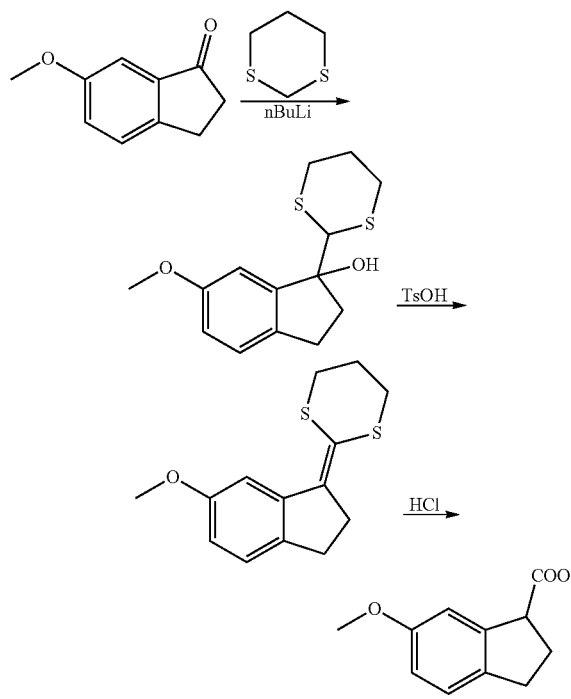
212
Example R^A-4c. Synthesis R^A Group Coupling Partner R^A-4
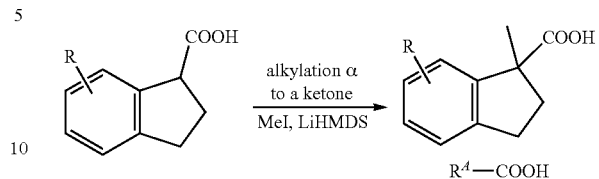
Example R^A-4d. Synthesis R^A Group Coupling Partner R^A-4. See Homologation. Ketone to acid
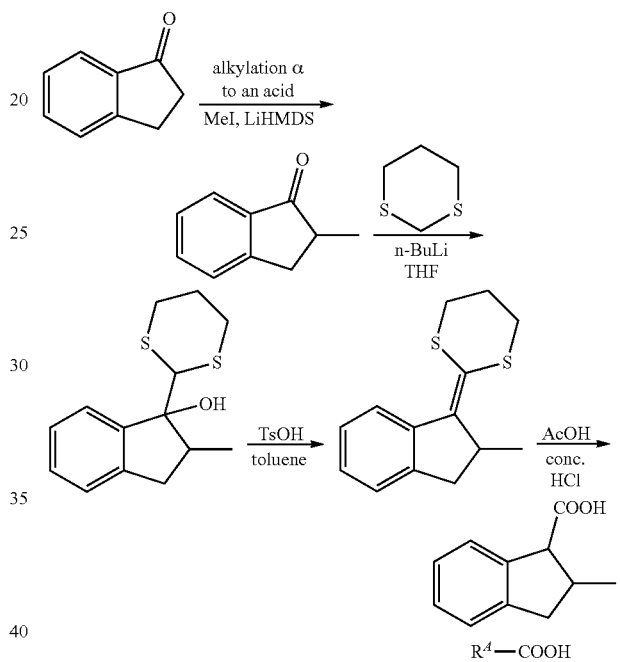
Example R^A-4e. Synthesis R^A Group Coupling Partner R^A-4
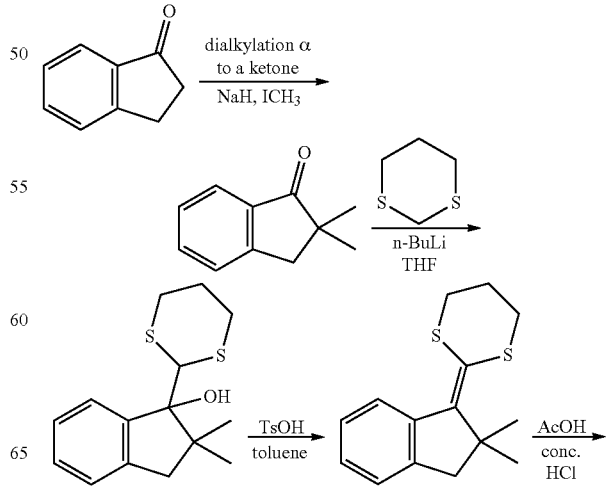

213
-continued

214
Example R^A-4h. Functionalization of R^A-4

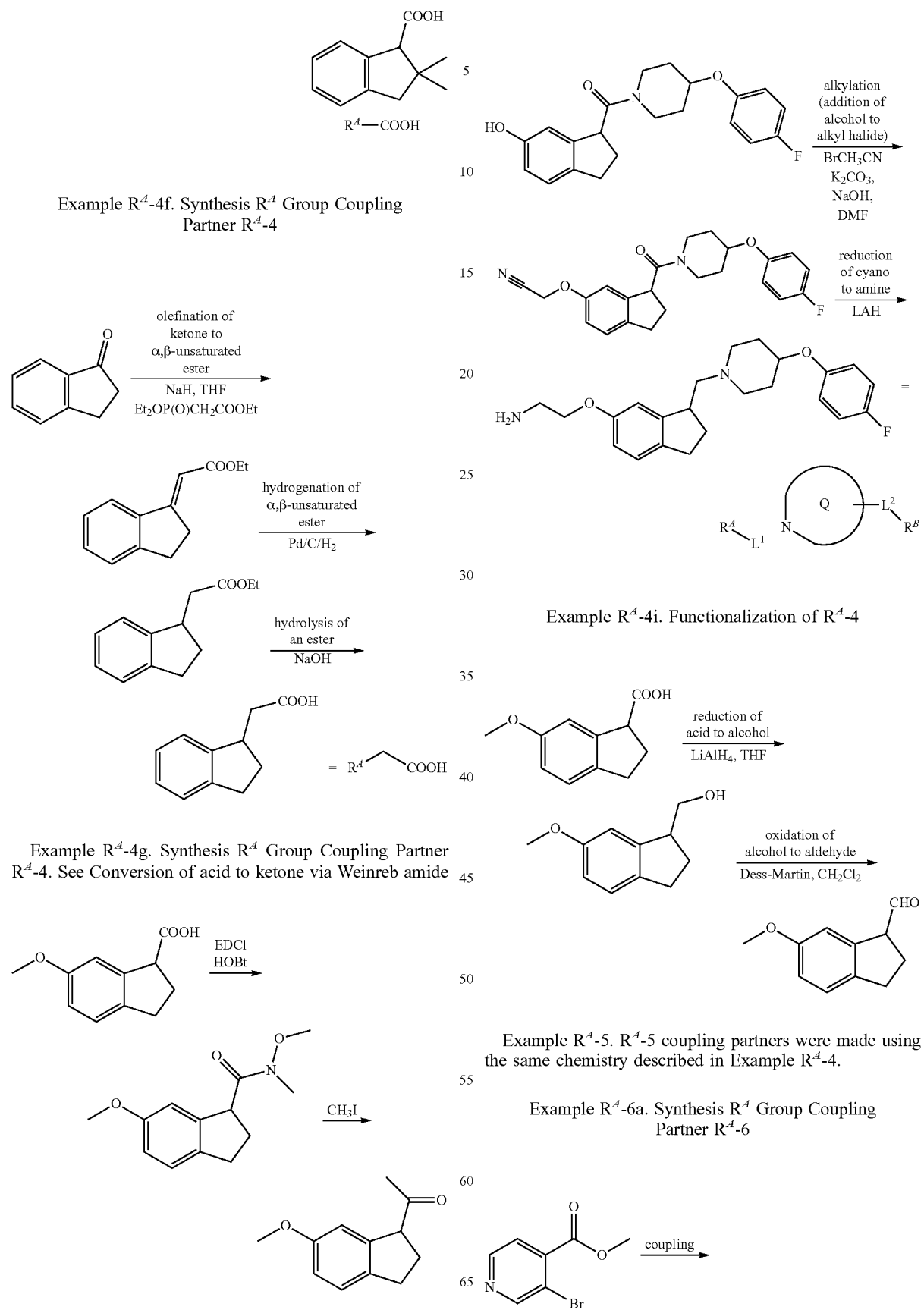

Example R^A-4f. Synthesis R^A Group Coupling Partner R^A-4

Example R^A-4i. Functionalization of R^A-4

Example R^A-4g. Synthesis R^A Group Coupling Partner R^A-4. See Conversion of acid to ketone via Weinreb amide Example R^A-5. R^A-5 coupling partners were made using the same chemistry described in Example R^A-4.

Example R^A-6a. Synthesis R^A Group Coupling Partner R^A-6

215
-continued

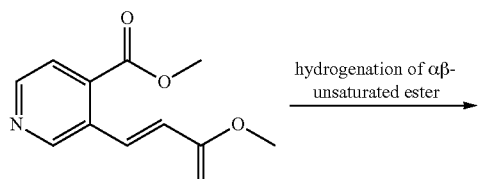
hydrogenation of αβ-unsaturated ester →

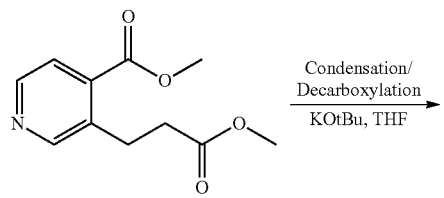
Condensation/Decarboxylation
KOtBu, THF →

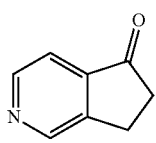

Example R^A-6b. R^A-6 coupling partners were made using the same chemistry described in Example R^A-4.

Example R^A-7a. Synthesis R^A Group Coupling Partner R^A-7

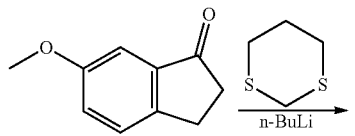

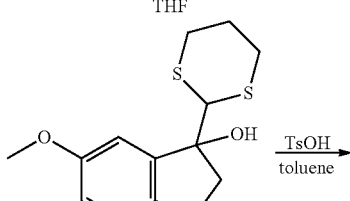
CuCN/LiClZn →

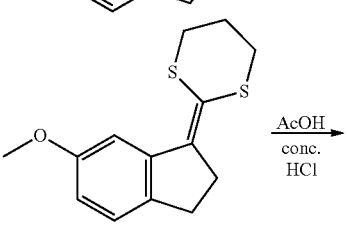

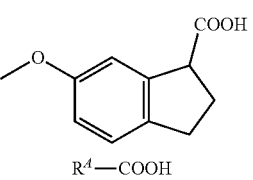
Dieckmann condensation
NaH →

216
-continued

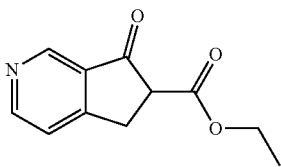
decarboxylation
conc. HCl →

Example R^A-7b). Synthesis R^A Group Coupling Partner R^A-7. See Homologation. Ketone to acid

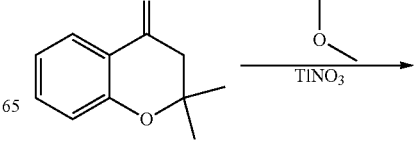
n-BuLi
THF →

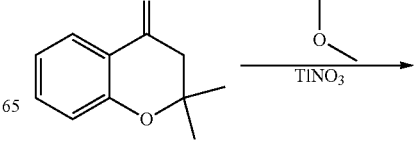
TsOH
toluene →

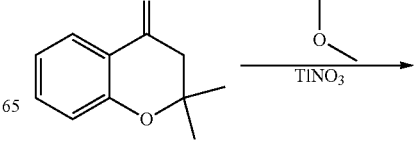
AcOH
conc. HCl →

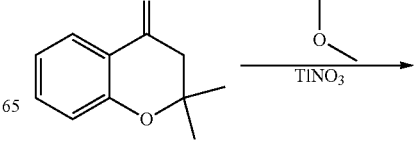

R^A—COOH

Example R^A-7c. R^A-7 coupling partners were made using the same chemistry described in Example R^A-4.

Example R^A-8. R^A-8 coupling partners were made using the same chemistry described in Example R^A-4.

Example R^A-9a. Synthesis R^A Group Coupling Partner R^A-9

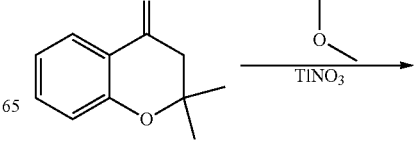
TlNO₃ →

-continued

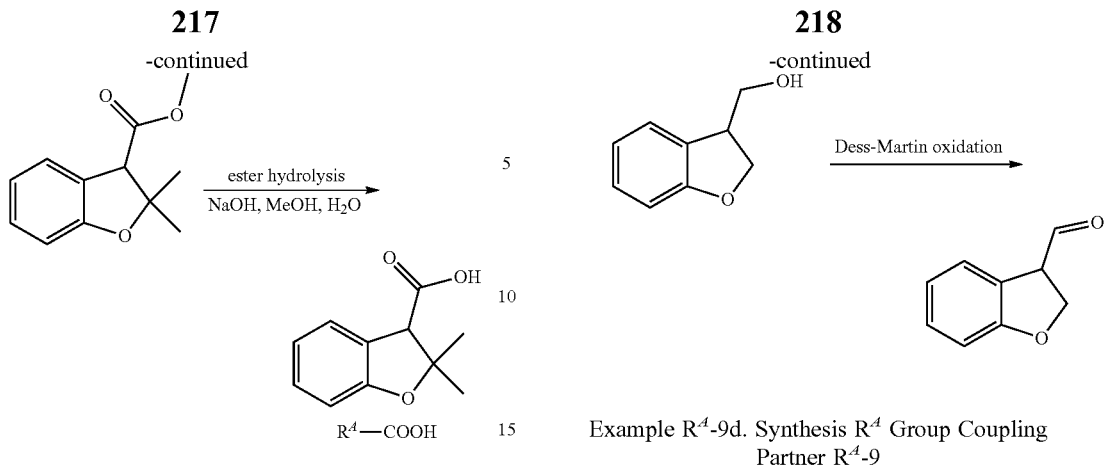

Example R<sup>A</sup>-9b. Synthesis R<sup>A</sup> Group Coupling Partner R<sup>A</sup>-9

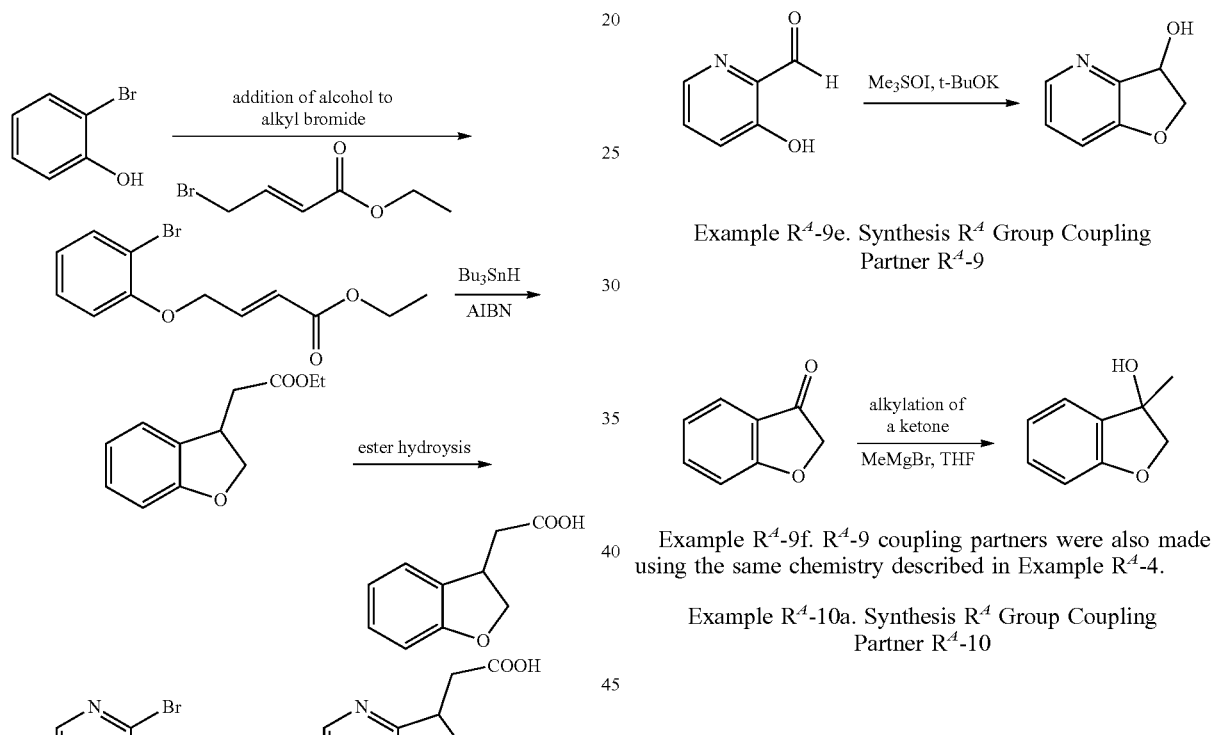

Example R<sup>A</sup>-9c. Synthesis R<sup>A</sup> Group Coupling Partner R<sup>A</sup>-9

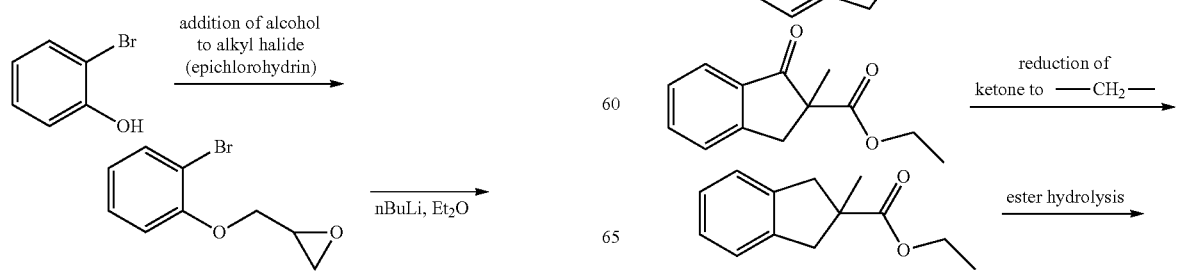

Example R<sup>A</sup>-9d. Synthesis R<sup>A</sup> Group Coupling Partner R<sup>A</sup>-9

Example R<sup>A</sup>-9e. Synthesis R<sup>A</sup> Group Coupling Partner R<sup>A</sup>-9

Example R<sup>A</sup>-9f. R<sup>A</sup>-9 coupling partners were also made using the same chemistry described in Example R<sup>A</sup>-4.

Example R<sup>A</sup>-10a. Synthesis R<sup>A</sup> Group Coupling Partner R<sup>A</sup>-10

-continued

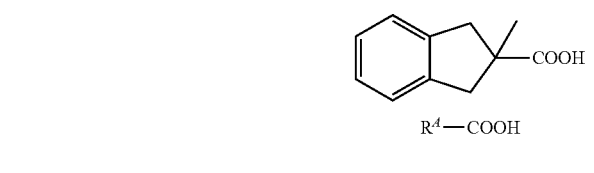

R$^A$—COOH

Example R$^A$-10b. Synthesis R$^A$ Group Coupling Partner R$^A$-10

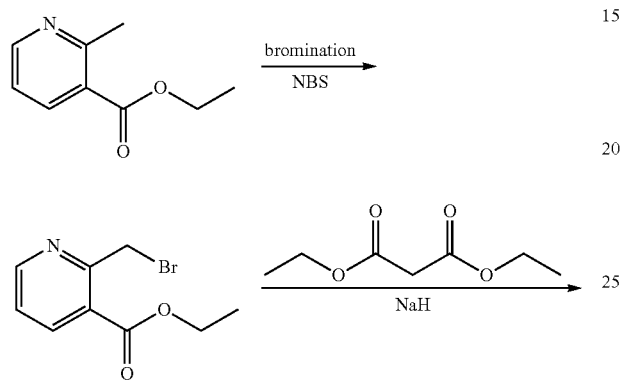

Example R$^A$-10c. Synthesis R$^A$ Group Coupling Partner R$^A$-10

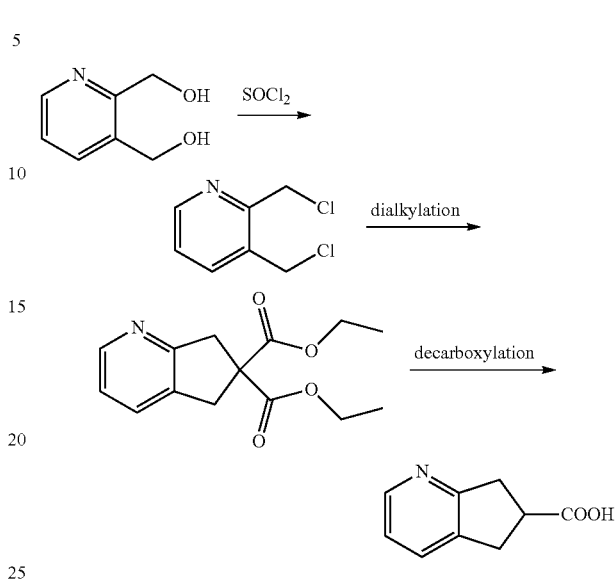

Example R$^A$-10d. Synthesis R$^A$ Group Coupling Partner R$^A$-10

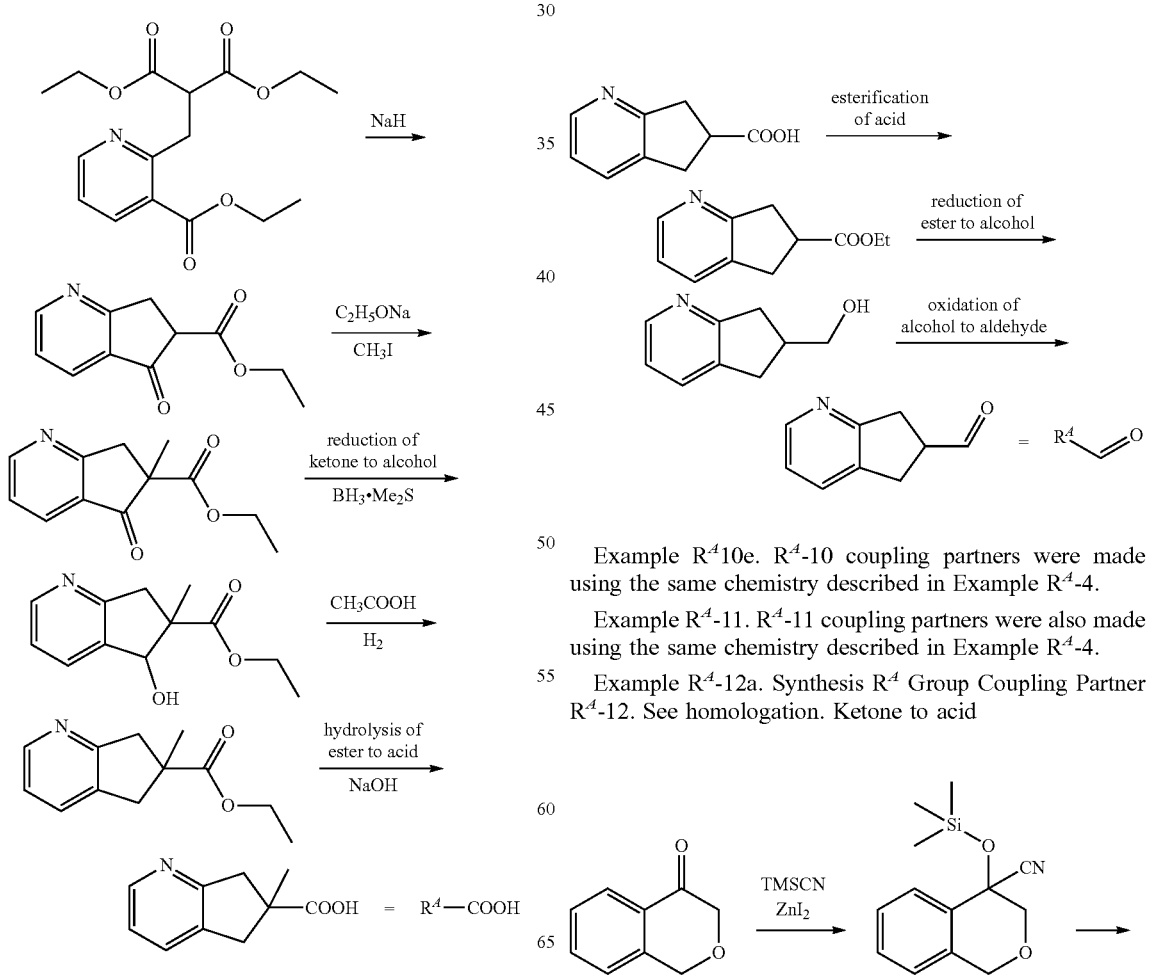

Example R$^A$10e. R$^A$-10 coupling partners were made using the same chemistry described in Example R$^A$-4.

Example R$^A$-11. R$^A$-11 coupling partners were also made using the same chemistry described in Example R$^A$-4.

Example R$^A$-12a. Synthesis R$^A$ Group Coupling Partner R$^A$-12. See homologation. Ketone to acid

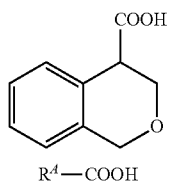

$R^A$—COOH

Example $R^A$-12b. Synthesis $R^A$ Group Coupling Partner $R^A$-12. See Example $R^A$-12

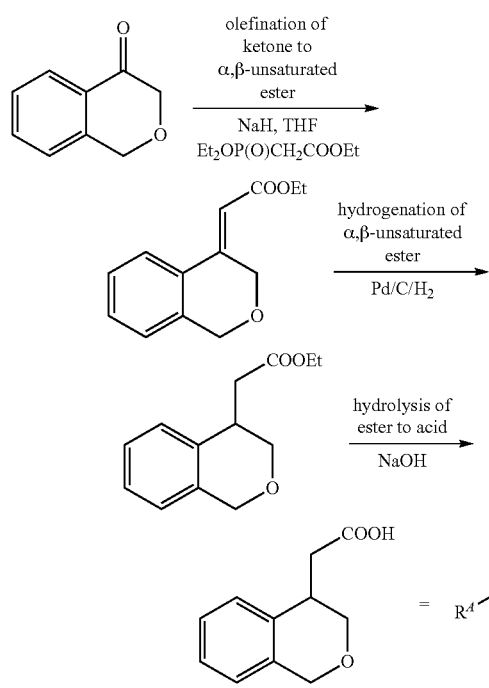

Example $R^A$-12c. Synthesis $R^A$ Group Coupling Partner $R^A$-12. See Example $R^A$-12.

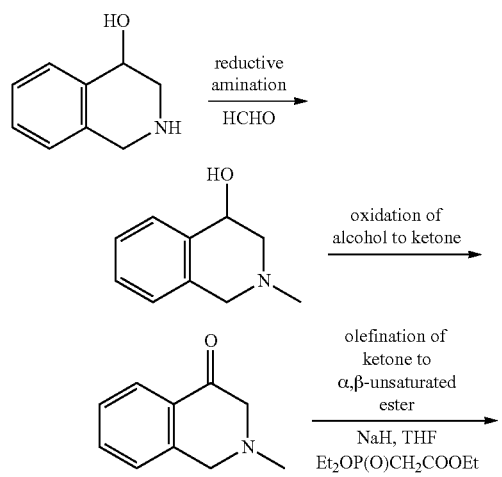

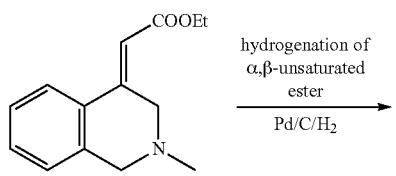

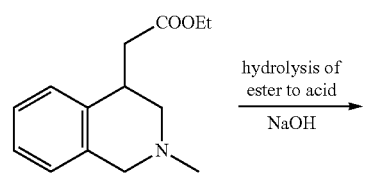

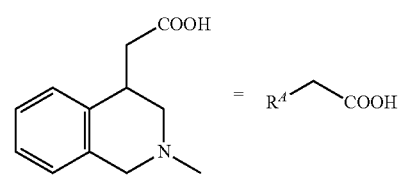

Example $R^A$-12d. $R^A$-12 coupling partners were also made using the same chemistry described in Example $R^A$-4.

Example $R^A$-13a. Synthesis $R^A$ Group Coupling Partner $R^A$-13

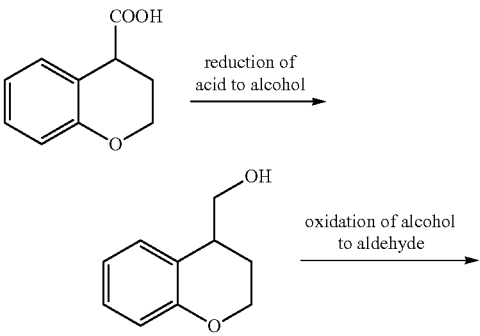

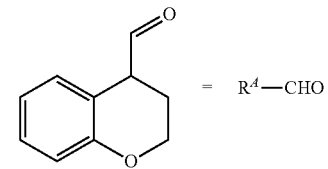

Example $R^A$-13b. Synthesis $R^A$ Group Coupling Partner $R^A$-13

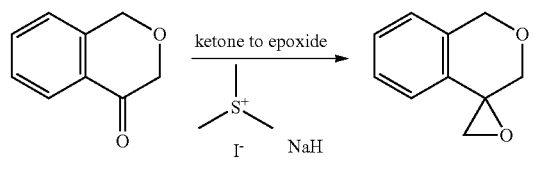

Example R$^A$-13c. Synthesis R$^A$ Group Coupling Partner R$^A$-13

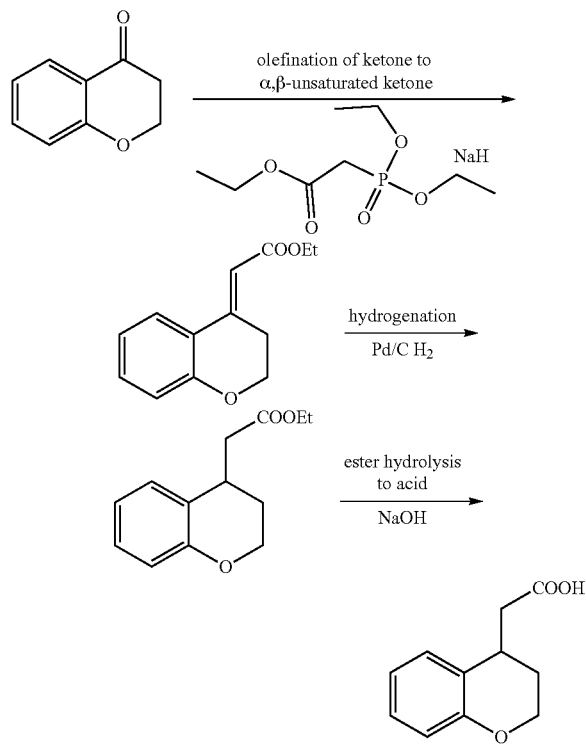

Example R$^A$-13d. R$^A$-13 coupling partners were also made using the same chemistry described in Example R$^A$-4.

Example R$^A$-17. Synthesis R$^A$ Group Coupling Partner R$^A$-17

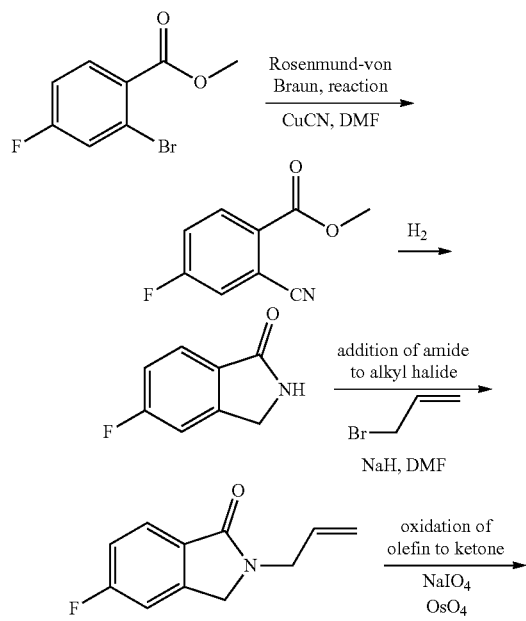

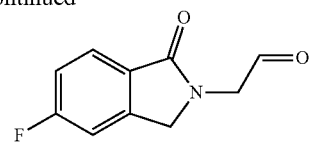

Example R$^A$-18. Synthesis R$^A$ Group Coupling Partner R$^A$-18

Example R$^A$-19. Synthesis R$^A$ Group Coupling Partner R$^A$-19

General Scheme

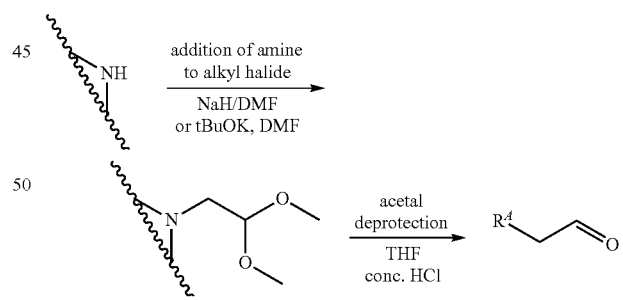

Representative Example

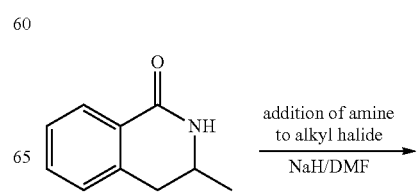

-continued

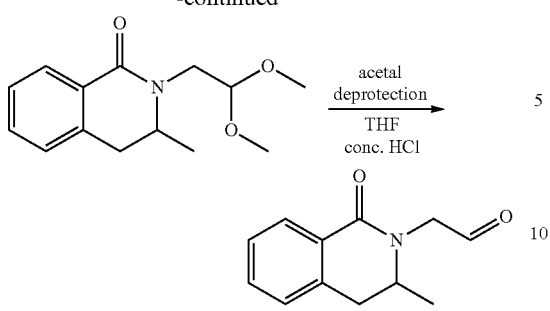

Example $R^A$-20. $R^A$-20 coupling partners were also made using the same chemistry described in Example $R^A$-18 and Example $R^A$-19.

Example $R^A$-21. Synthesis $R^A$ Group Coupling Partner $R^A$-21

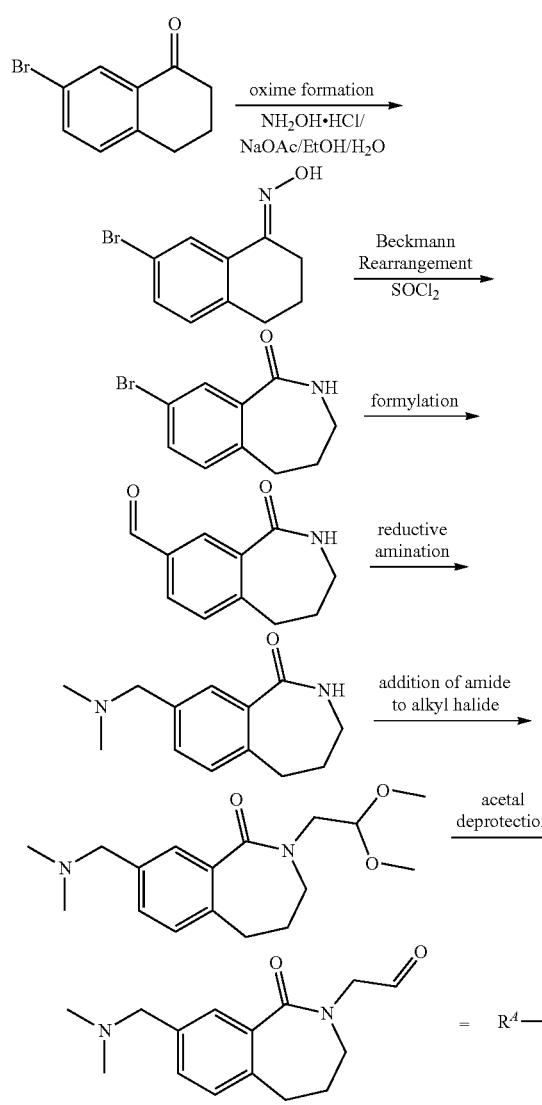

$= R^A—CHO$

Example $R^A$-24. $R^A$-24 coupling partners were also made using the same chemistry described in Example $R^A$-18 and Example $R^A$-19.

Example $R^A$-27. Synthesis $R^A$ Group Coupling Partner $R^A$-27

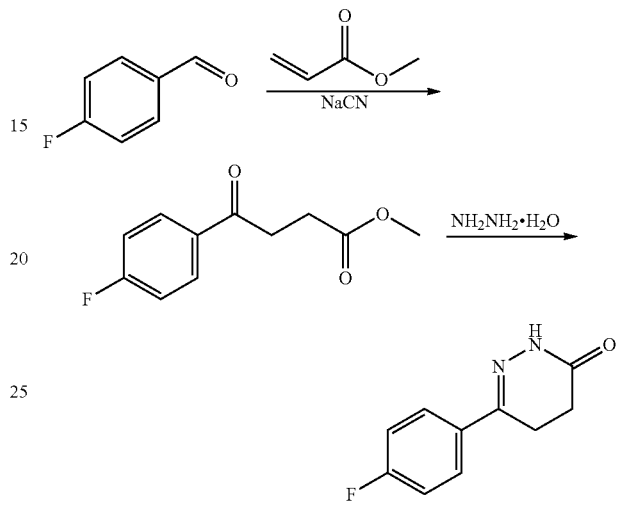

Example Q. Synthesis of Q Group coupling partners (Q) to be used in Examples $L^1$ and $L^2$. Compounds of the invention are made by coupling the $R^A$-coupling partners with the Q through linker $L^1$, and by coupling the $R^B$ coupling partners with the Q through linker $L^2$. Example Q contains the synthetic methods used to synthesis the Q coupling partners. Other Q coupling partners were commercially available.

Example Q-1. Synthesis of Q Group Coupling Partner Q-1

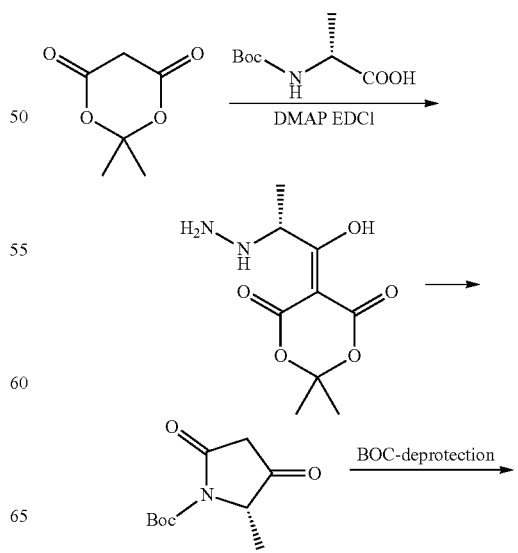

-continued

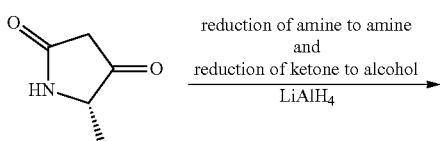
reduction of amine to amine and reduction of ketone to alcohol
LiAlH₄

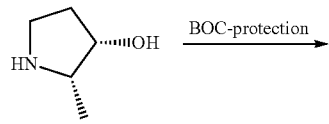
BOC-protection

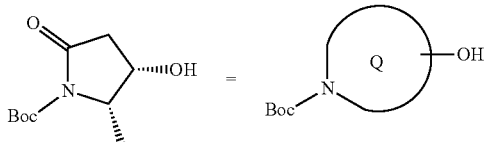

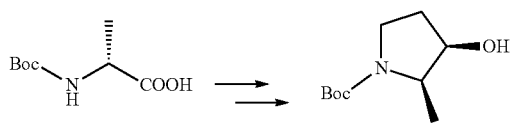

Example Q-3a. Synthesis of Q Group Coupling Partner Q-3

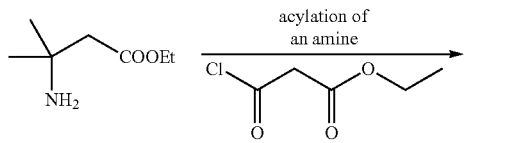
acylation of an amine

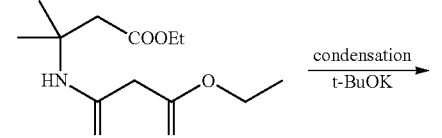
condensation
t-BuOK

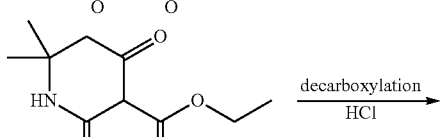
decarboxylation
HCl

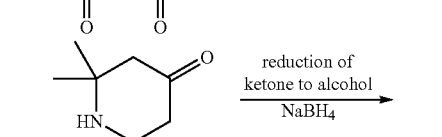
reduction of ketone to alcohol
NaBH₄

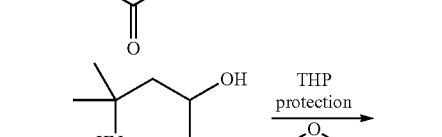
THP protection

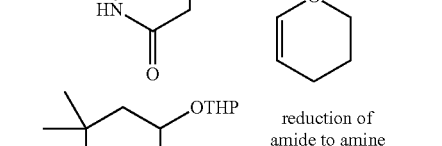
reduction of amide to amine
LAH

-continued

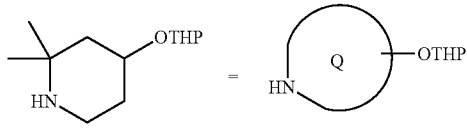

Example Q-3b. Synthesis of Q Group Coupling Partner Q-3

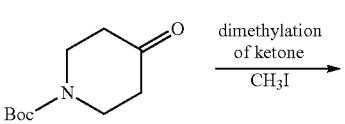
dimethylation of ketone
CH₃I

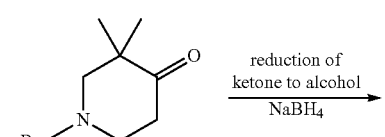
reduction of ketone to alcohol
NaBH₄

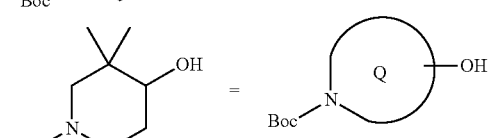

Example Q-3c. Synthesis of Q Group Coupling Partner Q-3

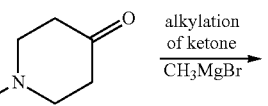
alkylation of ketone
CH₃MgBr

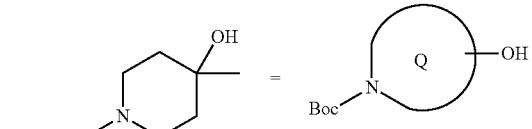

Example Q-3d. Synthesis of Q Group Coupling Partner Q-3

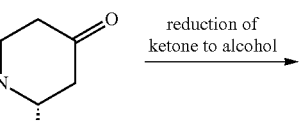
reduction of ketone to alcohol

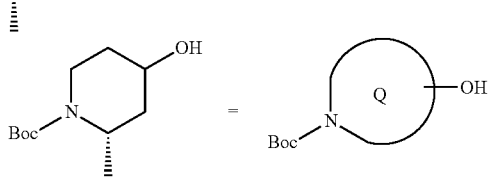

-continued
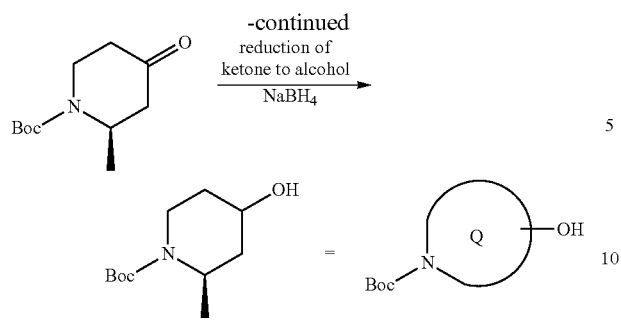
Example Q-3e. Synthesis of Q Group Coupling Partner Q-3
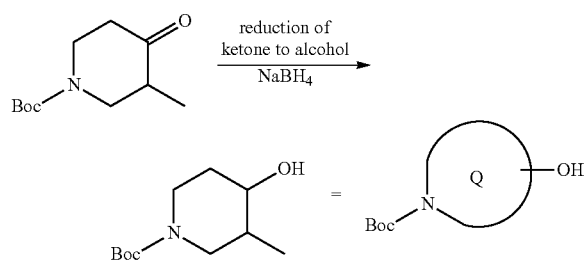
Example Q-3f. Synthesis of Q Group Coupling Partner Q-3
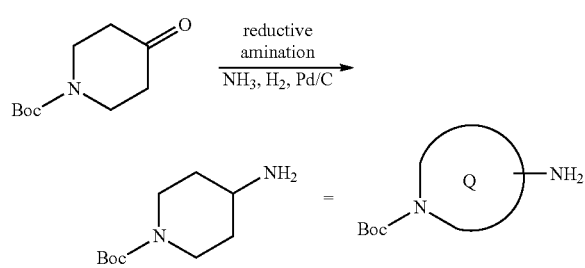
Example Q-4. Synthesis of Q Group Coupling Partner Q-4
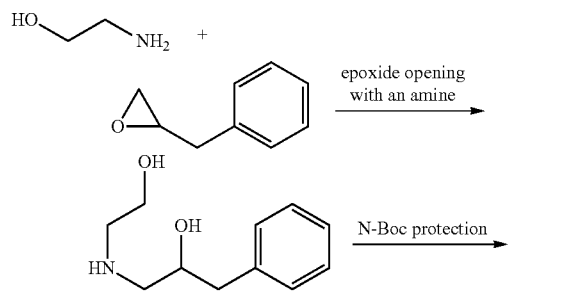
-continued
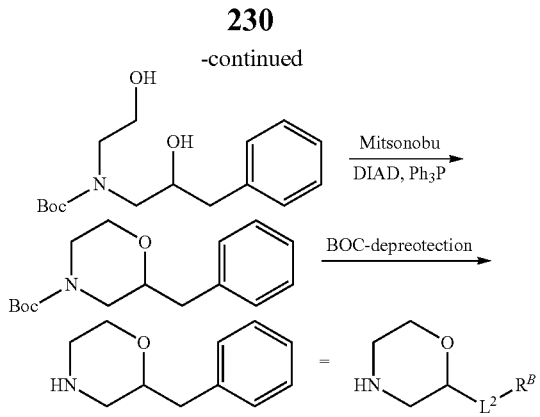
Example Q-6. Synthesis of Q Group Coupling Partner Q-6
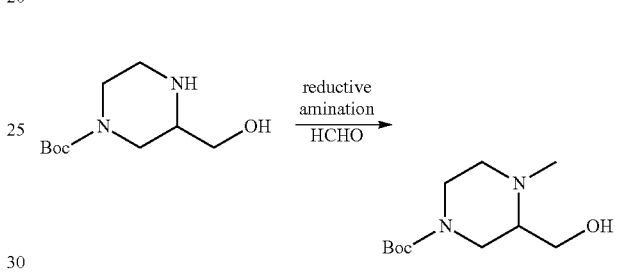
Example Q-8. Synthesis of Q Group Coupling Partner Q-8
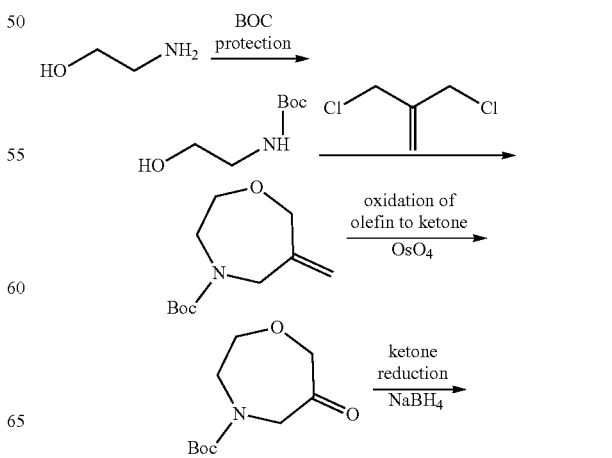
Example Q-9. Synthesis of Q Group Coupling Partner Q-9

-continued
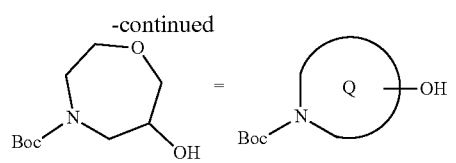
Example Q-10. Synthesis of Q Group Coupling Partner Q-10
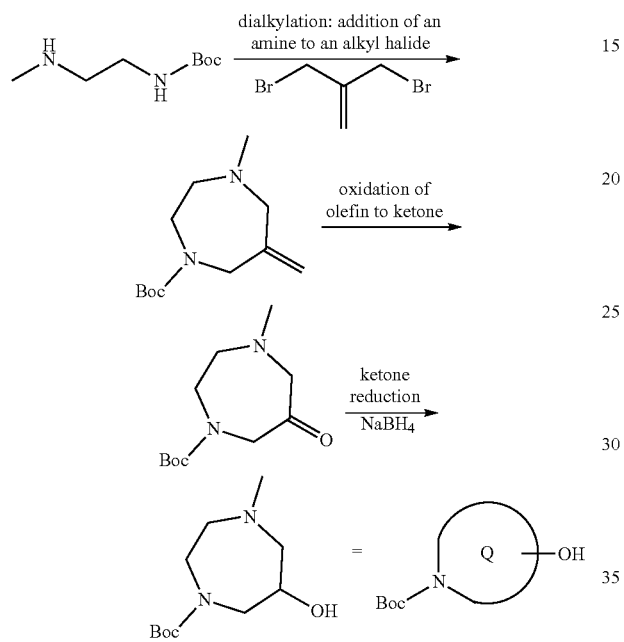
Example Q-19. Synthesis of Q Group Coupling Partner Q-19
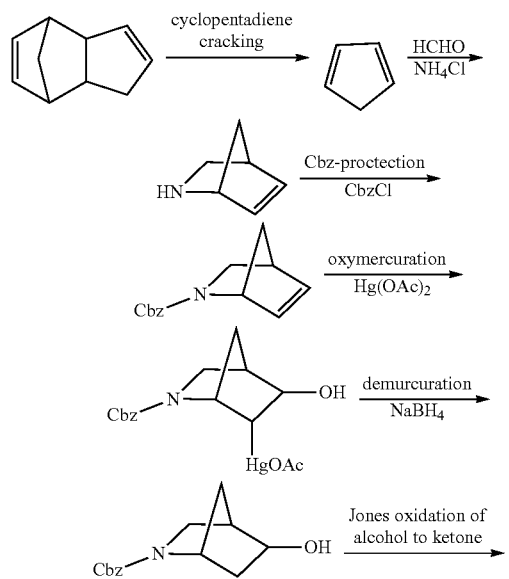
-continued
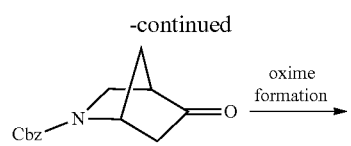
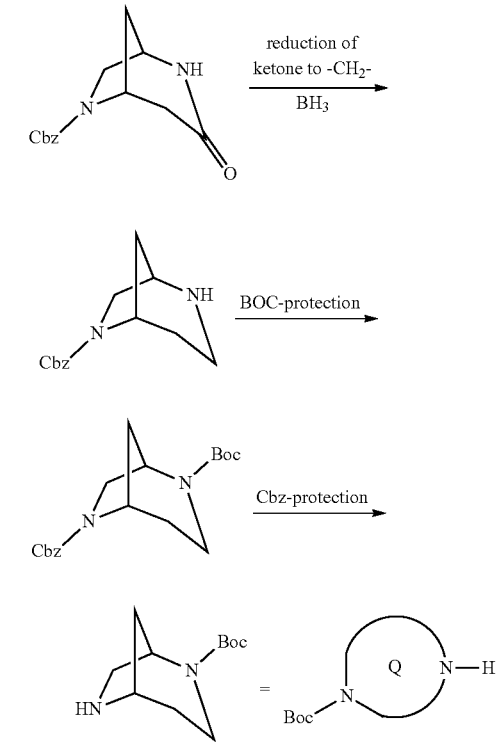
Example Q-31. Synthesis of Q Group Coupling Partner Q-31
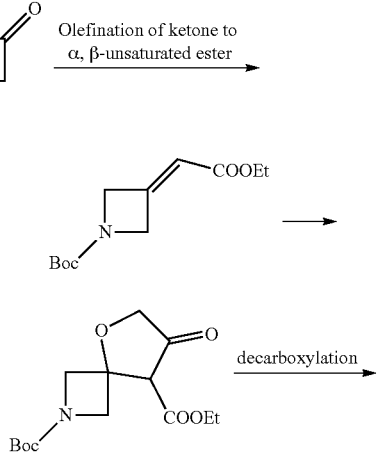

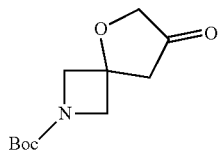
Example Q-32. See Example Q-31 for synthesis of Q-32A. Synthesis of Q Group Coupling Partner Q-32B.
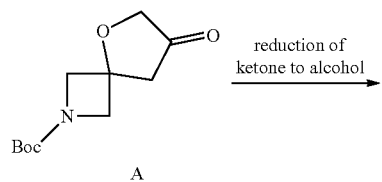
Example Q-33. Synthesis of Q Group Coupling Partner Q-33
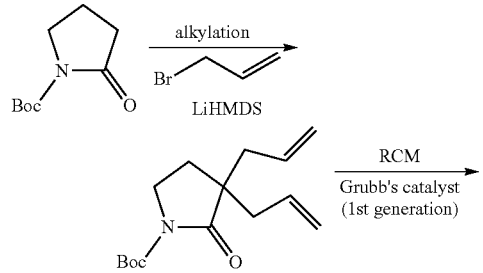
Example Q-34. Synthesis of Q Group Coupling Partner Q-34
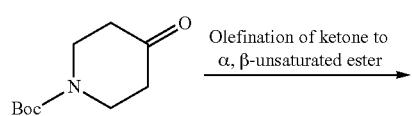
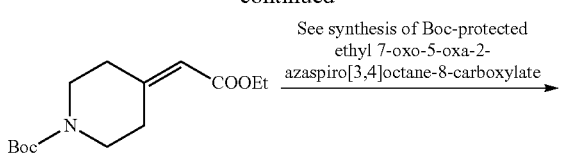
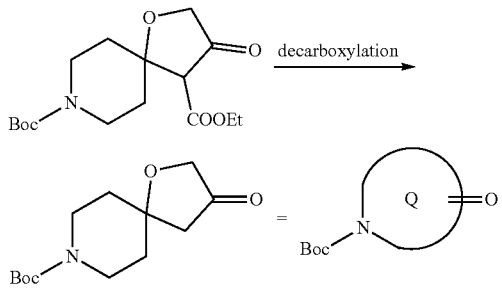
Example Q-41. Q Group Coupling Partner Q-41
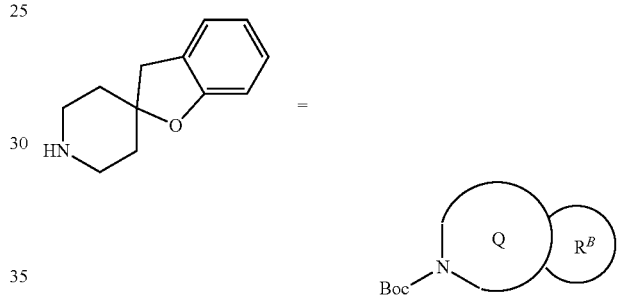
Example Q-43a. Synthesis of Q Group Coupling Partner Q-43
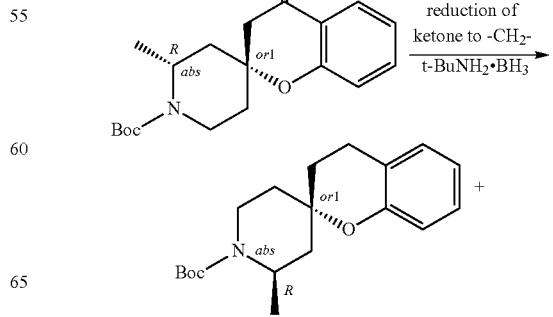

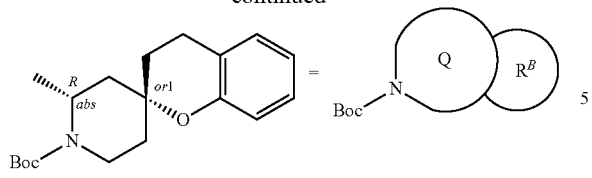

Example Q-43b. Synthesis of Q Group Coupling Partner Q-43

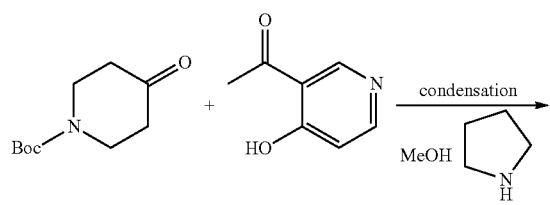

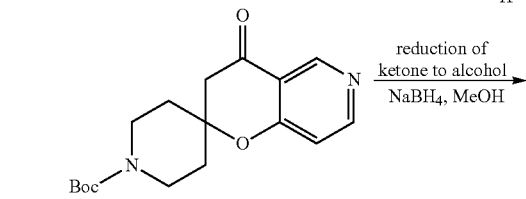

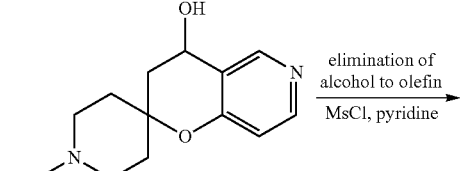

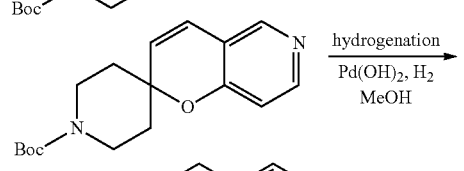

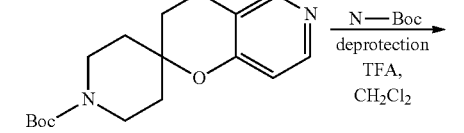

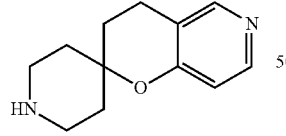

Example Q-45. Synthesis of Q Group Coupling Partner Q-45

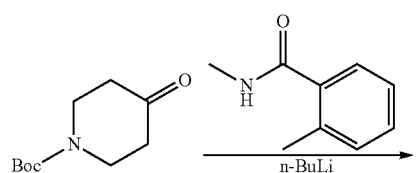

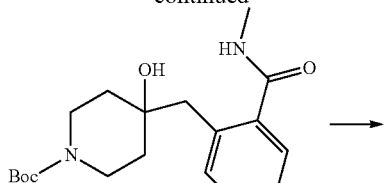

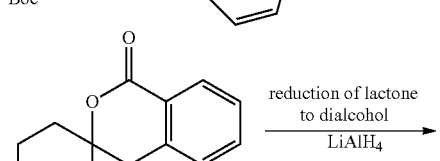

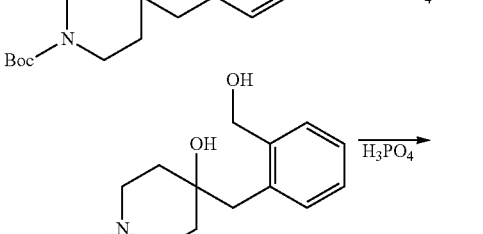

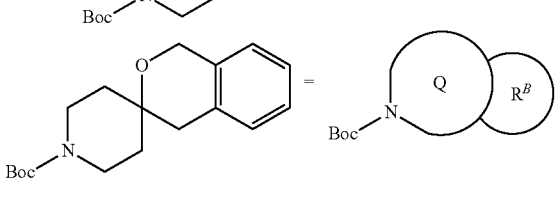

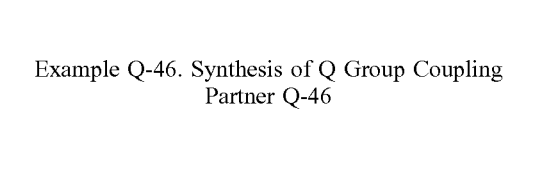

Example Q-46. Synthesis of Q Group Coupling Partner Q-46

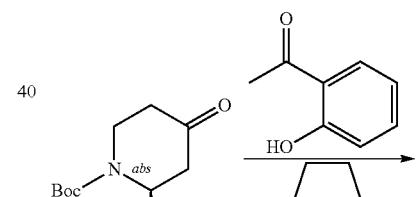

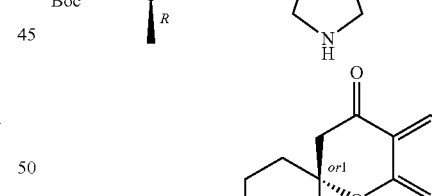

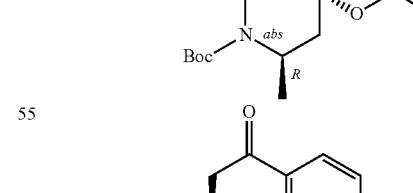

Example $R^B$. Synthesis of $R^B$ group coupling partners to be used in Example $L^2$. Compounds of the invention are made by coupling the $R^B$-coupling partners with the Q through linker $L^2$. Example $R^B$ contains the synthetic methods used to synthesis the $R^B$ coupling partners. Other $R^B$ coupling partners were commercially available.

Example RB-3a. Synthesis $R^B$ Group Coupling Partner $R^B$-3

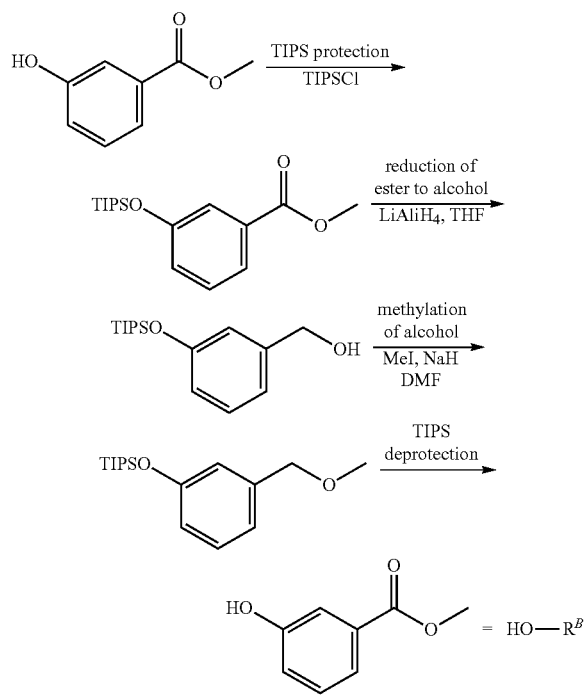

Example T. The routes to synthesize the compounds in Example $L^1$, Example $L^2$, Example $R^A$ and Example $R^B$ contain a variety of chemical transformations. Example T contains representative examples of these transformations.

Example T-1: BOC Protection

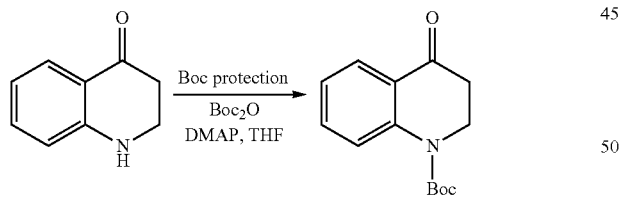

To a solution of 2,3-dihydroquinolin-4(1H)-one (300 mg, 2.04 mmol) and di-tert-butyl dicarbonate (0.53 g, 2.45 mmol) in THF (10 mL) was added N,N-dimethylpyridin-4-amine (0.25 g, 2.04 mmol). The reaction was stirred at ambient temperature overnight. TLC showed about 60% of starting material remained. The reaction was heated to 60° C. and stirred at that temperature overnight. The starting material was not consumed completely. The reaction was poured into water (40 mL) and then extracted with $CH_2Cl_2$ (3×40 mL). The combined organics were washed with brine, dried over $Na_2SO_4$, filtered and concentrated. The residue was purified by silica column chromatography (EtOAc: Hexane=1:6) to give the product (170 mg, 0.69 mmol) as pale oil.

Example T-2a: BOC Deprotection

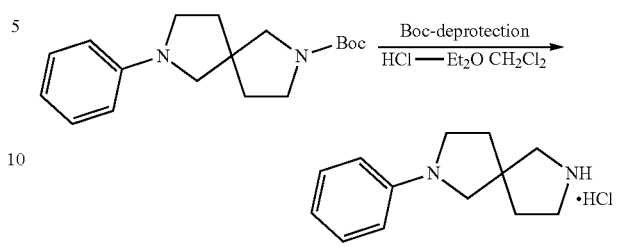

To a solution of tert-butyl 2-benzylmorpholine-4-carboxylate (900 mg, 3.24 mmol) in $CH_2Cl_2$ (2 mL) was added HCl-$Et_2O$ (3 mL). The reaction was stirred at ambient temperature for 2 h. The reaction mixture was concentrated to provide 2-benzylmorpholine hydrochloride (600 mg, 2.81 mmol) as a white solid.

Example T-2b: BOC Deprotection

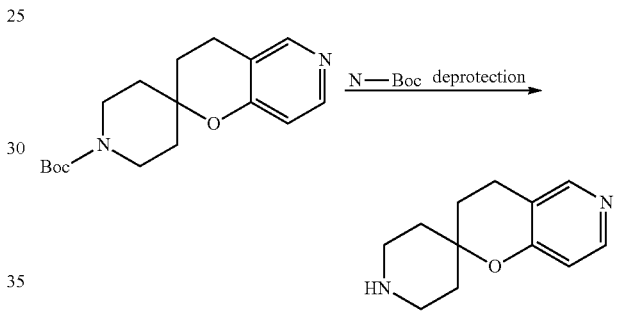

To a solution of tert-butyl 3',4'-dihydrospiro[piperidine-4,2'-pyrano[3,2-c]pyridine]-1-carboxylate (50 mg, 0.16 mmol) in $CH_2Cl_2$ (5 mL) was added TFA (1 mL). The reaction was stirred at ambient temperature for 2 h. TLC showed the starting material was consumed. Saturated aqueous $NaHCO_3$ (25 mL) was added to the reaction vessel and the mixture was extracted with $CH_2Cl_2$ (3×50 mL). The combined organics were dried over anhydrous $Na_2SO_4$, filtered and concentrated in vacuo. The crude product was used for next step without further purification.

Example T-3: Cbz Protection

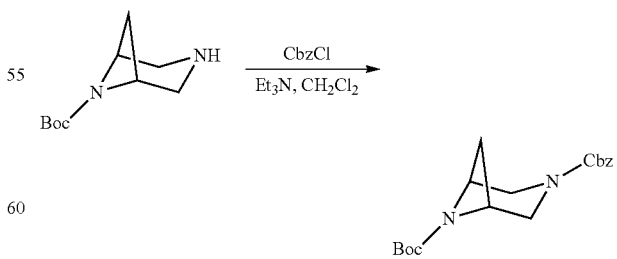

To a solution of (1R,5S)-tert-butyl 3,6-diazabicyclo[3.1.1]heptane-6-carboxylate (2.5 g, 12.61 mmol) in $CH_2Cl_2$ (20 mL) was added triethylamine (3.18 g, 31.53 mmol) and benzyl carbonochloridate (2.15 g, 12.61 mmol). The reaction was stirred at ambient temperature for 2 h. Water (20 mL) was added to the reaction vessel and was extracted with CH$_2$Cl$_2$ (3×15 mL). The layers were separated and the organic phase was washed with saturated aqueous NaCl (2×15 mL). The combined organics were dried over anhydrous Na$_2$SO$_4$, filtered and concentrated in vacuo. After concentration, the residue was purified to give the desired product (3.5 g, 10.53 mmol) as a yellow oil.

Example T-4: Cbz Deprotection

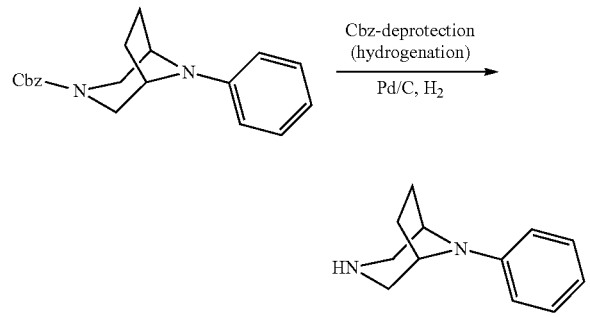

To a solution of (1R,5S)-benzyl 8-phenyl-3,8-diazabicyclo[3.2.1]octane-3-carboxylate (150 mg, 0.4653 mmol) in MeOH (10 mL) was added Pd/C (0.049 g, 0.0465 mmol) and H$_2$. The reaction was stirred at 40° C. for 4 h. The reaction mixture was filtered and concentrated in vacuo. The crude product (1R,5S)-8-phenyl-3,8-diazabicyclo[3.2.1]octane (0.072 g, 0.3824 mmol) was obtained as a colorless oil and used for the next step without purification.

Example T-5: Acetal Deprotection

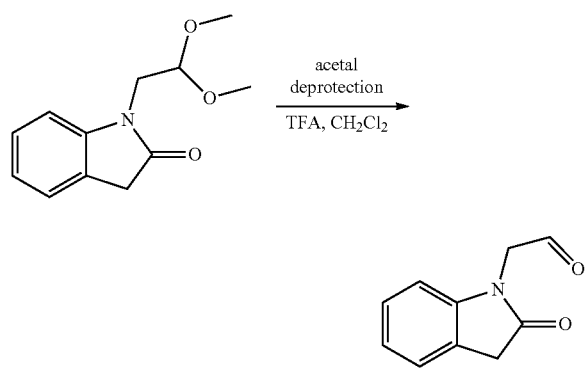

To a solution of 1-(2,2-dimethoxyethyl)indoline (88 mg, 0.43 mmol) in CH$_2$Cl$_2$ (5 mL) was added TFA (0.03 g, 0.22 mmol). The reaction was stirred at 30° C. for 4 h. The reaction mixture was quenched with Na$_2$CO$_3$(aq) extracted with CH$_2$Cl$_2$, and dried over anhydrous Na$_2$SO$_4$, The solvent was removed in vacuo. The residue was purified by silica gel column chromatography (Ethyl acetate:Hexane=3:1) to afford 40 mg product as yellow oil.

Example T-6: Mesylate Formation

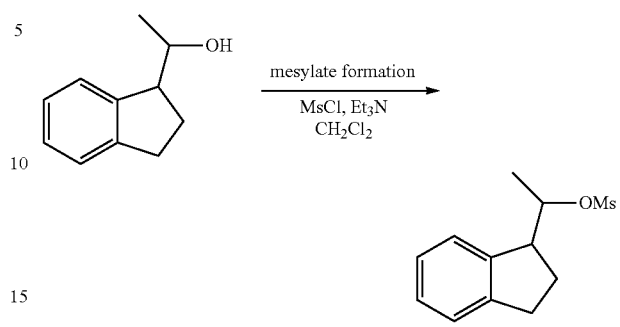

To a solution of 1-(2,3-dihydro-1H-inden-1-yl)ethanol (60 mg, 0.37 mmol) in CH$_2$Cl$_2$ (10 mL) was added methanesulfonyl chloride (0.13 g, 1.11 mmol) and triethylamine (0.07 g, 0.74 mmol). The reaction was stirred at ambient temperature for 30 min under N$_2$. Water (20 mL) was added to the reaction vessel and the resulting biphasic mixture was transferred to a separatory funnel. The layers were separated and the organic/aq phase was extracted with CH$_2$Cl$_2$ (3×100 mL). The combined organics were dried over anhydrous Na$_2$SO$_4$, filtered and concentrated in vacuo. The resulting oil was purified by flash column chromatography with hexane (80%) and EtOAc (20%) to provide 1-(2,3-dihydro-1H-inden-1-yl)ethyl methanesulfonate (0.06 g, 0.25 mmol) as a yellow oil.

Example T-7: Conversion of Alcohol to Alkyl Bromide

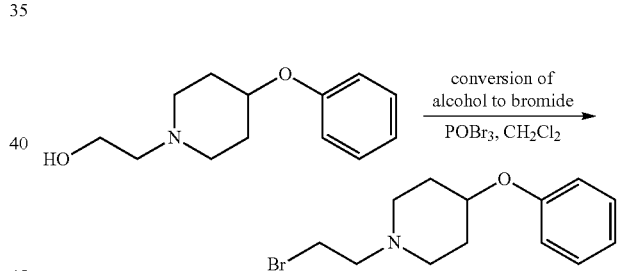

To a solution of 2-(4-phenoxypiperidin-1-yl)ethanol (30 mg, 0.14 mmol) in CH$_2$Cl$_2$ (5 mL) was added phosphoryl bromide (0.08 g, 0.28 mmol). The reaction mixture was heated to 40° C. and stirred at that temperature for 3 h. Saturated aqueous NaHCO$_3$ (20 mL) was added to the reaction vessel and adjusted pH=7. The mixture was extracted with CH$_2$Cl$_2$ (3×20 mL). The combined organics were dried over anhydrous Na$_2$SO$_4$, filtered and concentrated in vacuo. The crude product was used for next step without further purification.

Example T-8a: O-Methylation (A)

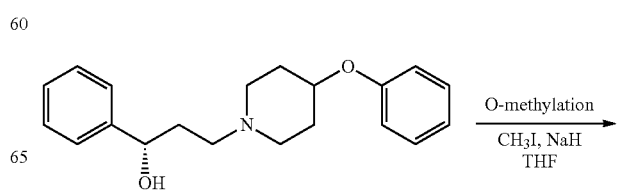

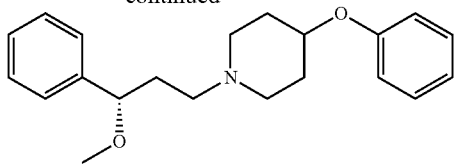

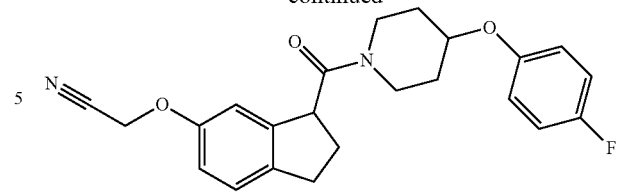

To a solution of 1-(3-methoxy-3-phenylpropyl)-4-phenoxypiperidine (120 mg, 0.37 mmol) in THF (5 mL) was added sodium hydride (0.04 g, 1.85 mmol). The reaction mixture was heated to 40° C. and stirred at that temperature for 30 min. CH$_3$I (0.26 g, 1.85 mmol) was added to the mixture. The reaction was stirred at this temperature for 30 min. Water (30 mL) was added to the reaction vessel and the resulting biphasic mixture was extracted with CH$_2$Cl$_2$ (3×30 mL). The organic phase was washed with saturated aqueous NaCl (1×25 mL). The combined organics were dried over anhydrous Na$_2$SO$_4$, filtered and concentrated in vacuo. The resulting oil was purified by flash column chromatography with a gradient elution of hexanes (50%) and EtOAc (50%) to ethyl acetate (100%) to provide the freebase as an oil. 2N HCl/Et$_2$O (4 mL) was added to the resulting oil and concentrated in vacuo to provide 1-(3-methoxy-3-phenylpropyl)-4-phenoxypiperidine hydrochloride (44 mg) as a white solid.

Example T-8b: O-Methylation (B)

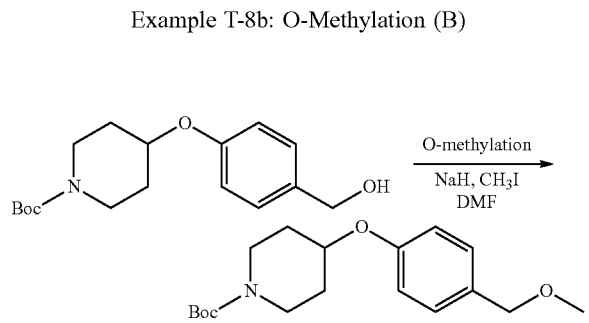

To a solution of tert-butyl 4-(4-(hydroxymethyl)phenoxy)piperidine-1-carboxylate (350 mg, 1.14 mmol) in DMF (5 mL) was added sodium hydride (0.14 g, 5.7 mmol) and iodomethane (0.81 g, 5.7 mmol). The reaction was stirred at ambient temperature for 1 h. Water (20 mL) was added to the reaction vessel and the resulting biphasic mixture was extracted with DCM (3×50 mL). The organic phase was washed with saturated aqueous NaCl (5×25 mL). The combined organics were dried over anhydrous Na$_2$SO$_4$, filtered and concentrated in vacuo. The resulting oil was purified by flash column chromatography with a gradient elution of hexanes (100%) to hexanes (90%) and EtOAc (10%) to provide tert-butyl 4-(4-(methoxymethyl)phenoxy)piperidine-1-carboxylate (350 mg, 1.09 mmol) as a colorless oil.

Example T-9: O-Alkylation (Addition of Alcohol to Alkyl Halide)

To a solution of (4-(4-fluorophenoxy)piperidin-1-yl)(6-hydroxy-2,3-dihydro-1H-inden-1-yl)methanone (220 mg, 0.62 mmol) in THF (30 mL) was added sodium hydride (0.06 g, 2.48 mmol) and 2-bromoacetonitrile (0.15 g, 1.24 mmol). The reaction was stirred at ambient temperature for 1 h. Water (20 mL) was added to the reaction vessel and the resulting biphasic mixture was extracted with ethyl acetate (3×60 mL). The organic phase was washed with saturated aqueous NaCl (1×50 mL). The combined organics were dried over anhydrous Na$_2$SO$_4$, filtered and concentrated in vacuo. The resulting oil was purified by flash column chromatography with a gradient elution of hexanes (95%) and EtOAc (5%) to hexanes (50%) and EtOAc (50%) to provide 2-((3-(4-(4-fluorophenoxy)piperidine-1-carbonyl)-2,3-dihydro-1H-inden-5-yl)oxy)acetonitrile (180 mg, 0.46 mmol) as a white solid.

Example T-10: O-Alkylation (Addition of Alcohol to an Alkyl Mesylate)

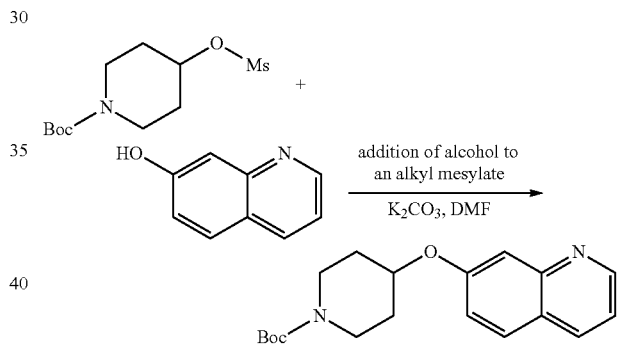

To a solution of quinolin-7-ol (100 mg, 0.69 mmol) in DMF (2 mL) was added tert-butyl 4-((methylsulfonyl)oxy)piperidine-1-carboxylate (0.23 g, 0.83 mmol) and K$_2$CO$_3$ (0.29 g, 2.07 mmol). The reaction mixture was heated to 90° C. and stirred at that temperature for 3 h. Water (15 mL) was added to the reaction vessel and the resulting biphasic mixture was extracted with ethyl acetate (3×50 mL). The organic phase was washed with saturated aqueous NaCl (5×25 mL). The combined organics were dried over anhydrous Na$_2$SO$_4$, filtered and concentrated in vacuo to provide tert-butyl 4-(quinolin-7-yloxy)piperidine-1-carboxylate (100 mg) as a brown oil.

Example T-11: O-Alkylation (Addition of Alcohol to an Alkyl Halide) (A)

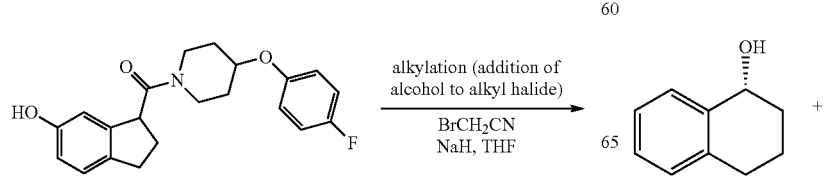

alkylation: addition of alcohol to an alkyl halide

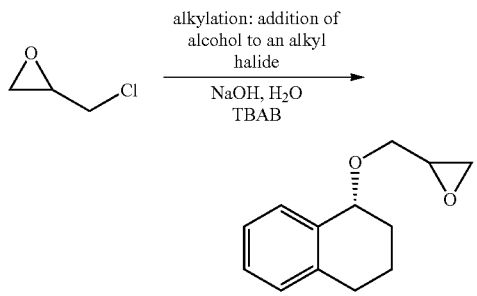

To a solution of 2-(chloromethyl)oxirane (0.17 g, 1.88 mmol) in NaOH (15 M) was added (R)-1,2,3,4-tetrahydronaphthalen-1-ol (0.07 g, 0.47 mmol). The reaction was stirred at ambient temperature for 3 h. TLC showed a new spot. GC-MS showed the product. Water was added to the mixture and extracted with EtOAc (3×50 mL). The combined organics were dried over anhydrous Na$_2$SO$_4$, filtered and concentrated in vacuo. The resulting oil was purified by flash column chromatography with an isocratic elution of hexanes (95%) and EtOAc (5%) to hexanes (85%) and EtOAc (15%) to provide 2-((((R)-1,2,3,4-tetrahydronaphthalen-1-yl)oxy)methyl)oxirane (65 mg, 0.32 mmol) as a colorless oil.

Example T-12: O-Alkylation (Addition of Alcohol to an Alkyl Halide) (B)

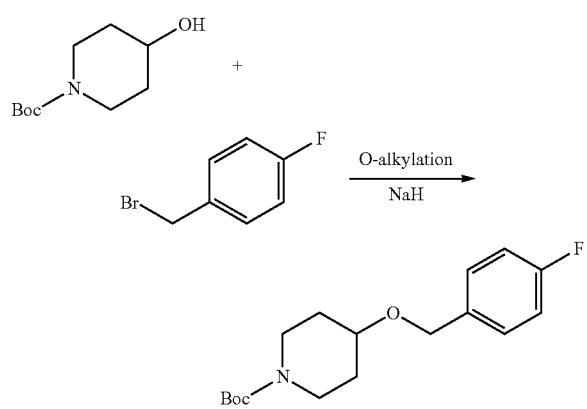

To a solution of tert-butyl 4-hydroxypiperidine-1-carboxylate (600 mg, 2.9812 mmol) in THF (10 mL) was added sodium hydride (0.2385 g, 5.9624 mmol) and 1-(bromomethyl)-4-fluorobenzene (0.6199 g, 3.2793 mmol). The reaction was stirred at 60° C. for 1 h. Water (20 mL) and EtOAc (100 mL) were added to the reaction vessel and the resulting biphasic mixture was transferred to a separatory funnel. The layers were separated and the organic phase was washed with saturated aqueous NaCl (2×20 mL). The combined organics were dried over anhydrous Na$_2$SO$_4$, filtered and concentrated in vacuo. The resulting oil was purified by flash column chromatography with a gradient elution of hexanes (100%) to hexanes (80%) and EtOAc (20%) to provide tert-butyl 4-((4-fluorobenzyl)oxy)piperidine-1-carboxylate (0.8 g, 2.5859 mmol) as a colorless oil.

Example T-13: Mitsunobu (Conversion of an Alcohol into an Ester) (A)

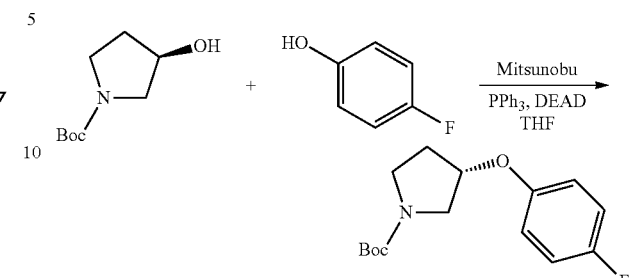

To a solution of (R)-tert-butyl 3-hydroxypyrrolidine-1-carboxylate (500 mg, 2.67 mmol) in THF (10 mL) was added 4-fluorophenol (0.3 g, 2.67 mmol), triphenylphosphine (0.84 g, 3.2 mmol) and diisopropyl azodiformate (0.59 g, 2.94 mmol). The reaction was stirred at ambient temperature for 24 h. TLC showed the starting material was consumed. The combined organics were filtered and concentrated in vacuo. The resulting oil was purified by flash column chromatography with an isocratic elution of EtOAc (10%) and hexanes (90%) to provide (S)-tert-butyl 3-(4-fluorophenoxy)pyrrolidine-1-carboxylate (530 mg) as a colorless oil.

Example T-14: Mitsunobu (Conversion of an Alcohol into an Ester) (A)

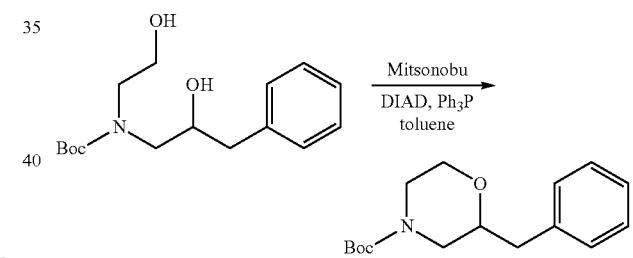

To a solution of tert-butyl (2-hydroxy-3-phenylpropyl)(2-hydroxyethyl)carbamate (1.3 g, 4.401 mmol) in toluene (25 mL) was added triphenylphosphine (1.385 g, 5.281 mmol). Then DIAD (1.067 g, 5.281 mmol) was added dropwise. The reaction mixture was heated to 30° C. and stirred at that temperature for 16 h. The reaction mixture was concentrated. The resulting oil was purified by flash column chromatography with a gradient elution of hexanes (94%) and EtOAc (6%) to hexanes (85%) and EtOAc (15%) to provide tert-butyl 2-benzylmorpholine-4-carboxylate (900 mg, 3.245 mmol) as a colorless oil.

Example T-15: N-Methylation

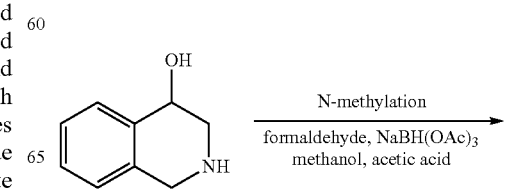

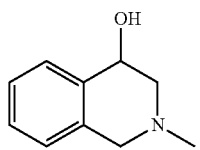

To a solution of 1,2,3,4-tetrahydroisoquinolin-4-ol (655 mg, 4.39 mmol) in MeOH (20 mL) was added formaldehyde (278 mg, 3.24 mmol), a drop of acetic acid. The reaction was stirred at ambient temperature for 30 min. NaBH(OAc)$_3$ (1.05 g, 4.98 mmol) was added to the reaction mixture. The reaction was stirred at ambient temperature for 16 h. Saturated aqueous NaHCO$_3$ (50 mL) was added to the reaction vessel and the resulting biphasic mixture was transferred to a separatory funnel. The layers were separated and the aqueous phase was washed with DCM (3×30 mL). The combined organics were dried over anhydrous Na$_2$SO$_4$, filtered and concentrated in vacuo. The resulting oil was purified by flash column chromatography with a gradient elution of DCM (100%) and MeOH (0%) to DCM (90%) and MeOH (10%) to provide 2-methyl-1,2,3,4-tetrahydroisoquinolin-4-ol (62.0 mg, 0.3803 mmol) as a yellow solid.

Example T-16: N-Alkylation (Addition of Amine to an Alkyl Mesylate)

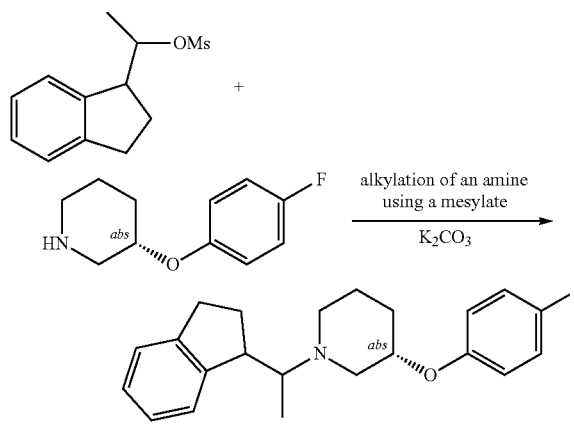

To a solution of 1-(2,3-dihydro-1H-inden-1-yl)ethyl methanesulfonate (60 mg, 0.25 mmol) in DMF (10 mL) was added (S)-3-(4-fluorophenoxy)piperidine (0.05 g, 0.25 mmol) and K$_2$CO$_3$ (0.07 g, 0.5 mmol). The reaction was stirred at 90° C. for 2 h under N$_2$. Water (30 mL) was added to the reaction vessel and the resulting biphasic mixture was transferred to a separatory funnel. The layers were separated and the organic/aq phase was extracted with EtOAc (3×100 mL). The combined organics were dried over anhydrous Na$_2$SO$_4$, filtered and concentrated in vacuo. The resulting was purified by reverse phase HPLC with MeOH (5%) and water (95%) to MeOH (40%) and water (60%) to provide (3S)-1-(1-(2,3-dihydro-1H-inden-1-yl)ethyl)-3-(4-fluorophenoxy)piperidine (10 mg, 0.03 mmol) as a colorless oil.

Example T-17: N-Alkylation (Addition of Amine to an Alkyl Halide) (A)

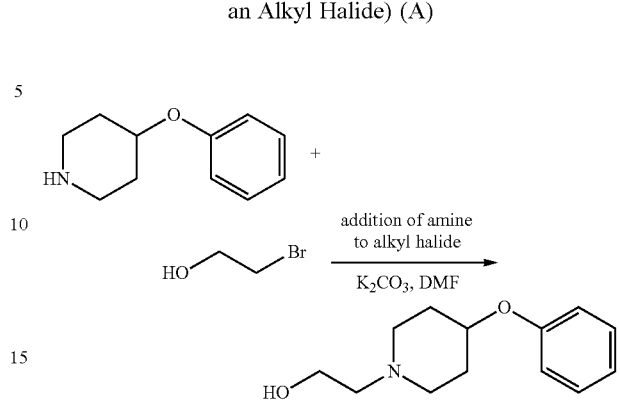

To a solution of 4-phenoxypiperidine (500 mg, 2.82 mmol) in DMF (6 mL) was added K$_2$CO$_3$ (0.78 g, 5.64 mmol) and 2-bromoethanol (0.39 g, 3.1 mmol). The reaction mixture was heated to 50° C. and stirred at that temperature for 3 h. TLC showed most of the product. The reaction was poured into water and extracted with DCM (3×40 mL). The combined organics were washed with saturated aqueous NaCl (2×20 mL). The combined organics were dried over anhydrous Na$_2$SO$_4$, filtered and concentrated in vacuo. The resulting oil was purified by flash column chromatography with a gradient elution of DCM (95%) and MeOH (5%) to DCM (85%) and MeOH (15%) to provide 2-(4-phenoxypiperidin-1-yl)ethanol (260 mg, 1.17 mmol) as a yellow solid.

Example T-18: N-Alkylation (Addition of Amine to an Alkyl Halide) (B)

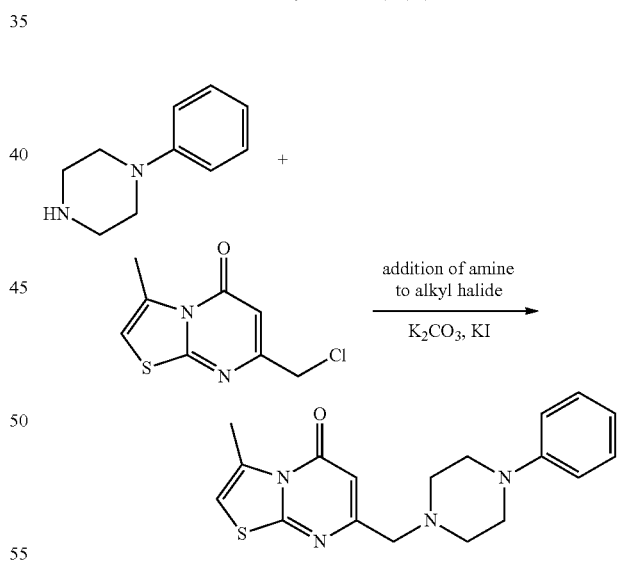

To a solution of 7-(chloromethyl)-3-methyl-5H-thiazolo [3,2-a]pyrimidin-5-one (100 mg, 465 μmol) in CH$_3$CN (10 mL) was added K$_2$CO$_3$ (255 mg, 1.85 mmol), KI (7.71 mg, 46.5 μmol) and 1-phenylpiperazine (82.9 mg, 511 μmol). The reaction was stirred at ambient temperature for 16 h. Water (30 mL) and EtOAc (100 ml) were added to the reaction vessel and the resulting biphasic mixture was transferred to a separatory funnel. The layers were separated and the organic phase was washed with saturated aqueous NaCl (2×50 mL). The combined organics were dried over anhydrous Na$_2$SO$_4$, filtered and concentrated in vacuo. The resulting solid was purified by flash column chromatography with a gradient elution of EtOAc (25%) and hexanes (75%) to EtOAc (50%) and hexanes (50%) to provide 3-methyl-7-((4-phenylpiperazin-1-yl)methyl)-5H-thiazolo[3,2-a]pyrimidin-5-one (98.0 mg, 287 μmol) as an off white solid.

Example T-19: Addition of Amide to Alkyl Halide (A)

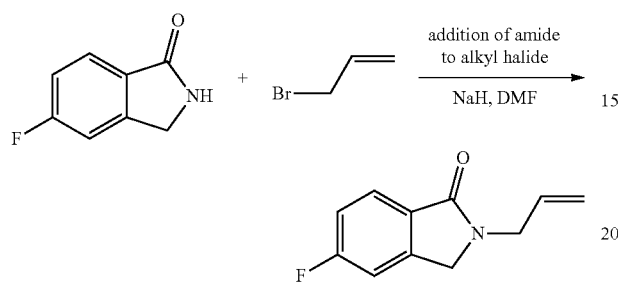

To a solution of 5-fluoroisoindolin-1-one (200 mg, 1.32 mmol) in DMF (5 mL) was added 3-bromoprop-1-ene (0.17 g, 1.45 mmol) and sodium hydride (0.03 g, 1.45 mmol) at 0° C. The reaction was stirred at 0° C. for 30 min. Water (20 mL) and EtOAc (30 mL) were added to the reaction vessel and the resulting biphasic mixture was transferred to a separatory funnel. The layers were separated and the aqueous phase was extracted with EtOAc (2×20 mL). The combined organics were dried over anhydrous Na₂SO₄, filtered and concentrated in vacuo. The resulting solid was purified by flash column chromatography with a gradient elution of EtOAc (10%) and hexanes (90%) to EtOAc (30%) and hexanes (70%) to provide 2-allyl-5-fluoroisoindolin-1-one (160 mg, 0.84 mmol) as a white solid.

Example T-20: N-Alkylation (Addition of an Amine to Alkyl Halide (B)

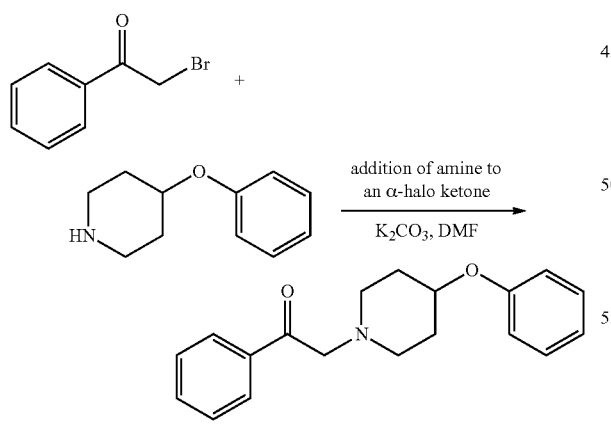

To a solution of 2-bromo-1-phenylethanone (100 mg, 0.5024 mmol) in DMF (2 mL) was added 4-phenoxypiperidine (0.1069 g, 0.6029 mmol) and K₂CO₃ (0.1389 g, 1.0048 mmol). The reaction was stirred at 80° C. for 16 h. Saturated aqueous NaCl (8 mL) and EtOAc (12 mL) was added to the reaction vessel and the resulting biphasic mixture was transferred to a separatory funnel. The layers were separated and the aqueous phase was extracted with EtOAc (3×10 mL). The combined organics were washed with brine (10 mL), dried over anhydrous Na₂SO₄, filtered and concentrated in vacuo. The resulting oil was purified by preparative thin layer chromatography with an isocratic elution of hexanes (80%) and EtOAc (20%) to provide 2-(4-phenoxypiperidin-1-yl)-1-phenylethanone (50 mg) as a yellow oil. The product was dissolved in HCl-Et₂O (2 mL) and stirred at room temperature for 5 min. The mixture was concentrated and the resulting solid was washed with Et₂O (3 mL) and dried in vacuo to give HCl salt (45 mg, 0.1508 mmol) as yellow solid.

Example T-21: N-Alkylation (Addition of an Amine to Alkyl Halide) (C)

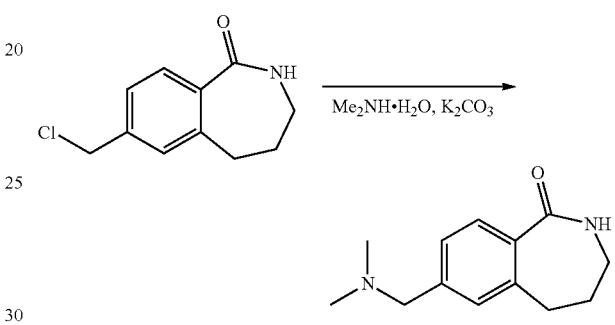

To a solution of 7-(chloromethyl)-2,3,4,5-tetrahydro-1H-benzo[c]azepin-1-one (60 mg, 0.29 mmol) in DMF (10 mL) was added potassium carbonate (0.16 g, 1.16 mmol) and dimethylamine hydrate (0.05 g, 0.87 mmol). The reaction mixture was heated to 120° C. and stirred at that temperature for 1 h. Water (20 mL) was added to the reaction vessel and was extracted with EtOAc (3×15 ml). The layers were separated and the organic phase was washed with saturated aqueous NaCl (2×15 mL). The combined organics were dried over anhydrous Na₂SO₄, filtered and concentrated in vacuo. After concentration, the desired product 50 mg (crude) was obtained as a yellow oil.

Example T-22: N-Alkylation (Addition of an Amide to an α-Halo-Ketone)

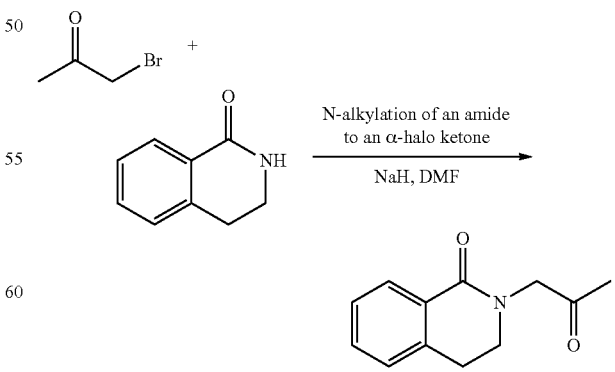

To a solution of 3,4-dihydroisoquinolin-1(2H)-one (200 mg, 1.36 mmol) in DMF (5 mL) was added sodium hydride (0.07 g, 2.72 mmol). The reaction was stirred at ambient temperature for 1 h. 1-bromopropan-2-one (0.28 g, 2.04 mmol) was added to the reaction mixture. The reaction was stirred at ambient temperature for 24 h. TLC and LC-MS showed only a small amount of the desired product. The reaction mixture was heated to 50° C. and stirred at that temperature for an additional 5 h.

Example T-23a: Epoxide Opening with an Amine
(A)

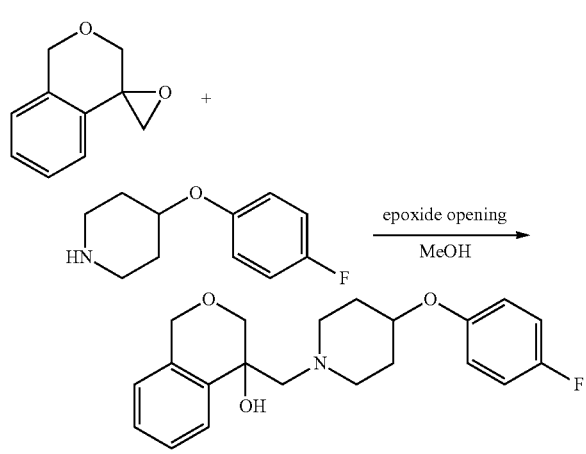

To a solution of spiro[isochroman-4,2'-oxirane] (50 mg, 0.3083 mmol) in MeOH (10 mL) was added 4-(4-fluorophenoxy)piperidine (0.0602 g, 0.3083 mmol). The reaction was stirred at 60° C. for 8 h. The reaction mixture was concentrated in vacuo. The resulting oil was purified by reverse phase HPLC with a gradient elution of MeOH (30%) and water (70%) to MeOH (70%) and water (30%) to provide 4-((4-(4-fluorophenoxy)piperidin-1-yl)methyl)isochroman-4-ol (50 mg, 0.1357 mmol) as an oil.

Example T-23b: Epoxide Opening with an Amine
(B)

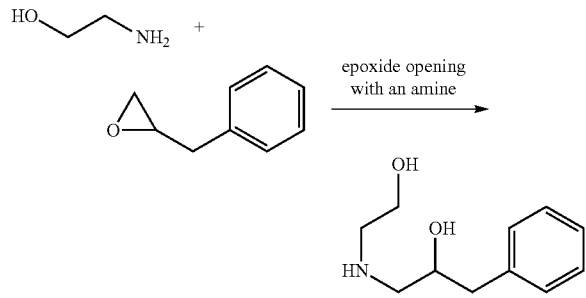

A solution of 2-benzyloxirane (1.5 g, 11.18 mmol) in 2-aminoethanol (2.73 g, 44.72 mmol) was stirred at ambient temperature for 16 h. Water (40 mL) was added to the reaction vessel and the aqueous phase was extracted with DCM (3×25 mL). The combined organics were washed with brine (15 mL), dried over anhydrous Na$_2$SO$_4$, filtered and concentrated to provide 1-((2-hydroxyethyl)amino)-3-phenylpropan-2-ol (1.7 g, 8.71 mmol) as a yellow oil.

Example T-23c: Epoxide Opening with an Amine
(C)

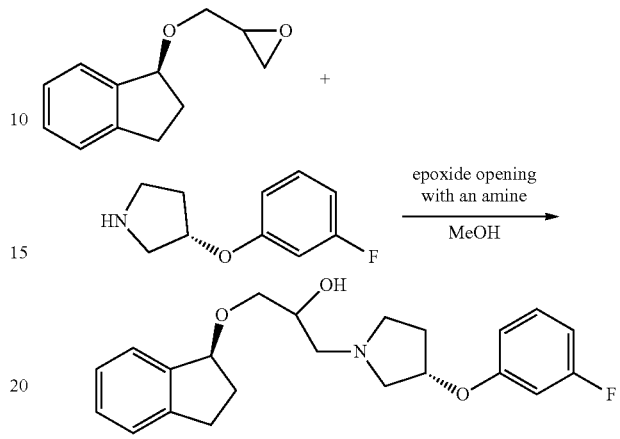

To a solution of 2-((((S)-2,3-dihydro-1H-inden-1-yl)oxy)methyl)oxirane (38 mg, 0.21 mmol) in CH$_3$OH (2 mL) was added (S)-3-(3-fluorophenoxy)pyrrolidine (0.04 g, 0.21 mmol). The reaction mixture was heated to 60° C. and stirred at that temperature for 4 h. The reaction mixture was concentrated in vacuo. The resulting oil was purified by preparative thin layer chromatography with an isocratic elution of EtOAc (95%) and MeOH (5%) to provide 1-(((S)-2,3-dihydro-1H-inden-1-yl)oxy)-3-((S)-3-(3-fluorophenoxy)pyrrolidin-1-yl)propan-2-ol (16 mg, 0.05 mmol) as a colorless oil.

Example T-24: Alkylation Alpha to an Acid

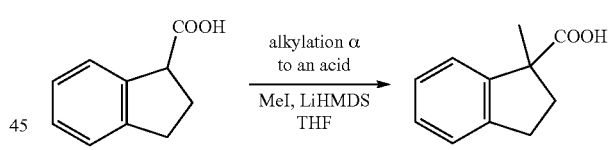

To a solution of 2,3-dihydro-1H-indene-1-carboxylic acid (1 g, 6.17 mmol) in THF (10 mL) was added dropwise lithium bis(trimethylsilyl)amide (2.06 g, 12.34 mmol) at −20° C. under N$_2$. The reaction was stirred at 35° C. for 1 h. A solution of iodomethane (1.14 g, 8.02 mmol) in THF (3 mL) was added slowly at 0° C. The reaction was stirred at 35° C. for 2 h. The mixture solution was acidified with 6 N HCl to pH=5 and the resulting biphasic mixture was transferred to a separatory funnel. The layers were separated and the aqueous phase was extracted with EtOAc (2×20 mL). The combined organics were dried over anhydrous Na$_2$SO$_4$, filtered and concentrated in vacuo. The resulting oil was purified by flash column chromatography with an isocratic elution of EtOAc (10%) and petroleum ether (90%) to provide 1-methyl-2,3-dihydro-1H-indene-1-carboxylic acid (0.45 g, 2.55 mmol) as a brown solid.

Example T-25: Alkylation of a Ketone

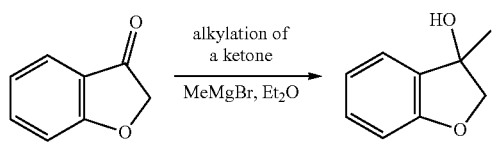

To a solution of benzofuran-3(2H)-one (700 mg, 5.2187 mmol) in ether (30 mL) was added methylmagnesium bromide (1.5557 g, 13.0468 mmol). The reaction was stirred at 15° C. for 1 h. The reaction mixture was treated with H₂O (30 mL). The aqueous layer was extracted with EtOAc (3×30 mL). The combined organic layers were washed with brine, dried over Na₂SO₄, filtered and concentrated in vacuo. The resulting oil was purified by column chromatography (EtOAc:Hexanes=1:10) to provide the desired product (500 mg, 2.83 mmol) as an oil.

Example T-26: Arylation of a Ketone

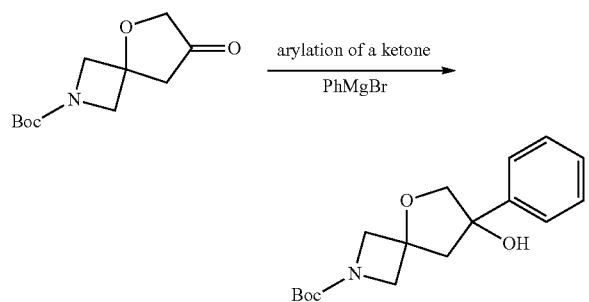

To a solution of tert-butyl 7-oxo-5-oxa-2-azaspiro[3.4]octane-2-carboxylate (500 mg, 2.20 mmol) in THF (10 mL) was added phenylmagnesium bromide (3.30 mL, 3.30 mmol) at 0° C. The reaction was stirred at that temperature for 1 h. Saturated aqueous NH₄Cl (10 mL) was added to the reaction vessel and the resulting mixture was extracted with EtOAc (3×20 mL). The combined organics were dried over anhydrous Na₂SO₄, filtered and concentrated in vacuo to provide tert-butyl 7-hydroxy-7-phenyl-5-oxa-2-azaspiro[3.4]octane-2-carboxylate (700 mg crude) as a pale yellow oil.

Example T-27: Alkylation Alpha to a Ketone

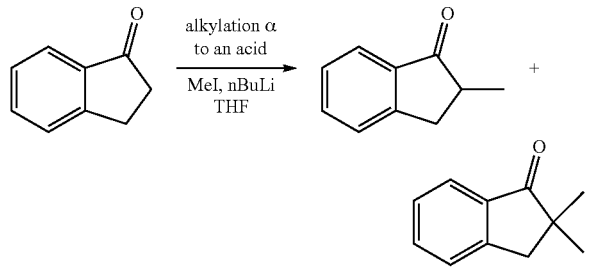

To a solution of 2,3-dihydro-1H-inden-1-one (2 g, 15.13 mmol) in THF (50 mL) was added iodomethane (2.15 g, 15.13 mmol) and butyllithium (0.97 g, 15.13 mmol). The reaction mixture was cooled to 0° C. and stirred at that temperature for 1 h. Na₂S₂O₃ (20 mL) was added to the reaction vessel and was extracted with DCM (3×15 ml). The layers were separated and the organic phase was washed with saturated aqueous NaCl (2×15 mL). The combined organics were dried over anhydrous Na₂SO₄, filtered and concentrated in vacuo. After concentration, the residue was purified by silica column chromatography with a gradient elution of hexane to hexane (90%) and EtOAc (10%) to give the product 2-methyl-2,3-dihydro-1H-inden-1-one (450 mg, 3.08 mmol) and 2,2-dimethyl-2,3-dihydro-1H-inden-1-one (900 mg, 5.62 mmol) as a yellow oil.

Example T-28: Alkylation Alpha to a Ketone with Allyl Bromide

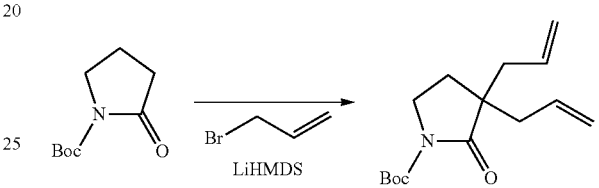

To a solution of tert-butyl 2-oxopyrrolidine-1-carboxylate (3 g, 16.2 mmol) in THF (30 mL) was added dropwise LiHMDS (27.54 mL 27.54 mmol) at −78° C. under N₂. The reaction was stirred at this temperature for 1 h. 3-bromoprop-1-ene (3.33 g, 27.54 mmol) was added dropwise to the reaction mixture. The reaction was stirred at −78° C. for 1 h. Saturated aqueous NH₄Cl (10 mL) and EtOAc (100 mL) were added to the reaction vessel and the resulting biphasic mixture was transferred to a separatory funnel. The layers were separated and the organic phase was washed with saturated aqueous NaCl (2×10 mL). The combined organics were dried over anhydrous Na₂SO₄, filtered and concentrated in vacuo. The resulting oil was purified by flash column chromatography with a gradient elution of hexanes (100%) to hexanes (90%) and EtOAc (10%) to provide tert-butyl 3,3-diallyl-2-oxopyrrolidine-1-carboxylate (1 g, 3.77 mmol) as a colorless oil.

Example T-29: Conversion of Amine to N-Substituted CH₂CHO

General Scheme

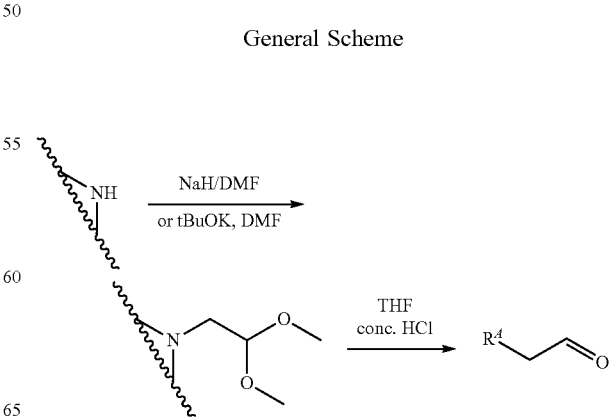

Representative Example

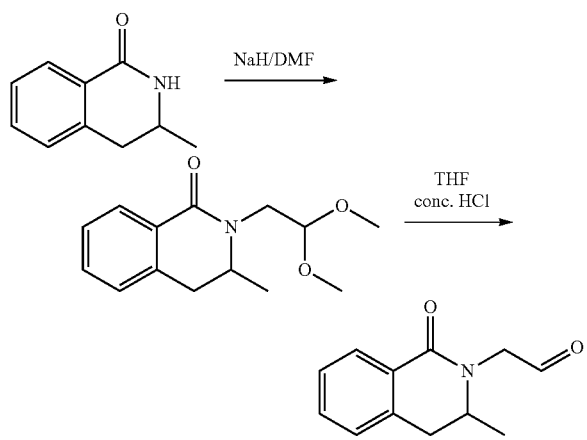

To a solution of 3-methyl-3,4-dihydroisoquinolin-1(2H)-one (170 mg, 1.05 mmol) in DMF (10 mL) was added 2-bromo-1,1-dimethoxyethane (0.35 g, 2.1 mmol) and sodium hydride (0.17 g, 4.2 mmol). The reaction was stirred at ambient temperature for 12 h. Water (50 mL) was added to the reaction vessel and was extracted with EtOAc (3×60 ml). The layers were separated and the organic phase was washed with saturated aqueous NaCl (2×50 mL). The combined organics were dried over anhydrous $Na_2SO_4$, filtered and concentrated in vacuo. The residue was concentrated to provide 2-(2,2-dimethoxyethyl)-3-methyl-3,4-dihydroisoquinolin-1(2H)-one (250 mg, 1 mmol) as a yellow oil.

To a solution of 2-(2,2-dimethoxyethyl)-3-methyl-3,4-dihydroisoquinolin-1(2H)-one (250 mg, 1 mmol) in THF (10 mL) was added hydrogen chloride (2.19 g, 60 mmol). The reaction was stirred at ambient temperature for 2 h. Water (50 mL) was added to the reaction vessel and was extracted with EtOAc (3×60 ml). The layers were separated and the organic phase was washed with saturated aqueous NaCl (2×50 mL). The combined organics were dried over anhydrous $Na_2SO_4$, filtered and concentrated in vacuo. The residue was concentrated to provide 2-(3-methyl-1-oxo-3,4-dihydroisoquinolin-2(1H)-yl)acetaldehyde (90 mg, 0.44 mmol) as a yellow oil.

Example T-30: Epoxide Formation from a Ketone by Corey-Chaykovsky Epoxidation

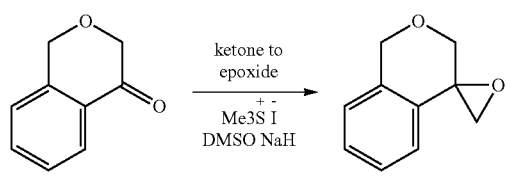 [SMILES: O=C1COCc2ccccc21 ; c1ccc2c(c1)COCC21CO1]

To a solution of trimethylsulfonium iodide (1.3774 g, 6.7496 mmol) in DMSO (10 mL) was added sodium hydride (0.243 g, 10.1244 mmol). After 20 min later isochroman-4-one (500 mg, 3.3748 mmol) was added. The reaction was stirred at 25° C. for 1 h. The reaction mixture was treated with $H_2O$ (30 mL). The aqueous layer was extracted with EtOAc (3×30 mL). The combined organic layers were washed with brine, dried over $Na_2SO_4$, filtered and concentrated in vacuo. The resulting oil was purified by column chromatography (EtOAc:Hexanes=1:10) to provide the desired product (350 mg, 1.9422 mmol) as an oil.

Example T-31: Olefination of Ketone to α,β-Unsaturated Ester

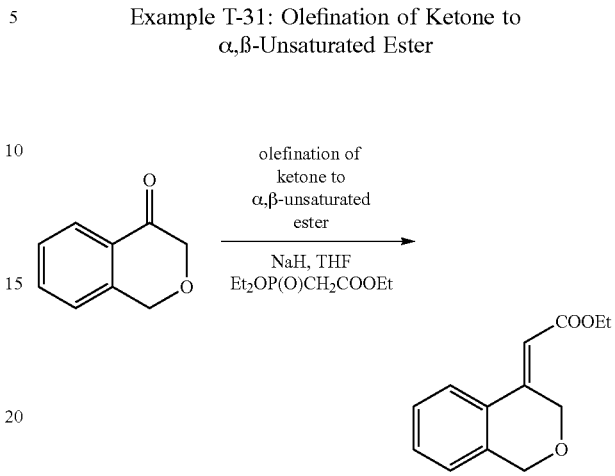

To a solution of sodium hydride (0.16 g, 6.74 mmol) in THF (30 mL) was added ethyl 2-(diethoxyphosphoryl)acetate (1.89 g, 8.43 mmol). The reaction was stirred at room temperature for 30 min. Isochroman-4-one (500 mg, 3.37 mmol) was added. The reaction was stirred at room temperature for 4 h. The solvent was then distilled off under reduced pressure. The residue was purified by silica gel column chromatography with EtOAc (5%) and hexanes (95%) to provide (Z)-ethyl 2-(isochroman-4-ylidene)acetate (600 mg) as a yellow oil.

Example T-32: Homologation: Ketone to Acid

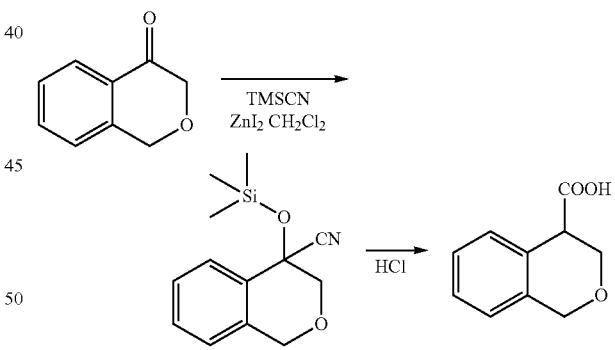

To a solution of isochroman-4-one (500 mg, 3.37 mmol) in DCM (20 mL) was added zinc(II) iodide (0.11 g, 0.34 mmol) and trimethylsilanecarbonitrile (1 g, 10.11 mmol). The reaction was stirred at ambient temperature for 12 h. The reaction mixture was concentrated in vacuo. The resulting oil was purified by flash column chromatography with a gradient elution of hexane (100%) to hexane (90%) and EtOAc (10%) to provide 4-((trimethylsilyl)oxy)isochroman-4-carbonitrile (0.4 g, 1.62 mmol) as a colorless oil.

To a solution of 4-((trimethylsilyl)oxy)isochroman-4-carbonitrile (400 mg, 1.62 mmol) in AcOH (4 mL) was added con hydrogen chloride (4 mL). The reaction mixture was heated to 130° C. and stirred at that temperature for 2 h. 1M aqueous NaOH (200 mL) and DCM (100 mL) were added to the reaction vessel and the resulting biphasic mixture was transferred to a separatory funnel. The layers were separated and the aqueous phase was washed with DCM (2×50 mL). The aqueous was adjusted to pH=3. DCM (100 mL) was added to the reaction vessel and the resulting biphasic mixture was transferred to a separatory funnel. The layers were separated and the organic phase was washed with saturated aqueous NaCl (2×25 mL). The combined organics were dried over anhydrous Na$_2$SO$_4$, filtered and concentrated in vacuo to provide isochroman-4-carboxylic acid (0.06 g, 0.34 mmol) as a colorless oil.

Example T-33: Homologation. Ketone to Cyano

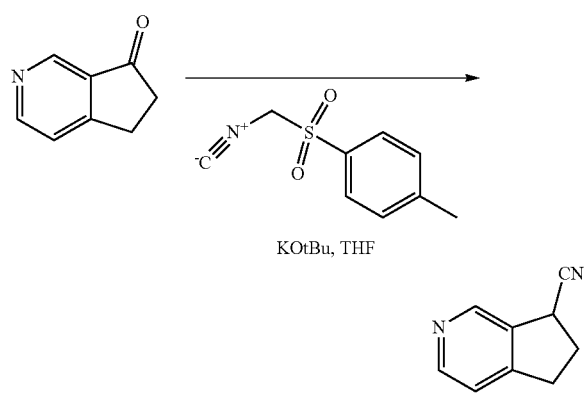

To a solution of 5H-cyclopenta[c]pyridin-7(6H)-one (300 mg, 2.25 mmol) in THF (10 mL) was added 1-((isocyanomethyl)sulfonyl)-4-methylbenzene (0.66 g, 3.38 mmol). The reaction was stirred at ambient temperature for 10 min. Then potassium 2-methylpropan-2-olate (0.5 g, 4.5 mmol) was added in five portions. The reaction was stirred at ambient temperature for 15 min. TLC showed the starting material was consumed. The organics were concentrated in vacuo and used for next step without further purification.

Example T-34: Homologation. Ketone to Acid

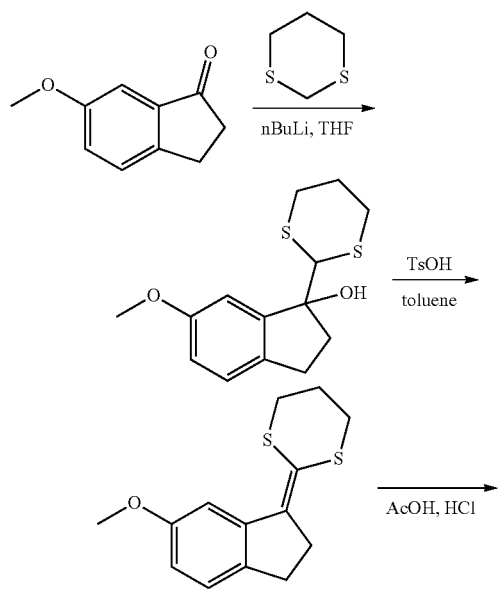

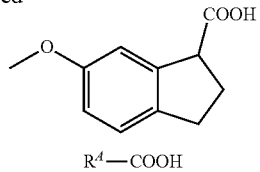

To a solution of 6-methoxy-2,3-dihydro-1H-inden-1-one (5.8 g, 35.76 mmol) in THF was added 1,3-dithiane (4.73 g, 39.34 mmol) and n-butyllithium (3.44 g, 53.64 mmol). The reaction mixture was cooled to 0° C. and stirred at that temperature for 12 h. Water (50 mL) was added to the reaction vessel and the reaction was extracted with EtOAc (3×55 ml). The layers were separated and the organic phase was washed with saturated aqueous NaCl (2×35 mL). The combined organics were dried over anhydrous Na$_2$SO$_4$, filtered and concentrated in vacuo. After concentration, the resulting oil was purified by silica column chromatography with a gradient elution of hexanes to hexanes (90%) and EtOAc (10%) to provide 1-(1,3-dithian-2-yl)-6-methoxy-2,3-dihydro-1H-inden-1-ol (10.1 g, 35.76 mmol) as a yellow power.

To a solution of 1-(1,3-dithian-2-yl)-6-methoxy-2,3-dihydro-1H-inden-1-ol (10.1 g, 35.76 mmol) in toluene (50 mL) was added 4-methylbenzenesulfonic acid (1.54 g, 8.94 mmol). The reaction mixture was heated to 50° C. and stirred at that temperature for 1 h. Water (20 mL) was added to the reaction vessel and the resulting biphasic mixture was extracted with ethyl acetate (2×100 mL). The organic phase was washed with saturated aqueous NaCl (2×25 mL). The combined organics were dried over anhydrous Na$_2$SO$_4$, filtered and concentrated in vacuo to provide 2-(6-methoxy-2,3-dihydro-1H-inden-1-ylidene)-1,3-dithiane (9.1 g, 34.42 mmol) as a yellow oil.

To a solution of 2-(6-methoxy-2,3-dihydro-1H-inden-1-ylidene)-1,3-dithiane (9.1 g, 34.42 mmol) in AcOH (50 mL) was added concentrated hydrochloric acid (25 mL). The reaction mixture was reflux and stirred at that temperature for 3 h then concentrated in vacuo to give the crude product. The resulting oil was purified by flash column chromatography with a gradient elution of hexanes (100%) to hexanes (50%) and EtOAc (50%) to provide 6-methoxy-2,3-dihydro-1H-indene-1-carboxylic acid (4.8 g, 25 mmol) as a yellow solid.

Example T-35: Deamination

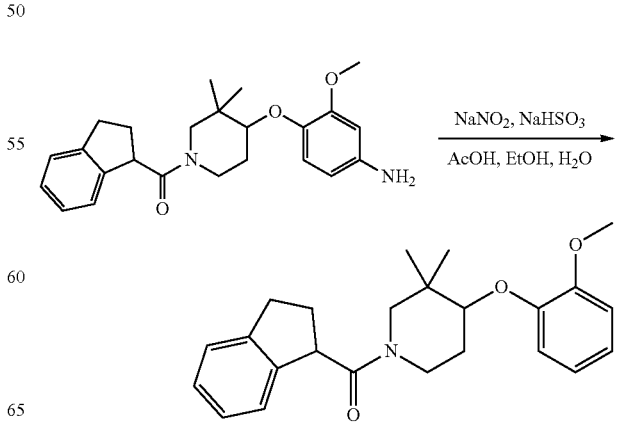

To a solution of (4-(4-amino-2-methoxyphenoxy)-3,3-dimethylpiperidin-1-yl)(2,3-dihydro-1H-inden-1-yl)methanone (200 mg, 0.51 mmol) in ethanol (5 mL) was added acetic acid (0.5 mL) and sodium nitrite (0.35 g, 5.1 mmol) in water dropwise. The reaction was stirred at ambient temperature for 10 min. To a solution of NaHSO3 (0.53 g, 5.1 mmol) in water (2 mL) was added to above mixture. The reaction was stirred at ambient temperature for 12 h. The resulting oil was purified by preparative thin layer chromatography with a gradient elution of EtOAc (30%) and hexanes (70%) to provide (2,3-dihydro-1H-inden-1-yl)(4-(2-methoxyphenoxy)-3,3-dimethylpiperidin-1-yl)methanone (0.03 g, 0.09 mmol) as a colorless oil.

Example T-36: Reduction of Ketone to Alcohol

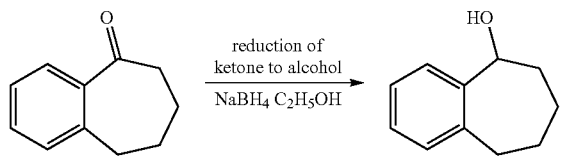 [SMILES: O=C1CCCCc2ccccc21 ; "reduction ofketone to alcohol" ; OC1CCCCc2ccccc21 ; "NaBH4 C2H5OH"]

To a solution of 6,7,8,9-tetrahydro-5H-benzonannulen-5-one (0.200 g, 1.248 mmol) in ethanol (5.0 mL) was added sodium tetrahydroborate (0.095 g, 2.496 mmol). The reaction was stirred at ambient temperature for 3 h. Saturated NH4Cl aqueous solution (30 mL) was added. The mixture was extracted with EtOAc (3×30 mL). The combined organics were washed with brine, dried over $Na_2SO_4$. After filtration, the solvent was evaporated to dry to give the desired product (200 mg, 1.233 mmol) as a white solid.

Example T-37: Reduction of Ketone to Alcohol (A)

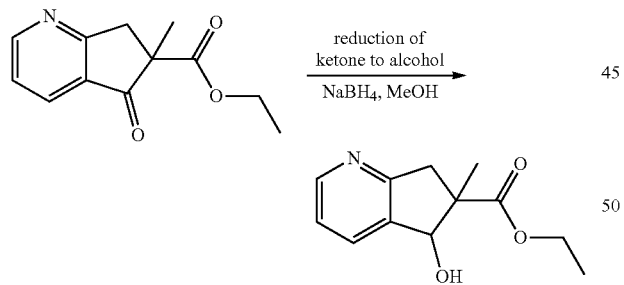

To a solution of ethyl 6-methyl-5-oxo-6,7-dihydro-5H-cyclopenta[b]pyridine-6-carboxylate (340 mg, 1.5508 mmol) in CH3OH (3 mL) was added NaBH4 (0.088 g, 2.3262 mmol) slowly at 0° C. The reaction was stirred at ambient temperature for 15 min. 6M aqueous HCl (1 mL) was added to the reaction vessel and then NH3H2O (1.5 mL) was added. The mixture was concentrated. The resulting solid was purified by flash column chromatography with a gradient elution of hexanes (90%) and EtOAc (10%) to hexanes (60%) and EtOAc (40%) to provide ethyl 5-hydroxy-6-methyl-6,7-dihydro-5H-cyclopenta[b]pyridine-6-carboxylate (0.22 g, 0.9943 mmol) as a yellow oil.

Example T-38: Reduction of Ketone to Alcohol (B)

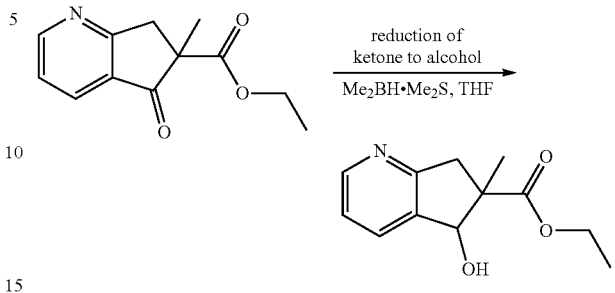

To a solution of ethyl 6-methyl-5-oxo-6,7-dihydro-5H-cyclopenta[b]pyridine-6-carboxylate (150 mg, 0.68 mmol) in THF (10 mL) was added Borane-methyl sulfide complex (0.1 g, 1.36 mmol). The reaction mixture was cooled to 0° C. and stirred at that temperature for 2 h. Water (20 mL) was added to the reaction vessel and was extracted with DCM (3×15 ml). The layers were separated and the organic phase was washed with saturated aqueous NaCl (2×15 mL). The combined organics were dried over anhydrous $Na_2SO_4$, filtered and concentrated in vacuo. After concentration, the residue was purified by silica column chromatography with a gradient elution of hexanes to hexanes (90%) and EtOAc (50%) to provide ethyl 5-hydroxy-6-methyl-6,7-dihydro-5H-cyclopenta[b]pyridine-6-carboxylate (110 mg, 0.5 mmol) as a yellow oil.

Example T-39: Reduction of Ketone to —CH2—

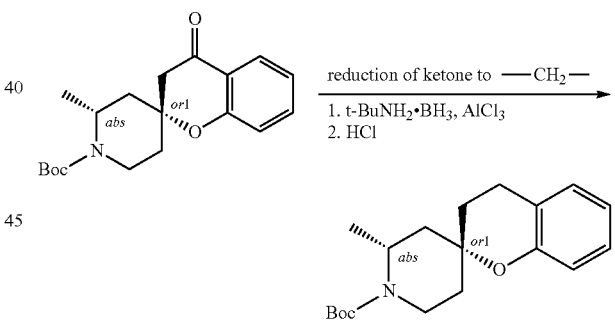

To a solution of aluminum trichloride (230 mg, 1.71 mmol) in DCM (20 mL) was added t-BuNH2BH3 (0.3 g, 3.42 mmol) at 0° C. under $N_2$. The reaction was stirred at 0° C. for 10 min. Then (2R,2'R)-tert-butyl 2'-methyl-4-oxospiro[chroman-2,4'-piperidine]-1'-carboxylate (190 mg, 0.57 mmol, the early eluting peak in preparative HPLC) in DCM (5 mL) was added. The reaction was stirred at room temperature overnight. Then HCl (6 M, 2 mL) was added. The reaction mixture was stirred at room temperature for 1 h. saturated aqueous NaHCO3 (30 mL) was added to the reaction vessel and the resulting biphasic mixture was transferred to a separatory funnel. The layers were separated and the aqueous phase was extracted with DCM:CH3OH (5:1, 5×50 mL). The combined organics were dried over anhydrous $Na_2SO_4$, filtered and concentrated in vacuo. The resulting oil was purified by flash column chromatography with a gradient elution of EtOAc (90%) and MeOH (10%)

to provide (2R,2'R)-2'-methylspiro[chroman-2,4'-piperidine] (0.11 g, 0.51 mmol) as a white oil.

Example T-40: Reductive Amination for Alkylation of an Amine (A)

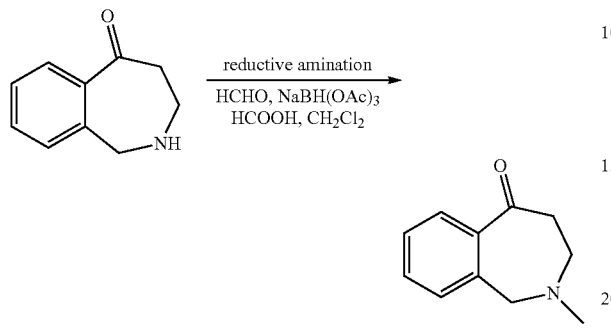

To a solution of 3,4-dihydro-1H-benzo[c]azepin-5(2H)-one (100 mg, 0.62 mmol) in DCM (8 mL) was added formaldehyde (40 mg, 1.24 mmol), formic acid (0.01 g, 0.12 mmol). The reaction was stirred at ambient temperature for 1 h. Sodium triacetoxyborohyride (260 mg, 1.24 mmol) was added to the mixture. The reaction was stirred at ambient temperature for 3 h. Water (20 mL) was added to the reaction vessel and extracted with DCM (3×40 mL). The combined organics was washed with water and dried over anhydrous Na₂SO₄, filtered and concentrated in vacuo. The resulting oil was purified by flash column chromatography with a gradient elution of DCM (99%) and MeOH (1%) to DCM (95%) and MeOH (5%) to provide 2-methyl-3,4-dihydro-1H-benzo[c]azepin-5(2H)-one (80 mg, 0.46 mmol) as a dark oil.

Example T-41: Reductive Amination for Alkylation of an Amine (B)

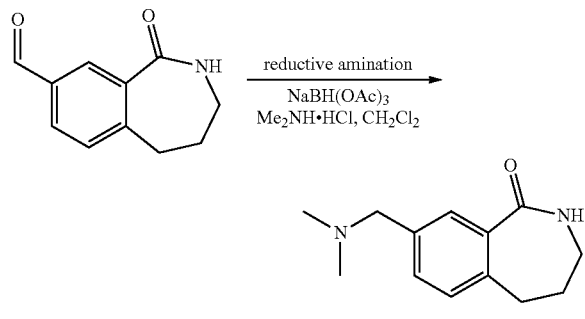

To a solution of 1-oxo-2,3,4,5-tetrahydro-1H-benzo[c]azepine-8-carbaldehyde (0.40 g, 2.11 mmol) and Dimethylamine hydrochloride (excess) in DCM (10 mL) was added sodium triacetoxyborohydride (STAB, excess) and AcOH (10 drops). The reaction was stirred at ambient temperature for 2 h. TLC showed the starting material was completely consumed. Saturated aq Na₂CO₃ (10 mL) was added to the mixture. The aqueous layer was extracted with EtOAc (3×15 mL). The combined organic layers were washed with brine, dried over Na₂SO₄, filtered and concentrated in vacuo. The resulting oil was purified by column chromatography (DCM:MeOH=10:1) to provide the desired product (0.15 g) as a yellow solid.

Example T-42: Reductive Amination for Alkylation of an Amine (C)

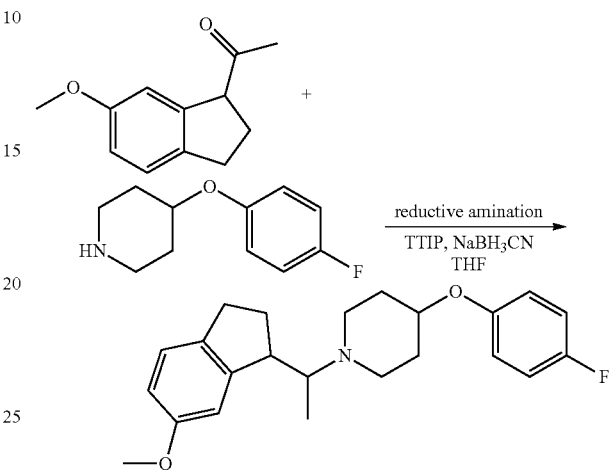

To a solution of 1-(6-methoxy-2,3-dihydro-1H-inden-1-yl)ethanone (90 mg, 0.47 mmol) in THF (1 mL) was added 4-(4-fluorophenoxy)piperidine (0.09 g, 0.47 mmol) and TTIP (0.4 g, 1.41 mmol). The reaction mixture was heated to 50° C. and stirred at that temperature for 2 h. NaBH₃CN (0.12 g, 1.88 mmol) was added to the solution. The reaction was stirred at ambient temperature for 30 min. 1M aqueous HCl (20 mL) and DCM (100 mL) were added to the reaction vessel and the resulting biphasic mixture was transferred to a separatory funnel. The layers were separated and the organic phase was washed with saturated aqueous NaHCO₃ (2×20 mL). The combined organics were dried over anhydrous Na₂SO₄, filtered and concentrated in vacuo. The resulting oil was purified by reverse phase HPLC with a gradient elution of MeOH (5%) and water (95%) to MeOH (40%) and water (60%) to provide 4-(4-fluorophenoxy)-1-(1-(6-methoxy-2,3-dihydro-1H-inden-1-yl)ethyl)piperidine (5 mg of the early eluting peak and 10 mg of the late eluting peak) as a colorless oil.

Example T-43: Reductive Amination: Ammonia Plus Ketone

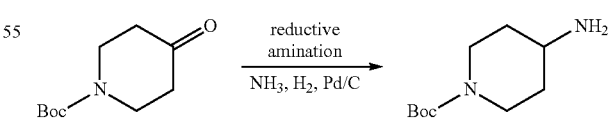

To a solution of tert-butyl-4-oxopiperidine-1-carboxylate (200 mg, 1.0038 mmol) in NH₃/isopropanol (10 mL) was added Pd/C (15 mg). The reaction was stirred at ambient temperature for 16 h under H₂.

The reaction was filtered and concentrated to provide tert-butyl-4-aminopiperidine-1-carboxylate (0.2 g, 0.9986 mmol) as a yellow oil.

Example T-44: Reduction of Amide to Amine

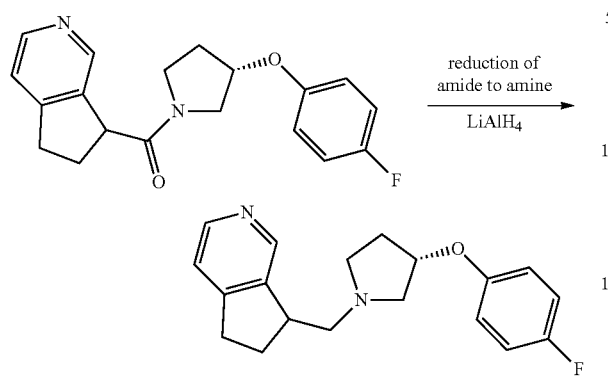

To a solution of ((6,7-dihydro-5H-cyclopenta[c]pyridin-7-yl)((S)-3-(4-fluorophenoxy)pyrrolidin-1-yl)methanone (12 mg, 0.03 mmol) in THF (5 mL) was added LiAlH$_4$ (3 mg, 0.06 mmol). The reaction was stirred at 25° C. for 1 h. One drop water and one drop 5 M NaOH were added. The mixture was stirred for 15 mins. The filtrate was concentrated in vacuo. The resulting oil was purified by flash column chromatography with a gradient elution of DCM (98%) and MeOH (2%) to DCM (95%) and MeOH (5%) to give 7-(((S)-3-(4-fluorophenoxy)pyrrolidin-1-yl)methyl)-6,7-dihydro-5H-cyclopenta[c]pyridine (6 mg) as a colorless oil.

Example T-45: Reduction of Alkyl Nitrile to Alkyl Amine

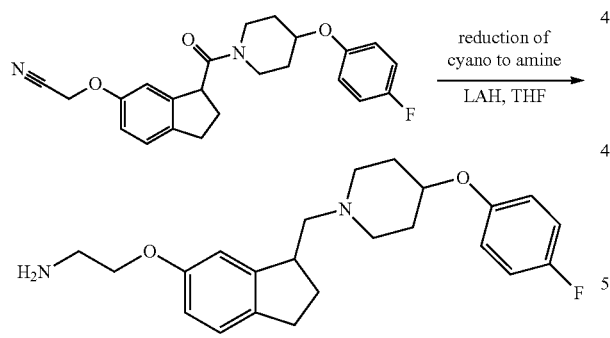

To a solution of 2-((3-(4-(4-fluorophenoxy)piperidine-1-carbonyl)-2,3-dihydro-1H-inden-5-yl)oxy)acetonitrile (120 mg) in THF (15 mL) was added LiAlH$_4$ (0.06 g, 1.5 mmol). The reaction was stirred at ambient temperature for 1 h. Water (20 mL) was added to the reaction vessel and the resulting biphasic mixture was extracted with DCM (3×40 mL). The organic phase was washed with saturated aqueous NaCl (1×20 mL). The combined organics were dried over anhydrous Na$_2$SO$_4$, filtered and concentrated in vacuo. The resulting oil was purified by preparative thin layer chromatography with an isocratic elution of DCM (90%) and MeOH (10%) to provide the freebase, which was taken forward to the next step of salt formation.

Example T-46: Reduction of Nitro to Amine

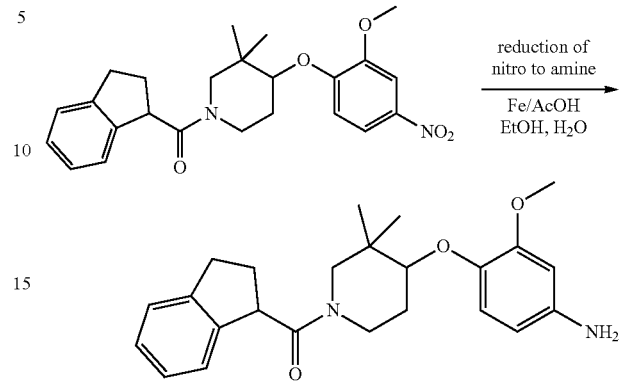

To a solution of (2,3-dihydro-1H-inden-1-yl)(4-(2-methoxy-4-nitrophenoxy)-3,3-dimethylpiperidin-1-yl)methanone (400 mg, 0.94 mmol) in EtOH (6 mL) was added acetic acid (2 mL), water (2 mL) and iron (0.31 g, 5.64 mmol). The reaction mixture was heated to 50° C. and stirred at that temperature for 1 h. TLC showed the product was consumed. Water (30 mL) was added to the reaction vessel and adjusted the pH=8. The mixture was transferred to a separatory funnel and extracted with DCM (3×50 ML). The layers were separated. The combined organics were dried over anhydrous Na$_2$SO$_4$, filtered and concentrated in vacuo. The resulting oil was purified by flash column chromatography with a gradient elution of DCM to provide (4-(4-amino-2-methoxyphenoxy)-3,3-dimethylpiperidin-1-yl)(2,3-dihydro-1H-inden-1-yl)methanone (0.2 g, 0.51 mmol) as a yellow oil.

Example T-47: Dehydroxylation

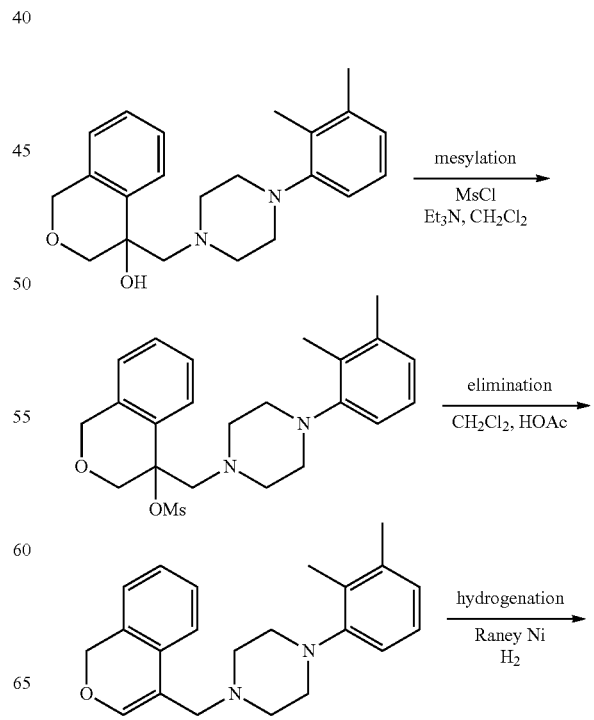

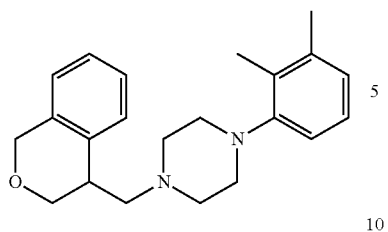

(A) To a solution of 4-((4-(2,3-dimethylphenyl)piperazin-1-yl)methyl)isochroman-4-ol (150 mg, 0.4256 mmol) in DCM (20 mL) was added triethylamine (0.1292 g, 1.2768 mmol) and methanesulfonyl chloride (0.0731 g, 0.6384 mmol). The reaction was stirred at 25° C. for 4 h.

(B) To a solution of 4-((4-(2,3-dimethylphenyl)piperazin-1-yl)methyl)isochroman-4-yl methanesulfonate (100 mg, 0.2323 mmol) in DCM (20 mL) was added acetic acid (0.0698 g, 1.1615 mmol). The reaction was stirred at 50° C. for 8 h. The reaction mixture was treated with $Na_2CO_3$ solution (30 mL). The aqueous layer was extracted with EtOAc (3×30 mL). The combined organic layers were washed with brine, dried over $Na_2SO_4$, filtered and concentrated in vacuo. The resulting oil was purified by column chromatography (EtOAc:Hexanes=1:10) to provide the desired product (50 mg, 0.1196 mmol) as an oil.

(C) To a solution of 1-((1H-isochromen-4-yl)methyl)-4-(2,3-dimethylphenyl)piperazine (50 mg, 0.1495 mmol) in MeOH (20 mL) was added Raney-Ni (0.0512 g, 0.598 mmol) and $H_2$. The reaction was stirred at 50° C. for 2 days. The reaction was filtered and concentrated in vacuo. The resulting oil was purified by column chromatography (EtOAc:Hexanes=1:10) to provide the product (15 mg) as an oil.

Example T-48: Reduction of Ester to Alcohol

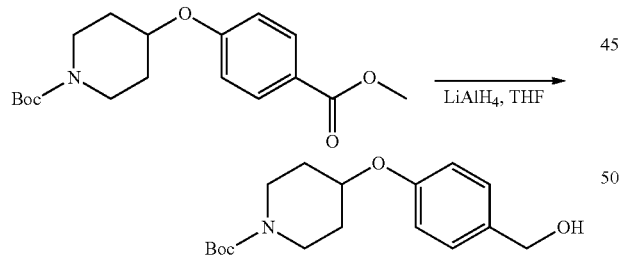

To a solution of tert-butyl 4-(4-(ethoxycarbonyl)phenoxy) piperidine-1-carboxylate (500 mg, 1.43 mmol) in THF (10 mL) was added $LiAlH_4$ (0.16 g, 4.29 mmol) at 0° C. The reaction was stirred at this temperature for 30 min. 1M aqueous NaOH (10 mL) was added to the reaction vessel and the resulting biphasic mixture was extracted with DCM (3×50 mL). The organic phase was washed with saturated aqueous NaCl (2×50 mL). The combined organics were dried over anhydrous $Na_2SO_4$, filtered and concentrated in vacuo to provide tert-butyl 4-(4-(hydroxymethyl)phenoxy) piperidine-1-carboxylate (350 mg, 1.14 mmol) as a colorless oil.

Example T-49: Reduction of Acid to Alcohol

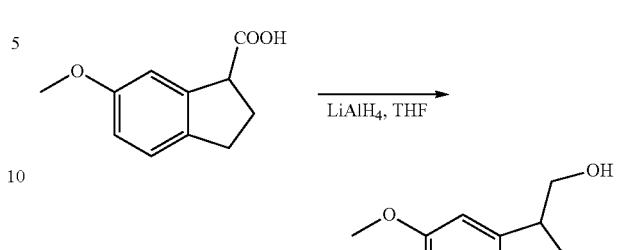

To a solution of 6-methoxy-2,3-dihydro-1H-indene-1-carboxylic acid (300 mg, 1.56 mmol) in THF (10 mL) was added $LiAlH_4$(0.18 g, 4.68 mmol). The reaction was stirred at room temperature for 2 h. Saturated aqueous $NH_4Cl$ (15 mL) was added to the reaction vessel and the resulting biphasic mixture was transferred to a separatory funnel. The layers were separated and the organic/aqueous phase was extracted with EtOAc (3×150 mL). The combined organics were dried over anhydrous $Na_2SO_4$, filtered and concentrated in vacuo. The resulting oil was purified by flash column chromatography with hexane (70%) and EtOAc (30%) to provide (6-methoxy-2,3-dihydro-1H-inden-1-yl) methanol (290 mg, 1.63 mmol) as a white oil.

Example T-50: Conversion of Acid to Ketone Via a Weinreb Amide

General Scheme

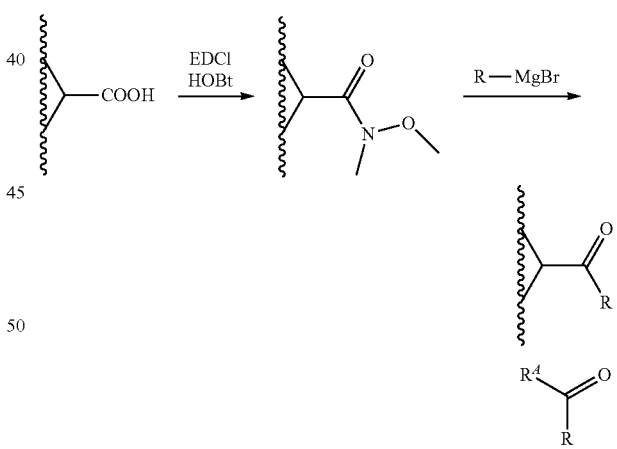

Representative Example

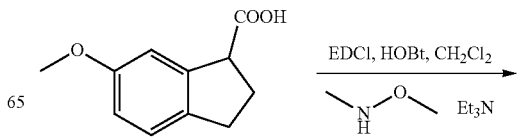

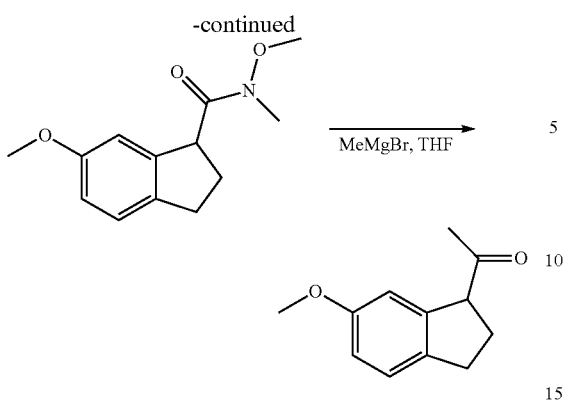

To a solution of 6-methoxy-2,3-dihydro-1H-indene-1-carboxylic acid (250 mg, 1.3 mmol) in DCM (20 mL) was added N,O-dimethylhydroxylamine hydrochloride (0.38 g, 3.9 mmol), triethylamine (0.66 g, 6.5 mmol), EDCI (0.5 g, 2.6 mmol) and HOBT (0.18 g, 1.3 mmol). The reaction was stirred at ambient temperature for 12 h. Saturated aqueous NaHCO$_3$ (10 mL) was added to the reaction vessel and the resulting biphasic mixture was transferred to a separatory funnel. The layers were separated and the organic phase was washed with saturated aqueous NaCl (2×5 mL). The combined organics were dried over anhydrous Na$_2$SO$_4$, filtered and concentrated in vacuo. The resulting oil was purified by flash column chromatography with a gradient elution of hexanes (100%) to hexanes (70%) and EtOAc (30%) to provide N,6-dimethoxy-N-methyl-2,3-dihydro-1H-indene-1-carboxamide (0.2 g, 0.85 mmol) as a yellow oil.

To a solution of N,6-dimethoxy-N-methyl-2,3-dihydro-1H-indene-1-carboxamide (200 mg, 0.85 mmol) in THF (3 mL) was added methylmagnesium bromide (0.12 g, 1.02 mmol) at 0° C. The reaction was stirred at ambient temperature for 1 h. Saturated aqueous NH$_4$Cl (10 mL) and EtOAc (50 mL) were added to the reaction vessel and the resulting biphasic mixture was transferred to a separatory funnel. The layers were separated and the organic phase was washed with saturated aqueous NaCl (2×10 mL). The combined organics were dried over anhydrous Na$_2$SO$_4$, filtered and concentrated in vacuo. The resulting oil was purified by flash column chromatography with a gradient elution of hexane (100%) to hexane (90%) and EtOAc (10%) to provide 1-(6-methoxy-2,3-dihydro-1H-inden-1-yl)ethanone (0.1 g, 0.53 mmol) as a yellow oil.

Example T-50a: Hydrogenation (A)

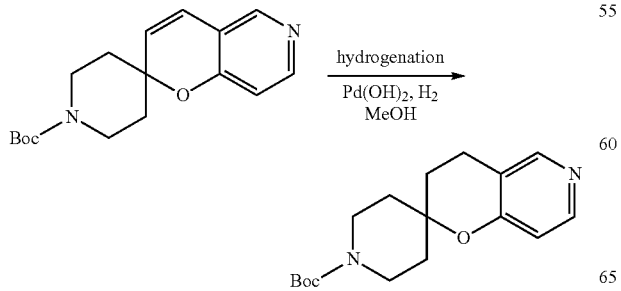

To a solution of tert-butyl spiro[piperidine-4,2'-pyrano[3,2-c]pyridine]-1-carboxylate (200 mg) in MeOH (5 mL) was added dihydroxypalladium/C (10 mg). The reaction mixture was heated to 40° C. and stirred under H$_2$ for 24 h. Another aliquot of dihydroxypalladium/C (10 mg) was added to the mixture. The reaction mixture was heated to 40° C. and stirred under H$_2$ for another 24 h. TLC showed the starting material was most consumed. After quickly purification and used for next step.

Example T-50b: Hydrogenation (B)

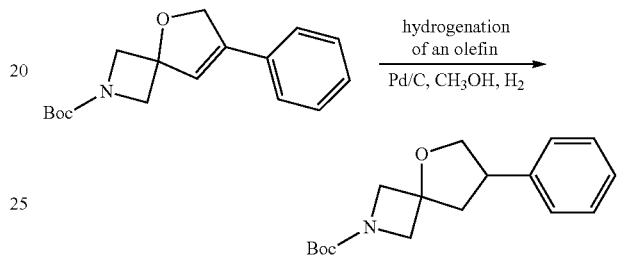

To a solution of tert-butyl 7-phenyl-5-oxa-2-azaspiro[3.4]oct-7-ene-2-carboxylate (700 mg, 1.21 mmol) in methanol (15 mL) was added 10% Pd/C (70 mg, 657 µmol). The reaction mixture was stirred at room temperature for 2 h under H$_2$ atmosphere. After filtration, the filtrate was concentrated and purified by flash column chromatography with an isocratic elution of EtOAc (10%) and hexanes (90%) to provide tert-butyl-7-phenyl-5-oxa-2-azaspiro[3.4]octane-2-carboxylate (300 mg, 1.03 mmol) as a colorless oil.

Example T-51: Hydrogenation of α,β-Unsaturated Ester

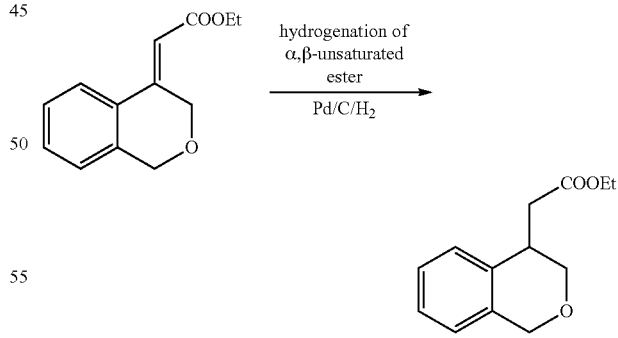

To a solution of (Z)-ethyl 2-(isochroman-4-ylidene)acetate (300 mg, 1.37 mmol) in ethanol (30 mL) was added Pd/C (30 mg). The reaction was stirred at ambient temperature for 3 h under H$_2$. The reaction mixture was filtered and concentrated in vacuo. The resulting oil was purified by flash column chromatography with a gradient elution of hexanes (100%) to hexanes (90%) and EtOAc (10%) to provide ethyl 2-(isochroman-4-yl)acetate (300 mg) as a white oil.

Example T-52: Nitration of an Aryl Group

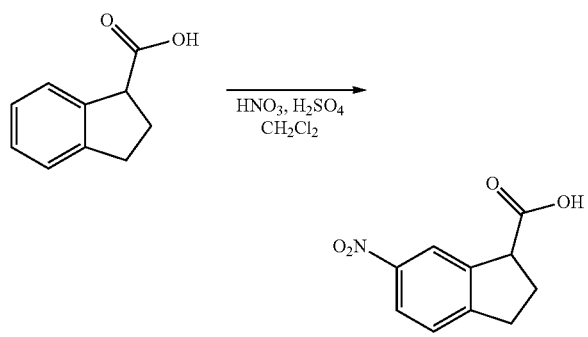

To a solution of 2,3-dihydro-1H-indene-1-carboxylic acid (3 g, 18.5 mmol) in DCM (4 mL) was added to sulfuric acid (20 mL) at −10° C. The mixture was stirred at that temperature for 15 min. Nitric acid (1.17 g, 18.5 mmol) in sulfuric acid (4 mL) was added to above mixture in one hour. The mixture was poured into ice water (50 mL) and extracted with DCM (5×50 mL). The combined organics were dried over anhydrous $Na_2SO_4$. After filtered and concentrated in vacuo, the resulting solid was purified by flash column chromatography with a gradient elution of EtOAc (10%) and hexanes (90%) to EtOAc (30%) and hexanes (70%) to provide 6-nitro-2,3-dihydro-1H-indene-1-carboxylic acid (2.5 g) as a white solid. HNMR showed contained ~20% of the isomers. After recrystallized in EtOAc/Hexanes (40:1), 1.0 g of the desired product was obtained as a white solid.

Example T-53: Formylation. Conversion of Aryl Halide to Aryl Aldehyde

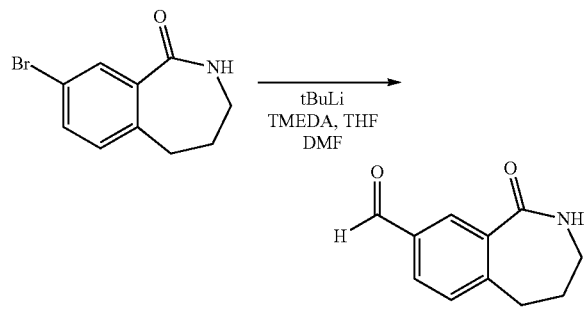

To a solution of 8-bromo-2,3,4,5-tetrahydro-1H-benzo[c]azepin-1-one (0.80 g, 3.33 mmol) and TMEDA (1.50 mL) in THF (30 mL) being cooled −70° C. under $N_2$ was added n-BuLi (2.93 mL, 2.5 N) via syringe over 15 min. The reaction was stirred at that temperature for 10 min t-BuLi (7.68 mL, 1.3 N) was added to the reaction mixture via syringe over 20 min. The reaction was stirred at that temperature for 2 h. DMF (0.77 mL) was added to the mixture. The reaction mixture was allowed to warm to room temperature. TLC showed the completely consumed starting material. Saturated aqueous $NH_4Cl$ (10 mL) was added to the mixture. The aqueous layer was extracted with EtOAc (3×15 mL). The combined organic layers were washed with brine, dried over $Na_2SO_4$, filtered and concentrated in vacuo. The resulting oil was purified by column chromatography (DCM:MeOH=10:1) to provide the desired product (0.40 g) as a yellow solid.

Example T-54: Oxidation of Alcohol to Aldehyde

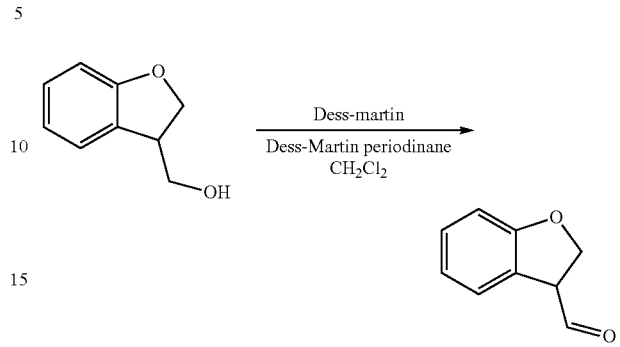

To a solution of (2,3-dihydrobenzofuran-3-yl)methanol (250 mg, 1.66 mmol) in DCM (8 mL) was added Dess-Martin periodinane (1.41 g, 3.32 mmol). The reaction was stirred at ambient temperature for 10 min. Water (20 mL) was added to the reaction vessel and was extracted with DCM (3×15 ml). The layers were separated and the organic phase was washed with saturated aqueous NaCl (2×15 mL). The combined organics were dried over anhydrous $Na_2SO_4$, filtered and concentrated in vacuo. After concentration, the residue was purified to give the desired product 2,3-dihydrobenzofuran-3-carbaldehyde (180 mg, 1.21 mmol) as a yellow oil.

Example T-55: Oxidation Olefin to Ketone

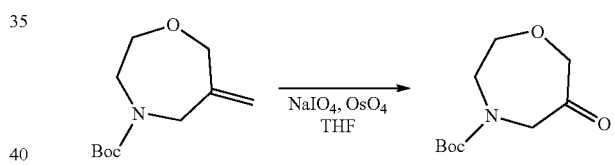

To a solution of tert-butyl 6-methylene-1,4-oxazepane-4-carboxylate (1.8 g, 8.44 mmol) in THF (30 mL) and $H_2O$ (30 mL) was added sodium periodate (3.61 g, 16.88 mmol) and osmium(VIII) oxide (0.11 g, 0.42 mmol). The reaction was stirred at ambient temperature for 4 h. Water (20 mL) was added to the reaction vessel and the resulting biphasic mixture was extracted with DCM (3×100 mL). The organic phase was washed with saturated aqueous NaCl (1×20 mL). The combined organics were dried over anhydrous $Na_2SO_4$, filtered and concentrated in vacuo. The resulting oil was purified by flash column chromatography with a gradient elution of hexanes (100%) to hexanes (40%) and EtOAc (60%) to provide tert-butyl 6-oxo-1,4-oxazepane-4-carboxylate (1.7 g, 7.9 mmol) as a colorless oil.

Example T-56: Hydroboration Oxidation of an Olefin to an Alcohol

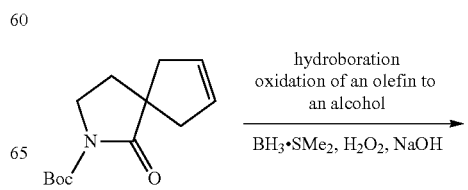

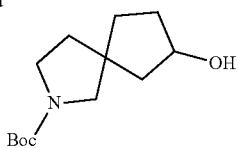

To a solution of tert-butyl 1-oxo-2-azaspiro[4.4]non-7-ene-2-carboxylate (700 mg, 2.95 mmol) in THF (5 mL) was added BH₃—SMe₂ (12 mL, 23.6 mmol). The reaction mixture was heated to 40° C. and stirred at that temperature for 16 h. The mixture was cooled to 0° C. Hydrogen peroxide (0.8 g, 23.6 mmol) and sodium hydroxide (0.94 g, 23.6 mmol) in 10 ml H₂O was added dropwise. The reaction was stirred at ambient temperature for 4 h. Water (10 mL) and DCM (100 mL) were added to the reaction vessel and the resulting biphasic mixture was transferred to a separatory funnel. The layers were separated and the organic phase was washed with saturated aqueous NaCl (2×20 mL). The combined organics were dried over anhydrous Na₂SO₄, filtered and concentrated in vacuo. The resulting oil was purified by flash column chromatography with a gradient elution of hexane (80%) and EtOAc (20%) to hexane (30%) and EtOAc (70%) to provide tert-butyl-7-hydroxy-2-azaspiro[4.4]nonane-2-carboxylate (0.7 g, 2.9 mmol) as a white solid.

Example T-57: Coupling of an Acid with an Amine to Form an Amide

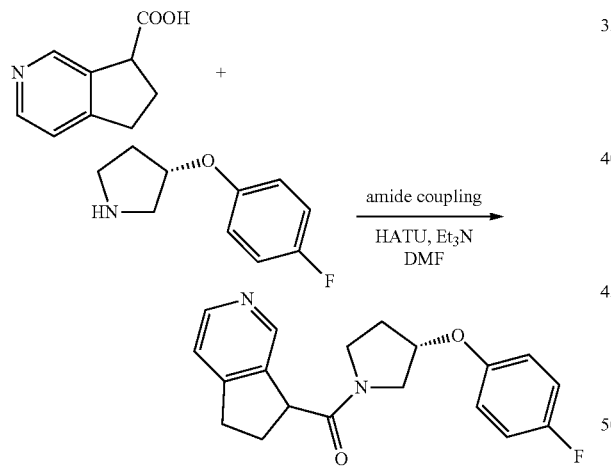

To a solution of 6,7-dihydro-5H-cyclopenta[c]pyridine-7-carboxylic acid hydrochloride (30 mg, 0.15 mmol) in DMF (5.0 mL) was added (S)-3-(4-fluorophenoxy)pyrrolidine (0.03 g, 0.165 mmol), o-(7-Azabenzotriazol-1-yl)-N,N,N',N'-tetramethyluronium hexafluorophosphate (0.09 g, 0.36 mmol) and triethylamine (0.05 g, 0.54 mmol). The reaction was stirred at ambient temperature for 8 h. Water (40 mL) was added to the reaction vessel and the resulting mixture was extracted with DCM (4×60 mL). The combined organics were washed with brine, dried over anhydrous Na₂SO₄, filtered and concentrated in vacuo. The resulting oil was purified by flash column chromatography with a gradient elution of EtOAc (100%) to EtOAc (90%) and MeOH (10%) to provide (6,7-dihydro-5H-cyclopenta[c]pyridin-7-yl)((S)-3-(4-fluorophenoxy)pyrrolidin-1-yl)methanone (12 mg, 0.04 mmol) as a pale yellow oil.

Example T-58: Ether Formation. Addition of an Alcohol to an Alkyl Bromide

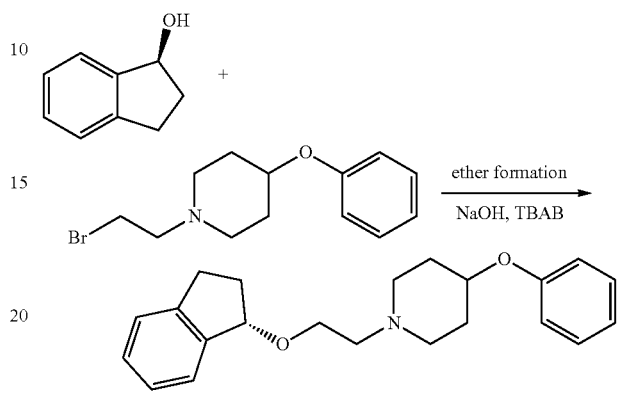

To a solution of 1-(2-bromoethyl)-4-phenoxypiperidine (60 mg, 0.22 mmol) in NaOH (0.88 g dissolved in 2 mL water) was added (S)-2,3-dihydro-1H-inden-1-ol (30 mg, 0.22 mmol) and tetra-n-butylammonium bromide (TBAB) (20 mg). The reaction was stirred at ambient temperature for 3 h. Water was added to the mixture and extracted with EtOAc (3×40 mL). The combined organics were dried over anhydrous Na₂SO₄, filtered and concentrated in vacuo. The resulting oil was purified by preparative thin layer chromatography with an isocratic elution of MeOH (5%) and DCM (95%) to provide (S)-1-(2-((2,3-dihydro-1H-inden-1-yl)oxy)ethyl)-4-phenoxypiperidine (15 mg, 0.04 mmol) as a colorless oil.

Example T-59: Buchwald Coupling of and Amine and an Aryl Halide

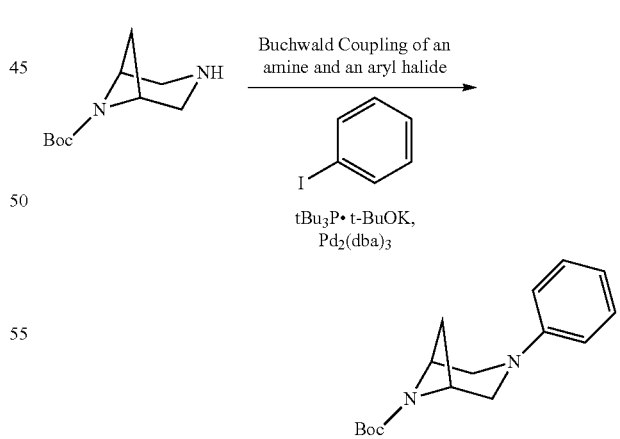

To a solution of (1R,5S)-tert-butyl 3,6-diazabicyclo[3.1.1]heptane-6-carboxylate (2 g, 10.0 mmol) in toluene (50 mL) was added iodobenzene (4.08 g, 20.0 mmol), tri-tert-butylphosphine (404 mg, 2.00 mmol) and potassium 2-methylpropan-2-olate (3.36 g, 30.0 mmol), potassium 2-methylpropan-2-olate (3.36 g, 30.0 mmol). The reaction was stirred at ambient temperature for 16 h under N₂. Water (50 mL) was added to the reaction vessel and the resulting biphasic mixture was transferred to a separatory funnel. The layers were separated and the aqueous phase was extracted with EtOAc (3×100 mL). The combined organics were dried over anhydrous Na$_2$SO$_4$, filtered and concentrated in vacuo. The resulting oil was purified by flash column chromatography with EtOAc (5%) and hexane (95%) to provide (1R,5S)-tert-butyl 3-phenyl-3,6-diazabicyclo[3.1.1]heptane-6-carboxylate (2.10 g, 7.65 mmol) as a pale yellow solid.

Example T-60: Coupling

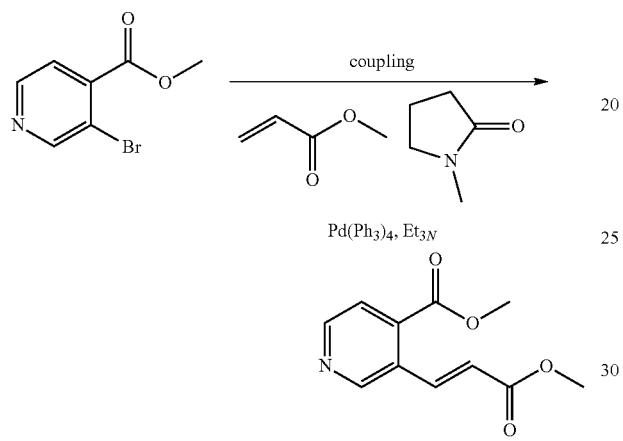

To a solution of methyl 3-bromoisonicotinate (7.5 g, 34.72 mmol) in 1-methylpyrrolidin-2-one (15 mL) was added methyl acrylate (14.25 g, 165.53 mmol), triethylamine (4.46 g, 44.1 mmol) and Pd(PPh$_3$)$_4$ (1.7 g, 1.47 mmol). The reaction mixture was heated to 90° C. and stirred at that temperature for 22 h in sealed tube. TLC showed the starting material was consumed completely. After the solvent was removed, water (150 mL) and EtOAc (150 mL) was added to the reaction vessel and the resulting biphasic mixture was transferred to a separatory funnel. The layers were separated and the aqueous phase was extracted with EtOAc (3×150 mL). The combined organics were washed with brine, dried over anhydrous Na$_2$SO$_4$, filtered and concentrated in vacuo. The resulting oil was purified by flash column chromatography with an isocratic elution of EtOAc (15%) and hexane (85%) to provide (E)-methyl 3-(3-methoxy-3-oxoprop-1-en-1-yl)isonicotinate (4.06 g, 18.35 mmol) as a pale yellow solid.

Example T-61: Ring-Closing Metathesis of a Diene to a Cyclic Olefin

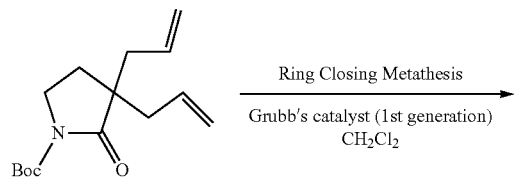

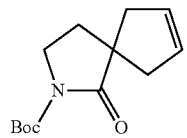

To a solution of tert-butyl 3,3-diallyl-2-oxopyrrolidine-1-carboxylate (1 g, 3.77 mmol) in DCM (20 mL) was added Grubb's 1$^{st}$ generation catalyst (0.31 g, 0.38 mmol). The reaction was stirred at ambient temperature for 4 h. The reaction mixture was concentrated in vacuo. The resulting oil was purified by flash column chromatography with a gradient elution of hexane (100%) to hexane (90%) and EtOAc (10%) to provide tert-butyl 1-oxo-2-azaspiro[4.4]non-7-ene-2-carboxylate (0.8 g, 3.37 mmol) as a white solid.

Example T-62: Sulfonamide Formation

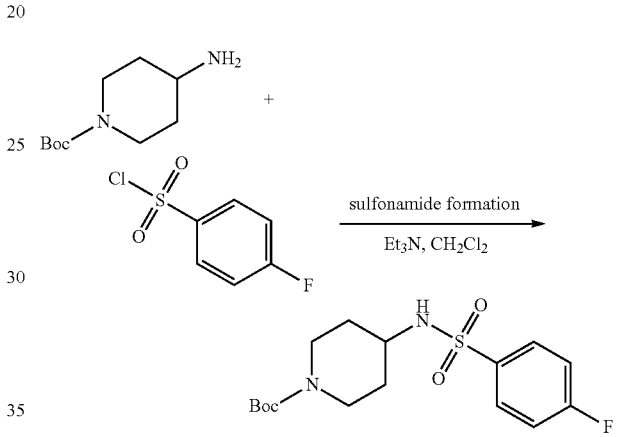

To a solution of tert-butyl 4-aminopiperidine-1-carboxylate (200 mg, 0.999 mmol) in DCM (3 mL) was added 4-fluorobenzene-1-sulfonyl chloride (0.214 g, 1.099 mmol). Then triethylamine (0.253 g, 2.498 mmol) was added slowly at 0° C. under N$_2$. The reaction was stirred at ambient temperature for 30 min. The mixture solution was concentrated. The resulting oil was purified by flash column chromatography with a gradient elution of petroleum ether (85%) and EtOAc (15%) to petroleum ether (75%) and EtOAc (25%) to provide tert-butyl 4-(4-fluorophenylsulfonamido)piperidine-1-carboxylate (0.25 g, 0.697 mmol) as a yellow oil.

Example T-63: Rosenmund-Von Braun Reaction

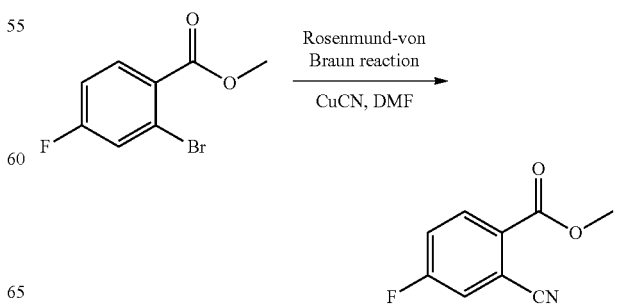

To a solution of methyl 2-bromo-4-fluorobenzoate (1.2 g, 5.15 mmol) in DMF (5 mL) was added cyanocopper (0.92 g, 10.3 mmol) under $N_2$. The reaction was stirred at 120 for 1.5 h under $N_2$. Then, the reaction was cooled to room temperature. 10% NaCN (10 mL) was added to the reaction. The mixture was extracted with DCM (3×30 mL). The layers were separated and the organic phase was washed with saturated aqueous NaCl (3×50 mL). The combined organic layers were dried over $Na_2SO_4$. After filtration, 850 mg of product was obtained as a white solid.

Example T-64a: Conversion of aryl-Br to aryl-CN (A)

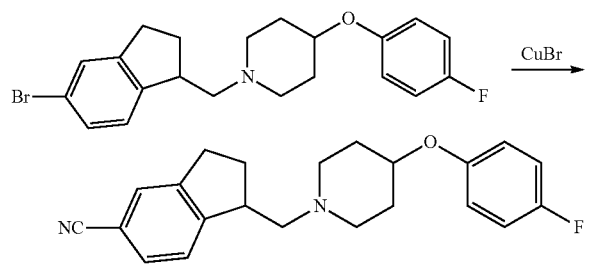

To a solution of 1-((5-bromo-2,3-dihydro-1H-inden-1-yl)methyl)-4-(4-fluorophenoxy)piperidine (170 mg, 0.4205 mmol) in DMA (2 mL) was added cyanocopper (0.113 g, 1.2615 mmol). The reaction was stirred at 150° C. for 1 h by microwave. Water (10 mL) was added to the reaction vessel and the resulting biphasic mixture was transferred to a separatory funnel. The layers were separated and the aqueous phase was extracted with EtOAc (3×20 mL). The combined organics were dried over anhydrous $Na_2SO_4$, filtered and concentrated in vacuo. The resulting oil was purified by flash column chromatography with a gradient elution of hexane (90%) and EtOAc (10%) to hexane (70%) and EtOAc (30%) to provide 1-((4-(4-fluorophenoxy)piperidin-1-yl)methyl)-2,3-dihydro-1H-indene-4-carbonitrile (0.0792 g, 0.226 mmol) as a brown oil.

Example T-64b: Conversion of aryl-Br to aryl-CN (B)

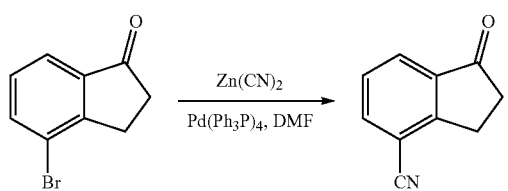

To a solution of 4-bromo-2,3-dihydro-1H-inden-1-one (300 mg, 1.4214 mmol) in dimethylamine (3 mL) was added dicyanozinc (0.1669 g, 1.4214 mmol) and $Pd(PPh_3)_4$ (0.0822 g, 0.0711 mmol). The reaction was stirred at 150° C. in microwave for 1 h. Water (20 mL) was added to the reaction vessel and the resulting biphasic mixture was transferred to a separatory funnel. The layers were separated and the aqueous phase was extracted with EtOAc (3×20 mL). The combined organics were dried over anhydrous $Na_2SO_4$, filtered and concentrated in vacuo. The resulting oil was purified by flash column chromatography with a gradient elution of EtOAc (5%) and hexane (95%) to EtOAc (10%) and EtOAc (90%) to provide 1-oxo-2,3-dihydro-1H-indene-4-carbonitrile (0.18 g, 1.1453 mmol) as a white solid.

Example T-65: Conversion of Nitrile to Ester

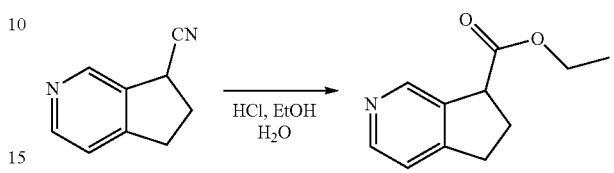

To a solution of 6,7-dihydro-5H-cyclopenta[c]pyridine-7-carbonitrile (100 mg, 0.69 mmol) in ethanol (25 mL) was added HCl (gas) at 0° C. The reaction was stirred at ambient temperature for 12 h. Water (10 mL) was added to the reaction vessel and the mixture was stirred at that temperature for 1 hour. The pH was adjusted to 8. The mixture was extracted with DCM (3×40 mL). The combined organics were dried over anhydrous $Na_2SO_4$, filtered and concentrated in vacuo. The resulting oil was purified by flash column chromatography with a gradient elution of EtOAc (5%) and hexane (95%) to EtOAc (30%) and hexane (70%) to provide crude ethyl 6,7-dihydro-5H-cyclopenta[c]pyridine-7-carboxylate as a yellow oil.

Example T-66: Conversion of Ester to Acid

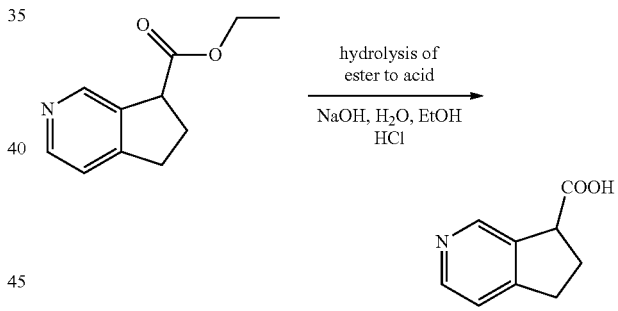

To a solution of ethyl 6,7-dihydro-5H-cyclopenta[c]pyridine-7-carboxylate (50 mg, 0.26 mmol) in methanol (5 mL) was added sodium hydroxide (0.02 g, 0.52 mmol) in $H_2O$ (2 mL). The reaction mixture was heated to 40° C. and stirred at that temperature for 1 h. The reaction mixture was acidified with 6M HCl. Then methanol was evaporated in vacuo and the residue was dried by freeze dryer to provide 6,7-dihydro-5H-cyclopenta[c]pyridine-7-carboxylic acid (35 mg, crude), which was directly used for the next step.

Example T-67: Acylation of an Amine

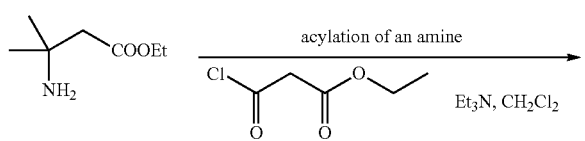

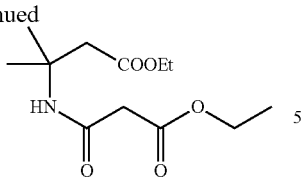

To a solution of ethyl 3-amino-3-methylbutanoate hydrochloride (2.8 g, 15.41 mmol) in DCM (40 mL) was added triethylamine (4.68 g, 46.23 mmol) and ethyl 3-chloro-3-oxopropanoate (3.48 g, 23.12 mmol) at 0° C. The reaction was stirred at ambient temperature for 24 h. Water (100 mL) was added to the reaction vessel and the resulting biphasic mixture was transferred to a separatory funnel. The layers were separated and the aqueous phase was extracted with DCM (2×100 mL). The combined organics were washed with 1 N HCl (70 mL) and sat. Na$_2$CO$_3$ (100 mL). The organic was dried over anhydrous Na$_2$SO$_4$, filtered and concentrated in vacuo to provide ethyl 3-(3-ethoxy-3-oxopropanamido)-3-methylbutanoate (3.8 g, 14.65 mmol) as a brown oil.

Example T-68: Condensation

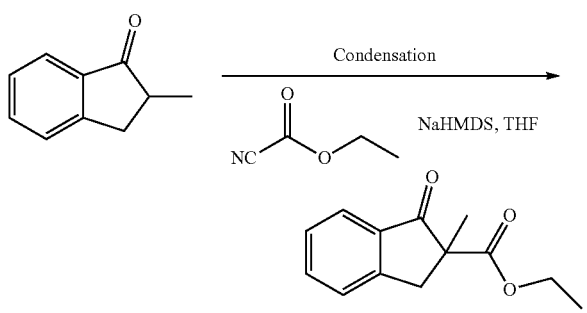

To a solution of 2-methyl-2,3-dihydro-1H-inden-1-one (1 g, 6.84 mmol) in THF (10 mL) was added sodium bis(trimethylsilyl)amide (1.25 g, 6.84 mmol) slowly. The reaction was stirred at −78° C. for 1 h. And then ethyl carbonocyanidate (0.68 g, 6.84 mmol) was added slowly. The reaction was stirred at −20° C. for 3 h. Saturated aqueous NH$_4$Cl (30 mL) and EtOAc (10 mL) was added to the reaction vessel and the resulting biphasic mixture was transferred to a separatory funnel. The layers were separated and the aqueous phase was extracted with EtOAc (2×20 mL). The combined organics were dried over anhydrous Na$_2$SO$_4$, filtered and concentrated in vacuo. The resulting oil was purified by flash column chromatography with an isocratic elution of petroleum ether (95%) and EtOAc (5%) to provide ethyl 2-methyl-1-oxo-2,3-dihydro-1H-indene-2-carboxylate (0.3 g, 1.37 mmol) as a yellow oil.

Example T-69: Dieckmann Condensation

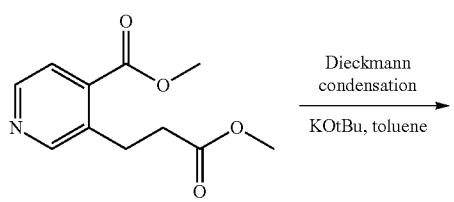

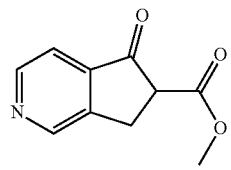

To a solution of methyl 3-(3-methoxy-3-oxopropyl)isonicotinate (500 mg, 2.24 mmol) in toluene (10 mL) was added potassium 2-methylpropan-2-olate (0.63 g, 5.6 mmol). The reaction mixture was heated to 100° C. and stirred at that temperature for 30 min. After cooling to room temperature, the solvent was evaporated to dry to give the crude product as a yellow solid which was directly used for the next step.

Example T-70

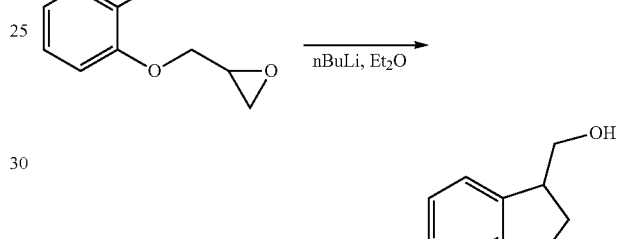

To a solution of 2-((2-bromophenoxy)methyl)oxirane (1 g, 4.37 mmol) in Et$_2$O (6 mL) was added butyllithium (0.31 g, 4.81 mmol). The reaction mixture was cooled to −78° C. and stirred at that temperature for 1 h. Water (20 mL) was added to the reaction vessel and was extracted with ethyl acetate (3×20 ml). The layers were separated and the organic phase was washed with saturated aqueous NaCl (2×20 mL). The combined organics were dried over anhydrous Na$_2$SO$_4$, filtered and concentrated in vacuo. After concentration, the residue was purified by silica column chromatography (Hexanes:EtOAc=1:1) to give the desired product (150 mg) as a yellow oil.

Example T-71

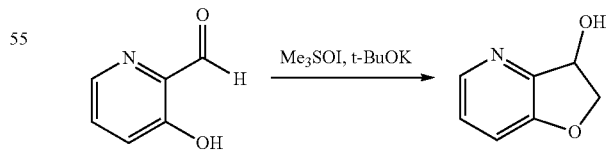

To a solution of Me$_3$SOI (0.1341 g, 0.6093 mmol) in DMSO (5 mL) was added potassium 2-methylpropan-2-olate (0.0684 g, 0.6093 mmol) after 30 min later 3-hydroxypicolinaldehyde (30 mg, 0.2437 mmol) was added. The reaction was stirred at 25° C. for 20 min. TLC showed new spots and the product was detected by GC-MS.

Example T-72

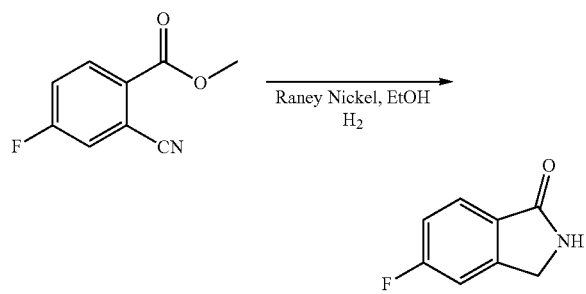

To a solution of methyl 2-cyano-4-fluorobenzoate (850 mg, 4.74 mmol) in ethanol (30 mL) was added Raney Nickel (1 g). The reaction was stirred at ambient temperature for 16 h under $H_2$ (50 psi). LCMS showed the desired product. After purification by silica gel chromatography eluted with DCM:MeOH=150:1→80:1 to give the product 500 mg as white solid.

Example T-73: Synthesis of Boc-Protected ethyl 7-oxo-5-oxa-2-azaspiro[3.4]octane-8-carboxylate

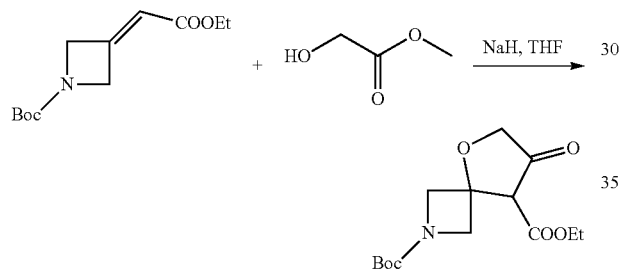

To a solution of methyl 2-hydroxyacetate (3.05 g, 33.82 mmol) in THF (20 mL) was added sodium hydride (0.81 g, 33.82 mmol). The reaction was stirred at ambient temperature for 30 min. The reaction mixture was concentrated in vacuo. tert-Butyl 3-(2-ethoxy-2-oxoethylidene)azetidine-1-carboxylate (6.8 g, 28.18 mmol) in DMSO (40 mL) was added at 0° C. The reaction was stirred at ambient temperature for 24 h. water (20 mL) and EtOAc (400 mL) was added to the reaction vessel and the resulting biphasic mixture was transferred to a separatory funnel. The layers were separated and the organic phase was washed with saturated aqueous NaCl (5×50 mL). The combined organics were dried over anhydrous $Na_2SO_4$, filtered and concentrated in vacuo to provide 2-tert-butyl 8-ethyl 7-oxo-5-oxa-2-azaspiro[3.4]octane-2,8-dicarboxylate (5.5 g, 18.38 mmol) as a yellow oil without further purification.

Example T-74: Condensation

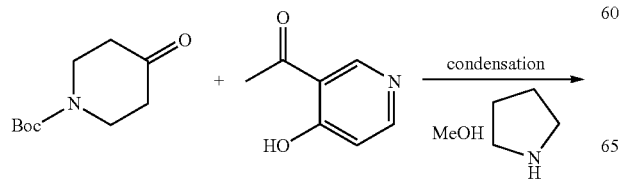

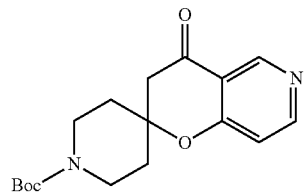

To a solution of 1-(4-hydroxypyridin-3-yl)ethanone (230 mg, 1.68 mmol) in MeOH (5 mL) was added pyrrolidine (0.24 g, 3.36 mmol) and tert-butyl 4-oxopiperidine-1-carboxylate (330 mg, 1.68 mmol). The reaction mixture was heated to 80° C. and stirred at that temperature for 3 h. The organics were concentrated in vacuo. The resulting oil was purified by flash column chromatography with a gradient elution of EtOAc (15%) and hexane (85%) to EtOAc (40%) and hexane (60%) to provide tert-butyl 4'-oxo-3',4'-dihydrospiro[piperidine-4,2'-pyrano[3,2-c]pyridine]-1-carboxylate (230 mg) as a yellow solid.

Example T-75: Synthesis of Boc-Protected spiro[isochromane-3,4'-piperidine]

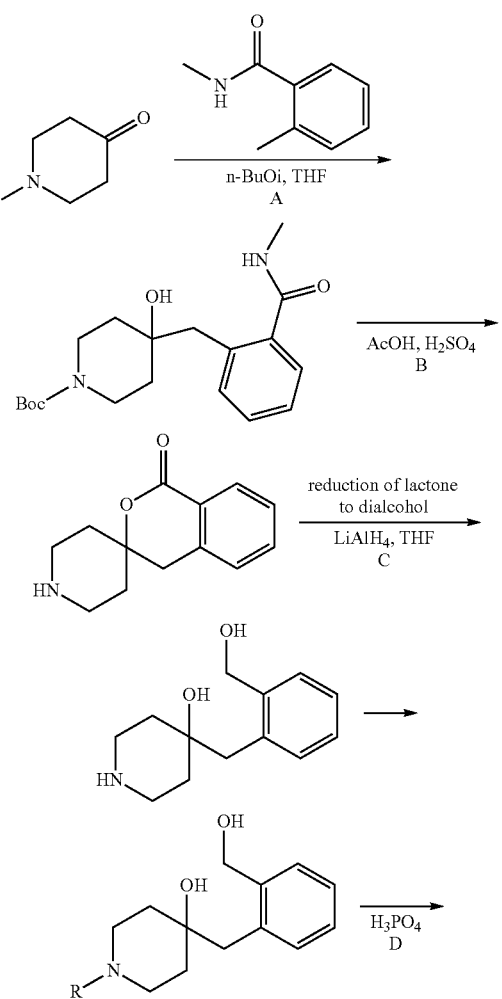

279
-continued

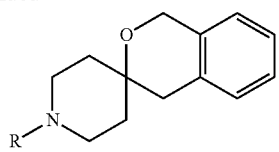

A. To a solution of N,2-dimethylbenzamide (500 mg, 3.351 mmol) in THF (10 mL) was added dropwise butyllithium (3.351 mL, 8.378 mmol) at −15° C. under N₂. The mixture was stirred at ambient temperature for 2 h. A solution of tert-butyl 4-oxopiperidine-1-carboxylate (1.202 g, 6.032 mmol) in THF (5 mL) was added dropwise. The reaction was stirred at ambient temperature for 2 h. Saturated aqueous NH₄Cl (20 mL) was added to the reaction vessel and the resulting biphasic mixture was transferred to a separatory funnel. The layers were separated and the aqueous phase was extracted with EtOAc (1×20 mL). The combined organics were dried over anhydrous Na₂SO₄, filtered and concentrated in vacuo. The resulting oil was purified by flash column chromatography with a gradient elution of hexanes (85%) and EtOAc (15%) to hexanes (70%) and EtOAc (30%) to provide tert-butyl 4-hydroxy-4-(2-(methylcarbamoyl)benzyl)piperidine-1-carboxylate (400 mg, 1.148 mmol).

B. To a solution of tert-butyl 4-hydroxy-4-(2-(methylcarbamoyl)benzyl)piperidine-1-carboxylate (2.2 g, 1.004 mmol) in AcOH/H₂O (15 mL/15 mL) was added sulfuric acid (8 mL) slowly. The reaction mixture was heated to 110° C. and stirred at that temperature for 2 h. The mixture solution was basified with 1M aqueous NaOH until the pH=10 and extracted with DCM (5×50 mL). The combined organics were dried over anhydrous Na₂SO₄, filtered and concentrated in vacuo to provide spiro[isochroman-3,4'-piperidin]-1-one (840 mg, 3.866 mmol) as a brown oil.

C. To a solution of spiro[isochroman-3,4'-piperidin]-1-one (820 mg, 3.774 mmol) in THF (10 mL) was added LiAlH₄ (0.286 g, 7.548 mmol) at 0° C. The reaction was stirred at 0° C. for 1 h. H₂O (40 uL) and aq. NaOH (20%) (30 uL) was added. The mixture solution was filtered. The filtrate was dried over anhydrous Na₂SO₄, filtered and concentrated in vacuo to provide 4-(2-(hydroxymethyl)benzyl)piperidin-4-ol (0.82 g, 3.705 mmol) as a yellow glass.

D. A solution of 1-((2,3-dihydro-1H-inden-1-yl)methyl)-4-(2-(hydroxymethyl)benzyl)piperidin-4-ol (120 mg, 0.3414 mmol) in H₃PO₄ (3 mL) was heated to and stirred at 110° C. for 1 h. The mixture solution was basified by 1M aqueous NaOH until the pH=8. The aqueous phase was extracted with DCM (3×40 mL). The combined organics were dried over anhydrous Na₂SO₄, filtered and concentrated in vacuo. The resulting oil was purified by preparative thin layer chromatography with an isocratic elution of DCM (97%) and MeOH (3%) to provide 1'-((2,3-dihydro-1H-inden-1-yl)methyl)spiro[isochroman-3,4'-piperidine] hydrochloride (0.026 g, 0.0703 mmol) as an off white solid.

280

Example T-76: Synthesis of Boc-Protected 2'-methylspiro[chromane-2,4'-piperidin]-4-one

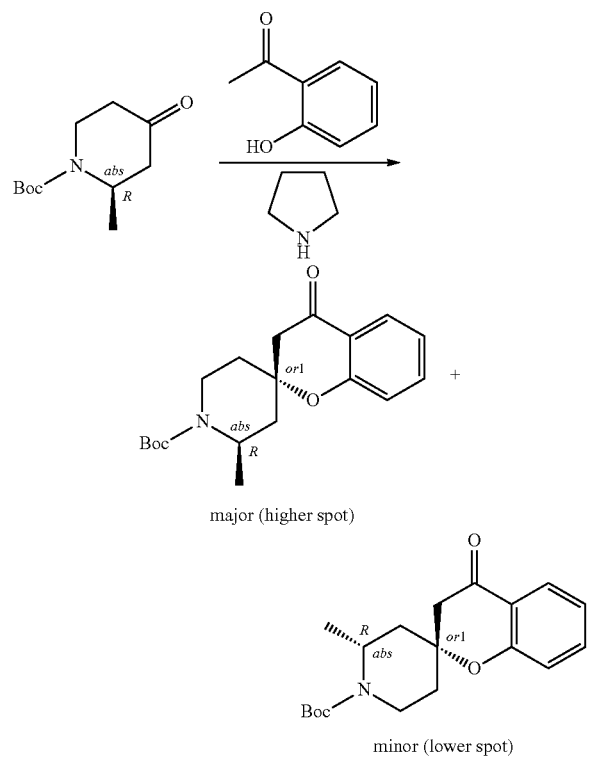

major (higher spot)

minor (lower spot)

To a solution of (R)-tert-butyl 2-methyl-4-oxopiperidine-1-carboxylate (1.2 g, 5.63 mmol) in CH₃OH (8 mL) was added 1-(2-hydroxyphenyl)ethanone (0.84 g, 6.19 mmol) and pyrrolidine (0.6 g, 8.44 mmol). The reaction mixture was heated to 70° C. and stirred at that temperature overnight. The reaction mixture was directly purified by flash column chromatography with a gradient elution of EtOAc (10%) and hexane (90%) to EtOAc (15%) and hexane (85%) to provide the mixture of Product 1 and Product 2 (1.5 g, 4.53 mmol). After further purification by reverse phase HPLC, product A (190 mg, 0.57 mmol) and product B (960 mg, 2.9 mmol) were obtained.

Example T-77

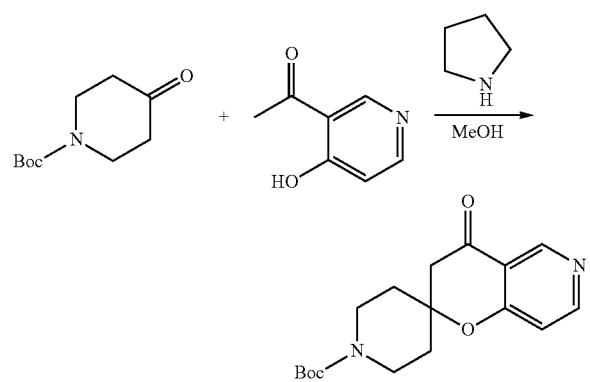

To a solution of 1-(4-hydroxypyridin-3-yl)ethanone (230 mg, 1.68 mmol) in MeOH (5 mL) was added pyrrolidine (0.24 g, 3.36 mmol) and tert-butyl 4-oxopiperidine-1-carboxylate (330 mg, 1.68 mmol). The reaction mixture was heated to 80° C. and stirred at that temperature for 3 h. The organics were concentrated in vacuo. The resulting oil was purified by flash column chromatography with a gradient elution of EtOAc (15%) and hexane (85%) to EtOAc (40%) and hexane (60%) to provide tert-butyl 4'-oxo-3',4'-dihydrospiro[piperidine-4,2'-pyrano[3,2-c]pyridine]-1-carboxylate (230 mg) as a yellow solid.

Example T-78: Oxime Formation and Beckmann Rearrangement to Convert Ketone to Amide General Scheme

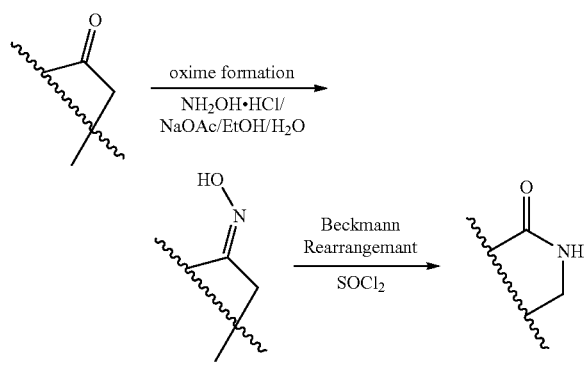

Representative Example

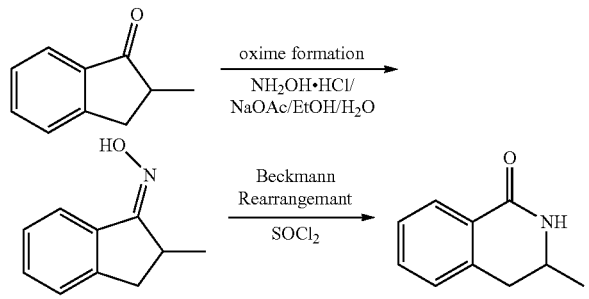

To a solution of 2-methyl-2,3-dihydro-1H-inden-1-one (900 mg, 6.16 mmol) in EtOH (15 mL) was added sodium acetate (1.52 g, 18.48 mmol) and Hydroxylamine hydrochloride (0.86 g, 12.32 mmol). The reaction mixture was reflux and stirred at that temperature for 3 h. Water (50 mL) was added to the reaction vessel and was extracted with EtOAc (3×60 ml). The layers were separated and the organic phase was washed with saturated aqueous NaCl (2×50 mL). The combined organics were dried over anhydrous $Na_2SO_4$, filtered and concentrated in vacuo. The residue was concentrated to provide (E)-2-methyl-2,3-dihydro-1H-inden-1-one oxime (0.4 g, 2.48 mmol) as a yellow oil.

To a solution of (E)-2-methyl-2,3-dihydro-1H-inden-1-one oxime (400 mg, 2.48 mmol) in $SOCl_2$ (10 mL) was reflux and stirred at ambient temperature for 30 min. Water (50 mL) was added to the reaction vessel and was extracted with EtOAc (3×60 ml). The layers were separated and the organic phase was washed with saturated aqueous NaCl (2×50 mL). The combined organics were dried over anhydrous $Na_2SO_4$, filtered and concentrated in vacuo. The residue was concentrated to provide 3-methyl-3,4-dihydroisoquinolin-1(2H)-one (170 mg, 1.06 mmol) as a yellow oil.

Example T-79: Bromination

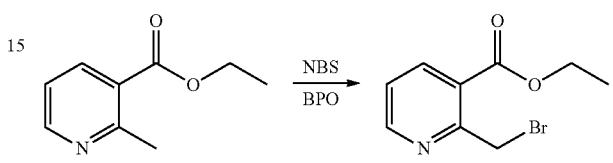

To a solution of ethyl 2-methylnicotinate (1 g, 6.05 mmol) in $CCl_4$ (30 ml) was added N-bromosuccinimide (2.15 g, 12.1 mmol) and benzoyl peroxide (2.19 g, 9.07 mmol). The reaction mixture was heated to 100° C. and stirred at that temperature for 6 h. Water (20 mL) was added to the reaction vessel and was extracted with DCM (3×20 mL). The layers were separated and the organic phase was washed with saturated aqueous NaCl (2×20 mL). The combined organics were dried over anhydrous $Na_2SO_4$, filtered and concentrated in vacuo. After concentration, the residue was purified by silica column chromatography (Hexanes:EtOAc=10:1) to give the desired product (1 g) as a yellow oil.

Example T-80: Chlorination

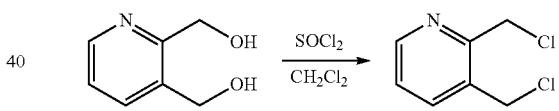

To a solution of pyridine-3,4-diyldimethanol (500 mg, 1.7966 mmol) in DCM (20 mL) was added sulfurous dichloride (0.3206 g, 2.6949 mmol). The reaction was stirred at 60° C. for 3 h and then evaporated in vacuo to give 2,3-bis(chloromethyl)pyridine hydrochloride (200 mg) which was used directly without further purification.

Example T-81: Dialkylation

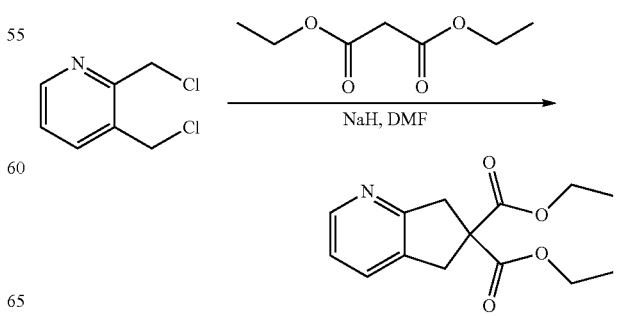

To a solution of diethyl malonate (0.4522 g, 2.8235 mmol) in DMF (20 mL) was added sodium hydride (0.2353 g, 5.8823 mmol) at 0° C. After 20 min, 2,3-bis(chloromethyl)pyridine hydrochloride (500 mg, 2.3529 mmol) was added. The reaction was stirred at 100° C. for 3 h. The reaction mixture was treated with H₂O (30 mL). The aqueous layer was extracted with EtOAc (3×30 mL). The combined organic layers were washed with brine, dried over Na₂SO₄, filtered and concentrated in vacuo. The resulting oil was purified by column chromatography (DCM:MeOH=1: 30) to provide the desired product (600 mg, 2.051 mmol) as an oil.

Example T-82

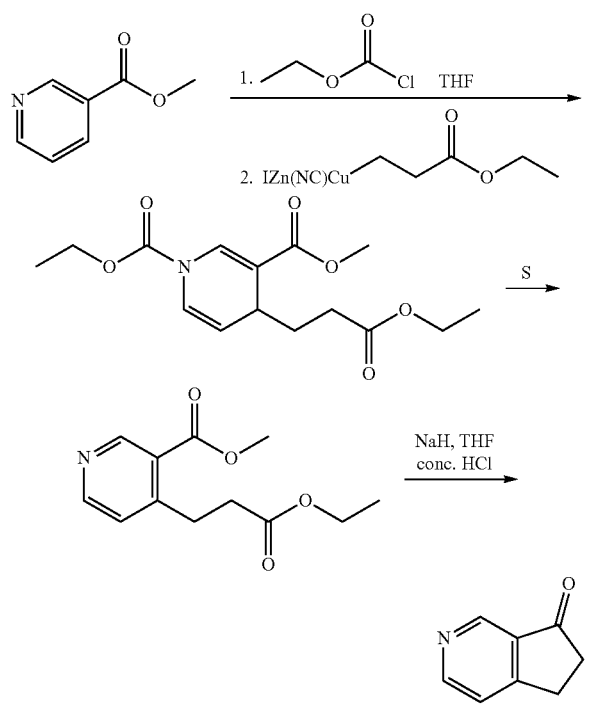

To a solution of methyl nicotinate (8 g, 58.34 mmol) in THF (40 mL) was added ethyl carbonochloridate (6.33 g, 58.34 mmol). The reaction mixture was cooled to 0° C. and stirred at that temperature for 30 min. The solution of C₆H₉CuINO₂Zn in THF cooled to −78° C. was added to the above mixture dropwise. The reaction was stirred at ambient temperature for 12 h until to room temperature. Saturated aqueous NaHCO₃ (100 mL) was added to the reaction vessel. The solid was filtered. The organic layer concentrated in vacuo. The solid was formed and filtered again. The aqueous phase was extracted with EtOAc (5×50 mL). The combined organics were dried over anhydrous Na₂SO₄, filtered and concentrated in vacuo. The resulting oil was purified by flash column chromatography with a gradient elution of EtOAc (5%) and hexane (95%) to EtOAc (10%) and hexane (90%) to provide 1-ethyl 3-methyl 4-(3-ethoxy-3-oxopropyl)pyridine-1,3(4H)-dicarboxylate (6.5 g, 20.88 mmol) as a colorless oil.

To a solution of 1-ethyl 3-methyl 4-(3-ethoxy-3-oxopropyl)pyridine-1,3(4H)-dicarboxylate (6.5 g, 20.88 mmol) in xylene (20 mL) was added sulfur (2.01 g, 62.64 mmol). The reaction mixture was heated to 140° C. and stirred at that temperature for 12 h. TLC showed the starting material was consumed. The organics were concentrated in vacuo. The resulting oil was purified by flash column chromatography with a gradient elution of EtOAc (5%) and hexane (95%) to EtOAc (10%) and hexane (90%) to provide methyl 4-(3-ethoxy-3-oxopropyl)nicotinate (4.3 g, 18.12 mmol) as a yellow oil.

To a solution of methyl 4-(3-ethoxy-3-oxopropyl)nicotinate (200 mg, 0.84 mmol) in THF (20 mL) was added sodium hydride (0.08 g, 3.36 mmol). The reaction mixture was heated to 60° C. under N₂ and stirred at that temperature for 3 h. The organics were concentrated in vacuo. 12 M HCl (4 mL) was added to the above mixture at 0° C. The reaction was stirred at that temperature for 10 min. And then the mixture was heated to 100° C. and stirred at that temperature for 30 min. Saturated aqueous NaHCO₃ (75 mL) was added to the reaction vessel and adjusted pH=8. The mixture was extracted with (3×50 mL). The combined organics were dried over anhydrous Na₂SO₄, filtered and concentrated in vacuo. The product was used for next step without further purification.

Example T-83

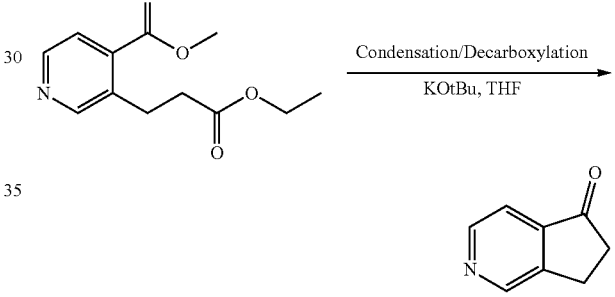

To a solution of methyl 3-(3-ethoxy-3-oxopropyl)isonicotinate (300 mg, 1.26 mmol) in THF (5.0 mL) was added potassium 2-methylpropan-2-olate (0.28 g, 2.52 mmol). The reaction was stirred at ambient temperature for 1 h. The solvent was evaporated to dry. Then conc HCl (5 mL) was added. The reaction was stirred at 100° C. for 2 h. After stirring at 100° C. for another 16 h, saturated aqueous NaHCO₃ (40 mL) and EtOAc (50 mL) were added to the reaction vessel and the resulting biphasic mixture was transferred to a separatory funnel. The layers were separated and the aqueous phase was extracted with EtOAc (2×50 mL). The combined organics were washed with brine, dried over anhydrous Na₂SO₄, filtered and concentrated in vacuo. The resulting oil was purified by flash column chromatography with an isocratic elution of EtOAc (35%) and hexane (65%) to provide 6,7-dihydro-5H-cyclopenta[c]pyridin-5-one (0.03 g, 0.23 mmol) as a gray oil.

Example T-84: Oxymercuration-Demercuration

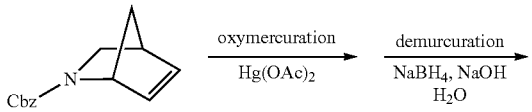

285

-continued

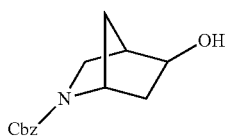

To a solution of diacetoxymercury (13.9 g, 43.62 mmol) in H₂O (44 mL) was added THF (35 mL). Then (1R,4S)-benzyl 2-azabicyclo[2.2.1]hept-5-ene-2-carboxylate (10 g, 43.62 mmol) was added dropwise at 0° C. The reaction was stirred at ambient temperature for 16 h. 3M aqueous NaOH (45 mL) was added to the reaction vessel. The mixture solution was used directly for the next step.

A solution of 0.5 M NaBH₄ in 3N NaOH was added to the mixture at 0° C. The reaction was stirred at ambient temperature for 30 min. The mercury was allowed to settle, and the supernatant liquid decanted and extracted with Et₂O (3×80 mL). The combined organics were dried over anhydrous Na₂SO₄, filtered and concentrated in vacuo. The resulting oil was purified by flash column chromatography with a gradient elution of EtOAc (20%) and petroleum ether (80%) to EtOAc (50%) and petroleum ether (50%) to provide (1R,4R)-benzyl 5-hydroxy-2-azabicyclo[2.2.1]heptane-2-carboxylate (3.5 g, 14.15 mmol) as a colorless oil.

Example T-85

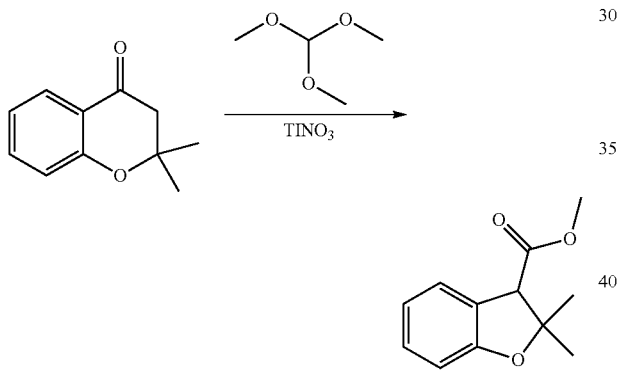

To a solution of 2,2-dimethylchroman-4-one (1.58 g, 8.97 mmol) in trimethoxymethane (30 mL) was added thallium (III) nitrate trihydrate (4.98 g, 11.21 mmol). The reaction was stirred at ambient temperature for 1 day. The reaction mixture was filtered and concentrated in vacuo. The resulting oil was purified by flash column chromatography with an isocratic elution of petroleum ether (100%) to provide methyl 2,2-dimethyl-2,3-dihydrobenzofuran-3-carboxylate (1 g, 4.83 mmol) as a yellow oil.

Example T-86a: Elimination of Alcohol to Olefin (A)

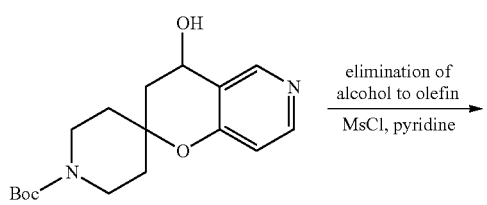

286

-continued

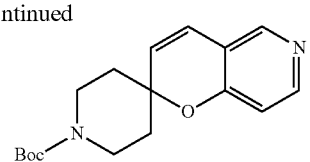

To a solution of tert-butyl 4'-hydroxy-3',4'-dihydrospiro[piperidine-4,2'-pyrano[2,3-c]pyridine]-1-carboxylate (120 mg, 0.37 mmol) in pyridine (10 mL) was added methanesulfonyl chloride (0.25 g, 2.22 mmol). The reaction mixture was heated to 40 and stirred at that temperature for 16 h. TLC showed the starting material was consumed. The organics concentrated in vacuo. The resulting oil was purified by flash column chromatography with a gradient elution of EtOAc (10%) and hexanes (90%) to EtOAc (50%) and hexanes (50%) to provide tert-butyl spiro[piperidine-4,2'-pyrano[3,2-c]pyridine]-1-carboxylate (70 mg) as a yellow solid. Some product tert-butyl 4'-chloro-3',4'-dihydrospiro[piperidine-4,2'-pyrano[3,2-c]pyridine]-1-carboxylate was obtained mixed with the alcohol product, and was removed in the next step.

Example T-86B: Elimination of Alcohol to Olefin (B)

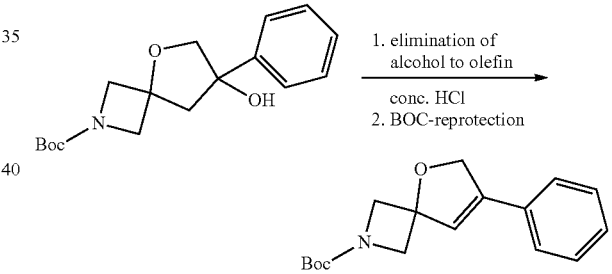

Elimination: To a solution of tert-butyl 7-hydroxy-7-phenyl-5-oxa-2-azaspiro[3.4]octane-2-carboxylate (700 mg, 1.60 mmol) in THF (4 mL) was added conc. HCl (3 mL, 36.0 mmol). The reaction mixture was heated to 60° C. and stirred at that temperature for 2 h. Water (15 mL) was added to the reaction vessel and the resulting mixture was extracted with DCM (2×15 mL). The aqueous solution was neutralized with Na₂CO₃ aqueous solution.

Boc-reprotection: Na₂CO₃ (339 mg, 3.20 mmol) and Boc₂O (523 mg, 2.40 mmol) and EtOAc (15 mL) were added. The reaction was stirred at ambient temperature for 1 h. The reaction vessel and the resulting biphasic mixture were transferred to a separatory funnel. The layers were separated and the aqueous phase was extracted with EtOAc (2×20 mL). The combined organics were dried over anhydrous Na₂SO₄, filtered and concentrated in vacuo to provide tert-butyl 7-phenyl-5-oxa-2-azaspiro[3.4]oct-7-ene-2-carboxylate (350 mg, 1.21 mmol) as a pale yellow oil.

Example T-87: Conversion of Ester to Amide

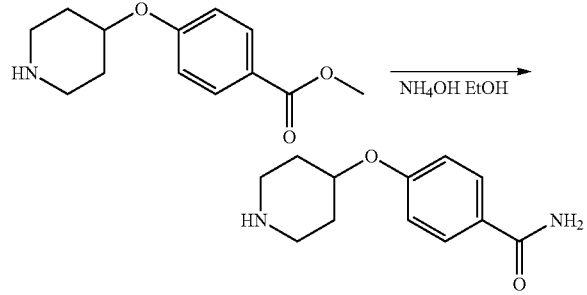

To a solution of methyl 4-(piperidin-4-yloxy)benzoate (500 mg, 2.13 mmol) in EtOH (2 mL) was added NH₄OH (10 mL). The reaction mixture was heated to 80° C. and stirred at that temperature for 2 days. DCM (10 mL) was added to the reaction vessel and the resulting biphasic mixture was transferred to a separatory funnel. The layers were separated and the aqueous phase was extracted with DCM (3×10 mL). The combined organics were dried over anhydrous Na₂SO₄, filtered and concentrated to provide 4-(piperidin-4-yloxy)benzamide (185 mg, 0.84 mmol) as a orange solid.

Example T-88: Synthesis of 6-aryl-4,5-dihydropyridazin-3(2H)-one

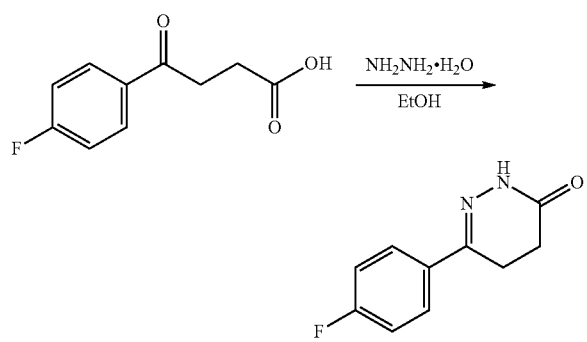

To a solution of 4-(4-fluorophenyl)-4-oxobutanoic acid (3 g, 15.29 mmol) in ethanol (30 mL) was added hydrazine hydrate (1.24 g, 19.78 mmol). The reaction mixture was heated to 80° C. and stirred at that temperature overnight. After cooling to room temperature, the reaction mixture was filtered. The filtrate was washed with ethanol (2×10 mL) to provide 6-(4-fluorophenyl)-4,5-dihydropyridazin-3(2H)-one (2.3 g, 11.97 mmol) as a pale yellow solid.

Example T-89: Synthesis of 2-azabicyclo[2.2.1]hept-5-ene

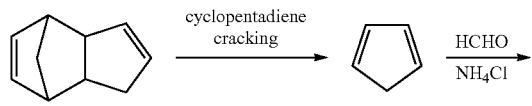

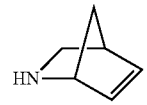

To a solution of cyclopenta-1,3-diene (140 g, 2117.97 mmol) in H₂O (1 L) was added NH₄Cl (339.88 g, 6353.91 mmol) and HCHO (257.81 g, 37%). The reaction was stirred at ambient temperature for 40 h. The reaction mixture was neutralized with solid Na₂CO₃. The mixture solution was used directly for the next step without work-up.

Example T-90

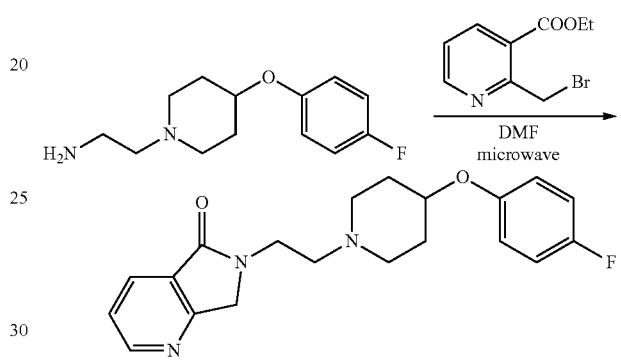

To a solution of 2-(4-(4-fluorophenoxy)piperidin-1-yl)ethanamine (100 mg, 0.42 mmol) in DMF (3 ml) was added ethyl 2-(bromomethyl)nicotinate (0.1 g, 0.42 mmol). The reaction mixture was microwaved to 150° C. for 15 min. Water (20 mL) was added to the reaction vessel and was extracted with EtOAc (3×20 ml). The layers were separated and the organic phase was washed with saturated aqueous NaCl (2×20 mL). The combined organics were dried over anhydrous Na₂SO₄, filtered and concentrated in vacuo. After concentration, the residue was purified by prep HPLC to give the desired product (20 mg) as a red oil.

Example T-91: HCl Salt Formation

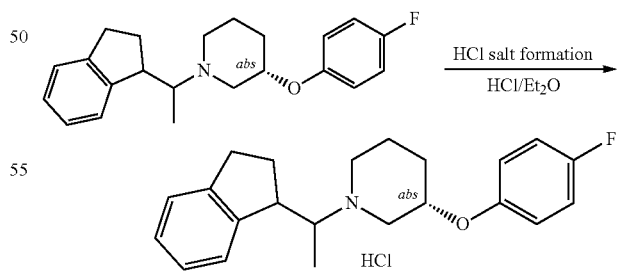

To a solution of (3S)-1-(1-(2,3-dihydro-1H-inden-1-yl)ethyl)-3-(4-fluorophenoxy)piperidine (10 mg, 0.03 mmol) in methanol (2 mL) was added HCl/Et₂O (2 mL). The reaction was stirred at ambient temperature for 30 min. The solvent was evaporated to give the viscous oil. The resulting oil was resolved in DCM (1 mL). Et₂O (5 mL) was added, then the solution was evaporated to dryness in vacuo to provide (3S)-1-(1-(2,3-dihydro-1H-inden-1-yl)ethyl)-3-(4-fluoro-phenoxy)piperidine hydrochloride (7 mg, 0.03 mmol) as a white solid.

Example 56. Synthesis of 4-((4-(2,3-dimethylphenyl)piperazin-1-yl)methyl)isochroman-4-ol

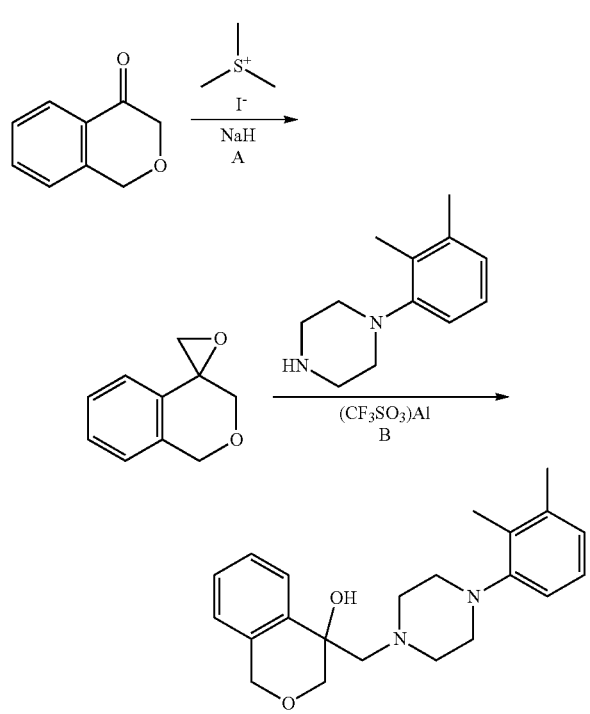

A. To a solution of trimethylsulfonium iodide (0.2755 g, 1.35 mmol) in DMSO (10 mL) was added sodium hydride (0.0486 g, 2.025 mmol). After 10 min later isochroman-4-one (100 mg, 0.675 mmol) was added. The reaction was stirred at 25° C. for 1 h. The reaction mixture was treated with H₂O (30 mL). The aqueous layer was extracted with EtOAc (3×30 mL). The combined organic layers were washed with brine, dried over Na₂SO₄, filtered and concentrated in vacuo. The crude product was used directly for the next step without purification.

B. To a solution of crude spiro[isochroman-4,2'-oxirane] (100 mg, 0.6166 mmol) in toluene (20 mL) was added 1-(2,3-dimethylphenyl)piperazine (0.1173 g, 0.6166 mmol) and Al(CF₃SO₃)₃ (0.0543 g, 0.3083 mmol). The reaction was stirred at 80° C. for 12 h. The reaction mixture was treated with H₂O (50 mL). The aqueous layer was extracted with EtOAc (3×30 mL). The combined organic layers were washed with brine, dried over Na₂SO₄, filtered and concentrated in vacuo. The resulting oil was purified by column chromatography (EtOAc:Hexanes=1:10) to provide 4-((4-(2,3-dimethylphenyl)piperazin-1-yl)methyl)isochroman-4-ol (31 mg, 0.0843 mmol) as a white solid.

Example 62. Synthesis of 4-((4-(2,3-dimethylphenyl)piperazin-1-yl)methyl)isochroman-4-ol

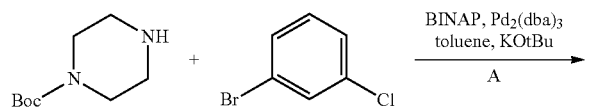

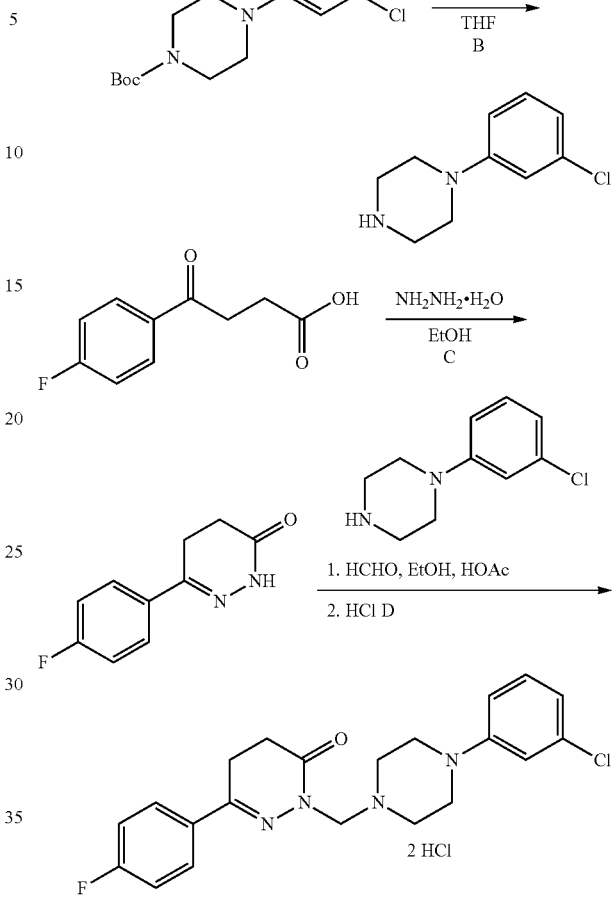

A. To a solution of 1-bromo-3-chlorobenzene (1.5 g, 7.83 mmol) in toluene (30 mL) was added tert-butyl piperazine-1-carboxylate (2.92 g, 15.66 mmol), (±)-2,2'-bis(diphenylphosphino)-1,1'-binaphthalene (0.49 g, 0.78 mmol), tris(dibenzylideneacetone)dipalladium (0.36 g, 0.39 mmol) and potassium 2-methylpropan-2-olate (2.64 g, 23.49 mmol). The reaction mixture was heated to and stirred at that temperature for 16 h under N₂ atmosphere. Water (100 mL) was added to the reaction vessel and the resulting biphasic mixture was extracted with EtOAc (3×200 mL). The combined organics were washed with brine, dried over anhydrous Na₂SO₄, filtered and concentrated in vacuo to provide tert-butyl 4-(3-chlorophenyl)piperazine-1-carboxylate (1.5 g, 5.05 mmol) as a brown oil.

B. To a solution of tert-butyl 4-(3-chlorophenyl)piperazine-1-carboxylate (1.5 g, 5.05 mmol, crude) in THF (50 mL) was added con. hydrogen chloride (20 mL). The reaction was stirred at ambient temperature for 1 h. Saturated aqueous NaHCO₃ (75 mL) was added to the reaction vessel and the resulting biphasic mixture was transferred to a separatory funnel. The layers were separated and the aqueous phase was extracted with DCM:CH₃OH (5:1, 4×100 mL). The combined organics were dried over anhydrous Na₂SO₄, filtered and concentrated in vacuo. The resulting oil was purified by flash column chromatography with a gradient elution of DCM (100%) and MeOH (0%) to DCM (90%) and MeOH (10%) to provide 1-(3-chlorophenyl)piperazine (0.4 g, 2.03 mmol) as a white oil.

C. To a solution of 4-(4-fluorophenyl)-4-oxobutanoic acid (3 g, 15.29 mmol) in ethanol (30 mL) was added hydrazine hydrate (1.24 g, 19.78 mmol). The reaction mixture was heated to 80° C. and stirred at that temperature overnight. After cooling to room temperature, the reaction mixture was filtered. The filtrate was washed with ethanol (2×10 mL) to provide 6-(4-fluorophenyl)-4,5-dihydropyridazin-3(2H)-one (2.3 g, 11.97 mmol) as a pale yellow solid.

D. To a solution of 1-(3-chlorophenyl)piperazine (100 mg, 0.51 mmol) in ethanol (15 mL) was added 6-(4-fluorophenyl)-4,5-dihydropyridazin-3(2H)-one (0.15 g, 0.77 mmol), HCHO (0.3 mL, 3 mmol) and acetic acid (15 mg, 0.33 mmol). The reaction mixture was heated to 40° C. and stirred at that temperature for 24 h. Water (50 mL) was added to the reaction vessel and the resulting mixture was extracted with DCM (4×50 mL). The combined organics were dried over anhydrous Na₂SO₄, filtered and concentrated in vacuo. The resulting oil was purified by flash column chromatography with a gradient elution of EtOAc (10%) and hexanes (90%) to EtOAc (25%) and hexanes (75%) (added 0.5% Et₃N) to provide 2-((4-(3-chlorophenyl)piperazin-1-yl)methyl)-6-(4-fluorophenyl)-4,5-dihydropyridazin-3(2H)-one (0.08 g, 0.21 mmol) as a colorless oil. The product was converted to the HCl salt with HCl/Et₂O.

Example 97. Synthesis of 1-((6-methoxy-1-methyl-2,3-dihydro-1H-inden-1-yl)methyl)-4-(2-methoxyphenoxy)piperidine

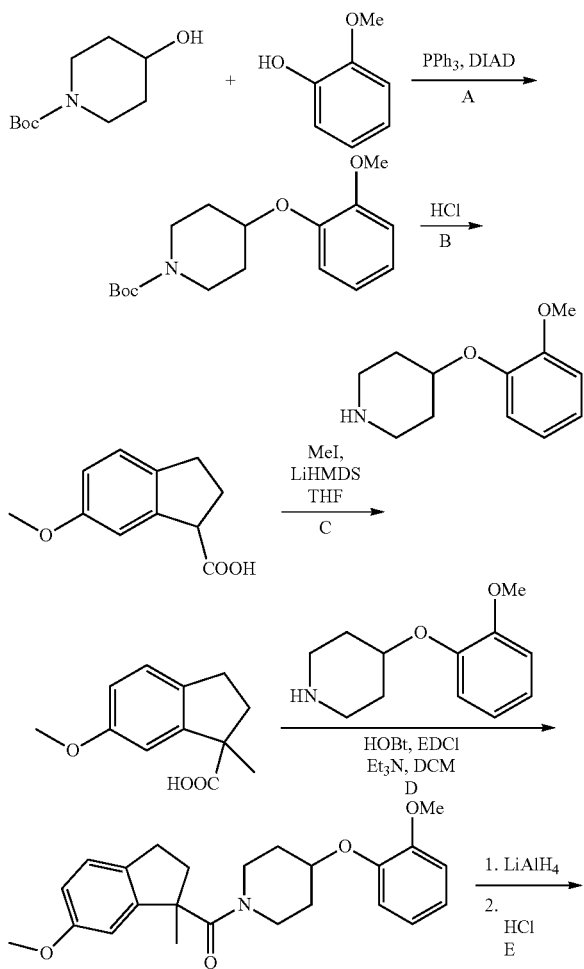

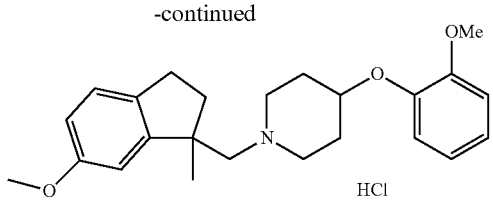

A. To a solution of 2-methoxyphenol (3.0 g, 24.17 mmol) in THF (50 mL) was added tert-butyl 4-hydroxypiperidine-1-carboxylate (4.86 g, 24.17 mmol), triphenylphosphine (7.61 g, 29 mmol) and DIAD (3.16 g, 24.17 mmol). The reaction was stirred at room temperature for 12 h under N₂ atmosphere. The solvent was concentrated in vacuo. The resulting oil was purified by flash column chromatography with an isocratic elution of hexanes (80%) and EtOAc (20%) to provide tert-butyl 4-(2-methoxyphenoxy) piperidine-1-carboxylate (7.2 g, 23.42 mmol) as a yellow oil.

B. To a solution of tert-butyl 4-(2-methoxyphenoxy) piperidine-1-carboxylate (7.2 g, 23.42 mmol) in THF (10 mL) was added hydrogen chloride (6 M, 10 mL). The reaction was stirred at room temperature for 2 h. 1M aqueous NaOH (150 mL) was added to the reaction vessel. The layers were separated and the org/aq phase was extracted with EtOAc (3×125 mL). The combined organics were dried over anhydrous Na₂SO₄, filtered and concentrated in vacuo. The resulting oil was purified by flash column chromatography with EtOAc (50%) and hexanes (50%) to provide 4-(2-methoxyphenoxy)piperidine (1.56 g, 7.53 mmol) as a yellow solid.

C. To a solution of 6-methoxy-2,3-dihydro-1H-indene-1-carboxylic acid (300 mg, 1.56 mmol, see Example T-34) in THF (8 mL) was added dropwise lithium bis(trimethylsilyl)amide (0.65 g, 3.9 mmol) at −20° C. under N₂. The reaction was stirred at 35° C. for 1 h. A solution of iodomethane (0.29 g, 2.03 mmol) in THF (3 mL) was added slowly at 0° C. The reaction was stirred at 35° C. for 2 h. The mixture solution was acidified with 6 N HCl to pH=5 and the resulting biphasic mixture was transferred to a separatory funnel. The layers were separated and the aqueous phase was extracted with EtOAc (2×20 mL). The combined organics were dried over anhydrous Na₂SO₄, filtered and concentrated in vacuo. The resulting oil was purified by flash column chromatography with an isocratic elution of EtOAc (10%) and petroleum ether (90%) to provide 6-methoxy-1-methyl-2,3-dihydro-1H-indene-1-carboxylic acid (0.2 g, 0.97 mmol) as a yellow solid.

D. To a solution of 6-methoxy-1-methyl-2,3-dihydro-1H-indene-1-carboxylic acid (70 mg, 0.339 mmol) in DCM (3 mL) was added 4-(2-methoxyphenoxy)piperidine (0.077 g, 0.373 mmol), 1H-benzo[d][1,2,3]triazol-1-ol (0.046 g, 0.339 mmol), EDCI (0.13 g, 0.678 mmol) and triethylamine (0.103 g, 1.017 mmol). The reaction was stirred at ambient temperature for 16 h. Saturated aqueous NaCl (3 mL) and DCM (5 mL) was added to the reaction vessel and the resulting biphasic mixture was transferred to a separatory funnel. The layers were separated and the organic phase was washed with saturated aqueous NaCl (1×3 mL). The DCM was dried over anhydrous Na₂SO₄, filtered and concentrated in vacuo. The resulting oil was purified by flash column chromatography with an isocratic elution of petroleum ether (85%) and EtOAc (15%) to provide (6-methoxy-1-methyl-2,3-dihydro-1H-inden-1-yl)(4-(2-methoxyphenoxy)piperidin-1-yl)methanone (0.085 g, 0.215 mmol) as a colorless oil.

E. To a solution of (6-methoxy-1-methyl-2,3-dihydro-1H-inden-1-yl)(4-(2-methoxyphenoxy)piperidin-1-yl)methanone (85 mg, 0.215 mmol) in THF (2 mL) was added AlLiH$_4$ (0.016 g, 0.43 mmol) at 0° C. The reaction was stirred at 0° C. for 1 h. H$_2$O (40 uL) and aq. NaOH (20%) (30 uL) was added. The mixture solution was filtered. The filtrate was dried over anhydrous Na$_2$SO$_4$, filtered and concentrated in vacuo. The resulting oil was purified by flash column chromatography with an isocratic elution of EtOAc (15%) and petroleum ether (85%) to provide 1-((6-methoxy-1-methyl-2,3-dihydro-1H-inden-1-yl)methyl)-4-(2-methoxyphenoxy)piperidine. The product was converted to HCl salt with HCl/Et$_2$O to provide desired product as hydrochloride (0.053 g, 0.127 mmol) as a yellow solid.

Example 113. Synthesis of 1-((6-methoxy-1-methyl-2,3-dihydro-1H-inden-1-yl)methyl)-4-(2-methoxyphenoxy)piperidine

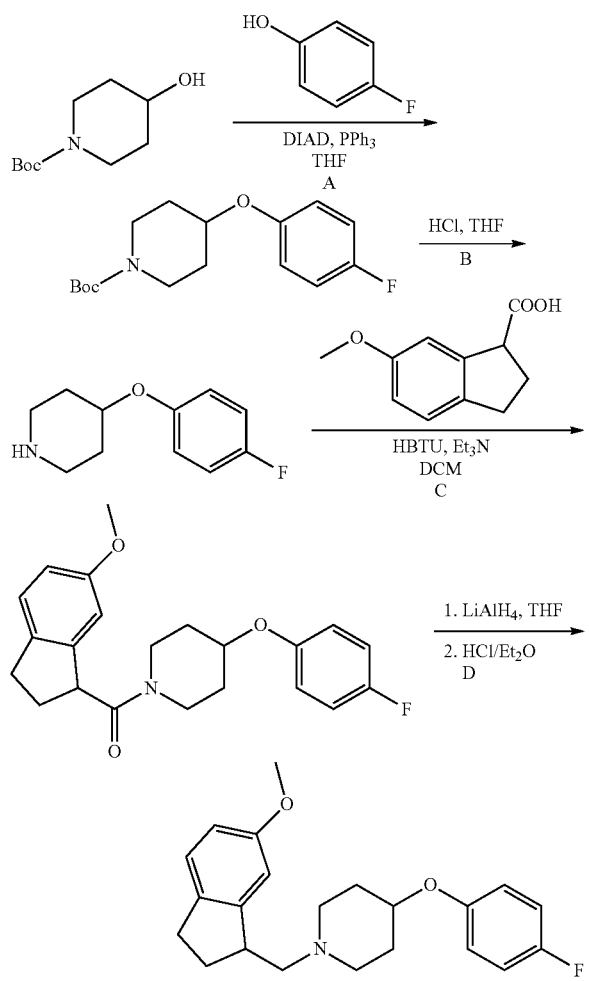

A. To a solution of 4-fluorophenol (7 g, 62.44 mmol) in THF (100 mL) was added tert-butyl 4-hydroxypiperidine-1-carboxylate (12.57 g, 62.44 mmol), triphenylphosphine (17.99 g, 68.68 mmol) and diisopropyl azodiformate (18.92 g, 93.66 mmol). The reaction was stirred at ambient temperature for 12 h. Water (50 mL) was added to the reaction vessel and was extracted with EtOAc (3×60 ml). The layers were separated and the organic phase was washed with saturated aqueous NaCl (2×50 mL). The combined organics were dried over anhydrous Na$_2$SO$_4$, filtered and concentrated in vacuo. The resulting oil was purified by silica column chromatography with a gradient elution of hexanes to hexanes (90%) and EtOAc (10%) to provide 1-(1,3-dithian-2-yl)-2-methyl-2,3-dihydro-1H-inden-1-ol (17 g, 57.56 mmol) as a yellow oil.

B. To a solution of tert-butyl 4-(4-fluorophenoxy)piperidine-1-carboxylate (17 g, 57.56 mmol) in THF (100 mL) was added HCl (21.01 g, 575.6 mmol). The reaction was stirred at ambient temperature for 1 h. Water (20 mL) was added to the reaction vessel and was extracted with DCM (6×20 ml). The layers were separated and the aqueous phase was added NaHCO$_3$ (20 mL). Then the reaction was extracted with DCM (3×20 ml). The layers were separated and the organic phase was washed with saturated aqueous NaCl (2×30 mL). The combined organics were dried over anhydrous Na$_2$SO$_4$, filtered and concentrated in vacuo. After concentrated, the residue was purified to give the desired product 4-(4-fluorophenoxy) piperidine (9 g, 46.1 mmol) as a yellow oil.

C. To a solution of 6-methoxy-2,3-dihydro-1H-indene-1-carboxylic acid (500 mg, 2.6 mmol) in DCM (30 mL) was added 4-(4-fluorophenoxy)piperidine (0.51 g, 2.6 mmol), triethylamine (0.53 g, 5.2 mmol) and HBTU (1.31 g, 5.2 mmol). The reaction was stirred at ambient temperature for 1 h. Water (10 mL) was added to the reaction vessel and the resulting biphasic mixture was transferred to a separatory funnel. The layers were separated and the organic phase was washed with saturated aqueous NaCl (1×5 mL). The combined organics were dried over anhydrous Na$_2$SO$_4$, filtered and concentrated in vacuo. The resulting oil was purified by flash column chromatography with a gradient elution of hexanes (100%) to hexanes (70%) and EtOAc (30%) to provide (4-(4-fluorophenoxy)piperidin-1-yl)(6-methoxy-2,3-dihydro-1H-inden-1-yl)methanone (550 mg, 1.49 mmol) as a yellow oil.

D. To a solution of (4-(4-fluorophenoxy)piperidin-1-yl)(6-methoxy-2,3-dihydro-1H-inden-1-yl)methanone (550 mg, 1.49 mmol) in THF (10 mL) was added LiAlH$_4$ (0.23 g, 5.96 mmol). The reaction was stirred at ambient temperature for 30 min. 1M aqueous NaOH (10 mL) was added to the reaction vessel and the resulting biphasic mixture was extracted with DCM (3×50 mL). The organic phase was washed with saturated aqueous NaCl (2×20 mL). The combined organics were dried over anhydrous Na$_2$SO$_4$, filtered and concentrated in vacuo. The resulting oil was purified by flash column chromatography with a gradient elution of hexanes (100%) to hexanes (85%) and EtOAc (15%) to provide the freebase as a oil. 2 N HCl/Et$_2$O was added to provide 4-(4-fluorophenoxy)-1-((6-methoxy-2,3-dihydro-1H-inden-1-yl)methyl)piperidine hydrochloride (320 mg, 0.82 mmol) as a white solid.

Example 119. Synthesis of 1-((7-fluoro-2,3-dihydro-1H-inden-1-yl)methyl)-4-(4-fluorophenoxy)piperidine

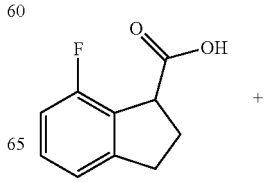

+

295

-continued

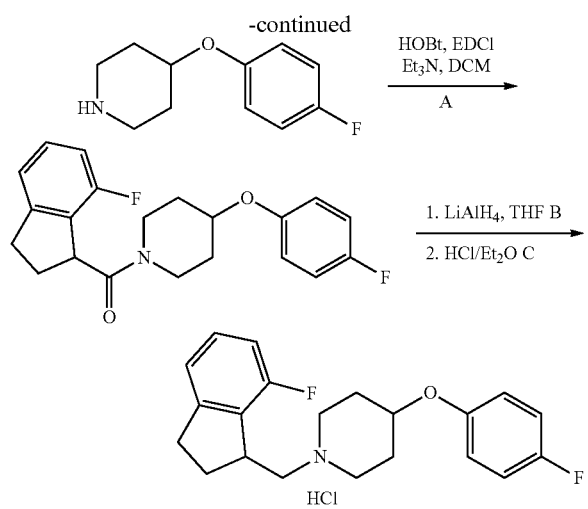

A. To a solution of 4-(4-fluorophenoxy)piperidine (160 mg, 0.82 mmol) in DCM (15 mL) was added 7-fluoro-2,3-dihydro-1H-indene-1-carboxylic acid (150 mg, 0.83 mmol, synthesized according to Example T-34), triethyl amine (0.21 g, 2.05 mmol) and hydroxybenzotriazole (0.17 g, 1.23 mmol). 1-Ethyl-3-(3-dimethyllaminopropyl)carbodiimide hydrochloride (0.31 g, 1.64 mmol). Water (20 mL) was added to the reaction vessel and was extracted with EtOAc (3×20 ml). The layers were separated and the organic phase was washed with saturated aqueous NaCl (2×20 mL). The combined organics were dried over anhdrous $Na_2SO_4$, filtered and concentrated in vacuo. After concentrated, the residue was purified by silica column chromatography (Hexane:EtOAc=1:1) to give the desired product (130 mg) as a yellow oil.

B. To a solution of (7-fluoro-2,3-dihydro-1H-inden-1-yl) (4-(4-fluorophenoxy)piperidin-1-yl)methanone (130 mg, 0.36 mmol) in THF (10 ml) was added Lithium aluminum hydride (0.04 g, 1.08 mmol). 0.5 M aqueous NaOH (20 mL) was added to the reaction vessel and was extracted with DCM (3×20 ml). The layers were separated and the organic phase was washed with saturated aqueous NaCl (2×20 mL). The combined organics were dried over anhdrous $Na_2SO_4$, filtered and concentrated in vacuo. After concentrated, the residue was purified by silica column chromatography (Hexane:EA=1:1) to give the desired product (89 mg) as a yellow oil.

C. To a solution of 1-((7-fluoro-2,3-dihydro-1H-inden-1-yl)methyl)-4-(4-fluorophenoxy)piperidine in methanol (2 mL) was added HCl/Et$_2$O (2 mL). The reaction was stirred at ambient temperature for 30 min. The solvent was evaporated to give the viscous oil. The resulting oil was resolved in CH$_2$Cl$_2$ (1 mL). And then Et$_2$O (5 mL) was added. Most of the solvent was sucked out. The remaining was evaporated to dry in vacuo to provide 1-((7-fluoro-2,3-dihydro-1H-inden-1-yl)methyl)-4-(4-fluorophenoxy)piperidine hydrochloride (75 mg, 0.36 mmol) as a white solid.

296

Example 121. Synthesis of 3-((4-(4-fluorophenoxy) piperidin-1-yl)methyl)-2,3-dihydro-1H-indene-5-carbonitrile

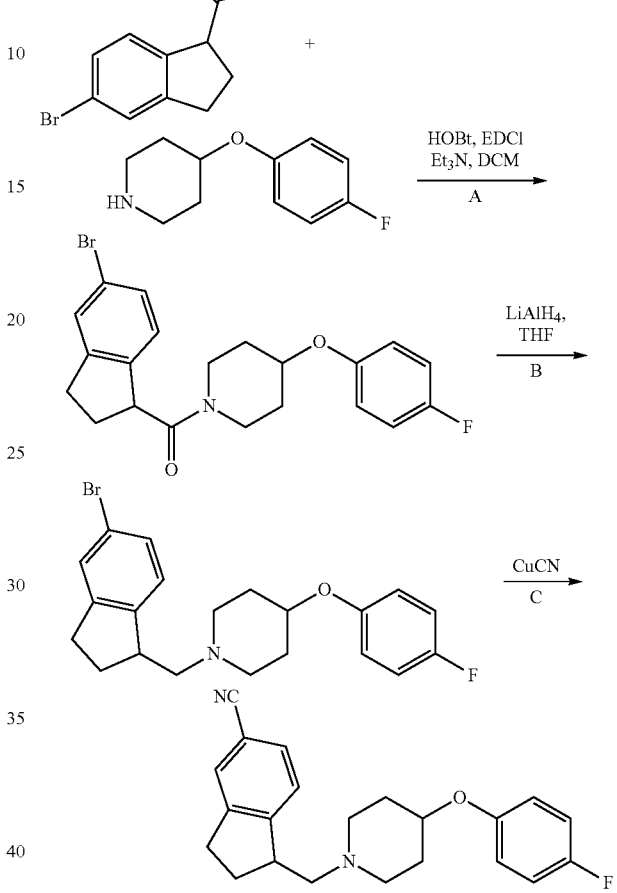

A. To a solution of 5-bromo-2,3-dihydro-1H-indene-1-carboxylic acid (180 mg, 0.747 mmol, synthesized according to Example T-34) in DCM (3 mL) was added 4-(4-fluorophenoxy)piperidine (0.146 g, 0.747 mmol), 1H-benzo[d][1,2,3]triazol-1-ol (0.101 g, 0.747 mmol), triethylamine (0.227 g, 2.241 mmol) and EDCI (0.287 g, 1.494 mmol). The reaction was stirred at ambient temperature for 16 h. Water (5 mL) and DCM (5 mL) was added to the reaction vessel and the resulting biphasic mixture was transferred to a separatory funnel. The layers were separated and the aqueous phase was extracted with DCM (2×5 mL). The organics were dried over anhydrous $Na_2SO_4$, filtered and concentrated in vacuo. The resulting oil was purified by flash column chromatography with a gradient elution of petroleum ether (85%) and EtOAc (15%) to petroleum ether (80%) and EtOAc (20%) to provide (5-bromo-2,3-dihydro-1H-inden-1-yl)(4-(4-fluorophenoxy)piperidin-1-yl)methanone (0.25 g, 0.598 mmol) as a yellow oil.

B. To a solution of 2-(6,7-dihydro-5H-cyclopenta[b]pyridin-7-yl)-1-(4-(4-fluorophenoxy)piperidin-1-yl)ethanone (220 mg, 0.621 mmol) in THF (2 mL) was added AlLiH$_4$ (0.047 g, 1.242 mmol) at 0° C. The reaction was stirred at 0° C. for 1 h. H$_2$O (40 uL) and aq. NaOH (20%) (30 uL) was added. The mixture solution was filtered. The filtrate was dried over anhydrous Na₂SO₄, filtered and concentrated in vacuo. The resulting oil was purified by flash column chromatography with an isocratic elution of EtOAc (15%) and petroleum ether (85%) to provide 1-((6-methoxy-1-methyl-2,3-dihydro-1H-inden-1-yl)methyl)-4-(2-methoxyphenoxy)piperidine hydrochloride (0.053 g, 0.127 mmol) as a yellow solid.

C. To a solution of 1-((5-bromo-2,3-dihydro-1H-inden-1-yl)methyl)-4-(4-fluorophenoxy)piperidine (150 mg, 0.371 mmol) in DMA (2 mL) was added cyanocopper (0.1 g, 1.113 mmol). The reaction was stirred at 150° C. for 1 h under microwave-irradiation. Saturated aqueous NaCl (10 mL) and EtOAc (5 mL) was added to the reaction vessel and the resulting biphasic mixture was transferred to a separatory funnel. The layers were separated and the aqueous phase was extracted with EtOAc (2×5 mL). The combined organics were washed with saturated aqueous NaCl (3×5 mL), dried over anhydrous Na₂SO₄, filtered and concentrated in vacuo. The resulting oil was purified by flash column chromatography with a gradient elution of petroleum ether (85%) and EtOAc (15%) to petroleum ether (75%) and EtOAc (25%) to provide 1-((4-(4-fluorophenoxy)piperidin-1-yl)methyl)-2,3-dihydro-1H-indene-5-carbonitrile (0.008 g, 0.023 mmol) as a yellow solid.

Example 122. Synthesis of 1-((4-(4-fluorophenoxy)piperidin-1-yl)methyl)-2,3-dihydro-1H-indene-4-carbonitrile

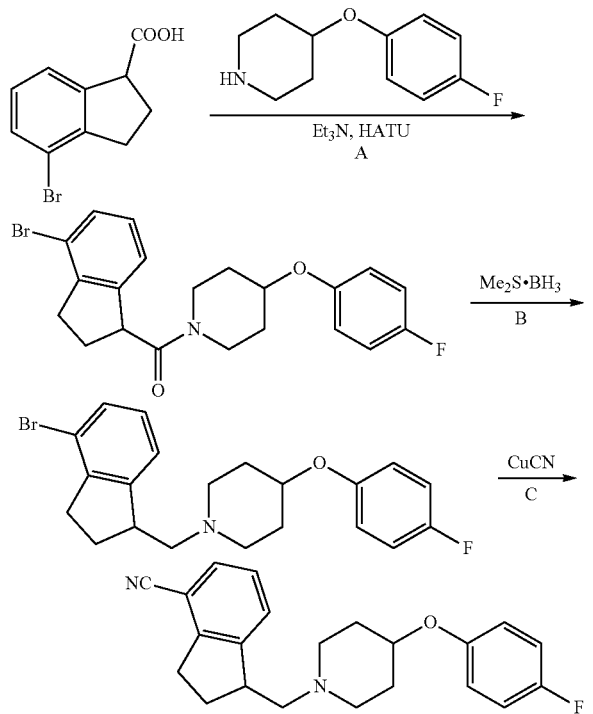

A. To a solution of 4-bromo-2,3-dihydro-1H-indene-1-carboxylic acid (1 g, 4.148 mmol, synthesized according to Example T-34) in DCM (30 mL) was added 4-(4-fluorophenoxy)piperidine (0.8098 g, 4.148 mmol), triethylamine (1.0493 g, 10.37 mmol) and HATU (2.3658 g, 6.222 mmol). The reaction was stirred at ambient temperature for 5 h. Water (30 mL) was added to the reaction vessel and the resulting biphasic mixture was transferred to a separatory funnel. The layers were separated and the aqueous phase was extracted with EtOAc (3×30 mL). The combined organics were dried over anhydrous Na₂SO₄, filtered and concentrated in vacuo. The resulting oil was purified by flash column chromatography with a gradient elution of hexanes (90%) and EtOAc (10%) to hexanes (70%) and EtOAc (30%) to provide (4-bromo-2,3-dihydro-1H-inden-1-yl)(4-(4-fluorophenoxy)piperidin-1-yl)methanone (1.08 g, 2.5819 mmol) as a colorless oil.

B. To a solution of (4-bromo-2,3-dihydro-1H-inden-1-yl)(4-(4-fluorophenoxy)piperidin-1-yl)methanone (1 g, 2.3906 mmol) in THF (30 mL) was added DMSB (0.9081 g, 11.953 mmol). The reaction was stirred at 0-20° C. for 2 h. Saturated aqueous Na₂CO₃ (30 mL) was added to the reaction vessel and the resulting biphasic mixture was transferred to a separatory funnel. The layers were separated and the aqueous phase was extracted with EtOAc (3×30 mL). The combined organics were dried over anhydrous Na2SO4, filtered and concentrated in vacuo. The resulting oil was purified by flash column chromatography with a gradient elution of hexanes (90%) and EtOAc (10%) to hexanes (50%) and EtOAc (50%) to provide 1-((4-bromo-2,3-dihydro-1H-inden-1-yl)methyl)-4-(4-fluorophenoxy)piperidine (0.63 g, 1.5582 mmol) as a colorless oil.

C. To a solution of 1-((4-bromo-2,3-dihydro-1H-inden-1-yl)methyl)-4-(4-fluorophenoxy)piperidine (200 mg, 0.4947 mmol) in DMA (5 mL) was added cyanocopper (0.2215 g, 2.4735 mmol). The reaction was stirred at 150° C. for 1 h by microwave. Water (20 mL) was added to the reaction vessel and the resulting biphasic mixture was transferred to a separatory funnel. The layers were separated and the aqueous phase was extracted with EtOAc (3×20 mL). The combined organics were dried over anhydrous Na₂SO₄, filtered and concentrated in vacuo. The resulting oil was purified by flash column chromatography with a gradient elution of hexanes (90%) and EtOAc (10%) to hexanes (70%) and EtOAc (30%) to provide 1-((4-(4-fluorophenoxy)piperidin-1-yl)methyl)-2,3-dihydro-1H-indene-4-carbonitrile (0.0792 g, 0.226 mmol).

Example 147/148. Synthesis of (2S,4R)-1-((2,3-dihydro-1H-inden-2-yl)methyl)-4-(2-methoxyphenoxy)-2-methylpiperidine and (2S,4S)-1-((2,3-dihydro-1H-inden-2-yl)methyl)-4-(2-methoxyphenoxy)-2-methylpiperidine

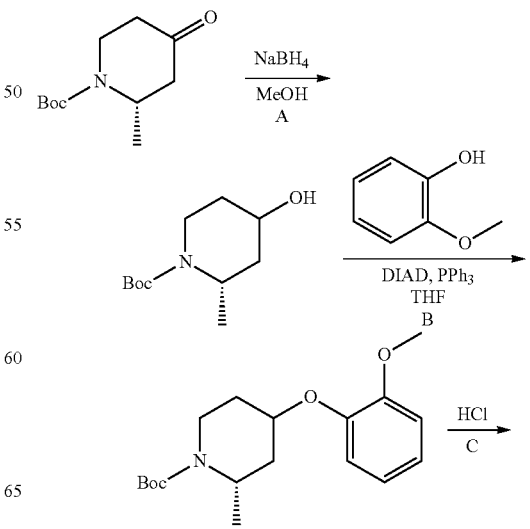

-continued

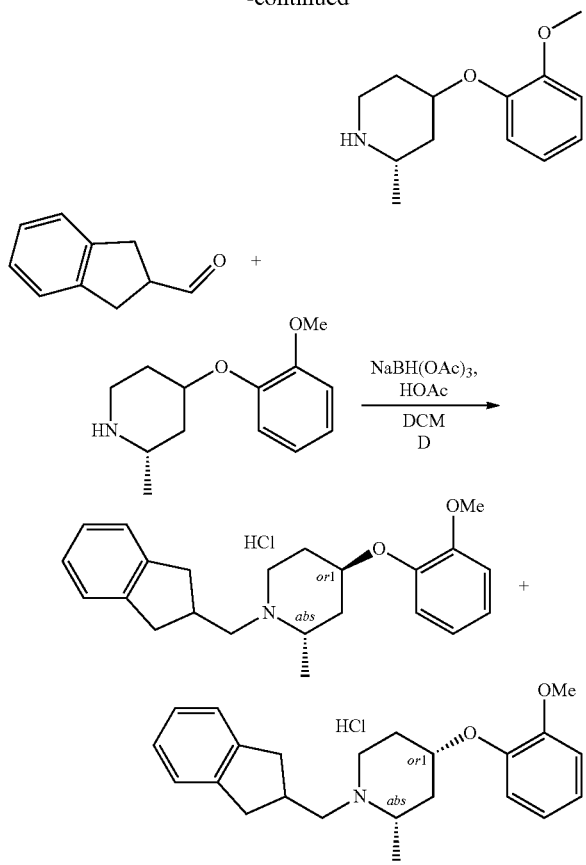

A. To a solution of (S)-tert-butyl 2-methyl-4-oxopiperidine-1-carboxylate (1 g, 4.69 mmol) in MeOH (20 mL) was added NaBH₄ (0.44 g, 11.73 mmol). The reaction was stirred at ambient temperature for 2 h. Water (1.5 mL) was added to the reaction vessel the org/aq phase was extracted with EtOAc (3×100 mL). The combined organics were dried over anhydrous Na₂SO₄, filtered and concentrated in vacuo to provide 0.99 g of crude product which was used directly in the next step.

B. To a solution of (2S)-tert-butyl 4-hydroxy-2-methylpiperidine-1-carboxylate (450 mg, 2.0902 mmol) in THF (30 mL) was added 2-methoxyphenol (0.2595 g, 2.0902 mmol), triphenylphosphine (0.6579 g, 2.5082 mmol) and DIAD (0.5072 g, 2.5082 mmol). The reaction was stirred at 50° C. for 12 h. Water (30 mL) was added to the reaction vessel and the resulting biphasic mixture was transferred to a separatory funnel. The layers were separated and the aqueous phase was extracted with EtOAc (3×20 mL). The combined organics were dried over anhydrous Na₂SO₄, filtered and concentrated in vacuo. The resulting oil was purified by flash column chromatography with an isocratic elution of hex (95%) and EtOAc (5%) to provide (2,9-tert-butyl 4-(2-methoxyphenoxy)-2-methylpiperidine-1-carboxylate (0.4 g, 1.2445 mmol) as a oil.

C. To a solution of (2S)-tert-butyl 4-(2-methoxyphenoxy)-2-methylpiperidine-1-carboxylate (500 mg, 1.5556 mmol) in THF (20 mL) was added 6 N HCl 10 mL. The reaction was stirred at 40° C. for 12 h. saturated aqueous Na₂CO₃ (20 mL) was added to the reaction vessel and the resulting biphasic mixture was transferred to a separatory funnel. The layers were separated and the aqueous phase was extracted with EtOAc (3×20 mL). The combined organics were dried over anhydrous Na₂SO₄, filtered and concentrated in vacuo to provide (2S)-4-(2-methoxyphenoxy)-2-methylpiperidine (0.27 g, 1.2201 mmol) as a colorless oil.

D. To a solution of 2,3-dihydro-1H-indene-2-carbaldehyde (150 mg, 1.0261 mmol) in DCM (10 mL) was added (2S)-4-(2-methoxyphenoxy)-2-methylpiperidine (0.2498 g, 1.1287 mmol), acetic acid (0.1849 g, 3.0783 mmol) and NaBH(OAc)3 (0.3262 g, 1.5392 mmol). The reaction was stirred at ambient temperature for 12 h. saturated aqueous Na₂CO₃ (20 mL) was added to the reaction vessel and the resulting biphasic mixture was transferred to a separatory funnel. The layers were separated and the aqueous phase was extracted with EtOAc (3×20 mL). The combined organics were dried over anhydrous Na₂SO₄, filtered and concentrated in vacuo. The resulting oil was purified by flash column chromatography with a gradient elution of hexanes (95%) and EtOAc (5%) to hexanes (90%) and EtOAc (5%) to provide (2S,4R)-1-((2,3-dihydro-1H-inden-2-yl)methyl)-4-(2-methoxyphenoxy)-2-methylpiperidine (0.0148 g, 0.0422 mmol) and (2S,4S)-1-((2,3-dihydro-1H-inden-2-yl)methyl)-4-(2-methoxyphenoxy)-2-methylpiperidine (0.0104 g, 0.0295 mmol).

Example 155. Synthesis of (2S,4R)-1-((2,3-dihydro-1H-inden-2-yl)methyl)-4-(2-methoxyphenoxy)-2-methylpiperidine

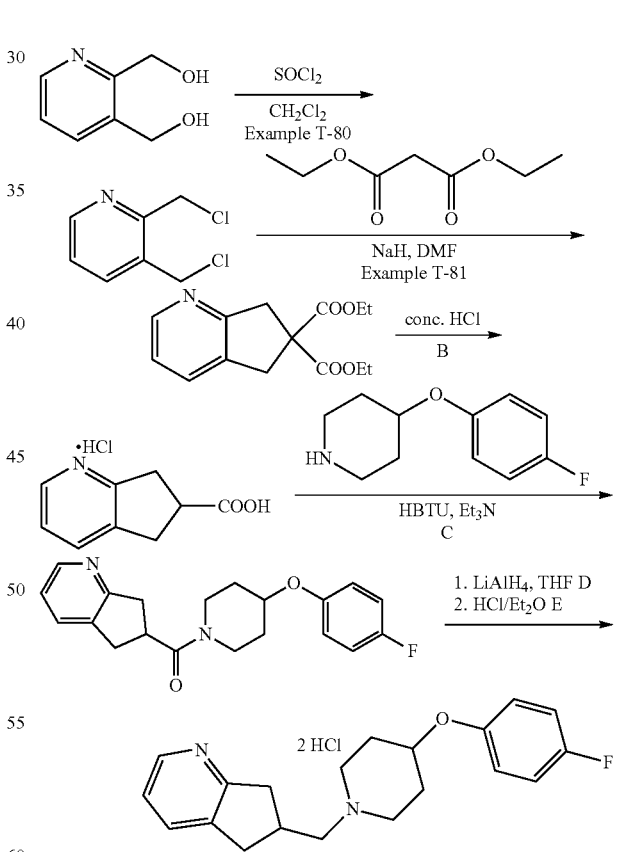

A. Diethyl 5,7-dihydro-6H-cyclopenta[b]pyridine-6,6-dicarboxylate was synthesized in two steps from pyridine-2,3-diyldimethanol according to Examples T-80 and T-81.

B. To a solution of diethyl 5,7-dihydro-6H-cyclopenta[b]pyridine-6,6-dicarboxylate (350 mg, 1.3293 mmol) in conc. HCl 25 mL was stirred at 100° C. for 2 h and then evaporated in vacuo to give the crude 6,7-dihydro-5H-cyclopenta[b]pyridine-6-carboxylic acid hydrochloride as a black oil which was used directly without further purification 200 mg.

C. To a solution of crude 6,7-dihydro-5H-cyclopenta[b]pyridine-6-carboxylic acid hydrochloride (300 mg, 1.5027 mmol) in DMF (20 mL) was added 4-(4-fluorophenoxy)piperidine (0.2934 g, 1.5027 mmol), HBTU (0.57 g, 2.2541 mmol) and Et₃N (0.5312 g, 5.2595 mmol). The reaction was stirred at ambient temperature for 12 h. Water (50 mL) was added to the reaction vessel and the resulting biphasic mixture was transferred to a separatory funnel. The layers were separated and the aqueous phase was extracted with EtOAc (3×25 mL). The combined organics were dried over anhydrous Na₂SO₄, filtered and concentrated in vacuo. The crude product (300 mg) was used for the next step without purification.

D. To a solution of crude (6,7-dihydro-5H-cyclopenta[b]pyridin-6-yl)(4-(4-fluorophenoxy)piperidin-1-yl)methanone (400 mg, 1.1751 mmol) in THF (20 mL) was added LiAlH₄ (0.1003 g, 2.6439 mmol). The reaction was stirred at ambient temperature for 30 min. Water (30 mL) was added to the reaction vessel and the resulting biphasic mixture was transferred to a separatory funnel. The layers were separated and the aqueous phase was extracted with EtOAc (3×25 mL). The combined organics were dried over anhydrous Na₂SO₄, filtered and concentrated in vacuo. The resulting oil was purified by reverse phase HPLC with a gradient elution of water (70%) and MeOH (30%) to water (20%) and MeOH (80%) to provide 6-((4-(4-fluorophenoxy)piperidin-1-yl)methyl)-6,7-dihydro-5H-cyclopenta[b]pyridine (0.0784 g, 0.2402 mmol) as a colorless oil.

E. To a solution of 6-((4-(4-fluorophenoxy)piperidin-1-yl)methyl)-6,7-dihydro-5H-cyclopenta[b]pyridine (80 mg, 0.2451 mmol) in Et₂O (10 mL) was added Et₂O/HCl (1 mL). The reaction was stirred at ambient temperature for 10 min. The reaction was concentrated in vacuo to provide 6-((4-(4-fluorophenoxy)piperidin-1-yl)methyl)-6,7-dihydro-5H-cyclopenta[b]pyridine dihydrochloride (0.0911 g, 0.2282 mmol).

Example 165. Synthesis of 1-(chroman-4-ylmethyl)-4-(4-fluorophenoxy)piperidine

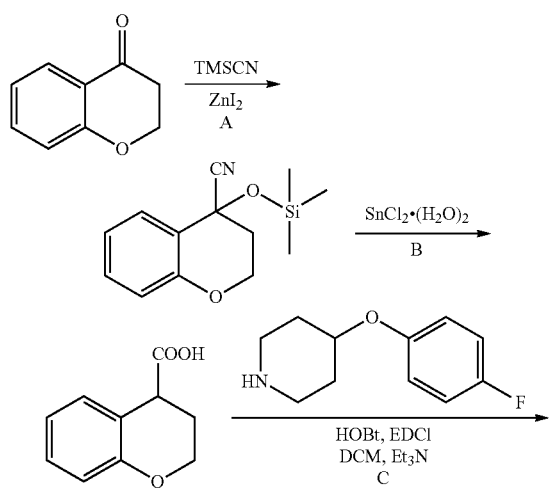

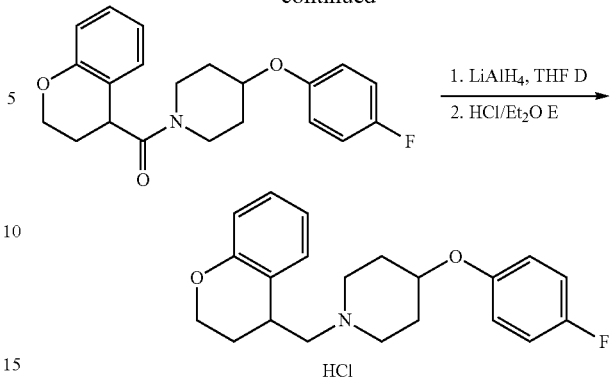

A. To a solution of chroman-4-one (2 g, 13.5 mmol) in DCM (30 mL) was added trimethylsilanecarbonitrile (2.01 g, 20.25 mmol) and zinc(II) iodide (4.31 g, 13.5 mmol). The reaction was stirred at ambient temperature for 8 h. Water (40 mL) was added to the reaction vessel and the resulting biphasic mixture was transferred to a separatory funnel. The layers were separated and the org/aq phase was extracted with DCM (3×200 mL). The combined organics were dried over anhydrous Na₂SO₄, filtered and concentrated in vacuo to provide 1.9 g of crude product.

B. To a solution of 4-((trimethylsilyl)oxy)chroman-4-carbonitrile (1.9 g, 7.68 mmol) in HCl (5.0 mL) and AcOH (5.0 mL) was added SnCl₂(H₂O)₂ (4.32 g, 19.2 mmol). The reaction was stirred at 80° C. for 24 h. water (40 mL) was added to the reaction vessel the org/aq phase was extracted with DCM (3×150 mL). The combined organics were dried over anhydrous Na₂SO₄, filtered and concentrated in vacuo. The resulting oil was purified by flash column chromatography with isocratic evolution of EtOAc (40%) and hex (60%) to provide chroman-4-carboxylic acid (1.2 g, 6.7 mmol) as a yellow oil.

C. To a solution of chroman-4-carboxylic acid (100 mg, 0.56 mmol) and 4-(4-fluorophenoxy)piperidine (110 mg, 0.56 mmol) in DCM (10.0 mL) was added 1-(3-dimethylaminopropyl)-3-ethylcarbodiimide hydrochloride (0.11 g, 0.56 mmol), N-Hydroxybenzotrizole (0.08 g, 0.56 mmol) and triethylamine (0.11 g, 1.12 mmol). The reaction was stirred at ambient temperature for 2 h. Water (20 mL) was added and then extracted with DCM (3×30 mL). The combined organics were washed with brine, dried over Na₂SO₄. After filtered and concentrated, the residue was purified by silica column chromatography (EtOAc:hexanes=1.5:1) to give the desired product (100 mg, 0.28 mmol) as colorless oil.

D. To a solution of chroman-4-yl(4-(4-fluorophenoxy)piperidin-1-yl)methanone (100 mg, 0.28 mmol) in THF (5 mL) was added LiAlH₄ (0.02 g, 0.56 mmol). The reaction was stirred at 25° C. for 2 h. One drop water and one drop 5 M NaOH were added. The mixture was stirred for 15 mins. The filtrate was concentrated in vacuo. The resulting oil was purified by flash column chromatography with a gradient elution of EtOAc (10%) and hexanes (90%) to EtOAc (30%) and hexanes (70%) to give 1-(chroman-4-ylmethyl)-4-(4-fluorophenoxy)piperidine (90 mg) as a colorless oil.

E. To a solution of 1-(chroman-4-ylmethyl)-4-(4-fluorophenoxy)piperidine (90 mg, 0.26 mmol) in methanol (2 mL) was added HCl/Et₂O (2 mL). The reaction was stirred at ambient temperature for 30 min. The solvent was evaporated to give the viscous oil. The resulting oil was resolved in CH₂Cl₂ (2 mL). And then Et₂O (5 mL) was added. Most of the solvent was sucked out. The remaining was evaporated to dry in vacuo to provide 1-(chroman-4-ylmethyl)-4-(4-fluorophenoxy)piperidine hydrochloride (75 mg, 0.2 mmol) as a white solid.

Example 171. Synthesis of 1-(2-(2,3-dihydro-1H-inden-1-yl)ethyl)-4-(4-fluorophenoxy)piperidine

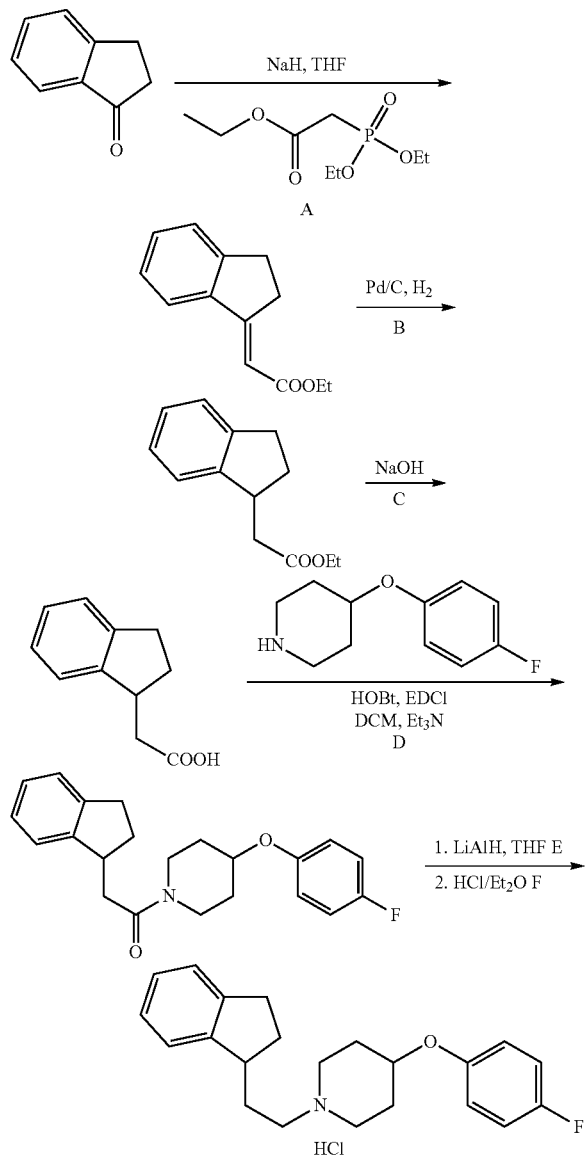

A. To a solution of sodium hydride (1.5 g, 11.35 mmol) in THF (50 mL) was added ethyl 2-(diethoxyphosphoryl)acetate (5.09 g, 22.7 mmol). The reaction was stirred at 0° C. temperature for 30 min. The 2,3-dihydro-1H-inden-1-one (1.5 g, 11.35 mmol) in THF (50 mL) was added to the above mixture. The reaction mixture was heated to 40° C. and stirred at that temperature for 2 h. TLC showed the SM was consumed. Saturated aqueous NH$_4$Cl (20 mL) was added to the reaction vessel and the mixture was extracted with EtOAc (3×30 mL). The combined organics were dried over anhydrous Na$_2$SO$_4$, filtered and concentrated in vacuo. The resulting oil was purified by flash column chromatography with a gradient elution of EtOAc (5%) and hexanes (95%) to EtOAc (15%) and hexanes (85%) to provide (E)-ethyl 2-(2,3-dihydro-1H-inden-1-ylidene)acetate (1.3 g, 6.43 mmol) as a colorless oil.

B. To a solution of (E)-ethyl 2-(2,3-dihydro-1H-inden-1-ylidene)acetate (1.3 g, 6.43 mmol) in CH$_3$OH (30 mL) was added Pd/C (0.15 g). The reaction was stirred at ambient temperature for 4 h under H$_2$. The reaction mixture was filtered and concentrated in vacuo. The resulting oil was purified by flash column chromatography with a gradient elution of hexanes (100%) to hexanes (90%) and EtOAc (10%) to provide ethyl 2-(2,3-dihydro-1H-inden-1-yl)acetate (1.2 g, 5.87 mmol) as a colorless oil.

C. To a solution of ethyl 2-(2,3-dihydro-1H-inden-1-yl) acetate (1.1 g, 5.39 mmol) in CH$_3$OH (20 mL) was added sodium hydroxide (0.65 g, 16.17 mmol) and H$_2$O (2 mL). The reaction mixture was heated to 40° C. and stirred at that temperature for 2 h then was concentrated in vacuo. 1M aqueous HCl (30 mL) was added to the reaction vessel and the resulting biphasic mixture was extracted with DCM (3×50 mL). The organic phase was washed with saturated aqueous NaCl (2×25 mL). The combined organics were dried over anhydrous Na$_2$SO$_4$, filtered and concentrated in vacuo to provide 2-(2,3-dihydro-1H-inden-1-yl)acetic acid (900 mg, 5.11 mmol) as a white solid.

D. To a solution of 2-(2,3-dihydro-1H-inden-1-yl)acetic acid (500 mg, 2.84 mmol) in DCM (30 mL) was added 4-(4-fluorophenoxy)piperidine (0.4 g, 2.03 mmol), triethylamine (0.62 g, 6.09 mmol) and HOBT (0.38 g 2.84 mmol) and EDCl (0.54 g 2.84 mmol). The reaction was stirred at ambient temperature for 2 h. Water (25 mL) and DCM (100 mL) were added to the reaction vessel and the resulting biphasic mixture was transferred to a separatory funnel. The layers were separated and the organic phase was washed with saturated aqueous NaCl (2×30 mL). The combined organics were dried over anhydrous Na$_2$SO$_4$, filtered and concentrated in vacuo to provide 2-(2,3-dihydro-1H-inden-1-yl)-1-(4-(4-fluorophenoxy)piperidin-1-yl)ethanone (0.7 g, 1.98 mmol) as a yellow oil.

E. To a solution of 2-(2,3-dihydro-1H-inden-1-yl)-1-(4-(4-fluorophenoxy)piperidin-1-yl)ethanone (350 mg, 0.99 mmol) in THF (20 mL) was added LiAlH$_4$ (80 mg, 1.98 mmol). The reaction was stirred at 25° C. for 1 h. 0.1 mL water and 0.2 mL 5 M NaOH were added. The mixture was stirred for 15 mins. The filtrate was concentrated in vacuo. The resulting oil was purified by flash column chromatography with a gradient elution of EtOAc (5%) and hexanes (95%) to EtOAc (15%) and hexanes (85%) to give 1-(2-(2,3-dihydro-1H-inden-1-yl)ethyl)-4-(4-fluorophenoxy)piperidine (300 mg, 085 mmol) as a colorless oil.

F. To a solution of 1-(2-(2,3-dihydro-1H-inden-1-yl)ethyl)-4-(4-fluorophenoxy)piperidine (300 mg, 085 mmol) in methanol (0.5 mL) was added HCl/Et$_2$O (10 mL). The reaction was stirred at ambient temperature for 30 min. The solvent was evaporated to give the viscous oil. The resulting oil was resolved in CH$_2$Cl$_2$ (0.5 mL). And then Et$_2$O (15 mL) was added. Most of the solvent was sucked out. The remaining was evaporated to dry in vacuo to 1-(2-(2,3-dihydro-1H-inden-1-yl)ethyl)-4-(4-fluorophenoxy)piperidine hydrochloride (280 mg, 082 mmol) as a white solid.

Example 175. Synthesis of 7-(2-(4-(4-fluorophenoxy)piperidin-1-yl)ethyl)-6,7-dihydro-5H-cyclopenta[b]pyridine

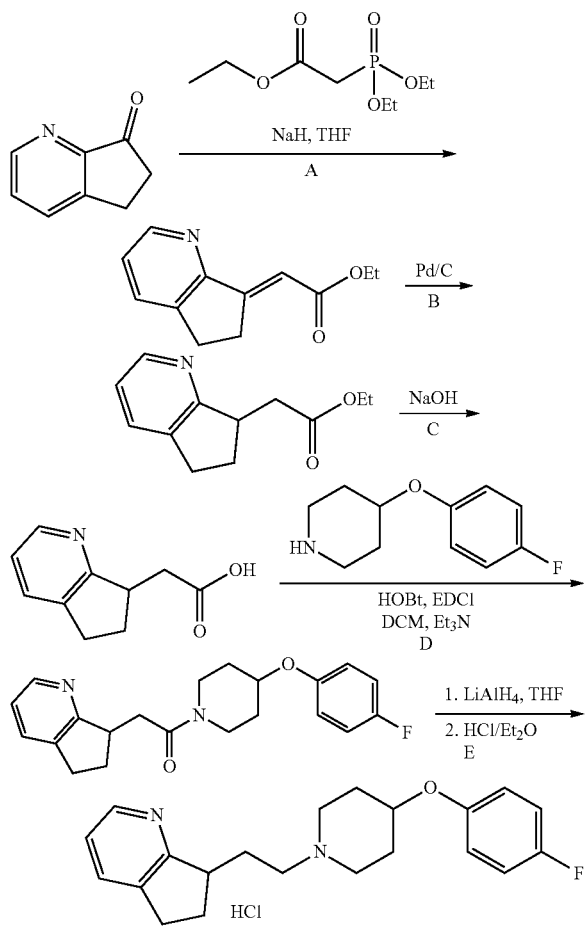

A. To a solution of sodium hydride (0.23 g, 5.64 mmol) in THF (8 mL) was added ethyl 2-(diethoxyphosphoryl)acetate (1.69 g, 7.52 mmol) in THF (1 mL) slowly at 0° C. under $N_2$. The mixture was stirred at ambient temperature for 30 min. Then 5H-cyclopenta[b]pyridin-7(6H)-one (500 mg, 3.76 mmol) in THF (10 mL) was added. The reaction was stirred at 50° C. for 2 h. Saturated aqueous $NH_4Cl$ (5 mL) was added to the reaction vessel and the resulting biphasic mixture was transferred to a separatory funnel. The layers were separated and the aqueous phase was extracted with EtOAc (2×15 mL). The combined organics were dried over anhydrous $Na_2SO_4$, filtered and concentrated in vacuo. The resulting oil was purified by flash column chromatography with a gradient elution of petroleum ether (90%) and EtOAc (10%) to petroleum ether (85%) and EtOAc (15%) to provide (Z)-ethyl 2-(5H-cyclopenta[b]pyridin-7(6H)-ylidene)acetate (0.32 g, 1.57 mmol) as a yellow oil.

B. To a solution of (Z)-ethyl 2-(5H-cyclopenta[b]pyridin-7(6H)-ylidene)acetate (1.1 g, 5.41 mmol) in $CH_3OH$ (30 mL) was added Pd/C (0.3 g). The reaction was stirred at ambient temperature for 12 h under $H_2$. The reaction mixture was filtered and concentrated in vacuo. The resulting oil was purified by flash column chromatography with a gradient elution of hexanes (100%) to hexanes (90%) and EtOAc (10%) to provide ethyl 2-(6,7-dihydro-5H-cyclopenta[b]pyridin-7-yl)acetate (1.1 g, 5.36 mmol) as a colorless oil.

C. To a solution of ethyl 2-(6,7-dihydro-5H-cyclopenta[b]pyridin-7-yl)acetate (1.1 g, 5.36 mmol) in $CH_3OH$ (10 mL) and $H_2O$ (3 mL) was added sodium hydroxide (0.64 g, 16.08 mmol). The reaction was stirred at ambient temperature for 8 h. Water (20 mL) was added to the reaction vessel and the resulting biphasic mixture was adjusted to pH=5. The layers were extracted with DCM (3×100 mL) and the organic phase was washed with saturated aqueous NaCl (2×30 mL). The combined organics were dried over anhydrous $Na_2SO_4$, filtered and concentrated in vacuo to provide 2-(6,7-dihydro-5H-cyclopenta[b]pyridin-7-yl)acetic acid (0.6 g, 3.39 mmol) as a yellow oil.

D. To a solution of 2-(6,7-dihydro-5H-cyclopenta[b]pyridin-7-yl)acetic acid (360 mg, 2.03 mmol) in DCM (30 mL) was added 4-(4-fluorophenoxy)piperidine (0.4 g, 2.03 mmol), triethylamine (0.62 g, 6.09 mmol) and HATU (1.54 g, 4.06 mmol). The reaction was stirred at ambient temperature for 2 h. Water (25 mL) and DCM (100 mL) were added to the reaction vessel and the resulting biphasic mixture was transferred to a separatory funnel. The layers were separated and the organic phase was washed with saturated aqueous NaCl (2×30 mL). The combined organics were dried over anhydrous $Na_2SO_4$, filtered and concentrated in vacuo to provide 2-(6,7-dihydro-5H-cyclopenta[b]pyridin-7-yl)-1-(4-(4-fluorophenoxy)piperidin-1-yl)ethanone (0.45 g, 1.27 mmol) as a yellow oil.

E. To a solution of 2-(6,7-dihydro-5H-cyclopenta[b]pyridin-7-yl)-1-(4-(4-fluorophenoxy)piperidin-1-yl)ethanone (450 mg, 1.27 mmol) in THF (15 mL) was added $LiAlH_4$ (0.14 g, 3.81 mmol). The reaction was stirred at ambient temperature for 10 min. 1M aqueous NaOH (5 mL) and DCM (100 mL) were added to the reaction vessel and the resulting biphasic mixture was transferred to a separatory funnel. The layers were separated and the organic phase was washed with saturated aqueous NaCl (2×10 mL). The combined organics were dried over anhydrous $Na_2SO_4$, filtered and concentrated in vacuo. The resulting oil was purified by flash column chromatography with a gradient elution of DCM (100%) to DCM (90%) and MeOH (10%) to provide 7-(2-(4-(4-fluorophenoxy)piperidin-1-yl)ethyl)-6,7-dihydro-5H-cyclopenta[b]pyridine (0.35 g, 1.03 mmol) as a yellow oil. $HCl/Et_2O$ (2 mL) was added to provide the product (370 mg) as a white solid.

Example 178. Synthesis of 1-(2-(2,3-dihydro-1H-inden-2-yl)ethyl)-4-(4-fluorophenoxy)piperidine

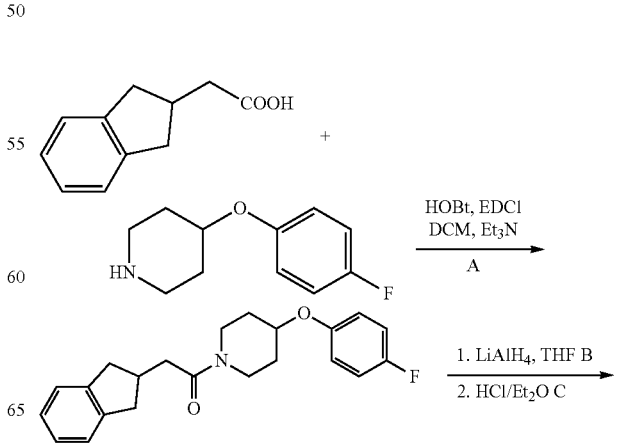

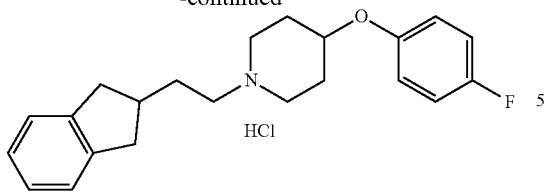

A. To a solution of 4-(4-fluorophenoxy)piperidine (100 mg, 0.512 mmol) in DCM (3 mL) was added 2-(2,3-dihydro-1H-inden-2-yl)acetic acid (0.09 g, 0.512 mmol), 1H-benzo[d][1,2,3]triazol-1-ol (0.069 g, 0.512 mmol), EDCI (0.197 g, 1.024 mmol) and triethylamine (0.155 g, 1.536 mmol). The reaction was stirred at ambient temperature for 16 h. Saturated aqueous NaCl (4 mL) and DCM (5 mL) was added to the reaction vessel and the resulting biphasic mixture was transferred to a separatory funnel. The layers were separated and the organic phase was washed with saturated aqueous NaCl (1×3 mL). The DCM was dried over anhydrous Na$_2$SO$_4$, filtered and concentrated in vacuo. The resulting oil was purified by flash column chromatography with a gradient elution of hexanes (90%) and EtOAc (10%) to hexanes (75%) and EtOAc (25%) to provide 2-(2,3-dihydro-1H-inden-2-yl)-1-(4-(4-fluorophenoxy)piperidin-1-yl)ethanone (120 mg, 0.34 mmol) as a colorless oil.

B. To a solution of 2-(2,3-dihydro-1H-inden-2-yl)-1-(4-(4-fluorophenoxy)piperidin-1-yl)ethanone (120 mg, 0.3395 mmol) in THF (3 mL) was added AlH$_4$Li (0.0258 g, 0.679 mmol) slowly at 0° C. The reaction was stirred at ambient temperature for 30 min. H$_2$O (40 uL) and aq. NaOH (20%) (30 uL) was added. The mixture solution was filtered. The filtrate was dried over anhydrous Na$_2$SO$_4$, filtered and concentrated in vacuo. The resulting oil was purified by flash column chromatography with a gradient elution of DCM (99%) and MeOH (1%) to DCM (98%) and MeOH (2%) to provide 1-(2-(2,3-dihydro-1H-inden-2-yl)ethyl)-4-(4-fluorophenoxy)piperidine (110 mg, 0.3241 mmol) as a colorless oil.

C. To a solution of 1-(2-(2,3-dihydro-1H-inden-2-yl)ethyl)-4-(4-fluorophenoxy)piperidine (110 mg, 0.3241 mmol) in DCM (0.5 mL) was added HCl-Et$_2$O (2 mL). The reaction was stirred at ambient temperature for 5 min. The mixture solution was concentrated and washed with Et$_2$O (5 mL). The resulting solid was concentrated to provide 1-(2-(2,3-dihydro-1H-inden-2-yl)ethyl)-4-(4-fluorophenoxy)piperidine hydrochloride (100 mg, 0.266 mmol) as a white solid.

Example 179. Synthesis of 1-(2-(isochroman-4-yl)ethyl)-4-phenoxypiperidine

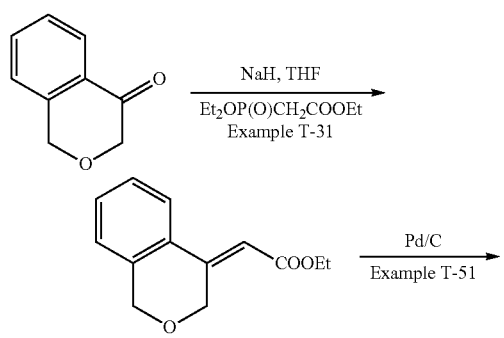

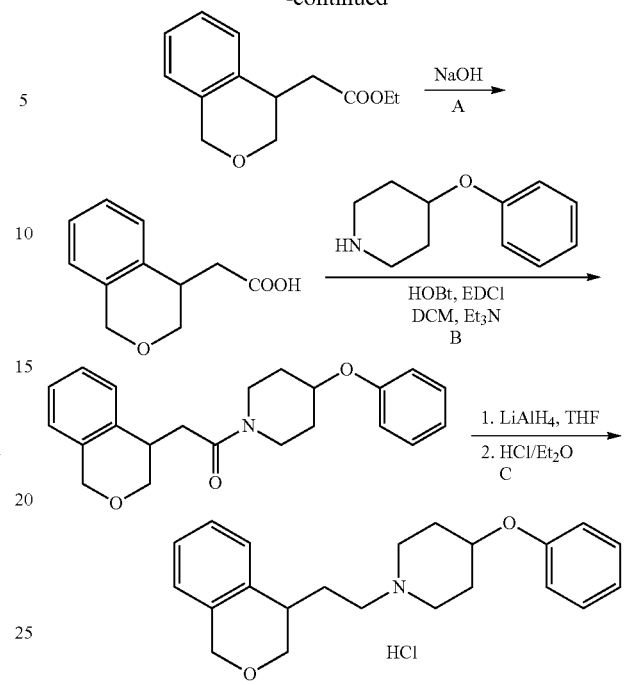

A. To a solution of ethyl 2-(isochroman-4-yl)acetate (500 mg, 2.27 mmol, see Examples T-31 and T-51) in MeOH (30 mL) was added sodium hydroxide (0.13 g, 3.18 mmol). The reaction was stirred at 65° C. for 2 h. The solvent was then distilled off under reduced pressure. 0.1M aqueous HCl (40 mL) was added to the reaction vessel. The aqueous phase was extracted with EtOAc (3×200 mL). The combined organics were dried over anhydrous Na$_2$SO$_4$, filtered and concentrated in vacuo. The resulting oil was purified by flash column chromatography with EtOAc (40%) and hexanes (60%) to provide 2-(isochroman-4-yl)acetic acid (190 mg) as a yellow oil.

B. To a solution of 2-(isochroman-4-yl)acetic acid (120 mg, 0.62 mmol) in DCM (20 mL) was added triethylamine (0.19 g, 1.86 mmol), 4-phenoxypiperidine (0.11 g, 0.62 mmol) and EDCI (0.24 g, 1.24 mmol). The reaction was stirred at ambient temperature for 5 h. Water (20 mL) was added to the reaction vessel and the resulting biphasic mixture was extracted with DCM (3×50 mL). The organic phase was washed with saturated aqueous NaCl (2×20 mL). The combined organics were dried over anhydrous Na$_2$SO$_4$, filtered and concentrated in vacuo to provide 2-(isochroman-4-yl)-1-(4-phenoxypiperidin-1-yl)ethanone (100 mg) as a yellow oil.

C. To a solution of 2-(isochroman-4-yl)-1-(4-phenoxypiperidin-1-yl)ethanone (190 mg, 0.54 mmol) in THF (5 mL) was added LiAlH$_4$ (0.08 g, 2.16 mmol). The reaction was stirred at room temperature for 30 min. saturated aqueous NH$_4$Cl (25 mL) was added to the reaction vessel and the resulting biphasic mixture was transferred to a separatory funnel. The layers were separated and the org/aq phase was extracted with EtOAc (3×150 mL). The combined organics were dried over anhydrous Na$_2$SO$_4$, filtered and concentrated in vacuo. The resulting oil was purified by flash column chromatography with DCM (95%) and MeOH (5%) to provide 1-(2-(isochroman-4-yl)ethyl)-4-phenoxypiperidine (120 mg) as a yellow oil. Converted to HCl salt with HCl/Et$_2$O.

Example 194. Synthesis of 2-(2-(4-(3-chlorophenoxy)piperidin-1-yl)ethyl)-3,4-dihydroisoquinolin-1(2H)-one

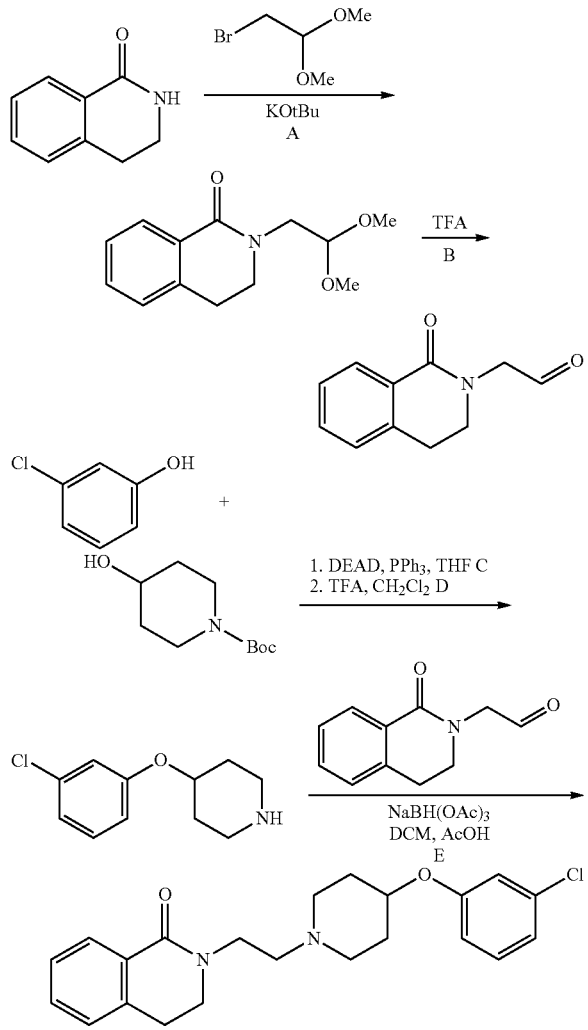

A. To a solution of 3,4-dihydroisoquinolin-1(2H)-one (5.00 g, 33.97 mmol), t-Bu-OK (5.72 g, 50.96 mmol) and TBAB (5.48 g, 16.99 mmol) in THF/DMF (30/5 mL) was added 2-bromo-1,1-dimethoxyethane (11.48 g, 67.94 mmol). The reaction mixture was heated to 70° C. and stirred at that temperature overnight. TLC showed 20% of the starting material was still remained. 2-bromo-1,1-dimethoxyethane (3.0 g) was added to the mixture. The reaction was stirred for another 6 h at 70° C. TLC showed about 10~20% of starting material was still remained. The reaction mixture was treated with H$_2$O (30 mL). The aqueous layer was extracted with EtOAc (3×30 mL). The combined organic layers were washed with brine, dried over Na$_2$SO$_4$, filtered and concentrated in vacuo. The resulting oil was purified by column chromatography (hexanes:EtOAc=6:1) to provide the desired product (5.00 g) as a yellow oil.

B. To a solution of 2-(2,2-dimethoxyethyl)-3,4-dihydroisoquinolin-1(2H)-one (2.5 g, 10.6257 mmol) in DCM (10 mL) was added TFA (6.0577 g, 53.1285 mmol). The reaction was stirred at ambient temperature for 12 h. saturated aqueous Na$_2$CO$_3$ (40 mL) was added to the reaction vessel and the resulting biphasic mixture was transferred to a separatory funnel. The layers were separated and the aqueous phase was extracted with DCM (3×30 mL). The combined organics were dried over anhydrous Na$_2$SO$_4$, filtered and concentrated in vacuo. The resulting oil was purified by flash column chromatography with a gradient elution of hex (95%) and EtOAc (5%) to hexanes (85%) and EtOAc (15%) to provide 2-(1-oxo-3,4-dihydroisoquinolin-2(1H)-yl)acetaldehyde (1.2 g, 6.3421 mmol) as a colorless oil.

C. To a solution of 3-chlorophenol (2 g, 15.56 mmol) in THF (15 mL) was added triphenylphosphine (4.49 g, 17.12 mmol), DEAD (3.52 g, 20.23 mmol) and tert-butyl 4-hydroxypiperidine-1-carboxylate (4.07 g, 20.23 mmol). The reaction mixture was heated to 55° C. and stirred at that temperature for 12 h. After concentrated, the residue was directly purified by silica column chromatography (EtOAc:Hexanes=1:80~1:20) to provide product of tert-butyl 4-(3-chlorophenoxy)piperidine-1-carboxylate (4 g).

D. The product was dissolved in DCM (20 mL) and added TFA (4 mL). The reaction was stirred at ambient temperature for 1 h. Saturated Na$_2$CO$_3$ aqueous solution (20 mL) and water (20 mL) was added to the reaction vessel and the mixture was extracted with DCM (3×50 mL). The combined organics were dried over anhydrous Na$_2$SO$_4$, filtered and concentrated in vacuo. The resulting oil was purified by flash column chromatography with a gradient elution of DCM (99%) and MeOH (1%) to DCM (95%) and MeOH (5%) to provide 4-(3-chlorophenoxy)piperidine (3 g) as a yellow solid.

E. To a solution of 4-(3-chlorophenoxy)piperidine (250 mg, 1.18 mmol) in DCM (15 mL) was added 2-(1-oxo-3,4-dihydroisoquinolin-2(1H)-yl)acetaldehyde (250 mg, 1.3 mmol), acetic acid (0.07 g, 1.18 mmol). The reaction was stirred at ambient temperature for 30 min. NaBH(OAc)$_3$ (500 mg, 2.36 mmol) was added to the mixture. The reaction was stirred at ambient temperature for 1 h. Water (30 mL) and saturated Na$_2$CO$_3$ aqueous solution (10 mL) were added to the reaction vessel. Then the mixture was extracted with DCM (3×40 mL). The combined organics was washed with brine and dried over anhydrous Na$_2$SO$_4$, filtered and concentrated in vacuo. The resulting oil was purified by silica column chromatography (DCM:CH$_3$OH=200:1~80:1) to give the desired product (213 mg, 0.55 mmol) as pale yellow oil.

Example 209. Synthesis of 8-chloro-2-(2-(4-(4-fluorophenoxy)piperidin-1-yl)ethyl)-2,3,4,5-tetrahydro-1H-benzo[c]azepin-1-one

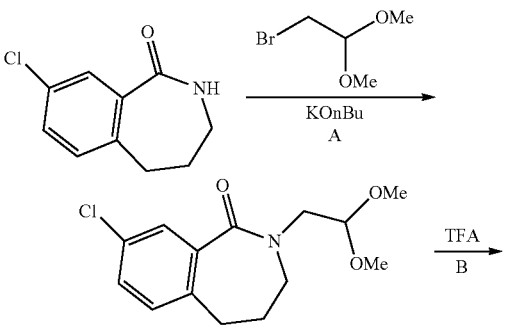

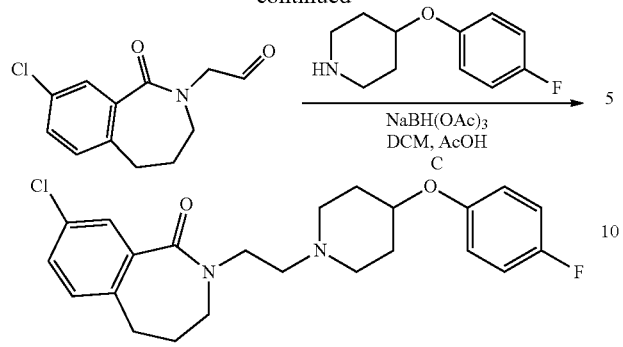

A. To a solution of 8-chloro-2,3,4,5-tetrahydro-1H-benzo[c]azepin-1-one (630 mg, 3.22 mmol) in DMF (10 mL) was added 2-bromo-1,1-dimethoxyethane (1.088 g, 6.44 mmol), potassium butan-1-olate (1.084 g, 9.66 mmol) and TBAB (0.311 g, 0.966 mmol). The reaction mixture was heated to 150° C. and stirred at that temperature for 20 h. TLC showed that starting material was consumed completely and a new major spot was found. H₂O was added and the mixture solution was extracted by EtOAc (30 mL×3). Then combined the organic layers were washed with H₂O (12 mL), dried over Na₂SO₄, concentrated and purified by silica gel chromatography eluted with hexanes:EtOAc=5:1 to give 580 mg of product.

B. A solution of 8-chloro-2-(2,2-dimethoxyethyl)-2,3,4,5-tetrahydro-1H-benzo[c]azepin-1-one (580 g, 2044.048 mmol) in TFA/DCM (2 mL/3 mL) was stirred at ambient temperature for 2 h. TLC showed that SM was consumed completely. The mixture solution was concentrated and H₂O was added. The aqueous solution was basified with sat. Na₂CO₃ till pH=8 and extracted by EtOAc (25 mL×3). Combined the organic layers were dried over Na₂SO₄, concentrated and purified by chromatography eluted with hexanes:EtOAc=3:1 to 1:1 to give 400 mg of product.

C. To a solution of 4-(4-fluorophenoxy)piperidine (200 mg, 1.024 mmol) in DCM (5 mL) was added 2-(8-chloro-1-oxo-4,5-dihydro-1H-benzo[c]azepin-2(3H)-yl)acetaldehyde (0.254 g, 1.07 mmol) and acetic acid (0.061 g, 1.019 mmol). The solution was stirred at room temperature for 20 min. Then NaBH(AcO)₃ (0.54 g, 2.547 mmol) was added. The reaction was stirred at ambient temperature for 2 h. Water (10 mL) was added to the reaction vessel and the resulting biphasic mixture was transferred to a separatory funnel. The layers were separated and the aqueous phase was extracted with DCM (3×20 mL). The combined organics were dried over anhydrous Na₂SO₄, filtered and concentrated in vacuo. The residue was purified by silica gel chromatography eluted with DCM:MeOH=100:1 to 60:1 to give 200 mg of crude product. The crude product was dissolved in HCl-Et₂O (20 mL) and stirred at room temperature for 10 min. The mixture solution was concentrated. The residue was washed with Et₂O (15 mL). The HCl solid was dissolved in DCM and basified with sat. Na₂CO₃. The mixture solution was transferred to a separatory funnel. The layers were separated and the aqueous phase was extracted with DCM (2×5 mL). The combined organics were dried over anhydrous Na₂SO₄, filtered and concentrated to give 180 mg of product.

Example 213. Synthesis of 7-bromo-2-(2-(4-(4-fluorophenoxy)piperidin-1-yl)ethyl)-2,3,4,5-tetrahydro-1H-benzo[c]azepin-1-one

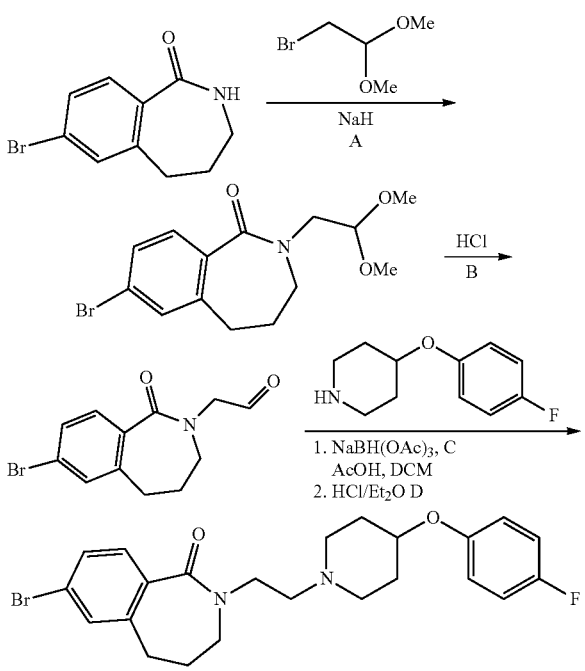

A. To a solution of 7-bromo-2,3,4,5-tetrahydro-1H-benzo[c]azepin-1-one (200 mg, 0.83 mmol) in DMF (6 mL) was added 2-bromo-1,1-dimethoxyethane (0.28 g, 1.66 mmol) and sodium hydride (0.08 g, 3.32 mmol). The reaction mixture was heated to 40° C. and stirred at that temperature for 16 h. Water (20 mL) was added to the reaction vessel and was extracted with EtOAc (3×20 ml). The layers were separated and the organic phase was washed with saturated aqueous NaCl (2×20 mL). The combined organics were dried over anhdrous Na₂SO₄, filtered and concentrated in vacuo. After concentration, give the desired product (190 mg) as a yellow oil.

B. To a solution of 7-bromo-2-(2,2-dimethoxyethyl)-2,3,4,5-tetrahydro-1H-benzo[c]azepin-1-one (190 mg, 0.58 mmol) in THF (4 mL) was added hydrogen chloride (4 mL). The reaction was stirred at ambient temperature for 15 min. Water (20 mL) was added to the reaction vessel and was extracted with EtOAc (3×20 ml). The layers were separated and the organic phase was washed with saturated aqueous NaCl (2×20 mL). The combined organics were dried over anhdrous Na₂SO₄, filtered and concentrated in vacuo. After concentrated, give the desired product (140 mg) as a yellow oil.

C. To a solution of 2-(7-bromo-1-oxo-4,5-dihydro-1H-benzo[c]azepin-2(3H)-yl)acetaldehyde (140 mg, 0.5 mmol) in DCM (10 mL) was added 4-(4-fluorophenoxy)piperidine (0.12 g, 0.6 mmol), acetic acid (0.03 g, 0.5 mmol) and sodium triacetoxyborohydride (0.21 g, 1 mmol). The reaction was stirred at ambient temperature for 1 h. Water (20 mL) was added to the reaction vessel and was extracted with DCM (3×15 ml). The layers were separated and the organic phase was washed with saturated aqueous NaCl (2×15 mL). The combined organics were dried over anhdrous Na₂SO₄, filtered and concentrated in vacuo. After concentration, the residue was purified by silica column chromatography (Hexane:EtOAc=1:3) to give the desired product (150 mg) as a yellow oil.

D. To a solution of 7-bromo-2-(2-(4-(4-fluorophenoxy) piperidin-1-yl)ethyl)-2,3,4,5-tetrahydro-1H-benzo[c]azepin-1-one (150 mg, 0.33 mmol) in HCl/Et$_2$O (3 ml). The reaction was stirred at ambient temperature for 10 min. The solvent was evaporated to give the viscous oil. The resulting oil was dissolve in MeOH (0.01 g, 0.18 mmol) and Et$_2$O (4 ml). Most of the solvent was sucked out. The remaining was evaporated to dry in vacuo to provide 7-bromo-2-(2-(4-(4-fluorophenoxy)piperidin-1-yl)ethyl)-2,3,4,5-tetrahydro-1H-benzo[c]azepin-1-one hydrochloride (140 mg) as a white solid.

Example 242. Synthesis of 1-((6-methoxy-2,3-dihydro-1H-inden-1-yl)methyl)-4-((2-methylbenzyl)oxy)piperidine

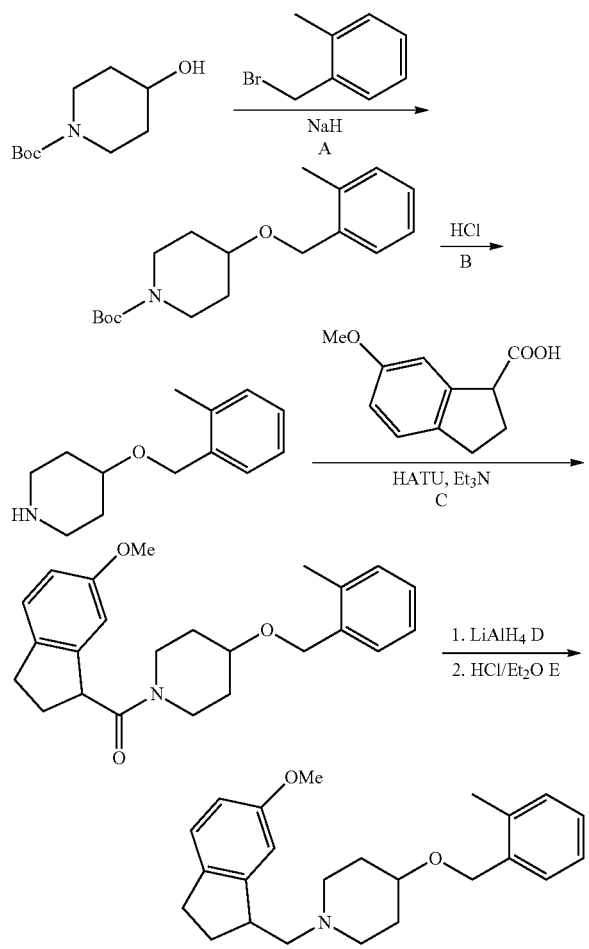

A. To a solution of tert-butyl 4-hydroxypiperidine-1-carboxylate (250 mg, 1.2422 mmol) in THF (10 mL) was added sodium hydride (0.1242 g, 3.1055 mmol) and 1-(bromomethyl)-2-methylbenzene (0.2529 g, 1.3664 mmol). The reaction was stirred at 60° C. for 12 h. Water (30 mL) was added to the reaction vessel and the resulting biphasic mixture was transferred to a separatory funnel. The layers were separated and the aqueous phase was extracted with EtOAc (3×20 mL). The combined organics were dried over anhydrous Na$_2$SO$_4$, filtered and concentrated in vacuo. The crude product 350 mg was used for the next step without purification.

B. To a solution of tert-butyl 4-((2-methylbenzyl)oxy) piperidine-1-carboxylate (350 mg, 0.9168 mmol) in THF (10 mL) was added 6 N HCl 10 mL. The reaction was stirred at 60° C. for 3 h. Saturated aqueous Na$_2$CO$_3$ (20 mL) was added to the reaction vessel and the resulting biphasic mixture was transferred to a separatory funnel. The layers were separated and the aqueous phase was extracted with EtOAc (3×15 mL). The combined organics were dried over anhydrous Na$_2$SO$_4$, filtered and concentrated in vacuo. The crude product 150 mg was used for the next step without purification.

C. To a solution of 6-methoxy-2,3-dihydro-1H-indene-1-carboxylic acid (200 mg, 1.0405 mmol) in DCM (20 mL) was added 4-((2-methylbenzyl)oxy)piperidine (0.2136 g, 1.0405 mmol), HATU (0.3762 g, 1.5608 mmol) and triethylamine (0.3159 g, 3.1215 mmol). The reaction was stirred at ambient temperature for 12 h. Saturated aqueous NH$_4$Cl (20 mL) was added to the reaction vessel and the resulting biphasic mixture was transferred to a separatory funnel. The layers were separated and the aqueous phase was extracted with DCM (3×20 mL). The combined organics were dried over anhydrous Na$_2$SO$_4$, filtered and concentrated in vacuo. The crude product was used for the next step without purification.

D. To a solution of (6-methoxy-2,3-dihydro-1H-inden-1-yl)(4-((2-methylbenzyl)oxy)piperidin-1-yl)methanone (350 mg, 0.9223 mmol) in THF (20 mL) was added LiAlH$_4$ (0.2721 g, 3.6892 mmol). The reaction was stirred at ambient temperature for 2 h. After the reaction mixture was cooled to 0° C., the reaction mixture was quenched by addition of 0.27 mL of H$_2$O, followed by 0.27 mL of 15% aqueous NaOH. After stirring at room temperature for 15 min, the solid was removed by filtration. The filtrate was concentrated to dryness to give crude product. The resulting oil was purified by flash column chromatography with a gradient elution of hexanes (90%) and EtOAc (10%) to hexanes (60%) and EtOAc (40%) to provide 1-((6-methoxy-2,3-dihydro-1H-inden-1-yl)methyl)-4-((2-methylbenzyl)oxy)piperidine (0.0637 g, 0.1743 mmol) as a colorless oil.

E. To a solution of 1-((6-methoxy-2,3-dihydro-1H-inden-1-yl)methyl)-4-((2-methylbenzyl)oxy)piperidine (0.0637 g, 0.1743 mmol) in CH$_2$Cl$_2$ (10 mL) was added HCl/Et$_2$O (10 mL). The reaction was stirred at ambient temperature for 30 min. The reaction mixture was concentrated in vacuo to provide 1-((6-methoxy-2,3-dihydro-1H-inden-1-yl)methyl)-4-(2-methylbenzyloxy)piperidine hydrochloride (65 mg, 0.1621 mmol).

Example 247. Synthesis of 4-((4-fluorobenzyl)oxy)-1-((6-methoxy-2,3-dihydro-1H-inden-1-yl)methyl) piperidine

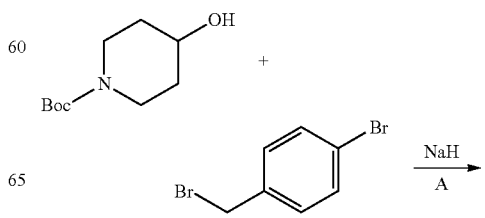

-continued

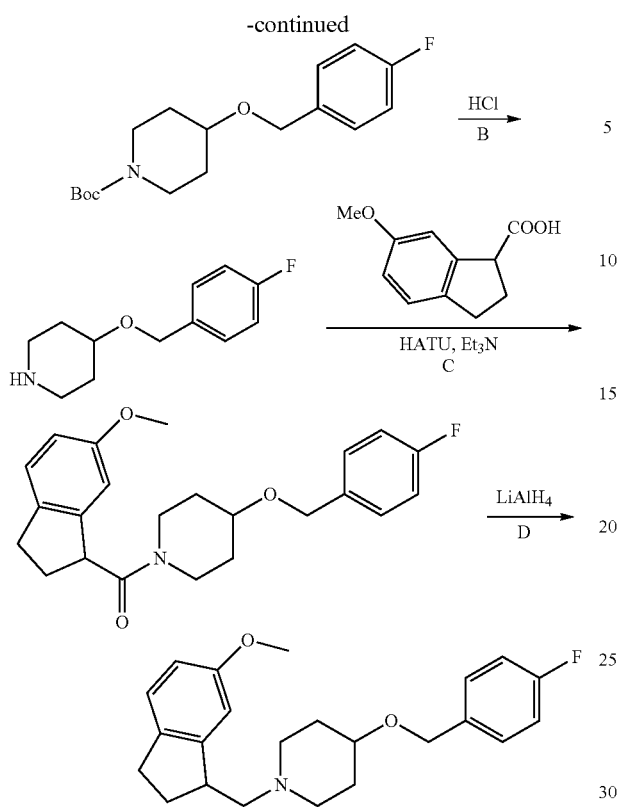

A. To a solution of tert-butyl 4-hydroxypiperidine-1-carboxylate (600 mg, 2.9812 mmol) in THF (10 mL) was added sodium hydride (0.2385 g, 5.9624 mmol) and 1-(bromomethyl)-4-fluorobenzene (0.6199 g, 3.2793 mmol). The reaction was stirred at 60° C. for 1 h. Water (20 mL) and EtOAc (100 mL) were added to the reaction vessel and the resulting biphasic mixture was transferred to a separatory funnel. The layers were separated and the organic phase was washed with saturated aqueous NaCl (2×20 mL). The combined organics were dried over anhydrous $Na_2SO_4$, filtered and concentrated in vacuo.

The resulting oil was purified by flash column chromatography with a gradient elution of hexanes (100%) to hexanes (80%) and EtOAc (20%) to provide tert-butyl 4-((4-fluorobenzyl)oxy)piperidine-1-carboxylate (0.8 g, 2.5859 mmol) as a colorless oil.

B. To a solution of tert-butyl 4-((4-fluorobenzyl)oxy)piperidine-1-carboxylate (800 mg, 2.59 mmol) in THF (2 mL) was added con hydrogen chloride (2 mL). The reaction was stirred at ambient temperature for 1 h. Saturated aqueous $NaHCO_3$ (30 mL) and DCM (200 mL) were added to the reaction vessel and the resulting biphasic mixture was transferred to a separatory funnel. The layers were separated and the organic phase was washed with saturated aqueous NaCl (2×20 mL). The combined organics were dried over anhydrous $Na_2SO_4$, filtered and concentrated in vacuo to provide 4-((4-fluorobenzyl)oxy)piperidine (0.5 g, 2.39 mmol) as a green oil.

C. To a solution of 4-((4-fluorobenzyl)oxy)piperidine (60 mg, 0.2867 mmol) in DCM (20 mL) was added 6-methoxy-2,3-dihydro-1H-indene-1-carboxylic acid (0.0551 g, 0.2867 mmol), HBTU (0.087 g, 0.344 mmol) and $Et_3N$ (0.0579 g, 0.5734 mmol). The reaction was stirred at ambient temperature for 12 h. 0.1M aqueous HCl (20 mL) and DCM (100 mL) were added to the reaction vessel and the resulting biphasic mixture was transferred to a separatory funnel. The layers were separated and the organic phase was extracted with saturated aqueous NaCl (2×20 mL). The combined organics were dried over anhydrous $Na_2SO_4$, filtered and concentrated in vacuo to provide (4-((4-fluorobenzyl)oxy)piperidin-1-yl)(6-methoxy-2,3-dihydro-1H-inden-1-yl)methanone (0.08 g, 0.2086 mmol) as a yellow oil.

D. To a solution of (4-((4-fluorobenzyl)oxy)piperidin-1-yl)(6-methoxy-2,3-dihydro-1H-inden-1-yl)methanone (160 mg, 0.42 mmol) in THF (10 mL) was added $LiAlH_4$ (0.08 g, 2.1 mmol). The reaction was stirred at ambient temperature for 10 min. 1M aqueous NaOH (10 mL) and DCM (100 mL) were added to the reaction vessel and the resulting biphasic mixture was transferred to a separatory funnel. The layers were separated and the organic phase was washed with saturated aqueous NaCl (2×20 mL). The combined organics were dried over anhydrous $Na_2SO_4$, filtered and concentrated in vacuo. The resulting oil was purified by preparative thin layer chromatography with an isocratic elution of hex (55%) and EtOAc (45%) to provide 4-((4-fluorobenzyl)oxy)-1-((6-methoxy-2,3-dihydro-1H-inden-1-yl)methyl)piperidine (0.11 g, 0.31 mmol) as a yellow solid.

Example 249. Synthesis of 1-(chroman-4-ylmethyl)-4-((4-fluorobenzyl)oxy)piperidine

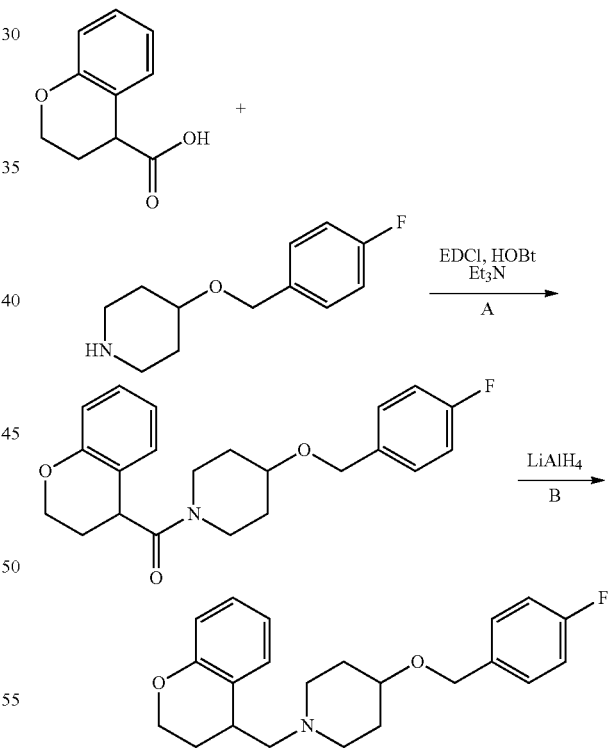

A. To a solution of chroman-4-carboxylic acid (100 mg, 0.56 mmol) in DCM (10 mL) was added 4-((4-fluorobenzyl)oxy)piperidine (0.13 g, 0.62 mmol), triethylamine (0.11 g, 1.12 mmol), HOBT (0.03 g, 1.12 mmol) and EDCI (0.2 g, 1.12 mmol). The reaction was stirred at ambient temperature for 3 h. Saturated aqueous $NaHCO_3$ (20 mL) and DCM (100 mL) were added to the reaction vessel and the resulting biphasic mixture was transferred to a separatory funnel. The layers were separated and the organic phase was washed with saturated aqueous NaCl (2×20 mL). The combined organics were dried over anhydrous Na$_2$SO$_4$, filtered and concentrated in vacuo to provide chroman-4-yl(4-((4-fluorobenzyl)oxy)piperidin-1-yl)methanone (0.16 g, 0.43 mmol) as a yellow oil.

B. To a solution of chroman-4-yl(4-((4-fluorobenzyl)oxy)piperidin-1-yl)methanone (160 mg, 0.43 mmol) in THF (10 mL) was added LiAlH$_4$ (0.08 g, 2.15 mmol). The reaction was stirred at ambient temperature for 10 min. 1M aqueous NaOH (10 mL) and DCM (100 mL) were added to the reaction vessel and the resulting biphasic mixture was transferred to a separatory funnel. The layers were separated and the organic phase was washed with saturated aqueous NaCl (2×20 mL). The combined organics were dried over anhydrous Na$_2$SO$_4$, filtered and concentrated in vacuo. The resulting oil was purified by preparative thin layer chromatography with an isocratic elution of hexanes (55%) and EtOAc (45%) to provide 1-(chroman-4-ylmethyl)-4-((4-fluorobenzyl)oxy)piperidine (0.11 g, 0.32 mmol) as a colorless oil.

Example 250. Synthesis of 4-fluoro-N-(1-((6-methoxy-2,3-dihydro-1H-inden-1-yl)methyl)piperidin-4-yl)benzenesulfonamide

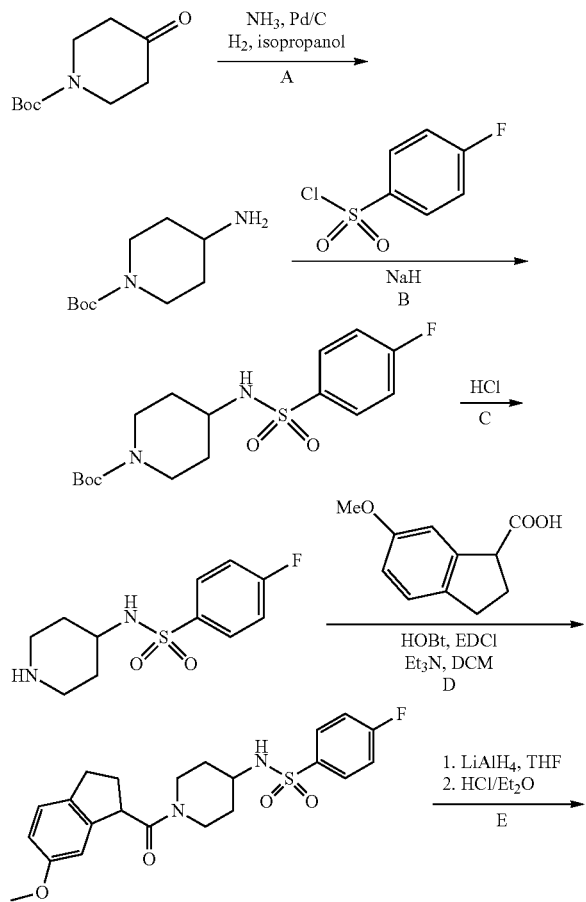

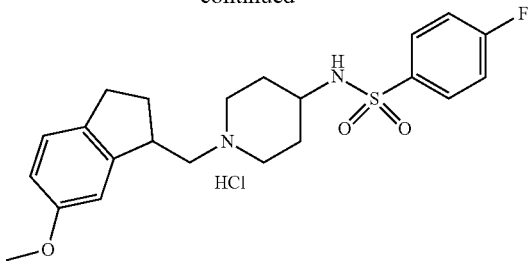

A. To a solution of tert-butyl 4-oxopiperidine-1-carboxylate (200 mg, 1.0038 mmol) in NH$_3$/isopropanol (10 mL) was added Pd/C (15 mg). The reaction was stirred at ambient temperature for 16 h under H$_2$. The reaction was filtered and concentrated to provide tert-butyl 4-aminopiperidine-1-carboxylate (0.2 g, 0.9986 mmol) as a yellow oil.

B. To a solution of tert-butyl 4-aminopiperidine-1-carboxylate (200 mg, 0.999 mmol) in DCM (3 mL) was added 4-fluorobenzene-1-sulfonyl chloride (0.214 g, 1.099 mmol). Then triethylamine (0.253 g, 2.498 mmol) was added slowly at 0° C. under N$_2$. The reaction was stirred at ambient temperature for 30 min. The mixture solution was concentrated. The resulting oil was purified by flash column chromatography with a gradient elution of petroleum ether (85%) and EtOAc (15%) to petroleum ether (75%) and EtOAc (25%) to provide tert-butyl 4-(4-fluorophenylsulfonamido)piperidine-1-carboxylate (0.25 g, 0.697 mmol) as a yellow oil.

C. To a solution of tert-butyl 4-(4-fluorophenylsulfonamido)piperidine-1-carboxylate (250 mg, 0.6975 mmol) in DCM (3 mL) was added HCl-Et$_2$O (5 mL). The reaction was stirred at ambient temperature for 24 h. The mixture solution was concentrated, washed with Et$_2$O (5 mL) and concentrated to provide 4-fluoro-N-(piperidin-4-yl)benzenesulfonamide (150 mg, 0.5807 mmol) as a yellow solid.

D. To a solution of 6-methoxy-2,3-dihydro-1H-indene-1-carboxylic acid (100 mg, 0.52 mmol) in DCM (2 mL) was added 4-fluoro-N-(piperidin-4-yl)benzenesulfonamide (0.134 g, 0.52 mmol), 1H-benzo[d][1,2,3]triazol-1-ol (0.07 g, 0.52 mmol), triethylamine (0.158 g, 1.56 mmol) and EDCI (0.2 g, 1.04 mmol). The reaction was stirred at ambient temperature for 16 h. Water (5 mL) and DCM (5 mL) was added to the reaction vessel and the resulting biphasic mixture was transferred to a separatory funnel. The layers were separated and the aqueous phase was extracted with DCM (2×5 mL). The organics were dried over anhydrous Na$_2$SO$_4$, filtered and concentrated in vacuo. The resulting oil was purified by flash column chromatography with a gradient elution of EtOAc (35%) and petroleum ether (65%) to EtOAc (55%) and petroleum ether (45%) to provide 4-fluoro-N-(1-(6-methoxy-2,3-dihydro-1H-indene-1-carbonyl)piperidin-4-yl)benzenesulfonamide (0.1 g, 0.23 mmol) as a yellow oil.

E. To a solution of 4-fluoro-N-(1-(6-methoxy-2,3-dihydro-1H-indene-1-carbonyl)piperidin-4-yl)benzenesulfonamide (100 mg, 0.2312 mmol) in THF (2 mL) was added LiAlH$_4$ (0.0176 g, 0.4624 mmol) at 0° C. The reaction was stirred at 0° C. for 1 h. H$_2$O (20 uL) and aq. NaOH (20%) (20 uL) was added. The mixture solution was filtered. The filtrate was dried over anhydrous Na$_2$SO$_4$, filtered and concentrated in vacuo. The resulting oil was purified by flash column chromatography with a gradient elution of petroleum ether (85%) and EtOAc (15%) to petroleum ether (70%) and EtOAc (30%) to provide 4-fluoro-N-(1-((6- methoxy-2,3-dihydro-1H-inden-1-yl)methyl)piperidin-4-yl) benzenesulfonamide (0.0585 g, 0.1398 mmol) as a yellow oil. The oil was dissolved in DCM (0.5 mL) and HCl-Et$_2$O (2 mL) was added. The mixture was stirred for 2 min, and then concentrated to give 60 mg of product.

Example 254. Synthesis of (3S)-1-((2,3-dihydro-1H-inden-1-yl)methyl)-3-(4-fluorophenoxy)piperidine

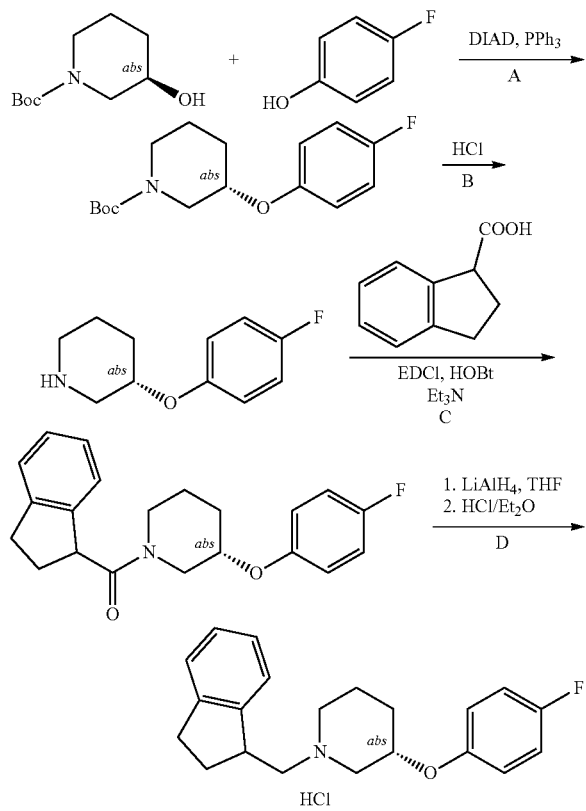

A. To a solution of (R)-tert-butyl 3-hydroxypiperidine-1-carboxylate (3 g, 14.91 mmol) in THF (30 mL) was added 4-fluorophenol (1.67 g, 14.91 mmol) and triphenylphosphine (3.91 g, 14.91 mmol). DIAD (3.01 g, 14.91 mole) was added dropwise at 0° C. under N$_2$. Then the reaction was stirred at room temperature for 12 h. The solvent was then distilled off under reduced pressure. The residue was purified by silica gel column chromatography (hexane:ethyl acetate=10:1) to provide the product 2.4 g as yellow oil.

B. To a solution of (S)-tert-butyl 3-(4-fluorophenoxy) piperidine-1-carboxylate (2.4 g, 8.13 mmol) in THF (15 mL) was added hydrogen chloride (6 N, 15 ml). The reaction was stirred at room temperature for 5 h. 1M aqueous NaOH (10 mL) was added to the reaction vessel and the resulting biphasic mixture was transferred to a separatory funnel. The layers were separated and the organic phase was extracted with DCM (3×100 mL). The combined organics were dried over anhydrous Na$_2$SO$_4$, filtered and concentrated in vacuo. The resulting oil was purified by flash column chromatography (hexanes:EtOAc=10:1) to provide (S)-3-(4-fluorophenoxy)piperidine (890 mg) as a yellow oil.

C. To a solution of 2,3-dihydro-1H-indene-1-carboxylic acid (100 mg, 0.62 mmol) in DCM (20 mL) was added HOBT (0.04 g, 1.24 mmol), and triethylamine (0.16 g, 1.55 mmol). The reaction was stirred at room temperature for 4 h. Water (30 mL) was added to the reaction vessel and was extracted with DCM (3×125 mL). The combined organics were dried over anhydrous Na$_2$SO$_4$, filtered and concentrated in vacuo. The resulting oil was purified by flash column chromatography with hexanes (70%) and EtOAc (30%) to provide (2,3-dihydro-1H-inden-1-yl)((S)-3-(4-fluorophenoxy)piperidin-1-yl)methanone (150 mg) as a yellow oil.

D. To a solution of (2,3-dihydro-1H-inden-1-yl)((S)-3-(4-fluorophenoxy)piperidin-1-yl)methanone (150 mg, 0.44 mmol) in THF (10 mL) was added LiAlH$_4$ (0.07 g, 1.76 mmol). The reaction was stirred at room temperature for 30 min under N$_2$. Saturated aqueous NH$_4$Cl (20 mL) was added to the reaction vessel and the resulting biphasic mixture was transferred to a separatory funnel. The layers were separated and the org/aq phase was washed with EtOAc (3×150 mL). The combined organics were dried over anhydrous Na$_2$SO$_4$, filtered and concentrated in vacuo. The resulting oil was purified by flash column chromatography with EtOAc (90%) and hexanes (10%) to provide (3S)-1-((2,3-dihydro-1H-inden-1-yl)methyl)-3-(4-fluorophenoxy)piperidine (114 mg) as a yellow oil.

Example 271. Synthesis of 1-((2,3-dihydro-1H-inden-1-yl)methyl)-4-(4-fluorophenoxy)azepane

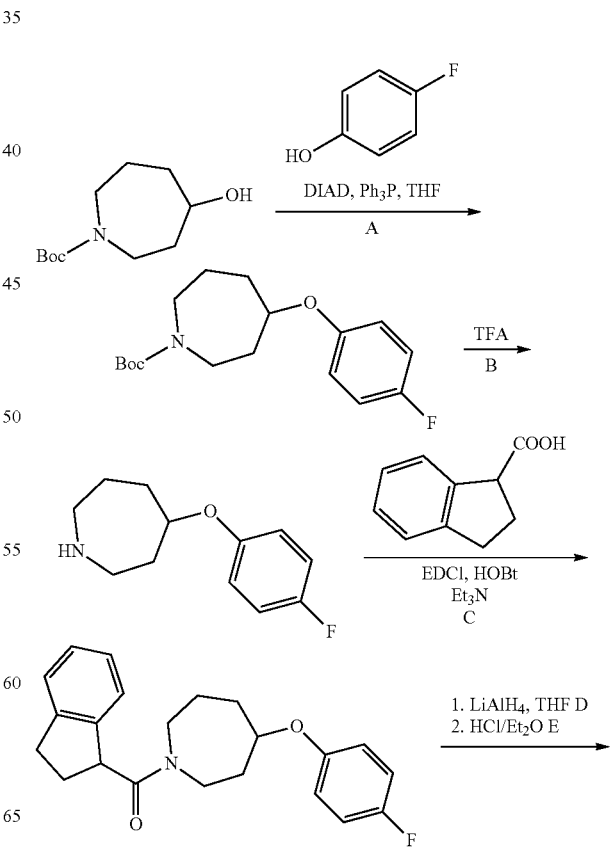

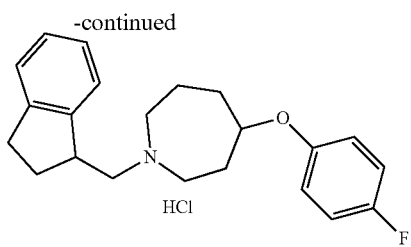

A. To a solution of tert-butyl 4-hydroxyazepane-1-carboxylate (400 mg, 1.86 mmol) in THF (8 mL) was added 4-fluorophenol (210 mg, 1.86 mmol), triphenylphosphine (0.73 g, 2.79 mmol). The reaction was stirred at ambient temperature for 5 min. Diisopropyl azodiformate (0.41 g, 2.05 mmol) was added to the above mixture dropwise. The reaction was stirred at ambient temperature for 3 h. TLC showed the starting material was consumed. The combined organics were concentrated in vacuo. The resulting oil was purified by flash column chromatography with an isocratic elution of EtOAc (10%) and hexanes (90%) to provide tert-butyl 4-(4-fluorophenoxy)azepane-1-carboxylate (440 mg) as a colorless oil.

B. To a solution of tert-butyl 4-(4-fluorophenoxy)azepane-1-carboxylate (400 mg, 1.29 mmol) in DCM (10 mL) was added trifluoroacetic acid (1 mL). The reaction was stirred at ambient temperature for 2 h. TLC showed the starting material was consumed. Saturated aqueous NaHCO$_3$ (10 mL) was added to the reaction vessel. And the mixture was extracted with DCM (3×20 mL). The combined organics were dried over anhydrous Na$_2$SO$_4$, filtered and concentrated in vacuo. The resulting oil was purified by flash column chromatography with a gradient elution of EtOAc (25%) and hexanes (75%) to DCM (95%) and MeOH (5%) to provide 4-(4-fluorophenoxy)azepane (0.14 g, 0.67 mmol) as a yellow oil.

C. To a solution of 4-(4-fluorophenoxy)azepane (80 mg, 0.38 mmol) in DCM (8 mL) was added 2,3-dihydro-1H-indene-1-carboxylic acid (0.06 g, 0.38 mmol), N-Hydroxybenzotriazole (0.08 g, 0.57 mmol), 1-(3-dimethylaminopropyl)-3-ethylcarbodiimide hydrochloride (0.15 g, 0.76 mmol) and triethylamine (0.08 g, 0.76 mmol). The reaction was stirred at ambient temperature for 3 h. Water (30 mL) and DCM (30 mL) were added to the reaction vessel and the resulting biphasic mixture was transferred to a separatory funnel. The layers were separated and the aqueous phase was extracted with DCM (2×30 mL). The combined organics were washed with saturated aqueous NaCl (1×25 mL). The combined organics were dried over anhydrous Na$_2$SO$_4$, filtered and concentrated in vacuo to provide (2,3-dihydro-1H-inden-1-yl)(4-(4-fluorophenoxy)azepan-1-yl)methanone (120 mg, 0.34 mmol) as a pale yellow oil.

D. To a solution of (2,3-dihydro-1H-inden-1-yl)(4-(4-fluorophenoxy)azepan-1-yl)methanone (120 mg, 0.34 mmol) in THF (5.0 mL) was added LiAlH$_4$ (0.03 g, 0.68 mmol) at 0° C. The reaction was warmed to room temperature and stirred for 30 min. Saturated aqueous NH$_4$Cl (20 mL) was added to the reaction vessel and the resulting biphasic mixture was extracted with CH$_2$Cl$_2$ (3×30 mL). The organic phase was washed with saturated aqueous NaCl (1×50 mL). The combined organics were dried over anhydrous Na$_2$SO$_4$, filtered and concentrated in vacuo. The resulting oil was purified by flash column chromatography with a gradient elution of EtOAc (20%) and hexanes (80%) to EtOAc (30%) and hexanes (70%) to provide 1-((2,3-dihydro-1H-inden-1-yl)methyl)-4-(4-fluorophenoxy)azepane (60 mg, 0.18 mmol) as a colorless oil.

E. To a solution of 1-((2,3-dihydro-1H-inden-1-yl)methyl)-4-(4-fluorophenoxy)azepane (60 mg, 0.18 mmol) in methanol (2 mL) was added HCl/Et$_2$O (2 mL). The reaction was stirred at ambient temperature for 30 min. The solvent was evaporated to give the viscous oil. The resulting oil was resolved in CH$_2$Cl$_2$ (1 mL). And then Et$_2$O (5 mL) was added. Most of the solvent was sucked out. The remaining was evaporated to dry in vacuo to provide 1-((2,3-dihydro-1H-inden-1-yl)methyl)-4-(4-fluorophenoxy)azepane hydrochloride (0.06 g, 0.16 mmol) as a white solid.

Example 287. Synthesis of (S)-1-(cyclohexyloxy)-3-((1R,5S)-3-phenyl-3,8-diazabicyclo[3.2.1]octan-8-yl)propan-2-ol

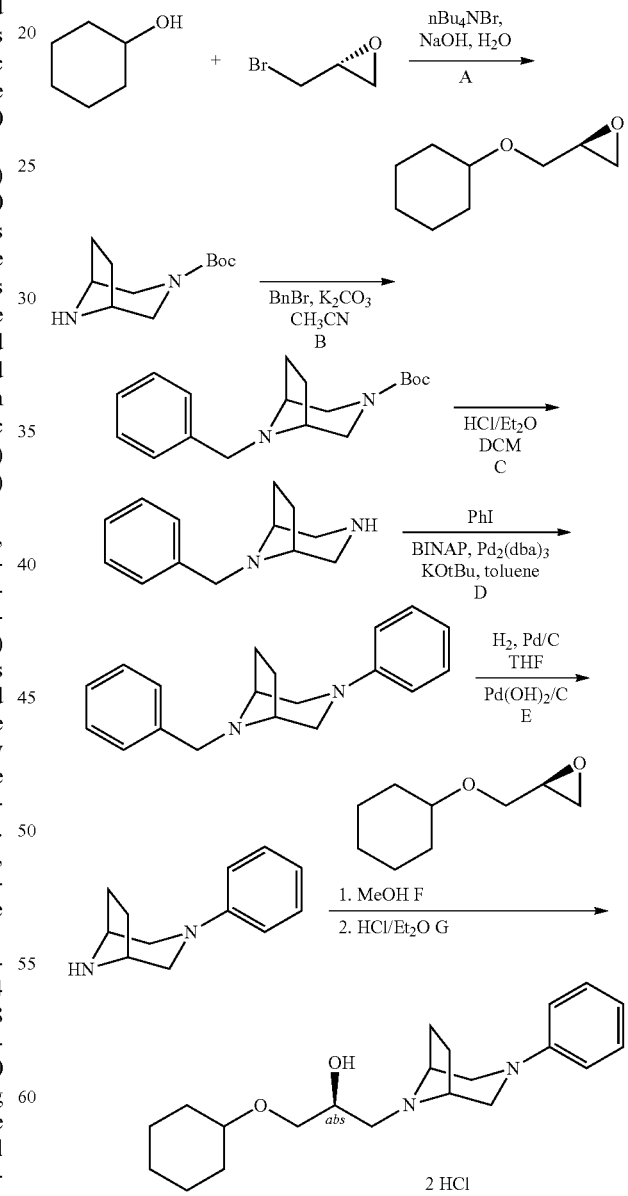

A. To a solution of (R)-2-(chloromethyl)oxirane (10 g, 108.08 mmol) in NaOH aqueous solution (21.62 g/50 mL)

was added cyclohexanol (10.83 g, 108.08 mmol) and tetrabutylammonium bromide (1.74 g, 5.4 mmol). The reaction was stirred at ambient temperature for 3 h. Water (50 mL) was added to the reaction vessel and extracted with EtOAc (3×50 mL). The layers were separated and the organic phase was washed with saturated aqueous NaCl (2×100 mL). The combined organics were dried over anhydrous Na$_2$SO$_4$, filtered and concentrated in vacuo. The resulting oil was purified by flash column chromatography with an isocratic elution of petroleum ether (100%) to provide (S)-2-((cyclohexyloxy)methyl)oxirane (1.25 g) as a yellow oil.

B. To a solution of (1R,5S)-tert-butyl 3,8-diazabicyclo[3.2.1]octane-3-carboxylate (1 g, 4.710 mmol) in CH$_3$CN (25 mL) was added (bromomethyl)benzene (966.6 mg, 5.652 mmol) and K$_2$CO$_3$ (650.9 mg, 4.710 mmol). The reaction was stirred at 60° C. for 12 h. The reaction was concentrated. H$_2$O (50 mL) was added. The aqueous phase was extracted with DCM (3×75 mL). The combined organics were dried over anhydrous Na$_2$SO$_4$, filtered and concentrated in vacuo. The resulting oil was purified by flash column chromatography with a gradient elution of hex (92%) and EtOAc (8%) to hexanes (85%) and EtOAc (15%) to provide (1R,5S)-tert-butyl 8-benzyl-3,8-diazabicyclo[3.2.1]octane-3-carboxylate (1.200 g, 3.968 mmol) as a yellow oil.

C. To a solution of (1R,5S)-tert-butyl 8-benzyl-3,8-diazabicyclo[3.2.1]octane-3-carboxylate (2.5 g, 8.26 mmol) in DCM (5 mL) was added HCl/Et$_2$O (5 mL). The reaction was stirred at ambient temperature for 3 h. The solution was concentrated in vacuo to provide (1R,5S)-8-benzyl-3,8-diazabicyclo[3.2.1]octane (1.70 g, 8.40 mmol) as a white solid.

D. To a solution of (1R,5S)-8-benzyl-3,8-diazabicyclo[3.2.1]octane (1.2 g, 5.93 mmol) in toluene (40 mL) was added iodobenzene (2.40 g, 11.8 mmol), potassium 2-methylpropan-2-olate (1.32 g, 11.8 mmol), BINAP (733 mg, 1.18 mmol) and Pd$_2$(dba)3 (1.07 g, 1.18 mmol). The reaction was stirred at 90° C. for 12 h. Water (75 mL) was added to the reaction vessel and the resulting biphasic mixture was transferred to a separatory funnel. The layers were separated and the aqueous phase was extracted with DCM (3×100 mL). The combined organics were dried over anhydrous Na$_2$SO$_4$, filtered and concentrated in vacuo. The resulting oil was purified by flash column chromatography with a gradient elution of hexanes (98%) and EtOAc (2%) to hex (90%) and EtOAc (10%) to provide (1R,5S)-8-benzyl-3-phenyl-3,8-diazabicyclo[3.2.1]octane (1.60 g, 5.74 mmol) as a brown solid.

E. To a solution of (1R,5S)-8-benzyl-3-phenyl-3,8-diazabicyclo[3.2.1]octane (1.8 g, 6.46 mmol) in THF (50 mL) was added Pd/C (152 mg, 1.29 mmol) and Pd(OH)$_2$/C (180 mg, 1.29 mmol) under H$_2$ (5 atm). The reaction mixture was heated to 60° C. and stirred at that temperature for 12 h. The solution was filtered and then directly to the next step.

F. To a solution of (S)-2-((cyclohexyloxy)methyl)oxirane (43 mg, 0.26 mmol) in MeOH (1.5 mL) was added (1R,5S)-3-phenyl-3,8-diazabicyclo[3.2.1]octane (0.05 g, 0.26 mmol). The reaction mixture was heated to 50° C. and stirred at that temperature for 12 h. TLC showed the SM was consumed. The reaction mixture was concentrated in vacuo. The resulting oil was purified by preparative thin layer chromatography with an isocratic elution of DCM (95%) and MeOH (5%) to provide (S)-1-(cyclohexyloxy)-3-((1R,5S)-3-phenyl-3,8-diazabicyclo[3.2.1]octan-8-yl)propan-2-ol (52 mg) as a yellow oil.

G. To a solution of (S)-1-(cyclohexyloxy)-3-((1R,5S)-3-phenyl-3,8-diazabicyclo[3.2.1]octan-8-yl)propan-2-ol (52 mg) in methanol (1 mL) was added HCl/Et$_2$O (3 mL). The reaction was stirred at ambient temperature for 30 min. The solvent was evaporated to give the viscous oil. The resulting oil was resolved in MeOH (0.5 mL). And then Et$_2$O (5 mL) was added. Most of the solvent was sucked out. The remaining was evaporated to dry in vacuo to provide (S)-1-(cyclohexyloxy)-3-((1R,5S)-3-phenyl-3,8-diazabicyclo[3.2.1]octan-8-yl)propan-2-ol hydrochloride (54 mg) as a white solid.

Example 288. Synthesis of (R)-1-(cyclohexyloxy)-3-((1R,5S)-3-phenyl-3,8-diazabicyclo[3.2.1]octan-8-yl)propan-2-ol

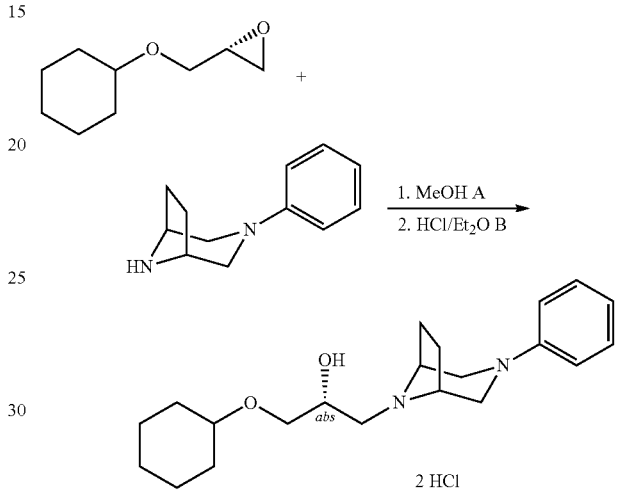

A. To a solution of (R)-2-((cyclohexyloxy)methyl)oxirane (43.5 mg, 0.26 mmol) in MeOH (1.5 mL) was added (1R,5S)-3-phenyl-3,8-diazabicyclo[3.2.1]octane (0.05 g, 0.26 mmol). The reaction mixture was heated to 50° C. and stirred at that temperature for 12 h. The reaction mixture was concentrated in vacuo. The resulting oil was purified by preparative thin layer chromatography with an isocratic elution of DCM (95%) and MeOH (5%) to provide (R)-1-(cyclohexyloxy)-3-((1R,5S)-3-phenyl-3,8-diazabicyclo[3.2.1]octan-8-yl)propan-2-ol (61 mg) as a yellow oil.

B. To a solution of (R)-1-(cyclohexyloxy)-3-((1R,5S)-3-phenyl-3,8-diazabicyclo[3.2.1]octan-8-yl)propan-2-ol (61 mg) in methanol (1 mL) was added HCl/Et$_2$O (3 mL). The reaction was stirred at ambient temperature for 30 min. The solvent was evaporated to give the viscous oil. The resulting oil was resolved in MeOH (0.5 mL). And then Et$_2$O (5 mL) was added. Most of the solvent was sucked out. The remaining was evaporated to dry in vacuo to provide (R)-1-(cyclohexyloxy)-3-((1R,5S)-3-phenyl-3,8-diazabicyclo[3.2.1]octan-8-yl)propan-2-ol hydrochloride (50 mg) as a white solid.

Example 310. Synthesis of (1R,4R)-2-((6-methoxy-2,3-dihydro-1H-inden-1-yl)methyl)-5-phenyl-2,5-diazabicyclo[2.2.2]octane

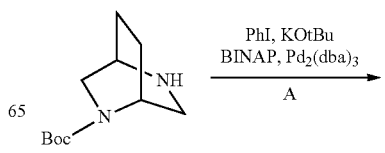

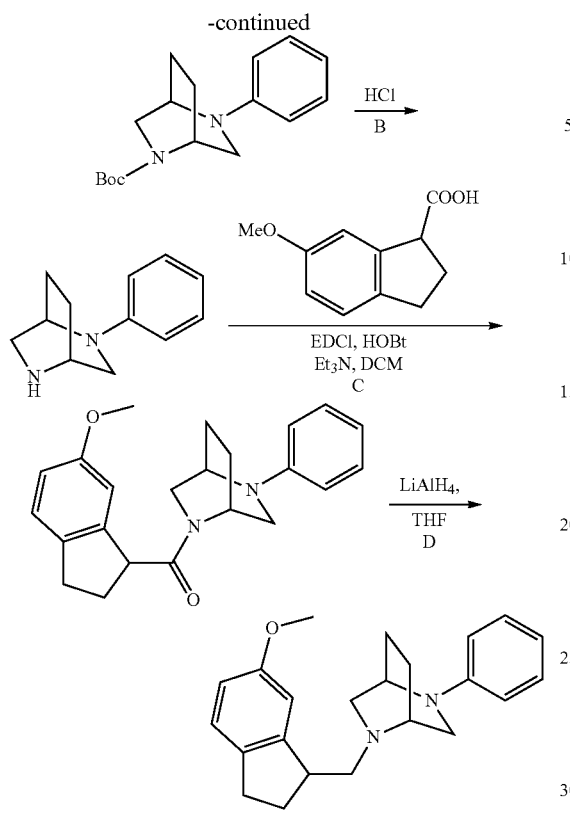

A. To a solution of (1S,4S)-tert-butyl 2,5-diazabicyclo[2.2.2]octane-2-carboxylate (500 mg, 2.36 mmol) in PhMe (30 mL) was added iodobenzene (1.44 g, 7.08 mmol), potassium 2-methylpropan-2-olate (0.79 g, 7.08 mmol) and Pd$_2$(dba)$_3$ (0.22 g, 0.24 mmol), BINAP (0.29 g, 0.47 mmol). The reaction were filtered and concentrated in vacuo. The resulting oil was purified by flash column chromatography with EtOAc (30%) and hexanes (70%) to provide (1S,4S)-tert-butyl 5-phenyl-2,5-diazabicyclo[2.2.2]octane-2-carboxylate (0.6 g, 2.08 mmol) as a yellow oil.

B. To a solution of (1S,4S)-tert-butyl 5-phenyl-2,5-diazabicyclo[2.2.2]octane-2-carboxylate (1.1 g, 3.81 mmol) in THF (3 mL) was added conc. hydrogen chloride (3 mL). The reaction was stirred at ambient temperature for 2 h. Water (15 mL) was added to the reaction vessel and the resulting biphasic mixture was adjusted to pH=9. The mixture was extracted with DCM (3×100 mL). The organic phase was washed with saturated aqueous NaCl (2×25 mL). The combined organics were dried over anhydrous Na$_2$SO$_4$, filtered and concentrated in vacuo to provide (1S,4S)-2-phenyl-2,5-diazabicyclo[2.2.2]octane (0.65 g, 3.45 mmol) as a yellow oil.

C. To a solution of (1S,4S)-2-phenyl-2,5-diazabicyclo[2.2.2]octane (430 mg, 2.284 mmol) in DCM (40 mL) was added 6-methoxy-2,3-dihydro-1H-indene-1-carboxylic acid (0.3951 g, 2.0556 mmol), 1H-benzo[d][1,2,3]triazol-1-ol (0.3086 g, 2.284 mmol), EDCI (0.6568 g, 3.426 mmol) and triethylamine (0.6934 g, 6.852 mmol). The reaction was stirred at ambient temperature for 16 h. Saturated aqueous NaHCO$_3$ (10 mL) was added to the reaction vessel and the resulting biphasic mixture was transferred to a separatory funnel. The layers were separated and the aqueous phase was extracted with DCM (2×100 mL). The combined organics were dried over anhydrous Na$_2$SO$_4$, filtered and concentrated in vacuo to provide (6-methoxy-2,3-dihydro-1H-inden-1-yl)((1S,4S)-5-phenyl-2,5-diazabicyclo[2.2.2]octan-2-yl)methanone (0.7 g, 1.9312 mmol) as a yellow oil.

D. To a solution of (6-methoxy-2,3-dihydro-1H-inden-1-yl)((1S,4S)-5-phenyl-2,5-diazabicyclo[2.2.2]octan-2-yl)methanone (100 mg, 0.2759 mmol) in THF (5 mL) was added AlLiH$_4$ (0.0262 g, 0.6898 mmol) under N$_2$. The reaction was stirred at ambient temperature for 30 min. H$_2$O (30 uL) was added and the mixture solution was filtered. The filtrate was dried over Na$_2$SO$_4$, concentrated and purified by silica gel chromatography eluted with hexanes:EtOAc=5:1 to give 40 mg of product as HCl salt.

Example 345. Synthesis of (2S)-1-(cyclohexyloxy)-3-(7-phenyl-2,7-diazaspiro[4.4]nonan-2-yl)propan-2-ol

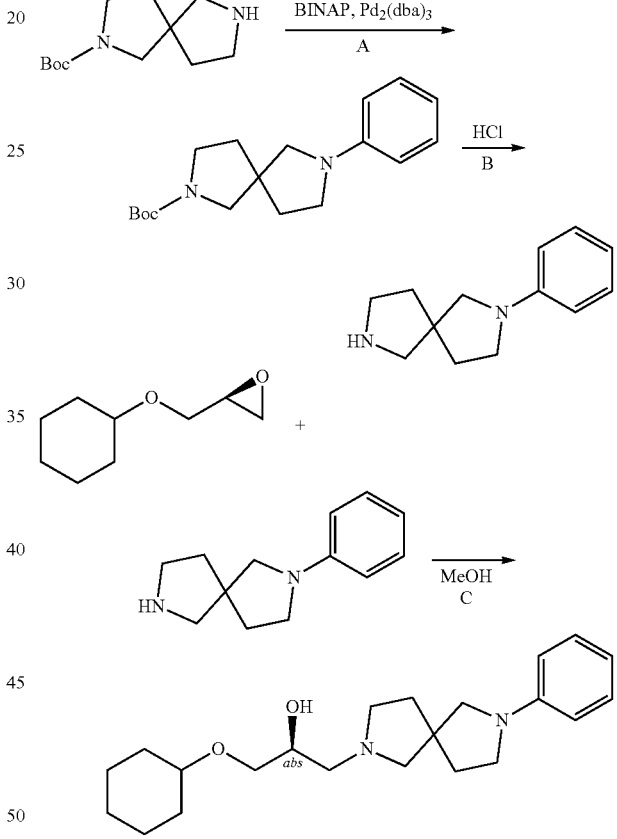

A. To a solution of tert-butyl 2,7-diazaspiro[4.4]nonane-2-carboxylate (400 mg, 1.77 mmol) in toluene (10 mL) was added iodobenzene (0.43 g, 2.12 mmol), potassium 2-methylpropan-2-olate (0.5 g, 4.43 mmol), tris(dibenzylideneacetone)dipalladium (0.08 g, 0.09 mmol) and BINAP (0.22 g, 0.35 mmol). The reaction mixture was heated to 80° C. and stirred at that temperature for 12 h. TLC showed the SM was consumed. The reaction mixture was filtered and concentrated in vacuo. The resulting oil was purified by flash column chromatography with a gradient elution of hexanes (98%) and EtOAc (2%) to hex (95%) and EtOAc (5%) to provide tert-butyl 7-phenyl-2,7-diazaspiro[4.4]nonane-2-carboxylate (0.3 g, 1 mmol) as a brown oil.

B. To a solution of tert-butyl 7-phenyl-2,7-diazaspiro[4.4]nonane-2-carboxylate (200 mg, 0.66 mmol, crude) in THF (10 mL) was added conc. hydrogen chloride (5 mL). The reaction was stirred at ambient temperature for 1 h. Saturated aqueous NaHCO₃ (50 mL) was added to the reaction vessel and the resulting biphasic mixture was extracted with DCM:CH₃OH (5:1, 4×50 mL). The combined organics were dried over anhydrous Na₂SO₄, filtered and concentrated in vacuo to provide 2-phenyl-2,7-diazaspiro[4.4]nonane (0.12 g, 0.58 mmol) as a yellow oil.

C. To a solution of 2-phenyl-2,7-diazaspiro[4.4]nonane (190 mg, 0.94 mmol) in methanol (15 mL) was added (S)-2-((cyclohexyloxy)methyl)oxirane (0.16 g, 1.03 mmol). The reaction was stirred at 50° C. for 12 h. TLC showed a new major spot. LCMS showed the desired product. After concentration, the residue was purified by silica gel chromatography eluted with DCM:MeOH=150:1 to 70:1 to give the desired product 129 mg as oil.

Example 375. Synthesis of 8-((2,3-dihydro-1H-inden-1-yl)methyl)-3-phenyl-1-oxa-8-azaspiro[4,5]decane

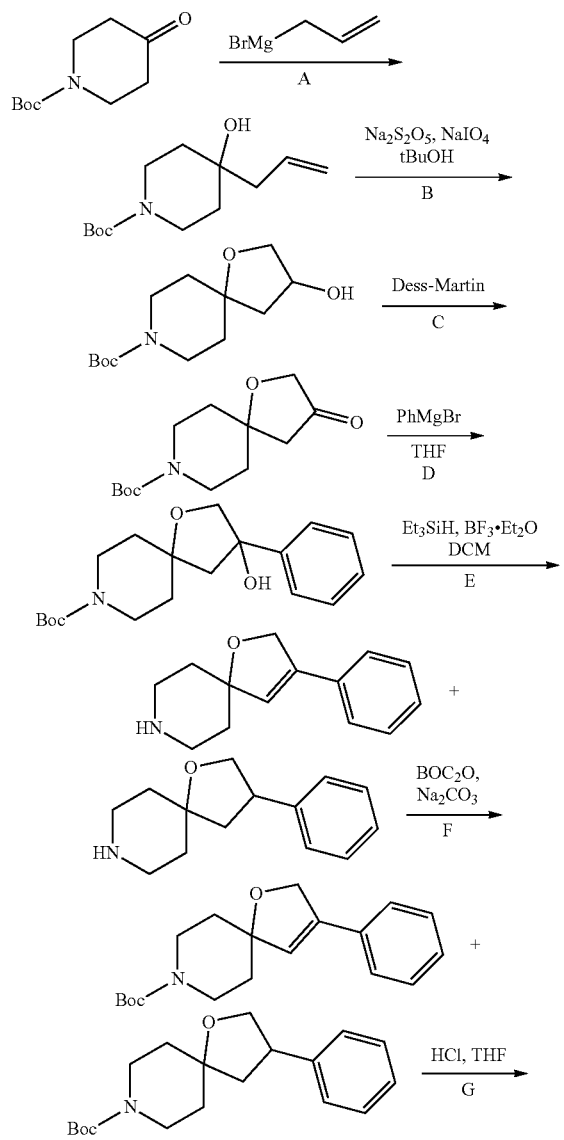

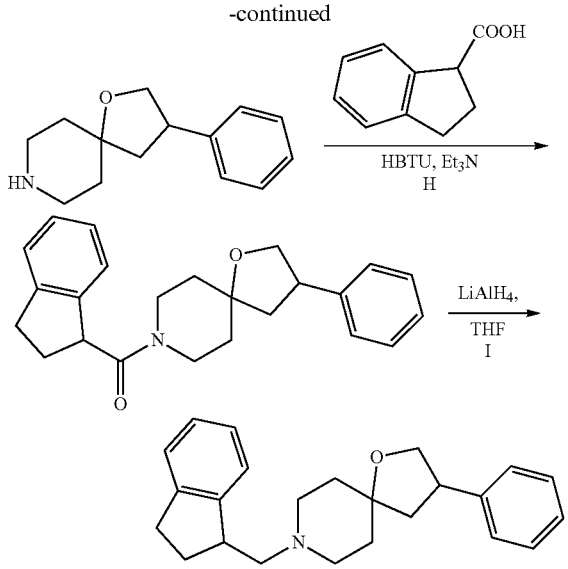

A. To a solution of tert-butyl 4-oxopiperidine-1-carboxylate (6.0 g, 30.11 mmol) in THF (40 mL) was added dropwised allylmagnesium bromide (33.2 mL, 33.12 mmol). The reaction was stirred at 0° C. for 2 h. saturated aqueous NH₄Cl (50 mL) and EtOAc (300 mL) were added to the reaction vessel and the resulting biphasic mixture was transferred to a separatory funnel. The layers were separated and the organic phase was washed with saturated aqueous NaCl (2×50 mL). The combined organics were dried over anhydrous Na₂SO₄, filtered and concentrated in vacuo. The resulting oil was purified by flash column chromatography with a gradient elution of hex (100%) to hexanes (80%) and EtOAc (20%) to provide tert-butyl 4-allyl-4-hydroxypiperidine-1-carboxylate (5 g, 20.72 mmol) as a colorless oil.

B. To a solution of tert-butyl 4-allyl-4-hydroxypiperidine-1-carboxylate (45 g, 186 mmol) in t-BuOH/H₂O (400 mL/200 mL) was added sodium periodate (43.6 g, 204 mmol). Na₂S₂O₅ (38.7 g, 204 mmol) was added in portions during a period of 20 min. The reaction was stirred at ambient temperature for 24 h.

Na₂S₂O₃ was added until the brown solution changed to colorless. The aqueous was extracted with EtOAc (3×300 mL). The combined organics were dried over anhydrous Na₂SO₄, filtered and concentrated in vacuo. The resulting oil was purified by flash column chromatography with a gradient elution of hexanes (90%) and EtOAc (10%) to hexanes (55%) and EtOAc (45%) to provide tert-butyl 3-hydroxy-1-oxa-8-azaspiro[4.5]decane-8-carboxylate (10.5 g, 40.8 mmol) as a brown oil.

C. To a solution of tert-butyl 3-hydroxy-1-oxa-8-azaspiro[4.5]decane-8-carboxylate (5.2 g, 20.2 mmol) in DCM (200 mL) was added Dess-Martin periodinane (12.8 g, 30.3 mmol) at 25° C. The reaction was stirred at ambient temperature for 3 h. Saturated aqueous Na₂CO₃ (100 mL) was added to the reaction vessel and the resulting biphasic mixture was transferred to a separatory funnel. The layers were separated and the aqueous phase was extracted with DCM (50 mL). The combined organics were washed with brine, dried over anhydrous Na₂SO₄, filtered and concentrated in vacuo. The resulting oil was purified by flash column chromatography with a gradient elution of EtOAc (5%) and hexanes (95%) to EtOAc (10%) and hexanes (90%) to provide tert-butyl 3-oxo-1-oxa-8-azaspiro[4.5]decane-8-carboxylate (2.00 g, 7.83 mmol) as a white solid.

D. To a solution of tert-butyl 3-oxo-1-oxa-8-azaspiro[4.5] decane-8-carboxylate (500 mg, 1.95 mmol) in THF (20 mL) was added phenylmagnesium bromide (3.90 mL, 3.90 mmol) at 0° C. The reaction mixture was stirred at this temperature for 1 h. saturated aqueous NH$_4$Cl (20 mL) and EtOAc (50 mL) were added to the reaction vessel and the resulting biphasic mixture was transferred to a separatory funnel. The layers were separated and the organic phase was washed with saturated aqueous NaCl (2×30 mL). The combined organics were dried over anhydrous Na$_2$SO$_4$, filtered and concentrated in vacuo to provide tert-butyl 3-hydroxy-3-phenyl-1-oxa-8-azaspiro[4.5]decane-8-carboxylate (500 mg, crude) as a yellow oil.

E. To a solution of tert-butyl 3-hydroxy-3-phenyl-1-oxa-8-azaspiro[4.5]decane-8-carboxylate (1.3 g, 3.9 mmol) in DCM (20 mL) was added triethylsilane (1.84 g, 15.82 mmol), Boron trifluoride ethylether (3.5 mL, 34.77 mmol) at −70° C. The reaction mixture was stirred at that temperature for 3 h. Water (20 mL) was added to the reaction vessel and the resulting biphasic mixture was transferred to a separatory funnel. The layers were separated and the aqueous phase was extracted with DCM (2×30 mL). The combined organics were washed with brine, dried over anhydrous Na$_2$SO$_4$, filtered and concentrated in vacuo to provide 3-phenyl-1-oxa-8-azaspiro[4.5]dec-3-ene (0.35 g, 1.63 mmol) and 3-phenyl-1-oxa-8-azaspiro[4.5]decane (0.42 g, 2.77 mmol) as a yellow oil.

F. To a solution of 3-phenyl-1-oxa-8-azaspiro[4.5]dec-3-ene and 3-phenyl-1-oxa-8-azaspiro[4.5]decane (400 mg crude, 1.85 mmol) in THF (20 mL) and H$_2$O (10 mL) was added di-tert-butyl dicarbonate (604 mg, 2.77 mmol) and sodium carbonate (588 mg, 5.55 mmol). The reaction was stirred at ambient temperature for 1 h. Water (20 mL) and EtOAc (30 mL) were added to the reaction vessel and the resulting biphasic mixture was transferred to a separatory funnel. The layers were separated and the organic phase was washed with saturated aqueous NaCl (2×30 mL). The combined organics were dried over anhydrous Na$_2$SO$_4$, filtered and concentrated in vacuo. The resulting oil was purified by flash column chromatography with a gradient elution of hexanes (100%) to hexanes (80%) and EtOAc (20%) to provide tert-butyl 3-phenyl-1-oxa-8-azaspiro[4.5]dec-3-ene-8-carboxylate and tert-butyl 3-phenyl-1-oxa-8-azaspiro [4.5]decane-8-carboxylate (400 mg mixture, 1.27 mmol) as a colorless solid.

G. To a solution of tert-butyl 3-phenyl-1-oxa-8-azaspiro [4.5]decane-8-carboxylate (0.56 g, 1.76 mmol) in THF (10 mL) was added hydrogen chloride (2 mL, 12 M, 1.76 mmol) at room temperature for 30 min.

DCM (40 mL) and water (25 mL) were added to the reaction vessel and the resulting biphasic mixture was transferred to a separatory funnel. The layers were separated. The aqueous phase was adjusted to pH=9, and extracted with DCM (2×50 mL). The organics were dried over anhydrous Na$_2$SO$_4$, filtered and concentrated in vacuo to provide 3-phenyl-1-oxa-8-azaspiro[4.5]decane (0.35 g, 1.61 mmol) as a yellow oil.

H. To a solution of 3-phenyl-1-oxa-8-azaspiro[4.5]decane (40 mg, 0.18 mmol) in DCM (5 mL) was added 2,3-dihydro-1H-indene-1-carboxylic acid (0.03 g, 0.18 mmol), triethylamine (0.03 g, 0.27 mmol) and HBTU (0.08 g, 0.32 mmol). The reaction was stirred at ambient temperature for 30 min. Saturated aqueous NaHCO$_3$ (20 mL) and DCM (100 mL) were added to the reaction vessel and the resulting biphasic mixture was transferred to a separatory funnel. The layers were separated and the organic phase was washed with saturated aqueous NaCl (2×50 mL). The combined organics were dried over anhydrous Na$_2$SO$_4$, filtered and concentrated in vacuo to provide (2,3-dihydro-1H-inden-1-yl)(3-phenyl-1-oxa-8-azaspiro[4.5]decan-8-yl)methanone (0.02 g, 0.06 mmol) as a yellow oil.

I. To a solution of (2,3-dihydro-1H-inden-1-yl)(3-phenyl-1-oxa-8-azaspiro[4.5]decan-8-yl)methanone (30 mg, 0.08 mmol) in THF (5 mL) was added LiAlH$_4$ (0 g, 0.08 mmol). The reaction was stirred at ambient temperature for 30 min. Saturated aqueous NaCl (20 mL) and DCM (100 mL) were added to the reaction vessel and the resulting biphasic mixture was transferred to a separatory funnel. The layers were separated and the organic phase was washed with saturated aqueous NaCl (2×20 mL). The combined organics were dried over anhydrous Na$_2$SO$_4$, filtered and concentrated in vacuo. The resulting oil was purified by preparative thin layer chromatography with an isocratic elution of hexanes (70%) and EtOAc (30%) to provide 8-((2,3-dihydro-1H-inden-1-yl)methyl)-3-phenyl-1-oxa-8-azaspiro[4.5]decane (0.01 g, 0.03 mmol) as a white solid.

Example 380. Synthesis of 8-((2,3-dihydro-1H-inden-1-yl)methyl)-3-phenoxy-1-oxa-8-azaspiro[4.5]decane

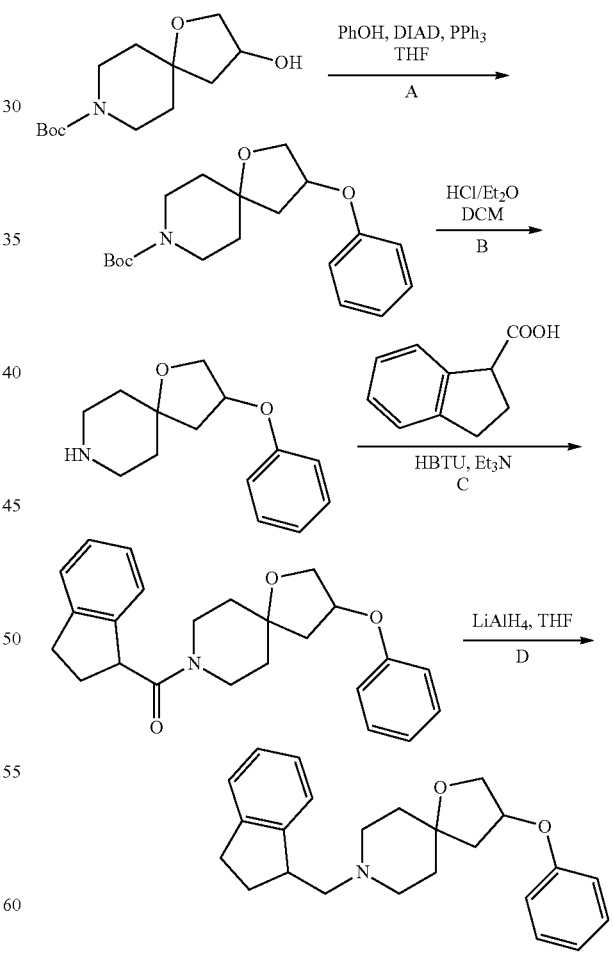

A. To a solution of tert-butyl 3-hydroxy-1-oxa-8-azaspiro [4.5]decane-8-carboxylate (1.5 g, 5.83 mmol) in THF (20 mL) was added phenol (0.6 g, 6.41 mmol), DIAD (1.53 g, 7.58 mmol) and PPh$_3$ (1.68 g, 6.41 mmol). The reaction mixture was heated to 50° C. and stirred at that temperature for 12 h. The mixture of solution was concentrated in vacuo. The resulting oil was purified by flash column chromatography with a gradient elution of hexanes (100%) to hexanes (90%) and EtOAc (10%) to provide tert-butyl 3-phenoxy-1-oxa-8-azaspiro[4.5]decane-8-carboxylate (1.14 g, 3.42 mmol) as a white solid.

B. To a solution of tert-butyl 3-phenoxy-1-oxa-8-azaspiro[4.5]decane-8-carboxylate (1.2 g, 3.6 mmol) in DCM (6 mL) was added HClEt$_2$O (20 mL). The reaction was stirred at ambient temperature for 12 h.

The solution was concentrated in vacuo to provide 3-phenoxy-1-oxa-8-azaspiro[4.5]decane (0.78 g, 3.33 mmol) of HCl salt as a white solid.

C. To a solution of 3-phenoxy-1-oxa-8-azaspiro[4.5]decane (50 mg, 0.24 mmol) in DCM (5 mL) was added 2,3-dihydro-1H-indene-1-carboxylic acid (0.03 g, 0.21 mmol), triethylamine (0.03 g, 0.32 mmol) and HBTU (0.12 g, 0.32 mmol). The reaction was stirred at ambient temperature for 2 h. Saturated aqueous NaHCO$_3$ (20 mL) and DCM (30 mL) were added to the reaction vessel and the resulting biphasic mixture was transferred to a separatory funnel. The layers were separated and the organic phase was washed with saturated aqueous NaCl (1×20 mL). The combined organics were dried over anhydrous Na$_2$SO$_4$, filtered and concentrated in vacuo to provide (2,3-dihydro-1H-inden-1-yl)(3-phenoxy-1-oxa-8-azaspiro[4.5]decan-8-yl)methanone (50 mg, 0.13 mmol) as a yellow oil.

D. To a solution of (2,3-dihydro-1H-inden-1-yl)(3-phenoxy-1-oxa-8-azaspiro[4.5]decan-8-yl)methanone (50 mg, 0.13 mmol) in THF (10 mL) was added LiAlH$_4$ (0.02 g, 0.52 mmol). The reaction was stirred at ambient temperature for 1 h. 1M aqueous NaOH (5 mL) and DCM (100 mL) were added to the reaction vessel and the resulting biphasic mixture was transferred to a separatory funnel. The layers were separated and the organic phase was washed with saturated aqueous NaCl (2×20 mL). The combined organics were dried over anhydrous Na$_2$SO$_4$, filtered and concentrated in vacuo. The resulting oil was purified by preparative thin layer chromatography with an isocratic elution of hexanes (60%) and EtOAc (40%) to provide 8-((2,3-dihydro-1H-inden-1-yl)methyl)-3-phenoxy-1-oxa-8-azaspiro[4.5]decane (0.03 g, 0.08 mmol) as a colorless oil.

Example 396. Synthesis of 1'-((2,3-dihydro-1H-inden-2-yl)methyl)-3H-spiro[benzofuran-2,4'-piperidine]

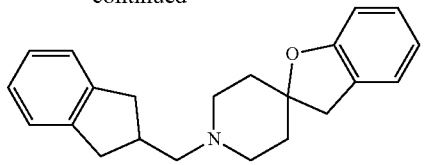

A. To a solution of 3H-spiro[benzofuran-2,4'-piperidine] (50 mg, 0.264 mmol) in DCM (5.0 mL) was added 2,3-dihydro-1H-indene-2-carboxylic acid (0.043 g, 0.264 mmol), N-Hydroxybenzotriazole (0.054 g, 0.396 mmol) and 1-(3-dimethylaminopropyl)-3-ethylcarbodiimide hydrochloride (0.101 g, 0.528 mmol) and Et$_3$N (0.053 g, 0.528 mmol). The reaction was stirred at ambient temperature for 3 h.

Water (30 mL) and DCM (30 mL) were added to the reaction vessel and the resulting biphasic mixture was transferred to a separatory funnel. The layers were separated and the aqueous phase was extracted with DCM (2×30 mL). The combined organics were washed with saturated aqueous NaCl (1×25 mL). The combined organics were dried over anhydrous Na$_2$SO$_4$, filtered and concentrated in vacuo to provide (2,3-dihydro-1H-inden-2-yl)(3H-spiro[benzofuran-2,4'-piperidin]-1'-yl)methanone (100 mg, purity: 70%, 0.21 mmol) as a colorless oil.

B. To a solution of (2,3-dihydro-1H-inden-2-yl)(3H-spiro[benzofuran-2,4'-piperidin]-1'-yl)methanone (70 mg, 0.21 mmol) in THF (5.0 mL) was added LiAlH$_4$ (0.016 g, 0.42 mmol) at 0° C. The reaction was warmed to room temperature and stirred for 1 h. Saturated aqueous NH$_4$Cl (20 mL) was added to the reaction vessel and the resulting biphasic mixture was extracted with CH$_2$Cl$_2$ (3×30 mL). The organic phase was washed with saturated aqueous NaCl (1×50 mL). The combined organics were dried over anhydrous Na$_2$SO$_4$, filtered and concentrated in vacuo. The resulting oil was purified by flash column chromatography with a gradient elution of EtOAc (10%) and hexanes (90%) to EtOAc (25%) and hexanes (75%) to provide 1-((2,3-dihydro-1H-inden-1-yl)methyl)-4-(4-fluorophenoxy)azepane (50 mg, 0.157 mmol) as a pale yellow oil.

Example 401. Synthesis of 1'-((2,3-dihydro-1H-inden-1-yl)methyl)spiro[chromane-2,4'-piperidine]

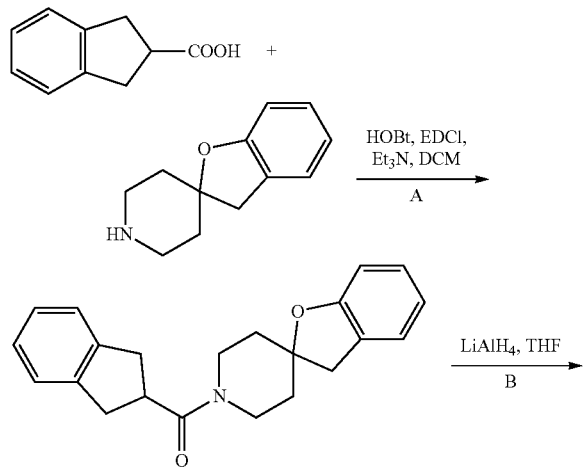

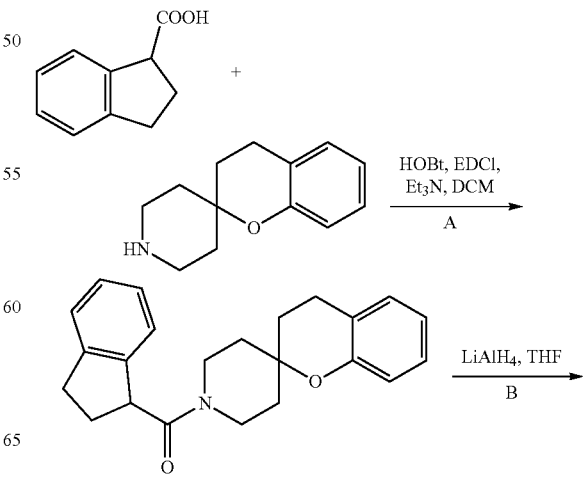

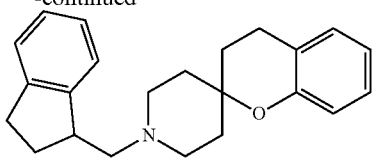

A. To a solution of 2,3-dihydro-1H-indene-1-carboxylic acid (130 mg, 0.8 mmol) in DCM (10.0 mL) was added spiro[chroman-2,4'-piperidine] (0.16 g, 0.8 mmol), N-Hydroxybenzotriazole (0.16 g, 1.2 mmol) and 1-(3-dimethylaminopropyl)-3-ethylcarbodiimide hydrochloride (0.31 g, 1.6 mmol) and Et$_3$N (0.16 g, 1.6 mmol). The reaction was stirred at ambient temperature for 3 h. Water (30 mL) and DCM (30 mL) were added to the reaction vessel and the resulting biphasic mixture was transferred to a separatory funnel. The layers were separated and the aqueous phase was extracted with DCM (2×50 mL). The combined organics were washed with saturated aqueous NaCl (1×25 mL). The combined organics were dried over anhydrous Na$_2$SO$_4$, filtered and concentrated in vacuo to provide (2,3-dihydro-1H-inden-1-yl)(spiro[chroman-2,4'-piperidin]-1'-yl)methanone (260 mg, purity: 90%, 0.27 mmol) as a pale yellow oil.

B. To a solution of (2,3-dihydro-1H-inden-1-yl)(spiro[chroman-2,4'-piperidin]-1'-yl)methanone (260 mg, purity: 90%, 0.66 mmol) in THF (10.0 mL) was added LiAlH$_4$ (0.05 g, 1.32 mmol) at 0° C. The reaction was warmed to room temperature and stirred for 1 h. Saturated aqueous NH$_4$Cl (30 mL) was added to the reaction vessel and the resulting biphasic mixture was extracted with CH$_2$Cl$_2$ (3×40 mL). The organic phase was washed with saturated aqueous NaCl (1×50 mL). The combined organics were dried over anhydrous Na$_2$SO$_4$, filtered and concentrated in vacuo. The resulting oil was purified by flash column chromatography with a gradient elution of EtOAc (10%) and hexanes (90%) to EtOAc (25%) and hexanes (75%) to provide 1'-((2,3-dihydro-1H-inden-1-yl)methyl)spiro[chroman-2,4'-piperidine] (200 mg, 0.60 mmol) as a colorless oil.

Example 422. Synthesis of 2-(2-(spiro[chromane-2,4'-piperidin]-1'-yl)ethyl)-3,4-dihydroisoquinolin-1(2H)-one

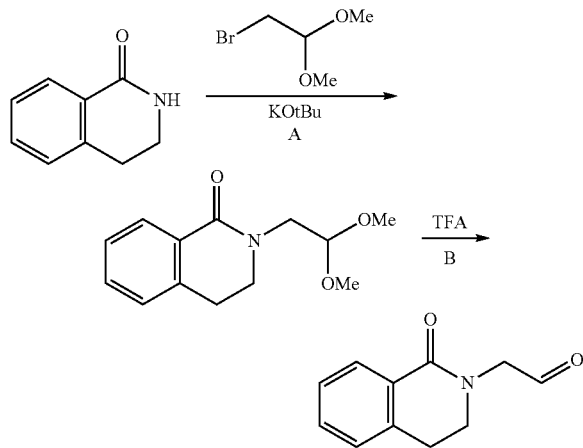

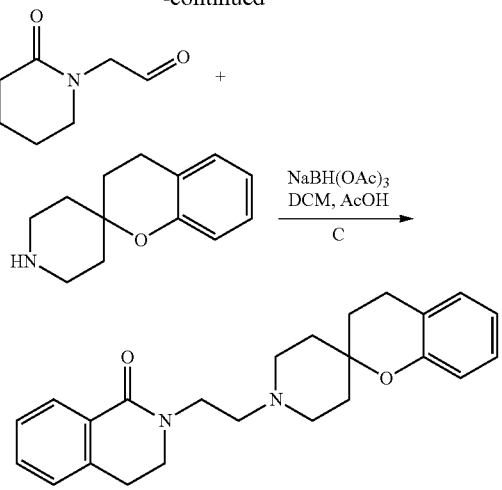

A. To a solution of 3,4-dihydroisoquinolin-1(2H)-one (5.00 g, 33.97 mmol), t-Bu-OK (5.72 g, 50.96 mmol) and TBAB (5.48 g, 16.99 mmol) in THF/DMF (30/5 mL) was added 2-bromo-1,1-dimethoxyethane (11.48 g, 67.94 mmol). The reaction mixture was heated to 70° C. and stirred at that temperature overnight. TLC showed 20% of the SM was still remained. 2-bromo-1,1-dimethoxyethane (3.0 g) was added to the mixture. The reaction was stirred for another 6 h at 70° C. The reaction mixture was treated with H$_2$O (30 mL). The aqueous layer was extracted with EtOAc (3×30 mL). The combined organic layers were washed with brine, dried over Na$_2$SO$_4$, filtered and concentrated in vacuo. The resulting oil was purified by column chromatography (Hexanes:EtOAc=6:1) to provide the desired product (5.00 g) as a yellow oil.

B. To a solution of 2-(2,2-dimethoxyethyl)-3,4-dihydroisoquinolin-1(2H)-one (2.5 g, 10.6257 mmol) in DCM (10 mL) was added TFA (6.0577 g, 53.1285 mmol). The reaction was stirred at ambient temperature for 12 h. Saturated aqueous Na$_2$CO$_3$ (40 mL) was added to the reaction vessel and the resulting biphasic mixture was transferred to a separatory funnel. The layers were separated and the aqueous phase was extracted with DCM (3×30 mL). The combined organics were dried over anhydrous Na$_2$SO$_4$, filtered and concentrated in vacuo. The resulting oil was purified by flash column chromatography with a gradient elution of hexanes (95%) and EtOAc (5%) to hexanes (85%) and EtOAc (15%) to provide 2-(1-oxo-3,4-dihydroisoquinolin-2(1H)-yl)acetaldehyde (1.2 g, 6.3421 mmol) as a colorless oil.

C. To a solution of spiro[chroman-2,4'-piperidine] (30 mg, 0.15 mmol) in DCM (8 mL) was added 2-(1-oxo-3,4-dihydroisoquinolin-2(1H)-yl)acetaldehyde (30 mg, 0.15 mmol), acetic acid (0.01 g, 0.15 mmol). The reaction was stirred at ambient temperature for 1 h. Sodium triacetoxyborohyride (60 mg, 0.3 mmol) was added to the mixture. The reaction was stirred at ambient temperature for 3 h. Water (20 mL) was added to the reaction vessel and extracted with DCM (3×40 mL). The combined organics was washed with water and dried over anhydrous Na$_2$SO$_4$, filtered and concentrated in vacuo. The resulting oil was purified by flash column chromatography with a gradient elution of DCM (99%) and MeOH (1%) to DCM (95%) and MeOH (5%) to provide 2-(2-(spiro[chroman-2,4'-piperidin]-1'-yl)ethyl)-3,4-dihydroisoquinolin-1(2H)-one (10 mg, 0.03 mmol) as a colorless oil. HCl/Et$_2$O was added to the above mixture to obtain the HCl salt.

Example 432. Synthesis of (S)-1'-(2-((2,3-dihydro-1H-inden-1-yl)oxy)ethyl)spiro[chromane-2,4]-piperidine]

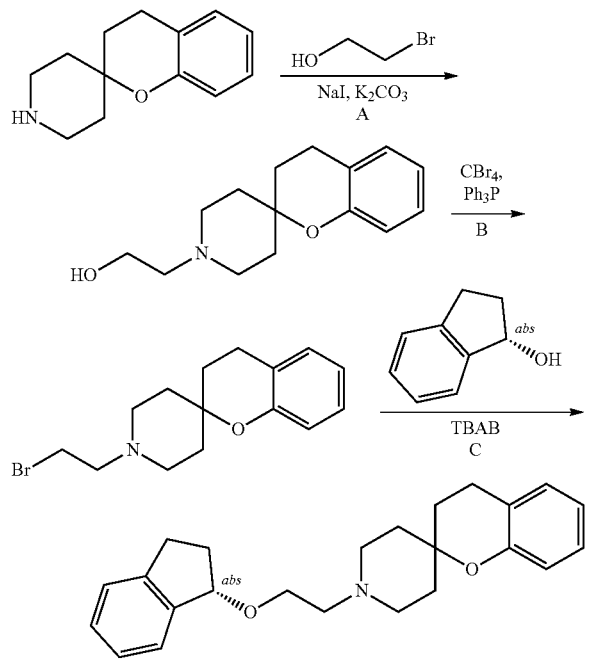

A. To a solution of spiro[chroman-2,4'-piperidine] (500 mg, 2.46 mmol) in DMF (30 mL) was added 2-bromoethanol (0.34 g, 2.71 mmol), K₂CO₃ (0.34 g, 2.46 mmol) and sodium iodide (0.37 g, 2.46 mmol). The reaction mixture was heated to 90° C. and stirred at that temperature for 2 h. Water (50 mL) and DCM (400 mL) was added to the reaction vessel and the resulting biphasic mixture was transferred to a separatory funnel. The layers were separated and the organic phase was washed with saturated aqueous NaCl (5×50 mL). The combined organics were dried over anhydrous Na₂SO₄, filtered and concentrated in vacuo to provide 2-(spiro[chroman-2,4'-piperidin]-1'-yl)ethanol (300 mg, 1.54 mmol) as a colorless oil.

B. To a solution of 2-(spiro[chroman-2,4'-piperidin]-1'-yl)ethanol (300 mg, 1.21 mmol) in DCM (20 mL) was added perbromomethane (0.48 g, 1.45 mmol) and triphenylphosphine (0.47 g, 1.81 mmol). The reaction was stirred at 0-20° C. for 12 h. Water (50 ml) was added to the reaction. The mixture was extracted with DCM (3×100 mL). The combined organics were dried over anhydrous Na₂SO₄, filtered and concentrated in vacuo. The resulting oil was purified by flash column chromatography with MeOH (10%) and DCM (90%) to provide 1'-(2-bromoethyl)spiro[chroman-2,4'-piperidine] (300 mg, 0.97 mmol) as a white solid.

C. To a solution of 1'-(2-bromoethyl)spiro[chroman-2,4'-piperidine] (300 mg, 0.97 mmol) in NaOH (1 g/2 ml) (5 mL) and 1,4-dioxane (0.25 ml) was added (S)-2,3-dihydro-1H-inden-1-ol (0.14 g, 1.07 mmol) and TBAB (1.56 g, 4.85 mmol). The reaction was stirred at ambient temperature for 12 h. Water (50 mL) was added to the reaction vessel. The mixture was extracted with DCM (3×100 mL). The combined organics were dried over anhydrous Na₂SO₄, filtered and concentrated in vacuo. The resulting oil was purified by flash column chromatography DCM (95%) and MeOH (5%) to provide (S)-1'-(2-((2,3-dihydro-1H-inden-1-yl)oxy)ethyl)spiro[chroman-2,4'-piperidine] (90 mg, 0.25 mmol) as a yellow oil.

Example 437. Synthesis of (S)-1-(cyclohexyloxy)-3-(spiro[chromane-2,4'-piperidin]-1'-yl)propan-2-ol

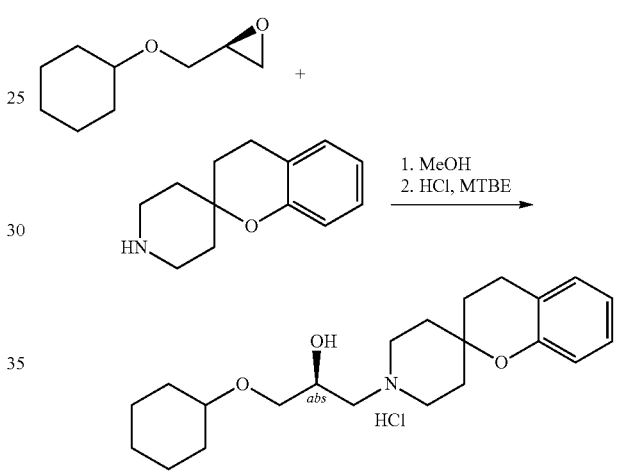

To a solution of spiro[chroman-2,4'-piperidine] (120 mg, 0.5903 mmol) in MeOH (20 mL) was added (S)-2-((cyclohexyloxy)methyl)oxirane (0.0922 g, 0.5903 mmol). The reaction was stirred at 60° C. for 12 h. The reaction mixture was concentrated in vacuo. The resulting oil was purified by reverse phase HPLC with a gradient elution of MeOH (30%) and water (70%) to MeOH (70%) and water (30%) to provide the product 116 mg as an oil. Than added HCl/MTBE 5 mL to provide the desired product (S)-1-(cyclohexyloxy)-3-(spiro[chroman-2,4'-piperidin]-1'-yl)propan-2-ol hydrochloride 100 mg as a solid.

Example 447. Synthesis of 6-(4-(4-fluorophenoxy)phenyl)-N-(2-(piperidin-1-yl)ethyl)picolinamide

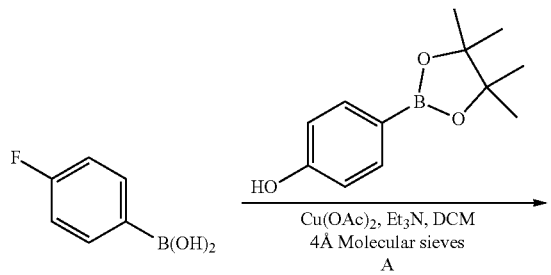

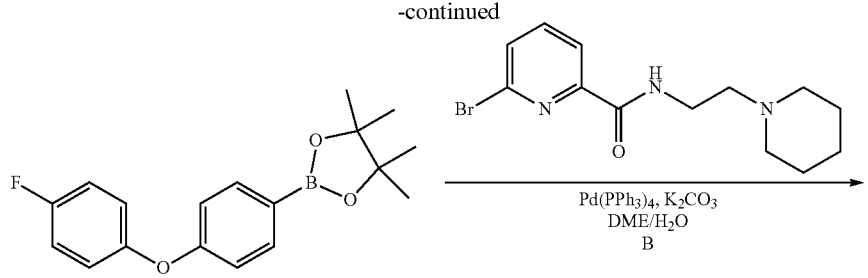

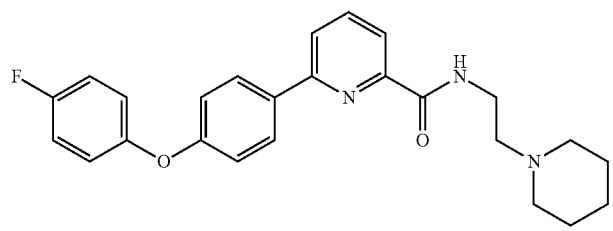

To a solution of (4-fluorophenyl)boronic acid (1.00 g, 7.15 mmol) and 4-(4,4,5,5-tetramethyl-1,3,2-dioxaborolan-2-yl)phenol (0.79 g, 3.58 mmol) in DCM (30 mL) was added Cu(OAc)$_2$ (0.65 g, 3.58 mmol), Et$_3$N (1.81 g, 17.9 mmol) and 4 Å molecular sieves (1.50 g). The reaction was stirred at ambient temperature overnight. The reaction mixture was filtered, and the filter cake was washed with EtOAc (3×20 mL). The combined organic layers were concentrated and the crude product was purified by column chromatography (Hex:EtOAc=10:1) to provide the desired product (0.49 g) as a yellow solid. The desired product was directly used the next step without further purification.

To a solution of 2-(4-(4-fluorophenoxy)phenyl)-4,4,5,5-tetramethyl-1,3,2-dioxaborolane (0.15 g, 0.48 mmol) and 6-bromo-N-(2-(piperidin-1-yl)ethyl)picolinamide (0.14 g, 0.44 mmol; prepared from 6-bromopicolinic acid and 2-(piperidin-1-yl)ethanamine according to Example T-54) in DME/H$_2$O (5 mL/1 mL) was added K$_2$CO$_3$ (0.18 g, 1.31 mmol) and Pd(PPh$_3$)$_4$ (0.05 g, 0.04 mmol). The reaction mixture was degassed for 2 min and refilled with N$_2$ three times, then the reaction mixture was stirred and heated to reflux overnight. The reaction mixture was treated with H$_2$O (10 mL) and extracted with EtOAc (3×10 mL). The combined organic layers were washed with brine, dried over Na$_2$SO$_4$, filtered and concentrated in vacuo. The resulting oil was purified by prep HPLC to provide the desired product (0.035 g, 0.10 mmol).

Example LC. LC Conditions. Compound purity was evaluated by HPLC analysis using a Sunfire C18 4.6×150 mm, 5 μM column. Methods A, B, C and D are defined in the following table. In all methods, flow rate: 0.8 mL/min, Run time: 25.10 min, Detection: 220/254 nM. Gradient: Time 0.01: 10% A, 90% B; Time 0.5 min: 10% A, 90% B; Time 8.00 min: 90% A, 10% B; Time 20.00 min: 90% A, 10% B; Time 20.10 min: 10% A, 90% B; Time 25.00: 10% A, 90% B; Time 25.10: end run.

|  | Mobile Phase A | Mobile Phase B |
|---|---|---|
| Method A | Methanol | 0.01% Trifluoroacetic acid (TFA) in water |
| Method B | Methanol | water |
| Method C | Methanol | 0.1% NH$_3$•H$_2$O in water |
| Method D | acetonitrile | 0.01% TFA in water |

Example CS: Chiral Separation Conditions. Mixtures of enantiomers and mixtures of diasteriomers were separation using Supercritical Fluid Chromatography (SFC). Methods E-H are defined in the following table.

TABLE 6

Chiral HPLC methods.

|  | Column | Solvent | Flow |
|---|---|---|---|
| Method E | 4.6 × 100 mm ChiralPak AD-H | Isocratic: 25% isopropanol with 0.1% isopropylamine | 75% CO$_2$ at 4 mL/min |
| Method F | 3 × 25 cm ChiralPak AD-H | Isocratic: 30% isopropanol w/0.5% isopropylamine | 75% CO$_2$ at 4 mL/min |
| Method G | 4.6 × 25 cm ChiralPak OJ-H | Isocratic: Methanol with 0.1% diethylamine | 75% CO$_2$ at 2.25 mL/min |
| Method H | 4.6 × 25 cm ChiralPak AD-H | Isocratic: Methanol with 0.1% diethylamine | 75% CO$_2$ at 2.25 mL/min |

TABLE 7

| Compound Separated | Separation Conditions and comments | Cmpd # | Peak # | Chiral Retention time (min) | Salt | Amount (mg) | % ee |
|---|---|---|---|---|---|---|---|
| 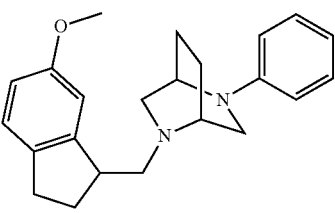 [SMILES: COc1ccc2c(c1)C(CN1CC3CCC1CN3c1ccccc1)CC2] 310 | Separated with prep Method F. Analytical data with Method E. Note: Peak 1 and Peak 4 are enantiomers. Peak 3 and Peak 2 are enantiomers | 311 312 313 314 | Peak 1 Peak 2 Peak 3 Peak 4 | 1.8 min 2.2 min 2.4 min 3.1 min | HCl HCl HCl HCl | 82 43 55 82 mg | 99% 100% 99.1% 100% |
| 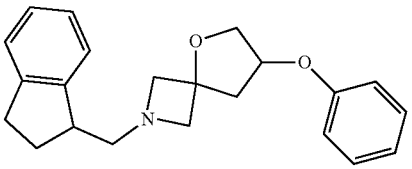 [SMILES: c1ccc(OC2COC3(C2)CN(CC2CCc4ccccc42)C3)cc1] 362 | Separated and analytical data with Method G. Peak 3 required second purification, by Method H. | 364 365 367 366 | Peak 1 Peak 2 Peak 3 Peak 4 | 2.77 min 3.42 min 3.81 min 7.02 min | HCl HCl HCl HCl | 48 19 44 49 | 98% 95% 99% 100% |
| 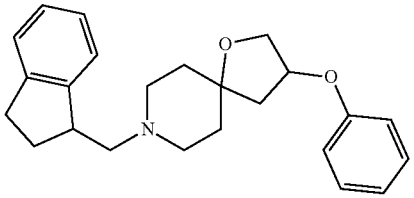 [SMILES: c1ccc(OC2COC3(CCN(CC4CCc5ccccc54)CC3)C2)cc1] 380 | Separated first with Method G. Peak 3 required second purification, by Method H. Separation method for analytical data | 381 382 384 383 | Peak 1 Peak 2 Peak 3 Peak 4 | 3.33 min 4.12 min 4.49 min 5.52 min | HCl HCl HCl HCl | 70 64 62 47 | 100% 97% 96.2% 100% |
| 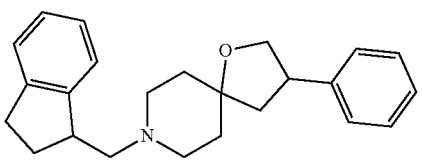 [SMILES: c1ccc(C2COC3(CCN(CC4CCc5ccccc54)CC3)C2)cc1] 375 | Separated and analytical with Method H. | 376 377 378 379 | Peak 1 Peak 2 Peak 3 Peak 4 | 4.03 min 4.64 min 5.39 min 5.67 min | HCl HCl HCl HCl | 38 56 29 38 | 100% 97% 98.7% 100% |

Pharmacology Assays

In vitro method for NaV1.2 inhibition assays: The methods utilized to assess the inhibitory activity of compounds on NaV1.2 were based on the methods described by Liu et al. [Liu Y, Beck E J, & Flores C M (2011): Validation of a patch clamp screening protocol that simultaneously measures compound activity in multiple states of the voltage-gated sodium channel Nav1.2. Assay Drug Development Technology 9, 628-634]. For these electrophysiology assays, a cell line (Chinese Hamster Ovarian K-1 cells (CHO K-1)) engineered to stably express human sodium channel NaV1.2 was purchased from Millipore Corporation (catalog no. CYL3023). The electrophysiology measurements were performed using automated patch-clamp methods on a Q-Patch HTX instrument by scientists at Evotec AG under contract with Sunovion.

The solutions utilized for the Qpatch experiments were similar buffered solutions to those described by Liu et al. [Liu Y, Beck E J, & Flores C M (2011)]. The extracellular solution contained 140 millimolar sodium chloride, 4 millimolar potassium chloride, 2 millimolar calcium chloride, 1 millimolar magnesium chloride, 10 millimolar 4-(2-hydroxyethyl)-1-piperazineethanesulfonic acid (HEPES), and 10 millimolar glucose (pH adjusted to 7.4 with sodium hydroxide). The intracellular solution contained 100 millimolar cesium fluoride, 45 millimolar cesium chloride, 10 millimolar HEPES, 5 millimolar ethylene glycol tetraacetic acid (EGTA), and 5 millimolar glucose (pH adjusted to 7.2 with cesium hydroxide).

The biophysical experiments of Lui et al. [Liu Y, Beck E J, & Flores C M (2011)] were replicated to assess the fast, slow and total inactivation characteristics of the human Nav1.2 channel Fast Inactivation:
100 milliseconds (msec) pre-pulse from −90 millivolts (mV) to +70 mV.
Mean $V_{1/2}$ for fast inactivation=−41.6±1.2 mV
Slow Inactivation
10 second pre-pulse from −90 mV to +20 mV
Recovery time=300 msec
Mean $V_{1/2}$ for slow inactivation=−52.2±0.7 mV
Total Inactivation
10 second pre-pulse from −90 mV to +20 mV
Recovery time=0 msec
Mean $V_{1/2}$ for total inactivation=−60.3±2.2 mV These results were comparable to values reported by Liu with a slight difference in the $V_{1/2}$ for fast inactivation (Liu reported −48.4 mV for rat NaV1.2), which may be caused by species differences.

Based upon results from studies of the fast, slow and total inactivation characteristics of the human Nav1.2 channel, a voltage protocol involving a sequence of consecutive pulses of current was used to measure channel activity in several states [Liu Y, Beck E J, & Flores C M (2011)]. The monolayer of CHO K-1 cells stably expressing human sodium channel NaV1.2 (hNaV1.2 CHO cells) was maintained in the Qpatch instrument at a potential of −100 millivolts (mV) except when the voltage protocol was being executed. The first pulse in the protocol involved a 100 millisecond depolarization to 0 mV to enable measurement of channel availability in the closed state (state A). The potential was then maintained at −90 mV for 15 milliseconds, followed by a five millisecond period of depolarization to 0 mV to enable measurement of channel availability after partial recovery from fast inactivation (state B). Next, the potential was maintained at −90 mV for 300 milliseconds, followed by ten seconds at −50 mV, 15 milliseconds at −90 mV, and finally another five millisecond period of depolarization to 0 mV to enable measurement of channel availability after additional recovery from fast inactivation and significant entry into the slow inactivated state (state C). Finally, after an additional 300 millisecond period at −90 mV, another five millisecond period of depolarization to 0 mV was employed to enable measurement of channel availability after partial recovery from the slow inactivated state (state D). Measurements of activity at state C were used to assess the activity of the NaV1.2 channel in the slow inactivated state. Comparison of activity after addition of test compounds or reference compounds with activity after addition of vehicle only provided a measure of percent remaining activity from which percent inhibition was calculated. Test and reference compounds were added as solutions in DMSO, which had no effect on observed channel activities up to the highest concentration used (0.3%). A slight modification of this protocol was utilized to provide measurements as a function of compound concentration, which enabled $IC_{50}$ values to be determined. $IC_{50}$ values were calculated by non-linear least squares regression of the data (percent inhibition of ion channel NaV1.2 activity in the slow inactivated state) onto equation (1):

$$\% \text{ inhibition} = 100\%/(1+(IC_{50}/[\text{compound}])) \quad \text{equation (1)}$$

The $IC_{50}$ values measured with several reference compound showed good inter-test reproducibility (Table 8), and agreed with published values for these compounds [Liu Y, Beck E J, & Flores C M (2011); Sheets P L, Heers C, Stoehr T, Cummins T R. Differential block of sensory neuronal voltage-gated sodium channels by lacosamide, lidocaine, and carbamazepine. J Pharmacol Exp Ther. 2008 July; 326(1):89-99.].

TABLE 8

Inter-test reproducibility for $IC_{50}$ (μM) for NaV1.2 slow inactivated state

| Reference compound | Test 1 | Test 2 | Test 3 | Test 4 |
|---|---|---|---|---|
| carbamazepine | 19 | 22 | | |
| lacosamide | 65 | 65 | | |
| lamotrigine | 34 | 33 | 25 | |
| lidocaine | 33 | 51 | 56 | |

TABLE 8-continued

Inter-test reproducibility for $IC_{50}$ (μM) for NaV1.2 slow inactivated state

| Reference compound | Test 1 | Test 2 | Test 3 | Test 4 |
|---|---|---|---|---|
| phenytoin | 27 | 17 | 17 | |
| sipatrigine | 1.6 | 2.8 | 0.6 | 0.5 |

In Vitro Method for 5-HT2A Assays:

The methods utilized to assess the inhibitory activity of compounds on recombinant human serotonin receptor 5-HT2A was based upon previously published approaches [Jerman J C, Brough S J, Gager T, Wood M, Coldwell M C, Smart D, Middlemiss D N. Pharmacological characterisation of human 5-HT2 receptor subtypes. European Journal of Pharmacology 2001 Feb. 23; 414(1):23-30; Le Poul E, Hisada S, Mizuguchi Y, Dupriez V J, Burgeon E, Detheux M. Adaptation of aequorin functional assay to high throughput screening. J Biomolecular Screening 2002 February; 7(1):57-65.] The 5-HT2A receptor signals through Gq-phospholipase signaling cascade, which leads to a transient increase in free intracellular $Ca^{2-}$ concentration. Both 5-HT2A assay methods rely upon monitoring these changes in $Ca^{2+}$ concentration.

In method A [Le Poul E, Hisada S, Mizuguchi Y, Dupriez V J, Burgeon E, Detheux M. (2002)], CHO-K1 cells engineered to stably co-express both recombinant human 5-HT2A and mitochondrial apoaequorin are used. Cell grown to mid-log phase are detached from culture flasks into a suspension with a solution of EDTA in phosphate buffered saline, pelleted by gentle centrifugation and re-suspended in assay buffer (Dulbecco's Modification of Eagle's Medium (DMEM)/Ham's F-12 medium buffered with HEPES, and including 0.1% w/v protease-free bovine serum albumin at a concentration of $10^6$ cells per milliliter. The suspended cells are incubated at ambient temperature (about 18° C.) for at least four hours with coelenterazine. The reference agonist alpha-methyl-serotonin is tested to evaluate the performance of the assay on each day of the test, and to determine the working value of $EC_{50}$ (the agonist concentration which generated a hal-maximal response). For agonist testing, 50 microliters of cell suspension is mixed with 50 microliters of a solution containing test compound or reference agonist in a 96-well standard geometry microtiter plate. The resulting emission of light was recorded using a Hamamatsu Functional Drug Screening System 6000 (FDSS 6000) luminometer. For antagonist testing, 100 microliters of the solution of reference agonist (to yield an agonist concentration, $EC_{80}$, sufficient to cause the cells to generate an 80% maximal luminescence response in the absence of any antagonist) is injected into the mix of cells and test compound, 15 minutes after the first injection. The resulting emission of light is recorded using Hamamatsu FDSS 6000 luminometer. $IC_{50}$ values are calculated (from compound concentration dependent inhibition of agonist-induced 5-HT2A-dependent light emission) by non-linear least squares regression of the data (percent inhibition) onto equation (1) above.

In method B [Jerman J C, Brough S J, Gager T, Wood M, Coldwell M C, Smart D, Middlemiss D N. (2001)], CHO-K1 cells which had been engineered to stably co-express recombinant human 5-HT2A are used in assay done similarly to method A. In method B, the cells are loaded with a fluorogenic $Ca^{2+}$ indicator dye by pre-incubation. Addition of the reference agonist serotonin causes a transient increase in fluorescence in a suspension of the loaded cells, which can be detected using the Molecular Devices fluorometric imaging plate reader (FLIPR), a high-throughput platform for 96-well cell-based assays. Addition of test compounds that are 5-HT2A antagonists, prior to the addition of the agonist (to yield an agonist concentration, $EC_{80}$, sufficient to cause the cells to generate an 80% maximal fluorescence response in the absence of any antagonist), reduces the amount of fluorescence detected by the FLIPR upon agonist addition. $IC_{50}$ values are calculated (from compound concentration dependent inhibition of agonist-induced 5-HT2A-dependent fluorescence) by non-linear least squares regression of the data (percent inhibition) onto equation (1) above. Values of $IC_{50}$ determined by methods A and B were statistically equivalent within experimental variability of $IC_{50}$ determinations, which varied less than three-fold between assay runs done on different days.

The data from pharmacology assays are given in Table 9.

TABLE 9

Pharmacological Data

| | NaV1.2 (% inh), 10 µM | NaV1.2 (% inh), 1 µM | NaV1.2 $IC_{50}$, µM | 5HT2A $IC_{50}$, µM |
|---|---|---|---|---|
| 1 | | | | 2.30 |
| 2 | | | | 1.25 |
| 3 | | −5 | | 1.88 |
| 4 | | | | 1.45 |
| 5 | | | | 5.88 |
| 6 | | | | 3.00 |
| 7 | | | | 1.01 |
| 8 | | | 7.45 | 0.98 |
| 9 | | 1 | | 0.60 |
| 10 | | 3 | | 0.31 |
| 11 | | 29 | | 0.59 |
| 12 | | | 3.23 | 0.30 |
| 13 | | | | 1.93 |
| 14 | | | | 7.47 |
| 15 | | | | >16.7 |
| 16 | | | | 1.85 |
| 17 | | | | 0.40 |
| 18 | | | | 0.02 |
| 19 | | | | 0.56 |
| 20 | | | | 0.01 |
| 21 | | | | 2.56 |
| 22 | | | | 2.34 |
| 23 | | | | >16.7 |
| 24 | | | | >16.7 |
| 25 | 83 | | | 0.17 |
| 26 | 70 | | | 0.17 |
| 27 | | | | 2.80 |
| 28 | | | | 10.04 |
| 29 | | | | >16.7 |
| 30 | | | | >16.7 |
| 31 | | | | >16.7 |
| 32 | | | | >16.7 |
| 33 | | | | >10.0 |
| 34 | | | | 4.66 |
| 35 | | | | 7.13 |
| 36 | | | 0.25 | 1.76 |
| 37 | | | | 9.01 |
| 38 | | | | 3.17 |
| 39 | | | | 4.30 |
| 40 | | | | 1.60 |
| 41 | | | | 7.13 |
| 42 | | | 0.75 | 0.83 |
| 43 | | | | 2.08 |
| 44 | | | 0.24 | 0.14 |
| 45 | 85 | | | 0.61 |
| 46 | | 41 | | 0.03 |
| 47 | | | 0.36 | 0.10 |
| 48 | | | | 2.22 |
| 49 | | | | 2.55 |
| 50 | | | 1.29 | 0.06 |
| 51 | | | | 0.49 |
| 52 | | | 1.69 | 0.14 |
| 53 | | | 1.93 | 0.23 |
| 54 | | | 2.64 | 0.00 |
| 55 | | | 4.12 | 0.01 |
| 56 | | | 0.43 | 0.13 |
| 57 | 83 | | | 0.10 |
| 58 | | | | 0.49 |
| 59 | | | | 0.80 |
| 60 | | | | |
| 61 | 8 | | | 0.20 |
| 62 | | | 5.27 | 0.05 |
| 63 | | 16 | | 0.45 |
| 64 | 93 | | | 0.04 |
| 65 | | | | |
| 66 | 55 | | | 0.89 |
| 67 | 85 | | | 0.01 |
| 68 | | | 0.73 | 0.004 |
| 69 | 91 | | | 0.003 |
| 70 | | | 1.70 | 0.004 |
| 71 | | | | |
| 72 | | | | |
| 73 | 91 | | | 0.002 |
| 74 | | | 50.85 | 0.06 |
| 75 | 21 | | | >4.2 |
| 76 | | | 0.24 | 0.02 |
| 77 | | | 9.02 | 0.21 |
| 78 | | | 4.66 | >10.0 |
| 79 | | | | 0.36 |
| 80 | | | 0.17 | 0.06 |
| 81 | | | 0.16 | 0.03 |
| 82 | | | 1.35 | 0.04 |
| 83 | | | 0.02 | 2.87 |
| 84 | | | | >16.7 |
| 85 | | 24 | | >11.9 |
| 86 | | | | >16.7 |
| 87 | | 15 | | 3.63 |
| 88 | | | 31.20 | 0.58 |
| 89 | | | 0.44 | 0.07 |
| 90 | | | 59.50 | 0.01 |
| 91 | | | 0.17 | 0.02 |
| 92 | | | 0.01 | 0.23 |
| 93 | | | | |
| 94 | | | | |
| 95 | | 9 | | 0.15 |
| 96 | | | | >10.0 |
| 97 | | | 0.08 | |
| 98 | | 37 | | 0.01 |
| 99 | | | | 0.45 |
| 100 | | | 2.60 | 0.71 |
| 101 | | | 0.37 | 0.08 |
| 102 | 82 | | | 0.15 |
| 103 | | | 3.13 | 0.22 |
| 104 | | 46 | | 0.26 |
| 105 | | | | 0.43 |
| 106 | | | >10.0 | 0.01 |
| 107 | | | 1.99 | 0.004 |
| 108 | | | | 0.74 |
| 109 | | | | 1.92 |
| 110 | | | | 4.04 |
| 111 | | | | 0.21 |
| 112 | | | 1.44 | 0.004 |
| 113 | | | 0.55 | 0.002 |
| 114 | 52 | | | 0.07 |
| 115 | | | 2.58 | <0.001 |
| 116 | | | 2.34 | 0.01 |
| 117 | | 1 | | 0.58 |
| 118 | | | | 1.78 |
| 119 | | | 0.18 | 0.02 |
| 120 | | | | 0.44 |
| 121 | | | 2.09 | 0.07 |
| 122 | | | 0.11 | 0.09 |
| 123 | | 71 | | 0.44 |
| 124 | | 34 | | 0.12 |
| 125 | | −3 | | 0.08 |
| 126 | | | | >3.16 |
| 127 | | | | >12 |
| 128 | 72 | | | 0.05 |
| 129 | | | 1.06 | 0.40 |
| 130 | | | | >10.0 |

TABLE 9-continued

Pharmacological Data

| | NaV1.2 (% inh), 10 μM | NaV1.2 (% inh), 1 μM | NaV1.2 IC$_{50}$, μM | 5HT2A IC$_{50}$, μM |
|---|---|---|---|---|
| 131 | | −1 | | 0.29 |
| 132 | | | | 0.04 |
| 133 | | | | 0.29 |
| 134 | | 14 | | 0.02 |
| 135 | | | | 0.12 |
| 136 | | 50 | | 0.06 |
| 137 | | 44 | | 0.04 |
| 138 | | 10 | | 0.13 |
| 139 | | −10 | | 0.18 |
| 140 | | | 0.51 | 0.63 |
| 141 | | | 1.01 | 0.20 |
| 142 | | | 0.91 | 0.30 |
| 143 | | | | 0.08 |
| 144 | | | 0.54 | 0.27 |
| 145 | | | | 0.01 |
| 146 | | | | >1.0 |
| 147 | | | 1.53 | 0.07 |
| 148 | | | | 1.44 |
| 149 | | | | 0.30 |
| 150 | | 14 | | 0.72 |
| 151 | | | | >10.0 |
| 152 | | | | 0.22 |
| 153 | | | | 0.76 |
| 154 | | 35 | | 0.17 |
| 155 | | | 1.00 | 0.04 |
| 156 | | | | 2.01 |
| 157 | | | | >10.0 |
| 158 | | −15 | | 0.15 |
| 159 | 77 | | | 0.02 |
| 160 | | 32 | | 0.13 |
| 161 | | 12 | | 0.05 |
| 162 | | 32 | | 0.09 |
| 163 | | | | 0.26 |
| 164 | | | | 0.86 |
| 165 | | | 0.91 | 0.02 |
| 166 | | −2 | | 0.31 |
| 167 | | 13 | | 0.09 |
| 168 | | 2 | | 0.13 |
| 169 | | 10 | | 0.28 |
| 170 | | 5 | | 1.11 |
| 171 | | | 0.04 | 0.06 |
| 172 | | 34 | | 0.12 |
| 173 | | | 3.17 | 0.01 |
| 174 | | 12 | | 0.01 |
| 175 | | | 0.44 | 0.01 |
| 176 | | 41 | | 0.08 |
| 177 | | 34 | | 0.01 |
| 178 | | | 1.90 | 0.03 |
| 179 | | | 0.61 | 0.06 |
| 180 | | 8 | | 0.32 |
| 181 | | | | >10.0 |
| 182 | | 52 | | 0.20 |
| 183 | | | 1.59 | 0.04 |
| 184 | | 35 | | 0.08 |
| 185 | | 19 | | 0.01 |
| 186 | | −3 | | 0.01 |
| 187 | | 14 | | 0.07 |
| 188 | | 32 | | 0.05 |
| 189 | | 0 | | 0.18 |
| 190 | | 25 | | 0.01 |
| 191 | 52 | 18 | | 0.05 |
| 192 | 15 | | | 2.84 |
| 193 | 66 | | | 0.33 |
| 194 | | | 0.23 | 0.11 |
| 195 | | | 1.50 | 0.26 |
| 196 | 67 | | | 0.36 |
| 197 | 47 | | | 1.25 |
| 198 | | | | 0.41 |
| 199 | | | | >8.7 |
| 200 | 73 | | | 0.01 |
| 201 | 39 | | | 2.17 |
| 202 | 62 | | | 0.174 |
| 203 | 14 | | | 0.07 |
| 204 | | | | 0.56 |
| 205 | 76 | | | 0.45 |
| 206 | 46 | | | >1.3 |
| 207 | 38 | | | 0.03 |
| 208 | | | 1.21 | 0.01 |
| 209 | | | 0.27 | 0.02 |
| 210 | | | 1.07 | 0.02 |
| 211 | 50 | | | 0.27 |
| 212 | 48 | | | 0.01 |
| 213 | | | 0.18 | 0.08 |
| 214 | | | | 0.04 |
| 215 | | 25 | | 0.19 |
| 216 | | 34 | | 0.15 |
| 217 | | 58 | | 0.28 |
| 218 | 72 | | | 0.44 |
| 219 | 54 | | | 0.01 |
| 220 | 12 | | | 0.49 |
| 221 | | | 1.00 | 0.98 |
| 222 | | | 1.30 | 0.06 |
| 223 | 68 | | | 0.03 |
| 224 | 81 | | | 0.17 |
| 225 | 88 | | | 0.25 |
| 226 | | | | 0.02 |
| 227 | 53 | | | 0.14 |
| 228 | 52 | | | 0.14 |
| 229 | | | 1.08 | 0.03 |
| 230 | 87 | | | 0.39 |
| 231 | | | | 0.79 |
| 232 | 76 | | | 0.22 |
| 233 | | | | 0.05 |
| 234 | | | | 0.03 |
| 235 | | | 0.34 | 0.19 |
| 236 | | | 0.55 | 0.35 |
| 237 | | | | 0.60 |
| 238 | | 47 | | 0.24 |
| 239 | | | | 3.51 |
| 240 | | | 0.96 | 0.11 |
| 242 | | | 0.23 | 0.09 |
| 243 | | | 0.10 | 0.36 |
| 244 | | | 0.16 | 0.06 |
| 245 | | | | 0.41 |
| 246 | | | | 0.98 |
| 247 | | | 0.27 | 0.10 |
| 248 | | | | >3.16 |
| 249 | | | 0.63 | 0.21 |
| 250 | | | 0.20 | 0.07 |
| 251 | | 23 | | 0.37 |
| 252 | | | | >16.7 |
| 253 | | 21 | | 1.17 |
| 254 | | | 0.77 | 0.52 |
| 255 | | 14 | | 0.36 |
| 256 | | | | 3.99 |
| 257 | | | | >10.0 |
| 258 | | | | 1.50 |
| 259 | | | | >13.3 |
| 260 | | | | 1.81 |
| 261 | | 22 | | 0.35 |
| 262 | | | | 1.63 |
| 263 | | | | >12.9 |
| 264 | | | | 0.94 |
| 265 | | | | >13.1 |
| 266 | | | | >12.9 |
| 267 | | | | 10.43 |
| 268 | | | | 2.12 |
| 269 | | | | 2.17 |
| 270 | | 56 | | 0.11 |
| 271 | | 44 | | 0.23 |
| 272 | | | 0.83 | 0.01 |
| 273 | | | | 0.02 |
| 274 | | 27 | | 0.19 |
| 275 | | 2 | | 0.40 |
| 276 | | | 0.44 | 0.40 |
| 277 | | 31 | | 0.10 |
| 278 | | | | >3.16 |
| 279 | | | | >10.0 |
| 280 | | | | 4.89 |
| 281 | | | 1.79 | 1.36 |

TABLE 9-continued

Pharmacological Data

| | NaV1.2 (% inh), 10 μM | NaV1.2 (% inh), 1 μM | NaV1.2 IC$_{50}$, μM | 5HT2A IC$_{50}$, μM |
|---|---|---|---|---|
| 286 | | | 1.25 | 0.01 |
| 287 | | | 0.58 | 0.03 |
| 288 | | | 0.44 | 0.04 |
| 289 | | | | 0.02 |
| 290 | | | | 0.002 |
| 291 | | | | >10.0 |
| 292 | | | | >10.0 |
| 293 | | | | 1.02 |
| 294 | 47 | | | 0.28 |
| 295 | | 2 | | >16.7 |
| 296 | | | | >10.0 |
| 297 | | −4 | | >16.7 |
| 298 | | | | >11 |
| 299 | | | 3.57 | 1.72 |
| 300 | | | | >10.0 |
| 301 | | | | >10.0 |
| 302 | | | | >2.7 |
| 303 | | | 1.82 | 2.60 |
| 304 | | 4 | | 7.05 |
| 305 | | | | >14.5 |
| 306 | 60 | | | 1.66 |
| 307 | | | | 10.40 |
| 308 | 27 | | | 4.02 |
| 309 | 52 | | | 4.81 |
| 310 | | | 0.70 | 0.03 |
| 311 | | | | 0.01 |
| 312 | | | | 0.43 |
| 313 | | | | >10.0 |
| 314 | | | | >10.0 |
| 315 | | 5 | | 5.28 |
| 316 | | | 0.08 | 3.17 |
| 317 | | | 1.83 | 0.49 |
| 318 | 48 | | | >5.3 |
| 319 | | | 0.04 | 1.21 |
| 320 | | | | >10.0 |
| 321 | | | | >10.0 |
| 322 | | | | >3.16 |
| 323 | | | | >3.16 |
| 324 | | | | >3.16 |
| 325 | | | 0.22 | 0.25 |
| 326 | | | | >3.16 |
| 327 | | | | >3.16 |
| 328 | | 31 | | 5.31 |
| 329 | | 36 | | >16.7 |
| 330 | | | | >16.7 |
| 331 | | | 0.31 | 1.64 |
| 332 | | | | >16.7 |
| 333 | | | | >16.7 |
| 334 | | | | >16.7 |
| 335 | | | 0.12 | 0.04 |
| 336 | | | | 3.28 |
| 337 | | −2 | | 0.45 |
| 338 | | | | >10.0 |
| 339 | | | 2.27 | 0.87 |
| 340 | | 25 | | 0.10 |
| 341 | | | | 3.12 |
| 342 | | | | 2.08 |
| 343 | | | | 2.46 |
| 344 | | | 0.43 | 0.11 |
| 345 | | | 1.90 | 0.24 |
| 346 | | | 0.32 | 0.27 |
| 347 | | | 3.19 | 0.03 |
| 348 | | | | 7.34 |
| 349 | | | | >16.7 |
| 350 | | | 1.68 | 0.61 |
| 351 | | | | >16.7 |
| 352 | | | | >5.3 |
| 353 | | | | >16.7 |
| 354 | | | | 1.94 |
| 355 | | | | >16.7 |
| 356 | | | 0.61 | 0.25 |
| 357 | | | | 11.00 |
| 358 | | | >10.0 | 0.87 |
| 359 | | 16 | | 0.55 |
| 360 | | 4 | | 0.13 |
| 361 | | | 2.71 | 0.02 |
| 362 | | | 6.37 | 0.50 |
| 363 | | 48 | | 0.62 |
| 364 | | | 0.69 | 0.08 |
| 365 | | | 2.18 | 0.22 |
| 366 | | | | 1.00 |
| 367 | | | 0.39 | 0.28 |
| 368 | | | 0.38 | 0.15 |
| 369 | 64 | | | 0.29 |
| 370 | | | 2.01 | 0.10 |
| 371 | | | | 0.09 |
| 372 | | | | 0.09 |
| 373 | | | 2.42 | 0.44 |
| 374 | | 9 | | 0.25 |
| 375 | | | 0.35 | 0.26 |
| 376 | | | 0.51 | 0.02 |
| 377 | | | 0.79 | 0.03 |
| 378 | | | 0.77 | 0.06 |
| 379 | | | 0.29 | 0.04 |
| 380 | | | 0.12 | 0.15 |
| 381 | | | 0.29 | 0.02 |
| 382 | | | 1.21 | 0.06 |
| 383 | | | 0.11 | 0.34 |
| 384 | | | 0.29 | 0.30 |
| 385 | | 16 | | 0.54 |
| 386 | | | | 3.76 |
| 387 | | 29 | | 0.03 |
| 388 | | | 1.75 | 0.22 |
| 389 | | | | 8.58 |
| 390 | | | 0.59 | 0.75 |
| 391 | | | | 14.1+ |
| 392 | | | | 1.59 |
| 393 | 93 | | | 1.80 |
| 394 | | | | >10.9 |
| 395 | | | | >10.0 |
| 396 | | | 0.17 | 0.09 |
| 397 | | | | 2.76 |
| 398 | | | | 9.65+ |
| 399 | 92 | | | 1.83 |
| 400 | 102 | | | 2.29 |
| 401 | | | 0.11 | 0.05 |
| 402 | | | 0.07 | 1.07 |
| 403 | | −4 | | 0.004 |
| 404 | | 14 | | 0.11 |
| 405 | | 18 | | 0.18 |
| 406 | | 7 | | 0.04 |
| 407 | | | | 3.64 |
| 408 | | | | 0.74 |
| 409 | | | 2.83 | 0.93 |
| 410 | | | 0.48 | 0.10 |
| 411 | | 37 | | 1.20 |
| 412 | | 18 | | 1.86 |
| 413 | | | | 1.10 |
| 414 | | 29 | | 0.26 |
| 415 | | | | 2.15 |
| 416 | | | | 1.05 |
| 417 | 94 | | | 0.69 |
| 418 | | | 1.13 | 0.16 |
| 419 | | 6 | | 0.22 |
| 420 | | 0 | | 0.25 |
| 421 | | 29 | | 0.13 |
| 422 | | | 0.40 | 0.07 |
| 423 | | | | 2.81 |
| 424 | | | | 0.05 |
| 425 | | | | 0.12 |
| 426 | | 41 | | 0.16 |
| 427 | 81 | | | 0.04 |
| 428 | 86 | | | 0.19 |
| 429 | | | 1.34 | 0.37 |
| 431 | | | | 0.71 |
| 432 | | | 0.36 | 0.15 |
| 433 | | | | 0.32 |
| 434 | | | | 0.73 |
| 435 | | | | 0.37 |
| 436 | | | 0.26 | 0.02 |

349

TABLE 9-continued

Pharmacological Data

| | NaV1.2 (% inh), 10 µM | NaV1.2 (% inh), 1 µM | NaV1.2 IC$_{50}$, µM | 5HT2A IC$_{50}$, µM |
|---|---|---|---|---|
| 437 | | | 3.41 | 0.09 |
| 438 | | | 1.31 | 0.15 |
| 439 | | | 0.50 | 0.01 |
| 440 | | −8 | | 0.08 |
| 441 | | 17 | | 0.03 |
| 442 | | 37 | | 0.59 |
| 443 | | | 3.37 | 0.22 |
| 444 | | | | 1.44 |
| 445 | | −2 | | 0.30 |
| 446 | | 11 | | 0.61 |
| 447 | 99 | | | 1.26 |

It may be found upon examination that additional species and genera not presently excluded from the claims to pharmaceutical compositions and chemical compounds are not patentable to the inventors in this application. In that case, the subsequent exclusion of species and genera in applicants' claims are to be considered artifacts of patent prosecution and not reflective of the inventors' concept or description of their invention. The invention, in a composition aspect, is all compounds of formula I except those that are in the public's possession.

The invention claimed is:

1. A compound of formula I

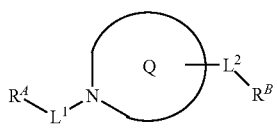

wherein
Q is piperidine attached to L$^1$ at a nitrogen, wherein substituents, when present, are selected from the group consisting of halogen, hydroxy, (C$_1$-C$_6$)alkyl, (C$_1$-C$_6$)alkoxy, and oxo;
R$^A$ is selected from the group consisting of (1) an optionally substituted bicyclic carbocycle containing an aromatic 6-membered ring and a non-aromatic 5-membered ring; and (2) an optionally substituted, bicyclic heterocycle selected from the group consisting of a cyclopenta[b]pyridine, a dihydrobenzofuran, a dihydrofuro[3,2-b]pyridine, a cyclopenta[c]pyridine, an indoline, a pyrrolo[3,4-b]pyridine, and an isoindoline;
L$^1$ is —(CH$_2$CHR$^1$)—, wherein R$^1$ is hydrogen or methyl;
L$^2$ is —O—; and
R$^B$ is an optionally substituted aromatic carbocycle wherein substituents, when present, are selected from the group consisting of halogen, cyano, (C$_1$-C$_6$)alkyl, (C$_1$-C$_6$)alkoxy, (C$_1$-C$_6$)oxaalkyl, —C(=O)NH$_2$, and di(C$_1$-C$_6$)alkylamino.

2. A compound according to claim 1 wherein R$^A$ is an optionally substituted bicyclic carbocycle containing an aromatic 6-membered ring and a non-aromatic 5-membered ring.

3. A compound according to claim 1 wherein R$^A$ is an optionally substituted bicyclic heterocycle selected from the group consisting of a cyclopenta[b]pyridine, a dihydrobenzofuran, a dihydrofuro[3,2-b]pyridine, a cyclopenta[c]pyridine, an indoline, a pyrrolo[3,4-b]pyridine, and an isoindoline.

350

4. A compound according to claim 1 wherein L$^1$ is —CH$_2$CH$_2$—.

5. A compound according to claim 1 wherein R$^A$ is selected from the group consisting of indane, dihydrobenzofuran, 3-methyldihydrobenzofuran, methylindane, haloindane, cyanoindane, and methoxyindane.

6. A compound according to claim 1 wherein R$^B$ is selected from the group consisting of benzene, halobenzene, methylbenzene, dimethylbenzene, and methoxybenzene.

7. A compound according to claim 1 wherein the piperidine Q is unsubstituted or is substituted with one or two methyls.

8. A compound according to claim 1 wherein R$^A$ is indane.

9. A compound according to claim 1 wherein R$^B$ is halobenzene.

10. A compound according to claim 1 wherein R$^B$ is dimethylbenzene.

11. A compound according to claim 1 selected from the group consisting of:

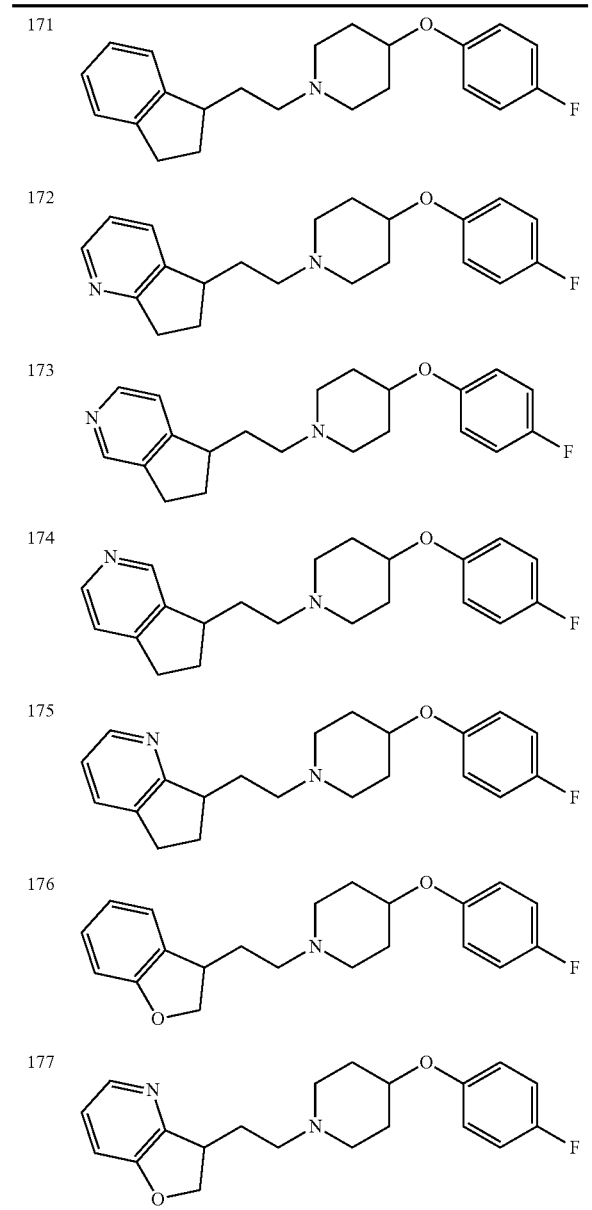

| | |
|---|---|
| 178 | 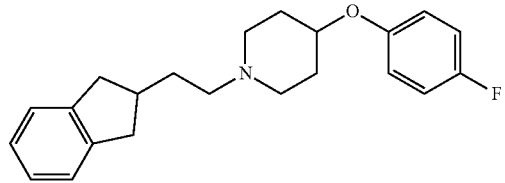 [SMILES: Fc1ccc(OC2CCN(CCC3Cc4ccccc4C3)CC2)cc1] |
| 185 | 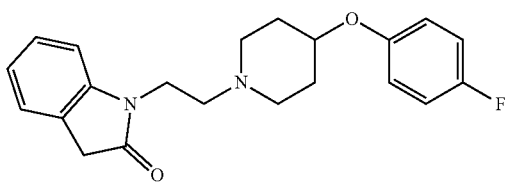 [SMILES: O=C1Cc2ccccc2N1CCN1CCC(Oc2ccc(F)cc2)CC1] |
| 186 | 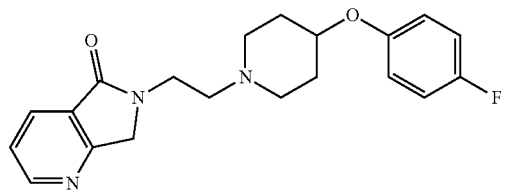 [SMILES: O=C1c2cccnc2CN1CCN1CCC(Oc2ccc(F)cc2)CC1] |
| 187 | 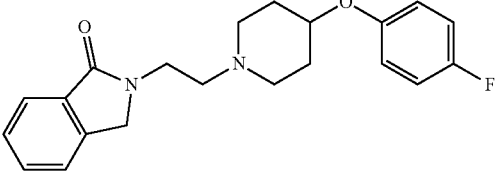 |
| 188 | 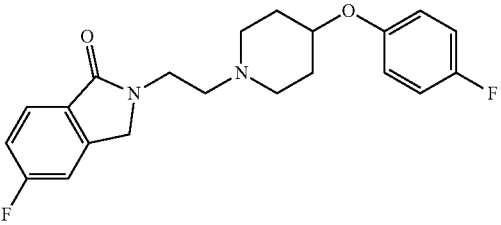 [SMILES: O=C1c2ccc(F)cc2CN1CCN1CCC(Oc2ccc(F)cc2)CC1] |
| 189 | 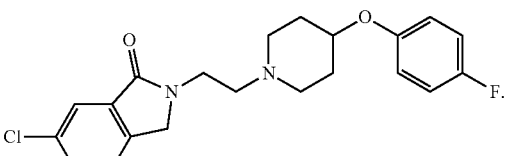 |
* * * * *